US005472933A

United States Patent [19]

Zimmerman et al.

[11] Patent Number: 5,472,933

[45] Date of Patent: Dec. 5, 1995

[54] HERBICIDAL PYRROLESULFONYLUREAS

[75] Inventors: William T. Zimmerman, Landenberg, Pa.; Bruce A. Lockett, Newark, Del.; John Cuomo, Salt Lake City, Utah

[73] Assignee: E. I. Du Pont de Nemours and Company, Wilmington, Del.

[21] Appl. No.: 974,581

[22] PCT Filed: Aug. 22, 1991

[86] PCT No.: PCT/US91/05822

§ 371 Date: Feb. 24, 1993

§ 102(e) Date: Feb. 24, 1993

[87] PCT Pub. No.: WO92/04319

PCT Pub. Date: Mar. 19, 1992

Related U.S. Application Data

[63] Continuation-in-part of Ser. No. 573,074, Aug. 29, 1990, abandoned.

[51] Int. Cl.$^6$ ......................... C07D 403/12; A01N 43/66

[52] U.S. Cl. ............................ 504/213; 544/83; 544/113; 544/198; 544/207; 544/209; 544/212; 544/219

[58] Field of Search ............................ 544/83, 113, 198, 544/207, 209, 212, 219; 504/213

[56] References Cited

U.S. PATENT DOCUMENTS

| | | | |
|---|---|---|---|
| 4,368,067 | 1/1983 | Budzinski et al. | 71/92 |
| 4,401,816 | 8/1983 | Levitt | 544/320 |
| 4,518,776 | 5/1985 | Meyer et al. | 544/206 |
| 4,549,898 | 10/1985 | Böhner et al. | 71/90 |
| 4,639,264 | 1/1987 | Töpfl | 71/87 |
| 4,685,961 | 8/1987 | Töpfl et al. | 71/92 |
| 4,737,184 | 4/1988 | Pasteris | 71/90 |
| 4,756,742 | 7/1988 | Thompson | 71/90 |

FOREIGN PATENT DOCUMENTS

| | | |
|---|---|---|
| 0126711 | 11/1984 | European Pat. Off. . |
| 0161211 | 11/1985 | European Pat. Off. . |

*Primary Examiner*—John M. Ford

[57] ABSTRACT

This invention relates to certain herbicidal pyrrolesulfonylureas, compositions thereof and a method for their use as herbicides or plant growth regulants.

17 Claims, No Drawings

HERBICIDAL PYRROLESULFONYLUREAS

CROSS-REFERENCE TO RELATED APPLICATION

This application is a continuation-in-part of U.S. Ser. No. 07/573,074 filed Aug. 29, 1990, now abandoned.

BACKGROUND OF THE INVENTION

The present invention relates to herbicidal pyrrolesulfonylureas, compositions thereof and a method for their use as preemergence and/or postemergence herbicides or plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

The "sulfonylurea" herbicides are an extremely potent class of herbicides discovered within the last few years which generally consist of a sulfonylurea bridge, —$SO_2NHCONH$—, linking two aromatic or heteroaromatic rings.

U.S. Pat. No. 4,368,067 discloses herbicidal sulfonylureas of the formula

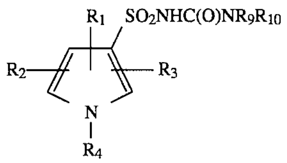

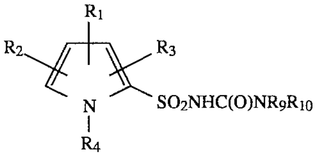

wherein:

$R_1$ is H, $C_1$–$C_4$ alkyl, $NO_2$, CN, $C(O)CCl_3$, $SO_2R_{11}$, $C(O)R_5$ or $CO_2H$;

$R_2$ is H or $C_1$–$C_4$ alkyl;

$R_3$ is H, $C_1$–$C_4$ alkyl, Cl or Br;

$R_4$ is H, $C_1$–$C_4$ alkyl, cyanoethyl, $C_5$–$C_6$ cycloalkyl, benzyl, phenyl substituted with Cl or $NO_2$, or $C(O)R_6$;

$R_5$ is $C_1$–$C_4$ alkyl or $C_1$–$C_4$ alkoxy;

$R_6$ is $C_1$–$C_4$ alkyl, $C_1$–$C_4$ alkoxy or $NR_7R_8$; and $R_7$ and $R_8$ are independently $C_1$–$C_2$ alkyl.

U.S. Pat. No. 4,549,898 discloses herbicidal sulfonamides of the formula

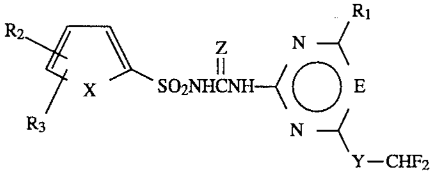

wherein:

X is O, S, $NR_4$ or —$C(R_5)$=N—;

$R_2$ is H, $C_1$–$C_3$ alkyl, $C_1$–$C_3$ haloalkyl, halogen, $NO_2$, $C_1$–$C_3$ alkoxy, $C(W)R_8$, $SO_2NR_6R_7$, $S(O)_n$—$C_1$–$C_3$ alkyl or $C(O)R_9$;

$R_4$ is H, $C_1$–$C_4$ alkyl, $C_1$–$C_4$ cyanoalkyl, $C_3$–$C_6$ cycloalkyl, benzyl, $C(O)C_1$–$C_4$ alkoxy, $C(O)NR_6R_7$ or $C(O)C_1$–$C_4$ alkyl which is unsubstituted or substituted by 1 to 3 halogen atoms;

$R_6$ is H, $C_1$–$C_6$ alkyl, $C_1$–$C_4$ cyanoalkyl, $OCH_3$ or $OCH_2CH_3$;

$R_7$ is H, $C_1$–$C_6$ alkyl or $C_3$–$C_6$ alkenyl; or $R_6$ and $R_7$, together with the nitrogen atom to which they are attached, form a 5- or 6-membered saturated heterocyclic ring which may contain an oxygen; and Y is O or S.

EP-A-126,711 discloses herbicidal sulfonamides of the formula

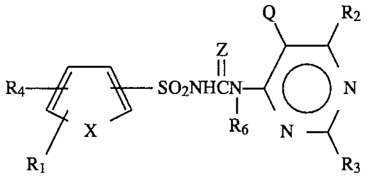

wherein:

Q is halogen, $C_1$–$C_4$ alkyl, $C_1$–$C_4$ haloalkyl, $C_1$–$C_4$ alkoxy, $C_1$–$C_4$ haloalkoxy, $NO_2$, $NH_2$, $C_1$–$C_4$ alkylamino, $C_1$–$C_4$ dialkylamino, CN, $C_1$–$C_4$ alkoxycarbonyl, CHO, $C_2$–$C_4$ alkoxyalkyl, $C_1$–$C_4$ alkylthio, $C_1$–$C_4$ alkylsulfinyl, $C_1$–$C_4$ alkylsulfonyl, $C_1$–$C_4$ alkenyl or $C_1$–$C_4$ alkynyl;

$R_1$ is H, halogen, $NO_2$, $CR_6(OC_1$–$C_4$ alkyl$)_2$,

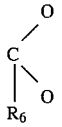 ($C_3$–$C_5$ alkylene), $C(W)R_6$, $SO_2NR_7R_8$, $C(O)R_9$ or $(Y)mR_{10}$;

X is O, S, $NR_5$, $C(R_5)$=N, CH=CH or

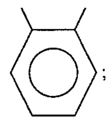 ;

and $R_5$ is H, $C_1$–$C_4$ alkyl or $C_3$–$C_4$ alkenyl.

EP-A-161,211 discloses herbicidal sulfonamides of the formula

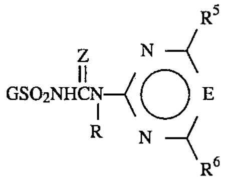

wherein:

G is

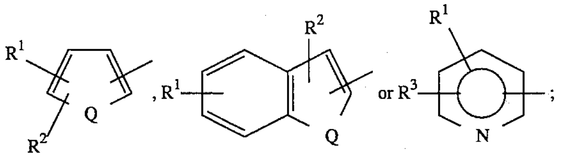

$R^2$ is

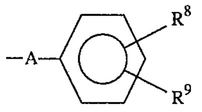

Q is O, S or $NR^7$;

A is O, S, SO, $SO_2$ or $-(CR_{10}R_{11})_m-$;

m is 0, 1 or 2;

$R^7$ is H, $C_1$–$C_4$ alkyl, $C_3$–$C_6$ cycloalkyl, benzyl or phenyl; and $R^{10}$ and $R^{11}$ are independently H or $C_1$–$C_4$ alkyl.

SUMMARY OF THE INVENTION

The invention comprises compounds of Formula I, agriculturally suitable compositions thereof and a method of use as preemergence and/or postemergence herbicides or plant growth regulants.

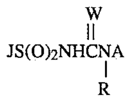

I wherein:

J is

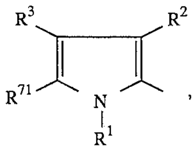

,

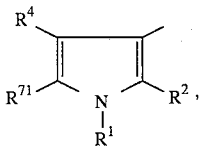

, or

J-1 J-2

-continued

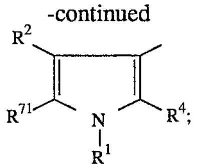

J-3

W is O or S;

R is H or $CH_3$;

$R^1$ is H; $CH_3$; $CH_2OCH_3$; $CH_2OC_2H_5$; $CH_2CN$; $CH_2SCH_3$, $CH_2SC_2H_5$; $C_2$–$C_6$ alkyl optionally substituted with one $C_1$–$C_2$ alkoxy, $C_1$–$C_2$ alkylthio, CN or one or more halogens; $C_3$–$C_4$ alkenyl; $C_3$–$C_4$ haloalkenyl; $C_3$–$C_6$ cycloalkyl; $C(O)R^5$; $N(CH_3)_2$; or $Q^1$;

$R^2$ is $C_1$–$C_4$ alkyl optionally substituted with one CN, $C_2$–$C_3$ alkylcarbonyl, methoxycarbonyl, $C_1$–$C_2$ alkoxy, $C_1$–$C_2$ alkylthio, $C_1$–$C_2$ alkylsulfonyl, $S(O)_2NR^6R^7$, OH or one or more halogens; $C_2$–$C_4$ alkenyl optionally substituted with one $C_1$–$C_2$ alkoxy, $C_1$–$C_2$ alkylthio, CN or one or more halogens; $(CH_2)_mQ^2$; CN; $C(O)R^8$; $C(O)OR^9$; $C(O)NR^{10}R^{11}$; $C(R^{12})$=$NOR^{13}$; $C(R^{14})(OR^{15})(OR^{16})$; $S(O)_nR^{17}$; $S(O)_2NR^{18}R^{19}$; $NO_2$; halogen or $OR^{73}$;

$R^3$ is H, halogen or $C_1$–$C_4$ alkyl;

$R^4$ is H, $C_1$–$C_4$ alkyl optionally substituted with one CN, $C_2$–$C_3$ alkylcarbonyl, methoxycarbonyl, $C_1$–$C_2$ alkoxy, $C_1$–$C_2$ alkylthio, $C_1$–$C_2$ alkylsulfonyl, $S(O)_2NR^6R^7$, OH or one or more halogens; $C_2$–$C_4$ alkenyl optionally substituted with one $C_1$–$C_2$ alkoxy, $C_1$–$C_2$ alkylthio, CN or one or more halogens; CN; $C(O)R^8$; $C(O)OR^9$; $C(O)NR^{10}R^{11}$; $C(R^{12})$=$NOR^{13}$; $S(O)_nR^{17}$; $S(O)_2NR^{18}R^{19}$; or halogen;

$R^5$ is $C_1$–$C_4$ alkyl, $C_1$–$C_4$ alkoxy or $NR^{20}R^{21}$;

$R^6$ is H, $C_1$–$C_2$ alkyl or $OCH_3$;

$R^7$ is $C_1$–$C_2$ alkyl; or $R^6$ and $R^7$ can be taken together as $-(CH_2)_3-$ or $-(CH_2)_4-$;

$R^8$ is H, $C_1$–$C_3$ alkyl or cyclopropyl;

$R^9$ is $CH_3$; $C_2$–$C_3$ alkyl optionally substituted with one $C_1$–$C_2$ alkoxy, OH, CN or one or more halogens; $C_3$–$C_4$ alkenyl; or propargyl;

$R^{10}$ is H, $C_1$–$C_3$ alkyl or $OCH_3$;

$R^{11}$ is $C_1$–$C_3$ alkyl; or $R^{10}$ and $R^{11}$ can be taken together as $-(CH_2)_3-$, $-(CH_2)_4-$, $-(CH_2)_5-$ or $-(CH_2)_2O(CH_2)_2-$;

$R^{12}$ is H, $C_1$–$C_3$ alkyl, allyl, halogen, CN, $N_3$, $C_1$–$C_2$ alkoxy, $C_1$–$C_2$ alkylthio or SCN;

$R^{13}$ is $C_1$–$C_3$ alkyl or allyl;

$R^{14}$ is H or $C_1$–$C_3$ alkyl;

$R^{15}$ and $R^{16}$ are independently $C_1$–$C_2$ alkyl;

$R^{17}$ is $C_1$–$C_4$ alkyl, optionally substituted with one $C_1$–$C_2$ alkoxy, $C_1$–$C_2$ alkylthio, CN or one or more halogens; $C_3$–$C_4$ alkenyl; or cyclopropylmethyl;

$R^{18}$ is H, $C_1$–$C_3$ alkyl or $OCH_3$;

$R^{19}$ is H or $C_1$–$C_2$ alkyl; or $R^{18}$ and $R^{19}$ can be taken together as $-(CH_2)_3-$, $-(CH_2)_4-$ or $-(CH_2)_5-$;

$R^{20}$ and $R^{21}$ are independently $C_1$–$C_2$ alkyl; or $R^{20}$ and $R^{21}$ can be taken together as $-(CH_2)_3-$, $-(CH_2)_4-$, $-(CH_2)_5-$ or $-(CH_2)_2O(CH_2)_2-$;

$R^{71}$ is H, halogen or $CF_3$;

$R^{73}$ is $C_1$–$C_4$ alkyl optionally substituted with one or more halogens, CN, $C_1$–$C_2$ alkoxy, or $C_1$–$C_2$ alkylthio; $C(O)R^{74}$; $SO_2R^{75}$; $C_3$–$C_4$ alkenyl; or propargyl;

$R^{74}$ is $C_1$–$C_4$ alkyl optionally substituted with $C_1$–$C_2$ alkoxy, one or more halogens, or CN; $C_3$–$C_4$ alkenyl; or $C_1$–$C_3$ alkoxy;

$R^{75}$ is $C_1$–$C_3$ alkyl or $CF_3$;

m is 0 or 1;

n is 0, 1 or 2;

$Q^1$ is phenyl, phenyl substituted with one to two groups selected from halogen and $CH_3$, or a fully unsaturated 5- or 6-membered heterocyclic ring containing 1 to 4 heteroatoms selected from 0–1 S, 0–1 O and 0–4 N and a fully unsaturated 5- or 6-membered heterocyclic ring optionally substituted with one to two groups selected from $C_1$–$C_4$ alkyl, $C_3$–$C_4$ alkenyl, halogen, $C_1$–$C_3$ alkoxy, $C_1$–$C_2$ haloalkoxy, $C_1$–$C_3$ alkylthio, $C_3$–$C_4$ alkenylthio and $C_1$–$C_2$ haloalkylthio, said $Q^1$ bound through a carbon atom;

$Q^2$ is phenyl optionally substituted with one to two groups selected from halogen and methyl; a saturated 5- or 6-membered heterocyclic ring containing 1 to 2 heteroatoms selected from 0–2 O and 0–2 S optionally substituted with 1–2 $C_1$–$C_3$ alkyl groups; a partially saturated 5- or 6-membered heterocyclic ring containing 1 to 2 heteroatoms selected from 0–2 O, 0–2 S and 0–2 N optionally substituted with one to two $C_1$–$C_3$ alkyl groups; or a fully unsaturated 5- or 6-membered heterocyclic ring containing 1 to 4 heteroatoms selected from 0–1 S, 0–1 O and 0–4 N, optionally "phenyl substituted with one to two groups selected from halogen and $CH_3$, a saturated heterocyclic ring containing 1 to 2 heteroatoms selected from 0–2 O, and 0–2 S substituted with one to two $C_1$–$C_3$ alkyl groups, a partially saturated heterocyclic ring containing 1 to 2 heteroatoms selected from 0–2 O, 0–2 S and 0–2 N substituted with one to two alkyl groups, and an unsaturated 5- or 6-membered heterocyclic ring containing 1 to 4 heteroatoms selected from 0–1 S, 0–1 O and 0–4 N" substituted with one to two groups selected from $C_1$–$C_4$ alkyl, $C_3$–$C_4$ alkenyl, halogen, $C_1$–$C_3$ alkoxy, $C_1$–$C_2$ haloalkoxy, $C_1$–$C_3$ alkylthio, $C_3$–$C_4$ alkenylthio and $C_1$–$C_2$ haloalkylthio;

A is

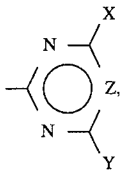
A-1

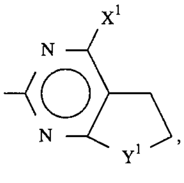
A-2

-continued

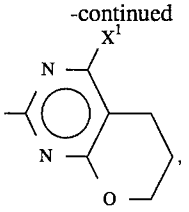
A-3

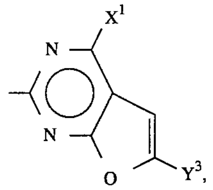
A-4

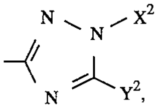
A-5

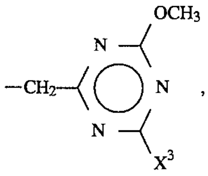
A-6

, or

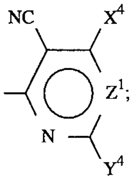
A-7

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ alkylthio, $C_1$–$C_4$ haloalkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

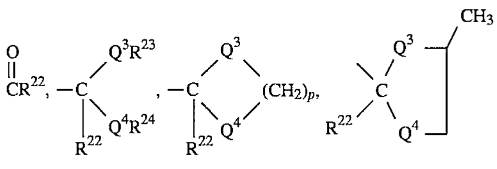

or $N(OCH_3)CH_3$;

p is 2 or 3;

$Q^3$ and $Q^4$ are independently O or S;

$R^{22}$ is H or $C_1$–$C_3$ alkyl;

$R^{23}$ and $R^{24}$ are independently $C_1$–$C_3$ alkyl;

Z is CH or N;

$Z^1$ is CH or N;

$Y^1$ is O or $CH_2$;

$X^1$ is $CH_3$, $OCH_3$ or $OCF_2H$;

$X^2$ is $CH_3$, $CH_2CH_3$ or $CH_2CF_3$;

$Y^2$ is $OCH_3$, $OCH_2CH_3$, $SCH_3$, $SCH_2CH_3$, $CH_3$ or $CH_2CH_3$;

$X^3$ is $CH_3$ or $OCH_3$;

$Y^3$ is H or $CH_3$;

$X^4$ is $CH_3$, $OCH_3$, $OCH_2CH_3$, $CH_2OCH_3$ or Cl; and $Y^4$ is $CH_3$, $OCH_3$, $OCH_2CH_3$ or Cl;

and their agriculturally suitable salts; provided that:

(a) when X and/or Y is $C_1$ haloalkoxy, then Z is CH;

(b) when m is zero, $Q^2$ is bound through carbon to the pyrrole ring in J;

(c) when X is F, Cl, Br or I, then Z is CH and Y is $OCH_3$, $OCH_2CH_3$, $N(OCH_3)CH_3$, $NHCH_3$, $N(CH_3)_2$ or $OCF_2H$;

(d) when W is S, then R is H, A is A-1 and Y is $CH_3$, $OCH_3$, $OCH_2CH_3$, $CH_2OCH_3$, $CH_2CH_3$, $CF_3$, $SCH_3$, $OCH_2CH{=}CH_2$, $OCH_2C{\equiv}CH$, $OCH_2CH_2OCH_3$, $CH(OCH_3)_2$ or

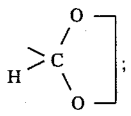

(e) when the total number of carbon atoms of X and Y is greater than four, then the number of carbons of $Q^1$ and $Q^2$ for each is less than or equal to eight;

(f) when A is A-2, A-3, A-4, A-5, A-6 or A-7, then R is H;

(g) when J is J-1, A is A-1 and X and/or Y is alkyl, then $R^2$ is other than CN or $NO_2$;

(h) when J is J-1, A is A-2, A-3 or A-4 and $R^1$ is $C(O)R^5$, then $R^2$ is other than alkyl; and (i) when J is J-1, A is A-1 and X and/or Y is $C_1$ haloalkoxy, then $R^2$ is other than $C(O)OR^9$.

In the above definitions, the term "alkyl", used either alone or in compound words such as "alkylthio" or "haloalkyl", includes straight chain and branched alkyl, e.g., methyl, ethyl, n-propyl, isopropyl and the different butyl isomers.

Alkoxy includes methoxy, ethoxy, n-propyloxy, isopropyloxy and the different butoxy isomers.

Alkenyl includes straight chain and branched alkenes, e.g., 1-propenyl, 2-propenyl, 3-propenyl and the different butenyl isomers.

Alkylsulfonyl includes methylsulfonyl and ethylsulfonyl.

Alkylthio, etc. are used analogously to the above examples.

Cycloalkyl includes cyclopropyl, cyclobutyl, cyclopentyl and cyclohexyl.

The term "halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated by the $C_i$–$C_j$ prefix where i and j are n-tubers from 1 to 6. For example, $C_1$–$C_2$ alkylsulfonyl would designate methylsulfonyl through ethylsulfonyl; $C_2$–$C_3$ alkoxycarbonyl would designate methoxy and ethoxy attached through a carbonyl radical.

Compounds of the invention preferred for reasons including ease of synthesis and/or greater herbicidal efficacy are:

1. Compounds of Formula I wherein $Q^1$ is the fully unsaturated substituted or unsubstituted heterocyclic ring, and $Q^1$ is selected from pyridinyl, pyrimidinyl, thienyl, furanyl, 1,2,4 -triazolyl, 1,2,3-thiadiazolyl, oxazolyl, thiazolyl, imidazolyl or tetrazolyl, and $Q^2$ is the substituted or unsubstituted heterocyclic ring containing 1 to 2 heteroatoms or the substituted or unsubstituted partially saturated heterocyclic ring containing 1 to 2 heteroatoms and $Q^2$ is elected from 1,3-dioxolanyl, 1,3-dioxanyl, pyridinyl, pyrimidinyl, thienyl, furanyl, 1,2,4-triazolyl, 1,2,3-thiadiazolyl, oxazolyl, thiazolyl, imidazolyl or tetrazolyl.

2. Compounds of Preferred 1 wherein;

$Q^1$ is

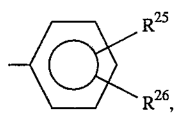

$Q^1$-1

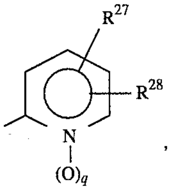

$Q^1$-2

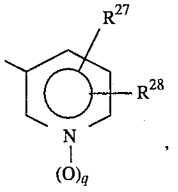

$Q^1$-3

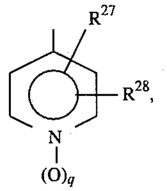

$Q^1$-4

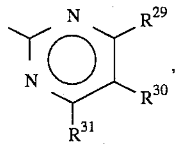

$Q^1$-5

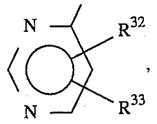

$Q^1$-6

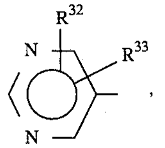

$Q^1$-7

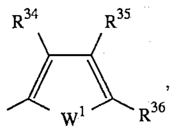

$Q^1$-8

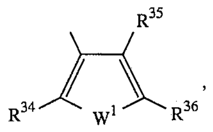

$Q^1$-9

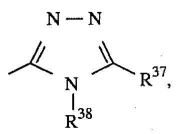

$Q^1$-10

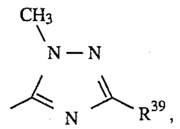

$Q^1$-11

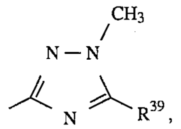

$Q^1$-12

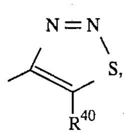

$Q^1$-13

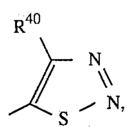

$Q^1$-14

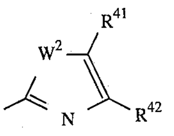

$Q^1$-15

-continued

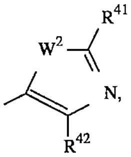

$Q^1$-16

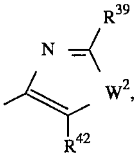

$Q^1$-17

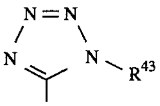

$Q^1$-18 or

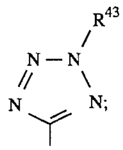

$Q^1$-19 q is 0 or 1;
$R^{25}$ and $R^{26}$ are independently H, $CH_3$ or Cl;
$R^{27}$ and $R^{28}$ are independently H, F, or $CH_3$;
$R^{29}$ is H, $CH_3$ or $OCH_3$;
$R^{30}$ is H or $CH_3$;
$R^{31}$, $R^{32}$ and $R^{33}$ are independently H, $CH_3$ or $OCH_3$;
$R^{34}$, $R^{35}$ and $R^{36}$ are independently H, $CH_3$, $CH_2CH_3$, Cl, Br, $OCH_3$ or $OCH_2CH_3$;
$R^{37}$ is H or $C_1$–$C_2$ alkyl;
$R^{38}$ is $CH_3$;
$R^{39}$ is H, $C_1$–$C_2$ alkyl, $OCH_3$ or $SCH_3$;
$R^{40}$ is H, $CH_3$ or $CH_2CH_3$;
$R^{41}$ and $R^{42}$ are independently H or $CH_3$;
$R^{43}$ is H, $CH_3$, $CH_2CH_3$ or $C_3H_7$;
$W^1$ is O or S;
$W^2$ is O, S or $NR^{44}$;
$R^{44}$ is H or $CH_3$;
$Q^2$ is

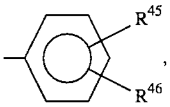

$Q^2$-1

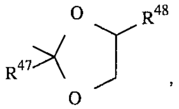

$Q^2$-2

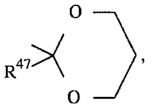

$Q^2$-3

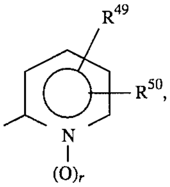

$Q^2$-4

-continued

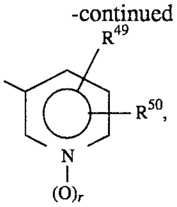

$Q^2$-5

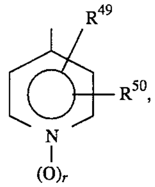

$Q^2$-6

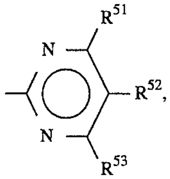

$Q^2$-7

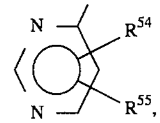

$Q^2$-8

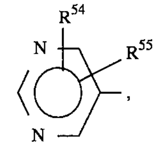

$Q^2$-9

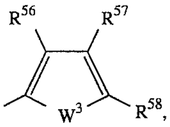

$Q^2$-10

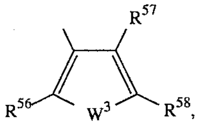

$Q^2$-11

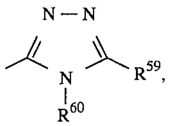

$Q^2$-12

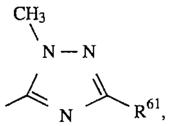

$Q^2$-13

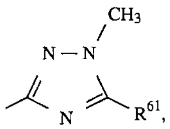

$Q^2$-14

-continued

Q²-15

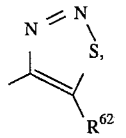

Q²-16

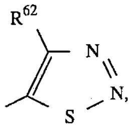

Q²-17

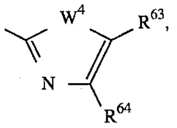

Q²-18

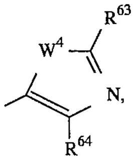

Q²-19

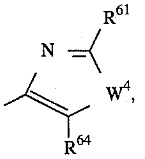

Q²-20

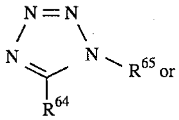

Q²-21

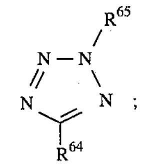

r is 0 or 1;

$R^{45}$ and $R^{46}$ are independently H, $CH_3$ or Cl;

$R^{47}$ is H or $C_1$–$C_3$ alkyl;

$R^{48}$ is H or $CH_3$;

$R^{49}$ and $R^{50}$ are independently H or $CH_3$;

$R^{51}$ is H, $CH_3$ or $OCH_3$;

$R^{52}$ is H or $CH_3$;

$R^{53}$ $R^{54}$ and $R^{55}$ are independently H, $CH_3$ or $OCH_3$;

$R^{56}$, $R^{57}$ and $R^{58}$ are independently H, $CH_3$, $CH_2CH_3$, Cl, Br, $OCH_3$ or $OCH_2CH_3$;

$R^{59}$ is H or $C_1$–$C_2$ alkyl;

$R^{60}$ is $CH_3$;

$R^{61}$ is H, $C_1$–$C_2$ alkyl, $OCH_3$ or $SCH_3$;

$R^{62}$ is H, $CH_3$ or $CH_2CH_3$;

$R^{63}$ and $R^{64}$ are independently H or $CH_3$;

$R^{65}$ is H, $CH_3$, $CH_2CH_3$ or $C_3H_7$;

$W^3$ is O or S;

$W^4$ is O, S or $NR^{66}$; and $R^{66}$ is H or $CH_3$;

3. Compounds of Preferred 2 wherein:

W is O;

$R^1$ is H, $C_1$–$C_6$ alkyl, allyl, $CH_2OCH_3$, $CH_2OC_2H_5$, $CH_2SCH_3$ phenyl, 2-pyridyl, 3-pyridyl, 4-pyridyl, $C(O)OCH_3$ or $C(O)N(CH_3)_2$;

X is $C_1$–$C_2$ alkyl, $C_1$–$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$; and Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C{\equiv}CH$, $OCH_2CH_2OCH_3$, $CH_2SCH_3$, $C(O)R^{22}$,

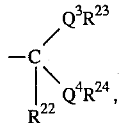 , 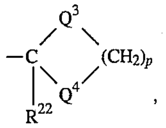 , 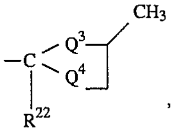 , $OCF_2H$, $SCF_2H$, cyclopropyl, $C{\equiv}CH$ or $C{\equiv}CH_3$.

4. Compounds of Preferred 3 wherein:

$R^3$ is H, $CH_3$, Cl or Br; and $R^4$ is H, $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)NR^{10}R^{11}$, $C(R^{12}){=}NOR^{13}$, $C(R^{14})(OR^{15})(OR^{16})$, $S(O)_nR^{17}$, $S(O)_2NR^{18}R^{19}$, F, Cl or Br;

$R^8$ is H or $C_1$–$C_2$ alkyl;

$R^9$ is $C_1$–$C_2$ alkyl or $CH_2CH_2Cl$;

$R^{10}$ is H or $CH_3$;

$R^{11}$ is $CH_3$;

$R^{12}$ is H, $CH_3$, $C_2H_5$ or Cl;

$R^{13}$ is $CH_3$;

$R^{14}$ is H or $C_1$–$C_2$ alkyl;

$R^{15}$ and $R^{16}$ are $CH_3$;

$R^{17}$ is $C_1$–$C_2$ alkyl;

$R^{18}$ is H or $CH_3$;

$R^{19}$ is $CH_3$; and n is 0 or 2.

5. Compounds of Preferred 4 wherein:

$R^2$ is $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)NR^{10}R^{11}$, $C(R^{12}){=}NOR^{13}$, $C(R^{14})(OR^{15})(OR^{16})$, $S(O)_nR^{17}$, $S(O)_2NR^{18}R^{19}$, F, Cl, Br or $OR^{73}$.

6. Compounds of Preferred 5 wherein:

R is H; and $R^{71}$ is H.

7. Compounds of Preferred 6 wherein:

J is J-1.

8. Compounds of Preferred 6 wherein:

J is J-2.

9. Compounds of Preferred 6 wherein:

J is J-3.

10. Compounds of Preferred 7 wherein:

$R^2$ is $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)N(CH_3)_2$, $S(O)_2CH_3$, $S(O)_2C_2H_5$, $S(O)_2N(CH_3)_2$, $C_1$–$C_2$ alkoxy, $OC(O)CH_3$, or $OSO_2CH_3$;

$R^4$ is H, $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)N(CH_3)_2$, $S(O)_2CH_3$, $S(O)_2C_2H_5$ or $S(O)_2N(CH_3)_2$;

$R^8$ is $C_1$–$C_2$ alkyl;

$R^9$ is $C_1$–$C_2$ alkyl;

$Q^2$ is $Q^2$-1, $Q^2$-4, $Q^2$-5, $Q^2$-6, $Q^2$-10, $Q^2$-11, $Q^2$-20 or $Q^2$-21;

$R^{45}$, $R^{46}$, $R^{49}$, $R^{50}$, $R^{56}$, $R^{57}$ and $R^{58}$ are H;

$R^{65}$ is $CH_3$;

$W^3$ is S; and r is 0.

11. Compounds of Preferred 8 wherein:

$R^2$ is $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)N(CH_3)_2$, $S(O)_2CH_3$, $S(O)_2C_2H_5$, $S(O)_2N(CH_3)_2$, $C_1$–$C_2$ alkoxy, $OC(O)CH_3$, or $OSO_2CH_3$;

$R^4$ is H, $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)N(CH_3)_2$, $S(O)_2CH_3$ or $S(O)_2N(CH_3)_2$;

$R^8$ is $C_1$–$C_2$ alkyl;

$R^9$ is $C_1$–$C_2$ alkyl;

$Q^2$ is $Q^2$-1, $Q^2$-4, $Q^2$-5, $Q^2$-6, $Q^2$-10, $Q^2$-11, $Q^2$-20 or $Q^2$-21;

$R^{45}$, $R^{46}$, $R^{49}$, $R^{50}$, $R^{56}$, $R^{57}$ and $R^{58}$ are H;

$R^{65}$ is $CH_3$;

$W^3$ is S; and r is 0.

12. Compounds of Preferred 9 wherein:

$R^2$ is $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)N(CH_3)_2$, $S(O)_2CH_3$, $S(O)_2C_2H_5$, $S(O)_2N(CH_3)_2$, $C_1$–$C_2$ alkoxy, $OC(O)CH_3$, or $OSO_2CH_3$;

$R^4$ is H, $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)N(CH_3)_2$, $S(O)_2CH_3$ or $S(O)_2N(CH_3)_2$;

$R^8$ is $C_1$–$C_2$ alkyl;

$R^9$ is $C_1$–$C_2$ alkyl;

$Q^2$ is $Q^2$-1, $Q^2$-4, $Q^2$-5, $Q^2$-6, $Q^2$-10, $Q^2$-11, $Q^2$-20 or $Q^2$-21;

$R^{45}$, $R^{46}$, $R^{49}$, $R^{50}$, $R^{56}$, $R^{57}$ and $R^{58}$ are H;

$R^{65}$ is $CH_3$;

$W^3$ is S; and r is 0.

13. Compounds of Preferred 10 wherein:

A is A-1;

X is $CH_3$, $OCH_3$, $OCH_2CH_3$, $OCH_2CF_3$ or Cl; and

Y is $CH_3$, $OCH_3$, $NHCH_3$ or $N(CH_3)_2$.

14. Compounds of Preferred 11 wherein:

A is A-1;

X is $CH_3$, $OCH_3$, $OCH_2CH_3$, $OCH_2CF_3$ or Cl; and

Y is $CH_3$, $OCH_3$, $NHCH_3$ or $N(CH_3)_2$.

15. Compounds of Preferred 12 wherein

A is A-1;

X is $CH_3$, $OCH_3$, $OCH_2CH_3$, $OCH_2CF_3$ or Cl; and

Y is $CH_3$, $OCH_3$, $NHCH_3$ or $N(CH_3)_2$.

Compounds of the invention specifically preferred for reasons of greatest ease of synthesis and/or greatest herbicidal efficacy are:

Methyl 3-[[[[(4,6-dimethoxy-2-pyrimidinyl)amino]carbonyl] amino]sulfonyl]-1-methyl-1H-pyrrole-2-carboxylate;

Methyl 3-[[[[[4-ethoxy-6-(methylamino)-1,3,5-triazin-2-yl] amino]carbonyl]amino]-sulfonyl]-1-methyl-1H-pyrrole-2-carboxylate;

$N^3$-[[(4-ethyl-6-methoxy-1,3,5-triazin-2-yl)-amino]carbonyl] $N^2$,$N^2$,1-trimethyl-1H-pyrrole-2,3-disulfonamide;

$N^3$-[[(4,6-dimethoxy-2-pyrimidinyl)amino]carbonyl] $N^2$,$N^2$,1-trimethyl-1H-pyrrole-2,3-disulfonamide;

Methyl 1-ethyl-2-[[[[(4-methoxy-6-methyl-1,3,5-triazin-2-yl)-amino] carbonyl]amino]sulfonyl]-1H-pyrrole-3-carboxylate;

2-(ethylsulfonyl)-N-[[(4-methoxy-6-methyl-1,3,5-triazin-2-yl)amino] carbonyl]-1-methyl-1H-pyrrole-3-sulfonamide; and 2-[[[[(4,6-dimethoxy-2 pyrimidinyl)amino]carbonyl]-amino]sulfonyl] N,N,1-trimethyl-1H-pyrrole-3-carboxamide.

The invention also comprises novel compounds, such as the bromopyrrolesulfonamides of Formula II, useful as intermediates to the compounds of Formula I.

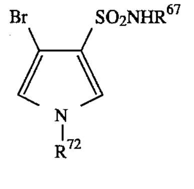

II wherein:

$R^{67}$ is H, $C(CH_3)_3$ or $Si(CH_3)_2C(CH_3)_3$; and $R^{72}$ is H or $Si(CH(CH_3)_2)_3$.

Another embodiment of the invention is the process for preparing any of the above compounds, said process comprising reacting (a) the compounds of Equation 1 in an inert polar aprotic solvent for 5 minutes to 24 hours or more at 20° to 80° C.

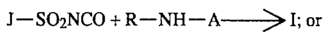

2 3

(b) the compounds of Equation 2 in an inert solvent followed by treatment with aqueous acid

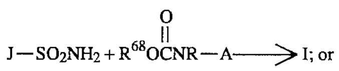

4 5

(c) the compounds of Equation 3 in an inert solvent for 0.5 to 24 hours

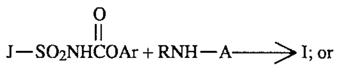

6 3

(d) the compounds of Equation 4 in an inert solvent at 20° to 80° C. for 0.5 to 24 hours and in the presence of 1 to 1.4 equivalents of a base

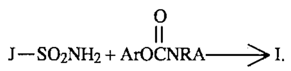

4 3

DETAILED DESCRIPTION OF THE INVENTION

Synthesis

The sulfonylureas of Formula I can be prepared by a number of methods. These methods are described below along with the appropriate references for greater detail.

Equation 1

$$J—SO_2NCO + R—NH—A \longrightarrow I$$

2 3

One of the methods of synthesis of sulfonylureas of Formula I is depicted in Equation 1 where J, R, and A are as defined above. A sulfonylisocyanate of Formula 2 is contacted with a heterocyclic amine of Formula 3 in an inert polar aprotic solvent, such as acetonitrile, dichloromethane, etc. for periods of several minutes to 24 hours or more, preferably at a temperature in the range of 20° to 80° C. to afford a sulfonylurea of Formula I.

U.S. Pat. Nos. 4,127,405; 4,257,802; and 4,221,585 disclose this equation and are herein incorporated by reference.

Equation 2

$$J—SO_2NH_2 + R^{68}O\overset{O}{\overset{||}{C}}NR—A \longrightarrow I$$

4 5

Another method of synthesis of compounds of Formula I is depicted in Equation 2 where J, R, and A are as defined previously and $R^{68}$ is lower alkyl such as methyl or ethyl. A sulfonamide of Formula 4 is contacted with an alkyl carbamate of Formula 5 in the presence of a trialkylaluminum in an inert solvent such as dichloromethane, 1,2-dichloroethane, etc., and subsequently treated with aqueous acid to afford a sulfonylurea of Formula I. This reaction is taught in European Patent Publication EP-A-83,975 (published Jul. 20, 1983).

Equation 3

$$J—SO_2NH\overset{O}{\overset{||}{C}}OAr + RNH—A \longrightarrow I$$

6 3

Alternatively, compounds of Formula I can be prepared by the method shown in Equation 3 where A, J, and R are as defined previously and Ar represents an aryl group, for example a phenyl group. In this reaction, a sulfonylcarbamate of Formula 6 is contacted with a heterocyclic amine of Formula 3 in an inert solvent such as p-dioxane for a period of 0.5 to 24 hours, as taught in European Patent Publication EP-A- 44,807.

Equation 4

$$J—SO_2NH_2 + ArO\overset{O}{\overset{||}{C}}NRA \longrightarrow I$$

4 7

A fourth method of preparation for compounds of Formula I is depicted in Equation 4 where A, R, and J are as defined previously and Ar represents an aryl group, for example a phenyl or substituted phenyl group. In this reaction, a sulfonamide of Formula 4 is contacted with a heterocyclic carbamate of Formula 7 in an inert solvent such as p-dioxane or acetonitrile preferably at temperatures in the range of from 20° to 80° C. for periods of 0.5 to 24 hours in the presence of 1 to 1.4 equivalents of a base such as 1,8-diazabicyclo[5.4.0]undec-7-ene (DBU). The resultant products are isolated by dilution of the reaction mixture with aqueous acid to afford sulfonylureas of Formula I. The reaction is taught in European Patent Publications EP-A-44,807, and EP-A-85,028.

Intermediate Compounds

Heterocyclic sulfonyl isocyanates of Formula 2 can be prepared by treatment of sulfonamides of Formula 4 by the procedures taught in U.S. Pat. No. 4,127,405. Heterocyclic carbamates of Formula 5 are prepared by procedures taught in European Patent Publication EP-A-83,975.

The sulfonylcarbamates of Formula 6 and heterocyclic carbamates of Formula 7 can be prepared by procedures taught in European Patent Publications EP-A-44,807, EP-A-72,347, EP-A-173,498 and U.S. Pat. No. 4,666,506 and references cited therein.

The intermediate pyrrole sulfonamides of Formula 4 can be prepared by a variety of methods, some of which are described in the sequence of reactions shown in Equations 5 through 24.

The sulfonamides of Formula 4 of this invention where J is J-1, J-2 or J-3 as defined above can be synthesized from the precursor sulfonamides of Formula 8 where J is as defined above and $R^{69}$ is a suitable protecting group such as tert-alkyl or trialkylsilyl, by appropriate methods known to one skilled in the art, as depicted in Equation 5.

Equation 5

$$J—SO_2NHR^{69} \xrightarrow{acid} J—SO_2NH_2$$

8 4

Sulfonamides of Formula 8 where J is J-2 or J-3, $R^1$ is as defined above or is a masked synthon thereof, $R^2$ is as defined above or is a masked synthon thereof, $R^{69}$ is as previously defined and $R^4$ is other than H, $X^5$ is a suitable leaving group such as but not limited to chloro, bromo, iodo, alkyl- or arylsulfonate, may be prepared by methods similar to the depiction in Equation 6. The general methodology described for the instance when J is J-2 is directly applicable to the instances where J is J-3. Further, the synthetic necessity, and selection of specific masked synthons for specific definitions of $R^1$ and $R^2$ are known to one skilled in the art, for the introduction of $R^4$ into the sulfonamide of Formula 9.

Equation 6

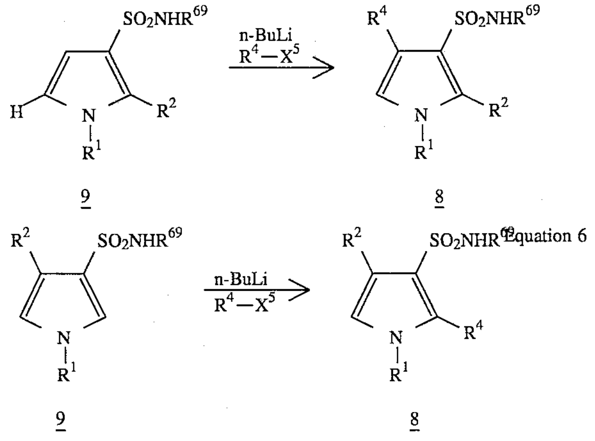

9 8

9 8

A sulfonomide of Formula 9 can be metalated on carbon using an excess of an organometallic base, preferably an organolithium reagent such as n-butyllithium, a-butyllithium/tetramethylethylenediamine (TMEDA) or lithium diisopropylamide in an inert solvent such as diethyl ether, dimethoxyethane (DME) or tetrahydrofuran (THE), under anhydrous conditions, preferably at a temperature in the range of −100° to −70° C., followed by quenching with the appropriate electrophilic reagent ($R^4$-$X^5$) affording sulfonamide of Formula 8 after standard aqueous workup.

A sulfonamide of Formula 9 where J is J-2, $R^1$, $R^2$ and $R^{69}$ are as previously defined, $X^5$ is a suitable leaving group such as but not limited to chloro, bromo, iodo, alkyl- or arylsulfonate, acid chloride or N,N-dialkylamide, can be prepared by methods similar to those depicted in Equation 7.

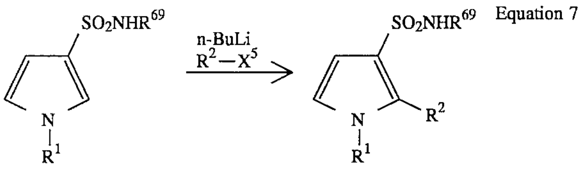

10 9

A sulfonamide of Formula 10 can be metalated on carbon using an excess of organometallic base, as described in *J. Org. Chem.*, vol. 50, p. 4362–4368, (1985) and *J. Chem Soc. Perkin Trans.*, I, p. 1343, (1982) and the references cited therein, preferably an organolithium reagent such as n-butyllithium, n-butyllithium/tetramethylethylenediamine (TMEDA) or lithium diisopropylamide, in an inert solvent such as diethyl ether, dimethoxyethane (DME) or tetrahydrofuran (THF), under anhydrous conditions, preferably at a temperature in the range of −100° to −70° C., followed by quenching with an appropriate electrophilic reagent ($R^2$-$X^5$) affording sulfonamide of Formula 8 after standard aqueous workup. A sulfonamide of Formula 9 where J is J-3, $R^1$, $R^2$ and $R^{69}$ are as previously defined, $X^5$ is a suitable leaving group such as but not limited to chloro, bromo, iodo, alkyl- or arylsulfonate, can be prepared by methods similar to those depicted in Equation 8.

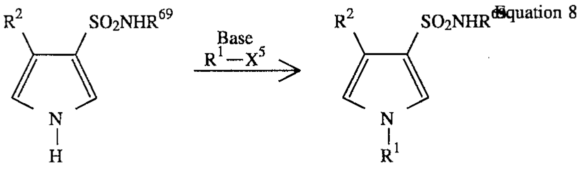

11 9

A sulfonamide of Formula 11 can be treated with a base such as an alkali metal alkoxide, hydride or tertiary amine and an appropriate electrophilic reagent ($R^1$-$X^5$) as shown in an inert solvent, preferably a polar aprotic solvent such as trimethylformamide (DMF) to afford a sulfonamide of Formula 9.

Sulfonamides of Formula 10, where J is J-2, $R^1$, $R^{69}$ and $X^5$ are as previously defined, can be prepared by methods similar to those depicted in Equation 9.

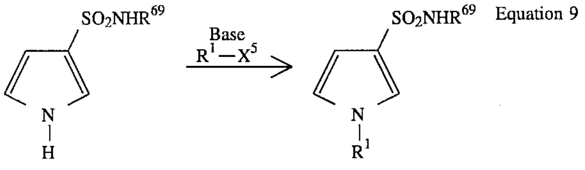

12 10

A sulfonamide of Formula 12 is treated with a base such as an alkali metal alkoxide, hydride or tertiary amine and an appropriate electrophilic reagent ($R^1$-$X^5$) as shown in an inert solvent, preferably a polar aprotic solvent such as dimethylformamide (DMF), at a temperature in the range of 20° to 80° C., for a period of 1 to 24 hours to afford a sulfonamide of Formula 10.

Pyrrole sulfonamides of Formula 12, where $R^{69}$ is a suitable protecting group as defined above are available from the corresponding bromopyrroles 13 as outlined in Equation 10, where $R^{70}$ is lower alkyl, such as isopropyl.

Equation 10

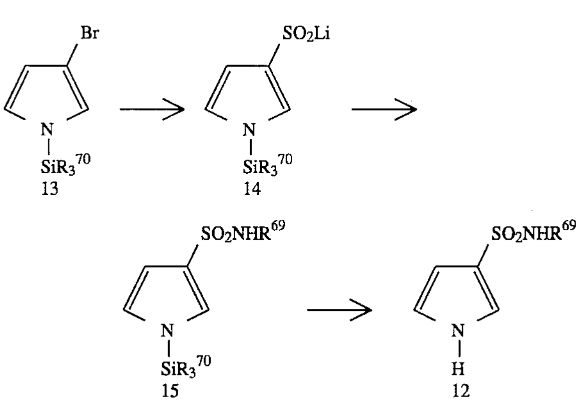

13 14 15 12

N-Silyl-protected pyrrole 13 where $R^{70}$ is preferably an isopropyl group, is treated with an alkyllithium reagent such as n-butyllithium as described in *Chem. Ber.*, Vol 122 p.169 (1989), and references cited therein. The resultant metalated species is treated with sulfur dioxide to afford sulfinate salt 14 which can be converted to sulfonamide 15 by any of several known methods, for example treatment with N-chlorosuccinimide followed by amination with an appropriate primary amine as disclosed in U.S. Pat. No. 4,481,029. The N-silyl group is then removed, most conveniently with an alkali fluoride or quaternary ammoniumfluoride salt to afford pyrrole-3-sulfonamide 12.

Sulfonamides of Formula 11, where J is J-3, $R^2$, $R^{69}$ and $X^5$ are as previously defined, can be prepared by methods similar to those depicted in Equation 11, where $R^{70}$ is lower alkyl, such as isopropyl.

Equation 11

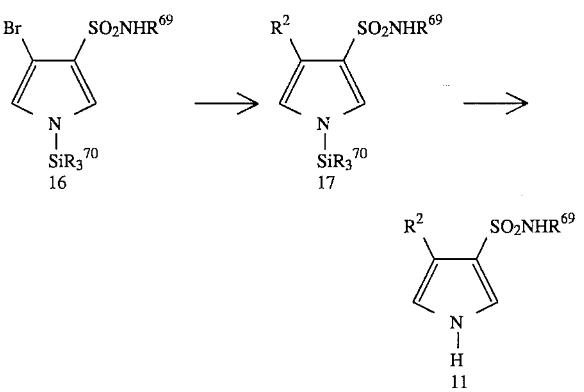

16 17 11

A sulfonamide of Formula 16 undergoes metal-halogen exchange on carbon using an excess of organometallic base, as described in *J. Org. Chem.*, vol. 50, p. 4362–4368, (1985) and *J. Chem Soc. Perkin Trans.*, I, p. 1343, (1982) and the references cited therein, preferably an organolithium reagent such as n-butyllithium, n-butyllithium/tetramethylethylenediamine (TMEDA) in an inert solvent such as diethyl ether, dimethoxyethane (DME) or tetrahydrofuran (THF), under anhydrous conditions, preferably at a temperature in the range of −100° to −70° C., followed by quenching with an appropriate electrophilic reagent ($R^2$-$X^5$) affording intermediate sulfonamide of Formula 17. The N-silyl group is then removed, most conveniently with an alkali fluoride or quaternary ammonium fluoride salt to afford sulfonamide 11.

A pyrrole sulfonamide of Formula 16, where $R^{69}$ is a suitable protecting group as defined above can be prepared from the corresponding bromopyrrole 13 as outlined in Equation 12, where $R^{70}$ is lower alkyl, such as isopropyl.

Equation 12

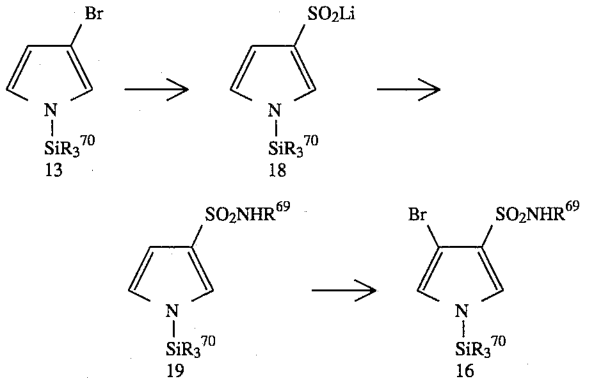

13 18 19 16

N-silyl-protected pyrrole 13 where $R^{70}$ is preferably an isopropyl group, is treated with an alkyllithium reagent such as n-butyllithium as described in *Chem. Ber.*, Vol. 122, p. 169 (1989), and references cited therein. The resultant metalated species is treated with sulfur dioxide to afford sulfinate salt 18 which can be converted to sulfonamide 19 by any of several known methods, for example treatment with N-chlorosuccinimide in a solvent such as acetic acid, methylene chloride/$H_2O$, 1,1,2-trichlorotrifluoroethene/$H_2O$ at a temperature from 0° C. to ambient temperature followed by amination with an appropriate primary amine as disclosed in U.S. Pat. No. 4,481,029. Sulfonamide 19 can be converted to a compound of Formula 16 by treatment with N-bromosuccinimide in an inert solvent such as tetrahydrofuran (THF), under anhydrous conditions, preferably at a temperature in the range of −100° to −70° C. as described in *J., Org. Chem.*, Vol. 55, No. 26, pp. 637–28 (1990) and the references cited therein.

In the cases where $R^2$ is not directly obtainable as an electrophilic reagent ($R^2$-X5), wherein $R^2$ is defined as $-S(O)_2NR^{18}R^{19}$, $-CONR^{10}R^{11}$, $C(R^{12})=NOR^{13}$, $-S(O)_n-R^{17}$, $C(O)R^8$, $(CH_2)_m-Q^2$ or —CN the desired compounds can be obtained through a series of functional group transformations known to one skilled in the art. The general methodology described for the instance when J is J-2 is directly applicable to the instances where J is J-1 or J-3 with modifications known to one skilled in the art. Therefore, only the instances where J is J-2, $R^1$ is $CH_3$ and $R^{69}$ is a suitable protecting group such as tert-alkyl or trialkylsilyl will be described in Equations 13 to 19.

Equation 13 depicts a sequence of reactions whereby one can obtain a sulfonamide of Formula 21 where J is J-2, $R^{11}$ and $R^{69}$ are as previously defined and $R^2$ is $-S(O)_2NR^{18}R^{19}$ wherein $R^{18}$ and $R^{19}$ are as defined above.

Equation 13

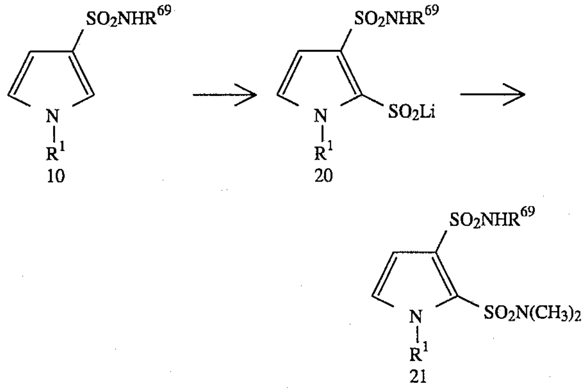

10 20 21

A precursor sulfonamide of Formula 10 can be metalated on carbon using an excess of organometallic base, similar to that described in *J. Org. Chem.*, vol. 50, p. 4362–4368, (1985) and *J. Chem Soc. Perkin Trans.*, I, p. 1343, (1982) and the references cited therein, preferably an organolithium reagent such as n-butyllithium, n-butyllithium/tetramethylethylenediamine (TMEDA) or lithium diisopropylamide, in an inert solvent such as diethyl ether, dimethoxyethene (DME) or tetrahydrofuran (THF), under anhydrous conditions, preferably at a temperature in the range of −100° to −70° C. The resultant metelated species is treated with sulfur dioxide to afford sulfinate salt 20 which can be converted to sulfonamide 21 by any of several known methods, for example treatment with N-chlorosuccinimide followed by amination with an appropriate amine in an analogous manner to that disclosed in U.S. Pat. No. 4,481,029.

In an analogous manner Equation 14 outlines a sequence wherein one can prepare a sulfonamide of Formula 22 where J is J-2, $R^1$ and $R^{69}$ are as previously defined and $R^2$ is $-C(O)NR^{10}R^{11}$.

Equation 14

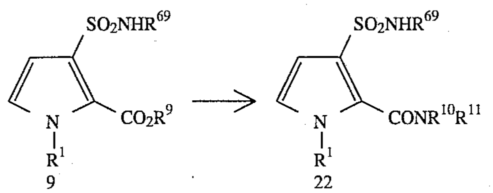

9 22

A precursor sulfonamide of Formula 9 where $R^2$ is defined for example as $-C(O)OR^9$ where $R^9$ is preferably methyl or ethyl, can be converted to amide 22 by any of several known methods, for example contacting the ester with an appropriate amine in the presence of an organometallic base in an analogous manner to that disclosed in *Tetrahedron Letters*, No. 21, p. 1791, (1970).

Equation 15 outlines a sequence whereby one can prepare a sulfonamide of Formula 23 where J is J-2, $R^1$ and $R^{69}$ are as previously defined and $R^2$ is —CN.

Equation 15

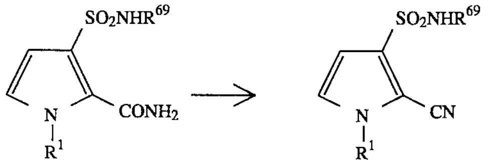

9 23

A precursor sulfonamide of Formula 9 where $R^2$ is defined for example as $—CONH_2$ can be converted to nitrile 23 by any of several known methods, for example contacting the amide with triphenylphosphine and $CCl_4$ in an inert solvent, in an analogous manner to that disclosed in *Tetrahedron Letters*, No. 21, p. 4383, (1970), or by dehydration with thionyl chloride as described in *Org. Syn.*, coll. vol. IV, p. 436, (1963).

Equation 16 depicts a sequence whereby one can prepare a sulfonamide of Formula 25 where J is J-2, $R^1$ and $R^{69}$ are as previously defined, $R^2$ is $(CH_2)_m$-$Q^2$, $Q^2$ is $Q^2$-1, $Q^2$-4, $Q^2$-5, $Q^2$-6, $Q^2$-7, $Q^2$-8, $Q^2$-9, $Q^2$-10 or $Q^2$-11, r is 0, m is 0 and M is $ZnCl_x$, $ZnBr_x$, or $B(OH)_2$.

Equation 16

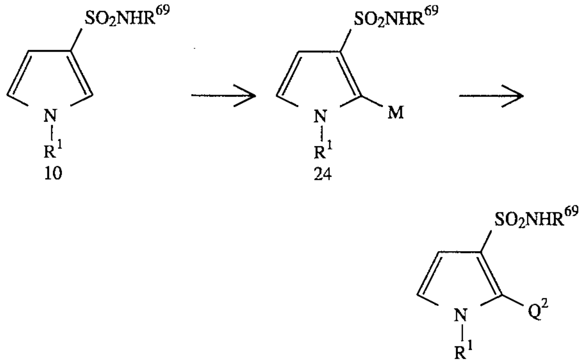

10 24

25

A sulfonamide of Formula 10 can be metalated on carbon using an excess of organometallic base, similar to that described in *J. Org. Chem.*, vol. 50, p. 4362–4368, (1985) and *J. Chem Soc. Perkin Trans.*, I, p. 1343, (1982) and the references cited therein, preferably an organolithium reagent such as n-butyllithium, n-butyllithium/tetramethylethylenediamine (TMEDA) or lithium diisopropylamide, in an inert solvent such as diethyl ether, dimethoxyethane (DME) or tetrahydrofuran (THF), under anhydrous conditions, preferably at a temperature in the range of −100° to −70° C. The metalated species can be transmetalated with anhydrous zinc chloride, by methods similar to those described in *Tetrahedron Letters*, Vol.29, No.39, pp. 5013–5016, (1988). The transmetalated species 24 can be coupled to an arylhalide substrate, for instance 2-bromopyridine, in the presence of excess zinc chloride and a palladium catalyst to afford the biaryl species of Formula 25. Alternatively, the metalated species can be quenched with an alkyl borate, for instance trimethylborate affording the corresponding 2-boronic acid species 24 upon hydrolysis. The pyrrole boronic acid species can be coupled to an arylhalide substrate by methods similar to those described in *Tetrahedron Letters*, vol. 26, No. 49, pp. 5997–6000, (1985) and *Tetrahedron Letters*, vol. 29, No. 43, p. 5459–5462, (1988) and the references cited therein, for instance 2-bromopyridine in the presence of a palladium catalyst and a base, in an inert solvent such as toluene or dimethoxyethane (DME), at reflux temperature for periods of 1 to 24 hours affording the biaryl species of Formula 25.

Equation 17 outlines a sequence whereby one can prepare a sulfonamide of Formula 27 where J is J-2, $R^1$ and $R^{69}$ are as previously defined, $R^2$ is $—C(R^{12})=NOR^{13}$, $R^{12}$ is H and $R^{13}$ is as previously defined.

Equation 17

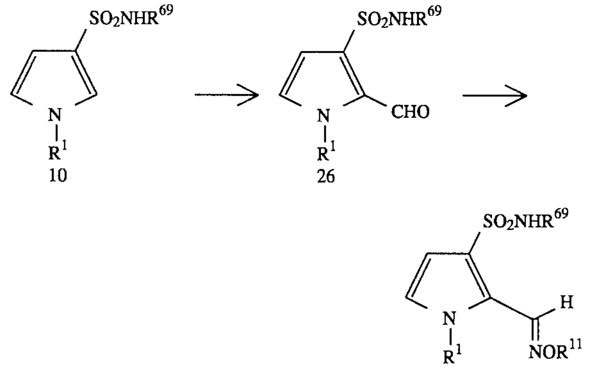

10 26

27

A sulfonamide of Formula 10 can be metalated on carbon using an excess of organometallic base, similar to that described in *J. Org. Chem.*, vol. 50, p. 4362–4368, (1985) and *J. Chem Soc. Perkin Trans.*, I, p. 1343, (1982) and the references cited therein, preferably an organolithium reagent such as n-butyllithium, n-butyllithium/tetramethylethylenediamine (TMEDA) or lithium diisopropylamide, in an inert solvent such as diethyl ether, dimethoxyethane (DME) or tetrahydrofuran (THF), under anhydrous conditions, preferably at a temperature in the range of −100° to −70° C. The metalated species, quenched with dimethylformamide (DMF) affords the corresponding pyrrole-2-aldehyde 26 following aqueous workup. The aldehyde species 26 is contacted with an alkoxy amine ($H_2N—OR^{13}$), for instance methoxylamine hydrochloride in the presence of a base, for example sodium acetate, in an inert solvent such as acetone, tetrahydrofuran, dioxane or methanol. The reaction is carried out at temperatures in the range of 20° C. to reflux for a period of 1 to 24 hours and optionally in the presence of a phase transfer catalyst such as a crown ether.

Equation 18 depicts a sequence whereby one can prepare a sulfonamide of Formula 29 where J is J-2, $R^1$ and $R^{69}$ are as previously defined and $R^2$ is $—C(O)R^8$ where $R^8$ is as defined above.

Equation 18

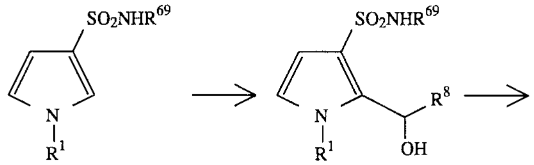

10 28

-continued

Equation 18

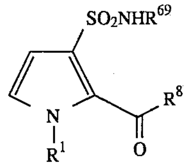

29

A sulfonamide of Formula 10 can be metalated on carbon using an excess of organometallic base, similar to that described in *J. Org. Chem.*, vol. 50, p. 4362–4368, (1985) and *J. Chem Soc. Perkin Trans.*, I, p. 1343, (1982) and the references cited therein, preferably an organolithium reagent such as n-butyllithium, n-butyllithium/tetramethylethylenediamine (TMEDA) or lithium diisopropylamide, in an inert solvent such as diethyl ether, dimethoxyethane (DME) or tetrahydrofuran (THF), under anhydrous conditions, preferably at a temperature in the range of −100° to −70° C. The metalated species, quenched with an aldehyde ($R^8$-CHO) affords the alcohol 28 following aqueous workup. Alcohol 28 can be oxidized to a ketone of Formula 29 by contact with one of several oxidants known to one skilled in the art, for example tetra-n-propylammonium perruthenate/N-methylmorpholine N-oxide as described in *Aldrichimica Acta*, Vol. 23, No. 1, p. 13–17, (1990) and the references cited therein.

Equation 19 outlines a sequence whereby one can prepare a sulfonamide of Formula 31 where J is J-2, $R^1$ and $R^{69}$ are as previously defined and $R^2$ is —$S(O)_n$-$R^{17}$, where $R^{17}$ is as defined above and n is 1 or 2.

Equation 19

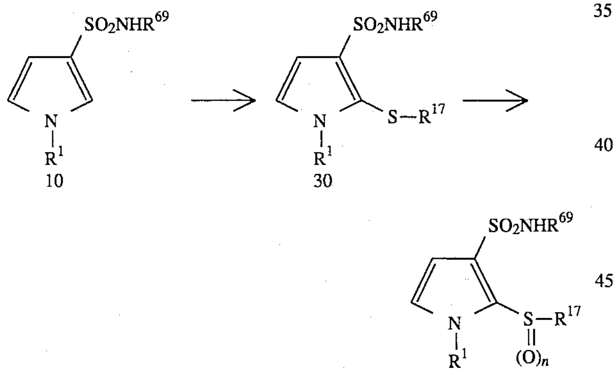

10 30 31

A sulfonamide of Formula 10 can be metalated on carbon using an excess of organometallic base, similar to that described in *J. Org. Chem.*, vol. 50, p. 4362–4368, (1985) and *J. Chem Soc. Perkin Trans.*, I, p. 1343, (1982) and the references cited therein, preferably an organolithium reagent such as n-butyllithium, n-butyllithium/tetramethylethylenediamine (TMEDA) or lithium diisopropylamide, in an inert solvent such as diethyl ether, dimethoxyethane (DME) or tetrahydrofuran (THF), under anhydrous conditions, preferably at a temperature in the range of −100° to −70° C. The metalated species, quenched with an appropriate disulfide ($R^{17}$-S-S-$R^{17}$) affords thioether 30 following aqueous workup. The thioether can be oxidized selectively to the corresponding sulfoxide or sulfone of Formula 31 by contact with one of several suitable oxidants such as a peroxy acid or hydrogen peroxide.

Pyrrole sulfonamide precursors of Formula 36 where J is J-1, $R^3$ is H or alkyl and $R^{69}$ is a trialkylsilyl protecting group can be prepared from the corresponding N-substituted pyrrole 32 as outlined in Equation 20.

Equation 20

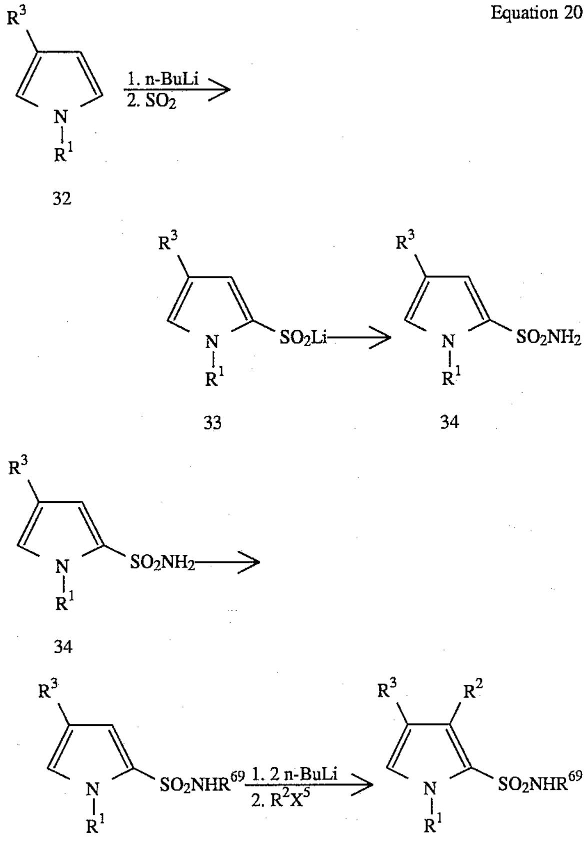

32 33 34 34 35 36

Pyrroles of Formula 32 are generally known in the art or can be prepared by a variety of known alkylation or acylation procedures such as those reviewed in "Pyrroles", R. Alan Jones, Ed., "The Chemistry of Heterocyclic Compounds", Vol. 48, Part 1 (John Wiley & Sons, Inc., 1990, New York) p. 397. Metalation of pyrroles 32 is likewise known to produce reactive 2-lithio intermediates as described in *Synthetic Communications*, Vol. 12, p. 231 (1982) and in *J. Org. Chem.*, Vol. 46, p. 157 (1981) and references cited therein. Treatment of these reactive metalated species with sulfur dioxide affords sulfinate salts 33. These can be converted to sulfonamides 34 by methods described above, or directly by treatment with hydroxylamine-O-sulfonic acid in aqueous media as described in *Synthesis*, p. 1031 (1986). Treatment of sulfonamides 34 with a base and a trialkylsilyl chloride such as t-butyldimethylsilyl chloride affords the protected sulfonamides 35. Metalation of 35 with two equivalents of an organometallic base such as n-butyllithium, lithium diisopropylamide or lithium 2,2,6,6 -tetramethylpiperidide (LTMP) and quenching with an appropriate electrophilic reagent $R^2X^5$ affords substituted sulfonamides 36. Directed metalations of this type on 1,2-disubstituted pyrroles have been described in *J. Org. Chem.*, Vol. 50, p. 4362 (1985) and *J. Chem. Soc. Perkin Trans.* I, p. 1343 (1982) and references cited therein. When 32 contains $R^1$ groups that are incompatible with strongly basic conditions of the subsequent reactions, such as when $R^1$ is $CO_2CH_3$ or $C(O)CH_3$, a suitable protecting group in place of $R^1$ can be substituted such as those described in *J. Org. Chem.*, Vol 46, p. 157 (1981), ibid., p.

3760, and in *Tetrahedron*, Vol. 42, p. 3723 (1986). This protecting group can be removed at a suitable point in the synthesis, such as after the synthesis of sulfonamide 36, and replaced with the appropriate $R^1$ group by standard alkylation or acylation methods as described above. Intermediates 34 or 35 where $R^3$ is hydrogen can be directly halogenated to afford the corresponding substituted sulfonamides 34 or 35 where $R^3$ is halogen. Conversion of these intermediates to sulfonamides of Formula 36 where $R^3$ is halogen is best carried out using a substituted lithium amide base, such as lithium diisopropylamide, followed by treatment with an electrophillic reagent as described above.

Intermediate sulfonamides of Formula 38 where J is J-1 and $R^{71}$ is other than H can be prepared as depicted in Equation 21 from the corresponding sulfonamides 36, where $X^6$ is chloro, bromo or iodo.

Equation 21

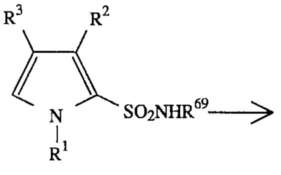

36

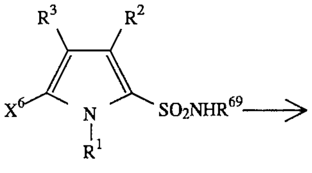

37

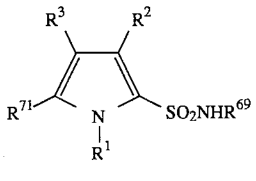

38

Treatment of sulfonamides 36 with a halogenating agent affords sulfonamides 37 where $X^6$ is chloro, bromo, or iodo. Further treatment of 37 where $X^6$ is bromo or iodo with an alkyllithium in an inert solvent followed by an alkyl halide affords sulfonamides 38 where $R^{71}$ is lower alkyl. Likewise treatment of 37 with an alkyllithium reagent and subsequently with a mild fluorinating agent such as that described in *J. Am. Chem. Soc.*, Vol. 106, p. 452 (1984) affords sulfonamides 38 wherein $R^{71}$ is a fluoro substituent. Compounds of 37 where $X^6$ is bromo or iodo to 38 where $R^{71}$ is $CF_3$ can be accomplished by first treatment with an alkyllithium reagent followed by quenching with carbon dioxide to afford an intermediate acid 37 where $R^{71}$ is COOH, and subsequent reaction with sulfur tetrafluoride or the like.

An intermediate pyrrole of Formula 40 where $R^1$ is defined as $Q^1$ above, can be prepared by the method outlined in Equation 22.

Equation 22

$Q^1-NH_2$ +

39

-continued

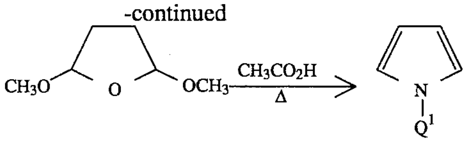

40

Amine 39 can be condensed with 2,5-dimethoxy tetrahydrofuran by the method described in *Org. Syn.*, coll. vol. V, pp. 716–717, affording pyrrole 40.

Intermediate sulfonamides of Formula 44 where J is J-1, $R^3$ is H, $R^1$ is $Q^1$ and $R^{69}$ is a trialkylsilyl protective group can be prepared from the corresponding N-substituted pyrrole 40 as depicted in Equation 23.

Equation 23

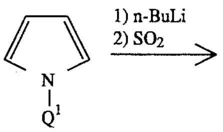

40

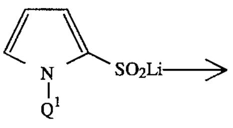

41

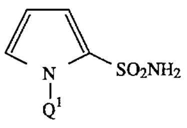

42

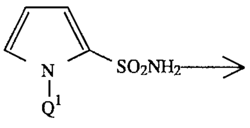

42

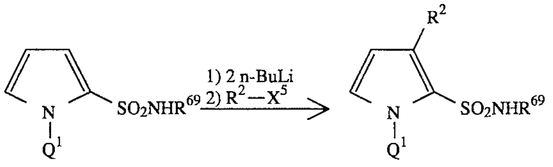

43

44

Pyrroles of Formula 40 can be metalated on carbon using an organometallic base, as described in *Org. React.*, vol. 26, p. 21 (1979) and the references cited therein, preferably using an organolithium reagent such as n-butyllithium, lithium diisopropyl amide, or n-butyllithium/tetramethylethylenediamine. Treatment of the metalated species with sulfur dioxide affords the sulfinate salts 41. These can be converted to sulfonamides 42 by methods described above. Treatment of 42 with a base and a trialkylsilyl chloride affords protected sulfonamides 43. Metalation of 43 with two equivalents of an organometallic base as described above, and quenching with an appropriate electrophilic reagent $R^2X^5$ affords substituted sulfonamides 44.

Intermediate sulfonamides of Formula 49 where J is J-2, $R^4$ is H, $R^1$ is $Q^1$ and $R^{69}$ is a trialkylsilyl protecting group can be prepared from the corresponding N-substituted pyrrole 40 as outlined in Equation 24.

Equation 24

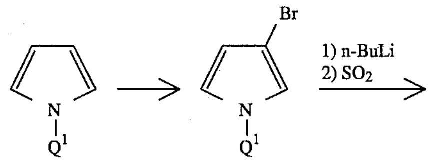

40 45

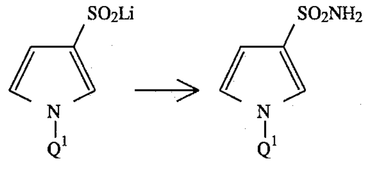

46 47

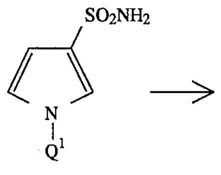

47

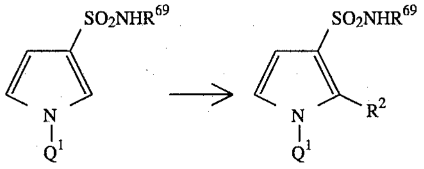

48 49

Pyrroles of Formula 40 can be brominated by methods similar to those reviewed in "Pyrroles," R. Alan Jones, Ed., "The Chemistry of Heterocyclic Compounds," vol. 48, Prt. 1 (John Wiley & Sons, Inc., 1990, New York) p. 372, affording 3-bromo pyrroles of Formula 45. Pyrroles of Formula 45 can undergo metal halogen exchange by the methods described above with an organometallic base, preferably an organolithium reagent. Treatment of the metalated species with sulfur dioxide affords sulfinite salts 46. These salts can be converted to sulfonamides 47 by methods described above. Treatment of 47 with a base and a trialkylsilyl chloride affords protected sulfonamides 48. Metalation of 48 with two equivalents of an organometallic base such as n-butyllithium, lithium diisopropyl amide or n-butyllithium/tetramethylethylenediamine and quenching with an appropriate electrophilic reagent $R^2X^5$ affords substituted sulfonamides 49. Directed metalation of 1,3-disubstituted pyrroles is described above.

Compounds of Formula 53 can be prepared by the method outlined in Equation 25.

Equation 25

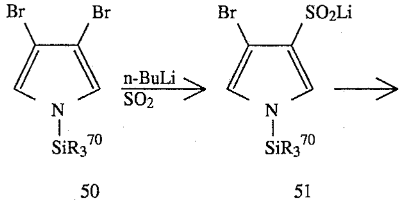

50 51

-continued

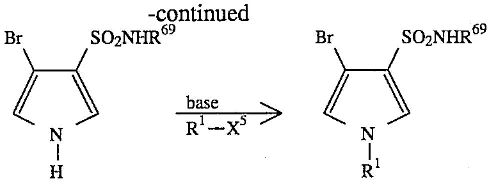

52 23

Compound 50, prepared by the method described in *J. Org. Chem.*, 55, 6317 (1990), is treated with 1 equivalent of an alkyllithium reagent such as n-butyllithium, and the resulting metalated species is treated with sulfur dioxide to obtain sulfinate salt 51 which can be converted to sulfonomide 52 by any of several known methods. For example treatment with N-chlorosuccinimide in acetic acid, followed by amination. The sulfonamide 52 is treated with a base such as an alkali metal alkoxide, hydride or tertiary amine and an appropriate electrophilic reagent ($R^1$-$X^5$) as shown in an inert solvent, to give a sulfonomide of Formula 53.

Sulfonamides of Formula 54 or 55 can be prepared by methods similar to those depicted in Equation 26.

Equation 26

53 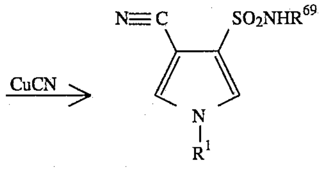

54

53 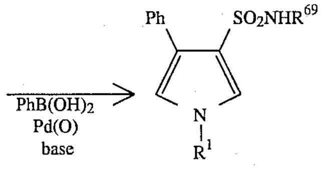

55

Sulfonamide 53 can be treated with cupric cyanide in a polar aprotic solvent preferably DMF, at a temperature in the range of 100° to 155° C. For a period of 6 to 28 hours to afford a sulfonamide of Formula 54. Treatment of sulfonamide 53 with an aryl boronic acid in the presence of a palladium (O) catalyst, such as tetrakis (triphenylphosphine) palladium, and an inorganic base, such as sodium carbonate, by methods similar to those described in *Synthetic Comm.*, 11 513 (1981), affords sulfonamides of Formula 55.

Sulfonamides of Formula 11 may also be prepared by the method depicted in Equation 27.

Equation 27

50 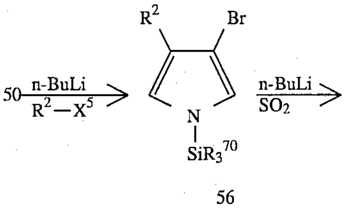

56

-continued

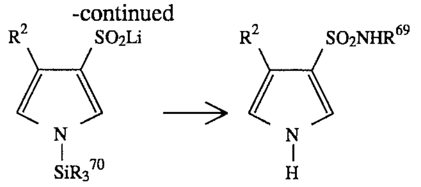

57 11

N-Silyl-protected pyrrole 50 where $R^{70}$ is preferably an isopropyl group, is treated with an alkyllithium reagent such as n-butyllithium, and the resulting metalated species is treated with an appropriate electrophilic reagent ($R^2$-$X^5$) as shown in an inert solvent to afford compound 56. Similar treatment of compound 56 with an alkyllithium reagent such as n-butyllithium and quenching of the metalated species thus formed with sulfur dioxide affords the sulfinate salt 57 which can be converted to sulfonamide 11 by any of several known methods as described above.

The synthesis of heterocyclic amine derivatives such as those depicted in Formulas 3, 5 and 7 are either known, or can be prepared by obvious methods known to one skilled in the art. For a review of the synthesis and reactions of 2-amino- and 2-methylaminopyrimidines see *The Chemistry of Heterocyclic Compounds*, vol 16, Wiley-Interscience, New York (1962). For a review of the synthesis and reactions of 2-amino- and 2-methylamino-s-triazines, see *The Chemistry of Heterocyclic Compounds*, vol 13, Wiley-Interscience, New York (1959), F. C. Schaefer U.S. Pat. No. 3,154,537 and F. C. Schaefer and K. R. Huffman *J. Org. Chem.*, 28, 1812 (1963). *J. Chem. Soc.*, 2031 (1966), EP-A-173,498 and U.S. Pat. No. 4,666,506 describes further methods. The synthesis of the bicyclic amines of Formula 3 where A is A-2 and A-3 is taught in U.S. Pat. No. 4,339,267. The synthesis of bicyclic amines of Formula 3, where A is A-4 is taught in European Patent Publication EP-A-46,667.

The synthesis of compounds of Formula 3 where A is A-5 are described European Patent Publication. EP-A-73,562. The synthesis of compounds of Formula 3 where A is A-6 are described European Patent Publication EP-A-94,260.

The compounds of Formula 3 where A is A-7 can be prepared by methods taught in EP-A-125,864 (published Nov. 21, 1984) or by suitable modifications that would be obvious to one skilled in the art.

The amines of Formula A where $X^1$ is $OCF_2H$ can be prepared by methods taught in EP-A-72,347, or by suitable modifications that would be obvious to one skilled in the art.

The pyrimidines of Formula 3 where A is A-1 (Z═CH) and where Y is

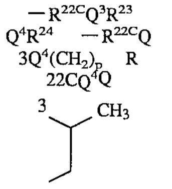

can be prepared according to the method taught in European Patent Publication EP-A-84,224 or suitable modifications thereof known to one skilled in the art.

Agricultural suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxides). Quaternary amine Salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., alkali metal or quaternary amine salt) through a column packed with a cation exchange resin containing the cation to be exchanged for that of the original salt and the desired product is eluted from the column. This method is particularly useful when the desired salt is water-soluble, e.g., potassium, sodium or calcium salt.

Acid addition salts useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Abbreviations for nuclear magnetic resonance (NMR) signals are: s=singlet, bs=broad singlet, d=doublet, t=triplet, m=multiplet, q=quartet, and peak positions are reported as parts per million downfield from internal tetramethylsilane. Infrared (IR) peak positions are given in reciprocal centimeters ($cm^{-1}$) and sh denotes shoulder.

EXAMPLE 1

N-(1,1-Dimethylethyl)-1-[tris(1-methylethyl)silyl] -1H-3-sulfonamide

A solution of 30.25 g (0.10 mol) of 3-bromo-N-triisopropylsilylpyrrole in 500 mL of anhydrous tetrahydrofuran (THF) under nitrogen atmosphere was cooled to −78° C. The colorless solution was treated with 44 mL of 2.38M n-butyllithium in hexanes (0.105 mol) dropwise at such a rate as to keep the temperature below −65° C. After ca. 1 hour at −78° C., liquified sulfur dioxide was added (25.8 ml, 0.6 mol). The amber solution was warmed to room temperature and stirred for ca. 1 hour. The THF was removed under reduced pressure. The resulting amber oil was dissolved in 500 mL glacial acetic acid, cooled to 20° C. and then treated with 13.35 g (0.1 mol) of N-chlorosuccinimide. After ca. 1 hour at room temperature the acetic acid was evaporated at reduced pressure and the residue was dissolved in ethyl acetate. This solution was washed successively with water, $NaHCO_3$ solution, brine, then dried ($MgSO_4$) and evaporated in vacuo. The resulting amber oil residue was dissolved in methylene chloride 500 mL cooled to −20° C. and treated with t-butylamine. The resulting dark brown turbid solution was allowed to warm to room temperature and stir overnight ca. 16 hours. The solution was washed with 1N HCl, dried ($MgSO_4$) and evaporated to a dark oil. Chromatography on silica gel (20% ethyl acetate/80% hexanes) afforded 10.48 g of the title compound as a cream colored solid, m.p. 103°–104° C. $^1H$ NMR ($CDCl_3$, 200 MHz.) δ: 7.28 (d,1H), 6.74(m,1H), 6.56(bs,1H), 4.39(bs,1H), 1.45(m, 3H), 1.23(s,9H), 1.08(d,18H).

EXAMPLE 2

N-(1,1-Dimethylethyl)-1H-pyrrole-3-sulfonamide

A solution of N-(1,1-dimethylethyl)-1-[tris-(1-methylethyl)silyl] -1H-3-sulfonamide (10.48 g, 0.0293 mol) in 100 mL diethyl ether under a nitrogen atmosphere was treated with tetrabutylammoniumfluoridehydrate 10.16 g (0.0388 mol) followed by 1.8 mL of glacial acetic acid. After stirring ca. 1.5 hours at room temperature, the reaction mixture was filtered through silica with diethyl ether rinse. The filtrate was concentrated in vacuo affording 4.1 g of the title compound as a white solid, m.p. 146°–148° C. $^1$H NMR ($CDCl_3$, 200 MHz.) δ: 8.58(bs,1H), 7.32(s,1H), 6.79(d,1H), 6.52(d,1H), 4.34(bs,1H), 1.26(s,9H).

EXAMPLE 3

N-(1,1-Dimethylethyl)-1-methyl-1H-pyrrole-3-sulfonamide

A solution of N-(1,1-dimethylethyl)-1H-pyrrole-3-sulfonamide 9 g (0.044 mol) in 90 mL N,N-dimethylforamide was cooled to 15° C. under a nitrogen atmosphere. To this was added 3.2 mL (0.053 mol) of methyl iodide followed by 5.43 g (0.048 mol) of potassium t-butoxide. The mixture was warmed at ca. 60° C. for 2 hours then allowed to cool to room temperature and stirred for ca. 2 hours. The reaction mixture was diluted with ethyl acetate, washed three times with 1N HCl, once with brine, dried ($MgSO_4$) and evaporated to an oily solid which was triturated with 5% diethyl ether/95% hexanes affording 6 g of the title compound as a beige solid, m.p. 134°–135° C. $^1$H NMR ($CDCl_3$, 200 MHz.) δ: 7.11(s,1H), 6.59(d,1H), 6.41(d,1H), 4.32(bs,1H), 3.67(s, 3H), 1.26(s,9H).

EXAMPLE 4

Methyl 3-[[(1,1-dimethylethyl)amino]sulfonyl]-1-methyl-1H-pyrrole-2-carboxylate To a solution of 1 g (4.62 mmol) of N-(1,1-dimethylethyl)-1-methyl-1H-pyrrole-3-sulfonamide in 150 mL THF under a nitrogen atmosphere cooled to −78° C. was added dropwise at such a rate as to keep the temperature below −65° C. 4.1 mL (9.48 mmol) 2.32M n-butyllithium in hexanes. The resulting amber turbid solution was stirred at −78° C. for ca. 30 minutes. Methyl chloroformate (0.37 mL, 4.86 mmol) was added in one portion and the resulting gold reaction mixture was allowed to warm to room temperature and stirred for ca. 1.5 hours. The gold reaction mixture was cooled to 0° C. and acidified with 1N HCl. The THF phase was separated washed with brine, dried ($MgSO_4$) and concentrated to an amber oil. The NMR of the crude reaction product was consistent with the title compound, additionally the NMR indicated that a trace of the starting material was also present. The crude material was combined with the product from a similar reaction run on the scale described below and chromatographed to give the title compound.

To a solution of 5 g (23 mmol) of N-(1,1-dimethylethyl)-1-methyl-1H-pyrrole-3-sulfonamide in 150 mL THF under nitrogen atmosphere cooled to −78° C. was added dropwise, at such a rate as to keep the temperature below −65° C., 20 mL (47.4 mmol) 2.32M n-butyllithium in hexanes. The resulting amber turbid solution was stirred at −78° C. for ca. 30 minutes. 1.87 mL (24.3 mmol) of methyl chloroformate was add in one portion and the resulting gold reaction mixture was allowed to warm to room temperature and stir for ca. 1.5 hours. The gold reaction mixture was cooled to 0° C. and acidified with 1N HCl. The THF phase was separated, washed with brine, dried ($MgSO_4$) and concentrated to an amber oil. The oil was combined with the crude product from the previous example and chromatographed on silica (30% ethyl acetate/70% hexanes) affording 3.53 g of the title compound as a solid. $^1$H NMR ($CDCl_3$, 200 MHz.) δ: 6.71(dd,2H), 5.72(bs,1H), 3.95(s,3H), 3.91(s,3H), 1.24(s, 9H).

EXAMPLE 5

Methyl 3-(aminosulfonyl)-1-methyl-1H-pyrrole-2-carboxylate

To a solution of 3.53 g of methyl 3-[[(1,1-dimethylethyl)amino] sulfonyl]-1-methyl-1H-pyrrole-2-carboxylate in 40 mL of methylene chloride under an nitrogen atmosphere was added 80 mL of trifluoroacetic acid (TFA). The gold solution was stirred at room temperature overnight ca. 16 hours. The gold solution was concentrated to an oily residue. Diethyl ether was added to the residue and removed by evaporation to remove residual TFA. The resulting solid was suspended in diethyl ether and filtered affording the title compound as a tan solid, m.p. 105°–107° C. $^1$H NMR (Acetone-$d_6$, 200 MHz.) δ: 7.01(d,1H), 6.51(d,1H), 6.28(bs,2H), 3.95(s,3H), 3.93(s,3H).

EXAMPLE 6

Methyl 3-[[[[(4,6-dimethoxy-2-pyrimidinyl)amino]carbonyl]-amino]sulfonyl-1-methyl-1H-pyrrole-2-carboxylate 0.22 g (1 mmol) of methyl 3-(aminosulfonyl)-1-methyl-1H-pyrrole-2-carboxylate and 0.28 g (1 mmol) of phenyl (4,6-dimethoxy-2-pyrimidinyl) carbamate were combined in 4 mL of acetonitrile, 0.2 mL (1.33 mmol) of 1,8-diazabicyclo[5.4.0]undec-7-ene (DBU) was added and the resulting amber reaction mixture was allowed to stand at room temperature overnight ca. 16 hours. The reaction mixture was diluted with 6 mL or water and ca. 2 mL or shaved ice, acidified with conc. HCl (ca. 8 drops) to pH 4. The resulting precipitate was filtered washed with water followed by diethyl ether and air dried affording 0.2 g of the title compound as a solid m.p. 182.5°–186.5° C. 1H NMR ($Me_2SO$-$d_6$, 200 MHz.) δ: 12.45(bs,1H), 10.45(bs,1H), 7.21(d,1H), 6.65(d,1H), 6.01(s,1H), 3.93(s,6H), 3.85(s,3H), 3.7(s,3H).

EXAMPLE 7

N-(1,1-Dimethylethyl)-1-methyl-2-(methylthio)-1H-pyrrole-3-sulfonamide

To a solution of 6.48 g (30 mmol) of N-(1,1-dimethylethyl)-1 -methyl-1H-pyrrole-3-sulfonamide in 150 mL THF under nitrogen atmosphere cooled to −78° C. was added dropwise at such a rate as to keep the temperature below −65° C. 25.52 mL (61.5 mmol) 2.41M n-butyllithium in hexanes. The reaction was stirred at −78° C. for ca. 30 minutes. To the reaction mixture was added 2.97 mL (33 mmol) of dimethyldisulfide in one portion and the resulting reaction mixture was allowed to warm to room temperature and stir for ca. 1.5 hours. The reaction mixture was cooled to 0° C. and acidified with 1N HCl. The THF phase was separated washed with brine, dried ($MgSO_4$) and concentrated in vacuo. The crude residue was chromatographed on silica (20% ethyl acetate/80% hexanes) affording 4.63 g of the title compound as an off white solid, m.p. 116°–119° C. $^1$H NMR ($CDCl_3$, 200 MHz.) δ: 6.72(d,1H), 6.58(d,1H), 4.96(bs,1H), 3.74(s,3H), 2.35(s,3H), 1.23(s,9H).

EXAMPLE 8

1-Methyl-2-(methylthio)-1H-pyrrole-3-sulfonamide

To a solution of 4.63 g (17.66 mmol) N-(1,1-dimethylethyl)-1 -methyl-2-(methylthio)-1H-pyrrole-3-sulfonamide in 50 mL of methylene chloride was added 50 mL of trifluoroacetic acid (TFA) under a nitrogen atmosphere. The orange reaction mixture was stirred at room temperature overnight ca. 16 hours. The reaction mixture was concentrated to a tan solid. Diethyl ether was added to the tan solid and was removed by evaporation to remove residual TFA. The solid was suspended in diethyl ether and filtered giving 2.9 g of the title compound as a solid, m.p. 135°–137° C. $^1$H NMR (Acetone-$d_6$, 200 MHz.) δ: 6.93(d,1H), 6.45(d,1H), 6.19(bs,2H), 3.78(s,3H), 2.33(s,3H).

EXAMPLE 9

2-Bromo-N-(1,1-dimethylethyl)-1-methyl-1H-pyrrole-3-sulfonamide

To a solution of 8.85 g (41 mmol) of N-(1,1-dimethylethyl)-1 -methyl-1H-pyrrole-3-sulfonamide in 200 mL diethyl ether under a nitrogen atmosphere cooled to −78° C. was added dropwise, at such a rate as to keep the temperature below −65° C., 36.0 mL (85 mmol) 2.41M n-butyllithium in hexanes. The reaction was stirred at −78° C. for ca. 15 minutes. To the reaction mixture was added 2.2 mL (41 mmol) of bromine dropwise. The light orange reaction mixture was allowed to warm to room temperature and stir for ca. 2 hours. The reaction mixture darkened as it stirred at room temperature. The reaction mixture was cooled to 0° C. and acidified with 1N HCl. The ether phase was separated, washed with brine, dried ($MgSO_4$) and concentrated in vacuo. The crude residue was chromatographed on silica (25% ethyl acetate/80% hexanes) affording 7.11 g of the title compound as an orange oil. $^1$H NMR ($CDCl_3$, 200 MHz.) δ: 6.73(d,1H), 6.62(d,1H), 3.63(s,3H), 1.24(s,9H).

EXAMPLE 10

2-Bromo-1-methyl-1H-pyrrole-3-sulfonamide

To a solution of 7.11 g (24 mmol) of 2-bromo-N-(1,1-dimethylethyl)-1-methyl-1H-pyrrole-3-sulfonamide in 50 mL methylene chloride under a nitrogen atmosphere was added 50 mL of TFA. The reaction mixture was allowed to stir at room temperature overnight ca. 16 hours. The reaction mixture was concentrated in vacuo. Three portions of diethyl ether were added to the crude residue and was removed by evaporation to remove residual TFA, which yielded 1.23 g of the title compound as a light brown solid. $^1$H NMR (Acetone-$d_6$, 200 MHz.) δ: 7.36(d,1H), 6.49(d,1H), 6.3(bs, 2H) 3.68(s,3H).

EXAMPLE 11

N-(1,1-Dimethylethyl)-2-formyl-1-methyl-1H-pyrrole-3-sulfonamide

To a solution of 12.96 g (60 mmol) of N-(1,1-dimethylethyl)-1 -methyl-1H-pyrrole-3-sulfonamide in 300 mL THF under a nitrogen atmosphere cooled to −78° C. was added dropwise, at such a rate as to keep the temperature below −65° C., 52.35 mL (123 mmol) 2.35M n-butyllithium in hexanes. The reaction was stirred at −78° C. for ca. 30 minutes. To the reaction mixture was added 4.64 mL (60 mmol) of N,N-dimethylformamide dropwise. The reaction mixture was allowed to warm to room temperature and stir for ca. 2 hours. The reaction mixture was cooled to 0° C. and acidified with 1N HCl. The THF phase was separated, washed with brine, dried ($MgSO_4$) and concentrated in vacuo. The crude residue was chromatographed on silica (25% ethyl acetate/80% hexanes) affording 5.72 g of the title compound as a white solid, m.p. 101.5°–103° C. $^1$H NMR ($CDCl_3$, 200 MHz.) δ: 10.25(s,1H), 6.81(d,1H), 6.6(d,1H), 4.93(bs,1H), 3.98(s,3H), 1.27(s,9H).

EXAMPLE 12

N-(1,1-Dimethylethyl)-2-[(methoxyimino)methyl]-1H-pyrrole-3-sulfonamide

To a suspension of 3.91 g (46.8 mmol) of methoxyamine hydrochloride in 60 mL of methanol was added 3.84 g (46.8 mmol) of sodium acetate. After stirring the white suspension for ca. 15 minutes 5.72 g (23 mmol) of N-(1,1-dimethylethyl)-2-formyl-1-methyl-1H-pyrrole-3-sulfonamide was added in one portion. The white suspension was heated at a gentle reflux overnight ca. 16 hours. The reaction mixture was cooled to room temperature and poured into 500 mL of water. The aqueous mixture was extracted with four 100 mL portions of methylene chloride. The combined extracts were washed with water, dried ($MgSO_4$) and concentrated in vacuo yielding 5.74 g of the title compound as a white solid, m.p. 99°–101° C. $^1$H NMR ($CDCl_3$, 200 MHz.) δ: 8.51(s, 1H), 6.66(d,1H), 6.54(d,1H), 4.82(bs,1H), 3.97(s,3H), 3.82(s,3H), 1.24(s,9H).

EXAMPLE 13

2-[(Methoxyimino)methyl]-1-methyl-1H-pyrrole-3-sulfonamide

To a solution of 5.74 g (21.9 mmol) of N-(1,1-dimethylethyl)-2 -[(methoxyimino)-methyl]-1H-pyrrole-3-sulfonamide in 75 mL methylene chloride under a nitrogen atmosphere was add 75 mL of TFA. The clear orange reaction mixture was allowed to stir at room temperature overnight ca. 16 hours. The orange reaction mixture was concentrated in vacuo. Three portions of diethyl ether were added to the residue and removed by evaporation to remove residual TFA, affording 3.49 g of the title compound as a gray solid, m.p. 120°–122° C. $^1$H NMR ($CDCl_3$, 200 MHz.) δ: 8.43(s, 1H), 6.66(d,1H), 6.54(d,1H), 6.1–6.7(bs,2H), 3.96(s,3H), 3.79(s,3H).

EXAMPLE 14

$N^3$-(1,1-Dimethylethyl)-$N^2$,$N^2$,1-trimethyl-1H-pyrrole-2,3-disulfonamide

A solution of 6.48 g (30 mmol) of N-(1,1-dimethylethyl)-1-methyl-1H-pyrrole-3-sulonamide in 150 mL of anhydrous tetrahydrofuran (THF) under nitrogen atmosphere was cooled to −78° C. The colorless reaction was treated with 61.5 mmol of 2.38M n-butyllithium in hexanes dropwise at such a rate as to keep the temperature below −65° C. After ca. 1 hour at −78° C., liquified sulfur dioxide was added (180 mmol). The amber solution was warmed to room temperature and stirred for ca. 1 hour. The THF was removed under reduced pressure. The residue was dissolved in 150 mL glacial acetic acid, cooled to 20° C. and then treated with 31 mmol of N-chlorosuccinimide. After ca. 1 hour at room temperature the acetic acid was evaporated at reduced pressure and the residue was dissolved in ethyl acetate. This solution was washed successively with water, $NaHCO_3$ solution, brine, dried ($MgSO_4$) and evaporated in vacuo. The residue was dissolved in methylene chloride (150 mL), cooled to −20° C. and treated with 75 mmol of liquified dimethylamine. The reaction mixture was allowed to warm to room temperature and stir overnight ca. 16 hours. The solution was washed with 1N HCl, dried ($MgSO_4$) and evaporated. The crude material was dissolved in acetonitrile and treated with activated charcoal, filtered and concentrated. The residue was triturated with hexanes/n-butyl chloride to yield 6.95 g of the title compound as a light brown solid, m.p. 98°–101° C. $^1H$ NMR ($CDCl_3$, 200 MHz.) δ: 6.79(d,1H), 6.69(d,1H), 5.77(bs,1H), 3.89(s,3H), 2.92(s,6H), 1.23(s,9H).

EXAMPLE 15

$N^2$,$N^2$,1-Trimethyl-1H-pyrrole-2,3-disulfonamide

To a solution of 6.95 g (21 mmol) of $N^3$-(1,1-dimethylethyl)$N^2$,$N^2$,1-trimethyl-1H-pyrrole-2,3-disulfonamide in 75 mL of methylene chloride under a nitrogen atmosphere was added 75 mL of TFA. The reaction mixture was allowed to stir at room temperature overnight ca. 16 hours. The reaction mixture was concentrated in vacuo. Three portions of diethyl ether were added to the solid residue and removed by evaporation to remove residual TFA. The solids were suspended in diethyl ether and filtered to yield 4.52 g of the title compound as a solid, m.p. 146°–148° C. $^1H$ NMR (Acetone-$d_6$, 200 MHz.) δ: 7.1(d,1H), 6.59(d,1H), 6.28(bs,2H), 3.95(s,3H), 2.93(s,6H).

EXAMPLE 16

N-[[(4-Ethyl-6-methoxy-1,3,5-triazinyl-2-yl)amino]-carbonyl-N,N,1-trimethyl-2,3-disulfonamide 0.27 g (1 mmol) of $N^2$,$N^2$,1-trimethyl-1H-pyrrole-2,3-disulfonamide and 0.28 g (1 mmol) of phenyl (4-ethyl-6-methoxy-2-triazinyl) carbamate were combined in 4 mL of acetonitrile 0.2 mL (1.33 mmol) of 1,8-diazabicyclo[5.4.0]undec-7-ene was added and the resulting amber reaction mixture was allowed to stand at room temperature overnight ca. 16 hours. The reaction mixture was diluted with 6 mL of water and ca. 2 mL of shaved ice, and was acidified With conc. HCl. The resulting precipitate was filtered, washed with water followed by diethyl ether, and air dried affording 0.19 g of the title compound as a solid, m.p. 159°–160.5° C. $^1H$ NMR ($Me_2SO$-$d_6$, 200 MHz.) δ: 12.52(bs,1H), 11.0(s,1H), 7.27(d,1H), 6.75(d,1H), 3.97(s,3H), 3.85(s,3H), 2.80(s,6H), 2.73(q,2H), 1.25(t,3H).

EXAMPLE 17

3-[[(1,1-Dimethylethyl)amino]sulfonyl]-N,N,1-trimethyl-1H-pyrrole-2-carboxamide To a solution of 6.48 g (30 mmol) of N-(1,1-dimethylethyl)-1 -methyl-1H-pyrrole-3-sulfonamide in 150 mL THF under a nitrogen atmosphere cooled to −78° C. was added dropwise, at such a rate as to keep the temperature below −60° C., 25 mL (61.5 mmol) 2.46M n-butyllithium in hexanes. The reaction mixture was stirred at −78° C. for ca. 30 minutes. To the reaction mixture was added dropwise a solution of 3.1 mL (33 mmol) of N,N-dimethylcarbamyl chloride in 10 mL of THF at such a rate as to maintain the temperature below −65° C. The reaction mixture was allowed to warm to room temperature and stir for ca. 1.5 hours. The reaction mixture was cooled to ca. 5° C. and 60 mL of 50% ammonium chloride solution was added. The reaction mixture was stirred for ca. 15 minutes. The pH was adjusted to ca. 3 with 1N HCl (ca. 30 mL), and the aqueous phase was separated from the THF phase and extracted with ethyl acetate. The combined THF and ethyl acetate extracts were washed with brine, dried ($MgSO_4$) and concentrated in vacuo to an oil. The oil was chromatographed on silica with (20% ethyl acetate/80% n-butyl chloride) affording 4.33 g of the title compound as a pale yellow solid. $^1H$ NMR($CDCl_3$, 200 MHz.) δ: 6.61(d,1H), 6.46(d,1H), 4.62(bs,1H), 3.59(s,3H), 3.1(s,3H), 2.95(s,3H), 1.24(s,9H).

EXAMPLE 18

3-(Aminosulfonyl)-N,N,1-trimethyl-1H-pyrrole-2-carboxamide

To a solution of 5.63 g of 3-[[(1,1-dimethylethyl)amino]sulfonyl] N,N,1-trimethyl-1H-pyrrole-2-carboxamide in 75 mL of methylene chloride was added 75 mL of TFA. The reaction mixture was allowed to stir at room temperature overnight ca. 16 hours. The reaction mixture was concentrated in vacuo. Three portions of diethyl ether were added to the residue and removed by evaporation to remove residual TFA, affording 4.21 g of the title compound as a gray solid, m.p. 185°–190.5° C. $^1H$ NMR($Me_2SO$-$d_6$, 200 MHz.) δ: 6.99(bs,2H), 6.88(d,1H), 6.34(d,1H), 3.47(s,3H), 2.96(s,3H), 2.81(s,3H).

EXAMPLE 19

N-(1,1-Dimethylethyl)-1-methyl-1H pyrrole-2-sulfonamide

A solution of 10 g (0.12 mol) of N-methyl-pyrrole in 120 mL of anhydrous THF under nitrogen atmosphere was cooled to below −70° C. then treated with 56 mL of 2.4M n-butyllithium in hexanes (0.13 mol) dropwise at such a rate as to keep the temperature below −60° C. The resulting brown colored mixture was stirred for 16 h at ambient temperature, then recooled to below −70° C. at which time liquified sulfur dioxide (9.0 mL, 0.21 mol) was added rapidly, causing an exotherm at −20° C. and the formation of a thick golden colored precipitate. After stirring for 1 h at ambient temperature, the THF was removed under reduced pressure. The solids were triturated with ether and collected by filtration with an ether rinse then dried under nitrogen. This intermediate sulfinate salt was added to a well stirred mixture of 350 mL water and 250 mL dichloromethane chilled to 0° C. N-Chlorosuccinimide was then added in portions so as to keep the temperature below 3° C. The mixture was stirred vigorously for 30 min at ambient temperature, after which time, the layers were separated and the organic layer was washed successively with 10% aq $NaHSO_3$, twice with aq $NaHCO_3$, dried ($MgSO_4$) and filtered. This dichloromethane solution was then cooled to 0° C. and stirred while 32 mL (0.30 mol) of t-butylamine was added over 2 min. After stirring for 1 h at ambient temperature, solids had precipitated from the brown solution which was then left stirring for 3 days. The mixture was diluted with more dichloromethane then washed three times with 1N HCl, once with saturated aq NaCl, dried ($MgSO_4$) and evaporated. The resulting solid residue was triturated and collected with a mixture of hexanes and n-chlorobutane to afford 7.4 g of the title compound as tan crystals, m.p. 125°–126° C. $^1H$ NMR ($CDCl_3$, 200 MHz.) δ: 6.82 (m,1H), 6.78 (m,1H), 6.10 (m,1H), 4.53 (bs,1H), 3.83 (s,3H), 1.23 (s,9H).

EXAMPLE 20

Methyl 2-[[(1,1-Dimethylethyl)amino]sulfonyl]-1-methyl-1H-pyrrole-3-carboxylate To a solution of 2.5 g (11.5 mmol) of N-(1,1-dimethylethyl)-1 -methyl-1H-pyrrole-2-sulfonamide in 50 mL THF under nitrogen atmosphere cooled to below −70° C. was added dropwise 13 mL (32.5 mmol) of 2.5M n-butyllithium at such a rate as to keep the temperature below −58° C. After stirring at −20° C. to −10° C. for 30 min then 1 h at 0° C., the mixture was recooled to −70° C. and treated with a solution of 1.63 g (17.3 mmol) of methyl chloroformate in 6 mL THF causing an exotherm to −57° C. The reaction mixture was stirred overnight at ambient temperature then diluted with 200 mL of ethyl acetate. This solution was washed successively with two 60 mL portions of 1N HCl, brine, then dried ($Na_2SO_4$) and evaporated to a dark oil. The crude product was purified by chromatography on silica gel (30% ethyl acetate/70% hexanes) then collected from hexanes to afford 0.45 g of the title compound, m.p. 105°–108° C. $^1H$ NMR ($CDCl_3$, 200 MHz.) δ: 7.00 (bs,1H), 6.61 (m,2H), 3.94 (s,3H), 3.85 (s,3H), 1.21 (s,9H).

EXAMPLE 21

Methyl 2-(Aminosulfonyl)-1-methyl-1H-pyrrole-3-carboxylate

A solution of 0.45 g (1.64 mmol) of methyl 2-[[(1,1 -dimethylethyl)amino]sulfonyl]-1-methyl-1H-pyrrole-3-carboxylate in 20 mL TFA was prepared and stirred at ambient temperature for 3 hours. The TFA was then removed under reduced pressure and chloroform added to the residue and evaporated again to remove residual TFA. The resulting solid was suspended in water, filtered, and dried under vacuum to afford 0.25 g of the title compound, m.p. 119°–121° C., (dec). $^1H$ NMR ($Me_2SO-d_6$, 200 MHz.) δ: 7.40 (bs,2H), 7.02 (d,1H), 6.48 (d,1H), 3.84 (s,3H), 3.76 (s,3H).

EXAMPLE 22

Methyl 2-[[[[(4,6-Dimethoxy-2-pyrimidinyl)amino] carbonyl]amino]sulfonyl-1-methyl-1H-pyrrole-3-carboxylate Methyl 2-(aminosulfonyl)-1-methyl-1H-pyrrole-3-carboxylate (0.10 g, 0.46 mmol) and 0.13 g (0.50 mmol) of phenyl (4,6-dimethoxy-2-pyrimidinyl)carbamate were combined in 2 mL of acetonitrile and 0.075 mL of DBU was added and the resulting amber solution was stirred at ambient temperature for 30 min. The reaction mixture was diluted with 15 mL of water and acidified with 0.5 mL 1N HCl and the resulting precipitate was collected by filtration and rinsed successively with water and ether, then dried to afford 0.15 g of the title compound as a white solid, m.p. 192°–193° C. (dec). $^1H$ NMR ($Me_2SO-d_6$, 200 MHz.) δ: 12.7 (NH), 10.7 (NH), 7.22 (d,1H), 6.60 (d,1H), 6.02 (s,1H), 3.98 (s,3H), 3.96 (s,6H), 3.68 (s,3H).

EXAMPLE 23

Methyl 2-[[[[(4-Methoxy-6-methyl-1,3,5-triazin-2-yl)amino]-carbonyl]amino]sulfonyl]-1-methyl-1H-pyrrole-3-carboxylate Methyl 2-(aminosulfonyl)-1-methyl-1H-pyrrole-3-carboxylate (0.10 g, 0.46 mmol) and 0.13 g (0.50 mmol) of phenyl (4-methoxy-6-methyl-1,3,5-triazin-2-yl)carbamate were combined in 2 mL of acetonitrile and 0.075 mL of DBU was added and the resulting amber solution was stirred at ambient temperature for 30 min. The reaction mixture was diluted with 15 mL of water and acidified with 0.5 mL 1N HCl and the resulting precipitate was collected by filtration and rinsed successively with water and ether, then dried to afford 0.13 g of the title compound as a white solid, m.p. 189°–190° C. (dec). $^1H$ NMR ($Me_2SO-d_6$, 200 MHz.) δ: 12.5 (NH), 11.1 (NH), 7.22 (d,1H), 6.60 (d,1H), 4.01 (s,3H), 3.98 (s,3H), 3.71 (s,3H), 2.49 (s,3H).

By applying the procedures of Examples 1 through 23 and Equations 1 through 24, one skilled in the art can prepare the compounds in Tables 1 through 5. In the following tables, abbreviations for various alkyl chains and rings have been used with the following corresponding definitions.

| | | | | |
|---|---|---|---|---|
| Et | = | ethyl | = | $CH_2CH_3$, |
| iPr | = | isopropyl | = | $CH(CH_3)_2$, |
| nPr | = | n-propyl | = | $CH_2CH_2CH_3$, |
| cPr | = | cyclopropyl | = | $CH(CH_2)_2$, |
| cBu | = | cyclobutyl | = | $CH(CH_2)_3$, |
| $cC_5H_9$ | = | cyclopentyl | = | $CH(CH_2)_4$. |
| t-Bu | = | tert-butyl | = | $C(CH_3)_3$ |
| n-Bu | = | n-butyl | = | $(CH_2)_3CH_3$ |
| $cC_6H_{11}$ | = | cyclohexyl | = | $CH(CH_2)_5$ |

TABLE 1

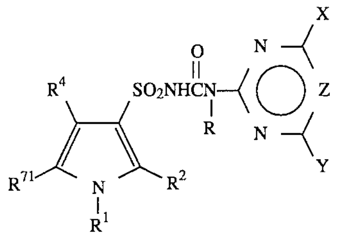

$R = H, R^1 = CH_3, R^2 = CO_2CH_3, R^4 = H, R^{71} = H$

| X | Y | Z | X | Y | Z |
|---|---|---|---|---|---|
| $CH_3$ | $CH_3$ | CH | $NHCH_3$ | $OCH_3$ | N |
| $CH_3$ | $OCH_3$ | CH | $N(CH_3)_2$ | $OCH_3$ | N |
| $OCH_3$ | $OCH_3$ | CH | $C_2H_5$ | $OC_2H_5$ | N |

TABLE 1-continued

| | | | | | |
|---|---|---|---|---|---|
| Cl | $OCH_3$ | CH | $NHCH_3$ | $OC_2H_5$ | N |
| $CH_3$ | $OC_2H_5$ | CH | $N(CH_3)_2$ | $OC_2H_5$ | N |
| $C_2H_5$ | $OCH_3$ | CH | $NHCH_3$ | $OCH_2CF_3$ | N |
| H | $OCH_3$ | CH | $N(CH_3)_2$ | $OCH_2CF_3$ | N |
| H | $OC_2H_5$ | CH | $CH_3$ | $OC_2H_5$ | N |
| $OCH_3$ | $CH_2OCH_3$ | CH | $CF_3$ | $OCH_3$ | N |
| $CH_3$ | $CH(OCH_3)_2$ | CH | $OCF_2H$ | $OCH_3$ | N |
| $OCHF_2$ | $OCH_3$ | CH | $CH_3$ | $OCH_2CH{=}CH_2$ | N |
| $OCH_3$ | $SCH_3$ | CH | | | |
| $CH_3$ | $OCH_3$ | N | | | |
| $OCH_3$ | $OCH_3$ | N | | | |

Z = CH

| X | Y | X | Y |
|---|---|---|---|
| $(CH_2)_3CH_3$ | $OCH_3$ | $OCH_3$ | $CH_2SO_2CH_3$ |
| iPr | $OCH_3$ | $OCH_3$ | cBu |
| $(CH_2)_4Cl$ | $OCH_3$ | $CH_3$ | $O(CH_2)_2CH{=}CH_2$ |
| SEt | SEt | $SCH_2CF_3$ | $OCH_3$ |
| $S(CH_2)_3CH_3$ | $OCH_3$ | $SCHF_2$ | $CH_3$ |
| $OCH_2OEt$ | $CH_3$ | $CF_3$ | $CF_3$ |
| $O(CH_2)_2OiPr$ | $OCH_3$ | $CH_2Cl$ | $OCH_3$ |
| $O(CH_2)_2OCH_3$ | $OC_2H_5$ | $CH_2Br$ | $OCH_3$ |
| $CH_2CH_2OCH_3$ | Et | $CH_2F$ | OEt |
| H | H | I | $OCH_3$ |
| Cl | $N(CH_3)_2$ | $OCH_2CHF_2$ | $CH_3$ |
| Br | $NHCH_3$ | NHiPr | $CH_3$ |
| $OCH_3$ | CN | $N(iPr)_2$ | $CH_3$ |
| $CH_3$ | $CH_2C{\equiv}CH$ | $OCH_2CF_3$ | $OCH_2CF_3$ |
| CH | $OCH_2C{\equiv}CH$ | $NEt_2$ | $NEt_2$ |
| $OCH_3$ | $OCH_2CH{=}CH_2$ | $OCH_3$ | $N_3$ |
| $NEt_2$ | $OCH_3$ | $CH_3$ | cPr |
| $OCH_2iPr$ | $OCH_3$ | $CH_3$ | $CH_2SEt$ |
| $NH_2$ | $CH_3$ | $OCH_3$ | $cC_5H_9$ |
| $N(CH_3)Et$ | $OCH_3$ | $O(CH_2)_3Cl$ | $O(CH_2)_3Cl$ |
| Cl | $OC_2H_5$ | | |
| Br | $OCH_3$ | | |
| $OCF_2H$ | $OCF_2H$ | | |
| $OCH_2CF_3$ | $OCF_2H$ | | |
| $OCH_2CF_3$ | $CH_3$ | | |
| $OCH_2CH_2CH_2F$ | $OCH_3$ | | |
| OiPr | $OCH_3$ | | |
| $CH_3$ | $N(OCH_3)CH_3$ | | |
| $O(CH_2)_3CH_3$ | $O(CH_2)_3CH_3$ | | |
| iPr | iPr | | |
| $OCH_3$ | cPr | | |

Z = N

| X | Y |
|---|---|
| $N(CH_3)_2$ | $N(CH_3)_2$ |
| OEt | NHnBu |
| $OCH_3$ | NHiPr |
| $OCH_2F$ | NHtBu |
| $OCH_3$ | $OCF_2Br$ |
| $NEt_2$ | $NEt_2$ |
| $OCH_3$ | $NEt_2$ |
| OEt | $NHCH_2CF_3$ |
| $OCH_3$ | $N(CH_2CF_3)_2$ |
| $OCH_3$ | StBu |
| $OCH_3$ | CN |
| $OCH_3$ | $N_3$ |
| OEt | cPr |
| $OCH_3$ | $OCH_2CH{=}CH_2$ |
| $CH_3$ | $CH_3$ |

$$Y = -\overset{O}{\overset{\|}{C}}R^{22}$$

| X | $R^{22}$ | Z |
|---|---|---|
| $CH_3$ | $CH_3$ | CH |
| $OCH_3$ | $CH_3$ | CH |
| $CH_3$ | H | CH |
| $OCH_3$ | H | CH |

TABLE 1-continued

| | | |
|---|---|---|
| $CH_3$ | $(CH_2)_2CH_3$ | CH |
| $CH_3$ | $CH_3$ | N |
| $OCH_3$ | $CH_3$ | N |
| $CH_3$ | H | N |
| OEt | H | CH |
| $OCH_3$ | Et | N |

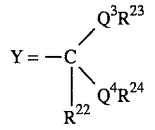

| X | $R^{22}$ | $Q^3R^{23}$ | $Q^4R^{24}$ | Z |
|---|---|---|---|---|
| $OCH_3$ | $CH_3$ | $OCH_3$ | $OCH_3$ | CH |
| $CH_3$ | $CH_3$ | $OCH_3$ | $OCH_3$ | CH |
| $OCH_3$ | Et | $OCH_3$ | $OCH_3$ | N |
| $OCH_3$ | $CH_3$ | SEt | SEt | CH |
| $CH_3$ | $CH_3$ | S-nPr | $SCH_3$ | CH |
| $OCH_3$ | nPr | $OCH_3$ | OiPr | CH |

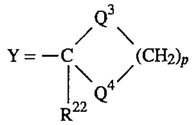

| X | $R^{22}$ | $Q^3$ | $Q^4$ | p | Z |
|---|---|---|---|---|---|
| $OCH_3$ | $CH_3$ | S | S | 2 | CH |
| $CH_3$ | $CH_3$ | O | O | 2 | CH |
| $CH_3$ | $CH_3$ | O | O | 3 | CH |
| $OCH_3$ | $CH_3$ | S | O | 2 | N |
| OEt | $CH_3$ | O | O | 2 | CH |
| $OCH_3$ | Et | S | O | 3 | N |

Z = CH

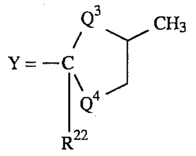

| Z | $R^{22}$ | $Q^3$ | $Q^4$ |
|---|---|---|---|
| $OCH_3$ | $CH_3$ | O | O |
| $CH_3$ | Et | O | O |
| $OCH_3$ | nPr | O | O |
| $CH_3$ | $CH_3$ | S | S |
| $OCH_3$ | Et | O | O |
| $OCH_3$ | $CH_3$ | S | O |

| $R^2 = CO_2CH_3$, $R^{71} = H$, $R = R^4 = H$, $R^1 = CH_2OCH_3$ | | | $R = H$, $R^1 = CH_3$, $R^{71} = H$, $R^2 = CO_2C_2H_5$, $R^4 = H$ | | |
|---|---|---|---|---|---|
| X | Y | Z | X | Y | Z |
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |

TABLE 1-continued

| | | | | | |
|---|---|---|---|---|---|
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH=CH_2$ | N | $CH_3$ | $OCH_2CH=CH_2$ | N |

| $R = R^4 = H$, $R^{71} = H$, $R^2 = SO_2CH_3$, $R^1 = CH_3$ | | | $R = H$, $R^4 = H$, $R^1 = CH_3$, $R^{71} = H$, $R^2 = SO_2N(CH_3)_2$ | | |
|---|---|---|---|---|---|
| X | Y | Z | X | Y | Z |
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH=CH_2$ | N | $CH_3$ | $OCH_2CH=CH_2$ | N |

| $R^1 = C_2H_5$, $R^{71} = H$, $R^2 = CO_2CH_3$, $R^4 = Br$ | | | | $R^1 = CH_3$, $R^4 = H$, $R^{71} = H$, $R^2 = $ 2-pyridyl | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1 = C_2H_5$, $R^{71} = H$, $R^2 = $ 2-thienyl, $R^4 = H$ | | | | $R^1 = CH_3$, $R^4 = H$, $R^{71} = H$, $R^2 = S(O)C_2H_5$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R = H$, $R^1 = CH_3$, $R^4 = H$, $R^{71} = H$, $R^2 = C(O)CH_3$ | | | $R = H$, $R^1 = CH_3$, $R^4 = H$, $R^{71} = H$, $R^2 = C(H)=NOCH_3$ | | |
|---|---|---|---|---|---|
| X | Y | Z | X | Y | Z |
| $CH_3$ | $CH_3$ | CH | $CH_3$ | $CH_3$ | CH |

TABLE 1-continued

| | | | | | |
|---|---|---|---|---|---|
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH{=}CH_2$ | N | $CH_3$ | $OCH_2CH{=}CH_2$ | N |

| $R^4$ = H, $R^{71}$ = H, $R^1$ = $C_2H_5$, $R^2$ = $NO_2$ | | | | $R^1$ = $CH_3$, $R^4$ = H, $R^{71}$ = H, $R^2$ = $CH_2OCH_3$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1$ = $CH_3$, $R^{71}$ = H, $R^2$ = $CH_2OC(O)CH_3$, $R^4$ = H | | | | $R^1$ = $CH_3$, $R^4$ = H, $R^{71}$ = H, $R^2$ = $CH_2SCH_3$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1$ = $CH_3$, $R^{71}$ = H, $R^2$ = $CH_2SO_2CH_3$, $R^4$ = H | | | | $R^1$ = $C_2H_5$, $R^4$ = H, $R^{71}$ = H, $R^2$ = $CH_2OH$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1$ = $CH_3$, $R^{71}$ = H, $R^2$ = $CHF_2$, $R^4$ = H | | | | $R^1$ = $CH_3$, $R^4$ = H, $R^{71}$ = H, $R^2$ = CN | | | |
|---|---|---|---|---|---|---|---|
| R | X | Y | Z | R | X | Y | Z |
| H | $CH_3$ | $CH_3$ | CH | H | $CH_3$ | $CH_3$ | CH |

TABLE 1-continued

| | | | | | | | |
|---|---|---|---|---|---|---|---|
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

$R = H$, $R^4 = CH_3$,
$R^{71} = H$, $R^1 = CH_3$ $R^2$ = 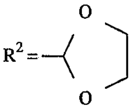

$R = H$, $R^4 = H$, $R^1 = CH_3$,
$R^{71} = H$, $R^2 = CHO$

| X | Y | Z | X | Y | Z |
|---|---|---|---|---|---|
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH{=}CH_2$ | N | $CH_3$ | $OCH_2CHOCH_2$ | N |

| $R = H$, $R^4 = H$, $R^{71} = H$, $R^1 = CH_3$, $R^2 = SCH_3$ | | | $R = H$, $R^4 = H$, $R^1 = CH_3$, $R^{71} = H$, $R^2 = C(O)N(CH_3)_2$ | | |
|---|---|---|---|---|---|
| X | Y | Z | X | Y | Z |
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$, | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH{=}CH_2$ | N | $CH_3$ | $OCH_2CH{=}CH_2$ | N |

TABLE 1-continued

| $R^1 = CH_3$, $R^{71} = H$, $R^2 = CH_2CH_2OCH_3$, $R^4 = H$ | | | | $R^1 = CH_2N(CH_3)_2$, $R^4 = H$, $R^{71} = H$, $R^2 = CO_2CH_3$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1 = CH_3$, $R^4 = H$, $R^{71} = H$, 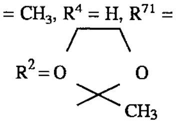 | | | | $R^1 = CH_3$, $R^4 = H$, $R^{71} = H$, 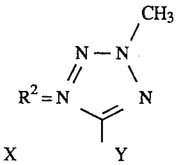 | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1 = H$, $R^{71} = H$, $R^2 = CO_2CH_3$, $R^4 = H$ | | | | $R^1 = H$, $R^4 = H$, $R^{71} = H$, $R^2 = SO_2N(CH_3)_2$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1 = R^4 = H$, $R^{71} = H$, $R^2 = CHO$ | | | | $R^1 = R^4 = H$, $R^{71} = H$, $R^2 = CO_2Et$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $X = Y = OCH_3$, $Z = CH$, $R = H$, $R^{71} = H$ | | |
|---|---|---|
| $R^1$ | $R^2$ | $R^4$ |
| $CH_2SCH_3$ | $CO_2CH_3$ | Br |
| $CH_2CH_2OCH_3$ | $CO_2CH_3$ | H |
| $CH_2CH_2CH_2CH_3$ | $CO_2CH_3$ | H |
| $c\text{-}C_5H_9$ | $SO_2N(CH_3)_2$ | F |
| $CH_2CF_3$ | $SO_2N(CH_3)_2$ | H |
| $CH_2CH_2CH_2Cl$ | $SO_2N(CH_3)_2$ | H |

TABLE 1-continued

| | | |
|---|---|---|
| $CH_2CH{=}CH_2$ | $SCH_3$ | Cl |
| $-CO_2$-t-Bu | $SCH_3$ | Br |
| $-N(CH_3)_2$ | $SCH_3$ | H |
| $-C(O)N(CH_3)_2$ | $SO_2CH_3$ | H |
| 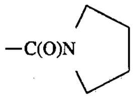 | $SO_2CH_3$ | Br |
| $-C(O)$-n-Pr | $SO_2CH_3$ | H |
| $-CO_2CH_3$ | $CH_3$ | F |
| $CH_3$ | $CO_2CH_3$ | $CO_2CH_3$ |
| $CH_3$ | $CH_2SO_2N(CH_3)_2$ | $CO_2CH_3$ |
| $CH_3$ | n-Bu | Br |
| $CH_2SCH_3$ | $CH_2CO_2CH_3$ | $CH_3$ |
| $CH_3$ | $CH_2CH_2CO_2CH_3$ | H |
| $CH_3$ | $CH_2CH_2CH_2OCH_2CH_3$ | H |
| $CH_3$ | $CH_2CH_2SCH_2CH_3$ | H |
| $CH_2CH_2F$ | $CH_2SO_2CH_2CH_3$ | H |
| $CH_3$ | $CH_2OH$ | Et |
| H | $CH_2Br$ | $CO_2CH_2CH_3$ |
| H | $CH_2Cl$ | F |
| Et | $CHF_2$ | Et |
| $CH_3$ | 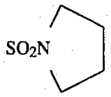 | H |

$X = CH_3$, $Y = OCH_3$, $Z = N$, $R = H$, $R^1 = CH_3$, $R^4 = H$, $R^2 = (CH_2)_mQ^2$, $R^{71} = H$

| m | $Q^2$ | $R^{45}$ | $R^{46}$ | $R^{47}$ | $R^{48}$ |
|---|---|---|---|---|---|
| 0 | $Q^2$-1 | H | H | — | — |
| 1 | $Q^2$-1 | H | H | — | — |
| 0 | $Q^2$-1 | 4-Cl | H | — | — |
| 0 | $Q^2$-1 | 4-$CH_3$ | H | — | — |
| 0 | $Q^2$-1 | 4-$CH_3$ | 2-Cl | — | — |
| 1 | $Q^2$-1 | 2-Cl | 4-Cl | — | — |
| 0 | $Q^2$-1 | 3-Cl | 4-Cl | — | — |
| 0 | $Q^2$-2 | — | — | $CH_3$ | $CH_3$ |
| 0 | $Q^2$-2 | — | — | n-Pr | H |
| 0 | $Q^2$-2 | — | — | Et | H |
| 0 | $Q^2$-3 | — | — | H | — |
| 0 | $Q^2$-3 | — | — | $CH_3$ | — |
| 0 | $Q^2$-3 | — | — | Et | — |

$X = OCH_3$, $Y = OCH_3$, $Z = N$, $R = H$, $R^1 = CH_3$, $R^4 = H$, $R^2 = (CH_2)_mQ^2$, $R^{71} = H$

| m | r | $Q^2$ | $R^{49}$ | $R^{50}$ | $R^{51}$ | $R^{52}$ | $R^{53}$ | $R^{54}$ | $R^{55}$ |
|---|---|---|---|---|---|---|---|---|---|
| 0 | 0 | $Q^2$-4 | H | H | — | — | — | — | — |
| 0 | 1 | $Q^2$-4 | 4-$CH_3$ | H | — | — | — | — | — |
| 0 | 0 | $Q^2$-4 | 5-$CH_3$ | H | — | — | — | — | — |
| 0 | 0 | $Q^2$-4 | 4-$CH_3$ | 6-$CH_3$ | — | — | — | — | — |
| 0 | 1 | $Q^2$-4 | 6-$CH_3$ | H | — | — | — | — | — |
| 0 | 1 | $Q^2$-5 | H | H | — | — | — | — | — |
| 0 | 0 | $Q^2$-5 | 6-$CH_3$ | H | — | — | — | — | — |
| 0 | 0 | $Q^2$-5 | 5-$CH_3$ | H | — | — | — | — | — |
| 0 | 1 | $Q^2$-6 | H | H | — | — | — | — | — |
| 0 | 0 | $Q^2$-6 | 2-$CH_3$ | H | — | — | — | — | — |
| 0 | — | $Q^2$-7 | — | — | H | H | H | — | — |
| 1 | — | $Q^2$-7 | — | — | $CH_3$ | H | $OCH_3$ | — | — |
| 0 | — | $Q^2$-7 | — | — | $OCH_3$ | H | H | — | — |
| 0 | — | $Q^2$-7 | — | — | H | $CH_3$ | H | — | — |
| 0 | — | $Q^2$-8 | — | — | — | — | — | H | H |
| 0 | — | $Q^2$-9 | — | — | — | — | — | 2-$CH_3$ | H |

$X = Y = OCH_3$, $Z = CH$, $R = R^4 = H$, $R^1 = CH_3$, $R^2 = (CH_2)_mQ^2$, $R^{71} = H$

| m | $Q^2$ | $W^3$ | $R^{56}$ | $R^{57}$ | $R^{58}$ |
|---|---|---|---|---|---|
| 0 | $Q^2$-10 | O | H | H | H |
| 0 | $Q^2$-10 | O | H | H | $OCH_3$ |

TABLE 1-continued

| | | | | | |
|---|---|---|---|---|---|
| 0 | $Q^2$-10 | O | H | $CH_3$ | H |
| 0 | $Q^2$-10 | S | H | H | H |
| 0 | $Q^2$-10 | S | $CH_3$ | H | H |
| 1 | $Q^2$-10 | S | H | H | OEt |
| 0 | $Q^2$-10 | S | Cl | H | H |
| 0 | $Q^2$-10 | S | H | H | Et |
| 0 | $Q^2$-10 | S | H | H | Br |
| 0 | $Q^2$-11 | O | H | H | H |
| 0 | $Q^2$-11 | O | H | H | $CH_3$ |
| 0 | $Q^2$-11 | O | $CH_3$ | H | H |
| 0 | $Q^2$-11 | S | H | H | H |
| 0 | $Q^2$-11 | S | H | $CH_3$ | H |
| 0 | $Q^2$-11 | S | H | H | Cl |

$X = CH_3$, $Y = OCH_3$, $Z = CH$, $R = R^4 = H$,
$R^1 = CH_3$, $R^2 = (CH_2)_mQ^2$, m = O, $R^{71} = H$

| $Q^2$ | $W^4$ | $R^{59}$ | $R^{60}$ | $R^{61}$ | $R^{62}$ | $R^{63}$ | $R^{64}$ | $R^{65}$ |
|---|---|---|---|---|---|---|---|---|
| $Q^2$-12 | — | H | $CH_3$ | — | — | — | — | — |
| $Q^2$-12 | — | $CH_3$ | $CH_3$ | — | — | — | — | — |
| $Q^2$-13 | — | — | — | H | — | — | — | — |
| $Q^2$-13 | — | — | — | $CH_3$ | — | — | — | — |
| $Q^2$-13 | — | — | — | $OCH_3$ | — | — | — | — |
| $Q^2$-14 | — | — | — | H | — | — | — | — |
| $Q^2$-14 | — | — | — | $OCH_3$ | — | — | — | — |
| $Q^2$-15 | — | — | — | — | H | — | — | — |
| $Q^2$-15 | — | — | — | — | Et | — | — | — |
| $Q^2$-16 | — | — | — | — | H | — | — | — |
| $Q^2$-16 | — | — | — | — | $CH_3$ | — | — | — |
| $Q^2$-17 | N—H | — | — | — | — | H | H | — |
| $Q^2$-17 | $NCH_3$ | — | — | — | — | H | H | — |
| $Q^2$-18 | $NCH_3$ | — | — | — | — | H | H | — |
| $Q^2$-19 | NH | — | — | $SCH_3$ | — | — | H | — |
| $Q^2$-19 | $NCH_3$ | — | — | $OCH_3$ | — | — | H | — |
| $Q^2$-20 | — | — | — | — | — | — | — | H |
| $Q^2$-20 | — | — | — | — | — | — | — | $CH_3$ |
| $Q^2$-20 | — | — | — | — | — | — | — | OEt |
| $Q^2$-21 | — | — | — | — | — | — | — | Et |
| $Q^2$-21 | — | — | — | — | — | — | — | H |
| $Q^2$-21 | — | — | — | — | — | — | — | $OCH_3$ |

$X = Y = OCH_3$, $Z = CH$, $R = R^4 = H$, $R^2 = CO_2CH_3$, $R^{71} = H$

| | |
|---|---|
| $Q^1$-1 | $R^{25} = R^{26} = H$ |
| $Q^1$-1 | $R^{25}$ = 4-Cl, $R^{26} = H$ |
| $Q^1$-2 | q = O, $R^{27} = R^{28}$ -H |
| $Q^1$-3 | q = O, $R^{27}$ = 6-$CH_3$, $R^{28} = H$ |
| $Q^1$-4 | q = O, $R^{27} = R^{28} = H$ |
| $Q^1$-5 | $R^{29} = R^{30} = R^{31} = H$ |
| $Q^1$-6 | $R^{32} = R^{33} = H$ |
| $Q^1$-8 | $W^1$ = O, $R^{34} = R^{35} = R^{36} = H$ |
| $Q^1$-8 | $W^1$ = S, $R^{34} = R^{35} = R^{36} = H$ |
| $Q^1$-9 | $W^1$ = S, $R^{34} = R^{35} = R^{36} = H$ |
| $Q^1$-10 | $R^{37} = H$, $R^{38} = CH_3$ |
| $Q^1$-11 | $R^{39} = SCH_3$ |
| $Q^1$-15 | $W^2$ = S, $R^{63} = R^{64} = H$ |
| $Q^1$-21 | $R^{65} = CH_3$ |

TABLE 2

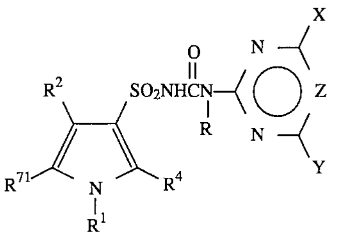

$R = H$, $R^1 = CH_3$, $R^2 = SO_2N(CH_3)_2$, $R^4 = H$, $R^{71} = H$

| X | Y | Z | X | Y | Z |
|---|---|---|---|---|---|
| $CH_3$ | $CH_3$ | CH | $NHCH_3$ | $OCH_3$ | N |

TABLE 2-continued

| | | | | | |
|---|---|---|---|---|---|
| $CH_3$ | $OCH_3$ | CH | $N(CH_3)_2$ | $OCH_3$ | N |
| $OCH_3$ | $OCH_3$ | CH | $C_2H_5$ | $OC_2H_5$ | N |
| Cl | $OCH_3$ | CH | $NHCH_3$ | $OC_2H_5$ | N |
| $CH_3$ | $OC_2H_5$ | CH | $N(CH_3)_2$ | $OC_2H_5$ | N |
| $C_2H_5$ | $OCH_3$ | CH | $NHCH_3$ | $OCH_2CF_3$ | N |
| H | $OCH_3$ | CH | $N(CH_3)_2$ | $OCH_2CF_3$ | N |
| H | $OC_2H_5$ | CH | $CH_3$ | $OC_2H_5$ | N |
| $OCH_3$ | $CH_2OCH_3$ | CH | $CF_3$ | $OCH_3$ | N |
| $CH_3$ | $CH(OCH_3)_2$ | CH | $OCF_2H$ | $OCH_3$ | N |
| $OCHF_2$ | $OCH_3$ | CH | $CH_3$ | $OCH_2CH{=}CH_2$ | N |
| $OCH_3$ | $SCH_3$ | CH | | | |
| $CH_3$ | $OCH_3$ | N | | | |
| $OCH_3$ | $OCH_3$ | N | | | |

Z = CH

| X | Y | X | Y |
|---|---|---|---|
| $(CH_2)_3CH_3$ | $OCH_3$ | $OCH_3$ | $CH_2SO_2CH_3$ |
| iPr | $OCH_3$ | $OCH_3$ | cBu |
| $(CH_2)_4Cl$ | $OCH_3$ | $CH_3$ | $O(CH_2)_2CH{=}CH_2$ |
| SEt | SEt | $SCH_2CF_3$ | $OCH_3$ |
| $S(CH_2)_3CH_3$ | $OCH_3$ | $SCHF_2$ | $CH_3$ |
| $OCH_2OEt$ | $CH_3$ | $CF_3$ | $CF_3$ |
| $O(CH_2)_2OiPr$ | $OCH_3$ | $CH_2Cl$ | $OCH_3$ |
| $O(CH_2)_2OCH_3$ | $OC_2H_5$ | $CH_2Br$ | $OCH_3$ |
| $CH_2CH_2OCH_3$ | Et | $CH_2F$ | OEt |
| H | H | I | $OCH_3$ |
| Cl | $N(CH_3)_2$ | $OCH_2CHF_2$ | $CH_3$ |
| Br | $NHCH_3$ | NHiPr | $CH_3$ |
| $OCH_3$ | CN | $N(iPr)_2$ | $CH_3$ |
| $CH_3$ | $CH_2C{\equiv}CH$ | $OCH_2CF_3$ | $OCH_2CF_3$ |
| $CH_3$ | $OCH_2C{\equiv}CH$ | $NEt_2$ | $NEt_2$ |
| $OCH_3$ | $OCH_2CH{=}CH_2$ | $OCH_3$ | $N_3$ |
| $NEt_2$ | $OCH_3$ | $CH_3$ | cPr |
| $OCH_2iPr$ | $OCH_3$ | $CH_3$ | $CH_2SEt$ |
| $NH_2$ | $CH_3$ | $OCH_3$ | $cC_5H_9$ |
| $N(CH_3)Et$ | $OCH_3$ | $O(CH_2)_3Cl$ | $O(CH_2)_3Cl$ |
| Cl | $OC_2H_5$ | | |
| Br | $OCH_3$ | | |
| $OCF_2H$ | $OCF_2H$ | | |
| $OCH_2CF_3$ | $OCF_2H$ | | |
| $OCH_2CF_3$ | $CH_3$ | | |
| $OCH_2CH_2CH_2F$ | $OCH_3$ | | |
| OiPr | $OCH_3$ | | |
| $CH_3$ | $N(OCH_3)CH_3$ | | |
| $O(CH_2)_3CH_3$ | $O(CH_2)_3CH_3$ | | |
| iPr | iPr | | |
| $OCH_3$ | cPr | | |

| $R^2 = CO_2CH_3$, $R^{71} = H$, $R = R^4 = H$, $R^1 = CH_3$ | | | $R = H$, $R^1 = CH_3$, $R^{71} = H$, $R^2 = CO_2C_2H_5$, $R^4 = H$ | | |
|---|---|---|---|---|---|
| X | Y | Z | X | Y | Z |
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |

TABLE 2-continued

| | | | | | |
|---|---|---|---|---|---|
| $OCF_2H$ | $OCH_3$ | N | $OCF_2H$ | $OCH_3$ | N |
| $CH_3$ | $OCH_2CH{=}CH_2$ | N | $CH_3$ | $OCH_2CH{=}CH_2$ | N |

| $R = R^4 = H$, $R^{71} = H$, $R^2 = SO_2CH_3$, $R^1 = CH_3$ | | | $R = R^4 = H$, $R^1 = CH_3$, $R^2 = Br$, $R^{71} = H$ | | |
|---|---|---|---|---|---|
| X | Y | Z | X | Y | Z |
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH{=}CH_2$ | N | $CH_3$ | $OCH_2CH{=}CH_2$ | N |

| $R^1 = CH_3$, $R^4 = H$, $R^{71} = H$, $R^2 = C(O)CH_3$ | | | | $R^1 = CH_3$, $R^4 = H$, $R^{71} = H$, $R^2 = C(H)NOCH_3$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

$R^1 = CH_3$, $R^4 = H$, $R^{71} = H$

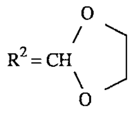

$R^1 = CH_3$, $R^4 = H$, $R^{71} = H$, $R^2 = SCH_3$

| R | X | Y | Z | R | X | Y | Z |
|---|---|---|---|---|---|---|---|
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1 = CH_3$, $R^4 = H$, $R^{71} = H$, $R^2 = CHO$ | | | | $R^1 = CH_3$, $R^4 = H$, $R^{71} = H$, $R^2 = CHF_2$ | | | |
|---|---|---|---|---|---|---|---|
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |

TABLE 2-continued

| | | | | | | | |
|---|---|---|---|---|---|---|---|
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |
| $R^1 = CH_3$, $R^4 = H$, $R^{71} = H$, $R^2 = CH_2OCH_3$ | | | | $R^1 = CH_3$, $R^4 = H$, $R^{71} = H$, $R^2 = CH_2CN$ | | | |
| R | X | Y | Z | R | X | Y | Z |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

$X = Y = OCH_3$, $Z = CH$, $R = H$, $R^{71} = H$

| $R^1$ | $R^2$ | $R^4$ |
|---|---|---|
| $CH_3$ | $S(O)CH_3$ | $CO_2CH_3$ |
| H | $S(O)CH_3$ | H |
| $CH_2OCH_3$ | $CH_2CO_2CH_3$ | H |
| $CH_3$ | $CH_2OH$ | Cl |
| H | $CH_2OH$ | $CH_3$ |
| $CH_3$ | $CH_2Cl$ | Br |
| $CH_3$ | 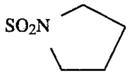 | H |
| $CH_3$ | $CH_2CH_2OCH_2CH_3$ | Cl |
| $CO_2$-t-Bu | Cl | H |
| C(O)NH-t-Bu | Br | H |
| C(O)Et | n-Pr | H |
| c-$C_6H_{11}$ | $-CHF_2$ | H |
| $CH_2CH_2Cl$ | $CO_2Et$ | Br |
| Et | $CH(OCH_3)_2$ | $CH_3$ |
| $CH_3$ | $C(O)N(CH_3)_2$ | H |
| $CH_2OCH_3$ | $C(O)N(CH_3)_2$ | H |
| $CH_2CH{=}CH_2$ | $CH_2CH_2OCH_3$ | H |
| $CH_2N(CH_3)_2$ | $CH_2CO_2CH_3$ | H |
| $CH_2SCH_3$ | $CO_2CH_2OCH_3$ | H |
| $CH_2$-c-Pr | $S(O)CH_2CH{=}CH_2$ | H |
| $CH_2CF_2H$ | $NO_2$ | H |
| $CH_2CH_2C(OCH_3)CH_3$ | $CH_2CH_2CN$ | H |
| $CH_3$ | $CH_2-C_6H_5$ | Br |
| $CH_3$ | CN | H |
| $CH_3$ | $CH_2CH_2C(O)CH_3$ | H |

TABLE 3

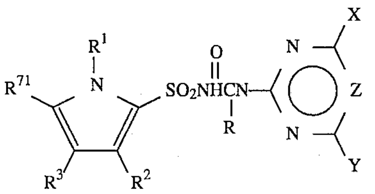

| X | Y | Z | X | Y | Z |
|---|---|---|---|---|---|
| $R{=}H$, $R^1{=}CH_3$, $R^2{=}CO_2CH_3$, $R^3{=}H$, $R^{71}{=}H$ | | | | | |
| $CH_3$ | $CH_3$ | CH | $NHCH_3$ | $OCH_3$ | N |
| $CH_3$ | $OCH_3$ | CH | $N(CH_3)_2$ | $OCH_3$ | N |
| $OCH_3$ | $OCH_3$ | CH | $C_2H_5$ | $OC_2H_5$ | N |
| Cl | $OCH_3$ | CH | $NHCH_3$ | $OC_2H_5$ | N |
| $CH_3$ | $OC_2H_5$ | CH | $N(CH_3)_2$ | $OC_2H_5$ | N |

TABLE 3-continued

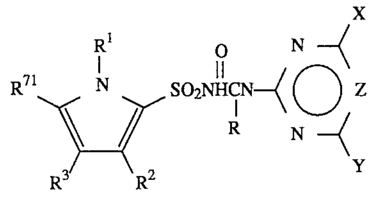

| | | | | | |
|---|---|---|---|---|---|
| $C_2H_5$ | $OCH_3$ | CH | $NHCH_3$ | $OCH_2CF_3$ | N |
| H | $OCH_3$ | CH | $N(CH_3)_2$ | $OCH_2CF_3$ | N |
| H | $OC_2H_5$ | CH | $CH_3$ | $OC_2H_5$ | N |
| $OCH_3$ | $CH_2OCH_3$ | CH | $CF_3$ | $OCH_3$ | N |
| $CH_3$ | $CH(OCH_3)_2$ | CH | $OCF_2H$ | $OCH_3$ | N |
| $OCHF_2$ | $OCH_3$ | CH | $CH_3$ | $OCH_2CH{=}CH_2$ | N |
| $OCH_3$ | $SCH_3$ | CH | | | |
| $CH_3$ | $OCH_3$ | N | | | |
| $OCH_3$ | $OCH_3$ | N | | | |

| X | Y | X | Y |
|---|---|---|---|
| | Z=CH | | |
| $(CH_2)_3CH_3$ | $OCH_3$ | $OCH_3$ | $CH_2SO_2CH_3$ |
| iPr | $OCH_3$ | $OCH_3$ | cBu |
| $(CH_2)_4Cl$ | $OCH_3$ | $CH_3$ | $O(CH_2)_2CH{=}CH_2$ |
| SEt | SEt | $SCH_2CF_3$ | $OCH_3$ |
| $S(CH_2)_3CH_3$ | $OCH_3$ | $SCHF_2$ | $CH_3$ |
| $OCH_2OEt$ | $CH_3$ | $CF_3$ | $CF_3$ |
| $O(CH_2)_2OiPr$ | $OCH_3$ | $CH_2Cl$ | $OCH_3$ |
| $O(CH_2)_2OCH_3$ | $OC_2H_5$ | $CH_2Br$ | $OCH_3$ |
| $CH_2CH_2OCH_3$ | Et | $CH_2F$ | OEt |
| H | H | I | $OCH_3$ |
| Cl | $N(CH_3)_2$ | $OCH_2CHF_2$ | $CH_3$ |
| Br | $NHCH_3$ | NHiPr | $CH_3$ |
| $OCH_3$ | CN | $N(iPr)_2$ | $CH_3$ |
| $CH_3$ | $CH_2C{=}CH$ | $OCH_2CF_3$ | $OCH_2CF_3$ |
| $CH_3$ | $OCH_2C{=}CH$ | $NEt_2$ | $NEt_2$ |
| $OCH_3$ | $OCH_2CH{=}CH_2$ | $OCH_3$ | $N_3$ |
| $NEt_2$ | $OCH_3$ | $CH_3$ | cPr |
| $OCH_2iPr$ | $OCH_3$ | $CH_3$ | $CH_2SEt$ |
| $NH_2$ | $CH_3$ | $OCH_3$ | $cC_5H_9$ |
| $N(CH_3)Et$ | $OCH_3$ | $O(CH_2)_3Cl$ | $O(CH_2)_3Cl$ |
| Cl | $OC_2H_5$ | | |
| Br | $OCH_3$ | | |
| $OCF_2H$ | $OCF_2H$ | | |
| $OCH_2CF_3$ | $OCF_2H$ | | |
| $OCH_2CF_3$ | $CH_3$ | | |
| $OCH_2CH_2CH_2F$ | $OCH_3$ | | |
| OiPr | $OCH_3$ | | |
| $CH_3$ | $N(OCH_3)CH_3$ | | |
| $O(CH_2)_3CH_3$ | $O(CH_2)_3CH_3$ | | |
| iPr | iPr | | |
| $OCH_3$ | cPr | | |

| X | Y | Z | X | Y | Z |
|---|---|---|---|---|---|
| $R{=}R^3{=}H$, $R^{71}{=}H$, $R^1{=}CH_2OCH_2CH_3$, $R^2{=}CO_2Et$ | | | $R{=}H$, $R^1{=}CH_3$, $R^{71}{=}Cl$, $R^3{=}H$, $R^2{=}CO_2Et$ | | |
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |

TABLE 3-continued

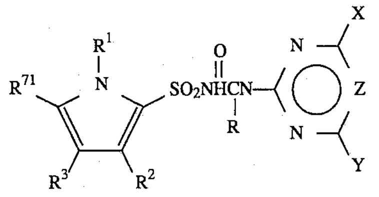

| | | | | | |
|---|---|---|---|---|---|
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH{=}CH_2$ | N | $CH_3$ | $OCH_2CH{=}CH_2$ | N |
| $R{=}R^3{=}H$, $R^{71}{=}H$, $R^1{=}CH_3$, $R^2{=}SO_2CH_3$ | | | $R{=}R^3{=}H$, $R^1{=}CH_3$, $R^{71}{=}H$, $R^2{=}SO_2N(CH_3)_2$ | | |
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH{=}CH_2$ | N | $CH_3$ | $OCH_2CH{=}CH_2$ | N |
| $R{=}R^3{=}H$, $R^{71}{=}H$, $R^2{=}C(O)CH_3$ | | | $R{=}R^3{=}H$, $R^1{=}CH_3$, $R^{71}{=}H$, $R^2{=}C(OCH_3){=}NOCH_3$ | | |
| $CH_3$ | $CH_3$ | CH | $CH_3$ | $CH_3$ | CH |
| $CH_3$ | $OCH_3$ | CH | $CH_3$ | $OCH_3$ | CH |
| $OCH_3$ | $OCH_3$ | CH | $OCH_3$ | $OCH_3$ | CH |
| Cl | $OCH_3$ | CH | Cl | $OCH_3$ | CH |
| $CH_3$ | $OC_2H_5$ | CH | $CH_3$ | $OC_2H_5$ | CH |
| $C_2H_5$ | $OCH_3$ | CH | $C_2H_5$ | $OCH_3$ | CH |
| H | $OCH_3$ | CH | H | $OCH_3$ | CH |
| H | $OC_2H_5$ | CH | H | $OC_2H_5$ | CH |
| $OCH_3$ | $CH_2OCH_3$ | CH | $OCH_3$ | $CH_2OCH_3$ | CH |
| $CH_3$ | $CH(OCH_3)_2$ | CH | $CH_3$ | $CH(OCH_3)_2$ | CH |
| $OCHF_2$ | $OCH_3$ | CH | $OCHF_2$ | $OCH_3$ | CH |
| $OCH_3$ | $SCH_3$ | CH | $OCH_3$ | $SCH_3$ | CH |
| $CH_3$ | $OCH_3$ | N | $CH_3$ | $OCH_3$ | N |
| $OCH_3$ | $OCH_3$ | N | $OCH_3$ | $OCH_3$ | N |
| $NHCH_3$ | $OCH_3$ | N | $NHCH_3$ | $OCH_3$ | N |
| $N(CH_3)_2$ | $OCH_3$ | N | $N(CH_3)_2$ | $OCH_3$ | N |
| $C_2H_5$ | $OC_2H_5$ | N | $C_2H_5$ | $OC_2H_5$ | N |
| $NHCH_3$ | $OC_2H_5$ | N | $NHCH_3$ | $OC_2H_5$ | N |
| $N(CH_3)_2$ | $OC_2H_5$ | N | $N(CH_3)_2$ | $OC_2H_5$ | N |
| $NHCH_3$ | $OCH_2CF_3$ | N | $NHCH_3$ | $OCH_2CF_3$ | N |
| $N(CH_3)_2$ | $OCH_2CF_3$ | N | $N(CH_3)_2$ | $OCH_2CF_3$ | N |
| $CH_3$ | $OC_2H_5$ | N | $CH_3$ | $OC_2H_5$ | N |
| $CF_3$ | $OCH_3$ | N | $CF_3$ | $OCH_3$ | N |
| $OCF_2H$ | $OCH_3$ | N | $OCF_2H$ | $OCH_3$ | N |
| $CH_3$ | $OCH_2CH{=}CH_2$ | N | $CH_3$ | $OCH_2CH{=}CH_2$ | N |

TABLE 3-continued

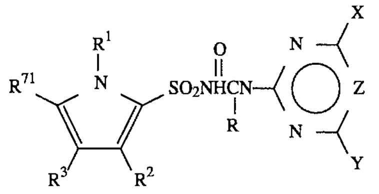

| R | X | Y | Z | R | X | Y | Z |
|---|---|---|---|---|---|---|---|
| $R^1=CH_3$, $R^3=H$, $R^{71}=H$, $R^2=NO_2$ | | | | $R^1=CH_3$, $R^3=H$, $R^{71}=H$, $R^2=S(O)Et$ | | | |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |
| $R^1=CH_3$, $R^3=H$, $R^{71}=H$, $R^2=CHO$ | | | | $R^1=CH_3$, $R^3=H$, $R^{71}=H$, $R^2=C(O)N(CH_3)_2$ | | | |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |
| $R^1=CH_3$, $R^3=H$, $R^{71}=H$, $R^2=Cl$ | | | | $R^1=CH_3$, $R^3=H$, $R^{71}=H$, $R^2=CH_2OCH_3$ | | | |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |
| $R^1=CH_3$, $R^3=H$, $R^{71}=H$, $R^2=SC_2H_5$ | | | | $R^1=CH_3$, $R^3=H$, $R^{71}=H$, $R^2=CHF_2$ | | | |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |
| $R^1=C_2H_5R^3=R^{71}=H$, $R^2=OCH_3$ | | | | $R^1=CH_3$, $R^3=R^{71}=H$, $R^2=OC(O)CH_3$ | | | |
| H | $CH_3$ | $CH_3$ | CH | H | $CH_3$ | $CH_3$ | CH |
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |
| $R^1=CH_3$, $R^3=R^{71}=H$, $R^2=OSO_2CH_3$ | | | | $R^1=CH_3$, $R^3=R^{71}=H$, $R^2=OiPr$ | | | |
| H | $CH_3$ | $CH_3$ | CH | H | $CH_3$ | $CH_3$ | CH |

TABLE 3-continued

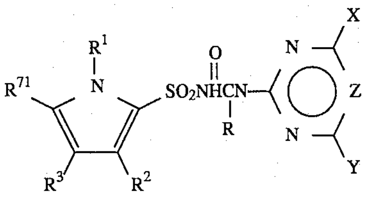

| | | | | | | | |
|---|---|---|---|---|---|---|---|
| H | $CH_3$ | $OCH_3$ | CH | H | $CH_3$ | $OCH_3$ | CH |
| H | $OCH_3$ | $OCH_3$ | CH | H | $OCH_3$ | $OCH_3$ | CH |
| H | Cl | $OCH_3$ | CH | H | Cl | $OCH_3$ | CH |
| $CH_3$ | $OCH_3$ | $OCH_3$ | CH | $CH_3$ | $OCH_3$ | $OCH_3$ | CH |
| H | $CH_3$ | $OCH_3$ | N | H | $CH_3$ | $OCH_3$ | N |
| H | $OCH_3$ | $OCH_3$ | N | H | $OCH_3$ | $OCH_3$ | N |
| H | $NHCH_3$ | $OC_2H_5$ | N | N | $NHCH_3$ | $OC_2H_5$ | N |
| H | $N(CH_3)_2$ | $OC_2H_5$ | N | H | $N(CH_3)_2$ | $OC_2H_5$ | N |
| $CH_3$ | $OCH_3$ | $OCH_3$ | N | $CH_3$ | $OCH_3$ | $OCH_3$ | N |

| $R^1$ | $R^2$ | $R^3$ |
|---|---|---|
| $X=Y=OCH_3$, $Z=CH$, $R=H$, $R^{71}=H$ | | |
| $CH_3$ | $CO_2Et$ | F |
| $CH_3$ | $CO_2Et$ | $CH_3$ |
| $CH_2OCH_3$ | $SO_2Et$ | Cl |
| $CH_3$ | $CH_2CH_2C(O)CH_3$ | H |
| Et | $CO_2CH_2OCH_3$ | H |
| $CH_2CH_{2F}$ | $NO_2$ | H |
| $CH_2CH_2OCH_3$ | $SO_2NHEt$ | H |
| Et | $CH(OCH_3)_2$ | Br |
| $CH_3$ | C(O)-n-Pr | F |
| $CH_3$ | $CH_2C(O)CH_3$ | H |
| $CH_3$ | CN | H |
| $CH_2OCH_3$ | CN | H |

TABLE 4

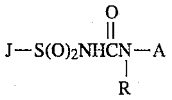

$R=H$, $R^1=CH_3$, $R^3=R^4=H$, $R^2=CO_2CH_3$, $R^{71}=H$

| J | A | $X^1$ | $Y^1$ | $Y^3$ |
|---|---|---|---|---|
| J-1 | A-2 | $CH_3$ | O | — |
| J-1 | A-2 | OEt | O | — |
| J-2 | A-2 | $OCH_3$ | O | — |
| J-2 | A-2 | $OCH_3$ | $CH_2$ | — |
| J-1 | A-3 | $CH_3$ | — | — |
| J-3 | A-3 | $CH_3$ | — | — |
| J-1 | A-4 | $CH_3$ | — | $CH_3$ |
| J-2 | A-4 | $OCH_3$ | — | $CH_3$ |
| **J** | **A** | **$X^2$** | **$Y^2$** | **$X^3$** |
| J-1 | A-5 | $CH_3$ | $CH_3$ | — |
| J-1 | A-6 | — | — | $OCH_3$ |
| J-2 | A-5 | $CH_3$ | $SCH_3$ | — |
| J-2 | A-6 | — | — | $CH_3$ |
| J-3 | A-6 | $CH_3$ | $OCH_3$ | — |
| J-3 | A-5 | $CH_2CF_3$ | $OCH_3$ | — |
| **J** | **A** | **$X^4$** | **$Y^4$** | **$Z^1$** |
| J-1 | A-7 | $CH_3$ | $CH_3$ | CH |
| J-1 | A-7 | $OCH_3$ | $CH_3$ | CH |
| J-2 | A-7 | $OCH_3$ | $OCH_3$ | N |
| J-2 | A-7 | $CH_3$ | $OC_2H_5$ | CH |
| J-3 | A-7 | Cl | $CH_3$ | CH |
| J-3 | A-7 | $CH_3$ | $CH_3$ | N |

TABLE 5

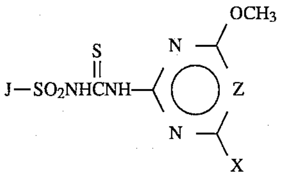

$R^3 = R^4 = H$, $R^1 = CH_3$, $R^{71} = H$

| J | $R^2$ | Z | X |
|---|---|---|---|
| J-1 | $CO_2CH_3$ | CH | $OCH_3$ |
| J-1 | $CO_2CH_3$ | N | $CH_3$ |
| J-1 | $SO_2N(CH_3)_2$ | CH | $OCH_3$ |
| J-1 | $SO_2CH_3$ | N | $CH_3$ |
| J-2 | $CO_2CH_3$ | CH | Cl |
| J-2 | $CO_2CH_3$ | CH | $OCH_3$ |
| J-2 | $SO_2N(CH_3)_2$ | N | $CH_3$ |
| J-2 | CHO | N | $OCH_3$ |
| J-2 | $CO_2CH_3$ | CH | $OCH_3$ |
| J-3 | $CO_2CH_3$ | CH | $CH_3$ |
| J-3 | $SO_2N(CH_3)_2$ | N | $CH_3$ |
| J-3 | $C(O)CH_3$ | N | $OCH_3$ |

The procedures of Examples 1 through 18 and Equations 1 through 21 were followed in the synthesis of the following compounds.

INDEX TABLE

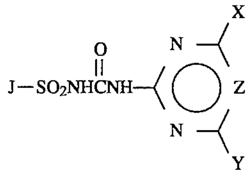

| J is J-2, $R^1$ is $CH_3$, $R^4$ and $R^{71}$ are H | | | | | |
|---|---|---|---|---|---|
| CMPD | $R^2$ | X | Y | Z | m.p. (°C.) |
| 1 | $CO_2CH_3$ | $CH_3$ | $CH_3$ | CH | 188–190 |
| 2 | $CO_2CH_3$ | $CH_3$ | $OCH_3$ | CH | 186–188 |
| 3 | $CO_2CH_3$ | $OCH_3$ | $OCH_3$ | CH | 182.5–186.5 |
| 4 | $CO_2CH_3$ | Cl | $OCH_3$ | CH | 186–188.5 |
| 5 | $CO_2CH_3$ | $CH_3$ | $OCH_3$ | N | 189–190 |
| 6 | $CO_2CH_3$ | $OCH_3$ | $OCH_3$ | N | 182–183 |
| 7 | $CO_2CH_3$ | $NHCH_3$ | OEt | N | 173–179 |
| 8 | $CO_2CH_3$ | OEt | OEt | N | 179–180.5 |
| 9 | $SCH_3$ | $CH_3$ | $CH_3$ | CH | 140–164 |
| 10 | $SCH_3$ | $CH_3$ | $OCH_3$ | CH | 176–178 |
| 11 | $SCH_3$ | $OCH_3$ | $OCH_3$ | CH | 181–183 |
| 12 | $SCH_3$ | Cl | $OCH_3$ | CH | 165–167 |
| 13 | $SCH_3$ | $CH_3$ | $OCH_3$ | N | 180–183 |
| 14 | $SCH_3$ | $OCH_3$ | $OCH_3$ | N | 174–176 |
| 15 | $SCH_3$ | $NHCH_3$ | OEt | N | 124–126 |
| 16 | $SCH_3$ | $NHCH_3$ | $OCH_2CF_3$ | N | 165–169 |
| 17 | $SCH_3$ | $N(CH_3)_2$ | $OCH_2CF_3$ | N | 116–125 |
| 18 | $SCH_3$ | Et | OEt | N | 120–123 |
| 19 | $SCH_3$ | Et | $OCH_3$ | N | 129–130.6 |
| 20 | Br | $CH_3$ | $OCH_3$ | CH | 172–177.5 |
| 21 | Br | $OCH_3$ | $OCH_3$ | CH | 149–151.5 |
| 22 | Br | Cl | $OCH_3$ | CH | 168–175.6 |
| 23 | Br | $OCH_3$ | $OCH_3$ | N | 185–188 |
| 24 | Br | $OCH_3$ | $OCH_3$ | H | 180–186 |
| 25 | $SO_2N(CH_3)_2$ | $CH_3$ | $CH_3$ | CH | 200–205 |
| 26 | $SO_2N(CH_3)_2$ | $CH_3$ | $OCH_3$ | CH | 211–216 |
| 27 | $SO_2N(CH_3)_2$ | $OCH_3$ | $OCH_3$ | CH | 175.5–181 |
| 28 | $SO_2N(CH_3)_2$ | Cl | $OCH_3$ | CH | 169–172 |
| 29 | $SO_2N(CH_3)_2$ | $CH_3$ | $OCH_3$ | N | 184–190 |
| 30 | $SO_2N(CH_3)_2$ | $OCH_3$ | $OCH_3$ | N | 176.5–178.5 |
| 31 | $SO_2N(CH_3)_2$ | $NHCH_3$ | OEt | N | 128–132 |
| 32 | $SO_2N(CH_3)_2$ | $NHCH_3$ | $OCH_2CF_3$ | N | 144–146 |
| 33 | $SO_2N(CH_3)_2$ | $N(CH_3)_2$ | $OCH_2CF_3$ | N | 143–145 |
| 34 | $SO_2N(CH_3)_2$ | $N(CH_3)_2$ | $OCH_3$ | N | 189–191 |
| 35 | $SO_2N(CH_3)_2$ | Et | OEt | N | 138–140 |
| 36 | $SO_2N(CH_3)_2$ | Et | $OCH_3$ | N | 159–160.5 |
| 37 | $C(H){=}NOCH_3$ | $CH_3$ | $CH_3$ | CH | 193–196 |
| 38 | $C(H){=}NOCH_3$ | $CH_3$ | $OCH_3$ | CH | 195–197 |
| 39 | $C(H){=}NOCH_3$ | $OCH_3$ | $OCH_3$ | CH | 172–174 |
| 40 | $C(H){=}NOCH_3$ | Cl | $OCH_3$ | CH | 166–168 |
| 41 | $C(H){=}NOCH_3$ | $CH_3$ | $OCH_3$ | N | 168–170.6 |
| 42 | $C(H){=}NOCH_3$ | $OCH_3$ | $OCH_3$ | N | 187–189 |
| 43 | $C(H){=}NOCH_3$ | $NHCH_3$ | OEt | N | 193–195 |
| 44 | $C(H){=}NOCH_3$ | OEt | OEt | N | 189–192 |
| 45 | $C(H){=}NOCH_3$ | $NHCH_3$ | $OCH_2CF_3$ | N | 119–122 |
| 46 | $C(H){=}NOCH_3$ | $N(CH_3)_2$ | $OCH_2CF_3$ | N | 158–160 |
| 47 | $C(H){=}NOCH_3$ | $N(CH_3)_2$ | $OCH_3$ | N | 173–176 |
| 48 | $C(H){=}NOCH_3$ | Et | OEt | N | 166–156.5 |
| 49 | $C(H){=}NOCH_3$ | Et | $OCH_3$ | N | 137.5–145 |

| J is J-1, $R^3$ is H | | | | | | | |
|---|---|---|---|---|---|---|---|
| CMPD | $R^1$ | $R^2$ | $R^{71}$ | X | Y | Z | m.p. (°C.) |
| 50 | $CH_3$ | $CO_2CH_3$ | H | $OCH_3$ | $OCH_3$ | CH | 192–193 |
| 51 | $CH_3$ | $CO_2CH_3$ | H | $CH_3$ | $OCH_3$ | N | 189–190 |
| 52 | $CH_3$ | $CO_2CH_3$ | H | $CH_3$ | $CH_3$ | CH | 120–122 |
| 53 | $CH_3$ | $CO_2CH_3$ | H | $CH_3$ | $OCH_3$ | CH | 112–114 |
| 54 | $CH_3$ | $CO_2CH_3$ | H | $OCH_3$ | $OCH_3$ | N | 185–187 |
| 55 | $CH_3$ | $CO_2CH_3$ | H | Cl | $OCH_3$ | CH | 209–210 |
| 56 | $CH_3$ | $CO_2Et$ | H | $CH_3$ | $CH_3$ | CH | 210–211 |
| 57 | $CH_3$ | $CO_2Et$ | H | $CH_3$ | $OCH_3$ | CH | 197–198 |

-continued

INDEX TABLE

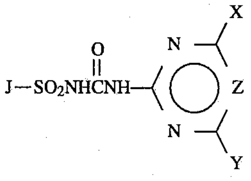

| | | | | | | | |
|---|---|---|---|---|---|---|---|
| 58 | $CH_3$ | $CO_2Et$ | H | $OCH_3$ | $OCH_3$ | CH | 176–179 |
| 59 | $CH_3$ | $CO_2Et$ | H | $CH_3$ | $OCH_3$ | N | 179–180 |
| 60 | $CH_3$ | $CO_2Et$ | H | $OCH_3$ | $OCH_3$ | N | 175–176 |
| 61 | $CH_3$ | $CO_2Et$ | H | Cl | $OCH_3$ | CH | 192–194 |
| 62 | $CH_3$ | $SO_2CH_3$ | H | $CH_3$ | $CH_3$ | CH | 209–120 |
| 63 | $CH_3$ | $SO_2CH_3$ | H | $CH_3$ | $OCH_3$ | CH | 209–210 |
| 64 | $CH_3$ | $SO_2CH_3$ | H | $OCH_3$ | $OCH_3$ | CH | 197–198 |
| 65 | $CH_3$ | $SO_2CH_3$ | H | $CH_3$ | $OCH_3$ | N | 192–193 |
| 66 | $CH_3$ | $SO_2CH_3$ | H | $OCH_3$ | $OCH_3$ | N | 194–195 |
| 67 | $CH_3$ | $SO_2CH_3$ | H | Cl | $OCH_3$ | CH | 212–214 |
| 68 | $CH_3$ | Cl | H | $CH_3$ | $OCH_3$ | CH | 187–188 |
| 69 | $CH_3$ | Cl | H | $OCH_3$ | $OCH_3$ | CH | 180–183 |
| 70 | $CH_3$ | Cl | H | $CH_3$ | $OCH_3$ | N | 167–168 |
| 71 | $CH_3$ | Cl | H | $OCH_3$ | $OCH_3$ | N | 181–182 |
| 72 | $CH_3$ | Cl | H | Cl | $OCH_3$ | CH | 190–192 |
| 73 | $CH_3$ | $SCH_3$ | H | $CH_3$ | $OCH_3$ | CH | 181–183 |
| 74 | $CH_3$ | $SCH_3$ | H | $OCH_3$ | $OCH_3$ | CH | 178–179 |
| 75 | $CH_3$ | $SCH_3$ | H | $CH_3$ | $OCH_3$ | N | 173–174 |
| 76 | $CH_3$ | $SCH_3$ | H | $CH_3$ | $OCH_3$ | N | 182–184 |
| 77 | $CH_3$ | $S(O)CH_3$ | H | $CH_3$ | $OCH_3$ | CH | 134–135 |
| 78 | $CH_3$ | $S(O)CH_3$ | H | $OCH_3$ | $OCH_3$ | CH | 150d |
| 79 | $CH_3$ | $S(O)CH_3$ | H | $CH_3$ | $OCH_3$ | N | 176d |
| 80 | $CH_3$ | $S(O)CH_3$ | H | $OCH_3$ | $OCH_3$ | N | 129d |
| 81 | $CH_3$ | $SO_2Et$ | H | $CH_3$ | $CH_3$ | CH | 206–209 |
| 82 | $CH_3$ | $SO_2Et$ | H | $CH_3$ | $OCH_3$ | CH | 176–179 |
| 83 | $CH_3$ | $SO_2Et$ | H | $OCH_3$ | $OCH_3$ | CH | 167–164 |
| 84 | $CH_3$ | $SO_2Et$ | H | $CH_3$ | $OCH_3$ | N | 180–182 |
| 85 | $CH_3$ | $SO_2Et$ | H | $OCH_3$ | $OCH_3$ | N | 178–182 |
| 86 | $CH_3$ | $SO_2Et$ | H | Cl | $OCH_3$ | CH | 205–207 |
| 87 | $CH_3$ | $SO_2$n-Pr | H | $CH_3$ | $CH_3$ | CH | 198–200 |
| 88 | $CH_3$ | $SO_2$n-Pr | H | $CH_3$ | $OCH_3$ | CH | 192–194 |
| 89 | $CH_3$ | $SO_2$n-Pr | H | $OCH_3$ | $OCH_3$ | CH | 196–199 |
| 90 | $CH_3$ | $SO_2$n-Pr | H | $CH_3$ | $OCH_3$ | N | 190–192 |
| 91 | $CH_3$ | $SO_2$n-Pr | H | $OCH_3$ | $OCH_3$ | N | 179–183 |
| 92 | $CH_3$ | $SO_2$n-Pr | H | Cl | $OCH_3$ | CH | 201–203 |
| 93 | $CH_3$ | SEt | H | $CH_3$ | $OCH_3$ | CH | 164–165 |
| 94 | $CH_3$ | SEt | H | $OCH_3$ | $OCH_3$ | CH | 161–166 |
| 95 | $CH_3$ | SEt | H | $CH_3$ | $OCH_3$ | N | 161–162 |
| 96 | $CH_3$ | SEt | H | $OCH_3$ | $OCH_3$ | N | 169–171 |
| 97 | $CH_3$ | S(n-Pr) | H | $CH_3$ | $OCH_3$ | CH | 149–150 |
| 98 | $CH_3$ | S(n-Pr) | H | $OCH_3$ | $OCH_3$ | CH | 159–160 |
| 99 | $CH_3$ | S(n-Pr) | H | $CH_3$ | $OCH_3$ | N | 154–155 |
| 100 | $CH_3$ | S(n-Pr) | H | $OCH_3$ | $OCH_3$ | N | 151–153 |
| 101 | $CH_3$ | $C(O)N(CH_3)_2$ | H | $CH_3$ | $CH_3$ | CH | 181–186 |
| 102 | $CH_3$ | $C(O)N(CH_3)_2$ | H | $CH_3$ | $OCH_3$ | CH | 160–162 |
| 103 | $CH_3$ | $C(O)N(CH_3)_2$ | H | $OCH_3$ | $OCH_3$ | CH | 192–194 |
| 104 | $CH_3$ | $C(O)N(CH_3)_2$ | H | $CH_3$ | $OCH_3$ | N | 167–169 |
| 105 | $CH_3$ | $C(O)N(CH_3)_2$ | H | $OCH_3$ | $OCH_3$ | N | 186–187 |
| 106 | $CH_3$ | $C(O)N(CH_3)_2$ | H | Cl | $OCH_3$ | CH | 178–181 |
| 107 | Et | $CO_2CH_3$ | H | $CH_3$ | $OCH_3$ | N | 175–176 |
| 108 | Et | $CO_2CH_3$ | H | $OCH_3$ | $OCH_3$ | N | 173–174 |
| 109 | Et | $CO_2CH_3$ | H | $CH_3$ | $CH_3$ | CH | 212–213 |
| 110 | Et | $CO_2CH_3$ | H | $CH_3$ | $OCH_3$ | CH | 190–191 |
| 111 | Et | $CO_2CH_3$ | H | $OCH_3$ | $OCH_3$ | CH | 178–180 |
| 112 | Et | $CO_2CH_3$ | H | Cl | $OCH_3$ | CH | 194–196 |
| 113 | $CH_3$ | $CO_2$iPr | H | $CH_3$ | $CH_3$ | CH | 199–200 |
| 114 | $CH_3$ | $CO_2$iPr | H | $CH_3$ | $OCH_3$ | CH | 203–204 |
| 115 | $CH_3$ | $CO_2$iPr | H | $OCH_3$ | $OCH_3$ | CH | 194–195 |
| 116 | $CH_3$ | $CO_2$iPr | H | $CH_3$ | $OCH_3$ | N | 183–184 |
| 117 | $CH_3$ | $CO_2$iPr | H | $OCH_3$ | $OCH_3$ | N | 186–187 |
| 118 | $CH_3$ | $CO_2$iPr | H | Cl | $OCH_3$ | CH | 200–202 |
| 119 | $CH_2OCH_3$ | $CO_2CH_3$ | H | $CH_3$ | $OCH_3$ | CH | 166–167 |
| 120 | $CH_2OCH_3$ | $CO_2CH_3$ | H | $OCH_3$ | $OCH_3$ | CH | 145–146 |
| 121 | $CH_2OCH_3$ | $CO_2CH_3$ | H | $CH_3$ | $OCH_3$ | N | 165–166 |
| 122 | $CH_2OCH_3$ | $CO_2CH_3$ | H | $OCH_3$ | $OCH_3$ | N | 165–166 |
| 123 | $CH_3$ | $CO_2CH_3$ | Cl | $CH_3$ | $CH_3$ | CH | 200–201 |

-continued

INDEX TABLE

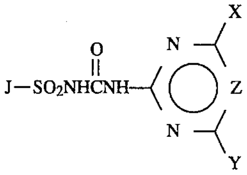

| | | | | | | | |
|---|---|---|---|---|---|---|---|
| 124 | $CH_3$ | $CO_2CH_3$ | Cl | $CH_3$ | $OCH_3$ | CH | 194–195 |
| 125 | $CH_3$ | $CO_2CH_3$ | Cl | $OCH_3$ | $OCH_3$ | CH | 182–183 |
| 126 | $CH_3$ | $CO_2CH_3$ | Cl | $CH_3$ | $OCH_3$ | N | 188–189 |
| 127 | $CH_3$ | $CO_2CH_3$ | Cl | $OCH_3$ | $OCH_3$ | N | 188–189 |
| 128 | $CH_3$ | $CO_2CH_3$ | Cl | Cl | $OCH_3$ | CH | 185–186 |
| 129 | $CH_3$ | $CO_2Et$ | Cl | $CH_3$ | $CH_3$ | CH | 193–194 |
| 130 | $CH_3$ | $CO_2Et$ | Cl | $CH_3$ | $OCH_3$ | CH | 191–192 |
| 131 | $CH_3$ | $CO_2Et$ | Cl | $OCH_3$ | $OCH_3$ | CH | 159–161 |
| 132 | $CH_3$ | $CO_2Et$ | Cl | $CH_3$ | $OCH_3$ | N | 166–167 |
| 133 | $CH_3$ | $CO_2Et$ | Cl | $OCH_3$ | $OCH_3$ | N | 167–169 |
| 134 | $CH_3$ | $CO_2Et$ | Cl | Cl | $OCH_3$ | CH | 175–177 |
| 135 | $CH_3$ | $CO_2Et$ | H | $NHCH_3$ | $OCH_2CH_3$ | N | 183–185 |
| 136 | $CH_3$ | $CO_2Et$ | H | $N(CH_3)_2$ | $OCH_2CF_3$ | N | 189–191 |
| 137 | $CH_3$ | $CO_2Et$ | H | $N(CH_3)_2$ | OEt | N | 171–173 |
| 138 | Et | $CO_2CH_3$ | H | $NHCH_3$ | OEt | N | 193–195 |
| 139 | Et | $CO_2CH_3$ | H | $N(CH_3)_2$ | $OCH_2CF_3$ | N | 196–197 |
| 140 | Et | $CO_2CH_3$ | H | $N(CH_3)_2$ | OEt | N | 175–177 |
| 141 | Et | $SO_2CH_3$ | H | $CH_3$ | $CH_3$ | CH | 212–213 |
| 142 | Et | $SO_2CH_3$ | H | $CH_3$ | $OCH_3$ | CH | 184–185 |
| 143 | Et | $SO_2CH_3$ | H | $OCH_3$ | $OCH_3$ | CH | 195–196 |
| 144 | Et | $SO_2CH_3$ | H | $CH_3$ | $OCH_3$ | N | 201–202 |
| 145 | Et | $SO_2CH_3$ | H | $OCH_3$ | $OCH_3$ | N | 186–187 |
| 146 | Et | $SO_2CH_3$ | H | Cl | $OCH_3$ | CH | 204–205 |
| 147 | Et | $SO_2Et$ | H | $CH_3$ | $CH_3$ | CH | 214–215 |
| 148 | Et | $SO_2Et$ | H | $CH_3$ | $OCH_3$ | CH | 196–197 |
| 149 | Et | $SO_2Et$ | H | $OCH_3$ | $OCH_3$ | CH | 205–206 |
| 150 | Et | $SO_2Et$ | H | $CH_3$ | $OCH_3$ | N | 191–192 |
| 151 | Et | $SO_2Et$ | H | $OCH_3$ | $OCH_3$ | N | 191–192 |
| 152 | Et | $SO_2Et$ | H | Cl | $OCH_3$ | CH | 189–197 |
| 153 | Et | $CO_2Et$ | H | $CH_3$ | $CH_3$ | CH | 209–210 |
| 154 | Et | $CO_2Et$ | H | $CH_3$ | $OCH_3$ | CH | 161–162 |
| 155 | Et | $CO_2Et$ | H | $OCH_3$ | $OCH_3$ | CH | 160–161 |
| 156 | Et | $CO_2Et$ | H | $CH_3$ | $OCH_3$ | N | 185–186 |
| 157 | Et | $CO_2Et$ | H | $OCH_3$ | $OCH_3$ | N | 166–167 |
| 158 | Et | $CO_2Et$ | H | Cl | $OCH_3$ | CH | 166–167 |
| 159 | Et | $C(O)N(CH_3)_2$ | H | $CH_3$ | $CH_3$ | CH | 169–171 |
| 160 | Et | $C(O)N(CH_3)_2$ | H | $CH_3$ | $OCH_3$ | CH | 150–159 |
| 161 | Et | $C(O)N(CH_3)_2$ | H | $OCH_3$ | $OCH_3$ | CH | 192–194 |
| 162 | Et | $C(O)N(CH_3)_2$ | H | $CH_3$ | $OCH_3$ | N | 174–175 |
| 163 | Et | $C(O)N(CH_3)_2$ | H | $OCH_3$ | $OCH_3$ | N | 176–178 |
| 164 | Et | $C(O)N(CH_3)_2$ | H | Cl | $OCH_3$ | CH | 197–198 |

J is J-3, $R^{71}$ is H

| CMPD | $R^1$ | $R^2$ | $R^4$ | X | Y | Z | m.p. (°C.) |
|---|---|---|---|---|---|---|---|
| 165 | $CH_3$ | Br | H | $CH_3$ | $CH_3$ | CH | 197–199 |
| 166 | $CH_3$ | Br | H | $CH_3$ | $OCH_3$ | CH | 206–208 |
| 167 | $CH_3$ | Br | H | $OCH_3$ | $OCH_3$ | CH | 203–205 |
| 168 | $CH_3$ | Br | H | Cl | $OCH_3$ | CH | 180–183 |
| 169 | $CH_3$ | Br | H | $CH_3$ | $OCH_3$ | N | 168–173 |
| 170 | $CH_3$ | Br | H | $OCH_3$ | $OCH_3$ | N | 200–202 |
| 171 | $CH_3$ | Br | H | $NHCH_3$ | OEt | N | 214–217 |
| 172 | $CH_3$ | $CO_2CH_3$ | H | $CH_3$ | $OCH_3$ | CH | 239–240.5 |
| 173 | $CH_3$ | $CO_2CH_3$ | H | $OCH_3$ | $OCH_3$ | CH | 246–248 |
| 174 | $CH_3$ | $CO_2CH_3$ | H | Cl | $OCH_3$ | CH | 232–234 |
| 175 | $CH_3$ | $CO_2CH_3$ | H | $CH_3$ | $OCH_3$ | N | 152–156 |
| 176 | $CH_3$ | $CO_2CH_3$ | H | $NHCH_3$ | OEt | N | 240–242 |
| 177 | $CH_3$ | $CO_2CH_3$ | H | $N(CH_3)_2$ | OEt | N | 197–199 |
| 178 | $CH_3$ | $CO_2CH_3$ | H | OEt | OEt | N | 180–182 |
| 179 | $CH_3$ | $CO_2CH_3$ | H | $N(CH_3)_2$ | $OCH_2CF_3$ | N | 204–206 |
| 180 | $CH_3$ | $CO_2CH_3$ | H | Et | OEt | N | 181–183 |
| 181 | $CH_3$ | $CO_2CH_3$ | H | Et | $OCH_3$ | N | 216–218 |
| 182 | $CH_3$ | $SO_2N(CH_3)_2$ | H | $CH_3$ | $CH_3$ | CH | 223–225 |
| 183 | $CH_3$ | $SO_2N(CH_3)_2$ | H | $CH_3$ | $OCH_3$ | CH | 207–209 |
| 184 | $CH_3$ | $SO_2N(CH_3)_2$ | H | $OCH_3$ | $OCH_3$ | CH | 204–206 |

-continued

INDEX TABLE

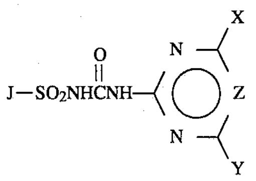

| | | | | | | | |
|---|---|---|---|---|---|---|---|
| 185 | $CH_3$ | $SO_2N(CH_3)_2$ | H | Cl | $OCH_3$ | CH | 206–208 |
| 186 | $CH_3$ | $SO_2N(CH_3)_2$ | H | $CH_3$ | $OCH_3$ | N | 185–187 |
| 187 | $CH_3$ | $SO_2N(CH_3)_2$ | H | $OCH_3$ | $OCH_3$ | N | 176–178 |
| 188 | $CH_3$ | $SO_2N(CH_3)_2$ | H | $NHCH_3$ | OEt | N | 166–168 |
| 189 | $CH_3$ | $SO_2N(CH_3)_2$ | H | $N(CH_3)_2$ | OEt | N | 143–146 |
| 190 | $CH_3$ | $SO_2N(CH_3)_2$ | H | OEt | OEt | N | 174–176 |
| 191 | $CH_3$ | $SO_2N(CH_3)_2$ | H | $N(CH_3)_2$ | $OCH_2CF_3$ | N | 178–180 |
| 192 | $CH_3$ | $SO_2N(CH_3)_2$ | H | $N(CH_3)_2$ | $OCH_3$ | N | 213–215 |
| 193 | $CH_3$ | $C(O)N(CH_3)_2$ | H | $CH_3$ | $OCH_3$ | CH | 190–196 |
| 194 | $CH_3$ | $C(O)N(CH_3)_2$ | H | $CH_3$ | $OCH_3$ | CH | 170–176 |
| 195 | $CH_3$ | $C(O)N(CH_3)_2$ | H | $OCH_3$ | $OCH_3$ | CH | 193–197 |
| 196 | $CH_3$ | $C(O)N(CH_3)_2$ | H | Cl | $OCH_3$ | CH | 143–145 |
| 197 | $CH_3$ | $C(O)N(CH_3)_2$ | H | $CH_3$ | $OCH_3$ | N | 123–125 |
| 198 | $CH_3$ | $C(O)N(CH_3)_2$ | H | $OCH_3$ | $OCH_3$ | N | 139.5–142.6 |
| 199 | $CH_3$ | $C(O)N(CH_3)_2$ | H | $NHCH_3$ | OEt | N | 189–296 |
| 200 | $CH_3$ | $C(O)N(CH_3)_2$ | H | $N(CH_3)_2$ | OEt | N | 154.5–162 |
| 201 | $CH_3$ | $C(O)N(CH_3)_2$ | H | OEt | OEt | N | 183–185 |
| 202 | $CH_3$ | $C(O)N(CH_3)_2$ | H | $N(CH_3)_2$ | $OCH_2CF_3$ | N | 127–129 |
| | | | J is J-2, $R^{71}$ is H | | | | |
| 203 | $CH_3$ | $SO_2CH_3$ | H | $CH_3$ | $CH_3$ | CH | 215–216 |
| 204 | $CH_3$ | $SO_2CH_3$ | H | $CH_3$ | $OCH_3$ | CH | 211–212 |
| 205 | $CH_3$ | $SO_2CH_3$ | H | $OCH_3$ | $OCH_3$ | CH | 224–226 |
| 206 | $CH_3$ | $SO_2CH_3$ | H | $CH_3$ | $OCH_3$ | N | 206–208 |
| 207 | $CH_3$ | $SO_2CH_3$ | H | $OCH_3$ | $OCH_3$ | N | 198–201 |
| 208 | $CH_3$ | $SO_2CH_3$ | H | Cl | $OCH_3$ | CH | 228–230 |
| 209 | $CH_3$ | $SO_2CH_3$ | H | $NHCH_3$ | OEt | N | 248–249 |
| 210 | $CH_3$ | $CO_2Et$ | H | $CH_3$ | $CH_3$ | CH | 205–206 |
| 211 | $CH_3$ | $CO_2Et$ | H | $CH_3$ | $OCH_3$ | CH | 192–194 |
| 212 | $CH_3$ | $CO_2Et$ | H | $OCH_3$ | $OCH_3$ | CH | 172–175 |
| 213 | $CH_3$ | $CO_2Et$ | H | $CH_3$ | $OCH_3$ | N | 192–194 |
| 214 | $CH_3$ | $CO_2Et$ | H | $OCH_3$ | $OCH_3$ | N | 171–173 |
| 215 | $CH_3$ | $CO_2Et$ | H | Cl | $OCH_3$ | CH | 197–198 |
| 216 | $CH_3$ | $CO_2Et$ | H | $NHCH_3$ | OEt | N | 184–187 |
| 217 | $CH_3$ | $C(O)CH_3$ | H | $CH_3$ | $CH_3$ | CH | 181–183 |
| 218 | $CH_3$ | $C(O)CH_3$ | H | $CH_3$ | $OCH_3$ | CH | 180–181 |
| 219 | $CH_3$ | $C(O)CH_3$ | H | $OCH_3$ | $OCH_3$ | CH | 152–156 |
| 220 | $CH_3$ | $C(O)CH_3$ | H | $CH_3$ | $OCH_3$ | N | 152–156 |
| 221 | $CH_3$ | $C(O)CH_3$ | H | $OCH_3$ | $OCH_3$ | N | 184–186 |
| 222 | $CH_3$ | $C(O)CH_3$ | H | Cl | $OCH_3$ | CH | 180–182 |
| 223 | $CH_3$ | $C(CH_3){=}NOCH_3$ | H | $CH_3$ | $COH_3$ | CH | 160–163 |
| 224 | $CH_3$ | $C(CH_3){=}NOCH_3$ | H | $OCH_3$ | $OCH_3$ | CH | 206–209 |
| 225 | $CH_3$ | $C(CH_3){=}NOCH_3$ | H | $CH_3$ | $OCH_3$ | N | 168–170 |
| 226 | $CH_3$ | $C(CH_3){=}NOCH_3$ | H | $OCH_3$ | $OCH_3$ | N | 90–113 |
| 227 | $CH_3$ | $C(CH_3){=}NOCH_3$ | H | Cl | $OCH_3$ | CH | 179–182 |
| 228 | Et | $CO_2CH_3$ | H | $CH_3$ | $CH_3$ | CH | 204–206 |
| 229 | Et | $CO_2CH_3$ | H | $CH_3$ | $OCH_3$ | CH | 189–191 |
| 230 | Et | $CO_2CH_3$ | H | $OCH_3$ | $OCH_3$ | CH | 178–180 |
| 231 | Et | $CO_2CH_3$ | H | $CH_3$ | $OCH_3$ | N | 175–177 |
| 232 | Et | $CO_2CH_3$ | H | $OCH_3$ | $OCH_3$ | N | 173–176 |
| 233 | Et | $CO_2CH_3$ | H | Cl | $OCH_3$ | CH | 198–200 |
| 234 | Et | $C(O)N(CH_3)_2$ | H | $CH_3$ | $CH_3$ | CH | 174–186 |
| 235 | Et | $C(O)N(CH_3)_2$ | H | $CH_3$ | $OCH_3$ | CH | 134–136 |
| 236 | Et | $C(O)N(CH_3)_2$ | H | $OCH_3$ | $OCH_3$ | CH | 170–176 |
| 237 | Et | $C(O)N(CH_3)_2$ | H | $CH_3$ | $OCH_3$ | N | 168–170 |
| 238 | Et | $C(O)N(CH_3)_2$ | H | $OCH_3$ | $OCH_3$ | N | 147–149 |
| 239 | Et | $C(O)N(CH_3)_2$ | H | Cl | $OCH_3$ | CH | 116–117 |
| 240 | Et | $SO_2Et$ | H | $CH_3$ | $CH_3$ | CH | 204–205 |
| 241 | Et | $SO_2Et$ | H | $CH_3$ | $OCH_3$ | CH | 200–201 |
| 242 | $CH_3$ | $SO_2Et$ | H | $OCH_3$ | $OCH_3$ | CH | 199–208 |
| 243 | $CH_3$ | $SO_2Et$ | H | $CH_3$ | $OCH_3$ | N | 194–195 |
| 244 | $CH_3$ | $SO_2Et$ | H | $OCH_3$ | $OCH_3$ | N | 189–190 |
| 245 | $CH_3$ | $SO_2Et$ | H | Cl | $OCH_3$ | CH | 200–202 |
| 246 | $CH_3$ | SEt | H | $CH_3$ | $CH_3$ | CH | 178–179 |
| 247 | $CH_3$ | SEt | H | $OCH_3$ | $OCH_3$ | CH | 164–169 |
| 248 | $CH_3$ | SEt | H | $CH_3$ | $OCH_3$ | N | 168–170 |

-continued

INDEX TABLE

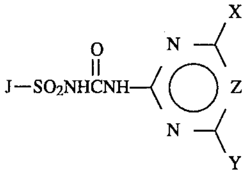

| | | | | | | | |
|---|---|---|---|---|---|---|---|
| 249 | $CH_3$ | SEt | H | $OCH_3$ | $OCH_3$ | N | 175–177 |
| 250 | $CH_3$ | $CO_2iPr$ | H | $CH_3$ | $CH_3$ | CH | 212–213 |
| 251 | $CH_3$ | $CO_2iPr$ | H | $CH_3$ | $OCH_3$ | CH | 188–194 |
| 252 | $CH_3$ | $CO_2iPr$ | H | $OCH_3$ | $OCH_3$ | CH | 158–162 |
| 253 | $CH_3$ | $CO_2iPr$ | H | $CH_3$ | $OCH_3$ | N | 202–205 |
| 254 | $CH_3$ | $CO_2iPr$ | H | $OCH_3$ | $OCH_3$ | N | 184–185 |
| 255 | $CH_3$ | $CO_2iPr$ | H | Cl | $OCH_3$ | CH | 191–192 |
| 256 | Et | $SO_2CH_3$ | H | $CH_3$ | $CH_3$ | CH | 184–188 |
| 257 | Et | $SO_2CH_3$ | H | $CH_3$ | $OCH_3$ | CH | 202–203 |
| 258 | Et | $SO_2CH_3$ | H | $OCH_3$ | $OCH_3$ | CH | 186–188 |
| 259 | Et | $SO_2CH_3$ | H | $CH_3$ | $OCH_3$ | N | 175–178 |
| 260 | Et | $SO_2CH_3$ | H | $OCH_3$ | $OCH_3$ | N | 172–176 |
| 261 | Et | $SO_2CH_3$ | H | Cl | $OCH_3$ | CH | 198–201 |
| 262 | Et | $SCH_3$ | H | $OCH_3$ | $OCH_3$ | CH | 150–155 |
| 263 | Et | $SCH_3$ | H | $CH_3$ | $OCH_3$ | N | 140–160 |
| 264 | Et | $CO_2Et$ | H | $CH_3$ | $CH_3$ | CH | 179–180 |
| 265 | Et | $CO_2Et$ | H | $CH_3$ | $OCH_3$ | CH | 168–170 |
| 266 | Et | $CO_2Et$ | H | $OCH_3$ | $OCH_3$ | CH | 167–168 |
| 267 | Et | $CO_2Et$ | H | $CH_3$ | $OCH_3$ | N | 158–159 |
| 268 | Et | $CO_2Et$ | H | $OCH_3$ | $OCH_3$ | N | 174–175 |
| 269 | Et | $CO_2Et$ | H | Cl | $OCH_3$ | CH | 181–182 |
| 270 | $CH_2OCH_3$ | $SO_2CH_3$ | H | $CH_3$ | $CH_3$ | CH | 182–189 |
| 271 | $CH_2OCH_3$ | $SO_2CH_3$ | H | $CH_3$ | $OCH_3$ | CH | 162–169 |
| 272 | $CH_2OCH_3$ | $SO_2CH_3$ | H | $OCH_3$ | $OCH_3$ | CH | 179–187 |
| 273 | $CH_2OCH_3$ | $SO_2CH_3$ | H | $CH_3$ | $OCH_3$ | N | 167–170 |
| 274 | $CH_2OCH_3$ | $SO_2CH_3$ | H | $OCH_3$ | $OCH_3$ | N | 195–198 |
| 275 | $CH_2OCH_3$ | $SO_2CH_3$ | H | Cl | $COH_3$ | CH | 187–192 |
| 276 | Et | $CO_2CH_3$ | H | $NHCH_3$ | OEt | N | 188–190 |
| 277 | Et | $CO_2CH_3$ | H | $N(CH_3)_2$ | OEt | N | 171–174 |
| 278 | Et | $CO_2CH_3$ | H | $N(CH_3)_2$ | $OCH2CF_3$ | N | 186–188 |
| 279 | $CH_3$ | $CO_2iPr$ | H | $N(CH_3)_2$ | $OCH_2CF_3$ | N | 167–169 |
| 280 | Et | $CO_2Et$ | H | $NHCH_3$ | OEt | N | 162–164 |
| 281 | Et | $CO_2Et$ | H | $N(CH_3)_2$ | $OCH_2CF_3$ | N | 178–180 |
| 282 | $CH_3$ | $CO_2Et$ | H | $N(CH_3)_2$ | $OCH_2CF_3$ | N | 173–174 |
| 283 | $CH_3$ | $CO_2CH_3$ | Br | $CH_3$ | $CH_3$ | CH | 148–150 |
| 284 | $CH_3$ | $CO_2CH_3$ | Br | $CH_3$ | $OCH_3$ | CH | 137–140 |
| 285 | $CH_3$ | $CO_2CH_3$ | Br | $OCH_3$ | $OCH_3$ | CH | 154–156 |
| 286 | $CH_3$ | $CO_2CH_3$ | Br | $CH_3$ | $OCH_3$ | N | 150–151 |
| 287 | $CH_3$ | $CO_2CH_3$ | Br | $OCH_3$ | $OCH_3$ | N | 157–160 |
| 288 | $CH_3$ | $CO_2CH_3$ | Br | Cl | $OCH_3$ | CH | 152–155 |
| 289 | $CH_3$ | $CO_2CH_3$ | Br | $N(CH_3)_2$ | OEt | N | 145–147 |

J is J-3, $R^{71}$ is H

| | | | | | | | |
|---|---|---|---|---|---|---|---|
| 290 | $CH_3$ | $SCH_3$ | H | $CH_3$ | $COH_3$ | CH | 217–220 |
| 291 | $CH_3$ | $SCH_3$ | H | $OCH_3$ | $OCH_3$ | CH | 230–235 |
| 292 | $CH_3$ | $SCH_3$ | H | $CH_3$ | $OCH_3$ | N | 186–189 |
| 293 | $CH_3$ | $SCH_3$ | H | Cl | $OCH_3$ | CH | 188–190 |
| 294 | $CH_3$ | $SCH_3$ | H | $N(CH_3)_2$ | OEt | N | 170–174 |
| 295 | $CH_3$ | Ph | H | $CH_3$ | $OCH_3$ | CH | 180–184 |
| 296 | $CH_3$ | Ph | H | $OCH_3$ | $OCH_3$ | CH | 223–226 |
| 297 | $CH_3$ | Ph | H | $CH_3$ | $OCH_3$ | N | 190–195 |
| 298 | $CH_3$ | Ph | H | Cl | $OCH_3$ | CH | 219–221 |
| 299 | $CH_3$ | Ph | H | $N(CH_3)_2$ | OEt | N | 117–120 |
| 300 | $CH_3$ | $SCH_3$ | $CO_2CH_3$ | $CH_3$ | $CH_3$ | CH | 169–171 |
| 301 | $CH_3$ | $SCH_3$ | $CO_2CH_3$ | $CH_3$ | $OCH_3$ | CH | 140–145 |
| 302 | $CH_3$ | $SCH_3$ | $CO_2CH_3$ | $OCH_3$ | $OCH_3$ | CH | 153–155 |
| 303 | $CH_3$ | $SCH_3$ | $CO_2CH_3$ | $CH_3$ | $OCH_3$ | N | 193–195 |
| 304 | $CH_3$ | $SCH_3$ | $CO_2CH_3$ | $OCH_3$ | $OCH_3$ | N | 158–160 |
| 305 | $CH_3$ | $SCH_3$ | $CO_2CH_3$ | Cl | OEt | N | 187–190 |
| 306 | $CH_3$ | $SCH_3$ | $CO_2CH_3$ | $NHCH_3$ | OEt | N | 158–160 |
| 307 | $CH_3$ | Ph | $CO_2CH_3$ | $CH_3$ | $CH_3$ | CH | 126–128 |
| 308 | $CH_3$ | Ph | $CO_2CH_3$ | $CH_3$ | $OCH_3$ | CH | 218–221 |
| 309 | $CH_3$ | Ph | $CO_2CH_3$ | $OCH_3$ | $OCH_3$ | CH | 224–226 |
| 310 | $CH_3$ | Ph | $CO_2CH_3$ | $CH_3$ | $OCH_3$ | N | 201–204 |
| 311 | $CH_3$ | Ph | $CO_2CH_3$ | $OCH_3$ | $OCH_3$ | N | 201–204 |
| 312 | $CH_3$ | Ph | $CO_2CH_3$ | Cl | $OCH_3$ | CH | 194–196 |

-continued

INDEX TABLE

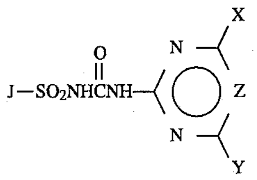

| | | | | | | | |
|---|---|---|---|---|---|---|---|
| 313 | $CH_3$ | Ph | $CO_2CH_3$ | $NHCH_3$ | OEt | N | 135–138 |
| 314 | $CH_3$ | Ph | $CO_2CH_3$ | $N(CH_3)_2$ | OEt | N | 189–193 |
| | | | J is J-2, $R^{71}$ is H | | | | |
| 315 | Ph | $CO_2CH_3$ | H | $CH_3$ | $CH_3$ | CH | 209–212 |
| 316 | Ph | $CO_2CH_3$ | H | $CH_3$ | $OCH_3$ | CH | 212–215 |
| 317 | Ph | $CO_2CH_3$ | H | $OCH_3$ | $OCH_3$ | CH | 185–188 |
| 318 | Ph | $CO_2CH_3$ | H | $CH_3$ | $OCH_3$ | N | 165–170 |
| 319 | Ph | $CO_2CH_3$ | H | $OCH_3$ | $OCH_3$ | N | 160–164 |
| 320 | Ph | $CO_2CH_3$ | H | Cl | $OCH_3$ | CH | 215–220 |
| 321 | Ph | $CO_2CH_3$ | H | $N(CH_3)_2$ | OEt | N | 154–160 |
| 322 | $CH_3$ | CN | H | $CH_3$ | $CH_3$ | CH | 218–221 |
| 323 | $CH_3$ | CN | H | $CH_3$ | $OCH_3$ | CH | 212–216 |
| 324 | $CH_3$ | CN | H | $OCH_3$ | $OCH_3$ | CH | 201–204 |
| 325 | $CH_3$ | CN | H | $CH_3$ | $OCH_3$ | N | 213–216 |
| 326 | $CH_3$ | CN | H | $OCH_3$ | $OCH_3$ | N | 216–220 |
| 327 | $CH_3$ | CN | H | Cl | $OCH_3$ | CH | 219–220 |
| 328 | $CH_3$ | CN | H | $NHCH_3$ | OEt | N | 159–161 |
| 329 | $CH_3$ | CN | H | $N(CH_3)_2$ | OEt | N | 211–215 |
| 330 | Ph | $SCH_3$ | H | $CH_3$ | $CH_3$ | CH | 216–220 |
| 331 | Ph | $SCH_3$ | H | $CH_3$ | $OCH_3$ | CH | 204–206 |
| 332 | Ph | $SCH_3$ | H | $OCH_3$ | $OCH_3$ | CH | 189–191 |
| 333 | Ph | $SCH_3$ | H | $CH_3$ | $OCH_3$ | N | 187–190 |
| 334 | Ph | $SCH_3$ | H | $OCH_3$ | $OCH_3$ | N | 208–211 |
| 335 | Ph | $SCH_3$ | H | Cl | $OCH_3$ | CH | 190–193 |
| 336 | Ph | $SCH_3$ | H | $NHCH_3$ | OEt | N | 189–191 |
| 337 | Ph | $SCH_3$ | H | $N(CH_3)_2$ | OEt | N | 185–187 |
| | | | J is J-3, $R^{71}$ is H | | | | |
| 338 | $CH_3$ | CN | $CO_2CH_3$ | $CH_3$ | $OCH_3$ | CH | >260 |
| 339 | $CH_3$ | CN | $CO_2CH_3$ | $OCH_3$ | $OCH_3$ | CH | 183–185 |
| 340 | $CH_3$ | CN | $CO_2CH_3$ | $CH_3$ | $OCH_3$ | N | 180–183 |
| 341 | $CH_3$ | CN | $CO_2CH_3$ | $OCH_3$ | $OCH_3$ | N | 231–235 |
| 342 | $CH_3$ | CN | $CO_2CH_3$ | Cl | $OCH_3$ | CH | >255 |
| | | | J is J-2, $R^{71}$ is H | | | | |
| 343 | Ph | $SO_2CH_3$ | H | $CH_3$ | $OCH_3$ | CH | 225–226 |
| 344 | Ph | $SO_2CH_3$ | H | $OCH_3$ | $OCH_3$ | CH | 212–216 |
| 345 | Ph | $SO_2CH_3$ | H | $CH_3$ | $OCH_3$ | N | 199–201 |
| 346 | Ph | $SO_2CH_3$ | H | $OCH_3$ | Cl | CH | 209–211 |
| | | | J is J-3, $R^{71}$ is H | | | | |
| 347 | $CH_3$ | CN | CHO | $CH_3$ | $OCH_3$ | CH | 179–180 |
| 348 | $CH_3$ | CN | CHO | $OCH_3$ | $OCH_3$ | CH | 181–184 |
| 349 | $CH_3$ | CN | CHO | $CH_3$ | $OCH_3$ | N | 229–233 |
| 350 | $CH_3$ | CN | CHO | Cl | $COH_3$ | CH | 155–159 |
| | | | J is J-2, $R^{71}$ is H | | | | |
| 351 | Ph | CHO | H | $CH_3$ | $CH_3$ | CH | 149–151 |
| 352 | Ph | CHO | H | $CH_3$ | $OCH_3$ | CH | 171–174 |
| 353 | Ph | CHO | H | $OCH_3$ | $OCH_3$ | CH | 146–150 |
| 354 | Ph | CHO | H | $CH_3$ | $OCH_3$ | N | 160–164 |
| 355 | Ph | CHO | H | OCH3 | $OCH_3$ | N | 147–160 |
| 356 | Ph | CHO | H | Cl | $OCH_3$ | CH | 161–165 |
| 357 | Ph | CHO | H | $N(CH_3)_2$ | OEt | N | 135–137 |
| | | | J is J-3, $R^{71}$ is H | | | | |
| 358 | $CH_3$ | CN | $CON(CH_3)_2$ | $CH_3$ | $OCH_3$ | CH | 92–95 |
| 359 | $CH_3$ | CN | $CON(CH_3)_2$ | $OCH_3$ | $OCH_3$ | CH | 168–171 |
| 360 | $CH_3$ | CN | $CON(CH_3)_2$ | $CH_3$ | OCH3 | N | 120–125 |
| 361 | $CH_3$ | CN | $CON(CH_3)_2$ | $OCH_3$ | Cl | CH | 165–170 |
| 362 | $CH_3$ | CN | $CON(CH_3)_2$ | $N(CH_3)_2$ | OEt | N | 129–131 |
| 363 | $CH_3$ | $CO_2CH_3$ | $SCH_3$ | $CH_3$ | $OCH_3$ | CH | 190–193 |
| 364 | $CH_3$ | $CO_2CH_3$ | $SCH_3$ | $OCH_3$ | $OCH_3$ | CH | 125–127 |
| 365 | $CH_3$ | $CO_2CH_3$ | $SCH_3$ | $CH_3$ | $OCH_3$ | N | 183–185 |
| 366 | $CH_3$ | $CO_2CH_3$ | $SCH_3$ | Cl | $OCH_3$ | CH | 168–170 |

-continued

INDEX TABLE

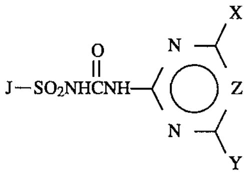

| | | | | | | | |
|---|---|---|---|---|---|---|---|
| 367 | $CH_3$ | $CO_2CH_3$ | $SCH_3$ | $N(CH_3)_2$ | OEt | N | 210–215 |
| 368 | H | $CO_2CH_3$ | H | $CH_3$ | $CH_3$ | CH | 215–217 |
| 369 | H | $CO_2CH,3$ | H | $CH_3$ | $OCH_3$ | CH | 200–202 |
| 370 | H | $CO_2CH_3$ | H | $OCH_3$ | $OCH_3$ | CH | 218–220 |
| 371 | H | $CO_2CH_3$ | H | Cl | $OCH_3$ | CH | 221–223 |
| 372 | H | $CO_2CH_3$ | H | $CH_3$ | $OCH_3$ | N | 138–142 |
| 373 | H | $CO_2CH_3$ | H | $OCH_3$ | $OCH_3$ | N | 230–234 |
| 374 | H | $CO_2CH_3$ | H | $NHCH_3$ | OEt | N | 146–148 |
| 375 | H | $CO_2CH_3$ | H | $N(CH_3)_2$ | OEt | N | 185–187 |
| 376 | $CH_3$ | $C(=O)CH_3$ | H | $CH_3$ | $CH_3$ | CH | 247–249 |
| 377 | $CH_3$ | $C(=O)CH_3$ | H | $CH_3$ | $OCH_3$ | CH | 245–247 |
| 378 | $CH_3$ | $C(=O)CH_3$ | H | $OCH_3$ | $OCH_3$ | CH | 233–235 |
| 379 | $CH_3$ | $C(=O)CH_3$ | H | Cl | $OCH_3$ | CH | 237–239 |
| 380 | $CH_3$ | $C(=O)CH_3$ | H | $CH_3$ | $OCH_3$ | N | 204–206 |
| 381 | $CH_3$ | $C(=O)CH_3$ | H | $OCH_3$ | $OCH_3$ | N | 216–218 |
| 382 | $CH_3$ | $C(=O)CH_3$ | H | $NHCH_3$ | OEt | N | 249–252 |
| 383 | $CH_3$ | $C(=O)CH_3$ | H | $N(CH_3)_2$ | OEt | N | 225–227 |
| | | | J is J-2, $R^{71}$ is H | | | | |
| 384 | $CH_3$ | $C(=O)N(CH_3)_2$ | H | $CH_3$ | $CH_3$ | CH | 159–166 |
| 385 | $CH_3$ | $C(=O)N(CH_3)_2$ | H | $CH_3$ | $OCH_3$ | CH | 131–136 |
| 386 | $CH_3$ | $C(=O)N(CH_3)_2$ | H | $OCH_3$ | $OCH_3$ | CH | 140–147 |
| 387 | $CH_3$ | $C(=O)N(CH_3)_2$ | H | Cl | $OCH_3$ | CH | 103–107 |
| 388 | $CH_3$ | $C(=O)N(CH_3)_2$ | H | $CH_3$ | $OCH_3$ | N | oil |
| 389 | $CH_3$ | $C(=O)N(CH_3)_2$ | H | $OCH_3$ | $OCH_3$ | N | oil |
| 390 | $CH_3$ | $C(=O)N(CH_3)_2$ | H | $NHCH_3$ | OEt | N | 140–142 |
| 391 | $CH_3$ | $C(=O)N(CH_3)_2$ | H | $N(CH_3)_2$ | OEt | N | 178–180 |
| 392 | $CH_3$ | $C(=O)N(CH_3)_2$ | H | OEt | OEt | N | 121–125 |
| 393 | $CH_3$ | $C(=O)N(CH_3)_2$ | H | $NHCH_3$ | $OCH_2CF_3$ | N | 156–160 |
| 394 | $CH_3$ | $C(=O)N(CH_3)_2$ | H | $N(CH_3)_2$ | $OCH_2CF_3$ | N | 250 |
| 395 | $CH_3$ | $C(=O)N(CH_3)_2$ | H | $N(CH_3)_2$ | $OCH_3$ | N | gum |
| 396 | $CH_3$ | $C(=O)N(CH_3)_2$ | H | Et | OEt | N | gum |
| 397 | $CH_3$ | $C(=O)N(CH_3)_2$ | H | Et | $OCH_3$ | N | gum |
| 398 | $CH_3$ | CHO | H | $CH_3$ | $OCH_3$ | CH | 140–141.5 |
| 399 | $CH_3$ | CHO | H | $OCH_3$ | $OCH_3$ | CH | 172–174.5 |
| 400 | $CH_3$ | CHO | H | Cl | $OCH_3$ | CH | 172–175 |
| 401 | $CH_3$ | CHO | H | $CH_3$ | $OCH_3$ | N | 156–160 |
| 402 | $CH_3$ | CHO | H | $OCH_3$ | $OCH_3$ | N | 173–177 |
| 403 | $CH_3$ | CHO | H | $NHCH_3$ | OEt | N | 176–179 |
| 404 | $CH_3$ | CHO | H | OEt | OEt | N | 102–104 |
| 405 | $CH_3$ | CHO | H | Et | OEt | N | 149–151.5 |
| 406 | $CH_3$ | CHO | H | Et | $OCH_3$ | N | 148–150 |

J is J-1, $R^3$ and $R^{71}$ is H

| CMPD | $R^1$ | $R^2$ | X | Y | Z | m.p. (°C.) |
|---|---|---|---|---|---|---|
| 407 | $(CH_2)_3CH_3$ | $CO_2CH_3$ | $CH_3$ | $CH_3$ | CH | 188–189 |
| 408 | $(CH_2)_3CH_3$ | $CO_2CH_3$ | $CH_3$ | $OCH_3$ | CH | 138–140 |
| 409 | $(CH_2)_3CH_3$ | $CO_2CH_3$ | $OCH_3$ | $OCH_3$ | CH | 139–140 |
| 410 | $(CH_2)_3CH_3$ | $CO_2CH_3$ | $CH_3$ | $OCH_3$ | N | 137–138 |
| 411 | $(CH_2)_3CH_3$ | $CO_2CH_3$ | $OCH_3$ | $OCH_3$ | N | 152–155 |
| 412 | $(CH_2)_3CH_3$ | $CO_2CH_3$ | Cl | $OCH_3$ | CH | 162–164 |
| 413 | $CH_3$ | $OC_2H_5$ | $CH_3$ | $OCH_3$ | CH | 180–181° d |
| 414 | $CH_3$ | $OC_2H_5$ | $OCH_3$ | $OCH_3$ | CH | 170–172° d |
| 415 | $CH_3$ | $OC_2H_5$ | $CH_3$ | $OCH_3$ | N | 178–179° d |
| 416 | $CH_3$ | $OC_2H_5$ | $OCH_3$ | $OCH_3$ | N | 176–177° d |
| 417 | $CH_3$ | CN | $CH_3$ | $CH_3$ | CH | 198–200° d |
| 418 | $CH_3$ | CN | $CH_3$ | $OCH_3$ | CH | 178–184° d |
| 419 | $CH_3$ | CN | $OCH_3$ | $OCH_3$ | CH | 199–201° d |
| 420 | $CH_3$ | CN | $CH_3$ | $OCH_3$ | N | 184–186° d |
| 421 | $CH_3$ | CN | $OCH_3$ | $OCH_3$ | N | 180–182° d |
| 422 | $CH_3$ | CN | Cl | $OCH_3$ | CH | 199–201° d |

-continued

INDEX TABLE

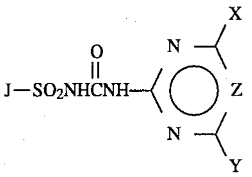

J is J-3, $R^{71}$ is H

| CMPD | $R^1$ | $R^2$ | $R^4$ | X | Y | Z | m.p. (°C.) |
|---|---|---|---|---|---|---|---|
| 423 | $CH_3$ | CN | CHO | $OCH_3$ | $CH_3$ | CH | 179–180 |
| 424 | $CH_3$ | CN | CHO | $OCH_3$ | $OCH_3$ | CH | 181–184 |
| 425 | $CH_3$ | CN | CHO | $OCH_3$ | $CH_3$ | N | 229–233 |
| 426 | $CH_3$ | CN | CHO | $OCH_3$ | Cl | CH | 155–169 |
| 427 | $CH_3$ | CN | $C(O)N(CH_3)_2$ | $OCH_3$ | $CH_3$ | CH | 92–95 |
| 428 | $CH_3$ | CN | $C(O)N(CH_3)_2$ | $OCH_3$ | $OCH_3$ | CH | 168–171 |
| 429 | $CH_3$ | CN | $C(O)N(CH_3)_2$ | $OCH_3$ | $CH_3$ | N | 120–123 |
| 430 | $CH_3$ | CN | $C(O)N(CH_3)_2$ | $OCH_3$ | Cl | CH | 165–170 |
| 431 | $CH_3$ | CN | $C(O)N(CH_3)_2$ | OEt | $N(CH_3)_2$ | N | 129–131 |
| 432 | $CH_3$ | $CO_2CH_3$ | $SCH_3$ | $OCH_3$ | $CH_3$ | CH | 190–193 |
| 433 | $CH_3$ | $CO_2CH_3$ | $SCH_3$ | $OCH_3$ | $OCH_3$ | CH | 125–127 |
| 434 | $CH_3$ | $CO_2CH_3$ | $SCH_3$ | $OCH_3$ | $CH_3$ | N | 183–185 |
| 435 | $CH_3$ | $CO_2CH_3$ | $SCH_3$ | $OCH_3$ | Cl | CH | 168–170 |
| 436 | $CH_3$ | $CO_2CH_3$ | $SCH_3$ | OEt | $N(CH_3)_2$ | N | 210–215 |
| 437 | $CH_3$ | CN | Br | $CH_3$ | $CH_3$ | CH | 153–156 |
| 438 | $CH_3$ | CN | Br | $OCH_3$ | $CH_3$ | CH | 168–171 |
| 439 | $CH_3$ | CN | Br | $OCH_3$ | $OCH_3$ | CH | 150–153 |
| 440 | $CH_3$ | CN | Br | $OCH_3$ | $CH_3$ | N | 159–162 |
| 441 | $CH_3$ | CN | Br | $OCH_3$ | $OCH_3$ | N | 164–167 |
| 442 | $CH_3$ | CN | Br | $OCH_3$ | Cl | CH | >210 |
| 443 | $CH_3$ | CN | Br | OEt | $N(CH_3)_2$ | N | >210 |
| 444 | $CH_3$ | $CH_3$ | $CO_2CH_3$ | $CH_3$ | $CH_3$ | CH | 205–209 |
| 445 | $CH_3$ | $CH_3$ | $CO_2CH_3$ | $OCH_3$ | $CH_3$ | CH | 196–200 |
| 446 | $CH_3$ | $CH_3$ | $CO_2CH_3$ | $OCH_3$ | $OCH_3$ | CH | 185–188 |
| 447 | $CH_3$ | $CH_3$ | $CO_2CH_3$ | $OCH_3$ | $CH_3$ | N | 201–202 |
| 448 | $CH_3$ | $CH_3$ | $CO_2CH_3$ | $OCH_3$ | $OCH_3$ | N | 186–186 |
| 449 | $CH_3$ | $CH_3$ | $CO_2CH_3$ | $OCH_3$ | Cl | CH | 175–178 |
| 450 | $CH_3$ | $CH_3$ | $CO_2CH_3$ | OEt | $N(CH_3)_2$ | N | 154–157° |
| 451 | $CH_3$ | CN | $C(O)CH_3$ | $OCH_3$ | $CH_3$ | CH | 159–162 |
| 452 | $CH_3$ | CN | $C(O)CH_3$ | $OCH_3$ | $OCH_3$ | CH | 175–178 |
| 453 | $CH_3$ | CN | $C(O)CH_3$ | $OCH_3$ | $CH_3$ | N | 180–182 |
| 454 | $CH_3$ | CN | $C(O)CH_3$ | $OCH_3$ | Cl | CH | >240 |
| 455 | $CH_3$ | CN | $SO_2Et$ | $OCH_3$ | $CH_3$ | CH | 168–170 |
| 456 | $CH_3$ | CN | $SO_2Et$ | $OCH_3$ | $OCH_3$ | CH | 161–164 |
| 457 | $CH_3$ | CN | $SO_2Et$ | $OCH_3$ | $CH_3$ | N | 170–174 |
| 458 | $CH_3$ | CN | $SO_2Et$ | $OCH_3$ | Cl | CH | 195–200 |
| 459 | $CH_3$ | CN | $SO_2Et$ | OEt | $N(CH_3)_2$ | N | >200 |
| 460 | $CH_3$ | $CO_2CH_3$ | Br | $OCH_3$ | $CH_3$ | N | 192–193 |
| 461 | $CH_3$ | $CO_2CH_3$ | Br | $OCH_3$ | $OCH_3$ | N | 193–197 |
| 462 | $CH_3$ | $CO_2CH_3$ | Br | $OCH_3$ | Cl | CH | 194–195 |
| 463 | $CH_3$ | $SO_2Et$ | H | $OCH_3$ | $CH_3$ | CH | 172–173 |
| 464 | $CH_3$ | $SO_2Et$ | H | $OCH_3$ | $OCH_3$ | CH | 183–184 |
| 465 | $CH_3$ | $SO_2Et$ | H | $CH_3$ | $OCH_3$ | N | 189–190 |
| 466 | $CH_3$ | $SO_2Et$ | H | $OCH_3$ | $OCH_3$ | N | 193–194 |

Formulations

Useful formulations of the Compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active | Weight Percent* | |
|---|---|---|---|
| | Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |

-continued

| | Active | Weight Percent* | |
|---|---|---|---|
| | Ingredient | Diluent(s) | Surfactant(s) |
| Aqueous Suspension | 10–50 | 40–84 | 1–20 |
| Dusts | 1–25 | 70–99 | 0–5 |
| Granules and Pellets | 0.1–95 | 5–99.9 | 1–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1963, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE A

| High Strength Concentrate | |
|---|---|
| methyl 3-[[[[(4,6-dimethoxy-2-pyrimidinyl)amino]-carbonyl]amino]sulfonyl]-1-methyl-lH-pyrrole-2-carboxylate | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE B

| Wettable Powder | |
|---|---|
| methyl 3[[[[[4-ethoxy-6-(methylamino)-1,3,5-triazin-2-yl]amino]carbonyl]amino]sulfonyl]-1-methyl-lH-pyrrole-2-carboxylate | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE C

| Aqueous Suspension | |
|---|---|
| methyl 3-[[[[(4,6-dimethoxy-2-pyrimidinyl)amino]-carbonyl]amino]sulfonyl]-l-methyl-1H-pyrrole-2-carboxylate | 50.0% |
| polyacrylic acid thickener | 0.3% |
| dodecylphenol polyethylene | 0.5% |
| glycol ether | 1% |
| disodium phosphate | |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE D

| Oil Suspension | |
|---|---|
| methyl 3[[[[[4-ethoxy-6-(methylamino)-1,3,5-triazin-2-yl]amino]carbonyl]amino]sulfonyl]-l-methyl-lH-pyrrole-2-carboxylate | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE E

| Oil Suspension | |
|---|---|
| methyl 3-[[[[(4,6-dimethoxy-2-pyrimidinyl)amino]-carbonyl]amino]sulfonyl]-1-methyl-1H-pyrrole-2-carboxylate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE F

| Aqueous Suspension | |
|---|---|
| methyl 3[[[[[4-ethoxy-6-methylamino)-1,3,5-triazin-2-yl]amino]carbonyl]amino]sulfonyl]-1-methyl-lH-pyrrole-2-carboxylate | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE G

| Wettable Powder | |
|---|---|
| methyl 3-[[[[(4,6-dimethoxy-2-pyrimidinyl)amino]-carbonyl]amino]sulfonyl]-1-methyl-lH-pyrrole-2-carboxylate | 40.4% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE H

| Granule | |
|---|---|
| wettable powder of Example G | 15% |
| gypsum | 69% |
| potassium sulfate | 16% |

The ingredients are blended in a rotating mixer and water sprayed on to accomplish granulation. When most of the material has reached the desired range of 1.0 to 0.42 cm (U.S.S. #18 to 40 sieves), the granules are removed, dried, and screened. Oversized material is crushed to produce additional material in the desired range. These granules contain % active ingredient.

EXAMPLE I

| Wettable Powder | |
|---|---|
| methyl 3[[[[[4-ethoxy-6-(methylamino)-1,3,5-triazin-2-yl]amino]carbonyl]amino]sulfonyl]-1-methyl-lH-pyrrole-2-carboxylate | 50% |
| sodium alkylnaphthalenesulfonate | 2% |
| low viscosity methyl cellulose | 2% |
| diatomaceous earth | 46% |

The ingredients are blended, coarsely hammer-milled and the air milled to produce particles of active essentially all below 10 microns in diameter. The product is reblended before packaging.

EXAMPLE J

| Extruded Pellet | |
|---|---|
| methyl 3-[[[[(4,6-dimethoxy-2-pyrimidinyl)amino]-carbonyl]amino]sulfonyl]-1-methyl-lH-pyrrole-2-carboxylate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE K

| Wettable Powder | |
|---|---|
| methyl 3[[[[[4-ethoxy-6-(methylamino)-1,3,5-triazin-2-yl]amino]carbonyl]amino]sulfonyl]-1-methyl-1H-pyrrole-2-carboxylate | 80% |
| sodium alkylnaphthalenesulfonate | 2% |
| sodium ligninsulfonate | 2% |
| synthetic amorphous silica | 3% |
| kaolinite | 13% |

The ingredients are blended and then ground in a hammer mill to produce particles with an average particle size less than 25 microns in diameter. The material is reblended and sired through a U.S.S. No. 50 sieve (0.3 mm opening) before being packaged.

EXAMPLE L

| High Strength Concentrate | |
|---|---|
| methyl 3-[[[[(4,6-dimethoxy-2-pyrimidinyl)amino]-carbonyl]amino]sulfonyl]-1-methyl-1H-pyrrole-2-carboxylate | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in a variety of ways.

EXAMPLE M

| Solution | |
|---|---|
| methyl 3[[[[4-ethoxy-6-(methylamino)-1,3,5-triazin-2-yl]amino]carbonyl]amino]sulfonyl]-1-methyl-lH-pyrrole-2-carboxylate | |
| sodium salt | 5% |
| water | 95% |

The salt is added directly to the water with stirring to produce the solution, which may then be packaged for use.

EXAMPLE N

| Solution | |
|---|---|
| methyl 3-[[[[(4,6-dimethoxy-2-pyrimidinyl)amino]-carbonyl]amino]sulfonyl]-1-methyl-1H-pyrrole-2-carboxylate | |
| sodium salt | 5% |
| water | 95% |

The salt is added directly to the water with sting to produce the solution, which may then be packaged for use.

Utility

Test results indicate compounds of this invention are active postemergence and preemergence herbicides. Compounds in this invention are useful for the control of selected grass and broadleaf weeds with tolerance to important agronomic crops which include, but are not limited to barley (*Hordeum vulgare*), cotton (*Gossypium hirsutum*), rape (*Brassica napus*), rice (*Oryza sativa*), and wheat (*Triticum aestivum*). Grass and broadleaf weed species controlled include, but are not limited to, bedstraw (Galium spp.), brome (Bromus spp.), lambsquarters (Chenopodium spp.), and umbrella sedge (Cyperus spp.). A few compounds in this invention are useful for the control of selected broadleaf weeds such as umbrella sedge in upland and paddy rice.

These compounds also have utility for control of vegetation in specified areas such as around storage tanks, parking lots, highways, and railways; in fallow crop areas; and in citrus and plantation crops such as banana, coffee, oil palm, and rubber. Alternatively, these compounds are useful to modify plant growth or as citrus abscission agents.

A herbicidally effective amount of the compounds of this invention is determined by a number of factors. These factors include: formulation selected, method of application, amount and type of vegetation present, growing conditions, etc. In general, a herbicidally effective amount of the subject compounds is applied at rates from 0.001 to 20 kg/ha with a preferred rate range of 0.004 to 0.25 kg/ha. One skilled in the art can easily determine application rates necessary for the desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)-phenoxy]-2-nitrobenzoic acid |
| acrolein | 2-propenal |
| alachlor | 2-chloro-N-(2,6-diethylphenyl)-N-(methoxymethyl)acetamide |
| anilofos | S-4-chloro-N-isopropylcarbaniloyl-methyl-O,O-dimethyl phosphorodithioate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]-carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-N-ethyl-2,6-dinitro-4-(trifluoromethyl)benzenamine |
| bensulfuron methyl | 2-[[[[[(4,6-dimethoxy-2-pyrimidinyl)amino]methylcarbonyl]-amino]sulfonyl]methyl]benzoic acid, methyl ester |
| bensulide | O,O-bis(1-methylethyl) S-[2-[(phenylsulfonyl)amino]-ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoro-methyl)phenyl]methanesulfonamide |
| benzoylprop | N-benzoyl-N-(3,4-dichlorophenyl)-DL, alanine |
| bifenox | methyl 5-(2,4-dichlorophenoxy)-2-nitrobenzoate |
| bromacil | 5-bromo-6-methyl-3-(1-methylpropyl)-2,4(lH,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methyl-propyl)-2,6-dinitrobenzenamine |
| butylate | S-ethyl bis(2-methylpropyl)-carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| CGA 142,464 | 3-(4,6-dimethoxy,-1,3,5-triazin-2-yl)-1-[2-(2-methoxyethoxy)-pehnyl-sulfonyl]-urea |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)ethylamino]carbonyl]- |

-continued

| Common Name | Chemical Name |
|---|---|
| | amino]sulfonyl]benzoic acid, ethyl ester |
| chlormethoxynil | 2,4-dichlorophenyl 4-nitro-3-methoxyphenyl ether |
| chlornitrofen | 2,4,6-trichlorophenyl-4-nitrophenyl ether |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo[2.2.1]heptane |
| clethodim | (E,E)-(±)-2-[1-[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]4,4-dimethyl-3-isoxazolidinone |
| cloproxydim | (E,E)-2-[1-[[(3-chloro-2-propenyl)oxy)imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(iso propylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop | (±)-2-[4-(2,4-dichlorophenoxy)phenoxy]propanoic acid, methyl ester |
| diethatyl | N-(chloroacetyl)-N-(2,6-diethylphenyl)glycine |
| difenzoquat | 1,2-dimethyl-3,5-diphenyl-1H-pyrazolium |
| dimepiperate | S-1-methyl-1-phenylethylpiperidine-1-carbothioate |
| dinitramine | $N^3$,$N^3$-diethyl-2,4-dinitro-6-(trifluoromethyl)-1,3-benzenediamine |
| dinoseb | 2-(1-methylpropyl)-4,6-dinitrophenol |
| diphenamid | N,N-dimethyl-a-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]pyrazinedium ion |
| diuron | N'-(3,4-dichlorophenyl)-N,N-dimethylurea |
| DNOC | 2-methyl-4,6-dinitrophenol |
| DSMA | disodium salt of MAA |
| dymron | N-(4-methylphenyl)-N'-(1-methyl-1-phenylethyl)urea |
| endothall | 7-oxabicyclo[2.2.1]heptane-2,3-dicarboxylic acid |
| EPTC | S-ethyl dipropylcarbamothioate |
| esprocarb | S-benzyl-N-ethyl-N-(1,2-dimethyl)- |

-continued

| Common Name | Chemical Name |
|---|---|
| (SC2957) | propyl)thiolcarbamate |
| ethalfluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl-5-benzofuranyl methanesulfonate |
| fenac | 2,3,6-trichlorobenzeneacetic acid |
| fenoxaprop | (±)-2-[4-[(6-chloro-2-benzoxazolyl)oxy]-phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)-phenyl]urea |
| fluorochloridone | 3-chloro-4-(chloromethyl)-1-[3-(trifluoromethyl)phenyl]-2-pyrrolidinone |
| fluorodifen | p-nitrophenyl a,a,a-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hydrogen (aminocarbonyl)-phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(lH,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-lH-imidazol-2-yl]-3-quinolinecarboxylic acid |
| imazethapyr | (±)-2-[4,5-dihydro-4-methyl-4-(l-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-lH-cyclopentapyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| MON 7200 | S,S-dimethyl-2-(difluoromethyl)-4-(2-methylpropyl)-6-(trifluoromethyl)- |

-continued

| Common Name | Chemical Name |
|---|---|
| | 3,5-pyridinedicarbothionate |
| mecoprop | (±)-2-(4-chloro-2-methylphenoxy)-propanoic acid |
| mefenacet | 2-(2-benzothiazolyloxy-N-methyl-N-phenylacetamide |
| mefluidide | N-[2,4-dimethyl-5-[[(trifluoromethyl)-sulfonyl]amino]phenyl]acetamide |
| methal-propalin | N-(2-methyl-2-propenyl)-2,6-dinitro-N-propyl-4-(trifluoromethyl)benzenamide |
| methabenz-thiazuron | 1,3-dimethyl-3-(2-benzothiazolyl)urea |
| metham | methylcarbamodithioic acid |
| methazole | 2-(3,4-dicblorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]-amino]sulfonyl]benzoic acid, methyl ester |
| MH | 1,2-dihydro-3,6-pyridazinedione |
| molinate | S-ethyl hexahydro-lH-azepine-1-carbothioate |
| monolinuron | 3-(p-chlorophenyl)-1-methoxy-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nicosulfuron | 2-[[(4,6-dimethoxypyrimidin-2-yl)-aminocarbonyl]aminosulfonyl]-N,N-dimethyl-3-pyridinecarboxamide |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aa,-4a,5a,7a,7aa-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitro-benzenesulfonamide |
| oxadiazon | 3-[2,4-dichloro-5-(1-methylethoxy).phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridinecarboxylic acid |
| PPG-1013 | 5-[2-chloro-4-(trifluoromethyl)-phenoxy]-2-nitroacetophenone oxime-O-acetic acid, methyl ester |
| pretilachlor | a-chloro-2,6-diethyl-N-(2-propoxyethyl)acetanilide |
| procyazine | 2-[[4-chloro-6-(cyclopropylamino)-1,3,5-triazine-2-yl]amino]-2-methylpropanenitrile |

-continued

| Common Name | Chemical Name |
|---|---|
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(l-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| pyrazolate | 4-(2,4-dichlorobenzoyl)-1,3-dimethylpyrazol-5-yl-p-toluenesulphonate |
| pyrazon | 5-amino-4-chloro-2-phenyl-3(2H)-pyridazinone |
| pyrazosulfuron ethyl | ethyl S-[3-(4,6-dimethoxypyrimidin-2-yl)ureadosulfonyl]-1-methylpyrazole-4-carboxylate |
| quinclorac | 3,7-dichloro-8-quinoline carboxylic acid |
| quizalofop ethyl | (±)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| SK-233 | 1-(a,a-dimethylbenzyl)-3-(4-methylphenyl)urea |
| sulfometuron methyl | 2-[[[[(4,6-dimethyl-2-pyrimidinyl)-amino]carbonyl]amino]sulfonyl]-benzoic acid, methyl ester |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthyl-azine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thifensul-furon methyl | 3-[[[[(4-methoxy-6-methyl-1,3,5-triazin-2-yl)amino]carbonyl]amino]sulfonyl]-2-thiophenecarboxylic acid, methyl ester |
| thiobencarb | S-[(4-chlorophenyl)methyl]diethylcarbamothioate |
| triallate | S-(2,3,3-trichloro-2-propenyl) bis(1-methylethyl)carbamothioate |
| tribenuron methyl | 2-[[[[N-(4-methoxy-6-methyl-1,3,5-triazine-2-yl)-N-methylamino]-carbonyl]amino]sulfonyl]benzoic acid, methyl ester |
| triclopyr | [(3,5,6-trichloro-2-pyridinyl)-oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseu- |

-continued

| Common Name | Chemical Name |
|---|---|
| | dourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Herbicidal properties of the subject compounds were discovered in a number of greenhouse tests. Test procedures and results follow.

TEST A

Seeds of barley (*Hordeum vulgare*), barnyardgrass (*Echinochloa crus-galli*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (Digitaria spp.), bedstraw (*Galium aparine*). giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

TEST A

| Rate (200 g/ha) POST- EMERGENCE | COMPOUND 165 | 166 | 167 | 168 | 169 | 170 | 171 |
|---|---|---|---|---|---|---|---|
| Barley | 9 | 9 | 9 | 7 | 9 | 9 | 9 |
| Barnyardgrass | 9 | 9 | 10 | 9 | 9 | 9 | 9 |
| Bedstraw | 8 | 9 | 9 | 9 | 10 | 10 | 8 |
| Blackgrass | 9 | 9 | 9 | 9 | 10 | 10 | 9 |
| Cheatgrass | 8 | 10 | 9 | 8 | 9 | 9 | 9 |
| Chickweed | 9 | 10 | 10 | 9 | 9 | 9 | 3 |
| Cocklebur | 9 | 9 | 9 | — | 10 | 10 | 7 |
| Corn | 10 | 10 | 10 | 10 | 9 | 10 | 9 |
| Cotton | 9 | 10 | 10 | 9 | 9 | 10 | 9 |
| Crabgrass | 9 | 10 | 8 | 5 | 10 | 10 | 8 |
| Giant foxtail | 9 | 10 | 9 | 9 | 10 | 10 | 9 |
| Lambsquarters | 10 | 10 | 10 | 10 | 10 | 10 | 9 |
| Morningglory | 10 | 10 | 10 | 10 | 10 | 10 | 8 |
| Nutsedge | 9 | 9 | 9 | 10 | 10 | 9 | 0 |
| Rape | 9 | 9 | 10 | 9 | 9 | 9 | 5 |
| Rice | 9 | 9 | 9 | 9 | 9 | 10 | 9 |
| Sorghum | 9 | 10 | 10 | 10 | 10 | 10 | 9 |
| Soybean | 9 | 9 | 9 | 9 | 9 | 9 | 9 |
| Sugar beet | 9 | 9 | 10 | 9 | 9 | 9 | 10 |
| Velvetleaf | 9 | 9 | 9 | 9 | 9 | 9 | 7 |
| Wheat | 10 | 8 | 9 | 8 | 9 | 9 | 9 |
| Wild buckwheat | 10 | 10 | 10 | 9 | 9 | 10 | 8 |
| Wild oat | 9 | 9 | 10 | 8 | 9 | 10 | 10 |

| Rate (100 g/ha) POST- EMERGENCE | COMPOUND 93 |
|---|---|
| Barley | 4 |
| Bedstraw | 6 |
| Blackgrass | 5 |
| Cheatgrass | 4 |
| Chickweed | 2 |
| Lambsquarters | 9 |
| Rape | 4 |
| Sugar beet | 8 |
| Wheat | 5 |
| Wild buckwheat | 9 |
| Wild oat | 5 |

| Rate (200 g/ha) PRE- EMERGENCE | COMPOUND 165 | 166 | 167 | 168 | 169 | 170 | 171 |
|---|---|---|---|---|---|---|---|
| Barley | 8 | 9 | 8 | 2 | 3 | 2 | 2 |
| Barnyardgrass | 9 | 9 | 9 | 9 | 9 | 9 | 7 |
| Bedstraw | 7 | 7 | 9 | 6 | 8 | 9 | 4 |
| Blackgrass | 7 | 8 | 9 | 8 | 3 | 9 | 0 |
| Cheatgrass | 8 | 8 | 9 | 8 | 4 | 8 | 0 |
| Chickweed | 9 | 9 | 9 | 8 | 9 | 9 | 2 |
| Cocklebur | — | 8 | 6 | 1 | 2 | 8 | 2 |
| Corn | 7 | 9 | 9 | 8 | 8 | 7 | 3 |
| Cotton | 8 | 8 | 7 | 3 | 5 | 9 | 2 |
| Crabgrass | 9 | 9 | 8 | 7 | 9 | 9 | 9 |
| Giant foxtail | 9 | 9 | 9 | 7 | 9 | 9 | 9 |
| Lambsquarters | 9 | 9 | 9 | 8 | 9 | 9 | 7 |
| Morningglory | 0 | 6 | 5 | 4 | 4 | 9 | 0 |
| Nutsedge | 9 | 9 | 9 | 9 | 0 | 10 | 3 |
| Rape | 9 | 9 | 9 | 9 | 9 | 9 | 2 |
| Rice | 9 | 9 | 9 | 9 | 10 | 9 | 9 |
| Sorghum | 9 | 9 | 9 | 9 | 9 | 9 | 7 |
| Soybean | 8 | 9 | 8 | 4 | 7 | 8 | 5 |
| Sugar beet | 9 | 9 | 9 | 8 | 9 | 9 | 7 |
| Velvetleaf | 3 | 8 | 8 | 8 | 1 | 7 | 2 |
| Wheat | 8 | 9 | 9 | 5 | 7 | 9 | 2 |
| Wild buckwheat | 7 | 7 | 8 | 3 | 7 | 9 | 0 |
| Wild oat | 8 | 8 | 9 | 3 | 4 | 6 | 0 |

| Rate (100 g/ha) PRE- EMERGENCE | COMPOUND 93 |
|---|---|
| Barley | 0 |
| Bedstraw | 0 |
| Blackgrass | 2 |
| Cheatgrass | 0 |
| Chickweed | 8 |
| Lambsquarters | 5 |
| Rape | 0 |
| Sugar beet | 5 |
| Wheat | 0 |
| Wild buckwheat | 0 |
| Wild oat | 0 |

| Rate (50 g/ha) POST- EMERGENCE | COMPOUND 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|
| Barley | 9 | 8 | 7 | 7 | 8 | 9 | 9 | 9 | 8 | 8 | 9 | 8 | 9 | 9 | 2 | 4 | 0 | 7 | 8 | 4 | 5 | 3 | 9 | 8 | 9 | 9 | 9 | 9 | 9 |
| Barnyardgrass | 9 | 9 | 9 | 9 | 10 | 9 | 9 | 9 | 9 | 9 | 10 | 10 | 10 | 9 | 2 | 3 | 2 | 7 | 9 | 7 | 2 | 7 | 9 | 8 | 9 | 9 | 9 | 9 | 10 |
| Bedstraw | 9 | 9 | 10 | 9 | 10 | 9 | 7 | 9 | 4 | 5 | 8 | 4 | 7 | 5 | 5 | 3 | 0 | 2 | 5 | 6 | 6 | 6 | 7 | 9 | 8 | 9 | 8 | 8 | 10 |
| Blackgrass | 8 | 8 | 9 | 8 | 9 | 9 | 9 | 8 | 8 | 9 | 9 | 9 | 9 | 9 | 7 | 4 | 3 | 8 | 9 | 3 | 8 | 5 | 10 | 8 | 10 | 10 | 9 | 9 | 8 |
| Cheatgrass | 9 | 9 | 9 | 7 | 9 | 9 | 9 | 9 | 8 | 9 | 9 | 9 | 9 | 5 | 6 | 4 | 5 | 7 | 7 | 4 | 8 | 3 | 9 | 6 | 9 | 10 | 9 | 9 | 9 |
| Chickweed | 9 | 8 | 9 | 8 | 9 | 9 | 6 | 9 | 10 | 10 | 10 | — | — | 10 | — | — | — | — | 10 | 8 | 9 | 7 | 10 | 10 | 10 | 10 | 10 | 7 | 10 |
| Cocklebur | 9 | 9 | 6 | 5 | 8 | 3 | 0 | 3 | 9 | 9 | 9 | 8 | 9 | 2 | 0 | 8 | 7 | 3 | 5 | 3 | 3 | 0 | 8 | 0 | — | — | — | — | — |
| Corn | 9 | 9 | 10 | 9 | 10 | 9 | 9 | 9 | 9 | 9 | 9 | 9 | 10 | 9 | 7 | 7 | 7 | 9 | 9 | 9 | 6 | 7 | 10 | 9 | 9 | 9 | 10 | 9 | 10 |
| Cotton | 9 | 9 | 9 | 9 | 9 | 9 | 10 | 9 | 9 | 9 | 9 | 9 | 9 | 9 | 4 | 5 | 0 | 4 | 9 | 5 | 3 | 1 | 9 | 9 | 9 | 9 | 10 | 9 | 9 |
| Crabgrass | 9 | 9 | 9 | 6 | 10 | 5 | 6 | 6 | — | — | — | — | — | — | — | — | — | — | — | 5 | 3 | 0 | 7 | 9 | 8 | 9 | 9 | 7 | 9 |
| Giant foxtail | 9 | 9 | 9 | 6 | 9 | 9 | 9 | 7 | 9 | 8 | 10 | 8 | 10 | 10 | 7 | 3 | 2 | 7 | 8 | 6 | 8 | 8 | 9 | 9 | 9 | 9 | 9 | 9 | 10 |
| Lambsquarters | 9 | 9 | 9 | 9 | 10 | 9 | 9 | 9 | 9 | 9 | 9 | 10 | 10 | 9 | 4 | 8 | 7 | 6 | 7 | 9 | 9 | 8 | 9 | 7 | 10 | 10 | 10 | 10 | 10 |
| Morningglory | 9 | 9 | 10 | 9 | 10 | 9 | 9 | 9 | 7 | 9 | 10 | 9 | 10 | 9 | 8 | 5 | 7 | 7 | 9 | 8 | 2 | 3 | 9 | 9 | 10 | 9 | 9 | 9 | 10 |
| Nutsedge | 9 | 9 | 10 | 9 | 10 | 9 | 3 | 7 | 8 | 9 | 5 | 6 | 2 | 5 | 0 | 0 | 0 | 0 | 2 | 4 | 7 | 0 | 3 | 5 | — | 9 | 9 | 9 | — |
| Rape | 6 | 9 | 9 | 8 | 9 | 9 | 0 | 0 | 7 | 9 | 9 | 8 | 9 | 9 | 0 | 8 | 2 | 0 | 9 | 7 | 9 | 7 | 9 | 10 | 9 | 9 | 9 | 9 | 9 |

TABLE A-continued

TEST A

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | 9 | 9 | 9 | 9 | 9 | 9 | 9 | 9 | 9 | 9 | 9 | 9 | 10 | 9 | 9 | 6 | 8 | 9 | 9 | 9 | 9 | 9 | 9 | 9 | 9 | 9 | 9 | 9 | 9 |
| Sorghum | 9 | 9 | 9 | 9 | 9 | 9 | 9 | 9 | 9 | 9 | 9 | 10 | 9 | 9 | 7 | 6 | 6 | 9 | 9 | 9 | 9 | 6 | 9 | 9 | 9 | 9 | 10 | 9 | 10 |
| Soybean | 9 | 9 | 9 | 7 | 9 | 9 | 8 | 9 | 9 | 9 | 9 | 9 | 9 | 9 | 3 | 3 | 4 | 5 | 6 | 8 | 7 | 0 | 9 | 9 | 9 | 9 | 9 | 9 | 9 |
| Sugar beet | 9 | 10 | 9 | 7 | 9 | 9 | 7 | 9 | 8 | 9 | 9 | 8 | 9 | 9 | 2 | 3 | 3 | 3 | 8 | 9 | 9 | 4 | 9 | 10 | 10 | 10 | 10 | 9 | 10 |
| Velvetleaf | 9 | 9 | 9 | 9 | 10 | 7 | 6 | 9 | 4 | 8 | 9 | 7 | 9 | 9 | 2 | 0 | 0 | 6 | 9 | 6 | 8 | 2 | 9 | 9 | 9 | 9 | 10 | 9 | 9 |
| Wheat | 9 | 8 | 6 | 7 | 7 | 9 | 8 | 8 | 9 | 9 | 9 | 8 | 9 | 9 | 2 | 1 | 0 | 8 | 9 | 4 | 5 | 3 | 9 | 9 | 8 | 9 | 9 | 8 | 9 |
| Wild buckwheat | 9 | 9 | 9 | 9 | 9 | 9 | 6 | 9 | 7 | 7 | 9 | 8 | 7 | 8 | 0 | 0 | 0 | 3 | 3 | 8 | 8 | 3 | 8 | 8 | 9 | 9 | 9 | 9 | 10 |
| Wild oat | 9 | 9 | 9 | 7 | 8 | 9 | 9 | 8 | 9 | 10 | 9 | 9 | 10 | 9 | 4 | 1 | 0 | 7 | 7 | 6 | 7 | 2 | 9 | 9 | 9 | 10 | 10 | 9 | 10 |

| Rate (50 g/ha) POST- | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| EMERGENCE | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 |
| Barley | 9 | 9 | 8 | 8 | 9 | 8 | 9 | 6 | 6 | 3 | 0 | 8 | 5 | 3 | 0 | 0 | 0 | 4 | 2 | 4 | 7 | 8 | 9 | 9 | 6 | 3 | 7 | 8 | 7 |
| Barnyardgrass | 9 | 9 | 9 | 8 | 9 | 9 | 9 | 2 | 8 | 3 | 3 | 9 | 6 | 1 | 3 | 1 | 3 | 1 | 1 | 6 | 9 | 9 | — | 9 | 9 | 9 | 9 | 9 | 9 |
| Bedstraw | 8 | 7 | 6 | 6 | 5 | 8 | 9 | 4 | 7 | 9 | 5 | 9 | 7 | 0 | 5 | 0 | 0 | 3 | 2 | 6 | 9 | 10 | 2 | 7 | 8 | 7 | 8 | 9 | 9 |
| Blackgrass | 7 | 8 | 7 | 6 | 9 | 10 | 9 | 0 | 3 | 2 | 0 | 4 | 3 | 4 | 2 | 2 | 0 | 3 | 0 | 0 | 9 | 9 | 2 | 9 | 7 | 7 | 8 | 9 | 9 |
| Cheatgrass | 9 | 8 | 7 | 8 | 9 | 8 | 8 | 4 | 5 | 3 | 0 | 6 | 5 | 2 | 3 | 0 | 3 | 5 | 0 | 2 | 9 | 9 | 3 | 9 | 7 | 6 | 7 | 8 | 9 |
| Chickweed | 9 | 6 | 6 | 9 | 10 | 8 | 10 | 6 | 9 | — | 3 | 10 | 10 | — | 10 | 0 | 2 | 9 | 4 | 9 | 9 | 10 | 4 | 10 | 10 | 8 | 3 | 10 | 9 |
| Cocklebur | — | — | — | — | — | — | — | — | — | — | — | — | — | — | — | — | — | — | — | — | 10 | 10 | — | 10 | 10 | 9 | 9 | 10 | 9 |
| Corn | 10 | 9 | 9 | 9 | 9 | 9 | 9 | 8 | 9 | 9 | 4 | 9 | 9 | 3 | 7 | 1 | 6 | 9 | 7 | 9 | 9 | 9 | — | 9 | 9 | 5 | 9 | 9 | 9 |
| Cotton | 10 | 9 | 9 | 8 | 8 | 9 | 9 | 0 | 7 | 9 | 5 | 9 | 9 | 0 | 3 | 0 | 0 | 2 | 0 | 9 | 9 | 9 | — | 9 | 9 | 9 | 9 | 9 | 9 |
| Crabgrass | 9 | 7 | 1 | 2 | 7 | 8 | 9 | 3 | 0 | 0 | 0 | 3 | 1 | 0 | 0 | 3 | 0 | 0 | 2 | 1 | 3 | 9 | — | 9 | 4 | 0 | 0 | 4 | 1 |
| Giant foxtail | 10 | 9 | 7 | 7 | 9 | 9 | 9 | 2 | 4 | 2 | 0 | 8 | 4 | 1 | 0 | 0 | 0 | 3 | 0 | 2 | 9 | 9 | — | 9 | 7 | 1 | 3 | 9 | 9 |
| Lambsquarters | 10 | 8 | 10 | 9 | 9 | 9 | 10 | 9 | 9 | 9 | 9 | — | 8 | 4 | 7 | 9 | 8 | 2 | 5 | 9 | 10 | 10 | 7 | 10 | 10 | 8 | 7 | — | 10 |
| Morningglory | 9 | 9 | 9 | 9 | 9 | 9 | 9 | 8 | 9 | 8 | 4 | 10 | 9 | 5 | 8 | 6 | 6 | 5 | 7 | 9 | 10 | 10 | — | 9 | 10 | 9 | 0 | 9 | 9 |
| Nutsedge | — | 2 | 0 | 0 | 0 | 0 | 8 | — | 6 | 8 | 0 | 5 | 0 | 0 | 0 | 0 | — | 0 | 0 | 0 | 9 | 10 | — | 9 | 9 | — | 9 | 9 | 10 |
| Rape | 10 | 7 | 3 | 8 | 8 | 1 | 9 | 7 | 8 | 8 | 8 | 10 | 10 | 2 | 2 | 0 | 4 | 6 | 0 | 9 | 9 | 10 | 8 | 9 | 9 | 9 | 9 | 9 | 10 |
| Rice | 9 | 9 | 9 | 9 | 10 | 9 | 9 | 8 | 8 | 7 | 2 | 9 | 9 | 4 | 3 | 1 | 3 | 9 | 4 | 8 | 9 | 10 | — | 9 | 9 | 8 | 9 | 9 | 9 |
| Sorghum | 10 | 9 | 9 | 9 | 9 | 9 | 9 | 4 | 8 | 2 | 0 | 9 | 4 | 1 | 1 | 0 | 0 | 3 | 1 | 3 | 8 | 9 | — | 9 | 9 | 3 | 9 | 9 | 9 |
| Soybean | 9 | 9 | 9 | 5 | 8 | 8 | 9 | 4 | 8 | 7 | 2 | 9 | 9 | 2 | 3 | 0 | 2 | 3 | 2 | 9 | 9 | 9 | — | 9 | 9 | 6 | 8 | 9 | 9 |
| Sugar beet | 10 | 9 | 8 | 9 | 9 | 9 | 9 | 9 | 10 | 8 | 9 | 10 | 9 | 3 | 9 | 8 | 8 | 9 | 8 | 9 | 10 | 9 | 7 | 9 | 9 | 8 | 7 | 9 | 9 |
| Velvetleaf | 9 | 7 | 8 | 7 | 6 | 8 | 9 | 9 | 9 | 9 | 2 | 9 | 8 | 1 | 7 | 2 | 0 | 1 | 4 | 5 | 9 | 10 | — | 9 | 8 | 9 | 9 | 10 | 10 |
| Wheat | 9 | 8 | 7 | 8 | 9 | 8 | 9 | 2 | 3 | 2 | 0 | 8 | 6 | 1 | 1 | 1 | 2 | 3 | 0 | 3 | 7 | 9 | 8 | 9 | 2 | 2 | 3 | 7 | 7 |
| Wild buckwheat | 10 | 3 | 0 | 6 | 3 | 6 | 8 | 8 | 7 | 9 | 9 | 9 | 9 | 0 | 3 | 2 | 0 | 5 | 2 | 6 | 7 | 10 | 2 | 8 | 8 | 7 | — | 8 | 7 |
| Wild oat | 10 | 9 | 9 | 9 | 9 | 9 | 9 | 3 | 6 | 4 | 0 | 9 | 6 | 1 | 0 | 0 | 0 | 5 | 0 | 3 | 8 | 9 | 8 | 8 | 7 | 0 | 8 | 8 | 7 |

| Rate (50 g/ha) POST- | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| EMERGENCE | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
| Barley | 8 | 7 | 2 | 8 | 9 | 8 | 8 | 6 | 3 | 9 | 0 | 5 | 0 | 0 | 7 | 7 | 4 | 2 | 8 | 6 | 5 | 2 | 9 | 9 | 8 | 8 | 8 | — | 4 |
| Barnyardgrass | 8 | 7 | 5 | 9 | 9 | 9 | 9 | 8 | 9 | 9 | 8 | 9 | 5 | 3 | 9 | 9 | 4 | 1 | 9 | 9 | 7 | 0 | 9 | 9 | 9 | 9 | 4 | 9 | 4 |
| Bedstraw | 9 | 10 | 8 | 5 | 8 | 8 | 7 | 8 | 8 | 5 | 7 | 9 | 9 | 6 | 7 | 9 | 8 | 8 | 6 | 8 | 4 | 2 | 6 | 8 | 9 | 8 | 8 | — | 3 |
| Blackgrass | 8 | 8 | 5 | 9 | 10 | 10 | 9 | 9 | 8 | 7 | 1 | 7 | 5 | 3 | 9 | 9 | 6 | 2 | 9 | 9 | 8 | 3 | 9 | 9 | 10 | 9 | 9 | — | 8 |
| Cheatgrass | 9 | 8 | 6 | 9 | 10 | 10 | 9 | 7 | 9 | 9 | 8 | 3 | 2 | 3 | 9 | 9 | 2 | 3 | 9 | 9 | 4 | 2 | 9 | 9 | 10 | 9 | 8 | — | 8 |

TABLE A-continued

TEST A

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Chickweed | 10 | 10 | 8 | 5 | 10 | 9 | 9 | 0 | 9 | — | 9 | 9 | 9 | — | 9 | 9 | 10 | 9 | 10 | 9 | 4 | 0 | 9 | 10 | 10 | 9 | 7 | — | 2 |
| Cocklebur | 10 | 10 | 9 | 9 | 10 | 10 | 9 | 9 | 10 | 9 | 9 | — | 9 | 8 | 9 | 9 | 9 | — | — | — | — | — | — | — | — | — | — | — | — |
| Corn | 9 | 9 | 3 | 0 | 9 | 9 | 9 | 9 | 3 | 9 | 5 | 9 | 9 | 2 | 7 | 9 | 9 | 7 | 5 | 9 | 6 | 2 | 0 | 7 | 9 | 9 | 9 | 1 | 0 |
| Cotton | 9 | 9 | 9 | 9 | 9 | 10 | 9 | 9 | 9 | 9 | 9 | 9 | 9 | 8 | 9 | 9 | 10 | 9 | 9 | 9 | 6 | 2 | 9 | 9 | 9 | 9 | 9 | 9 | 9 |
| Crabgrass | 6 | 0 | 0 | 5 | 5 | 9 | 10 | 4 | 2 | 6 | 2 | 6 | 3 | 0 | 4 | 5 | 2 | 0 | 6 | 7 | 0 | 0 | 5 | 7 | — | 6 | 3 | 3 | 2 |
| Giant foxtail | 8 | 5 | 0 | 7 | 9 | 9 | 9 | 5 | 5 | 8 | 5 | 8 | 2 | 1 | 9 | 10 | 8 | 6 | 9 | 9 | 7 | 0 | 8 | 9 | 9 | 9 | 3 | 6 | 2 |
| Lambsquarters | 9 | 9 | 7 | 9 | 10 | 10 | 9 | 9 | 10 | 9 | — | 9 | 9 | 8 | 9 | 9 | 9 | 8 | 9 | 9 | 8 | 3 | 10 | 10 | 10 | 10 | 9 | — | 7 |
| Morningglory | 9 | 9 | 9 | 9 | 10 | 10 | 9 | 9 | 9 | 9 | 9 | 9 | 10 | 7 | 9 | 10 | 7 | 8 | 9 | 9 | 7 | 5 | 10 | 10 | 10 | 9 | 9 | 10 | 9 |
| Nutsedge | 10 | 10 | 9 | 9 | 9 | 10 | 6 | 7 | 9 | — | 9 | 9 | — | 5 | 8 | 10 | 5 | 0 | 10 | 10 | 0 | 0 | 3 | 9 | 10 | 7 | 0 | 8 | 0 |
| Rape | 9 | 9 | 10 | 9 | 10 | 9 | 9 | 8 | 10 | 9 | 9 | 10 | 9 | 7 | 9 | 9 | 9 | 9 | 9 | 9 | 9 | 7 | 9 | 9 | 9 | 9 | 9 | — | 8 |
| Rice | 9 | 9 | 8 | 9 | 9 | 9 | 9 | 9 | 8 | 9 | 7 | 9 | 8 | 4 | 9 | 9 | 9 | 7 | 9 | 9 | 9 | 8 | 9 | 9 | 9 | 10 | 9 | 9 | 8 |
| Sorghum | 9 | 9 | 3 | 10 | 9 | 10 | 9 | 8 | 9 | 9 | 3 | 4 | 1 | 2 | 9 | 9 | 3 | 2 | 9 | 9 | 3 | 0 | 9 | 9 | 9 | 9 | 9 | 9 | 8 |
| Soybean | 9 | 9 | 7 | 9 | 9 | 9 | 9 | 8 | 9 | 9 | 9 | 9 | 9 | 1 | 9 | 9 | 8 | 8 | 9 | 9 | 6 | 3 | 9 | 9 | 9 | 9 | 9 | 9 | 6 |
| Sugar beet | 9 | 9 | 10 | 9 | 9 | 9 | 9 | 9 | 9 | 10 | 10 | 10 | 10 | 10 | 9 | 9 | 10 | 9 | 10 | 9 | 9 | 7 | 9 | 9 | 9 | 9 | 9 | — | 7 |
| Velvetleaf | 9 | 9 | 9 | 9 | 9 | 10 | 9 | 9 | 9 | 9 | 9 | 9 | 9 | 8 | 9 | 9 | 9 | 8 | 9 | 9 | 5 | 0 | 9 | 10 | 10 | 9 | 9 | 9 | 9 |
| Wheat | 7 | 3 | 1 | 9 | 9 | 9 | 9 | 9 | 2 | 6 | 0 | 0 | 0 | 0 | 7 | 7 | 3 | 0 | 8 | 9 | 8 | 2 | 8 | 9 | 9 | 9 | 8 | — | 4 |
| Wild buckwheat | 9 | 9 | 9 | 10 | 9 | 9 | 9 | 8 | 10 | 7 | 7 | 10 | 4 | 0 | 8 | 9 | 7 | 1 | 8 | 9 | 5 | 0 | 9 | 9 | 9 | 9 | 9 | — | 7 |
| Wild oat | 8 | 7 | 0 | 9 | 9 | 9 | 10 | 9 | 3 | 8 | 0 | 2 | 0 | 0 | 9 | 9 | 8 | 2 | 9 | 9 | 9 | 2 | 9 | 8 | 4 | 9 | 9 | — | 3 |

| Rate (50 g/ha) POST- | COMPOUND | | | | | | | | | | | | | | | | | | | | | | | | |
|---|---|---|---|---|---|---|---|---|---|---|---|---|---|---|---|---|---|---|---|---|---|---|---|---|---|
| EMERGENCE | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
| Barley | 7 | 8 | 8 | 3 | 3 | 8 | 8 | 9 | 8 | 8 | 8 | 6 | 4 | 7 | 9 | 9 | 9 | 9 | 3 | 9 | 9 | 9 | 9 | 9 | 8 |
| Barnyardgrass | 9 | 9 | 7 | 0 | 5 | 9 | 9 | 9 | 9 | 8 | 8 | 7 | 7 | 6 | 9 | 9 | 9 | 8 | 4 | 9 | 9 | 9 | 9 | 9 | 9 |
| Bedstraw | 8 | — | 8 | 8 | 7 | 8 | 9 | 9 | 8 | 7 | 9 | 7 | 7 | 5 | 9 | 9 | 7 | 8 | 7 | 9 | 9 | 9 | 9 | 8 | 9 |
| Blackgrass | 8 | 9 | 9 | 9 | 9 | 9 | 9 | 9 | 9 | 9 | 9 | 9 | 9 | 8 | 9 | 9 | 9 | 9 | 5 | 9 | 9 | 9 | 10 | 9 | 9 |
| Cheatgrass | 8 | 9 | 8 | 7 | 9 | 9 | 9 | 9 | 6 | 8 | 9 | 4 | 3 | 6 | 9 | 9 | 9 | 9 | 5 | 9 | 9 | 9 | 9 | 9 | 9 |
| Chickweed | 10 | 9 | 9 | 10 | 3 | 9 | 9 | 9 | 10 | 9 | 9 | 9 | 9 | 3 | 9 | 10 | 3 | 7 | 2 | 10 | 9 | 10 | 9 | 10 | — |
| Cocklebur | — | — | — | — | — | — | — | — | — | — | — | — | — | — | — | — | — | — | — | — | — | — | — | — | — |
| Corn | 5 | 9 | 9 | 9 | 0 | 9 | 9 | 9 | 9 | 9 | 9 | 9 | 7 | 0 | 0 | 0 | 0 | 9 | 0 | 9 | 9 | 9 | 9 | 9 | 6 |
| Cotton | 9 | 10 | 9 | 9 | 9 | 9 | 9 | 9 | 10 | 9 | 9 | 9 | 9 | 2 | 8 | 9 | 5 | 8 | 4 | 10 | 9 | 10 | 10 | 10 | 10 |
| Crabgrass | 5 | 6 | 6 | 2 | 0 | 8 | 7 | 8 | 5 | 3 | 5 | 2 | 1 | 2 | 3 | 1 | 5 | 7 | 0 | 9 | 9 | 9 | 9 | 8 | — |
| Giant foxtail | 5 | 8 | 8 | 3 | 0 | 9 | 9 | 9 | 9 | 8 | 9 | 5 | 4 | 3 | 7 | 7 | 7 | 8 | 0 | 9 | 7 | 9 | 10 | 9 | 6 |
| Lambsquarters | 8 | 9 | 9 | — | 5 | 9 | 9 | 10 | 9 | 9 | — | 8 | 7 | 8 | 9 | 10 | 3 | 8 | — | 10 | 10 | 10 | 10 | 10 | 9 |
| Morningglory | 10 | 9 | 9 | 9 | 9 | 9 | 10 | 9 | 9 | 9 | 10 | 9 | 9 | 8 | 9 | 9 | 9 | 9 | 8 | 9 | 9 | 8 | 10 | 10 | 9 |
| Nutsedge | 9 | 9 | — | 0 | — | — | — | — | — | — | — | — | — | — | 10 | 8 | 0 | 0 | 0 | 10 | 9 | 9 | 9 | 10 | 9 |
| Rape | 9 | 9 | 9 | 9 | 6 | 9 | 9 | 9 | 9 | 9 | 9 | 9 | 9 | 9 | 9 | 9 | 9 | 5 | 7 | 9 | 9 | 9 | 10 | 9 | 8 |
| Rice | 9 | 8 | 9 | 9 | 9 | 9 | 9 | 9 | 9 | 9 | 9 | 9 | 9 | 9 | 10 | 9 | 10 | 9 | 7 | 9 | 10 | 9 | 10 | 9 | 9 |
| Sorghum | 9 | 9 | 9 | 9 | 9 | 9 | 9 | 9 | 9 | 9 | 9 | 9 | 9 | 5 | 9 | 9 | 9 | 9 | 8 | 9 | 9 | 9 | 9 | 9 | 9 |
| Soybean | 9 | 8 | 9 | 9 | 3 | 9 | 9 | 9 | 9 | 8 | 9 | 9 | 9 | 0 | 3 | 9 | 0 | 2 | 1 | 9 | 9 | 9 | 9 | 9 | 9 |
| Sugar beet | 9 | 10 | 9 | 10 | 5 | 10 | 9 | 9 | 9 | 9 | 9 | 9 | 9 | 9 | 9 | 9 | 8 | 9 | 9 | 9 | 9 | 9 | 9 | 9 | 8 |
| Velvetleaf | 10 | 10 | 8 | 9 | 6 | 9 | 9 | 9 | 9 | 8 | 9 | 10 | 9 | 7 | 7 | 9 | 5 | 5 | 2 | 10 | 9 | 10 | 10 | 10 | 10 |
| Wheat | 4 | 4 | 4 | 4 | 1 | 9 | 9 | 9 | 9 | 9 | 9 | 3 | 3 | 6 | 9 | 9 | 9 | 9 | 4 | 9 | 9 | 9 | 9 | 9 | 8 |
| Wild buckwheat | 7 | 9 | 9 | 9 | 5 | — | — | — | — | 9 | — | 9 | 9 | 6 | 9 | — | — | — | — | 10 | 10 | 10 | — | — | 9 |
| Wild oat | 4 | 2 | 7 | 7 | 0 | 9 | 9 | 9 | 9 | 9 | 9 | 9 | 8 | 6 | 9 | 9 | 9 | 9 | 0 | 9 | 9 | 9 | 9 | 7 | 6 |

TABLE A-continued

TEST A

| Rate (50 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 113 | 114 | 115 | 116 | 117 | 118 | 119 | 120 | 121 | 122 | 123 | 124 | 125 | 126 | 127 | 128 | 129 | 130 | 131 | 132 | 133 | 134 |
| Barley | 7 | 8 | 7 | 6 | 3 | 0 | 9 | 8 | 9 | 9 | 7 | 8 | 4 | 3 | 0 | 2 | 0 | 1 | 1 | 3 | 1 | 2 |
| Barnyardgrass | 9 | 9 | 9 | 9 | 7 | 5 | 9 | 9 | 9 | 9 | 5 | 9 | 3 | 9 | 0 | 2 | 0 | 5 | 0 | 0 | 0 | 0 |
| Bedstraw | 8 | 9 | 10 | 8 | 9 | 8 | 8 | 7 | 8 | 9 | 3 | 2 | 3 | 7 | 9 | 2 | 3 | 6 | 7 | 8 | 8 | 7 |
| Blackgrass | 9 | 9 | 9 | 10 | 8 | 9 | 9 | 9 | 9 | 9 | 4 | 7 | 4 | 6 | 4 | 4 | 2 | 6 | 6 | 7 | 6 | 3 |
| Cheatgrass | 9 | 8 | 9 | 8 | 8 | 5 | 9 | 9 | 9 | 9 | 7 | 8 | 7 | 5 | 2 | 2 | 0 | 6 | 6 | 3 | 2 | 0 |
| Chickweed | 2 | 7 | 9 | 9 | 9 | 4 | 10 | 9 | 10 | 9 | 4 | 9 | 8 | 9 | 5 | 2 | 4 | 10 | 9 | 10 | 2 | 0 |
| Cocklebur | — | — | — | — | — | — | — | — | — | — | 6 | 9 | 10 | 10 | 6 | 10 | 4 | 9 | 10 | 10 | 9 | 9 |
| Corn | 9 | 9 | 9 | 9 | 4 | 0 | 9 | 9 | 9 | 9 | 0 | 5 | 2 | 9 | 7 | 0 | 0 | 6 | 5 | 9 | 7 | 2 |
| Cotton | 9 | 9 | 10 | 10 | 10 | 9 | 9 | 10 | 10 | 9 | 9 | 9 | 10 | 10 | 9 | 9 | 9 | 9 | 9 | 9 | 9 | 2 |
| Crabgrass | 5 | 8 | 4 | 6 | 0 | 3 | 9 | 8 | 9 | 9 | 2 | 4 | 2 | 2 | 2 | 0 | 0 | 0 | 0 | 0 | 0 | 0 |
| Giant foxtail | 7 | 9 | 7 | 8 | 2 | 2 | 9 | 9 | 9 | 9 | 2 | 3 | 1 | 3 | 1 | 0 | 0 | 2 | 2 | 0 | 0 | 0 |
| Lambsquarters | — | — | 9 | 9 | 9 | 7 | — | — | 10 | — | 9 | 10 | — | 10 | 9 | 9 | 7 | 9 | 10 | 10 | 10 | — |
| Morningglory | 8 | 9 | 10 | 10 | 10 | 9 | 10 | 10 | 10 | 10 | 5 | 9 | 10 | 9 | 10 | 9 | 1 | 6 | 9 | 10 | 10 | 9 |
| Nutsedge | — | 9 | 9 | 10 | 7 | 9 | 9 | 9 | 9 | 9 | — | 8 | 9 | 9 | 7 | 8 | — | 8 | 10 | 9 | 7 | 3 |
| Rape | 9 | 9 | 9 | 9 | 9 | 9 | 9 | 9 | 10 | 9 | 8 | 9 | 9 | 9 | 9 | 9 | 8 | 8 | 9 | 9 | 9 | 9 |
| Rice | 9 | 9 | 8 | 9 | 9 | 7 | 9 | 9 | 9 | 9 | 8 | 8 | 7 | 9 | 9 | 4 | 0 | 8 | 2 | 8 | 9 | 0 |
| Sorghum | 9 | 9 | 9 | 9 | 9 | 7 | 9 | 9 | 9 | 9 | 1 | 5 | 3 | 8 | 8 | 9 | 0 | 6 | 7 | 8 | 9 | 0 |
| Soybean | 2 | 9 | 9 | 9 | 9 | 1 | 9 | 9 | 9 | 9 | 7 | 9 | 8 | 8 | 8 | 3 | 6 | 9 | 9 | 9 | 9 | 1 |
| Sugar beet | 5 | 9 | 8 | 10 | 9 | 7 | 9 | 9 | 9 | 9 | 8 | 10 | 10 | 10 | 10 | 9 | 8 | 9 | 9 | 9 | 9 | 6 |
| Velvetleaf | 9 | 10 | 10 | 10 | 10 | 9 | 10 | 10 | 10 | 9 | 10 | 9 | 9 | 10 | 2 | 9 | 9 | 9 | 10 | 10 | 6 | 9 |
| Wheat | 3 | 5 | 7 | 3 | 0 | 0 | 9 | 9 | 9 | 9 | 2 | 2 | 0 | 0 | 0 | 2 | 0 | 0 | 0 | 2 | 1 | 0 |
| Wild buckwheat | 5 | 8 | 9 | 9 | 9 | 7 | 9 | 9 | 9 | 9 | 7 | 8 | 9 | 9 | 9 | 9 | 6 | 7 | 9 | 9 | 8 | 9 |
| Wild oat | 9 | 9 | 9 | 8 | 5 | 2 | 9 | 7 | 9 | 9 | 7 | 6 | 2 | 3 | 2 | 2 | 1 | 0 | 3 | 4 | 3 | 2 |

| Rate (50 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 135 | 136 | 137 | 138 | 139 | 140 | 141 | 142 | 143 | 144 | 145 | 146 | 147 | 148 | 149 | 150 | 151 | 152 | 165 | 166 | 167 | 168 |
| Barley | 9 | 7 | 8 | 9 | 7 | 9 | 8 | 9 | 8 | 9 | 5 | 7 | 9 | 9 | 9 | 9 | 7 | 5 | 8 | 8 | 9 | 3 |
| Barnyardgrass | 9 | 7 | 9 | 9 | 7 | 9 | 9 | 9 | 9 | 9 | 0 | 9 | 9 | 9 | 9 | 8 | 5 | 8 | 9 | 9 | 9 | 9 |
| Bedstraw | 9 | 9 | 9 | 9 | 8 | 7 | 8 | 9 | 9 | 9 | 7 | 8 | 9 | 9 | 9 | 9 | 9 | 9 | 7 | 9 | 9 | 9 |
| Blackgrass | 9 | 4 | 8 | 9 | 7 | 9 | 9 | 9 | 9 | 9 | 8 | 9 | 9 | 9 | 9 | 9 | 9 | 9 | 8 | 9 | 8 | 7 |
| Cheatgrass | 9 | 8 | 9 | 9 | 8 | 9 | 8 | 9 | 9 | 9 | 3 | 9 | 9 | 9 | 9 | 9 | 8 | 9 | 8 | 9 | 9 | 7 |
| Chickweed | 8 | 0 | 8 | 8 | 4 | 7 | 4 | 9 | 10 | 8 | 4 | 7 | 9 | 10 | 10 | 9 | 8 | 7 | 9 | 10 | 9 | 8 |
| Cocklebur | 9 | 9 | 8 | 9 | 9 | 9 | 9 | 10 | 10 | 9 | 8 | 10 | 10 | 10 | 10 | 10 | 9 | 10 | 9 | 9 | 9 | 8 |
| Corn | 8 | 8 | 9 | 9 | 5 | 9 | 2 | 9 | 9 | 9 | 8 | 8 | 0 | 6 | 9 | 9 | 9 | 3 | 9 | 10 | 10 | 9 |
| Cotton | 9 | 9 | 9 | 9 | 9 | 9 | 9 | 9 | 10 | 9 | 9 | 9 | 10 | 10 | 9 | 9 | 9 | 9 | 9 | 10 | 10 | 9 |
| Crabgrass | 2 | 2 | 3 | 6 | 0 | 2 | 1 | 6 | 9 | 3 | 0 | 2 | 3 | 2 | 6 | 2 | 2 | 2 | 9 | 8 | 4 | 3 |
| Giant foxtail | 7 | 4 | 7 | 9 | 6 | 9 | 3 | 8 | 9 | 9 | 2 | 5 | 7 | 6 | 9 | 9 | 6 | 3 | 9 | 9 | 9 | 9 |
| Lambsquarters | 8 | 9 | 9 | 9 | — | 9 | 9 | 9 | 10 | 9 | 9 | 10 | 10 | 10 | 10 | 10 | 9 | 9 | 10 | 9 | 10 | 9 |
| Morningglory | 9 | 9 | 10 | 9 | 10 | 10 | 2 | 9 | 9 | 9 | 9 | 9 | 10 | 9 | 10 | 10 | 10 | 10 | 5 | 10 | 10 | 10 |
| Nutsedge | 6 | 8 | 9 | — | 6 | 8 | 9 | 9 | 10 | 9 | 0 | 9 | 9 | 9 | 9 | 9 | 7 | 8 | 8 | 9 | 9 | 9 |
| Rape | 2 | 9 | 7 | 2 | 2 | 3 | 9 | 9 | 9 | 9 | 9 | 9 | 9 | 10 | 9 | 9 | 9 | 9 | 9 | 9 | 9 | 9 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Rice | 9 | 9 | 9 | 9 | 9 | 9 | 9 | 9 | 10 | 10 | 9 | 9 | 9 | 9 | 10 | 9 | 10 | 9 | 9 | 9 | 9 | 9 |
| Sorghum | 9 | 9 | 9 | 9 | 7 | 9 | 9 | 9 | 10 | 10 | 9 | 9 | 9 | 9 | 9 | 9 | 9 | 9 | 9 | 9 | 10 | 9 |
| Soybean | 9 | 9 | 8 | 9 | 9 | 9 | 9 | 9 | 9 | 9 | 9 | 9 | 9 | 9 | 9 | 9 | 9 | 9 | 9 | 9 | 9 | 9 |
| Sugar beet | 9 | 8 | 9 | 9 | 8 | 9 | 9 | 8 | 10 | 9 | 9 | 9 | 8 | 9 | 9 | 9 | 9 | 9 | 9 | 10 | 10 | 9 |
| Velvetleaf | 9 | 9 | 7 | 9 | 9 | 9 | 9 | 10 | 10 | 8 | 4 | 10 | 10 | 10 | 10 | 9 | 9 | 9 | 9 | 9 | 9 | 8 |
| Wheat | 8 | 8 | 9 | 9 | 8 | 9 | 9 | 9 | 9 | 9 | 9 | 8 | 9 | 9 | 9 | 9 | 8 | 4 | 7 | 8 | 8 | 6 |
| Wild buckwheat | — | — | — | — | — | — | — | — | — | — | — | — | — | — | — | — | — | — | 9 | 7 | 9 | 8 |
| Wild oat | 9 | 8 | 9 | 9 | 5 | 9 | 9 | 9 | 9 | 9 | 9 | 8 | 9 | 8 | 9 | 9 | 9 | 3 | 8 | 9 | 9 | 4 |

| Rate (50 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 169 | 170 | 171 | 172 | 173 | 174 | 175 | 176 | 177 | 178 | 179 | 180 | 181 | 182 | 183 | 184 | 185 | 186 | 187 | 188 | 189 | 190 |
| Barley | 7 | 4 | 9 | 9 | 9 | 8 | 9 | 8 | 9 | 9 | 7 | 8 | 8 | 9 | 9 | 9 | 9 | 9 | 9 | 8 | 9 | 9 |
| Barnyardgrass | 9 | 10 | 9 | 7 | 9 | 9 | 9 | 4 | 6 | 9 | 9 | 9 | 9 | 10 | 10 | 10 | 10 | 10 | 9 | 9 | 9 | 9 |
| Bedstraw | 8 | 10 | 6 | 8 | 9 | 8 | 7 | 2 | 3 | 5 | 7 | 7 | 7 | 8 | 9 | 9 | 9 | 9 | 9 | 8 | 8 | 8 |
| Blackgrass | 9 | 10 | 9 | 9 | 9 | 9 | 9 | 9 | 8 | 9 | 9 | 9 | 9 | 9 | 9 | 9 | 9 | 9 | 10 | 9 | — | 9 |
| Cheatgrass | 8 | 8 | 8 | 9 | 9 | 8 | 8 | 7 | 7 | 8 | 8 | 7 | 7 | 9 | 9 | 9 | 9 | 9 | 9 | 7 | 9 | 8 |
| Chickweed | 9 | 9 | 2 | 8 | 8 | 5 | 9 | 3 | 3 | 9 | 7 | 8 | 8 | 4 | 8 | 9 | 9 | 8 | 9 | 4 | 4 | 9 |
| Cocklebur | 9 | 9 | 7 | 9 | 9 | 9 | 7 | 2 | 6 | 2 | 6 | 1 | 6 | 9 | 10 | 10 | 10 | 10 | 9 | 3 | 9 | 9 |
| Corn | 10 | 10 | 9 | 9 | 10 | 10 | 9 | 9 | 9 | 9 | 8 | 10 | 10 | 10 | 10 | 10 | 9 | 10 | 10 | 9 | 9 | 9 |
| Cotton | 9 | 9 | 8 | 9 | 9 | 8 | 9 | 0 | 2 | 9 | 2 | 8 | 9 | 9 | 10 | 9 | 9 | 9 | 9 | 8 | 9 | 9 |
| Crabgrass | 9 | 9 | 8 | 8 | 9 | 7 | 9 | 6 | 7 | 9 | 6 | 9 | 9 | 9 | 10 | 10 | 9 | 10 | 9 | 8 | 9 | 8 |
| Giant foxtail | 9 | 10 | 9 | 9 | 9 | 9 | 9 | 8 | 9 | 9 | 6 | 9 | 9 | 9 | 10 | 10 | 9 | 10 | 9 | 9 | 9 | 9 |
| Lambsquarters | 10 | 9 | 9 | 10 | 10 | 10 | 10 | 5 | 7 | 7 | 7 | 6 | 7 | 10 | 10 | 10 | 10 | 9 | 10 | 7 | 8 | 9 |
| Morningglory | 10 | 10 | 9 | 9 | 9 | 9 | 9 | 2 | 6 | 8 | 5 | 9 | 9 | 9 | 10 | 10 | 10 | 10 | 9 | 9 | 9 | 9 |
| Nutsedge | 7 | 3 | 0 | 9 | 8 | 9 | 3 | 0 | 0 | 9 | — | 2 | — | 8 | 9 | 9 | 9 | 9 | — | 2 | 9 | 5 |
| Rape | 9 | 9 | 2 | 7 | 9 | 8 | 8 | 0 | 0 | 2 | 7 | 2 | 7 | 9 | 9 | 9 | 9 | 10 | 9 | 0 | 3 | 0 |
| Rice | 9 | 10 | 9 | 9 | 9 | 10 | 10 | 7 | 9 | 9 | 8 | 9 | 9 | 10 | 10 | 10 | 10 | 10 | 10 | 9 | 9 | 9 |
| Sorghum | 10 | 10 | 9 | 9 | 9 | 9 | 9 | 6 | 8 | 9 | 6 | 9 | 9 | 9 | 9 | 10 | 9 | 10 | 9 | 9 | 9 | 9 |
| Soybean | 9 | 9 | 9 | 9 | 9 | 9 | 9 | 1 | 8 | 9 | 7 | 9 | 9 | 9 | 9 | 9 | 9 | 9 | 9 | 6 | 8 | 9 |
| Sugar beet | 9 | 9 | 9 | 9 | 9 | 8 | 8 | 0 | 7 | 8 | 7 | 8 | 9 | 9 | 10 | 9 | 8 | 9 | 9 | 9 | 8 | 9 |
| Velvetleaf | 9 | 9 | 6 | 9 | 9 | 9 | 9 | 0 | 2 | 6 | 3 | 9 | 9 | 9 | 10 | 10 | 9 | 9 | 9 | 6 | 6 | 7 |
| Wheat | 9 | 9 | 9 | 9 | 9 | 4 | 9 | 8 | 8 | 9 | 8 | 8 | 9 | 9 | 9 | 9 | 7 | 9 | 9 | 7 | 8 | 8 |
| Wild buckwheat | 9 | 10 | 6 | 9 | 9 | 9 | — | — | — | — | — | — | — | — | — | — | — | — | — | — | — | — |
| Wild oat | 9 | 9 | 8 | 9 | 9 | 3 | 9 | 9 | 7 | 9 | 8 | 8 | 8 | 9 | 9 | 9 | 9 | 9 | 9 | 9 | 9 | 9 |

| Rate (50 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 191 | 192 | 203 | 204 | 205 | 206 | 207 | 208 | 209 | 210 | 211 | 212 | 213 | 214 | 215 | 216 | 217 | 218 | 219 | 220 | 221 | 222 |
| Barley | 9 | 9 | 9 | 10 | 9 | 9 | 9 | 9 | 9 | 9 | 9 | 9 | 9 | 9 | 7 | 9 | 9 | 9 | 6 | 8 | 5 | 0 |
| Barnyardgrass | 8 | 6 | 9 | 10 | 9 | 9 | 10 | 9 | 1 | 9 | 9 | 9 | 10 | 9 | 9 | 9 | 10 | 9 | 9 | 9 | 9 | 9 |
| Bedstraw | 7 | 7 | 9 | 9 | 9 | 9 | 9 | 9 | 5 | 8 | 10 | 10 | 10 | 10 | 9 | 6 | 7 | 8 | 8 | 8 | 6 | 7 |
| Blackgrass | 8 | 9 | 9 | 9 | 9 | 9 | 9 | 9 | 9 | 9 | 9 | 9 | 9 | 9 | 7 | 9 | 9 | 8 | 8 | 9 | 9 | 0 |
| Cheatgrass | 7 | 8 | 9 | 9 | 9 | 9 | 9 | 9 | 9 | 9 | 10 | 9 | 9 | 9 | 8 | 9 | 9 | 9 | 9 | 9 | 2 | 3 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Chickweed | 3 | 9 | 10 | 10 | 10 | 10 | 9 | 9 | 0 | 7 | 9 | 9 | 10 | 10 | 3 | 3 | 7 | 9 | 10 | 9 | 2 | 4 |
| Cocklebur | 9 | 9 | — | 9 | 10 | 9 | 7 | 9 | 1 | 9 | — | 9 | 9 | 8 | — | — | 7 | 2 | 9 | 5 | 0 | 4 |
| Corn | 9 | 9 | 10 | 10 | 10 | 10 | 10 | 9 | 7 | 9 | 9 | 10 | 10 | 9 | 9 | 9 | 9 | 9 | 8 | 10 | 9 | 8 |
| Cotton | 9 | 9 | 9 | 9 | 10 | 9 | 9 | 9 | 5 | 9 | 10 | 10 | 10 | 10 | 10 | 9 | 10 | 10 | 9 | 9 | 8 | 9 |
| Crabgrass | 2 | 9 | 9 | 10 | 10 | 9 | 10 | 9 | 3 | 8 | 6 | 7 | 6 | 3 | 2 | 2 | 8 | 5 | 2 | 6 | 6 | 0 |
| Giant foxtail | 8 | 9 | 9 | 10 | 10 | 10 | 10 | 10 | 7 | 9 | 9 | 10 | 9 | 8 | 7 | 9 | 9 | 8 | 7 | 9 | 6 | 4 |
| Lambsquarters | 9 | — | 10 | 10 | 10 | 10 | 10 | 10 | 5 | 9 | 10 | 10 | 10 | 10 | 9 | 9 | 10 | 10 | 9 | 9 | 5 | 10 |
| Morningglory | 9 | 9 | 9 | 9 | 10 | 9 | 10 | 9 | 7 | 9 | 9 | 10 | 9 | 10 | 9 | 9 | 10 | 10 | 10 | 9 | 7 | 10 |
| Nutsedge | 6 | 5 | 9 | 9 | — | 8 | 10 | 10 | — | 9 | 10 | — | 9 | — | 9 | 0 | 9 | 10 | 10 | 4 | — | — |
| Rape | 7 | 7 | 10 | 9 | 9 | 9 | 9 | 9 | 0 | 8 | 9 | 9 | 9 | 10 | 9 | 2 | 9 | 9 | 9 | 9 | 9 | 9 |
| Rice | 9 | 10 | 9 | 10 | 10 | 10 | 9 | 9 | 9 | 9 | 10 | 10 | 10 | 9 | 9 | 9 | 9 | 9 | 9 | 9 | 9 | 9 |
| Sorghum | 9 | 9 | 10 | 10 | 10 | 10 | 10 | 10 | 9 | 9 | 9 | 10 | 10 | 9 | 9 | 9 | 9 | 9 | 5 | 9 | 9 | 6 |
| Soybean | 9 | 9 | 9 | 9 | 9 | 9 | 8 | 9 | 1 | 9 | 9 | 9 | 9 | 9 | 9 | 7 | 9 | 9 | 9 | 9 | 9 | 8 |
| Sugar beet | 7 | 9 | 10 | 9 | 10 | 10 | 10 | 10 | 0 | 9 | 9 | 9 | 10 | 10 | 9 | 9 | 10 | 10 | 10 | 9 | 9 | 9 |
| Velvetleaf | 6 | 7 | 9 | 10 | 9 | 9 | 9 | 9 | 5 | 9 | 10 | 10 | 9 | 7 | 9 | 6 | 9 | 10 | 10 | 9 | 4 | 7 |
| Wheat | 8 | 9 | 10 | 10 | 9 | 10 | 9 | 9 | 8 | 9 | 9 | 9 | 9 | 9 | 8 | 8 | 9 | 9 | 6 | 9 | 9 | 2 |
| Wild buckwheat | — | — | 9 | 10 | 10 | 10 | 9 | 9 | 0 | 9 | 9 | 9 | 10 | 10 | 9 | 6 | 9 | 8 | 9 | 8 | 7 | 8 |
| Wild oat | 8 | 9 | 9 | 9 | 9 | 10 | 9 | 9 | 9 | 9 | 10 | 10 | 9 | 9 | 9 | 9 | 10 | 9 | 9 | 9 | 9 | 3 |

| Rate (50 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 223 | 224 | 225 | 226 | 227 | 228 | 229 | 230 | 231 | 232 | 233 | 234 | 235 | 236 | 237 | 238 | 239 | 240 | 241 | 242 | 243 | 244 |
| Barley | 9 | 9 | 9 | 9 | 8 | 8 | 8 | 7 | 9 | 9 | 8 | 0 | 5 | 8 | 0 | 0 | 0 | 10 | 9 | 9 | 9 | 9 |
| Barnyardgrass | 9 | 9 | 9 | 9 | 9 | 9 | 9 | 7 | 9 | 6 | 7 | 2 | 7 | 9 | 0 | 0 | 3 | 9 | 9 | 10 | 9 | 10 |
| Bedstraw | 8 | 8 | 8 | 7 | 7 | 7 | 9 | 9 | 9 | 8 | 8 | 0 | 6 | 7 | 0 | 0 | 3 | 9 | 9 | 9 | 9 | 9 |
| Blackgrass | 7 | 8 | 9 | 9 | 3 | 9 | 9 | 9 | 9 | 9 | 9 | 2 | 8 | 9 | 0 | 2 | 2 | 9 | 9 | 9 | 10 | 10 |
| Cheatgrass | 8 | 8 | 9 | 7 | 5 | 8 | 9 | 9 | 9 | 9 | 8 | 0 | 8 | 8 | 0 | 0 | 0 | 9 | 9 | 10 | 9 | 9 |
| Chickweed | 9 | 7 | 10 | 9 | 1 | 2 | 9 | 7 | 9 | 9 | 3 | 0 | 5 | 6 | 0 | 0 | 0 | 9 | 9 | 10 | 10 | 10 |
| Cocklebur | 9 | 10 | 9 | 9 | — | — | — | — | — | — | — | — | — | — | — | — | — | — | — | — | — | — |
| Corn | 9 | 9 | 10 | 10 | 9 | 9 | 9 | 9 | 9 | 9 | 6 | 0 | 5 | 9 | 0 | 0 | 1 | 9 | 9 | 9 | 10 | 9 |
| Cotton | 9 | 10 | 10 | 8 | 9 | 9 | 9 | 9 | 9 | 9 | 8 | 0 | 3 | 5 | 0 | 0 | — | 9 | 9 | — | 10 | 10 |
| Crabgrass | 2 | 8 | 2 | 5 | 2 | 6 | 2 | 6 | 7 | 7 | 0 | 2 | 2 | 7 | 0 | 0 | 2 | 9 | 10 | 10 | 10 | 10 |
| Giant foxtail | 8 | 6 | 9 | 8 | 5 | 9 | 9 | 9 | 9 | 8 | 8 | 0 | 8 | 8 | 0 | 0 | 5 | 9 | 9 | 10 | 10 | 10 |
| Lambsquarters | 9 | 9 | 10 | 9 | 9 | 9 | 9 | 9 | 9 | 9 | 9 | 0 | 4 | 7 | 0 | 2 | 0 | 9 | 10 | 10 | 10 | 10 |
| Morningglory | 10 | 9 | 10 | 9 | 9 | 9 | 9 | 10 | 9 | 9 | 9 | 0 | 7 | 9 | 0 | 0 | 3 | 10 | 10 | 9 | 10 | 10 |
| Nutsedge | 9 | 9 | 5 | 0 | — | 5 | 5 | 7 | 3 | 0 | 5 | 0 | 3 | 0 | 0 | — | 0 | 10 | 8 | 10 | 9 | 9 |
| Rape | 8 | 9 | 10 | 10 | 9 | 5 | 8 | 9 | 9 | 9 | 9 | 0 | 7 | 8 | 0 | 0 | 5 | 9 | 9 | 9 | 9 | 9 |
| Rice | 9 | 9 | 9 | 9 | 9 | 10 | 9 | 9 | 9 | 10 | 9 | 9 | 9 | 9 | 0 | 0 | 8 | 10 | 9 | 10 | 10 | 10 |
| Sorghum | 9 | 8 | 10 | 9 | 8 | 9 | 9 | 9 | 9 | 9 | 9 | 3 | 3 | 9 | 0 | 0 | 3 | 9 | 9 | 10 | 10 | 10 |
| Soybean | 9 | 8 | 9 | 9 | 8 | 9 | 9 | 8 | 9 | 9 | 8 | 0 | 1 | 4 | 0 | 0 | 0 | 9 | 9 | 9 | 9 | 9 |
| Sugar beet | 9 | 9 | 10 | 9 | 7 | 3 | 5 | 5 | 9 | 9 | 4 | 0 | 3 | 7 | 3 | 0 | 0 | 9 | 9 | 9 | 9 | 10 |
| Velvetleaf | 9 | 9 | 9 | 9 | 8 | 9 | 9 | 10 | 9 | 8 | 8 | 0 | 6 | 8 | 0 | 0 | 0 | 10 | 10 | 10 | 9 | 10 |
| Wheat | 9 | 8 | 9 | 9 | 7 | 9 | 8 | 7 | 9 | 10 | 5 | 0 | 5 | 7 | 0 | 0 | 0 | 9 | 8 | 9 | 9 | 9 |
| Wild buckwheat | 6 | 8 | 9 | 8 | 7 | — | — | 9 | 10 | 9 | 9 | 2 | 7 | — | — | — | — | — | 10 | — | 10 | — |
| Wild oat | 9 | 9 | 9 | 9 | 9 | 9 | 9 | 9 | 9 | 9 | 9 | 0 | 3 | 9 | 0 | 0 | 2 | 9 | 9 | 9 | 9 | 9 |

TABLE A-continued

TEST A

| Rate (50 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 245 | 246 | 247 | 248 | 249 | 250 | 251 | 252 | 253 | 254 | 255 | 256 | 257 | 258 | 259 | 260 | 261 | 262 | 263 | 264 | 265 | 266 |
| Barley | 9 | 9 | 9 | 9 | 9 | 7 | 7 | 8 | 8 | 8 | 4 | 9 | 9 | 9 | 9 | 9 | 9 | 7 | 9 | 9 | 9 | 9 |
| Barnyardgrass | 9 | 9 | 9 | 9 | 9 | 8 | 9 | 9 | 9 | 7 | 8 | 9 | 9 | 10 | 9 | 9 | 9 | 9 | 9 | 8 | 9 | 9 |
| Bedstraw | 10 | 8 | 9 | 8 | 7 | 7 | 9 | 8 | 8 | 8 | 8 | 9 | 9 | 9 | 8 | 8 | 9 | 7 | 10 | 8 | 8 | 8 |
| Blackgrass | 9 | 9 | 10 | 9 | 9 | 9 | 9 | 9 | 9 | 9 | 9 | 9 | 10 | 9 | 9 | 9 | 9 | 8 | 5 | 9 | 9 | 10 |
| Cheatgrass | 9 | 8 | 9 | 8 | 5 | 5 | 8 | 9 | 8 | 8 | 7 | 10 | 10 | 9 | 9 | 9 | 10 | 8 | 8 | 8 | 9 | 9 |
| Chickweed | 9 | 8 | 9 | 10 | 9 | 0 | 8 | 5 | 9 | 10 | 3 | 10 | 10 | 10 | 8 | 8 | 10 | 9 | 9 | 5 | 5 | 7 |
| Cocklebur | — | — | — | — | — | 2 | 3 | 9 | 9 | 9 | 2 | 5 | 8 | 10 | 5 | 0 | 10 | 4 | 8 | 7 | 9 | 7 |
| Corn | 9 | 9 | 9 | 9 | 9 | 9 | 9 | 10 | 9 | 9 | 8 | 10 | 10 | 10 | 10 | 10 | 10 | 9 | 10 | 9 | 9 | 9 |
| Cotton | 10 | 10 | 10 | 9 | 10 | 8 | 9 | 9 | 10 | 10 | 8 | 9 | 8 | 9 | 9 | 8 | 8 | 4 | 10 | 8 | 7 | 9 |
| Crabgrass | — | 9 | 9 | — | 8 | 2 | 6 | 7 | 7 | 2 | 0 | 9 | 8 | 9 | 7 | 9 | 8 | 0 | 3 | 2 | 2 | 2 |
| Giant foxtail | 10 | 9 | 10 | 9 | 9 | 6 | 9 | 9 | 9 | 7 | 4 | 9 | 9 | 9 | 9 | 9 | 9 | 9 | 8 | 7 | 9 | 9 |
| Lambsquarters | 10 | 10 | 10 | 10 | 9 | 5 | 8 | 8 | 10 | 10 | — | — | 10 | — | 10 | 10 | 10 | — | — | — | — | 9 |
| Morningglory | 10 | 9 | 9 | 9 | 10 | 8 | 10 | 10 | 10 | 10 | 10 | 10 | 10 | 10 | 9 | 9 | 9 | 10 | 10 | 9 | 9 | 9 |
| Nutsedge | 10 | 8 | 10 | 7 | 8 | 0 | — | — | 9 | 9 | 8 | 9 | — | — | 0 | 0 | — | — | 0 | 5 | — | — |
| Rape | 9 | 6 | 8 | 9 | 8 | 5 | 9 | 9 | 9 | 10 | 7 | 9 | 9 | 9 | 9 | 9 | 9 | 10 | 9 | 7 | 7 | 7 |
| Rice | 10 | 10 | 9 | 9 | 9 | 9 | 9 | 9 | 9 | 9 | 9 | 9 | 9 | 9 | 9 | 9 | 9 | 9 | 9 | 9 | 9 | 9 |
| Sorghum | 10 | 8 | 9 | 9 | 9 | 9 | 9 | 10 | 9 | 9 | 9 | 9 | 9 | 10 | 9 | 9 | 9 | 10 | 9 | 9 | 9 | 9 |
| Soybean | 9 | 5 | 8 | 9 | 9 | 7 | 9 | 9 | 9 | 9 | 7 | 9 | 9 | 9 | 9 | 9 | 9 | 9 | 9 | 9 | 9 | 9 |
| Sugar beet | 9 | 8 | 9 | 8 | 7 | 1 | 8 | 3 | 9 | 9 | 3 | 9 | 9 | 9 | 9 | 8 | 9 | 9 | 9 | 3 | 5 | 6 |
| Velvetleaf | 10 | 6 | 9 | 10 | 10 | 8 | 9 | 9 | 9 | 7 | 8 | 9 | 9 | 9 | 9 | 8 | 9 | 9 | 9 | 9 | 9 | 9 |
| Wheat | 9 | 8 | 8 | 9 | 9 | 7 | 8 | 8 | 6 | 5 | 3 | 9 | 9 | 9 | 9 | 9 | 9 | 5 | 9 | 9 | 8 | 8 |
| Wild buckwheat | — | — | — | — | — | 5 | — | 9 | 9 | 9 | 8 | 9 | 9 | 9 | 8 | 8 | 9 | 8 | 8 | 8 | 8 | 9 |
| Wild oat | 9 | 9 | 9 | 8 | 9 | 7 | 8 | 9 | 9 | 8 | 3 | 10 | 9 | 9 | 10 | 9 | 9 | 8 | 9 | 9 | 9 | 9 |

| Rate (50 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 267 | 268 | 269 | 270 | 271 | 272 | 273 | 274 | 275 | 276 | 277 | 278 | 279 | 280 | 281 | 282 | 283 | 284 | 285 | 286 | 287 | 288 |
| Barley | 9 | 9 | 8 | 9 | 9 | 9 | 9 | 9 | 9 | 8 | 7 | 5 | 3 | 9 | 0 | 6 | 9 | 9 | 9 | 9 | 9 | 9 |
| Barnyardgrass | 9 | 4 | 8 | 9 | 9 | 9 | 9 | 9 | 9 | 6 | 8 | 5 | 7 | 9 | 3 | 8 | 10 | 9 | 9 | 10 | 10 | 10 |
| Bedstraw | 9 | 9 | 8 | 9 | 10 | 9 | 7 | 6 | 9 | 5 | 7 | 4 | 7 | 6 | 8 | 8 | 9 | 9 | 9 | 9 | 9 | 9 |
| Blackgrass | 9 | 9 | 9 | 9 | 9 | 9 | 9 | 9 | 9 | 9 | 8 | 7 | 7 | 9 | 7 | 9 | 9 | 9 | 9 | 9 | 9 | 9 |
| Cheatgrass | 9 | 9 | 9 | 9 | 9 | 9 | 9 | 9 | 9 | 8 | 7 | 7 | 4 | 8 | 5 | 8 | 9 | 9 | 9 | 10 | 9 | 9 |
| Chickweed | 9 | 9 | 2 | 7 | 9 | 9 | 7 | 5 | 9 | 0 | 3 | 0 | 1 | 2 | 0 | 0 | 9 | 9 | 10 | 9 | 10 | 9 |
| Cocklebur | 9 | 10 | 0 | 5 | 7 | 8 | 0 | 1 | 10 | 2 | 3 | 0 | 4 | 6 | 0 | 7 | — | — | — | — | — | — |
| Corn | 9 | 9 | 9 | 10 | 10 | 10 | 9 | 9 | 9 | 9 | 7 | 0 | 0 | 8 | 2 | 6 | 9 | 9 | 9 | 9 | 9 | 9 |
| Cotton | 9 | 9 | 6 | 9 | 9 | 9 | 7 | 7 | 10 | 4 | 5 | 0 | 1 | 6 | 3 | 7 | 10 | 10 | 9 | 10 | 9 | 10 |
| Crabgrass | 4 | 4 | 0 | 9 | 9 | 9 | 8 | 3 | 9 | 3 | 3 | 0 | 0 | 3 | 0 | 0 | 9 | 9 | 9 | 9 | 9 | 10 |
| Giant foxtail | 9 | 8 | 5 | 9 | 9 | 9 | 8 | 9 | 9 | 5 | 3 | 0 | 0 | 9 | 2 | 4 | 10 | 9 | 10 | 10 | 10 | 10 |
| Lambsquarters | 10 | 10 | 8 | 10 | 10 | 10 | 8 | 7 | 10 | 9 | 8 | 5 | 7 | — | 7 | 10 | 10 | 10 | 10 | 10 | 10 | 10 |
| Morningglory | 9 | 10 | 9 | 9 | 10 | 9 | 8 | 7 | 9 | 8 | 8 | 3 | 7 | 6 | 5 | 7 | 9 | 10 | 10 | 9 | 9 | 9 |
| Nutsedge | — | — | 3 | 9 | 9 | — | — | — | 9 | 0 | 0 | 0 | 3 | 9 | 0 | 4 | — | 9 | 6 | 9 | 9 | 9 |
| Rape | 9 | 9 | 9 | 9 | 9 | 9 | 9 | 8 | 9 | 0 | 0 | 3 | 3 | 0 | 4 | 7 | 9 | 9 | 9 | 9 | 9 | 9 |

TABLE A-continued

TEST A

| | | | | | | | | | | | | | | | | | | | | | |
|---|---|---|---|---|---|---|---|---|---|---|---|---|---|---|---|---|---|---|---|---|---|
| Rice | 9 | 9 | 9 | 9 | 9 | 9 | 9 | 9 | 10 | 9 | 9 | 9 | 9 | 9 | 9 | 8 | 10 | 9 | 10 | 10 | 10 | 9 |
| Sorghum | 9 | 9 | 9 | 9 | 9 | 9 | 9 | 9 | 9 | 9 | 9 | 8 | 6 | 8 | 8 | 8 | 9 | 9 | 10 | 10 | 10 | 10 |
| Soybean | 9 | 9 | 8 | 9 | 9 | 9 | 8 | 7 | 9 | 2 | 3 | 5 | 8 | 7 | 6 | 9 | 9 | 9 | 9 | 9 | 9 | 9 |
| Sugar beet | 9 | 9 | 1 | 9 | 9 | 9 | 7 | 7 | 9 | 8 | 9 | 8 | 3 | 7 | 7 | 8 | 9 | 9 | 9 | 9 | 9 | 9 |
| Velvetleaf | 9 | 9 | 8 | 9 | 9 | 9 | 3 | 3 | 8 | 3 | 5 | 2 | 2 | 4 | 0 | 7 | 10 | 9 | 10 | 10 | 9 | 10 |
| Wheat | 9 | 9 | 4 | 9 | 9 | 9 | 9 | 9 | 9 | 8 | 6 | 2 | 0 | 7 | 0 | 6 | 9 | 9 | 9 | 9 | 9 | 9 |
| Wild buckwheat | 9 | 9 | 9 | 9 | 10 | 9 | 8 | 7 | 9 | 2 | — | 0 | 0 | 0 | 2 | 0 | — | 9 | 9 | 9 | 9 | 9 |
| Wild oat | 9 | 9 | 6 | 9 | 9 | 9 | 9 | 9 | 9 | 9 | 8 | 5 | 0 | 8 | 0 | 7 | 9 | 9 | 9 | 9 | 9 | 9 |

| Rate (50 g/ha) POST- | COMPOUND | | | | | | | | | | | | | | | | | | | | |
|---|---|---|---|---|---|---|---|---|---|---|---|---|---|---|---|---|---|---|---|---|---|
| EMERGENCE | 289 | 290 | 291 | 292 | 293 | 294 | 295 | 296 | 297 | 298 | 299 | 300 | 301 | 302 | 303 | 304 | 305 | 306 | 307 | 308 | 309 | 310 |
| Barley | 9 | 9 | 9 | 8 | 9 | 7 | 5 | 8 | 5 | 4 | 6 | 9 | 9 | 9 | 9 | 9 | 9 | 8 | 9 | 8 | 8 | 8 |
| Barnyardgrass | 9 | 9 | 9 | 9 | 9 | 6 | 6 | 8 | 9 | 7 | 0 | 9 | 9 | 9 | 9 | 9 | 9 | 9 | 9 | 8 | 9 | 9 |
| Bedstraw | 8 | 7 | 8 | 7 | 7 | 6 | 7 | 7 | 7 | 5 | 3 | 7 | 8 | 8 | 6 | 6 | 7 | 7 | 7 | 8 | 6 | 9 |
| Blackgrass | 9 | 9 | 9 | 9 | 9 | 8 | 8 | 8 | 8 | 6 | 4 | 9 | 9 | 9 | 9 | 9 | 9 | 8 | 9 | 9 | 9 | 9 |
| Cheatgrass | 9 | 8 | 9 | 8 | 8 | 6 | 6 | 8 | 7 | 4 | 3 | 9 | 9 | 9 | 9 | 9 | 9 | 8 | 7 | 8 | — | 7 |
| Chickweed | 9 | 9 | 8 | 9 | 6 | 5 | 6 | 5 | 9 | 3 | 5 | 9 | 9 | 10 | 9 | 8 | 9 | 9 | 2 | 0 | 2 | 4 |
| Cocklebur | — | — | — | — | — | — | — | — | — | — | — | — | — | — | — | — | — | — | 7 | 8 | 9 | 9 |
| Corn | 9 | 9 | 9 | 7 | 9 | 9 | 8 | 9 | 9 | 7 | 4 | 9 | 9 | 10 | 9 | 3 | 9 | 9 | 8 | 9 | 9 | 9 |
| Cotton | 9 | 9 | 9 | 9 | 10 | 8 | 8 | 9 | 9 | 9 | 0 | 9 | 9 | 9 | 9 | 9 | 9 | 9 | 9 | 9 | 9 | 9 |
| Crabgrass | 8 | 6 | 8 | 8 | 8 | 3 | 1 | 1 | 1 | 0 | 0 | 9 | 9 | 9 | 8 | 7 | 9 | 6 | 6 | 2 | 6 | 3 |
| Giant foxtail | 9 | 9 | 9 | 8 | 9 | 5 | 5 | 7 | 8 | 3 | 5 | 9 | 9 | 10 | 9 | 8 | 9 | 9 | 9 | 6 | 9 | 8 |
| Lambsquarters | 10 | 9 | 10 | 9 | 10 | 7 | 7 | 10 | 10 | 7 | 4 | — | — | 10 | 10 | 10 | 10 | 7 | 10 | 9 | 9 | 10 |
| Morningglory | 9 | 9 | 10 | 8 | 8 | 8 | 8 | 5 | 9 | 4 | 3 | 9 | 9 | 10 | 10 | 9 | 9 | 7 | 9 | 8 | 10 | 10 |
| Nutsedge | 7 | 3 | 8 | 3 | 5 | 2 | 0 | — | 1 | 0 | 0 | 5 | 9 | 9 | 5 | 0 | — | 5 | 8 | 9 | 9 | 9 |
| Rape | 2 | 9 | 9 | 10 | 9 | 2 | 7 | 8 | 9 | 5 | 0 | 9 | 10 | 9 | 9 | 9 | 9 | 5 | 9 | 7 | 10 | 10 |
| Rice | 9 | 9 | 9 | 8 | 9 | 5 | 8 | 9 | 9 | 9 | 4 | 10 | 9 | 9 | 9 | 8 | 9 | 9 | 9 | 9 | 10 | 9 |
| Sorghum | 9 | 9 | 9 | 9 | 9 | 9 | 9 | 9 | 9 | 6 | 4 | 9 | 9 | 9 | 9 | 9 | 9 | 9 | 9 | 8 | 9 | 10 |
| Soybean | 9 | 8 | 9 | 1 | 8 | 2 | 7 | 5 | 9 | 3 | 2 | 9 | 9 | 9 | 8 | 6 | 9 | 9 | 9 | 8 | 9 | 9 |
| Sugar beet | 9 | 9 | 9 | 9 | 9 | 7 | 8 | 9 | 9 | 6 | 3 | 9 | 9 | 9 | 9 | 8 | 9 | 7 | 7 | 7 | 9 | 8 |
| Velvetleaf | 8 | 9 | 9 | 9 | 8 | 6 | 8 | 8 | 9 | 3 | 0 | 9 | 9 | 10 | 9 | 9 | 9 | 9 | 9 | 9 | 8 | 9 |
| Wheat | 9 | 8 | 9 | 8 | 7 | 5 | 4 | 5 | 8 | 2 | 2 | 9 | 9 | 9 | 8 | 9 | 9 | 8 | 8 | 7 | 8 | 6 |
| Wild buckwheat | 9 | 8 | 9 | 9 | 9 | 3 | 7 | 8 | 9 | 7 | 0 | 9 | 9 | 7 | 9 | 9 | 7 | 7 | 8 | 7 | — | 9 |
| Wild oat | 9 | 9 | 9 | 8 | 8 | 5 | 8 | 8 | 7 | 2 | 5 | 9 | 9 | 9 | 8 | 9 | 9 | 9 | 9 | 8 | 9 | 9 |

| Rate (50 g/ha) POST- | COMPOUND | | | | | | | | | | | | | | | | | | | | |
|---|---|---|---|---|---|---|---|---|---|---|---|---|---|---|---|---|---|---|---|---|---|
| EMERGENCE | 311 | 312 | 313 | 314 | 315 | 316 | 317 | 318 | 319 | 320 | 321 | 322 | 323 | 324 | 325 | 326 | 327 | 328 | 329 | 330 | 331 | 332 |
| Barley | 9 | 8 | 8 | 5 | 0 | 0 | 0 | 1 | 0 | 0 | 0 | 9 | 9 | 9 | 9 | 9 | 8 | 5 | 8 | 0 | 0 | 0 |
| Barnyardgrass | 9 | 9 | 6 | 6 | 0 | 0 | 0 | 0 | 0 | 0 | 0 | 9 | 9 | 9 | 9 | 7 | 9 | 2 | 4 | 0 | 0 | 0 |
| Bedstraw | 9 | 8 | 7 | 6 | 0 | 6 | 7 | 6 | 5 | 2 | 0 | 8 | 9 | 9 | 8 | 8 | 9 | 7 | 8 | 0 | 0 | 0 |
| Blackgrass | 9 | 9 | 9 | 6 | 0 | 3 | 2 | 3 | 0 | 0 | 0 | 9 | 9 | 9 | 9 | 9 | 9 | 6 | 9 | 0 | 0 | 0 |
| Cheatgrass | 8 | 7 | 7 | 5 | 0 | 0 | 1 | 5 | 2 | 0 | 0 | 9 | 9 | 9 | 9 | 9 | 9 | 9 | 9 | 0 | 0 | 0 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Chickweed | 2 | 3 | 3 | 5 | 0 | 2 | 0 | 0 | 0 | 0 | 0 | 9 | 10 | 9 | 9 | 7 | 10 | 1 | 4 | 0 | 0 | 0 |
| Cocklebur | 9 | 9 | 3 | — | 0 | 7 | 8 | 9 | 9 | 8 | 0 | 9 | 10 | 10 | 7 | 2 | 10 | 0 | 6 | 0 | 0 | 0 |
| Corn | 9 | 8 | 4 | 0 | 0 | 0 | 0 | 6 | 6 | 0 | 0 | 9 | 9 | 9 | 9 | 9 | 9 | 9 | 9 | 0 | 0 | 0 |
| Cotton | 9 | 9 | 1 | 4 | 0 | 7 | 3 | 6 | 2 | 0 | 0 | 9 | 10 | 9 | 9 | 9 | 9 | 8 | 7 | 0 | 0 | 0 |
| Crabgrass | 3 | 3 | 0 | 0 | 0 | 0 | 0 | 0 | 0 | 0 | 0 | 9 | 9 | 9 | 7 | 4 | 5 | 0 | 7 | 0 | 0 | 0 |
| Giant foxtail | 8 | 9 | 6 | 2 | 0 | 0 | 0 | 3 | 0 | 0 | 0 | 9 | 9 | 9 | 9 | 4 | 9 | 8 | 9 | 0 | 0 | 0 |
| Lambsquarters | 10 | — | 7 | 6 | 0 | 7 | 8 | 7 | 4 | 0 | 0 | 10 | 10 | 10 | 9 | 7 | 10 | — | 7 | — | 0 | 0 |
| Morningglory | 10 | 9 | 8 | 4 | 0 | 8 | 7 | 7 | 7 | 2 | 0 | 9 | 10 | 10 | 9 | 6 | 9 | 2 | 7 | 0 | 0 | 0 |
| Nutsedge | 9 | 9 | 0 | 0 | 0 | 0 | 0 | 0 | 0 | 0 | 0 | 9 | 9 | 9 | 3 | — | 4 | 0 | 0 | 0 | 0 | 0 |
| Rape | 10 | 7 | 4 | 4 | 0 | 5 | 7 | 7 | 7 | 2 | 2 | 10 | 10 | 9 | 9 | 9 | 9 | 0 | 0 | 0 | 0 | 0 |
| Rice | 9 | 9 | 9 | 9 | 0 | 7 | 5 | 9 | 9 | 4 | 0 | 9 | 10 | 10 | 9 | 9 | 9 | 9 | 9 | 0 | 0 | 0 |
| Sorghum | 9 | 9 | 8 | 8 | 0 | 0 | 0 | 7 | 2 | 0 | 0 | 9 | 9 | 9 | 9 | 9 | 9 | 9 | 9 | 0 | 0 | 0 |
| Soybean | 9 | 8 | 8 | 6 | 0 | 0 | 0 | 5 | 2 | 0 | 0 | 9 | 9 | 9 | 9 | 9 | 9 | 7 | 9 | 0 | 0 | 0 |
| Sugar beet | 9 | 8 | 5 | 7 | 0 | 3 | 2 | 6 | 7 | 0 | 2 | 9 | 9 | 10 | 9 | 9 | 9 | 7 | 9 | 0 | 0 | 0 |
| Velvetleaf | 6 | 9 | 0 | 2 | 0 | 6 | 2 | 3 | 4 | 0 | 0 | 9 | 9 | 10 | 7 | 2 | 9 | 5 | 6 | 0 | 0 | 0 |
| Wheat | 8 | 5 | 5 | 3 | 0 | 0 | 0 | 3 | 0 | 0 | 0 | 9 | 9 | 9 | 9 | 9 | 8 | 7 | 9 | 0 | 0 | 0 |
| Wild buckwheat | 9 | 9 | 0 | — | — | — | — | — | — | — | — | — | — | — | — | — | — | — | — | — | — | — |
| Wild oat | 9 | 7 | 7 | 5 | 0 | 0 | 0 | 0 | 0 | 2 | 0 | 9 | 9 | 9 | 9 | 9 | 7 | 9 | 9 | 0 | 0 | 0 |

| Rate (50 g/ha) POST-EMERGENCE | COMPOUND 333 | 334 | 335 | 336 | 337 | 338 | 339 | 340 | 341 | 342 |
|---|---|---|---|---|---|---|---|---|---|---|
| Barley | 0 | 0 | 0 | 0 | 0 | 9 | 9 | 9 | 9 | 9 |
| Barnyardgrass | 0 | 0 | 0 | 0 | 0 | 10 | 10 | 9 | 9 | 10 |
| Bedstraw | 2 | 0 | 0 | 0 | 2 | 9 | 9 | 8 | 9 | 9 |
| Blackgrass | 0 | 0 | 0 | 0 | 0 | 9 | 9 | 9 | 9 | 10 |
| Cheatgrass | 0 | 0 | 0 | 0 | 0 | 9 | 9 | 9 | 9 | 9 |
| Chickweed | 0 | 3 | 2 | 0 | 2 | 10 | 10 | 7 | 2 | 9 |
| Cocklebur | 0 | 0 | 0 | 0 | 0 | 10 | 10 | 5 | 0 | 10 |
| Corn | 0 | 0 | 0 | 0 | 0 | 10 | 10 | 9 | 9 | 10 |
| Cotton | 0 | 0 | 0 | 0 | 0 | 9 | 9 | 5 | 3 | 10 |
| Crabgrass | 0 | 0 | 0 | 0 | 0 | 9 | 10 | 5 | 3 | 7 |
| Giant foxtail | 0 | 0 | 0 | 0 | 0 | 9 | 10 | 9 | 8 | 10 |
| Lambsquarters | 2 | 0 | 0 | 0 | 2 | 10 | 10 | 7 | 7 | 10 |
| Morningglory | 0 | 0 | 0 | 0 | 0 | 10 | 9 | 7 | 6 | 10 |
| Nutsedge | 0 | 0 | 0 | 4 | 0 | 9 | 9 | 3 | 1 | 10 |
| Rape | 2 | 4 | 0 | 0 | 1 | 9 | 9 | 8 | 8 | 9 |
| Rice | 4 | 0 | 0 | 0 | 0 | 9 | 9 | 9 | 9 | 10 |
| Sorghum | 0 | 0 | 0 | 0 | 0 | 9 | 9 | 9 | 9 | 10 |
| Soybean | 0 | 0 | 0 | 0 | 0 | 9 | 9 | 7 | 5 | 9 |
| Sugar beet | 1 | 2 | 0 | 0 | 1 | 10 | 9 | 7 | 5 | 9 |
| Velvetleaf | 0 | 0 | 0 | 0 | 0 | 10 | 9 | 3 | 0 | 10 |
| Wheat | 0 | 0 | 0 | 0 | 0 | 9 | 9 | 9 | 9 | 9 |
| Wild buckwheat | — | — | — | — | — | — | — | — | — | — |
| Wild oat | 0 | 0 | 0 | 0 | 0 | 9 | 9 | 9 | 9 | 9 |

TABLE A-continued

TEST A

| Rate (50 g/ha) PRE-EMERGENCE | COMPOUND 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|
| Barley | 4 | 7 | 7 | 3 | 9 | 2 | 0 | 1 | 0 | 0 | 0 | 0 | 0 | 0 | 0 | 0 | 0 | 0 | 0 | 0 | 0 | 0 | 0 | 0 | 8 | 8 | 8 | 9 | 6 |
| Barnyardgrass | 6 | 9 | 9 | 9 | 9 | 0 | 2 | 0 | 2 | 0 | 3 | 0 | 0 | 0 | 0 | 0 | 0 | 0 | 0 | 2 | 0 | 0 | 0 | 0 | 9 | 9 | 9 | 9 | 9 |
| Bedstraw | 4 | 9 | 9 | 9 | 9 | 8 | 0 | 6 | 0 | 7 | 0 | 0 | 0 | 0 | 0 | 2 | 0 | 3 | 0 | 9 | 2 | 2 | 0 | 0 | 9 | 9 | 9 | 9 | 8 |
| Blackgrass | 6 | 8 | 9 | 4 | 8 | 4 | 5 | 2 | 4 | 6 | 7 | 0 | 3 | 0 | 1 | 0 | 0 | 2 | 3 | 3 | 0 | 0 | 0 | 2 | 9 | 9 | 9 | 9 | 3 |
| Cheatgrass | 9 | 9 | 9 | 5 | 10 | 8 | 6 | 5 | 6 | 5 | 6 | 2 | 3 | 0 | 0 | 2 | 0 | 2 | 0 | 3 | 0 | 0 | 0 | 2 | 9 | 9 | 9 | 9 | 9 |
| Chickweed | 8 | 9 | 10 | 6 | 9 | 9 | 0 | 8 | — | — | 9 | 0 | 8 | 5 | 2 | 0 | 5 | 8 | — | 8 | 7 | 2 | 2 | 5 | 9 | 9 | 9 | 8 | 8 |
| Cocklebur | 0 | 0 | 0 | 0 | 8 | 10 | 0 | 4 | 0 | 0 | 2 | 0 | 0 | — | 0 | 0 | 0 | 4 | 0 | 0 | 0 | 0 | 0 | 0 | — | — | — | — | — |
| Corn | 6 | 9 | 9 | 9 | 9 | 4 | 2 | 0 | 1 | 6 | 7 | 0 | 1 | 0 | 0 | 0 | 0 | 0 | 0 | 2 | 0 | 0 | 0 | 0 | 9 | 9 | 9 | 9 | 9 |
| Cotton | 5 | 8 | 7 | 7 | 8 | 7 | 0 | 0 | 4 | 0 | 0 | 0 | 0 | 0 | 0 | 0 | 0 | 0 | 0 | 0 | 0 | 0 | 0 | 0 | 5 | 7 | 7 | 6 | 7 |
| Crabgrass | 8 | 9 | 8 | 4 | 8 | 7 | 0 | 0 | 1 | 0 | 2 | 0 | 0 | 0 | 0 | 0 | 0 | 0 | 0 | 0 | 0 | 0 | 0 | 0 | 9 | 9 | 10 | 9 | 10 |
| Giant foxtail | 1 | 9 | 6 | 3 | 3 | 2 | 2 | 2 | 2 | 2 | 3 | 0 | 0 | 2 | 0 | 0 | 0 | 2 | 0 | 0 | 2 | 0 | 0 | 0 | 9 | 9 | 9 | 9 | 9 |
| Lambsquarters | 9 | 9 | 9 | 8 | 9 | — | 0 | 6 | 6 | 6 | 9 | 6 | 6 | — | 5 | 0 | — | 3 | 6 | 3 | 0 | 0 | 0 | 0 | 9 | 10 | 10 | 10 | 9 |
| Morningglory | 0 | 5 | 8 | 5 | 9 | 5 | 2 | 2 | 0 | 2 | 0 | 0 | 0 | 0 | 0 | 0 | 0 | 0 | 0 | 1 | 0 | 0 | 0 | 0 | 6 | 9 | 8 | 9 | 9 |
| Nutsedge | 7 | 10 | 10 | 3 | 8 | 10 | 0 | 0 | 0 | 0 | 0 | 0 | 0 | 0 | 0 | 0 | 0 | 0 | 0 | 0 | 0 | 0 | 0 | — | 9 | 8 | 8 | 9 | 10 |
| Rape | 8 | 6 | 9 | 9 | 9 | 9 | 0 | 0 | 3 | 5 | 2 | 0 | 6 | 0 | 0 | 1 | 0 | 2 | 0 | 0 | 0 | 0 | 0 | 0 | 8 | 9 | 9 | 9 | 9 |
| Rice | 9 | 9 | 8 | 9 | 10 | 9 | 2 | 0 | 3 | 0 | 3 | 0 | 6 | 0 | 0 | 0 | 0 | 0 | 2 | 2 | 0 | 0 | 0 | 4 | 10 | 9 | 9 | 10 | 10 |
| Sorghum | 9 | 9 | 7 | 7 | 9 | 9 | 3 | 0 | 2 | 0 | 0 | 0 | 0 | 0 | 0 | 0 | 0 | 0 | 0 | 0 | 0 | 0 | 3 | 0 | 9 | 9 | 8 | 9 | 9 |
| Soybean | 2 | 7 | 6 | 7 | 8 | 2 | 0 | 2 | 4 | 2 | 4 | 0 | 2 | 0 | 0 | 0 | 0 | 0 | 3 | 1 | 0 | 0 | 0 | 0 | 8 | 8 | 8 | 8 | 9 |
| Sugar beet | 7 | 8 | 9 | 9 | 10 | 9 | 0 | 3 | 4 | 4 | 7 | 2 | 2 | 4 | 0 | 0 | 0 | 0 | 2 | 0 | 0 | 0 | 0 | 2 | 8 | 9 | 9 | 9 | 9 |
| Velvetleaf | 4 | 8 | 5 | 6 | 9 | 0 | 2 | 1 | 0 | 0 | 0 | 0 | 0 | 2 | 0 | 0 | 0 | 0 | 0 | 0 | 0 | 0 | 0 | 0 | 3 | 5 | 6 | 9 | 8 |
| Wheat | 8 | 8 | 9 | 2 | 9 | 5 | 1 | 0 | 0 | 2 | 0 | 0 | 0 | 0 | 0 | 0 | 0 | — | 0 | 0 | 0 | 0 | 0 | 0 | 9 | 9 | 8 | 3 | 7 |
| Wild buckwheat | 2 | 7 | 9 | 9 | 9 | 7 | 0 | 4 | 0 | 0 | 0 | 0 | 0 | 2 | 0 | 2 | 0 | 0 | 0 | 2 | 0 | 0 | 2 | 0 | 9 | 9 | 3 | 8 | 3 |
| Wild oat | 7 | 7 | 8 | 2 | 9 | 7 | 2 | 2 | 0 | 2 | 0 | 0 | 0 | 2 | 0 | 0 | 0 | 0 | 0 | 0 | 0 | 0 | 0 | 0 | 9 | 8 | 9 | 8 | 8 |

| Rate (50 g/ha) PRE-EMERGENCE | COMPOUND 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 |
|---|---|---|---|---|---|---|---|---|---|---|---|---|---|---|---|---|---|---|---|---|---|---|---|---|---|---|---|---|---|
| Barley | 2 | 2 | 0 | 0 | 2 | 8 | 8 | 0 | 2 | 0 | 0 | 0 | 0 | 0 | 0 | 0 | 0 | 0 | 0 | 0 | 3 | 7 | 2 | 8 | 2 | 2 | 4 | 4 | 2 |
| Barnyardgrass | 9 | 7 | 6 | 0 | 2 | 9 | 9 | 0 | 7 | 2 | 0 | 0 | 0 | 0 | 0 | 0 | 0 | 0 | 0 | 0 | 9 | 9 | 8 | 9 | 8 | 9 | 9 | 9 | 9 |
| Bedstraw | 8 | 6 | 6 | 7 | 0 | 7 | 8 | 2 | 3 | 0 | 0 | 0 | 0 | 0 | 0 | 0 | — | 2 | 0 | 0 | 8 | 8 | 5 | 8 | 8 | 7 | 7 | 9 | 9 |
| Blackgrass | 7 | 8 | 0 | 5 | 7 | 7 | 8 | 0 | 3 | 2 | 2 | 2 | 1 | 0 | 0 | 2 | 1 | 3 | 2 | 0 | 8 | 8 | 9 | 9 | 4 | 2 | 8 | 9 | 9 |
| Cheatgrass | 8 | 7 | 8 | 4 | 9 | 9 | 9 | 0 | 7 | 5 | 4 | 3 | 3 | 3 | 0 | 2 | 3 | 3 | 0 | 4 | 8 | 8 | 8 | 9 | 6 | 2 | 8 | 9 | 8 |
| Chickweed | 9 | 7 | 6 | 8 | 8 | 9 | 9 | 0 | 8 | 6 | 6 | 7 | 9 | 2 | 0 | 3 | 0 | 7 | 2 | 3 | — | 9 | 8 | 9 | 10 | 10 | 10 | 9 | 9 |
| Cocklebur | — | — | — | — | — | — | — | — | — | — | — | — | — | — | — | — | — | — | — | — | 9 | 9 | 8 | 9 | 9 | 0 | 6 | 9 | 8 |
| Corn | 9 | 6 | 3 | 2 | 9 | 9 | 9 | 1 | 2 | 2 | 0 | 0 | 0 | 0 | 0 | 0 | 0 | 0 | 0 | 0 | 8 | 8 | 0 | 9 | 9 | 3 | 7 | 9 | 9 |
| Cotton | 9 | 0 | 0 | 1 | 3 | 5 | 8 | 0 | 0 | 0 | 0 | 0 | 0 | 0 | 0 | 0 | 0 | 0 | 0 | 1 | 8 | 9 | 1 | 9 | 9 | 2 | 9 | 8 | 8 |
| Crabgrass | 9 | 7 | 6 | 1 | 9 | 9 | 9 | 0 | 0 | 0 | 0 | 0 | 0 | 0 | 0 | 0 | 0 | 0 | 0 | 0 | 6 | 9 | 6 | 9 | 5 | 2 | 1 | 7 | 2 |
| Giant foxtail | 9 | 9 | 5 | 2 | 9 | 9 | 9 | 0 | 5 | 0 | 0 | 0 | 0 | 0 | 0 | 0 | 0 | 0 | 0 | 0 | 9 | 9 | 5 | 9 | 1 | 0 | 2 | 9 | 6 |
| Lambsquarters | 8 | 9 | 9 | 7 | 10 | 10 | 10 | 4 | 8 | 9 | 0 | 10 | 3 | 0 | 0 | 0 | 0 | 0 | 4 | 2 | 9 | 9 | 8 | 10 | 9 | 8 | 9 | 9 | 9 |
| Morningglory | 9 | 2 | 0 | 0 | 1 | 9 | 9 | 0 | 0 | 0 | 0 | 0 | 0 | 0 | 0 | 0 | 0 | 0 | 0 | 0 | 7 | 9 | 2 | 9 | 9 | 8 | 0 | 2 | 6 |
| Nutsedge | 9 | 5 | 0 | 0 | 0 | 8 | 2 | 0 | 0 | 0 | 0 | 0 | 0 | — | 0 | 0 | 0 | 0 | 0 | 0 | 10 | 10 | 5 | 10 | 10 | 10 | — | 8 | — |
| Rape | 9 | 0 | 0 | 4 | 3 | 4 | 8 | 0 | 3 | 0 | 2 | 2 | 2 | 2 | 0 | 0 | 0 | 0 | 0 | 0 | 9 | 9 | 9 | 9 | 9 | 8 | 9 | 9 | 9 |

TABLE A-continued

TEST A

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | 10 | 8 | 7 | 4 | 7 | 9 | 10 | 0 | 8 | 5 | 4 | 8 | 3 | 0 | 0 | 0 | 0 | 2 | 0 | 3 | 9 | 10 | 9 | 9 | 9 | 9 | 8 | 8 | 9 |
| Sorghum | 9 | 6 | 2 | 2 | 2 | 9 | 9 | 0 | 2 | 1 | 0 | 0 | 0 | 0 | 0 | 0 | 0 | 0 | 0 | 0 | 7 | 6 | 3 | 9 | 3 | 1 | 7 | 9 | 4 |
| Soybean | 9 | 2 | 1 | 1 | 1 | 8 | 9 | 1 | 1 | 3 | 0 | 0 | 2 | 0 | 0 | 0 | 0 | 0 | 0 | 0 | 6 | 8 | 1 | 8 | 9 | 1 | 2 | 8 | 8 |
| Sugar beet | 9 | 4 | 7 | 6 | 8 | 9 | 9 | 2 | 9 | 2 | 1 | 2 | 3 | 2 | 0 | 2 | 0 | 2 | 0 | 2 | 9 | 9 | 9 | 9 | 9 | 9 | 9 | 9 | 9 |
| Velvetleaf | 9 | 1 | 1 | 0 | 1 | 2 | 9 | 0 | 0 | 0 | 0 | 0 | 0 | 0 | 0 | 0 | 0 | 0 | 0 | 0 | 8 | 9 | 5 | 9 | 0 | 4 | 5 | 8 | 7 |
| Wheat | 8 | 7 | 2 | 0 | 0 | 8 | 9 | 0 | 2 | 0 | 0 | 2 | 0 | 0 | 0 | 0 | 0 | 0 | 0 | 0 | 3 | 8 | 7 | 9 | 2 | 0 | 3 | 7 | 3 |
| Wild buckwheat | 8 | 2 | 0 | 0 | 0 | 3 | 2 | 0 | 2 | 0 | 2 | 0 | 3 | 0 | 0 | 0 | 0 | 0 | 0 | 0 | 1 | 7 | 6 | 8 | 9 | 0 | 7 | 9 | 9 |
| Wild oat | 9 | 8 | 2 | 3 | 8 | 9 | 9 | 0 | 2 | 2 | 0 | 0 | 2 | 0 | 0 | 0 | 0 | 2 | 0 | 0 | 4 | 8 | 8 | 9 | 8 | 0 | 8 | 8 | 5 |

| Rate (50 g/ha) PRE- | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| EMERGENCE | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
| Barley | 4 | 2 | 0 | 2 | 6 | 6 | 0 | 0 | 3 | 2 | 1 | 5 | 0 | 0 | 2 | 2 | 0 | 0 | 3 | 0 | 0 | 0 | 5 | 7 | 2 | 4 | 0 | 1 | 0 |
| Barnyardgrass | 5 | 6 | 4 | 9 | 9 | 9 | 6 | 0 | 8 | 7 | 7 | 1 | 0 | 0 | 0 | 6 | 0 | 1 | 4 | 9 | 0 | 0 | 5 | 9 | 9 | 8 | 3 | 9 | 3 |
| Bedstraw | 9 | 9 | 8 | 0 | 6 | 8 | 0 | 4 | 5 | 6 | 0 | 8 | 8 | 2 | 0 | 1 | 1 | 0 | 2 | 1 | 0 | 0 | 1 | 8 | 9 | 5 | 3 | 7 | 1 |
| Blackgrass | 7 | 6 | 5 | 4 | 8 | 9 | 4 | 1 | 5 | 6 | 2 | 3 | 3 | 0 | 0 | 5 | 0 | 2 | 5 | 7 | 3 | 0 | 9 | 9 | 9 | 7 | 2 | 9 | 3 |
| Cheatgrass | 8 | 7 | 6 | 7 | 8 | 8 | 7 | 5 | 7 | 8 | 7 | 6 | 0 | 0 | 7 | 8 | 0 | 2 | 8 | 9 | 1 | 0 | 9 | 9 | 9 | 7 | 2 | 9 | 8 |
| Chickweed | 10 | 10 | 9 | 5 | 9 | 9 | 3 | 0 | 9 | 9 | 8 | 8 | 7 | 5 | 5 | 7 | 0 | 0 | 5 | 7 | 2 | 0 | 7 | 9 | 9 | 7 | 0 | 7 | 1 |
| Cocklebur | 9 | 9 | 0 | 1 | 8 | 8 | 0 | — | 8 | 8 | 0 | 9 | 0 | 0 | 0 | — | 2 | 1 | 2 | 5 | 0 | 0 | — | — | — | — | — | — | — |
| Corn | 9 | 7 | 2 | 0 | 7 | 9 | 8 | 2 | 1 | 9 | 3 | 8 | 2 | 0 | 0 | 2 | 2 | 0 | 5 | 9 | 0 | 0 | 0 | 7 | 9 | 9 | 9 | 5 | 0 |
| Cotton | 9 | 9 | 5 | 0 | 7 | 8 | 1 | 0 | 4 | 8 | 0 | 8 | 7 | 0 | 1 | 2 | 0 | 2 | 0 | 1 | 0 | 0 | 7 | 5 | 8 | 3 | 0 | 5 | 0 |
| Crabgrass | 4 | 3 | 0 | 6 | 9 | 9 | 6 | 2 | 7 | 5 | 2 | 2 | 0 | 0 | 1 | 2 | 1 | 0 | 4 | 7 | 0 | 0 | 6 | 4 | 7 | 3 | 4 | 0 | 0 |
| Giant foxtail | 2 | 4 | 2 | 2 | 9 | 9 | 3 | 0 | 5 | 6 | 2 | 2 | 0 | 0 | 1 | 4 | 0 | 0 | 5 | 8 | 0 | 0 | 3 | 9 | 8 | 3 | 3 | 5 | 2 |
| Lambsquarters | 9 | 9 | 10 | 9 | 9 | 10 | 9 | 0 | 9 | 9 | 6 | — | 8 | 7 | 6 | 9 | 0 | 0 | 8 | 7 | 0 | 0 | 9 | 10 | 10 | 10 | 9 | 10 | 8 |
| Morningglory | 9 | 9 | 3 | 0 | 2 | 8 | 3 | 0 | 0 | 7 | 2 | 9 | 0 | 0 | 0 | 5 | 1 | 2 | 3 | 5 | 0 | 0 | 7 | 7 | 9 | 7 | 3 | 9 | 1 |
| Nutsedge | — | 9 | 8 | 5 | 10 | 10 | 0 | 0 | 10 | 10 | 0 | 0 | 0 | — | 0 | 0 | 0 | 0 | 4 | 10 | — | — | 9 | 10 | 10 | 5 | 6 | 10 | 0 |
| Rape | 9 | 9 | 9 | 5 | 9 | 9 | 1 | 0 | 9 | 8 | 3 | 7 | 9 | 2 | 2 | 2 | 0 | 0 | 3 | 7 | 1 | 0 | 9 | 9 | 9 | 4 | 0 | 9 | 1 |
| Rice | 9 | 9 | 9 | 9 | 10 | 8 | 10 | 8 | 9 | 7 | 8 | 7 | 2 | 1 | 4 | 7 | 0 | 0 | 7 | 8 | 0 | 0 | 8 | 8 | 9 | 9 | 8 | 9 | 0 |
| Sorghum | 5 | 3 | 2 | 6 | 8 | 9 | 4 | 2 | 9 | 7 | 0 | 2 | 2 | 0 | 2 | 1 | 0 | 0 | 4 | 5 | 0 | 0 | 8 | 9 | 9 | 9 | 5 | 9 | 3 |
| Soybean | 9 | 8 | 0 | 1 | 8 | 9 | 3 | 3 | 0 | 8 | 0 | 7 | 4 | 0 | 5 | 7 | 1 | 3 | 7 | 6 | 0 | 0 | 2 | 6 | 9 | 7 | 4 | 9 | 1 |
| Sugar beet | 9 | 9 | 9 | 4 | 9 | 9 | 5 | 5 | 9 | 8 | 7 | 9 | 9 | 4 | 4 | 8 | 3 | 2 | 9 | 8 | 1 | 0 | 8 | 9 | 9 | 9 | 8 | 9 | 8 |
| Velvetleaf | 9 | 8 | 2 | 2 | 7 | 7 | 5 | 0 | 5 | 6 | 2 | 8 | 0 | 0 | 0 | 2 | 1 | 0 | 0 | 3 | 0 | 0 | 5 | 9 | 9 | 4 | 0 | 1 | 1 |
| Wheat | 2 | 4 | 0 | 5 | 7 | 7 | 8 | 0 | 7 | 2 | 1 | 2 | 0 | 0 | 0 | 0 | 0 | 0 | 4 | 2 | 0 | 0 | 8 | 7 | 7 | 8 | 5 | 1 | 0 |
| Wild buckwheat | 9 | 8 | 7 | 3 | 3 | 3 | 0 | 3 | 0 | 0 | 0 | 3 | 0 | 0 | 0 | 1 | 2 | 0 | 1 | 4 | 0 | 0 | 6 | 9 | 9 | 9 | — | 7 | — |
| Wild oat | 8 | 8 | 0 | 5 | 6 | 6 | 6 | 0 | 6 | 4 | 2 | 2 | 0 | 0 | 2 | 3 | 0 | 0 | 3 | 3 | 0 | 0 | 7 | 6 | 3 | 7 | 1 | 2 | 0 |

| Rate (50 g/ha) PRE- | COMPOUND | | | | | | | | | | | | | | | | | | | | | | | | |
|---|---|---|---|---|---|---|---|---|---|---|---|---|---|---|---|---|---|---|---|---|---|---|---|---|---|
| EMERGENCE | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
| Barley | 0 | 0 | 0 | 0 | 0 | 1 | 2 | 3 | 0 | 2 | 1 | 1 | 0 | 0 | 4 | 7 | 2 | 1 | 0 | 5 | 6 | 8 | 8 | 7 | 0 |
| Barnyardgrass | 9 | 9 | 4 | 2 | 9 | 5 | 7 | 5 | 3 | 3 | 4 | 1 | 2 | 0 | 3 | 6 | 2 | 0 | 0 | 9 | 7 | 9 | 9 | 8 | 8 |
| Bedstraw | 3 | 8 | 0 | 0 | 0 | 0 | 0 | 0 | 2 | 3 | 5 | 2 | 5 | 0 | 2 | 7 | 2 | 2 | 0 | 8 | 8 | 7 | 8 | 5 | 2 |
| Blackgrass | 6 | 7 | 7 | 2 | 8 | 2 | 6 | 2 | 3 | 6 | 8 | 7 | 4 | 2 | 6 | 8 | 5 | 2 | 2 | 7 | 9 | 9 | 9 | 7 | 7 |
| Cheatgrass | 9 | 8 | 7 | 5 | 8 | 7 | 0 | 0 | 5 | 6 | 6 | 4 | 0 | 0 | 8 | 8 | 2 | 3 | 3 | 9 | 9 | 9 | 9 | 8 | 7 |

TABLE A-continued

TEST A

| | | | | | | | | | | | | | | | | | | | | | | | | | |
|---|---|---|---|---|---|---|---|---|---|---|---|---|---|---|---|---|---|---|---|---|---|---|---|---|---|
| Chickweed | 7 | 8 | 8 | 8 | 0 | 9 | 8 | — | 9 | 9 | 9 | 9 | 9 | 0 | 5 | 8 | 0 | 0 | 0 | 10 | 9 | 9 | 9 | 8 | 9 |
| Cocklebur | — | — | — | — | — | — | — | — | — | — | — | — | — | — | — | — | — | — | — | — | — | — | — | — | — |
| Corn | 6 | 9 | 9 | 9 | 0 | 4 | 7 | 8 | 7 | 6 | 7 | 8 | 7 | 0 | 0 | 0 | 0 | 0 | 0 | 9 | 8 | 9 | 9 | 8 | 7 |
| Cotton | 5 | 5 | 2 | 0 | 0 | 6 | 5 | 3 | 7 | 9 | 3 | 7 | 5 | 0 | — | 9 | 0 | 0 | 0 | 9 | 9 | 9 | 9 | 7 | 7 |
| Crabgrass | 2 | 3 | 0 | 0 | 0 | 7 | 5 | 2 | 2 | 6 | 5 | 0 | 0 | 0 | 1 | 3 | 1 | 0 | 0 | 8 | 8 | 9 | 9 | 7 | 8 |
| Giant foxtail | 5 | 3 | 0 | 0 | 0 | 5 | 7 | 0 | 1 | 2 | 7 | 0 | 0 | 0 | 3 | 3 | 0 | 0 | 0 | 8 | 3 | 8 | 9 | 6 | 2 |
| Lambsquarters | 9 | 9 | 9 | 9 | 9 | 9 | 6 | 9 | 9 | — | 9 | 7 | 9 | 0 | 9 | 9 | 0 | 2 | 3 | 9 | 10 | 9 | 9 | 9 | 9 |
| Morningglory | 2 | 8 | 6 | 7 | 2 | 1 | 1 | 9 | 4 | 0 | 1 | 2 | 3 | 0 | 7 | 8 | 0 | 0 | 0 | 10 | 9 | 9 | 8 | 9 | 6 |
| Nutsedge | 8 | 10 | 10 | 0 | 0 | 0 | 6 | 0 | 4 | 5 | 0 | 0 | 3 | 0 | 0 | 0 | 10 | 0 | — | 10 | 10 | 10 | 10 | 4 | 9 |
| Rape | 9 | 9 | 3 | 3 | 4 | 2 | 3 | 7 | 7 | 6 | 2 | 7 | 9 | 0 | 3 | 6 | 0 | 0 | 0 | 9 | 9 | 9 | 9 | 9 | 7 |
| Rice | 7 | 8 | 9 | 8 | 9 | 4 | 9 | 8 | 9 | 3 | 8 | 3 | 4 | 0 | 5 | 8 | 4 | 0 | 0 | 9 | 9 | 10 | 9 | 9 | 9 |
| Sorghum | 9 | 8 | 7 | 6 | 6 | 7 | 8 | 9 | 4 | 8 | 9 | 5 | 3 | 0 | 3 | 8 | 0 | 0 | 0 | 8 | 8 | 9 | 9 | 9 | 9 |
| Soybean | 5 | 7 | 5 | 3 | 0 | 2 | 5 | 7 | 7 | 1 | 3 | 4 | 7 | 0 | 0 | 1 | 0 | 0 | 0 | 9 | 8 | 8 | 8 | 8 | 5 |
| Sugar beet | 8 | 6 | 5 | 8 | 2 | 8 | 5 | 8 | 9 | 5 | 6 | 9 | 9 | 0 | 8 | 9 | 1 | 1 | 0 | 9 | 9 | 9 | 9 | 9 | 8 |
| Velvetleaf | 4 | 6 | 0 | 0 | 0 | 0 | 1 | 1 | 0 | 1 | 0 | 6 | 1 | 0 | 0 | 3 | 1 | 0 | 0 | 9 | 8 | 8 | 9 | 9 | 9 |
| Wheat | 0 | 0 | 2 | 3 | 0 | 3 | 6 | 0 | 0 | 3 | 6 | 0 | 0 | 0 | 8 | 8 | 2 | 2 | 0 | 6 | 6 | 9 | 7 | 5 | 0 |
| Wild buckwheat | 9 | 10 | 0 | — | — | 0 | 5 | 8 | 0 | 3 | 5 | 3 | 5 | 0 | 2 | 7 | 5 | 2 | 1 | 5 | 8 | 3 | 3 | 2 | 5 |
| Wild oat | 0 | 2 | 5 | 0 | 0 | 1 | 2 | 1 | 2 | 3 | 5 | 6 | 0 | 0 | 4 | 3 | 0 | 0 | 0 | 7 | 7 | 7 | 7 | 2 | 5 |

| Rate (50 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 113 | 114 | 115 | 116 | 117 | 118 | 119 | 120 | 121 | 122 | 123 | 124 | 125 | 126 | 127 | 128 | 129 | 130 | 131 | 132 | 133 | 134 |
| Barley | 5 | 7 | 0 | 2 | 0 | 0 | 8 | 7 | 7 | 7 | 1 | 2 | 2 | 1 | 1 | 1 | 0 | 0 | 0 | 2 | 0 | 0 |
| Barnyardgrass | 9 | 9 | 9 | 9 | 7 | 7 | 10 | 9 | 9 | 9 | 1 | 4 | 0 | 5 | 0 | 0 | 2 | 6 | 3 | 2 | 0 | 0 |
| Bedstraw | 7 | 8 | 8 | 9 | 9 | 7 | 7 | 3 | 8 | 7 | 2 | 5 | 3 | 8 | 6 | 1 | 2 | 0 | 0 | 8 | 7 | 2 |
| Blackgrass | 7 | 7 | 8 | 5 | 3 | 3 | 8 | 7 | 9 | 6 | 5 | 6 | 5 | 7 | 4 | 3 | 0 | 5 | 2 | 3 | 6 | 3 |
| Cheatgrass | 8 | 9 | 8 | 8 | 7 | 6 | 9 | 8 | 9 | 9 | 7 | 7 | 7 | 6 | 3 | 2 | 2 | 7 | 7 | 4 | 3 | 2 |
| Chickweed | 4 | 8 | 7 | 7 | 8 | 3 | 10 | 9 | 10 | 9 | 8 | 9 | — | 10 | 7 | 10 | 3 | 9 | 9 | 9 | 5 | 0 |
| Cocklebur | — | — | — | — | — | — | — | — | — | — | 3 | 3 | 2 | 5 | 3 | 0 | 2 | 5 | 7 | 8 | 6 | 0 |
| Corn | 9 | 9 | 9 | 9 | 6 | 5 | 9 | 9 | 10 | 9 | 0 | 5 | 0 | 0 | 0 | 0 | 0 | 2 | 5 | 8 | 2 | 0 |
| Cotton | 5 | 8 | 9 | 9 | 9 | 0 | 9 | 9 | 10 | 10 | 5 | 7 | 1 | — | 4 | 3 | 2 | 6 | 0 | 5 | 3 | 3 |
| Crabgrass | 4 | 5 | 3 | 7 | 3 | 2 | 9 | 6 | 9 | 9 | 2 | 1 | 1 | 2 | 2 | 0 | 3 | 2 | 2 | 2 | 6 | 0 |
| Giant foxtail | 3 | 9 | 5 | 8 | 1 | 3 | 9 | 9 | 8 | 7 | 2 | 3 | 1 | 2 | 1 | 0 | 3 | 0 | 2 | 2 | 2 | 0 |
| Lambsquarters | 6 | 9 | 9 | 9 | 10 | 9 | 10 | 10 | 10 | 10 | 7 | 9 | 9 | 10 | 9 | — | 9 | 9 | 7 | 9 | 9 | 5 |
| Morningglory | 5 | 9 | 9 | 9 | 9 | 6 | 9 | 9 | 9 | 10 | 2 | 2 | 2 | 8 | 3 | 0 | 1 | 2 | 3 | 7 | 6 | 0 |
| Nutsedge | 9 | 10 | 9 | 9 | 8 | 4 | 10 | 10 | 9 | 10 | 2 | 0 | 0 | 2 | — | 0 | 0 | 9 | 9 | 9 | 0 | 0 |
| Rape | 7 | 8 | 9 | 9 | 9 | 7 | 9 | 9 | 9 | 9 | 9 | 9 | 9 | 9 | 5 | 9 | 5 | 8 | 8 | 7 | 5 | 5 |
| Rice | 8 | 9 | 9 | 8 | 9 | 8 | 10 | 9 | 10 | 10 | 7 | 5 | 2 | 8 | 5 | 3 | 2 | 2 | 0 | 7 | 8 | 0 |
| Sorghum | 8 | 9 | 9 | 8 | 6 | 6 | 9 | 9 | 9 | 9 | 0 | 0 | 0 | 6 | 3 | 0 | 0 | 5 | 2 | 4 | 6 | 2 |
| Soybean | 1 | 8 | 7 | 9 | 9 | 1 | 9 | 9 | 9 | 9 | 1 | 2 | 0 | 1 | 0 | 0 | 0 | 2 | 3 | 2 | 1 | 0 |
| Sugar beet | 5 | 8 | 7 | 9 | 9 | 8 | 9 | 9 | 9 | 9 | 8 | 8 | 9 | 9 | 9 | 6 | 7 | 7 | 7 | 9 | 8 | 4 |
| Velvetleaf | 2 | 9 | 9 | 9 | 9 | 1 | 9 | 9 | 9 | 8 | 6 | 8 | 5 | 8 | 0 | 0 | 4 | 8 | 7 | 8 | 0 | 3 |
| Wheat | 2 | 6 | 2 | 2 | 2 | 0 | 8 | 7 | 8 | 8 | 2 | 2 | 2 | 2 | 2 | 0 | 0 | 0 | 0 | 0 | 0 | 2 |
| Wild buckwheat | 0 | 3 | 5 | 7 | 5 | 2 | 7 | 4 | 7 | 5 | 2 | 7 | 6 | 8 | 3 | 0 | 2 | 5 | 7 | 4 | 7 | 3 |
| Wild oat | 5 | 7 | 4 | 7 | 5 | 2 | 7 | 6 | 7 | 7 | 7 | 4 | 4 | 5 | 2 | 0 | 2 | 3 | 3 | 3 | 2 | 3 |

TABLE A-continued

TEST A

| Rate (50 g/ha) PRE-EMERGENCE | COMPOUND 135 | 136 | 137 | 138 | 139 | 140 | 141 | 142 | 143 | 144 | 145 | 146 | 147 | 148 | 149 | 150 | 151 | 152 | 165 | 166 | 167 | 168 |
|---|---|---|---|---|---|---|---|---|---|---|---|---|---|---|---|---|---|---|---|---|---|---|
| Barley | 4 | 0 | 4 | 8 | 2 | 3 | 7 | 8 | 7 | 6 | 1 | 2 | 5 | 7 | 9 | 0 | 0 | 0 | 4 | 8 | 8 | 2 |
| Barnyardgrass | 8 | 5 | 7 | 9 | 3 | 8 | 3 | 9 | 9 | 2 | 1 | 8 | 5 | 6 | 7 | 0 | 0 | 7 | 7 | 7 | 7 | 8 |
| Bedstraw | 7 | 7 | 9 | 7 | 5 | 5 | 4 | 7 | 8 | 8 | 5 | 9 | 6 | 8 | 9 | 8 | 5 | 9 | 2 | 8 | 6 | 0 |
| Blackgrass | 7 | 6 | 8 | 9 | 8 | 8 | 6 | 10 | 8 | 7 | 7 | 7 | 9 | 8 | 9 | 5 | 5 | 8 | 5 | 8 | 8 | 3 |
| Cheatgrass | 8 | 8 | 9 | 9 | 9 | 8 | 8 | 10 | 10 | 8 | 8 | 9 | 9 | 9 | 9 | 9 | 9 | 8 | 7 | 8 | 9 | 6 |
| Chickweed | 8 | 8 | 9 | 9 | 5 | 9 | 5 | 9 | 7 | 10 | 0 | 8 | 9 | 9 | — | 7 | 7 | 7 | 8 | 9 | 9 | 5 |
| Cocklebur | 0 | 0 | 2 | 5 | 2 | 1 | 7 | 9 | 9 | 5 | 2 | 9 | 5 | 9 | 7 | 2 | 2 | 0 | 3 | 3 | 2 | — |
| Corn | 6 | 3 | 6 | 7 | 0 | 4 | 3 | 9 | 9 | 9 | 8 | 9 | 0 | 5 | 5 | 8 | 6 | 3 | 3 | 8 | 7 | 2 |
| Cotton | 4 | 0 | — | 8 | 0 | 2 | 5 | 7 | 8 | 8 | 2 | 4 | 2 | 6 | 6 | 2 | 1 | 3 | 0 | 8 | 2 | 0 |
| Crabgrass | 0 | 0 | 0 | 2 | 2 | 3 | 2 | 7 | 9 | 3 | 0 | 5 | 7 | 2 | 5 | 0 | 1 | 0 | 7 | 8 | 6 | 5 |
| Giant foxtail | 3 | 0 | 2 | 6 | 2 | 5 | 9 | 9 | 9 | 4 | 0 | 3 | 2 | 3 | 3 | 0 | 0 | 0 | 9 | 8 | 7 | 2 |
| Lambsquarters | 9 | 8 | 9 | 9 | 9 | 8 | 7 | 9 | 9 | 5 | 7 | 9 | 8 | 9 | 9 | 9 | 5 | 9 | 8 | 9 | 8 | 8 |
| Morningglory | 6 | 3 | 6 | 8 | 3 | 6 | 2 | 6 | 9 | 8 | 6 | 9 | 8 | 8 | 8 | 5 | 4 | 3 | 0 | 4 | 3 | 0 |
| Nutsedge | 0 | 0 | 0 | 0 | 0 | 2 | 9 | 9 | 10 | 2 | 0 | 10 | 5 | 9 | 10 | 0 | 0 | 8 | 7 | 10 | 0 | 0 |
| Rape | 0 | 5 | 4 | 0 | 1 | 2 | 7 | 9 | 9 | 9 | 3 | 9 | 8 | 9 | 9 | 3 | 0 | 7 | 8 | 9 | 8 | 8 |
| Rice | 7 | 1 | 7 | 9 | 5 | 6 | 9 | 9 | 10 | 10 | 8 | 9 | 10 | 8 | 10 | 9 | 9 | 10 | 9 | 8 | 9 | 9 |
| Sorghum | 9 | 5 | 6 | 9 | 2 | 6 | 8 | 8 | 9 | 8 | 3 | 7 | 5 | 6 | 6 | 3 | 2 | 5 | 9 | 9 | 9 | 5 |
| Soybean | 2 | 0 | 2 | 3 | 2 | 0 | 7 | 9 | 9 | 8 | 4 | 9 | 7 | 9 | 9 | 8 | 6 | 6 | 2 | 7 | 4 | 0 |
| Sugar beet | 9 | 8 | 8 | 9 | 8 | 8 | 7 | 9 | 9 | 9 | 3 | 9 | 7 | 9 | 9 | 8 | 7 | 7 | 7 | 9 | 8 | 3 |
| Velvetleaf | 0 | 6 | 3 | 2 | 4 | 3 | 7 | 9 | 9 | 6 | 0 | 9 | 5 | 7 | 9 | 2 | 0 | 0 | 1 | 6 | 2 | 1 |
| Wheat | 7 | 3 | 7 | 8 | 5 | 7 | 7 | 8 | 8 | 9 | 6 | 5 | 6 | 7 | 9 | 4 | 4 | 3 | 2 | 8 | 8 | 2 |
| Wild buckwheat | — | — | — | — | — | — | — | — | — | — | — | — | — | — | — | — | — | — | 4 | 3 | 5 | 3 |
| Wild oat | 8 | 5 | 7 | 8 | 4 | 6 | 7 | 7 | 5 | 8 | 3 | 5 | 7 | 4 | 5 | 3 | 2 | 2 | 3 | 8 | 8 | 2 |

| Rate (50 g/ha) PRE-EMERGENCE | COMPOUND 169 | 170 | 171 | 172 | 173 | 174 | 175 | 176 | 177 | 178 | 179 | 180 | 181 | 182 | 183 | 184 | 185 | 186 | 187 | 188 | 189 | 190 |
|---|---|---|---|---|---|---|---|---|---|---|---|---|---|---|---|---|---|---|---|---|---|---|
| Barley | 0 | 0 | 0 | 2 | 3 | 0 | 0 | 0 | 0 | 0 | 0 | 0 | 0 | 8 | 6 | 5 | 3 | 7 | 2 | 0 | 0 | 0 |
| Barnyardgrass | 3 | 9 | 5 | 3 | 6 | 7 | 9 | 0 | 0 | 0 | 0 | 9 | 9 | 8 | 9 | 3 | 9 | 9 | 6 | 1 | 1 | 2 |
| Bedstraw | 6 | 6 | 0 | 2 | 5 | 1 | 0 | 0 | 0 | 2 | 0 | 2 | 2 | 9 | 8 | 2 | 7 | 8 | 6 | 0 | 2 | 5 |
| Blackgrass | 2 | 9 | — | 7 | 8 | 2 | 7 | 0 | 3 | 3 | 2 | 4 | 5 | 9 | 9 | 9 | 9 | 9 | 9 | 6 | 5 | 7 |
| Cheatgrass | 0 | 8 | — | 8 | 8 | 7 | 8 | 5 | 2 | 2 | 0 | 7 | 7 | 9 | 10 | 9 | 9 | 10 | 10 | 7 | 7 | 7 |
| Chickweed | 7 | 8 | 0 | 7 | 8 | 2 | 4 | 0 | 3 | 4 | 0 | 4 | 9 | 9 | 9 | — | 8 | 9 | 8 | 0 | — | 3 |
| Cocklebur | — | 5 | — | 0 | 2 | 0 | 2 | 0 | 0 | 0 | 0 | 0 | 0 | 7 | 8 | 7 | 8 | 8 | 8 | 2 | 0 | 0 |
| Corn | 0 | 5 | 1 | 5 | 8 | 6 | 6 | 0 | 0 | 0 | 0 | 7 | 8 | 9 | 9 | 9 | 9 | 9 | 9 | 3 | 9 | 4 |
| Cotton | 4 | 2 | 0 | 5 | 8 | 2 | 0 | 0 | 0 | 0 | 0 | 0 | 0 | 8 | 3 | 8 | 9 | 9 | 6 | 0 | 0 | 3 |
| Crabgrass | 5 | 5 | 7 | 9 | 8 | 6 | 9 | 2 | 0 | 0 | 0 | 9 | 9 | 9 | 10 | 9 | 9 | 10 | 9 | 8 | 5 | 6 |
| Giant foxtail | 7 | 8 | 8 | 9 | 8 | 5 | 7 | 6 | 0 | 4 | 0 | 9 | 9 | 9 | 10 | 9 | 9 | 9 | 9 | 8 | 7 | 6 |
| Lambsquarters | 7 | 9 | 7 | 9 | 9 | 5 | 9 | — | 0 | 3 | 2 | 3 | 5 | 8 | 9 | 9 | 9 | 9 | 5 | 4 | 3 | 5 |
| Morningglory | 2 | 5 | 0 | 6 | 3 | 6 | 4 | 0 | 0 | 1 | 0 | 0 | 2 | 6 | 6 | 6 | 9 | 7 | 4 | 0 | 4 | 3 |
| Nutsedge | 0 | 4 | 0 | 0 | 8 | 0 | 0 | 0 | 0 | 0 | 0 | 0 | 9 | 7 | 10 | 8 | 10 | 7 | 5 | 7 | 0 | 0 |
| Rape | 9 | 9 | 0 | 4 | 8 | 3 | 0 | 0 | 0 | 0 | 0 | 0 | 2 | 7 | 8 | 5 | 9 | 9 | 6 | 0 | 0 | 0 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Rice | 9 | 10 | 3 | 7 | 9 | 7 | 9 | 0 | 0 | 0 | 0 | 7 | 9 | 9 | 9 | 8 | 10 | 10 | 9 | 8 | 9 | 9 |
| Sorghum | 0 | 7 | 1 | 7 | 8 | 7 | 9 | 0 | 0 | 0 | 0 | 9 | 9 | 8 | 9 | 9 | 9 | 9 | 8 | 0 | 1 | 1 |
| Soybean | 3 | 4 | 0 | 5 | 8 | 4 | 3 | 0 | 0 | 0 | 0 | 0 | 1 | 9 | 9 | 9 | 8 | 9 | 9 | 2 | 6 | 2 |
| Sugar beet | 9 | 9 | 6 | 9 | 8 | 5 | 6 | 2 | 0 | 2 | 2 | 3 | 7 | 9 | 7 | 7 | 7 | 8 | 7 | 3 | 3 | 7 |
| Velvetleaf | 3 | 9 | 0 | 5 | 7 | 2 | 0 | 0 | 0 | 0 | 0 | 0 | 0 | 7 | 8 | 7 | 6 | 7 | 5 | 0 | 2 | 2 |
| Wheat | 2 | 4 | 0 | 7 | 7 | 0 | 6 | 0 | 0 | 2 | 0 | 7 | 6 | 7 | 7 | 6 | 0 | 8 | 8 | 0 | 2 | 6 |
| Wild buckwheat | 3 | 2 | 0 | — | — | — | — | — | — | — | — | — | — | — | — | — | — | — | — | — | — | — |
| Wild oat | 2 | 3 | 0 | 4 | 3 | 0 | 4 | 0 | 0 | 0 | 3 | 1 | 2 | 8 | 7 | 7 | 2 | 7 | 7 | 4 | 6 | 5 |

| Rate (50 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 191 | 192 | 203 | 204 | 205 | 206 | 207 | 208 | 209 | 210 | 211 | 212 | 213 | 214 | 215 | 216 | 217 | 218 | 219 | 220 | 221 | 222 |
| Barley | 0 | 0 | 8 | 9 | 8 | 9 | 7 | 8 | 2 | 0 | 2 | 7 | 5 | 3 | 1 | 2 | 3 | 1 | 0 | 0 | 0 | 0 |
| Barnyardgrass | 1 | 2 | 5 | 9 | 9 | 9 | 9 | 9 | 0 | 6 | 9 | 8 | 8 | 6 | 9 | 4 | 3 | 7 | 3 | 0 | 0 | 0 |
| Bedstraw | 5 | 0 | 0 | 8 | 9 | 9 | 8 | 9 | 4 | 5 | 8 | 8 | 8 | 9 | 6 | 0 | 1 | 8 | 2 | 0 | 0 | 1 |
| Blackgrass | 7 | 7 | 8 | 8 | 9 | 8 | 9 | 8 | 2 | 2 | 8 | 8 | 7 | 6 | 5 | 6 | 6 | 7 | 6 | 0 | 3 | 0 |
| Cheatgrass | 7 | 7 | 9 | 9 | 9 | 9 | 8 | 9 | 8 | 8 | 9 | 9 | 9 | 9 | 8 | 6 | 8 | 9 | 8 | 4 | 0 | 2 |
| Chickweed | 2 | 6 | 9 | 9 | 9 | 9 | 10 | 9 | 0 | 7 | 9 | 10 | 10 | 9 | 9 | 8 | 7 | 9 | 9 | 2 | 2 | 5 |
| Cocklebur | 0 | 0 | — | 8 | 10 | 10 | 9 | 9 | 8 | — | 8 | — | — | — | 0 | 0 | 0 | 0 | 0 | — | 0 | — |
| Corn | 3 | 7 | 9 | 9 | 9 | 9 | 9 | 9 | 0 | 8 | 9 | 9 | 9 | 9 | 7 | 8 | 3 | 2 | 0 | 5 | 0 | 0 |
| Cotton | 0 | 0 | 7 | 4 | 8 | 7 | 8 | 7 | 0 | 0 | 8 | 8 | 8 | 9 | 5 | 0 | 0 | — | 0 | 0 | 0 | 0 |
| Crabgrass | 6 | 9 | 9 | 9 | 9 | 9 | 9 | 9 | 3 | 8 | 9 | 7 | 9 | 4 | 5 | 3 | 6 | 3 | 2 | 0 | 2 | 3 |
| Giant foxtail | 6 | 9 | 8 | 9 | 9 | 9 | 9 | 9 | 3 | 6 | 9 | 9 | 8 | 2 | 3 | 5 | 5 | 2 | 0 | 0 | 2 | 0 |
| Lambsquarters | 0 | 5 | 9 | 9 | 10 | 9 | 8 | 9 | 5 | 8 | 9 | 9 | 9 | 9 | 8 | 7 | 9 | 9 | 9 | 6 | — | 9 |
| Morningglory | 3 | 3 | 7 | 9 | 9 | 9 | 4 | 9 | 2 | 1 | 3 | 2 | 3 | 9 | 2 | 0 | 3 | 2 | 1 | 0 | 1 | 0 |
| Nutsedge | 0 | 0 | 6 | 10 | 10 | 9 | 5 | 10 | 0 | 0 | 3 | 8 | 8 | 9 | 2 | 0 | 9 | 0 | 0 | 0 | 0 | 0 |
| Rape | 2 | 0 | 8 | 8 | 9 | 7 | 4 | 9 | 0 | 3 | 9 | 9 | 8 | 8 | 8 | 1 | 9 | 7 | 1 | 0 | 1 | 0 |
| Rice | 0 | 7 | 9 | 9 | 9 | 9 | 10 | 10 | 5 | 6 | 9 | 9 | 9 | 9 | 6 | 6 | 9 | 7 | 6 | 0 | 3 | 6 |
| Sorghum | 0 | 4 | 9 | 8 | 9 | 8 | 8 | 9 | 0 | 5 | 9 | 9 | 9 | 8 | 8 | 3 | 3 | 2 | 0 | 0 | 0 | 0 |
| Soybean | 2 | 8 | 9 | 8 | 8 | 8 | 8 | 8 | 0 | 3 | 7 | 7 | 9 | 8 | 2 | 2 | 4 | 4 | 0 | 1 | 0 | 0 |
| Sugar beet | 4 | 5 | 8 | 9 | 9 | 9 | 9 | 9 | 1 | 8 | 6 | 7 | 9 | 9 | 7 | 4 | 2 | 4 | 3 | 1 | 1 | 1 |
| Velvetleaf | 2 | 2 | 7 | 6 | 9 | 8 | 5 | 8 | 0 | 4 | 7 | 4 | 9 | 0 | 6 | 0 | 6 | 7 | 2 | 0 | 0 | 0 |
| Wheat | 0 | 2 | 7 | 9 | 9 | 9 | 8 | 8 | 0 | 7 | 9 | 8 | 6 | 1 | 3 | 6 | 8 | 8 | 0 | 0 | 0 | 0 |
| Wild buckwheat | — | — | 5 | 8 | 8 | 8 | 3 | 8 | 0 | 3 | 1 | 7 | 8 | 8 | 3 | 1 | 5 | 2 | 0 | 3 | 3 | 0 |
| Wild oat | 2 | 7 | 8 | 9 | 8 | 8 | 7 | 8 | 2 | 7 | 9 | 8 | 8 | 8 | 3 | 6 | 7 | 3 | 2 | 0 | 0 | 1 |

| Rate (50 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 223 | 224 | 225 | 226 | 227 | 228 | 229 | 230 | 231 | 232 | 233 | 234 | 235 | 236 | 237 | 238 | 239 | 240 | 241 | 242 | 243 | 244 |
| Barley | 1 | 1 | 0 | 0 | 0 | 5 | 5 | 2 | 4 | 5 | 0 | 0 | 0 | 0 | 0 | 0 | 0 | 8 | 8 | 8 | 8 | 8 |
| Barnyardgrass | 7 | 0 | 0 | 0 | 0 | 2 | 5 | 1 | 5 | 1 | 3 | 0 | 0 | 2 | 0 | 0 | 0 | 9 | 9 | 9 | 9 | 9 |
| Bedstraw | 7 | 6 | 0 | 0 | 0 | 3 | 2 | 3 | 3 | 0 | 3 | 2 | 0 | 0 | 0 | 4 | 3 | 7 | 7 | 7 | 8 | 8 |
| Blackgrass | 2 | 5 | 3 | 0 | 0 | 3 | 8 | 7 | 4 | 3 | 4 | 3 | 0 | 0 | 0 | 3 | 0 | 7 | 9 | 9 | 9 | 7 |
| Cheatgrass | 7 | 8 | 7 | 0 | 2 | 7 | 10 | 8 | 9 | 8 | 8 | 0 | 0 | 0 | 0 | 0 | 0 | 8 | 9 | 9 | 9 | 8 |

TABLE A-continued

| TEST A | | | | | | | | | | | | | | | | | | | | | | |
|---|---|---|---|---|---|---|---|---|---|---|---|---|---|---|---|---|---|---|---|---|---|---|
| Chickweed | 9 | 8 | 5 | 4 | 9 | 0 | 9 | 2 | 2 | 0 | 0 | 0 | 0 | 0 | 0 | 0 | 0 | 9 | 9 | 9 | 9 | 9 |
| Cocklebur | — | 0 | 0 | 0 | — | — | — | — | — | — | — | — | — | — | — | — | — | — | — | — | — | — |
| Corn | 2 | 8 | 0 | 0 | 0 | 2 | 8 | 8 | 4 | 3 | 1 | 0 | 2 | 2 | 0 | 0 | 2 | 9 | 9 | 9 | 9 | 9 |
| Cotton | 0 | 2 | 0 | 0 | 0 | 2 | 4 | 5 | 2 | 2 | 2 | 0 | 0 | 2 | 0 | 0 | 0 | 8 | 7 | 7 | 9 | 10 |
| Crabgrass | 0 | 3 | 0 | 0 | 0 | 2 | 5 | 3 | 6 | 6 | 2 | 0 | 0 | 2 | 0 | 0 | 0 | 9 | 9 | 9 | 9 | 9 |
| Giant foxtail | 5 | 7 | 0 | 0 | 0 | 3 | 7 | 1 | 5 | 2 | 0 | 0 | 0 | 2 | 0 | 0 | 0 | 9 | 9 | 9 | 9 | 9 |
| Lambsquarters | — | 8 | — | — | 7 | 9 | 9 | 7 | 4 | 5 | 0 | 7 | 0 | 0 | 0 | 2 | 2 | 9 | 9 | 9 | 9 | 9 |
| Morningglory | 3 | 2 | 0 | 0 | 0 | 5 | 6 | 6 | 7 | 5 | — | 0 | 0 | 1 | 0 | 0 | 0 | 7 | 6 | 8 | 8 | 8 |
| Nutsedge | 0 | 0 | 0 | 0 | 0 | 2 | 5 | 6 | 5 | 0 | 6 | 0 | 0 | 4 | 0 | 0 | — | 10 | 9 | 9 | 10 | 10 |
| Rape | 7 | 8 | 2 | 0 | 0 | 0 | 3 | 3 | 0 | 3 | 2 | 0 | 0 | 0 | 0 | 0 | 0 | 9 | 9 | 9 | 9 | 9 |
| Rice | 5 | 4 | 5 | 4 | 0 | 1 | 8 | 7 | 8 | 8 | 9 | 0 | 0 | 1 | 0 | 2 | 2 | 9 | 9 | 9 | 10 | 9 |
| Sorghum | 6 | 1 | 2 | 2 | 0 | 3 | 7 | 7 | 8 | 6 | 2 | 0 | 0 | 2 | 0 | 0 | 0 | 9 | 9 | 9 | 9 | 8 |
| Soybean | 3 | 5 | 3 | 2 | 0 | 4 | 7 | 2 | 5 | 4 | 2 | 0 | 0 | 0 | 0 | 0 | 0 | 9 | 9 | 9 | 8 | 9 |
| Sugar beet | 6 | 7 | 0 | 1 | 2 | 2 | 4 | 2 | 3 | 2 | 2 | 2 | 0 | 0 | 0 | 0 | 0 | 9 | 9 | 9 | 9 | 9 |
| Velvetleaf | 2 | 8 | 0 | 0 | 0 | 4 | 6 | 6 | 6 | 0 | 0 | 0 | 0 | 0 | 0 | 0 | 0 | 8 | 9 | 9 | 9 | 7 |
| Wheat | 0 | 2 | 0 | 0 | 0 | 3 | 6 | 6 | 7 | 7 | 3 | 0 | 0 | 0 | 0 | 0 | 0 | 8 | 7 | 7 | 8 | 8 |
| Wild buckwheat | 3 | 6 | 0 | 3 | 0 | 0 | 0 | 2 | 2 | 0 | 2 | 2 | — | 0 | 3 | 2 | 3 | 7 | 9 | 7 | 5 | 7 |
| Wild oat | 0 | 2 | 3 | 0 | 0 | 4 | 7 | 7 | 5 | 6 | 1 | 0 | 0 | 0 | 0 | 0 | 0 | 7 | 7 | 7 | 7 | 7 |

| Rate (50 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 245 | 246 | 247 | 248 | 249 | 250 | 251 | 252 | 253 | 254 | 255 | 256 | 257 | 258 | 259 | 260 | 261 | 262 | 263 | 264 | 265 | 266 |
| Barley | 8 | 3 | 2 | 0 | 0 | 0 | 5 | 1 | 5 | 0 | 0 | 8 | 5 | 8 | 5 | 0 | 8 | 0 | 0 | 0 | 2 | 0 |
| Barnyardgrass | 9 | 4 | 6 | 1 | 0 | 1 | 8 | 3 | 6 | 2 | 3 | 4 | 8 | 9 | 9 | 8 | 9 | 1 | 0 | 2 | 2 | 5 |
| Bedstraw | 8 | 2 | 3 | 5 | 2 | 0 | 8 | 5 | 8 | 7 | 7 | 7 | 7 | 7 | 3 | 2 | 9 | 3 | 2 | 3 | 3 | 3 |
| Blackgrass | 9 | 8 | 7 | 3 | 4 | 3 | 8 | 7 | 6 | 5 | 2 | 8 | 8 | 8 | 6 | 8 | 8 | 3 | 0 | 2 | 8 | 7 |
| Cheatgrass | 9 | 5 | 8 | 4 | 2 | 7 | 8 | 7 | 8 | 8 | 6 | 8 | 8 | 9 | 8 | 8 | 8 | 5 | 0 | 8 | 8 | 7 |
| Chickweed | 9 | 9 | 9 | 7 | 9 | 9 | 9 | 6 | 9 | 9 | 5 | 5 | 8 | 9 | 7 | 3 | 9 | 5 | 3 | 2 | 0 | 3 |
| Cocklebur | — | — | — | — | — | 0 | 2 | — | 6 | 5 | 0 | 1 | 0 | 2 | 1 | 5 | 7 | 0 | 0 | 2 | 0 | 2 |
| Corn | 9 | 4 | 8 | 5 | 3 | 2 | 8 | 9 | 9 | 8 | 5 | 9 | 9 | 9 | 9 | 9 | 9 | 2 | 0 | 4 | 8 | 6 |
| Cotton | 8 | 0 | 0 | 3 | 0 | 1 | 5 | 4 | 9 | 8 | 2 | 7 | 6 | 8 | 9 | 2 | 8 | 0 | 2 | 0 | 6 | 7 |
| Crabgrass | 9 | 7 | 9 | 7 | 2 | 2 | 8 | 4 | 3 | 4 | 0 | 9 | 7 | 8 | 8 | 7 | 8 | 0 | 0 | 2 | 4 | 0 |
| Giant foxtail | 9 | 4 | 9 | 4 | 3 | 1 | 8 | 7 | 3 | 2 | 0 | 6 | 8 | 9 | 7 | 8 | 8 | 1 | 0 | 2 | 5 | 5 |
| Lambsquarters | 9 | 9 | 7 | 9 | 9 | 8 | 9 | 7 | 10 | 9 | 6 | 9 | 9 | 9 | 9 | — | 8 | 7 | 3 | 5 | 9 | 5 |
| Morningglory | 8 | 0 | 3 | 2 | 2 | 1 | 1 | 3 | 9 | 8 | 1 | 8 | 8 | 8 | 3 | 1 | 8 | 0 | 0 | 5 | 3 | 4 |
| Nutsedge | 10 | 8 | 6 | — | — | 0 | 0 | 2 | 8 | 0 | 0 | 9 | 7 | 8 | 0 | 0 | 8 | 0 | 0 | 0 | 0 | 0 |
| Rape | 9 | 2 | 5 | 7 | 8 | 3 | 8 | 7 | 8 | 8 | 6 | 9 | 7 | 8 | 6 | 4 | 9 | 0 | 0 | 5 | 7 | 7 |
| Rice | 10 | 4 | 8 | 2 | 0 | 1 | 7 | 8 | 8 | 8 | 0 | 9 | 9 | 9 | — | 9 | 9 | 0 | 2 | 0 | 6 | 8 |
| Sorghum | 9 | 2 | 4 | 3 | 0 | 3 | 8 | 8 | 9 | 7 | 5 | 9 | 9 | 9 | 9 | 8 | 9 | 1 | 2 | 5 | 7 | 9 |
| Soybean | 8 | 0 | 2 | 5 | 0 | 1 | 5 | 7 | 7 | 8 | 1 | 7 | 7 | 8 | 8 | 5 | 4 | 0 | 2 | 2 | 7 | 3 |
| Sugar beet | 9 | 7 | 7 | 8 | 9 | 1 | 8 | 3 | 8 | 7 | 5 | 6 | 8 | 7 | 6 | 2 | 5 | 2 | 0 | 2 | 3 | 2 |
| Velvetleaf | 6 | 3 | 3 | 2 | 2 | 2 | 8 | 6 | 9 | 0 | 2 | 7 | 5 | 8 | 1 | 1 | 2 | 0 | 0 | 7 | 7 | 4 |
| Wheat | 7 | 5 | 5 | 0 | 0 | 0 | 6 | 6 | 0 | 2 | 0 | 7 | 7 | 8 | 7 | 6 | 7 | 0 | 0 | 5 | 2 | 2 |
| Wild buckwheat | 7 | 7 | 5 | 5 | 5 | 0 | — | 3 | 3 | 3 | 2 | 3 | 3 | 3 | 2 | 2 | 4 | 0 | 2 | 3 | 3 | 0 |
| Wild oat | 7 | 2 | 6 | 0 | 0 | 1 | 5 | 3 | 4 | 5 | 2 | 7 | 8 | 8 | 7 | 6 | 7 | 2 | 3 | 7 | 4 | 3 |

TABLE A-continued

TEST A

| Rate (50 g/ha) PRE-EMERGENCE | COMPOUND 267 | 268 | 269 | 270 | 271 | 272 | 273 | 274 | 275 | 276 | 277 | 278 | 279 | 280 | 281 | 282 | 283 | 284 | 285 | 286 | 287 | 288 |
|---|---|---|---|---|---|---|---|---|---|---|---|---|---|---|---|---|---|---|---|---|---|---|
| Barley | 4 | 2 | 0 | 9 | 7 | 8 | 0 | 2 | 9 | 0 | 0 | 0 | 0 | 0 | 0 | 1 | 9 | 8 | 2 | 4 | 9 | 8 |
| Barnyardgrass | 4 | 1 | 0 | 1 | 4 | 8 | 2 | 1 | 9 | 0 | 0 | 0 | 0 | 1 | 2 | 2 | 9 | 9 | 9 | 9 | 9 | 9 |
| Bedstraw | 3 | 6 | 2 | 3 | 3 | 3 | 0 | 0 | 0 | 0 | 0 | 0 | 2 | 0 | 0 | 2 | 8 | 7 | 9 | 9 | 7 | 8 |
| Blackgrass | 8 | 8 | 4 | 9 | 9 | 7 | 7 | 2 | 9 | 6 | 1 | 2 | 1 | 0 | 2 | 5 | 8 | 8 | 6 | 8 | 5 | 8 |
| Cheatgrass | 9 | 9 | 8 | 9 | 9 | 9 | 8 | 8 | 9 | 8 | 1 | 0 | 0 | 3 | 2 | 4 | 9 | 9 | 9 | 9 | 9 | 9 |
| Chickweed | — | 4 | 3 | 6 | 9 | 9 | 3 | 0 | 9 | 0 | 0 | 0 | 0 | 0 | 0 | 7 | 8 | 9 | 9 | 10 | 10 | 9 |
| Cocklebur | 6 | 1 | 0 | 1 | 1 | 2 | 2 | 0 | 7 | 0 | 0 | 0 | 4 | 0 | 0 | 0 | 8 | 7 | 8 | 7 | 7 | 7 |
| Corn | 7 | 6 | 1 | 9 | 8 | 8 | 2 | 2 | 9 | 0 | 0 | 0 | 0 | 2 | 7 | 2 | 9 | 9 | 6 | 6 | 9 | 9 |
| Cotton | 8 | 6 | 0 | 8 | 8 | 5 | 2 | 4 | 9 | 0 | — | 0 | 0 | 0 | 0 | 0 | 9 | 9 | 9 | 9 | 9 | 8 |
| Crabgrass | 2 | 2 | 0 | 9 | 9 | 9 | 4 | 0 | 9 | 2 | 0 | 0 | 0 | 0 | 0 | 0 | 9 | 9 | 9 | 9 | 9 | 9 |
| Giant foxtail | 3 | 2 | 0 | 2 | 8 | 9 | 2 | 0 | 9 | 1 | 0 | 0 | 2 | 1 | 0 | 0 | 9 | 9 | 10 | 9 | 9 | 8 |
| Lambsquarters | 9 | 8 | — | 9 | 9 | 10 | 0 | 0 | 9 | 0 | 0 | 0 | 0 | 5 | — | 9 | — | 9 | 9 | — | 9 | 9 |
| Morningglory | 8 | 9 | 0 | 5 | 7 | 2 | 2 | 0 | 8 | 0 | 0 | 0 | 0 | 2 | 3 | 0 | 9 | 7 | 7 | 9 | 9 | 9 |
| Nutsedge | 5 | 0 | 0 | 10 | 9 | 6 | 0 | 0 | 9 | 0 | 0 | 0 | 0 | 0 | 0 | 0 | 9 | 6 | 4 | 5 | 9 | 9 |
| Rape | 5 | 8 | 3 | 8 | 8 | 5 | 1 | 1 | 8 | 1 | 0 | 0 | 2 | 0 | 0 | 4 | 9 | 9 | 9 | 9 | 9 | 9 |
| Rice | 8 | 8 | 6 | 9 | 9 | 9 | 9 | 8 | 9 | 0 | 0 | 0 | 0 | 0 | 0 | 1 | 9 | 7 | 7 | 8 | 9 | 8 |
| Sorghum | 8 | 8 | 4 | 9 | 8 | 8 | 4 | 3 | 9 | 0 | 0 | 0 | 0 | 2 | 0 | 0 | 9 | 8 | 9 | 8 | 8 | 9 |
| Soybean | 7 | 6 | 0 | 6 | 7 | 5 | 0 | 1 | 6 | 0 | 0 | 0 | 0 | 1 | 0 | 2 | 9 | 8 | 6 | 7 | 7 | 4 |
| Sugar beet | 7 | 8 | 1 | 9 | 9 | 7 | 1 | 1 | 9 | 2 | 0 | 0 | 2 | 0 | 0 | 5 | 9 | 9 | 9 | 9 | 9 | 9 |
| Velvetleaf | 7 | 0 | 0 | 1 | 1 | 0 | 1 | 0 | 1 | 0 | 0 | 0 | 0 | 0 | 0 | 0 | 8 | 8 | 9 | 9 | 5 | 9 |
| Wheat | 5 | 2 | 0 | 7 | 8 | 8 | 4 | 2 | 8 | 2 | 0 | 0 | 0 | 0 | 0 | 0 | 8 | 8 | 3 | 7 | 8 | 6 |
| Wild buckwheat | 5 | 5 | 2 | — | 8 | 5 | 2 | 0 | 9 | — | — | — | — | — | — | — | 5 | 5 | 7 | 3 | 2 | 6 |
| Wild oat | 7 | 8 | 2 | 8 | 8 | 8 | 3 | 2 | 8 | 2 | 0 | 0 | 0 | 0 | 0 | 2 | 8 | 7 | 3 | 8 | 6 | 6 |

| Rate (50 g/ha) PRE-EMERGENCE | COMPOUND 289 | 290 | 291 | 292 | 293 | 294 | 295 | 296 | 297 | 298 | 299 | 300 | 301 | 302 | 303 | 304 | 305 | 306 | 307 | 308 | 309 | 310 |
|---|---|---|---|---|---|---|---|---|---|---|---|---|---|---|---|---|---|---|---|---|---|---|
| Barley | 2 | 2 | 4 | 0 | 1 | 0 | 0 | 0 | 0 | 0 | 0 | 2 | 3 | 7 | 0 | 0 | 7 | 0 | 1 | 0 | 0 | 0 |
| Barnyardgrass | 6 | 2 | 9 | 0 | 5 | 0 | 0 | 0 | 0 | 0 | 0 | 9 | 6 | 9 | 2 | 0 | 8 | 6 | 1 | 1 | 0 | 0 |
| Bedstraw | 9 | 1 | 4 | 0 | 2 | 2 | 0 | 2 | 0 | 3 | 0 | 0 | 0 | 2 | 0 | 3 | 0 | 0 | 2 | 2 | 0 | 2 |
| Blackgrass | 8 | 6 | 8 | 2 | 6 | 0 | 7 | 3 | 3 | 3 | 4 | 8 | 7 | 7 | 5 | 0 | 7 | 4 | 7 | 5 | 5 | 1 |
| Cheatgrass | 9 | 6 | 9 | 0 | 7 | 0 | 2 | 5 | 0 | 2 | 2 | 8 | 8 | 8 | 2 | 0 | 9 | 7 | 7 | 2 | 3 | 0 |
| Chickweed | 9 | 7 | 8 | 1 | 5 | 8 | 8 | 8 | 7 | 2 | 0 | 7 | 7 | 9 | 0 | 3 | 9 | 3 | 0 | 1 | 3 | 3 |
| Cocklebur | 7 | — | 0 | 0 | 0 | 0 | 0 | 0 | 0 | 0 | 0 | — | — | — | — | — | — | — | 0 | 3 | 3 | 6 |
| Corn | 9 | 2 | 8 | 0 | 2 | 0 | 0 | 0 | 0 | 0 | 0 | 9 | 8 | 9 | 1 | 2 | 9 | 8 | 5 | 4 | 0 | 0 |
| Cotton | 2 | 0 | 2 | 0 | 1 | 0 | 0 | 0 | 0 | 0 | 0 | 5 | 6 | 9 | 0 | 0 | 5 | 1 | 0 | 2 | 0 | 3 |
| Crabgrass | 9 | 7 | 9 | 2 | 2 | 0 | 6 | 0 | 0 | 0 | 0 | 7 | 9 | 9 | 7 | 0 | 9 | 6 | 2 | 4 | 0 | 1 |
| Giant foxtail | 8 | 4 | 9 | 2 | 7 | 0 | 1 | 0 | 0 | 0 | 0 | 9 | 8 | 9 | 4 | 2 | 9 | 3 | 6 | 2 | 0 | 2 |
| Lambsquarters | 9 | 8 | 9 | 3 | 8 | 2 | 7 | 9 | 10 | 5 | 4 | 9 | 10 | 9 | 5 | 0 | 10 | 8 | 7 | 5 | 9 | 3 |
| Morningglory | 2 | 0 | 2 | 0 | 0 | 0 | 0 | 0 | 0 | 0 | 0 | 0 | 7 | 8 | 2 | 1 | 8 | 1 | 2 | 2 | 1 | 4 |
| Nutsedge | 10 | 3 | 8 | 0 | 0 | 0 | 0 | 0 | 0 | 0 | 0 | 0 | 8 | 9 | 0 | 0 | 9 | 0 | 9 | 0 | 8 | 0 |
| Rape | 2 | 6 | 9 | 2 | 2 | 0 | 3 | 3 | 2 | 2 | 0 | 3 | 8 | 7 | 0 | 0 | 2 | 0 | 7 | 8 | 5 | 7 |

TABLE A-continued

| TEST A | | | | | | | | | | | | | | | | | | | | | | |
|---|---|---|---|---|---|---|---|---|---|---|---|---|---|---|---|---|---|---|---|---|---|---|
| Rice | 7 | 0 | 7 | 0 | 4 | 0 | 0 | 0 | 0 | 0 | 0 | 8 | 8 | 9 | 0 | 0 | 9 | 7 | 9 | 0 | 2 | 0 |
| Sorghum | 9 | 0 | 8 | 0 | 3 | 0 | 0 | 0 | 0 | 0 | 0 | 8 | 8 | 9 | 0 | 2 | 9 | 5 | 8 | 0 | 0 | 0 |
| Soybean | 3 | 1 | 6 | 0 | 1 | 0 | 3 | 0 | 0 | 0 | 0 | 2 | 7 | 8 | 2 | 0 | 5 | 1 | 2 | 3 | 2 | 7 |
| Sugar beet | 9 | 2 | 8 | 3 | 4 | 2 | 2 | 2 | 1 | 1 | 2 | 9 | 9 | 9 | 0 | 0 | 6 | 3 | 3 | 5 | 5 | 7 |
| Velvetleaf | 0 | 0 | 1 | 0 | 0 | 0 | 0 | 0 | 0 | 0 | 0 | 0 | 3 | 7 | 2 | 1 | 2 | 0 | 6 | 7 | 6 | 6 |
| Wheat | 5 | 4 | 6 | 0 | 2 | 0 | 0 | 0 | 0 | 0 | 0 | 6 | 7 | 8 | 2 | 0 | 7 | 2 | 0 | 0 | 0 | 0 |
| Wild buckwheat | 3 | 5 | 8 | 0 | 2 | 0 | 3 | 0 | 0 | 0 | 3 | 0 | 0 | 4 | 2 | 0 | 0 | 0 | — | — | — | — |
| Wild oat | 2 | 4 | 5 | 0 | 1 | 3 | 2 | 2 | 0 | 0 | 0 | 6 | 6 | 8 | 0 | 0 | 7 | 4 | 3 | 2 | 0 | 0 |
| Rate (50 g/ha) PRE- | COMPOUND | | | | | | | | | | | | | | | | | | | | | |
| EMERGENCE | 311 | 312 | 313 | 314 | 315 | 316 | 317 | 318 | 319 | 320 | 321 | 322 | 323 | 324 | 325 | 326 | 327 | 328 | 329 | 330 | 331 | 332 |
| Barley | 0 | 0 | 0 | 0 | 0 | 0 | 0 | 0 | 0 | 0 | 0 | 8 | 9 | 8 | 2 | 0 | 5 | 0 | 2 | 0 | 0 | 0 |
| Barnyardgrass | 4 | 0 | 0 | 0 | 0 | 0 | 0 | 0 | 0 | 0 | 0 | 2 | 4 | 7 | 2 | 0 | 9 | 2 | 2 | 0 | 0 | 0 |
| Bedstraw | 0 | 3 | 2 | 0 | 0 | 2 | 4 | 0 | 1 | 0 | 0 | 9 | 9 | 9 | 1 | 5 | 8 | 0 | 3 | 0 | 0 | 0 |
| Blackgrass | 3 | 7 | 1 | 2 | 0 | 0 | 0 | 0 | 0 | 0 | 0 | 8 | 9 | 9 | 7 | 6 | 9 | 3 | 7 | 0 | 0 | 0 |
| Cheatgrass | 0 | 5 | 0 | 2 | 0 | 0 | 0 | 0 | 0 | 0 | 0 | 9 | 9 | 9 | 8 | 7 | 9 | 7 | 9 | 0 | 0 | 0 |
| Chickweed | — | 0 | 0 | 0 | 0 | 5 | 0 | 0 | 0 | 0 | 0 | 9 | 9 | 9 | 8 | 7 | 9 | 5 | 7 | — | — | 0 |
| Cocklebur | 3 | 5 | 3 | 0 | 0 | 0 | 0 | 2 | 2 | 0 | 0 | 5 | 2 | 7 | 0 | 2 | 2 | 0 | 1 | 0 | 0 | 0 |
| Corn | 0 | 4 | 0 | 2 | 0 | 0 | 0 | 0 | 0 | 0 | 0 | 9 | 9 | 9 | 9 | 2 | 9 | 2 | 8 | 0 | 0 | 0 |
| Cotton | 6 | 5 | 4 | 6 | 0 | 0 | 0 | 0 | 0 | 0 | 0 | 8 | 9 | 9 | 5 | 0 | 8 | 4 | 3 | 0 | 0 | 0 |
| Crabgrass | 2 | 2 | 4 | 0 | 0 | 0 | 0 | 0 | 0 | 0 | 0 | 8 | 9 | 9 | 5 | 0 | 9 | 5 | 4 | 0 | 0 | 0 |
| Giant foxtail | 4 | 5 | 4 | 0 | 0 | 0 | 0 | 0 | 0 | 0 | 0 | 8 | 9 | 9 | 2 | 0 | 9 | 2 | 2 | 0 | 0 | 0 |
| Lambsquarters | 9 | 9 | 5 | 10 | 0 | 3 | 2 | 3 | 0 | 0 | 0 | 9 | 9 | 9 | 8 | — | 9 | 5 | 7 | 0 | 0 | 0 |
| Morningglory | 5 | 3 | 0 | 0 | 0 | 0 | 0 | 2 | 0 | 0 | 0 | 3 | 8 | 8 | 3 | 1 | 9 | 1 | 3 | 0 | 0 | 0 |
| Nutsedge | 2 | 3 | 0 | 0 | 0 | 0 | 0 | 0 | 0 | 0 | 0 | 8 | 9 | 9 | 3 | 0 | 8 | 0 | 0 | 0 | 0 | 0 |
| Rape | 5 | 7 | 0 | 0 | 0 | 0 | 0 | 0 | 0 | 0 | 0 | 9 | 9 | 9 | 2 | 2 | 9 | 0 | 0 | 0 | 0 | 0 |
| Rice | 2 | 0 | 0 | 0 | 0 | 0 | 0 | 0 | 0 | 0 | 0 | 9 | 9 | 9 | 10 | 8 | 9 | 5 | 7 | 0 | 0 | 0 |
| Sorghum | 2 | 0 | 0 | 0 | 0 | 0 | 0 | 0 | 0 | 0 | 0 | 9 | 9 | 9 | 7 | 0 | 9 | 3 | 4 | 0 | 0 | 0 |
| Soybean | 4 | 3 | 0 | 0 | 0 | 0 | 0 | 0 | 0 | 0 | 0 | 9 | 9 | 9 | 5 | 2 | 8 | 1 | 7 | 0 | 0 | 0 |
| Sugar beet | 7 | 6 | 0 | 0 | 0 | 0 | 0 | 0 | 0 | 0 | 0 | 9 | 9 | 9 | 7 | 8 | 9 | 2 | 2 | 0 | 0 | 0 |
| Velvetleaf | 3 | 6 | 0 | 0 | 0 | 0 | 0 | 0 | 1 | 0 | 0 | 7 | 8 | 9 | 1 | 0 | 8 | 0 | 0 | 0 | 0 | 0 |
| Wheat | 0 | 2 | 0 | 0 | 0 | 0 | 0 | 0 | 0 | 0 | 0 | 8 | 9 | 9 | 8 | 0 | 6 | 0 | 2 | 0 | 0 | 0 |
| Wild buckwheat | — | — | — | — | — | — | — | 0 | — | — | 0 | — | — | — | — | — | — | — | — | — | — | — |
| Wild oat | 3 | 2 | 0 | 0 | 0 | 0 | 0 | 0 | 0 | 0 | 0 | 8 | 9 | 9 | 8 | 4 | 6 | 2 | 8 | 0 | 0 | 0 |

| Rate (50 g/ha) PRE- | COMPOUND | | | | | | | | | |
|---|---|---|---|---|---|---|---|---|---|---|
| EMERGENCE | 333 | 334 | 335 | 336 | 337 | 338 | 339 | 340 | 341 | 342 |
| Barley | 0 | 0 | 0 | 0 | 0 | 8 | 9 | 2 | 2 | 7 |
| Barnyardgrass | 0 | 0 | 0 | 0 | 0 | 7 | 8 | 1 | 1 | 7 |
| Bedstraw | 0 | 2 | 0 | 0 | 0 | 5 | 1 | 0 | 0 | 2 |
| Blackgrass | 0 | 0 | 0 | 0 | 0 | 7 | 7 | 7 | 4 | 6 |
| Cheatgrass | 0 | 0 | 0 | 0 | 0 | 9 | 9 | 9 | 6 | 8 |

TABLE A-continued

TEST A

| | | | | | | | | | | |
|---|---|---|---|---|---|---|---|---|---|---|
| Chickweed | 0 | 0 | — | 0 | 0 | 9 | 9 | — | 0 | 10 |
| Cocklebur | 0 | 0 | 0 | 0 | 0 | 6 | 7 | 2 | 0 | 6 |
| Corn | 0 | 0 | 0 | 0 | 0 | 9 | 9 | 3 | 6 | 9 |
| Cotton | 0 | 0 | 0 | 0 | 0 | 7 | 8 | 1 | 0 | 5 |
| Crabgrass | 0 | 0 | 0 | 0 | 0 | 9 | 9 | 3 | 4 | 9 |
| Giant foxtail | 0 | 0 | 0 | 0 | 0 | 9 | 9 | 5 | 3 | 9 |
| Lambsquarters | 2 | 2 | 0 | 0 | 0 | 10 | 9 | 0 | 0 | 10 |
| Morningglory | 0 | 0 | 0 | 0 | 0 | 7 | 6 | 3 | 0 | 9 |
| Nutsedge | 0 | 0 | 0 | 0 | 0 | 7 | 10 | 0 | 4 | 9 |
| Rape | 0 | 0 | 0 | 0 | 0 | 9 | 9 | 2 | 2 | 9 |
| Rice | 0 | 0 | 0 | 0 | 0 | 9 | 10 | 9 | 7 | 10 |
| Sorghum | 0 | 0 | 0 | 0 | 0 | 8 | 9 | 2 | 0 | 9 |
| Soybean | 0 | 0 | 0 | 0 | 0 | 9 | 9 | 2 | 0 | 6 |
| Sugar beet | 0 | 0 | 0 | 0 | 0 | 9 | 9 | 1 | 3 | 10 |
| Velvetleaf | 0 | 0 | 0 | 0 | 0 | 5 | 7 | 0 | 0 | 6 |
| Wheat | 0 | 0 | 0 | 0 | 0 | 8 | 9 | 8 | 3 | 7 |
| Wild buckwheat | — | — | — | — | — | — | — | — | — | — |
| Wild oat | 0 | 0 | 0 | 0 | 0 | 8 | 7 | 8 | 2 | 5 |

| Rate (10 g/ha) POST- | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| EMERGENCE | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
| Barley | 8 | 7 | 6 | 5 | 7 | 8 | 7 | 8 | 7 | 7 | 8 | 7 | 8 | 4 | 2 | 3 | 3 | 2 | 4 | 0 | 0 | 0 | 0 | 2 | 8 | 8 | 8 | 8 | 9 |
| Barnyardgrass | 9 | 9 | 8 | 9 | 9 | 7 | 6 | 8 | 4 | 7 | 6 | 6 | 7 | 7 | 1 | 0 | 0 | 2 | 5 | 2 | 0 | 0 | 8 | 6 | 8 | 9 | 9 | 9 | 9 |
| Bedstraw | 8 | 8 | 9 | 8 | 9 | 9 | 2 | 8 | 2 | 3 | 3 | 3 | 5 | 3 | 2 | 0 | 0 | 0 | 2 | 5 | 3 | 2 | 2 | 5 | 7 | 5 | 8 | 7 | 8 |
| Blackgrass | 7 | 8 | 9 | 2 | 9 | 6 | 6 | 3 | 3 | 8 | 9 | 7 | 8 | 5 | 3 | 4 | 2 | 2 | 3 | 0 | 2 | 3 | 2 | 2 | 9 | 9 | 9 | 9 | 7 |
| Cheatgrass | 8 | 8 | 9 | 4 | 8 | 8 | 8 | 8 | 3 | 7 | 8 | 6 | 7 | 2 | 3 | 4 | 3 | 2 | 3 | 2 | 2 | 0 | 3 | 2 | 9 | 9 | 9 | 8 | 8 |
| Chickweed | 8 | 7 | 8 | 7 | 8 | 9 | 1 | 9 | 5 | — | — | — | — | 9 | 4 | — | — | 9 | — | 3 | 6 | 3 | 7 | 10 | 9 | 7 | 9 | 6 | — |
| Cocklebur | 3 | 5 | 5 | 0 | 2 | 2 | 0 | 3 | 9 | 9 | 6 | 2 | 7 | 0 | 0 | 3 | 4 | 3 | 3 | 2 | 0 | 0 | 7 | 0 | — | — | — | — | — |
| Corn | 9 | 9 | 9 | 9 | 9 | 9 | 9 | 9 | 9 | 9 | 9 | 9 | 10 | 9 | 7 | 4 | 1 | 8 | 9 | 7 | 3 | 1 | 9 | 9 | 9 | 9 | 9 | 9 | 10 |
| Cotton | 9 | 9 | 9 | 9 | 9 | 9 | 9 | 9 | 2 | 6 | 8 | 2 | 7 | 6 | 0 | 0 | 0 | 3 | 0 | 0 | 0 | 0 | 1 | 2 | 8 | 8 | 9 | 9 | 9 |
| Crabgrass | 9 | 7 | 9 | 0 | 2 | 2 | 2 | 4 | — | — | — | — | — | — | — | — | — | — | — | 2 | 0 | 0 | 2 | 6 | 5 | 2 | 8 | 4 | 8 |
| Giant foxtail | 8 | 9 | 7 | 3 | 7 | 5 | 7 | 4 | 7 | 7 | 9 | 8 | 6 | 7 | 4 | 0 | 0 | 5 | 7 | 3 | 2 | 2 | 7 | 6 | 9 | 8 | 9 | 8 | 9 |
| Lambsquarters | 9 | 9 | 9 | 8 | 8 | 9 | 8 | 9 | 9 | 8 | 8 | 9 | 8 | 7 | 3 | 7 | 5 | 4 | 4 | 5 | 5 | 3 | 8 | 3 | 10 | 10 | 8 | 8 | 10 |
| Morningglory | 9 | 9 | 9 | 9 | 9 | 8 | 8 | 9 | 5 | 8 | 9 | 0 | 6 | 8 | 5 | 2 | 1 | 6 | 7 | 2 | 1 | 0 | 1 | 4 | 9 | 9 | 10 | 9 | 10 |
| Nutsedge | 8 | 8 | 9 | 7 | 9 | 5 | 3 | 0 | 5 | — | 5 | 2 | 2 | 3 | 0 | 0 | 0 | 0 | 0 | 0 | 2 | 0 | 2 | 2 | 9 | 7 | 9 | 7 | 7 |
| Rape | 5 | 7 | 8 | 7 | 9 | 9 | 0 | 0 | 4 | 6 | 8 | 6 | 9 | 9 | 0 | 2 | 0 | 0 | 7 | 6 | 7 | 5 | 8 | 9 | 7 | 7 | 8 | 9 | 9 |
| Rice | 9 | 9 | 9 | 9 | 9 | 9 | 9 | 9 | 9 | 9 | 9 | 9 | 10 | 9 | 8 | 3 | 2 | 9 | 9 | 7 | 7 | 3 | 9 | 9 | 9 | 9 | 9 | 9 | 9 |
| Sorghum | 9 | 9 | 9 | 9 | 9 | 9 | 9 | 7 | 9 | 9 | 7 | 9 | 9 | 9 | 5 | 2 | 2 | 7 | 9 | 5 | 4 | 0 | 9 | 8 | 9 | 9 | 9 | 9 | 9 |
| Soybean | 9 | 9 | 8 | 6 | 9 | 9 | 3 | 8 | 6 | 6 | 9 | 5 | 9 | 8 | 1 | 1 | 2 | 3 | 3 | 1 | 1 | 0 | 5 | 4 | 8 | 8 | 9 | 9 | 9 |
| Sugar beet | 6 | 8 | 8 | 5 | 9 | 9 | 2 | 9 | 6 | 7 | 8 | 3 | 7 | 4 | 0 | 2 | 2 | 0 | 0 | 7 | 7 | 3 | 8 | 8 | 9 | 8 | 9 | 9 | 9 |
| Velvetleaf | 9 | 9 | 7 | 7 | 10 | 3 | 2 | 8 | 2 | 2 | 6 | 0 | 7 | 8 | 0 | 0 | 0 | 3 | 2 | 2 | 0 | 0 | 6 | 2 | 8 | 9 | 9 | 8 | 9 |
| Wheat | 7 | 7 | 7 | 3 | 7 | 7 | 7 | 8 | 6 | 7 | 9 | 6 | 9 | 6 | 1 | 2 | 0 | 3 | 4 | 2 | 2 | 2 | 3 | 3 | 8 | 9 | 8 | 8 | 9 |
| Wild buckwheat | 9 | 8 | 8 | 7 | 8 | 9 | 1 | 5 | 4 | 2 | 9 | 2 | 5 | 3 | 0 | 0 | 0 | 0 | 0 | 3 | 7 | 2 | 0 | 5 | 9 | 4 | 8 | 8 | 9 |
| Wild oat | 8 | 9 | 9 | 3 | 8 | 8 | 8 | 2 | 7 | 8 | 9 | 6 | 6 | 3 | 0 | 0 | 0 | 2 | 1 | 1 | 0 | 0 | 2 | 5 | 9 | 9 | 9 | 8 | 10 |

TABLE A-continued

TEST A

| Rate (10 g/ha) POST-EMERGENCE | COMPOUND 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 |
|---|---|---|---|---|---|---|---|---|---|---|---|---|---|---|---|---|---|---|---|---|---|---|---|---|---|---|---|---|---|
| Barley | 9 | 8 | 7 | 7 | 7 | 7 | 8 | 2 | 5 | 2 | 0 | 4 | 2 | 3 | 0 | 0 | 2 | 3 | 0 | 2 | 4 | 5 | 8 | 8 | 2 | 2 | 6 | 7 | 4 |
| Barnyardgrass | 9 | 7 | 5 | 3 | 3 | 9 | 9 | 0 | 1 | 1 | 0 | 7 | 2 | 0 | 0 | 0 | 0 | 0 | 0 | 2 | 9 | 9 | 9 | 9 | 7 | 7 | 8 | 8 | 8 |
| Bedstraw | 8 | 4 | 6 | 4 | 3 | 6 | 7 | 2 | 3 | 2 | 2 | 3 | 2 | 0 | 2 | 0 | 0 | 3 | 0 | 3 | 7 | 9 | — | 6 | 7 | 5 | 4 | 7 | 7 |
| Blackgrass | 8 | 8 | 4 | 2 | 7 | 8 | 9 | 0 | 0 | 0 | 0 | 2 | 3 | 2 | 3 | 2 | 0 | 0 | 0 | 0 | 9 | 8 | — | 8 | 2 | 4 | 4 | 8 | 5 |
| Cheatgrass | 9 | 7 | 7 | 6 | 8 | 5 | 5 | 0 | 0 | 2 | 0 | 2 | 3 | 0 | 3 | 0 | 0 | 2 | 0 | 2 | 9 | 7 | — | 7 | 3 | 3 | 5 | 7 | 6 |
| Chickweed | 9 | 4 | — | 8 | 7 | 4 | 9 | 0 | 6 | 8 | 0 | 9 | 9 | 3 | 5 | 0 | 0 | 0 | 0 | 9 | 9 | 9 | 4 | 9 | 10 | 7 | 0 | 7 | 5 |
| Cocklebur | — | — | — | — | — | — | — | — | — | — | — | — | — | — | — | — | — | — | — | — | 9 | 10 | 9 | 10 | 9 | 1 | 10 | 9 | 9 |
| Corn | 10 | 9 | 3 | 2 | 9 | 8 | 9 | 5 | 7 | 3 | 2 | 9 | 2 | 0 | 1 | 0 | 0 | 5 | 0 | 7 | 8 | 9 | 4 | 8 | 8 | 3 | 8 | 9 | 9 |
| Cotton | 9 | 2 | 3 | 0 | 5 | 9 | 9 | 0 | 0 | 0 | 0 | 1 | 5 | 0 | 0 | 0 | 0 | 0 | 0 | 0 | 9 | 9 | 9 | 9 | 9 | 8 | 9 | 9 | 9 |
| Crabgrass | 7 | 2 | 0 | 0 | 5 | 4 | 6 | 0 | 0 | 0 | 0 | 0 | 0 | 0 | 0 | 0 | 0 | 0 | 0 | 0 | 0 | 5 | 4 | 6 | 0 | 0 | 0 | 3 | 0 |
| Giant foxtail | 9 | 8 | 6 | 4 | 8 | 7 | 9 | 0 | 1 | 0 | 0 | 1 | 0 | 0 | 0 | 0 | 0 | 0 | 0 | 0 | 8 | 8 | 7 | 9 | 2 | 0 | 3 | 8 | 6 |
| Lambsquarters | 9 | — | 7 | 8 | 5 | 9 | 9 | 3 | 3 | 7 | 7 | 9 | — | 0 | 3 | 7 | 7 | 0 | 3 | 3 | 9 | 10 | 6 | 8 | 9 | 5 | 2 | 8 | — |
| Morningglory | 10 | 8 | 8 | 8 | 9 | 9 | 9 | 4 | 5 | 1 | 2 | 6 | 2 | 0 | 5 | 0 | 0 | 0 | 7 | 7 | 9 | 10 | 2 | 9 | 10 | 9 | 0 | 3 | 9 |
| Nutsedge | 5 | — | 0 | 0 | 0 | 0 | 0 | 0 | 0 | 0 | 0 | 0 | 0 | 0 | 0 | 0 | 0 | 0 | 0 | 5 | 9 | 9 | 4 | 9 | 8 | — | 9 | 9 | 9 |
| Rape | 10 | 2 | 2 | 5 | 7 | 0 | 9 | 6 | 5 | 7 | 6 | 9 | 8 | 2 | 0 | 0 | 4 | 4 | 0 | 6 | 9 | 9 | 7 | 9 | 9 | 8 | 9 | 8 | 9 |
| Rice | 9 | 9 | 9 | 7 | 9 | 9 | 9 | 2 | 2 | 0 | 0 | 9 | 9 | 0 | 0 | 0 | 0 | 2 | 0 | 0 | 9 | 9 | 9 | 9 | 9 | 8 | 8 | 9 | 8 |
| Sorghum | 10 | 9 | 4 | 3 | 7 | 9 | 9 | 0 | 1 | 0 | 0 | 5 | 1 | 0 | 0 | 0 | 0 | 1 | 0 | 0 | 8 | 9 | 9 | 9 | 7 | 3 | 7 | 9 | 8 |
| Soybean | 9 | 4 | 9 | 2 | 4 | 5 | 9 | 1 | 2 | 0 | 1 | 9 | 4 | 0 | 1 | 0 | 0 | 1 | 3 | 3 | 9 | 9 | 7 | 9 | 9 | 6 | 8 | 9 | 9 |
| Sugar beet | 10 | 7 | 5 | 6 | 8 | 7 | 9 | 7 | 8 | 8 | 8 | 9 | 8 | 2 | 7 | 6 | 7 | 0 | 4 | 9 | 8 | 10 | 3 | 8 | 9 | 7 | 7 | 7 | 8 |
| Velvetleaf | 9 | 3 | 1 | 1 | 2 | 8 | 9 | 3 | 5 | 5 | 0 | 3 | 2 | 0 | 0 | 0 | 0 | 0 | 0 | 2 | 9 | 10 | 9 | 9 | 5 | 8 | 9 | 8 | 9 |
| Wheat | 8 | 7 | 5 | 4 | 7 | 8 | 8 | 0 | 3 | 0 | 0 | 3 | 3 | 0 | 1 | 0 | 0 | 1 | 0 | 1 | 4 | 7 | 8 | 7 | 0 | 0 | 3 | 5 | 2 |
| Wild buckwheat | 8 | 0 | 0 | 2 | 2 | 2 | 5 | 5 | 4 | 5 | 7 | 8 | 7 | 0 | 0 | 0 | 0 | 3 | 2 | 2 | 5 | 10 | — | 4 | 8 | 6 | 3 | — | 4 |
| Wild oat | 10 | 8 | 7 | 7 | 9 | 9 | 9 | 0 | 2 | 0 | 0 | 4 | 2 | 0 | 1 | 0 | 0 | 1 | 0 | 0 | 5 | 9 | 8 | 7 | 2 | 0 | 6 | 4 | 0 |

| Rate (10 g/ha) POST-EMERGENCE | COMPOUND 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
|---|---|---|---|---|---|---|---|---|---|---|---|---|---|---|---|---|---|---|---|---|---|---|---|---|---|---|---|---|---|
| Barley | 4 | 2 | 0 | 7 | 7 | 5 | 4 | 3 | 1 | 9 | 0 | 5 | 0 | 0 | 3 | 3 | 0 | 0 | 4 | 3 | 2 | 0 | 7 | 7 | 7 | 6 | 3 | 2 | 2 |
| Barnyardgrass | 6 | 3 | 1 | 8 | 9 | 9 | 7 | 3 | 8 | 9 | 3 | 9 | 0 | 0 | 5 | 7 | 0 | 0 | 6 | 9 | 0 | 0 | 8 | 9 | 9 | 3 | 0 | 8 | 2 |
| Bedstraw | 8 | 8 | — | 2 | 8 | 7 | 4 | 7 | 5 | 3 | 7 | 7 | 6 | 0 | 5 | 7 | 4 | 5 | 4 | 7 | 0 | 0 | 3 | 6 | 9 | 7 | 7 | 7 | 0 |
| Blackgrass | 5 | 5 | 0 | 7 | 9 | 9 | 8 | 4 | 3 | 1 | 0 | 2 | 0 | 0 | 2 | 4 | 5 | 0 | 5 | 8 | 5 | 0 | 9 | 9 | 9 | 9 | 8 | 9 | 4 |
| Cheatgrass | 7 | 7 | — | 9 | 10 | 9 | 6 | 3 | 6 | 7 | 7 | 0 | 0 | 0 | 8 | 8 | 0 | 0 | 8 | 9 | 0 | 0 | 9 | 9 | 9 | 6 | 4 | 8 | 4 |
| Chickweed | 10 | 9 | 2 | 0 | 6 | 8 | 5 | 0 | 4 | — | — | — | — | — | 5 | 7 | 8 | 3 | — | 9 | 0 | 0 | 4 | 9 | 10 | 9 | 3 | 3 | 2 |
| Cocklebur | 10 | 10 | 9 | 5 | 9 | 9 | 7 | 7 | 9 | 9 | 6 | 9 | 9 | 2 | — | 9 | 9 | 7 | 9 | 9 | 0 | — | — | — | — | — | — | — | — |
| Corn | 8 | 5 | 0 | 0 | 7 | 9 | 9 | 7 | 0 | 9 | 2 | 9 | 7 | 0 | 3 | 7 | 6 | 2 | 0 | 7 | 1 | 1 | 0 | 1 | 5 | 7 | 7 | 0 | 0 |
| Cotton | 10 | 9 | 9 | 7 | 9 | 9 | 6 | 4 | 7 | 9 | 6 | 9 | 9 | 2 | 6 | 9 | 5 | 5 | 7 | 9 | 2 | 0 | 8 | 9 | 9 | 8 | 7 | 8 | 6 |
| Crabgrass | 1 | 0 | 0 | 3 | 8 | 3 | 2 | 0 | 0 | 3 | 0 | 1 | 0 | 0 | 0 | 1 | 0 | 0 | 1 | 3 | 0 | 0 | 1 | 5 | 5 | 4 | 3 | 2 | 0 |
| Giant foxtail | 2 | 0 | 0 | 6 | 9 | 8 | 7 | 0 | 4 | 4 | 3 | 3 | 2 | 0 | 7 | 9 | 5 | 0 | 7 | 9 | 3 | 0 | 6 | 9 | 7 | 4 | 0 | 4 | 0 |
| Lambsquarters | 9 | 9 | 3 | 9 | 10 | 9 | 7 | 5 | 9 | 8 | 9 | 10 | 7 | 7 | 8 | 9 | 9 | 2 | 9 | 9 | 5 | 0 | 9 | 9 | — | 9 | 9 | 8 | 1 |
| Morningglory | 9 | 10 | 8 | 7 | 9 | 10 | 8 | 6 | 9 | 10 | 9 | 9 | 10 | 2 | 9 | 9 | 0 | 1 | 9 | 9 | 2 | 0 | 9 | 9 | 9 | 9 | 8 | 9 | 9 |
| Nutsedge | 9 | 8 | 9 | 6 | 8 | 9 | 0 | 0 | 7 | — | — | 0 | 0 | 5 | 0 | 9 | — | 0 | — | 5 | 0 | 0 | 0 | — | — | 0 | 0 | — | 0 |
| Rape | 9 | 9 | 9 | 9 | 9 | 9 | 7 | 5 | 6 | 8 | 8 | 9 | 8 | 5 | 9 | 8 | 8 | 8 | 9 | 9 | 7 | 0 | 9 | 9 | 9 | 9 | 5 | 8 | 8 |

TABLE A-continued

TEST A

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rice | 9 | 9 | 6 | 9 | 8 | 9 | 9 | 9 | 4 | 8 | 4 | 8 | 5 | 0 | 7 | 8 | 1 | 0 | 9 | 9 | 9 | 0 | 9 | 9 | 9 | 9 | 9 | 9 | 3 |
| Sorghum | 7 | 6 | 2 | 9 | 9 | 9 | 8 | 4 | 9 | 9 | 1 | 3 | 0 | 0 | 5 | 8 | 0 | 0 | 7 | 9 | 0 | 0 | 9 | 9 | 9 | 9 | 9 | 9 | 5 |
| Soybean | 9 | 9 | 3 | 9 | 9 | 9 | 9 | 7 | 7 | 5 | 8 | 9 | 9 | 1 | 8 | 8 | 6 | 3 | 8 | 9 | 1 | 0 | 8 | 8 | 9 | 7 | 8 | 7 | 0 |
| Sugar beet | 9 | 9 | 9 | 8 | 9 | 9 | 6 | 4 | 7 | 9 | 9 | 10 | 10 | 9 | 9 | 9 | 8 | 9 | — | 9 | 5 | 2 | 8 | 9 | 10 | 9 | 9 | 9 | 0 |
| Velvetleaf | 9 | 9 | 9 | 9 | 9 | 9 | 6 | 4 | 9 | 9 | 9 | 9 | 9 | 5 | 6 | 8 | 7 | 6 | 7 | 9 | 0 | 0 | 9 | 10 | 10 | 8 | 6 | 8 | 5 |
| Wheat | 2 | 2 | 0 | 8 | 7 | 4 | 8 | 5 | 0 | 2 | 0 | 0 | 0 | 0 | 1 | 0 | 0 | 0 | 5 | 3 | 2 | 0 | 8 | 6 | 5 | 5 | 3 | 0 | 0 |
| Wild buckwheat | 9 | 8 | 0 | 10 | 7 | 8 | 8 | 5 | 7 | 2 | 7 | 6 | 2 | 0 | 0 | 8 | 2 | 0 | 4 | 9 | 0 | 0 | 7 | 7 | 7 | 8 | — | 7 | 3 |
| Wild oat | 4 | 2 | 0 | 8 | 7 | 4 | 8 | 5 | 0 | 5 | 0 | 0 | 0 | 0 | 6 | 3 | 7 | 0 | 7 | 6 | 2 | 0 | 8 | 5 | 3 | 7 | 5 | 0 | 0 |

| Rate (10 g/ha) POST- | COMPOUND | | | | | | | | | | | | | | | | | | | | | | | | |
|---|---|---|---|---|---|---|---|---|---|---|---|---|---|---|---|---|---|---|---|---|---|---|---|---|---|
| EMERGENCE | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
| Barley | 3 | 5 | 3 | 3 | 2 | — | 4 | 5 | 4 | 5 | 5 | 2 | 0 | 3 | 8 | 8 | 6 | 6 | 2 | 8 | 6 | 9 | 9 | 7 | 4 |
| Barnyardgrass | 7 | 8 | 2 | 0 | 1 | 7 | 6 | 5 | 2 | 2 | 2 | 1 | 1 | 2 | 8 | 8 | 1 | 2 | 2 | 8 | 6 | 9 | 9 | 9 | 8 |
| Bedstraw | 7 | 8 | 5 | 7 | 7 | — | 2 | 8 | 6 | 5 | 7 | 5 | 1 | 2 | 8 | 9 | 4 | 4 | 4 | 9 | 9 | 8 | 9 | 8 | 8 |
| Blackgrass | 9 | — | 5 | 7 | — | — | 7 | 6 | 5 | 8 | 8 | 5 | 6 | 5 | 9 | 9 | 6 | 9 | — | 9 | 8 | 9 | 9 | 9 | — |
| Cheatgrass | 9 | 9 | 3 | 2 | 3 | — | 5 | 0 | 0 | 4 | 5 | 2 | 0 | 3 | 9 | 8 | 5 | 7 | 3 | 9 | 8 | 9 | 9 | 9 | 8 |
| Chickweed | 4 | 6 | 7 | 8 | 2 | — | 3 | 9 | 3 | 1 | 2 | 2 | 2 | 2 | 8 | 8 | 0 | 2 | 0 | 9 | 9 | 9 | 9 | 9 | 8 |
| Cocklebur | — | — | — | — | — | — | — | — | — | — | — | — | — | — | — | — | — | — | — | — | — | — | — | — | — |
| Corn | 0 | 5 | 4 | 6 | 0 | 7 | 6 | 9 | 7 | 8 | 7 | 6 | 3 | 0 | 0 | 0 | 0 | 2 | 0 | 9 | 8 | 8 | 9 | 8 | 5 |
| Cotton | 9 | 9 | 6 | 7 | 8 | 9 | 9 | 9 | 9 | 9 | 9 | 9 | 9 | 0 | 7 | 9 | 0 | 0 | 4 | 10 | 9 | 9 | 9 | 10 | 10 |
| Crabgrass | 2 | 3 | 3 | — | 0 | 4 | 1 | 1 | 0 | 0 | 0 | 0 | 0 | 0 | 0 | 0 | 3 | 2 | 0 | 3 | 6 | — | 9 | 7 | 4 |
| Giant foxtail | 2 | 4 | 3 | 0 | 0 | 7 | 8 | 6 | 4 | 5 | 7 | 2 | 2 | 3 | 3 | 4 | 3 | 4 | 0 | 7 | 5 | 9 | 9 | 8 | 5 |
| Lambsquarters | 8 | 7 | 8 | 9 | 0 | — | 7 | 4 | 9 | 9 | 8 | 5 | — | 7 | 9 | 9 | — | 1 | 6 | 10 | — | 9 | 10 | 10 | 9 |
| Morningglory | 9 | 10 | 9 | 9 | 8 | 6 | 6 | 5 | 4 | 9 | 8 | 2 | 2 | 7 | 9 | 9 | 7 | 7 | 7 | 9 | 9 | 9 | 10 | 10 | 9 |
| Nutsedge | 8 | 9 | 0 | 0 | 0 | — | — | — | — | — | — | — | 0 | 0 | 8 | 8 | — | 0 | — | 8 | 8 | 9 | 9 | 7 | 3 |
| Rape | 8 | 7 | 8 | 7 | 7 | — | 3 | 7 | 8 | 7 | 6 | 8 | 8 | 8 | 9 | 6 | 6 | 0 | 2 | 9 | 9 | 7 | 10 | 9 | 7 |
| Rice | 5 | 9 | 9 | 9 | 7 | 8 | 9 | 9 | 9 | 8 | 8 | 8 | 7 | 7 | 9 | 9 | 9 | 9 | 4 | 9 | 9 | 9 | 9 | 9 | 8 |
| Sorghum | 9 | 9 | 8 | 6 | 6 | 8 | 9 | 9 | 7 | 8 | 9 | 9 | 5 | 2 | 9 | 9 | 9 | 8 | 4 | 9 | 9 | 9 | 9 | 9 | 9 |
| Soybean | 8 | 9 | 7 | 7 | 0 | 6 | 8 | 8 | 7 | 3 | 6 | 5 | 6 | 0 | 1 | 5 | 0 | 1 | 0 | 9 | 9 | 9 | 9 | 9 | 8 |
| Sugar beet | 9 | 8 | 8 | 9 | 3 | — | 9 | 9 | 9 | 9 | 8 | 9 | 9 | 8 | 9 | 9 | 0 | 5 | 8 | 9 | 9 | 7 | 8 | 9 | 8 |
| Velvetleaf | 9 | 9 | 6 | 4 | 0 | 6 | 7 | 8 | 7 | 9 | 4 | 9 | 7 | 4 | 5 | 8 | 1 | 2 | 0 | 10 | 8 | 10 | 10 | 10 | 10 |
| Wheat | 2 | 2 | 2 | 3 | 0 | — | 4 | 3 | 0 | 2 | 2 | 0 | 0 | 3 | 8 | 7 | 6 | 5 | 2 | 8 | 4 | 9 | 9 | 7 | 6 |
| Wild buckwheat | 7 | 6 | 9 | 7 | 3 | — | 9 | 8 | — | — | — | — | — | — | — | — | 4 | 1 | — | — | — | 9 | 9 | — | — |
| Wild oat | 2 | 0 | 7 | 7 | 0 | — | 2 | 4 | 3 | 7 | 6 | 3 | 2 | 2 | 7 | 3 | 9 | 8 | 0 | 9 | 9 | 9 | 9 | 5 | 4 |

| Rate (10 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 113 | 114 | 115 | 116 | 117 | 118 | 119 | 120 | 121 | 122 | 123 | 124 | 125 | 126 | 127 | 128 | 129 | 130 | 131 | 132 | 133 | 134 |
| Barley | 4 | 7 | 2 | 2 | 0 | 2 | 8 | 5 | 7 | 7 | 3 | 2 | 0 | 2 | 0 | 0 | 0 | 0 | 0 | 0 | 2 | 0 |
| Barnyardgrass | 6 | 9 | 7 | 7 | 1 | 1 | 9 | 9 | 9 | 8 | 1 | 8 | 2 | 4 | 0 | 0 | 0 | 0 | 0 | 0 | 0 | 0 |
| Bedstraw | 6 | 7 | 8 | 9 | 7 | 7 | 7 | 7 | 7 | 7 | 0 | 0 | 0 | 2 | 7 | 0 | 3 | 3 | 4 | 7 | 8 | — |
| Blackgrass | 8 | 8 | 8 | 8 | 6 | 5 | 9 | 9 | 8 | 9 | 3 | 5 | 2 | 2 | 0 | 0 | 0 | 5 | 2 | 4 | 3 | 0 |
| Cheatgrass | 8 | 8 | 9 | 5 | 0 | 2 | 9 | 8 | 9 | 8 | 5 | 5 | 3 | 2 | 0 | 0 | 0 | 3 | 0 | 0 | 0 | 0 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Chickweed | 0 | 5 | 3 | 9 | 9 | 2 | 9 | 8 | 9 | 9 | 0 | 0 | 4 | 9 | — | 0 | 0 | 2 | 4 | 8 | 0 | 0 |
| Cocklebur | — | — | — | — | — | — | — | — | — | — | 3 | 7 | 9 | 9 | 4 | 5 | 1 | 5 | 9 | 9 | 7 | 2 |
| Corn | 4 | 9 | 7 | 2 | 0 | 0 | 9 | 9 | 9 | 9 | 0 | 0 | 0 | 5 | 3 | 0 | 0 | 0 | 0 | 2 | 1 | 0 |
| Cotton | 9 | 9 | 9 | 9 | 9 | 7 | 9 | 9 | 9 | 9 | 9 | 9 | 9 | 10 | 8 | 8 | 6 | 6 | 6 | 7 | 4 | 0 |
| Crabgrass | 0 | 7 | 0 | 2 | 0 | 0 | 5 | 6 | 6 | 5 | 6 | 2 | 2 | 1 | 1 | 0 | 0 | 0 | 0 | 0 | 0 | 0 |
| Giant foxtail | 3 | 7 | 5 | 2 | 0 | 0 | 9 | 8 | 8 | 3 | 1 | 2 | 0 | 1 | 1 | 0 | 0 | 0 | 0 | 0 | 0 | 0 |
| Lambsquarters | 2 | — | 5 | — | — | 3 | — | 10 | 9 | 9 | 8 | 9 | — | — | 9 | 7 | — | 7 | — | 9 | 9 | 3 |
| Morningglory | 7 | 9 | 10 | 10 | 9 | 6 | 10 | 10 | 10 | 9 | 0 | 8 | 9 | 8 | 9 | 9 | 0 | 1 | 6 | 6 | 9 | 1 |
| Nutsedge | 0 | 7 | — | — | 0 | 2 | 9 | 9 | — | 5 | — | 8 | 9 | 9 | — | 3 | 0 | 7 | 9 | — | — | — |
| Rape | 8 | 9 | 8 | 9 | 9 | 8 | 8 | 9 | 9 | 9 | 4 | 8 | 9 | 9 | 7 | 7 | 5 | 8 | 9 | 8 | 6 | 5 |
| Rice | 8 | 9 | 7 | 8 | 8 | 3 | 9 | 9 | 9 | 9 | 8 | 7 | 3 | 9 | 9 | 2 | 0 | 2 | 0 | 0 | 9 | 0 |
| Sorghum | 7 | 9 | 9 | 9 | 7 | 3 | 9 | 9 | 9 | 9 | 0 | 0 | 0 | 7 | 8 | 6 | 0 | 2 | 0 | 0 | 2 | 0 |
| Soybean | 0 | 8 | 9 | 9 | 9 | 0 | 9 | 9 | 9 | 9 | 5 | 6 | 6 | 6 | 7 | 2 | 4 | 7 | 9 | 9 | 9 | 0 |
| Sugar beet | 2 | 6 | 5 | 9 | 9 | 4 | 9 | 9 | 9 | 9 | 5 | 7 | 9 | 9 | 9 | 5 | 5 | 6 | 6 | 9 | 8 | 4 |
| Velvetleaf | — | 9 | 9 | 9 | 9 | 7 | 10 | 10 | 10 | 9 | 9 | 9 | 9 | 9 | 0 | 9 | 8 | 5 | 9 | 9 | 0 | 0 |
| Wheat | 2 | 5 | 0 | 0 | 0 | 2 | 9 | 4 | 9 | 7 | 0 | 0 | 0 | 0 | 0 | 0 | 0 | 0 | 0 | 1 | 0 | 0 |
| Wild buckwheat | 5 | 3 | 5 | 9 | 9 | 6 | 7 | 8 | — | 9 | 6 | 5 | 8 | 9 | 8 | 8 | 5 | 3 | 7 | 7 | 7 | 6 |
| Wild oat | 4 | 7 | 1 | 3 | 2 | 0 | 8 | 3 | 8 | 8 | 4 | 3 | 0 | 1 | 5 | 0 | 0 | 0 | 1 | 1 | 1 | 2 |

| Rate (10 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 135 | 136 | 137 | 138 | 139 | 140 | 141 | 142 | 143 | 144 | 145 | 146 | 147 | 148 | 149 | 150 | 151 | 152 | 165 | 166 | 167 | 168 |
| Barley | 8 | 2 | 5 | 8 | 5 | 6 | 7 | 7 | 8 | 7 | 3 | 5 | 7 | 7 | 8 | 7 | 2 | 2 | 6 | 9 | 9 | 0 |
| Barnyardgrass | 7 | 4 | 8 | 7 | 3 | 7 | 6 | 9 | 9 | 2 | 0 | 6 | 9 | 9 | 9 | 3 | 0 | 4 | 8 | 9 | 9 | 9 |
| Bedstraw | 8 | 9 | 7 | 8 | 7 | 6 | 5 | 7 | 7 | 7 | 8 | 7 | 7 | 8 | 9 | 8 | 9 | 7 | 3 | 7 | 8 | 8 |
| Blackgrass | 7 | 0 | 7 | 9 | 3 | 9 | 8 | 9 | 9 | 9 | 8 | 9 | 9 | 9 | 9 | 9 | 9 | 9 | 8 | 8 | 9 | 0 |
| Cheatgrass | 7 | 8 | 8 | 9 | 8 | 9 | 7 | 7 | 9 | 6 | 3 | 8 | 9 | 9 | 9 | 9 | 7 | 7 | 8 | 9 | 10 | 4 |
| Chickweed | 5 | 0 | 4 | 7 | 0 | 5 | 5 | 6 | 8 | 6 | 0 | 3 | 7 | 9 | 10 | 9 | 7 | 3 | 5 | 8 | 10 | 3 |
| Cocklebur | 8 | 6 | 6 | 7 | 2 | 7 | 9 | 9 | 10 | 9 | 7 | 10 | 9 | 10 | 10 | 9 | 9 | 9 | 8 | 9 | 7 | 7 |
| Corn | 3 | 3 | 7 | 6 | 3 | 6 | 0 | 8 | 9 | 8 | 3 | 2 | 0 | 5 | 8 | 6 | 8 | 0 | 9 | 9 | 9 | 9 |
| Cotton | 9 | 6 | 9 | 9 | 7 | 9 | 8 | 9 | 9 | 8 | 8 | 9 | 9 | 9 | 9 | 9 | 9 | 9 | 7 | 9 | 9 | 9 |
| Crabgrass | 0 | 0 | 2 | 3 | 0 | 2 | 0 | 3 | 3 | 0 | 0 | 0 | 0 | 0 | 3 | 1 | 0 | 0 | 5 | 4 | 2 | 0 |
| Giant foxtail | 3 | 2 | 4 | 7 | 2 | 7 | 2 | 5 | 8 | 6 | 0 | 2 | 2 | 3 | 9 | 6 | 2 | 0 | 7 | 7 | 8 | 4 |
| Lambsquarters | 4 | 5 | 5 | 8 | 8 | 8 | 7 | 10 | 10 | 8 | 8 | 8 | 9 | 10 | 10 | 9 | 10 | 7 | 9 | 9 | 10 | 9 |
| Morningglory | 9 | 7 | 9 | 10 | 9 | 9 | 1 | 6 | 9 | 9 | 9 | 9 | 10 | 10 | 10 | 9 | 9 | 9 | 5 | 9 | 9 | 9 |
| Nutsedge | 4 | — | 6 | 9 | 0 | 5 | 8 | 9 | 9 | 9 | 0 | 9 | 9 | 9 | 9 | 9 | 7 | 9 | 6 | 7 | 9 | 7 |
| Rape | 0 | 3 | 3 | 0 | 0 | 0 | 8 | 9 | 8 | 9 | 8 | 9 | 9 | 9 | 9 | 9 | 9 | 9 | 7 | 8 | 9 | 8 |
| Rice | 9 | 8 | 9 | 9 | 9 | 8 | 9 | 9 | 9 | 9 | 9 | 9 | 9 | 9 | 9 | 9 | 9 | 9 | 9 | 9 | 9 | 9 |
| Sorghum | 9 | 8 | 9 | 9 | 4 | 8 | 9 | 9 | 9 | 9 | 7 | 9 | 9 | 9 | 9 | 9 | 8 | 9 | 8 | 9 | 9 | 7 |
| Soybean | 8 | 9 | 6 | 8 | 9 | 8 | 9 | 8 | 9 | 9 | 8 | 8 | 9 | 9 | 9 | 9 | 9 | 9 | 9 | 9 | 9 | 8 |
| Sugar beet | 9 | 7 | 9 | 9 | 8 | 8 | 7 | 9 | 9 | 9 | 9 | 9 | 7 | 9 | 9 | 9 | 9 | 7 | 7 | 10 | 7 | 6 |
| Velvetleaf | 6 | 7 | 6 | 8 | 9 | 8 | 9 | 9 | 10 | 6 | 3 | 9 | 10 | 10 | 10 | 9 | 8 | 9 | 9 | 9 | 9 | 8 |
| Wheat | 8 | 3 | 7 | 8 | 6 | 7 | 6 | 7 | 8 | 9 | 4 | 3 | 7 | 9 | 9 | 8 | 3 | 0 | 8 | 9 | 8 | 0 |
| Wild buckwheat | — | — | — | — | — | — | — | — | — | — | — | — | — | — | — | — | — | — | 7 | 7 | 10 | 8 |
| Wild oat | 9 | 3 | 8 | 9 | 3 | 7 | 7 | 6 | 8 | 9 | 8 | 5 | 8 | 5 | 7 | 9 | 4 | 2 | 7 | 9 | 9 | 1 |

TABLE A-continued

TEST A

| Rate (10 g/ha) POST-EMERGENCE | COMPOUND 169 | 170 | 171 | 172 | 173 | 174 | 175 | 176 | 177 | 178 | 179 | 180 | 181 | 182 | 183 | 184 | 185 | 186 | 187 | 188 | 189 | 190 |
|---|---|---|---|---|---|---|---|---|---|---|---|---|---|---|---|---|---|---|---|---|---|---|
| Barley | 3 | 4 | 8 | 9 | 9 | 6 | 7 | 7 | 4 | 6 | 4 | 4 | 3 | 8 | 8 | 9 | 8 | 9 | 9 | 8 | 8 | 8 |
| Barnyardgrass | 9 | 10 | 7 | 3 | 3 | 8 | 9 | 4 | 0 | 8 | 3 | 9 | 6 | 9 | 9 | 9 | 9 | 10 | 8 | 6 | 6 | 8 |
| Bedstraw | 8 | 8 | 7 | 5 | 8 | 7 | 5 | 2 | 2 | 0 | 0 | 3 | 6 | 8 | 9 | 9 | 7 | 8 | 8 | 7 | 7 | 7 |
| Blackgrass | 8 | 9 | 8 | 9 | 9 | 7 | 8 | 8 | 7 | 2 | 3 | 7 | 7 | 9 | 9 | 9 | 8 | 9 | — | 7 | 8 | 9 |
| Cheatgrass | 7 | 8 | 9 | 9 | 9 | 5 | 8 | 7 | 7 | 0 | 2 | 6 | 5 | 9 | 9 | 9 | 7 | 9 | 9 | 7 | 7 | 7 |
| Chickweed | 10 | 9 | 2 | 5 | 7 | 2 | 7 | 3 | 3 | 7 | 2 | 6 | 7 | 3 | 5 | 7 | 5 | 7 | 7 | 2 | 3 | 4 |
| Cocklebur | 7 | 9 | 2 | 5 | 6 | 6 | 2 | 0 | 0 | 0 | 0 | 0 | 0 | 9 | 9 | 10 | 9 | 9 | 8 | 0 | 8 | 8 |
| Corn | 9 | 10 | 9 | 8 | 9 | 9 | 9 | 8 | 3 | 5 | 1 | 9 | 9 | 9 | 9 | 9 | 9 | 9 | 9 | 9 | 9 | 9 |
| Cotton | 9 | 9 | 6 | 8 | 9 | 5 | 6 | 0 | 0 | 0 | 0 | 0 | 7 | 9 | 9 | 9 | 9 | 9 | 9 | 6 | 7 | 8 |
| Crabgrass | 6 | 9 | 7 | 7 | 8 | 4 | 8 | 5 | 3 | 2 | 2 | 6 | 8 | 9 | 8 | 9 | 7 | 9 | 8 | 5 | 5 | 5 |
| Giant foxtail | 8 | 10 | 6 | 8 | 9 | 8 | 9 | 6 | 5 | 9 | 2 | 8 | 9 | 9 | 9 | 9 | 9 | 9 | 9 | 7 | 7 | 8 |
| Lambsquarters | 10 | 10 | 9 | 10 | 10 | 8 | 8 | 2 | 3 | 2 | 5 | 4 | — | 10 | 10 | 10 | 10 | 9 | 7 | 7 | 8 | 8 |
| Morningglory | 9 | 10 | 7 | 8 | 8 | 7 | 7 | 0 | 0 | 0 | 0 | 8 | 9 | 9 | 10 | 10 | 10 | 9 | 9 | 7 | 9 | 9 |
| Nutsedge | 0 | 2 | 0 | 9 | 7 | 5 | 3 | — | — | 6 | 4 | 0 | 3 | 8 | 9 | 8 | 9 | 3 | 2 | 2 | 4 | 5 |
| Rape | 9 | 9 | 5 | 4 | 7 | 7 | 7 | 0 | 0 | 0 | 0 | 0 | 6 | 8 | 9 | 9 | 9 | 9 | 7 | 0 | 2 | 0 |
| Rice | 9 | 9 | 9 | 8 | 9 | 9 | 9 | 5 | 5 | 0 | 0 | 9 | 9 | 9 | 9 | 10 | 9 | 10 | 9 | 9 | 9 | 9 |
| Sorghum | 9 | 10 | 9 | 8 | 9 | 9 | 9 | 0 | 3 | 0 | 0 | 9 | 9 | 9 | 9 | 10 | 9 | 9 | 9 | 9 | 9 | 9 |
| Soybean | 9 | 9 | 2 | 8 | 9 | 7 | 5 | 0 | 6 | 2 | 0 | 5 | 8 | 8 | 9 | 9 | 6 | 9 | 9 | 1 | 9 | 7 |
| Sugar beet | 9 | 10 | 6 | 9 | 9 | 8 | 8 | 0 | 2 | 7 | 5 | 7 | 8 | 8 | 7 | 8 | 7 | 8 | 7 | 7 | 7 | 8 |
| Velvetleaf | 9 | 9 | 4 | 8 | 7 | 7 | 8 | 0 | 0 | 0 | 0 | 2 | 8 | 9 | 9 | 9 | 9 | 8 | 8 | 4 | 3 | 6 |
| Wheat | 8 | 9 | 7 | 9 | 9 | 2 | 7 | 7 | 5 | 4 | 3 | 7 | 7 | 8 | 8 | 8 | 2 | 9 | 9 | 7 | 8 | 8 |
| Wild buckwheat | 10 | 9 | 6 | 9 | 9 | 9 | — | — | — | — | — | — | — | — | — | — | — | — | — | — | — | — |
| Wild oat | 5 | 8 | 8 | 9 | 9 | 0 | 7 | 7 | 7 | 2 | 3 | 6 | 4 | 9 | 9 | 9 | 7 | 9 | 9 | 8 | 8 | 8 |

| Rate (10 g/ha) POST-EMERGENCE | COMPOUND 191 | 192 | 203 | 204 | 205 | 206 | 207 | 208 | 209 | 210 | 211 | 212 | 213 | 214 | 215 | 216 | 217 | 218 | 219 | 220 | 221 | 222 |
|---|---|---|---|---|---|---|---|---|---|---|---|---|---|---|---|---|---|---|---|---|---|---|
| Barley | 8 | 8 | 9 | 9 | 9 | 9 | 9 | 8 | 8 | 7 | 9 | 9 | 7 | 7 | 2 | 8 | 9 | 4 | 3 | 1 | 0 | 2 |
| Barnyardgrass | 6 | 2 | 9 | 9 | 9 | 9 | 9 | 9 | 0 | 9 | 9 | 9 | 9 | 2 | 9 | 8 | 9 | 8 | 9 | 8 | 2 | 6 |
| Bedstraw | 7 | 7 | 8 | 8 | 9 | 9 | 9 | 8 | 3 | 7 | 9 | 9 | 9 | 9 | 8 | 5 | 5 | 6 | 6 | 3 | 3 | 3 |
| Blackgrass | 7 | 9 | 9 | 9 | 9 | 9 | 9 | 9 | 8 | 7 | 9 | 9 | 9 | 8 | 5 | 9 | 9 | 3 | 5 | 8 | 8 | 0 |
| Cheatgrass | 5 | 7 | 9 | 9 | 10 | 9 | 7 | 9 | 7 | 9 | 9 | 9 | 9 | 9 | 7 | 8 | 8 | 8 | 5 | 5 | 0 | 2 |
| Chickweed | 0 | 6 | 9 | 9 | 9 | 9 | 9 | 9 | 0 | 2 | 4 | 7 | 10 | 10 | 3 | 0 | 0 | 5 | 7 | 3 | 0 | 0 |
| Cocklebur | 7 | 4 | 8 | — | 8 | — | — | — | — | 0 | — | 8 | 8 | — | 0 | — | — | — | — | — | 0 | 0 |
| Corn | 6 | 9 | 9 | 9 | 10 | 10 | 9 | 9 | 2 | 9 | 9 | 10 | 9 | 9 | 8 | 8 | 9 | 8 | 8 | 9 | 8 | 6 |
| Cotton | 7 | 8 | 8 | 8 | 9 | 9 | 8 | 9 | 0 | 7 | 9 | 10 | 10 | 10 | 9 | 6 | 6 | 9 | 9 | 2 | 0 | 4 |
| Crabgrass | 0 | 8 | 9 | 9 | 9 | 9 | 7 | 6 | 2 | 3 | 3 | 5 | 2 | 0 | 0 | 0 | 3 | 2 | 0 | 0 | 0 | 0 |
| Giant foxtail | 6 | 9 | 6 | 9 | 10 | 10 | 10 | 9 | 2 | 7 | 9 | 9 | 8 | 3 | 2 | 7 | 7 | 6 | 5 | 4 | 0 | 2 |
| Lambsquarters | 9 | 7 | 9 | 10 | 10 | 10 | 7 | 10 | 3 | 9 | 9 | 9 | 9 | 10 | 7 | 9 | 9 | 9 | 9 | 9 | 2 | 8 |
| Morningglory | 8 | 9 | 9 | 10 | 10 | 9 | 9 | 9 | 5 | 9 | 10 | 9 | 10 | 9 | 7 | 9 | 9 | 9 | 9 | 3 | 0 | 4 |
| Nutsedge | 3 | 3 | — | 9 | 10 | 4 | 2 | 9 | 0 | — | 2 | 10 | 9 | — | — | 0 | 7 | 7 | 9 | 0 | — | 0 |
| Rape | 5 | 5 | 9 | 10 | 9 | 9 | 9 | 9 | 0 | 5 | 8 | 9 | 10 | 10 | 9 | 0 | 8 | 7 | 8 | 9 | 8 | 8 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Rice | 9 | 9 | 9 | 9 | 9 | 9 | 9 | 9 | 9 | 9 | 9 | 9 | 9 | 9 | 9 | 9 | 9 | 9 | 9 | 9 | 8 | 7 |
| Sorghum | 6 | 9 | 9 | 9 | 10 | 10 | 9 | 9 | 4 | 9 | 9 | 10 | 9 | 9 | 9 | 9 | 9 | 6 | 2 | 8 | 4 | 0 |
| Soybean | 7 | 9 | 9 | 9 | 9 | 8 | 9 | 6 | 0 | 8 | 9 | 9 | 9 | 9 | 3 | 3 | 6 | 8 | 8 | 9 | 5 | 4 |
| Sugar beet | 7 | 8 | 9 | 10 | 9 | 10 | 10 | 10 | 0 | 4 | 7 | 8 | 10 | 9 | 7 | 8 | 9 | 9 | 9 | 8 | 4 | 8 |
| Velvetleaf | 5 | 2 | 8 | 9 | 9 | 9 | 9 | 9 | 0 | 9 | 9 | 9 | 9 | 6 | 9 | 3 | 9 | 9 | 9 | 2 | 0 | 5 |
| Wheat | 5 | 8 | 10 | 10 | 9 | 9 | 10 | 9 | 7 | 9 | 8 | 9 | 8 | 6 | 3 | 9 | 9 | 4 | 3 | 9 | 0 | 0 |
| Wild buckwheat | — | — | 9 | 8 | 9 | 9 | 9 | 9 | 0 | 8 | 6 | 8 | 9 | 9 | 8 | 2 | 9 | 7 | 9 | 0 | 3 | 9 |
| Wild oat | 7 | 9 | 9 | 9 | 9 | 10 | 9 | 9 | 7 | 9 | 9 | 10 | 9 | 9 | 3 | 9 | 10 | 9 | 9 | 2 | 0 | 0 |

| Rate (10 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 223 | 224 | 225 | 226 | 227 | 228 | 229 | 230 | 231 | 232 | 233 | 234 | 235 | 236 | 237 | 238 | 239 | 240 | 241 | 242 | 243 | 244 |
| Barley | 6 | 7 | 9 | 5 | 5 | 5 | 2 | 7 | 8 | 8 | 5 | 0 | 0 | 8 | 0 | 0 | 0 | 9 | 8 | 9 | 8 | 8 |
| Barnyardgrass | 6 | 7 | 9 | 3 | 5 | 7 | 7 | 3 | 8 | 1 | 3 | 0 | 0 | 2 | 0 | 0 | 0 | 8 | 9 | 9 | 9 | 9 |
| Bedstraw | 4 | 7 | 7 | 3 | 3 | 5 | 0 | 9 | 8 | 9 | 7 | 0 | 3 | 7 | 0 | 0 | 3 | 9 | 9 | 9 | — | 9 |
| Blackgrass | 3 | 3 | 8 | 6 | 0 | 9 | 7 | 9 | 9 | 9 | 9 | 0 | 3 | 8 | 0 | 0 | 0 | 9 | 9 | 9 | 9 | 10 |
| Cheatgrass | 7 | 5 | 5 | 2 | 5 | 5 | 7 | 8 | 9 | 9 | 8 | 0 | 2 | 8 | 0 | 0 | 0 | 9 | 9 | 9 | 9 | 9 |
| Chickweed | 2 | 1 | 8 | 7 | 0 | 2 | 2 | 3 | 3 | 5 | 0 | 0 | 2 | 5 | 0 | 0 | 0 | 9 | 9 | 9 | 10 | 10 |
| Cocklebur | — | 8 | 9 | — | — | — | — | — | — | — | — | — | — | — | — | — | — | — | — | — | — | — |
| Corn | 8 | 8 | 10 | 8 | 7 | 7 | 7 | 8 | 7 | 7 | 4 | 0 | 2 | 0 | 0 | 0 | 0 | 9 | 9 | 9 | 9 | 9 |
| Cotton | 9 | 9 | 8 | 7 | 8 | 5 | 7 | 7 | 9 | 8 | 7 | 0 | 0 | 2 | 0 | — | 2 | 9 | 9 | 9 | 10 | 9 |
| Crabgrass | 0 | 3 | 2 | 2 | 0 | 4 | 0 | — | — | 3 | 0 | 0 | — | — | 0 | 0 | 0 | 8 | 8 | 9 | 9 | 8 |
| Giant foxtail | 4 | 5 | 6 | 4 | 4 | 6 | 0 | 8 | 7 | 5 | 2 | 0 | 2 | 7 | 0 | 0 | 0 | 9 | 9 | 10 | 10 | 9 |
| Lambsquarters | 9 | 8 | 9 | 9 | 7 | 8 | 5 | 8 | 9 | 7 | 4 | 0 | 3 | 7 | 0 | 0 | 0 | 9 | 10 | 10 | 10 | 10 |
| Morningglory | 9 | 9 | 9 | 8 | 8 | 9 | 9 | 9 | 9 | 9 | 7 | 0 | 1 | 7 | 0 | 0 | 0 | 9 | 9 | 10 | 10 | 10 |
| Nutsedge | 0 | — | — | 0 | — | 5 | — | 0 | 0 | 0 | 0 | 0 | 0 | 0 | 0 | 0 | 0 | 9 | — | 9 | 3 | 5 |
| Rape | 6 | 8 | 9 | 9 | 8 | 3 | 0 | 7 | 9 | 9 | 5 | 0 | 1 | 5 | 0 | 0 | 0 | 9 | 8 | 9 | 9 | 9 |
| Rice | 9 | 8 | 9 | 9 | 8 | 9 | 9 | 9 | 9 | 9 | 9 | 3 | 5 | 9 | 0 | 0 | 0 | 9 | 9 | 9 | 9 | 9 |
| Sorghum | 7 | 4 | 8 | 3 | 3 | 8 | 9 | 9 | 9 | 9 | 7 | 0 | 0 | 8 | 0 | 0 | 0 | 9 | 9 | 10 | 10 | 9 |
| Soybean | 8 | 9 | 8 | 9 | 5 | 7 | 8 | 7 | 9 | 9 | 7 | 0 | 0 | 0 | 0 | 0 | 0 | 8 | 9 | 9 | 9 | 9 |
| Sugar beet | 6 | 6 | 9 | 7 | 5 | 0 | 2 | 4 | 8 | 6 | 0 | 0 | 2 | 5 | 0 | 0 | 0 | 9 | 8 | 10 | 9 | 9 |
| Velvetleaf | 9 | 9 | 9 | 7 | 5 | 9 | 9 | 9 | 9 | 7 | 1 | 0 | 0 | 3 | 0 | 0 | 0 | 9 | 9 | 10 | 9 | 9 |
| Wheat | 5 | 5 | 9 | 2 | 2 | 4 | 3 | 6 | 9 | 9 | 3 | 0 | 0 | 5 | 0 | 0 | 0 | 8 | 8 | 9 | 8 | 8 |
| Wild buckwheat | 2 | 7 | 9 | 8 | 5 | 7 | 0 | 8 | — | — | — | — | 3 | 7 | — | 3 | 9 | — | — | 10 | — | — |
| Wild oat | 8 | 7 | 9 | 6 | 0 | 7 | 5 | 8 | 9 | 9 | 7 | 0 | 1 | 8 | 0 | 0 | 0 | 9 | 9 | 9 | 9 | 9 |

| Rate (10 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 245 | 246 | 247 | 248 | 249 | 250 | 251 | 252 | 253 | 254 | 255 | 256 | 257 | 258 | 259 | 260 | 261 | 262 | 263 | 264 | 265 | 266 |
| Barley | 9 | 7 | 9 | 8 | 6 | 3 | 5 | 7 | 5 | 4 | 2 | 9 | 8 | 8 | 8 | 8 | 8 | 5 | 5 | 6 | 7 | 8 |
| Barnyardgrass | 9 | 6 | 8 | 6 | 6 | 4 | 9 | 7 | 8 | 2 | 2 | 8 | 9 | 9 | 9 | 7 | 9 | 3 | 8 | 6 | 7 | 5 |
| Bedstraw | 9 | 5 | 7 | 7 | 7 | 7 | 7 | 7 | 7 | 7 | 7 | 8 | 9 | 8 | 7 | 7 | 7 | 6 | 5 | 7 | 7 | 7 |
| Blackgrass | 9 | 7 | 9 | 8 | — | 7 | 9 | 9 | 7 | 7 | 7 | 9 | 9 | 9 | 9 | 9 | 9 | 8 | 2 | 7 | 8 | 9 |
| Cheatgrass | 9 | 6 | 8 | 4 | 3 | 6 | 8 | 9 | 7 | 6 | 5 | 9 | 9 | 9 | 9 | 5 | 9 | 8 | 4 | 7 | 8 | 8 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Chickweed | 5 | — | 7 | 9 | 7 | 0 | 5 | 5 | 8 | 9 | 0 | 6 | 9 | 9 | 6 | 5 | 6 | 5 | 5 | 0 | 4 | 4 |
| Cocklebur | — | — | — | — | — | 0 | 2 | 8 | 7 | 7 | 0 | 1 | 3 | 2 | 3 | 1 | 8 | 0 | 1 | 4 | 7 | 7 |
| Corn | 9 | 9 | 7 | 9 | 8 | 8 | 9 | 9 | 9 | 5 | 1 | 10 | 9 | 9 | 9 | 9 | 9 | 7 | 7 | 8 | 9 | 9 |
| Cotton | 9 | 9 | 10 | 9 | 9 | 2 | 8 | 8 | 8 | 9 | 5 | 1 | 5 | 4 | 2 | 2 | 4 | 1 | 9 | 2 | 5 | 8 |
| Crabgrass | — | 5 | 8 | — | 6 | 0 | 5 | 5 | 2 | 0 | 0 | 6 | 7 | 8 | 5 | 7 | 5 | 0 | 0 | 3 | 0 | 0 |
| Giant foxtail | 9 | 4 | 9 | 7 | 6 | 4 | 8 | 8 | 6 | 2 | 0 | 8 | 9 | 9 | 9 | 8 | 9 | 7 | 2 | 4 | 8 | 8 |
| Lambsquarters | 10 | 9 | 9 | 10 | 10 | — | 7 | — | — | 10 | 5 | 10 | 10 | 10 | — | — | 7 | 7 | 8 | 7 | 9 | — |
| Morningglory | 10 | 7 | 9 | 9 | 9 | 5 | 9 | 9 | 9 | 9 | 7 | 10 | 10 | 10 | 7 | 8 | 10 | 9 | 9 | 9 | 9 | 9 |
| Nutsedge | 10 | — | 9 | 4 | — | 0 | 3 | 0 | — | — | — | — | 5 | 9 | 0 | 0 | — | — | — | 0 | 5 | — |
| Rape | 9 | 5 | 5 | 8 | 8 | 5 | 7 | 9 | 9 | 9 | 7 | 9 | 7 | 7 | 8 | 7 | 8 | 7 | 9 | 5 | 5 | 6 |
| Rice | 9 | 9 | 9 | 9 | 9 | 8 | 9 | 9 | 9 | 9 | 8 | 9 | 9 | 9 | 10 | 10 | 9 | 7 | 9 | 8 | 9 | 9 |
| Sorghum | 9 | 4 | 9 | 9 | 7 | 8 | 9 | 9 | 9 | 8 | 8 | 9 | 9 | 9 | 9 | 9 | 9 | 7 | 9 | 8 | 9 | 9 |
| Soybean | 4 | 1 | 6 | 7 | 7 | 6 | 9 | 9 | 9 | 9 | 2 | 8 | 9 | 9 | 9 | 9 | 8 | 8 | 9 | 5 | 9 | 9 |
| Sugar beet | 9 | 8 | 9 | 8 | 8 | — | 5 | 3 | 9 | 8 | 0 | 4 | 5 | 7 | 7 | 5 | 6 | 5 | 7 | 0 | 3 | 5 |
| Velvetleaf | 9 | 2 | 8 | 9 | 8 | 5 | 9 | 8 | 9 | 2 | 5 | 9 | 9 | 9 | 7 | 7 | 7 | 3 | 9 | 8 | 8 | 8 |
| Wheat | 9 | 4 | 7 | 7 | 4 | 4 | 8 | 7 | 3 | 2 | 0 | 8 | 9 | 8 | 9 | 8 | 9 | 3 | 5 | 8 | 8 | 7 |
| Wild buckwheat | 9 | 9 | — | — | — | 5 | — | 9 | 9 | 9 | 7 | 9 | 9 | 8 | 7 | 8 | 8 | 9 | 4 | 8 | 5 | 8 |
| Wild oat | 9 | 5 | 8 | 7 | 6 | 5 | 5 | 5 | 7 | 7 | 2 | 9 | 9 | 9 | 9 | 9 | 9 | 7 | 6 | 7 | 7 | 8 |

| Rate (10 g/ha) POST- | COMPOUND | | | | | | | | | | | | | | | | | | | | | |
|---|---|---|---|---|---|---|---|---|---|---|---|---|---|---|---|---|---|---|---|---|---|---|
| EMERGENCE | 267 | 268 | 269 | 270 | 271 | 272 | 273 | 274 | 275 | 276 | 277 | 278 | 279 | 280 | 281 | 282 | 283 | 284 | 285 | 286 | 287 | 288 |
| Barley | 9 | 8 | 4 | 9 | 9 | 9 | 3 | 4 | 9 | 6 | 4 | 0 | 0 | 8 | 0 | 3 | 9 | 9 | 9 | 9 | 9 | 8 |
| Barnyardgrass | 7 | 1 | 5 | 8 | 9 | 9 | 1 | 2 | 9 | 3 | 3 | 2 | 4 | 6 | 0 | 7 | 9 | 9 | 9 | 9 | 9 | 9 |
| Bedstraw | 9 | 8 | 7 | 4 | 9 | 7 | 1 | 2 | 8 | 0 | 0 | 3 | 4 | 2 | 3 | 5 | 8 | 7 | 6 | 8 | 7 | 8 |
| Blackgrass | 9 | 9 | 8 | 9 | 9 | 9 | 9 | 9 | 9 | 7 | 2 | 3 | 5 | 7 | 5 | 5 | 9 | 9 | 9 | 9 | 9 | 8 |
| Cheatgrass | 9 | 9 | 7 | 9 | 9 | 9 | 9 | 8 | 9 | 8 | 2 | 0 | 2 | 7 | 2 | 5 | 9 | 9 | 9 | 9 | 9 | 9 |
| Chickweed | 8 | 8 | 0 | 4 | 7 | 9 | 2 | 2 | 8 | 0 | 0 | 0 | 0 | 0 | 0 | 0 | 0 | 9 | 10 | 9 | 9 | 8 |
| Cocklebur | 8 | 9 | 0 | 5 | 1 | 4 | 0 | 0 | 7 | 2 | 2 | 0 | 2 | 0 | 0 | 5 | — | — | — | — | — | — |
| Corn | 8 | 8 | 7 | 9 | 10 | 9 | 7 | 5 | 9 | 3 | 0 | 0 | 0 | 4 | 0 | 2 | 9 | 9 | 9 | 9 | 7 | 9 |
| Cotton | 9 | 9 | 1 | 9 | 7 | 8 | 0 | 2 | 9 | 2 | 0 | 0 | 0 | 0 | 0 | 5 | 9 | 9 | 9 | 9 | 10 | 10 |
| Crabgrass | 2 | 0 | 0 | 7 | 8 | 9 | 2 | 0 | 8 | 2 | 2 | 0 | 0 | 2 | 0 | 0 | 6 | 7 | 6 | 6 | 6 | 2 |
| Giant foxtail | 5 | 5 | 0 | 7 | 9 | 9 | 2 | 0 | 9 | 2 | 3 | 0 | 0 | 4 | 0 | 3 | 10 | 9 | 9 | 10 | 10 | 8 |
| Lambsquarters | — | — | — | — | 9 | 10 | 2 | 0 | 10 | 5 | 5 | 2 | 6 | 7 | 3 | 9 | 10 | 10 | 10 | 10 | 10 | 10 |
| Morningglory | 9 | 9 | 7 | 9 | 9 | 9 | 0 | 1 | 9 | 6 | 5 | 2 | 2 | 1 | 2 | 6 | 2 | 9 | 9 | 9 | 9 | 9 |
| Nutsedge | 0 | 0 | — | 8 | 8 | — | — | — | — | 0 | 0 | 0 | 0 | 0 | 0 | 0 | 6 | 9 | — | 3 | — | — |
| Rape | 9 | 9 | 7 | 9 | 9 | 9 | 0 | 1 | 9 | 0 | 0 | 0 | 0 | 0 | 0 | 5 | 9 | 9 | 9 | 9 | 10 | 9 |
| Rice | 9 | 9 | 5 | 10 | 9 | 9 | 9 | 9 | 9 | 9 | 9 | 6 | 5 | 9 | 8 | 7 | 9 | 9 | 9 | 10 | 10 | 9 |
| Sorghum | 9 | 9 | 8 | 9 | 9 | 9 | 9 | 9 | 9 | 9 | 9 | 0 | 0 | 7 | 2 | 8 | 9 | 9 | 9 | 10 | 9 | 9 |
| Soybean | 9 | 9 | 3 | 9 | 9 | 9 | 3 | 2 | 7 | 0 | 1 | 2 | 4 | 0 | 3 | 6 | 8 | 9 | 9 | 9 | 9 | 9 |
| Sugar beet | 9 | 9 | 0 | 9 | 8 | 9 | 1 | 1 | 8 | 2 | 4 | 5 | 3 | 3 | 7 | 7 | 8 | 8 | 9 | 9 | 9 | 9 |
| Velvetleaf | 9 | 7 | 0 | 7 | 8 | 9 | 0 | 0 | 3 | 0 | 2 | 0 | 0 | 0 | 0 | 4 | 9 | 9 | 10 | 9 | 7 | 9 |
| Wheat | 9 | 6 | 0 | 9 | 9 | 9 | 8 | 8 | 9 | 5 | 2 | 0 | 0 | 5 | 0 | 0 | 9 | 9 | 8 | 9 | 9 | 8 |
| Wild buckwheat | 9 | 9 | 9 | 8 | 8 | 9 | 2 | 2 | 9 | 0 | 0 | 0 | 0 | 0 | 0 | 0 | 9 | 9 | 9 | 9 | 9 | 9 |
| Wild oat | 9 | 9 | 3 | 9 | 9 | 9 | 8 | 8 | 9 | 8 | 5 | 0 | 0 | 7 | 0 | 4 | 9 | 9 | 9 | 9 | 9 | 9 |

TABLE A-continued

TEST A

| Rate (10 g/ha) POST-EMERGENCE | COMPOUND 289 | 290 | 291 | 292 | 293 | 294 | 295 | 296 | 297 | 298 | 299 | 300 | 301 | 302 | 303 | 304 | 305 | 306 | 307 | 308 | 309 | 310 |
|---|---|---|---|---|---|---|---|---|---|---|---|---|---|---|---|---|---|---|---|---|---|---|
| Barley | 9 | 7 | 9 | 4 | 8 | 2 | 2 | 6 | 3 | 2 | 4 | 9 | 8 | 9 | 7 | 5 | 8 | 6 | 8 | 7 | 5 | 7 |
| Barnyardgrass | 9 | 6 | 9 | 5 | 9 | 2 | 2 | 4 | 3 | 1 | 0 | 9 | 9 | 9 | 8 | 3 | 9 | 2 | 8 | 2 | 8 | 9 |
| Bedstraw | 7 | 3 | 5 | 3 | 4 | 3 | 2 | 3 | 5 | 0 | 0 | 7 | 5 | 7 | 3 | 5 | 6 | 6 | 6 | 6 | 6 | 6 |
| Blackgrass | 9 | 9 | 9 | 6 | 8 | 4 | 7 | 4 | 7 | 4 | 4 | 9 | 9 | 7 | 5 | 3 | 9 | 8 | 9 | 7 | 7 | 7 |
| Cheatgrass | 9 | 8 | 9 | 4 | 7 | 2 | 5 | 2 | 2 | 0 | 0 | 9 | 8 | 9 | 8 | 0 | 7 | 3 | 7 | 5 | 7 | 6 |
| Chickweed | 9 | 2 | 7 | 7 | 3 | 3 | 3 | 3 | 7 | 2 | 0 | 7 | 7 | 9 | 9 | 6 | 6 | 7 | 2 | 2 | 0 | 2 |
| Cocklebur | — | — | — | — | — | — | — | — | — | — | — | — | — | — | — | — | — | — | 5 | 1 | 8 | 9 |
| Corn | 9 | 6 | 9 | 6 | 9 | 2 | 1 | 2 | 2 | 2 | 0 | 5 | 9 | 9 | 1 | 0 | 8 | 6 | 7 | 6 | 8 | 9 |
| Cotton | 8 | 7 | 8 | 6 | 7 | 1 | 7 | 3 | 7 | 4 | 0 | 9 | 9 | 9 | 9 | 6 | 9 | 8 | 6 | 9 | 9 | 9 |
| Crabgrass | 7 | 2 | 9 | 2 | 5 | 1 | 1 | 1 | 0 | 0 | 0 | 5 | 7 | 8 | 5 | 4 | 7 | 2 | 4 | 2 | 6 | 0 |
| Giant foxtail | 9 | 6 | 9 | 6 | 8 | 3 | 3 | 4 | 3 | 3 | 2 | 8 | 9 | 9 | 3 | 2 | 9 | 3 | 7 | 3 | 7 | 6 |
| Lambsquarters | 9 | 7 | 10 | 7 | 8 | 5 | 8 | 7 | 9 | 5 | 5 | 9 | 9 | — | — | — | — | 4 | — | 8 | 8 | 9 |
| Morningglory | 9 | 6 | 9 | 6 | 5 | 6 | 3 | 2 | 2 | 2 | 1 | 5 | 9 | 9 | 8 | 3 | 9 | 3 | 6 | 3 | 9 | 10 |
| Nutsedge | 4 | 0 | — | 0 | 0 | 0 | 0 | 0 | 0 | — | 0 | — | 5 | 7 | 0 | 0 | 0 | — | 4 | 3 | 3 | 7 |
| Rape | 0 | 8 | 9 | 9 | 7 | 0 | 3 | 5 | 5 | 0 | 0 | 8 | 9 | 9 | 9 | 7 | 7 | 0 | 7 | 6 | 7 | 9 |
| Rice | 9 | 8 | 9 | 8 | 7 | 2 | 8 | 6 | 7 | 3 | 0 | 9 | 9 | 9 | 3 | 0 | 9 | 8 | 9 | 6 | 9 | 9 |
| Sorghum | 9 | 7 | 9 | 8 | 9 | 2 | 2 | 3 | 6 | 3 | 0 | 9 | 9 | 9 | 8 | 3 | 9 | 8 | 8 | 4 | 6 | 8 |
| Soybean | 9 | 2 | 6 | 1 | 6 | 1 | 4 | 2 | 4 | 2 | 0 | 7 | 8 | 7 | 1 | 0 | 8 | 2 | 8 | 8 | 8 | 9 |
| Sugar beet | 8 | 7 | 9 | 9 | 5 | 3 | 2 | 7 | 8 | 2 | 3 | 8 | 8 | 9 | 8 | 5 | 8 | 2 | 5 | 6 | 7 | 8 |
| Velvetleaf | 6 | 6 | 9 | 7 | 5 | 3 | 6 | 1 | 0 | 0 | 0 | 7 | 8 | 8 | 7 | 1 | 6 | 3 | 7 | 5 | 6 | 9 |
| Wheat | 9 | 7 | 9 | 5 | 3 | 0 | 1 | 3 | 2 | 0 | 2 | 9 | 9 | 9 | 3 | 1 | 7 | 0 | 5 | 3 | 7 | 4 |
| Wild buckwheat | 8 | 6 | 9 | 7 | 8 | 3 | 0 | 3 | 6 | 0 | 2 | 8 | 7 | 7 | 8 | 7 | 7 | 6 | 7 | 2 | 5 | 7 |
| Wild oat | 9 | 8 | 9 | 5 | 7 | 2 | 2 | 5 | 3 | 3 | 1 | 8 | 8 | 8 | 5 | 2 | 7 | 5 | 8 | 2 | 6 | 9 |

| Rate (10 g/ha) POST-EMERGENCE | COMPOUND 311 | 312 | 313 | 314 | 315 | 316 | 317 | 318 | 319 | 320 | 321 | 322 | 323 | 324 | 325 | 326 | 327 | 328 | 329 | 330 | 331 | 332 |
|---|---|---|---|---|---|---|---|---|---|---|---|---|---|---|---|---|---|---|---|---|---|---|
| Barley | 7 | 6 | 5 | 0 | 0 | 0 | 0 | 0 | 0 | 0 | 0 | 9 | 9 | 9 | 5 | 3 | 7 | 2 | 4 | 0 | 0 | 0 |
| Barnyardgrass | 9 | 9 | 2 | 2 | 0 | 0 | 0 | 0 | 0 | 0 | 0 | 3 | 6 | 9 | 4 | 0 | 8 | 0 | 1 | 0 | 0 | 0 |
| Bedstraw | 6 | 7 | 3 | 5 | 0 | 0 | 2 | 0 | 0 | 0 | 0 | 6 | 7 | 9 | 6 | 6 | 9 | 5 | 5 | 0 | 0 | 0 |
| Blackgrass | 9 | 8 | 2 | 2 | 0 | 0 | 0 | 0 | 0 | 0 | 0 | 7 | 9 | 8 | 5 | 4 | 3 | 0 | 3 | 0 | 0 | 0 |
| Cheatgrass | 8 | 8 | 3 | 0 | 0 | 0 | 0 | 0 | 0 | 0 | 0 | 9 | 9 | 9 | 7 | 5 | 8 | 7 | 8 | 0 | 0 | 0 |
| Chickweed | 0 | 0 | 0 | 0 | 0 | 0 | 0 | 0 | 0 | 0 | 0 | 8 | 9 | 9 | 7 | 6 | 9 | 0 | 2 | 0 | 0 | 0 |
| Cocklebur | 9 | 7 | 0 | 0 | 0 | 0 | 0 | 7 | 1 | 2 | 0 | 9 | 8 | 9 | 0 | 0 | 8 | 0 | 1 | 0 | 0 | 0 |
| Corn | 7 | 7 | 0 | 0 | 0 | 0 | 0 | 0 | 0 | 0 | 0 | 9 | 9 | 9 | 9 | 1 | 9 | 4 | 9 | 0 | 0 | 0 |
| Cotton | 9 | 7 | 2 | 0 | 0 | 0 | 0 | 0 | 0 | 0 | 0 | 9 | 9 | 9 | 9 | 0 | 9 | 2 | 3 | 0 | 0 | 0 |
| Crabgrass | 3 | 0 | 0 | 0 | 0 | 0 | 0 | 0 | 0 | 0 | 0 | 7 | 8 | 5 | 2 | 0 | 3 | 0 | 2 | 0 | 0 | 0 |
| Giant foxtail | 6 | 5 | 2 | 0 | 0 | 0 | 0 | 0 | 0 | 0 | 0 | 8 | 9 | 9 | 7 | 0 | 9 | 5 | 7 | 0 | 0 | 0 |
| Lambsquarters | 10 | — | 3 | 0 | 0 | 5 | 0 | 0 | 0 | 0 | 0 | 10 | — | 9 | 5 | 3 | 9 | 1 | 3 | 3 | 0 | 0 |
| Morningglory | 9 | 9 | 1 | 7 | 0 | 0 | 0 | 4 | 1 | 2 | 0 | 5 | 10 | 10 | 8 | 1 | 9 | 1 | 1 | 0 | 0 | 0 |
| Nutsedge | 2 | 4 | 0 | 0 | 0 | 0 | — | 0 | 0 | — | 0 | 5 | 8 | 8 | — | 0 | 7 | 0 | 0 | 0 | 0 | 0 |
| Rape | 7 | 7 | 3 | 2 | 0 | 0 | 2 | 4 | 2 | 0 | 0 | 9 | 9 | 9 | 9 | 8 | 9 | 0 | 0 | 0 | 0 | 0 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Rice | 9 | 7 | 7 | 4 | 0 | 2 | 2 | 4 | 0 | 0 | 0 | 9 | 9 | 9 | 9 | 9 | 9 | 8 | 9 | 0 | 0 | 0 |
| Sorghum | 9 | 8 | 3 | 3 | 0 | 0 | 0 | 0 | 0 | 0 | 0 | 9 | 9 | 9 | 9 | 1 | 9 | 1 | 8 | 0 | 0 | 0 |
| Soybean | 9 | 5 | 2 | 0 | 0 | 0 | 0 | 0 | 0 | 0 | 0 | 8 | 9 | 9 | 8 | 2 | 8 | 2 | 9 | 0 | 0 | 0 |
| Sugar beet | 8 | — | 5 | 3 | 0 | 0 | 2 | 3 | 2 | 0 | 0 | 9 | 9 | 9 | 8 | 7 | 9 | 3 | 5 | 0 | 0 | 0 |
| Velvetleaf | 2 | 8 | 0 | 0 | 0 | 0 | 0 | 0 | 0 | 0 | 0 | 9 | 10 | 9 | 0 | 0 | 8 | 0 | 0 | 0 | 0 | 0 |
| Wheat | 4 | 3 | 3 | 0 | 0 | 0 | 0 | 1 | 0 | 0 | 0 | 9 | 9 | 9 | 9 | 8 | 1 | 0 | 7 | 0 | 0 | 0 |
| Wild buckwheat | 9 | — | 0 | 2 | — | — | — | — | — | — | — | — | — | — | — | — | — | — | — | — | — | — |
| Wild oat | 8 | 5 | 3 | 0 | 0 | 0 | 0 | 1 | 0 | 0 | 0 | 9 | 9 | 9 | 9 | 4 | 2 | 7 | 8 | 0 | 0 | 0 |

| Rate (10 g/ha) POST- | COMPOUND | | | | | | | | | |
|---|---|---|---|---|---|---|---|---|---|---|
| EMERGENCE | 333 | 334 | 335 | 336 | 337 | 338 | 339 | 340 | 341 | 342 |
| Barley | 0 | 0 | 0 | 0 | 0 | 9 | 9 | 9 | 9 | 8 |
| Barnyardgrass | 0 | 0 | 0 | 0 | 0 | 9 | 9 | 6 | 3 | 8 |
| Bedstraw | 0 | 0 | 0 | 0 | 0 | 7 | 9 | 2 | 4 | 8 |
| Blackgrass | 0 | 0 | 0 | 0 | 0 | 9 | 9 | 9 | 9 | 7 |
| Cheatgrass | 0 | 0 | 0 | 0 | 0 | 9 | 9 | 9 | 7 | 8 |
| Chickweed | 0 | 0 | 0 | 0 | 0 | 9 | 10 | 5 | 0 | 8 |
| Cocklebur | 0 | 0 | 0 | 0 | 0 | 10 | 10 | 1 | 0 | 9 |
| Corn | 0 | 0 | 0 | 0 | 0 | 9 | 9 | 9 | 6 | 9 |
| Cotton | 0 | 0 | 0 | 0 | 0 | 9 | 10 | 0 | 0 | 9 |
| Crabgrass | 0 | 0 | 0 | 0 | 0 | 7 | 7 | 1 | 2 | 7 |
| Giant foxtail | 0 | 0 | 0 | 0 | 0 | 9 | 10 | 7 | 3 | 8 |
| Lambsquarters | 0 | 0 | 0 | 0 | 0 | 10 | 10 | 2 | 2 | 10 |
| Morningglory | 0 | 0 | 0 | 0 | 0 | 9 | 9 | 2 | 3 | 9 |
| Nutsedge | 0 | 0 | 0 | 0 | 0 | 8 | 8 | 0 | 1 | 5 |
| Rape | 0 | 0 | 0 | 0 | 0 | 9 | 9 | 8 | 5 | 9 |
| Rice | 0 | 0 | 0 | 0 | 0 | 9 | 9 | 9 | 9 | 9 |
| Sorghum | 0 | 0 | 0 | 0 | 0 | 9 | 9 | 9 | 6 | 10 |
| Soybean | 0 | 0 | 0 | 0 | 0 | 9 | 9 | 2 | 1 | 6 |
| Sugar beet | 0 | 0 | 0 | 0 | 0 | 9 | 10 | 1 | 3 | 9 |
| Velvetleaf | 0 | 0 | 0 | 0 | 0 | 9 | 10 | 1 | 0 | 8 |
| Wheat | 0 | 0 | 0 | 0 | 0 | 9 | 9 | 9 | 9 | 8 |
| Wild buckwheat | — | — | — | — | — | — | — | — | — | — |
| Wild oat | 0 | 0 | 0 | 0 | 0 | 9 | 9 | 9 | 9 | 8 |

| Rate (10 g/ha) PRE- | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| EMERGENCE | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
| Barley | 2 | 2 | 4 | 2 | 3 | 0 | 0 | 0 | 0 | 0 | 0 | 0 | 0 | 0 | 0 | 0 | 0 | 0 | 0 | 0 | 0 | 0 | 0 | 0 | 4 | 3 | 0 | 0 | 4 |
| Barnyardgrass | 0 | 5 | 3 | 3 | 2 | 0 | 0 | 0 | 0 | 0 | 0 | 0 | 0 | 0 | 0 | 0 | 0 | 0 | 0 | 0 | 0 | 0 | — | 0 | 8 | 7 | 3 | 9 | 8 |
| Bedstraw | 4 | 6 | 0 | 3 | 7 | 9 | 0 | 0 | 0 | 0 | 0 | 0 | 0 | 0 | 0 | 2 | 0 | 0 | 2 | 8 | — | 0 | — | — | 5 | 9 | 2 | 0 | 5 |
| Blackgrass | 2 | 4 | 4 | 3 | 5 | 2 | 0 | 1 | 0 | 2 | 3 | 0 | 2 | 2 | 1 | 0 | 0 | 0 | 0 | 2 | 0 | 0 | 0 | 0 | 8 | 8 | 8 | 9 | 5 |
| Cheatgrass | 3 | 5 | 5 | 2 | 9 | 4 | 1 | 1 | 0 | 0 | 2 | 2 | 0 | 0 | 0 | 0 | 0 | 0 | 0 | 2 | 0 | 0 | 0 | 0 | 9 | 9 | 8 | 8 | 9 |

TABLE A-continued

TEST A

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Chickweed | 2 | 9 | 9 | 0 | 5 | 5 | 0 | 8 | 0 | 0 | 9 | — | 0 | 5 | 9 | — | — | 0 | 5 | 4 | 5 | 0 | 2 | 0 | 9 | 9 | 8 | 7 | 8 |
| Cocklebur | 0 | 0 | 0 | 0 | 2 | 7 | — | 0 | 0 | 0 | 0 | 0 | 0 | 0 | 0 | 0 | 0 | 0 | 0 | — | 0 | 0 | — | 0 | — | — | — | — | — |
| Corn | 2 | 4 | 1 | 2 | 8 | 4 | 0 | 0 | 0 | 0 | 0 | 0 | 0 | 0 | 0 | 0 | 0 | 0 | 0 | 0 | 0 | 0 | — | 0 | 8 | 9 | 7 | 8 | 9 |
| Cotton | 0 | 0 | 2 | 2 | 3 | 0 | 0 | 0 | 0 | 0 | 0 | 0 | 0 | 0 | 0 | 0 | 0 | 0 | 0 | 0 | 0 | 0 | — | 0 | 2 | 7 | 5 | 0 | 2 |
| Crabgrass | 3 | 3 | 2 | 2 | 0 | 2 | 0 | 0 | 0 | 0 | 0 | 0 | 0 | 0 | 0 | 0 | 0 | 0 | 0 | 0 | 0 | 0 | — | 0 | 6 | 7 | 7 | 7 | 8 |
| Giant foxtail | 2 | 3 | 1 | 0 | 0 | — | 0 | 0 | 0 | 2 | 0 | 0 | 0 | 0 | 0 | 0 | 0 | 0 | 0 | 0 | 0 | 0 | — | 0 | 7 | 6 | 5 | 7 | 7 |
| Lambsquarters | 6 | 8 | 7 | 0 | 6 | 0 | 0 | 0 | 0 | 0 | 5 | 5 | 5 | 0 | 0 | 0 | 2 | 0 | 5 | 0 | 0 | 0 | 0 | 0 | 7 | 6 | 9 | 9 | 8 |
| Morningglory | 0 | 2 | 6 | 4 | 8 | 0 | 0 | 0 | 0 | 0 | 0 | 0 | 0 | 0 | 0 | 0 | 0 | 0 | 0 | 0 | 0 | 0 | — | 0 | 3 | 2 | 0 | 3 | 6 |
| Nutsedge | 3 | 2 | 0 | 2 | 0 | 7 | 0 | 0 | 0 | 0 | 0 | 0 | 0 | 0 | 0 | 0 | 0 | 0 | 0 | 0 | 0 | — | — | 3 | 0 | 0 | 0 | 0 | 3 |
| Rape | 1 | 2 | 8 | 7 | 8 | 0 | 0 | 0 | 0 | 0 | 0 | 0 | 1 | 0 | 0 | 0 | 2 | 0 | 0 | 0 | 0 | 0 | 0 | 0 | 3 | 9 | 4 | 8 | 5 |
| Rice | 2 | 2 | 8 | 8 | 8 | 7 | 0 | 0 | 0 | 0 | 0 | 0 | 0 | 0 | 0 | 0 | 0 | 0 | 0 | 0 | 0 | 0 | — | 0 | 9 | 7 | 3 | 9 | 9 |
| Sorghum | 2 | 2 | 0 | 4 | 3 | 2 | 0 | 0 | 0 | 0 | 0 | 0 | 0 | 0 | 0 | 0 | 0 | 0 | 0 | 0 | 0 | 0 | — | 0 | 6 | 6 | 3 | 8 | 4 |
| Soybean | 0 | 3 | 4 | 2 | 4 | 2 | 0 | 0 | 2 | 0 | 3 | 0 | 0 | 0 | 0 | 0 | 0 | 0 | 0 | 0 | 0 | 0 | — | 0 | 3 | 6 | 5 | 5 | 8 |
| Sugar beet | 5 | 7 | 4 | 6 | 3 | 1 | 0 | 0 | 2 | 2 | 0 | 0 | 1 | 3 | 0 | 0 | 2 | 0 | 0 | 0 | 0 | 0 | 0 | 0 | 8 | 8 | 8 | 6 | 8 |
| Velvetleaf | 3 | 4 | 3 | 2 | 3 | 0 | 0 | 0 | 0 | 0 | 0 | 0 | 0 | 0 | 0 | 0 | 0 | 0 | 0 | 0 | 0 | 0 | — | 0 | 1 | 1 | 2 | 1 | 3 |
| Wheat | 2 | 7 | 3 | 2 | 2 | 0 | 0 | 0 | 0 | 0 | 0 | 0 | 0 | 0 | 0 | 0 | 0 | 0 | 0 | 0 | 0 | 0 | 0 | 0 | 3 | 2 | 2 | 0 | 2 |
| Wild buckwheat | 2 | 5 | 3 | 2 | 3 | 2 | 0 | 0 | 0 | 0 | 0 | 0 | 0 | 0 | 0 | 0 | 0 | 0 | 2 | 2 | 0 | 0 | 0 | 0 | 3 | 2 | 2 | 0 | 2 |
| Wild oat | 3 | 4 | 5 | 0 | 3 | 2 | 1 | 1 | 0 | 0 | 0 | 0 | 0 | 0 | 0 | 0 | 0 | 0 | 0 | 0 | 0 | 0 | 0 | 0 | 7 | 8 | 3 | 2 | 3 |

| Rate (10 g/ha) PRE- | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| EMERGENCE | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 |
| Barley | 0 | 0 | 0 | 0 | 0 | 2 | 0 | 0 | 0 | 0 | 0 | 0 | 0 | 0 | 0 | 0 | 0 | 0 | 0 | 0 | 1 | 2 | 0 | 3 | 0 | 0 | 3 | 0 | 2 |
| Barnyardgrass | 4 | 2 | 0 | 0 | 0 | 1 | 3 | 0 | 1 | 0 | 0 | 0 | 0 | 0 | 0 | 0 | 0 | 0 | 0 | 0 | 9 | 9 | 5 | 9 | 2 | 7 | 3 | 9 | 8 |
| Bedstraw | 4 | 0 | 2 | 0 | 0 | 0 | 0 | 0 | 2 | 0 | 0 | 0 | 0 | 0 | 0 | 0 | 0 | 0 | 0 | 0 | 1 | 8 | 0 | 5 | 8 | 2 | 4 | 7 | 2 |
| Blackgrass | 2 | 3 | 0 | 0 | 0 | 4 | 0 | 0 | 0 | 0 | 2 | 0 | 1 | 2 | 0 | 2 | 1 | 2 | 0 | 1 | 7 | 6 | 0 | 8 | 2 | 0 | 3 | 8 | 4 |
| Cheatgrass | 7 | 3 | 0 | 0 | 3 | 9 | 6 | 0 | 0 | 2 | 3 | 2 | 2 | 0 | 0 | 3 | 2 | 2 | 0 | 2 | 7 | 7 | 0 | 6 | 0 | 0 | 4 | 8 | 6 |
| Chickweed | 9 | 0 | 0 | 0 | 2 | 6 | 6 | 0 | 3 | 0 | 0 | — | 0 | 0 | 0 | 5 | 0 | 0 | 0 | — | — | 9 | 3 | 9 | 10 | 10 | 0 | 9 | 8 |
| Cocklebur | — | — | — | — | — | — | — | — | — | — | — | — | — | — | — | — | — | — | — | — | 4 | 9 | 7 | 5 | 9 | 4 | 0 | 2 | 1 |
| Corn | 8 | 2 | 1 | 0 | 2 | 8 | 6 | 0 | 0 | 0 | 0 | 0 | 0 | 0 | 0 | 0 | 0 | 0 | 0 | 0 | 5 | 7 | 0 | 8 | 5 | 0 | 1 | 9 | 7 |
| Cotton | 3 | 0 | 0 | 0 | 0 | 0 | 3 | 0 | 0 | 0 | 0 | 0 | 0 | 0 | 0 | 0 | 0 | 0 | 0 | 0 | 6 | 9 | 0 | 8 | 3 | 0 | 0 | 6 | 2 |
| Crabgrass | 9 | 5 | 0 | 0 | 0 | 2 | 7 | 0 | 0 | 0 | 0 | 0 | 0 | 0 | 0 | 0 | 0 | 0 | 0 | 0 | 4 | 9 | 3 | 5 | 2 | 0 | 0 | 1 | 0 |
| Giant foxtail | 9 | 4 | 0 | 0 | 0 | 2 | 6 | 0 | 0 | 0 | 0 | 0 | 0 | 0 | 0 | 0 | 0 | 0 | 0 | 0 | 6 | 7 | 2 | 7 | 0 | 0 | 0 | 7 | 2 |
| Lambsquarters | 8 | 9 | 2 | 0 | 0 | 7 | 9 | 0 | 0 | 9 | — | 3 | 0 | 0 | 0 | 0 | 0 | 0 | 0 | 0 | 7 | 9 | 7 | 9 | 8 | — | 6 | 8 | 5 |
| Morningglory | 0 | 1 | 0 | 0 | 0 | 0 | 0 | 0 | 0 | 0 | 0 | 0 | 0 | 0 | 0 | 0 | 0 | 0 | 0 | 0 | 5 | 9 | 2 | 3 | 9 | 3 | 0 | 0 | 0 |
| Nutsedge | 7 | 0 | — | 0 | 0 | 0 | 0 | 0 | 0 | — | 0 | 0 | 0 | 0 | 0 | 0 | 0 | 0 | 0 | 0 | 9 | 9 | — | 5 | 0 | 0 | 0 | — | 5 |
| Rape | 0 | 0 | 0 | 0 | 2 | 0 | 2 | 0 | 2 | 0 | 0 | 0 | 0 | 0 | 0 | 0 | 0 | 0 | 0 | 0 | 7 | 9 | 2 | 8 | 8 | 8 | 5 | 9 | 8 |
| Rice | 9 | 4 | 0 | 0 | 3 | 8 | 8 | 2 | 2 | 0 | 0 | 2 | 0 | 0 | 0 | 0 | 0 | 0 | 0 | 0 | 9 | 10 | 8 | 9 | 9 | 7 | 5 | 8 | 8 |
| Sorghum | 2 | 2 | 0 | 0 | 0 | 5 | 7 | 0 | 0 | 0 | 0 | 0 | 0 | 0 | 0 | 0 | 0 | 0 | 0 | 0 | 5 | 5 | 2 | 2 | 2 | 1 | 1 | 6 | 1 |
| Soybean | 7 | 2 | 0 | 0 | 1 | 2 | 1 | 0 | 0 | 0 | 0 | 0 | 0 | 0 | 0 | 0 | 0 | 0 | 0 | 0 | 1 | 8 | 1 | 7 | 7 | 0 | 0 | 5 | 3 |
| Sugar beet | 8 | 2 | 3 | 2 | 4 | 8 | 9 | 0 | 2 | 2 | 0 | 0 | 2 | 0 | 0 | 0 | 0 | 0 | 0 | 0 | 7 | 9 | 5 | 8 | 9 | 7 | 6 | 7 | 7 |
| Velvetleaf | 2 | 0 | 0 | 0 | 0 | 0 | 1 | 0 | 0 | 0 | 0 | 0 | 0 | 0 | 0 | 0 | 0 | 0 | 0 | 0 | 2 | 8 | 2 | 6 | 0 | 0 | 0 | 5 | 1 |
| Wheat | 0 | 0 | 0 | 0 | 0 | 0 | 2 | 0 | 0 | 0 | 0 | 0 | 0 | 0 | 0 | 0 | 0 | 0 | 0 | 0 | 1 | 2 | 2 | 4 | 0 | 0 | 2 | 2 | 0 |
| Wild buckwheat | 0 | 0 | 0 | 3 | 0 | 2 | 0 | 0 | 0 | 0 | 0 | 0 | 0 | 0 | 0 | 0 | 0 | 0 | 0 | 0 | 0 | 7 | 0 | 3 | 7 | 0 | 2 | 4 | 2 |
| Wild oat | 0 | 0 | 0 | 0 | 0 | 2 | 0 | 0 | 0 | 0 | 0 | 0 | 0 | 0 | 0 | 0 | 0 | 0 | 0 | 0 | 2 | 5 | 0 | 5 | 2 | 0 | 2 | 3 | 3 |

TABLE A-continued

TEST A

| Rate (10 g/ha) PRE- | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| EMERGENCE | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
| Barley | 2 | 2 | 0 | 0 | 1 | 0 | 0 | 0 | 0 | 0 | 0 | 0 | 0 | 0 | 0 | 0 | 0 | 0 | 0 | 0 | 0 | 0 | 1 | 2 | 0 | 1 | 0 | 0 | 0 |
| Barnyardgrass | 1 | 2 | 2 | 0 | 9 | 9 | 0 | 0 | 5 | 2 | 0 | 0 | 0 | 0 | 0 | 0 | 0 | 0 | 0 | 2 | 0 | 0 | 2 | 6 | 7 | 2 | 3 | 3 | 2 |
| Bedstraw | 9 | 8 | 0 | — | 0 | 0 | 0 | 0 | 0 | 2 | 0 | 6 | 2 | 0 | 0 | 0 | 0 | 0 | 0 | 2 | 0 | 0 | 0 | 4 | 7 | 2 | 0 | 1 | 0 |
| Blackgrass | 6 | 3 | 2 | 2 | 4 | 5 | 3 | 0 | 2 | 2 | 0 | 0 | 0 | 0 | 0 | 0 | 0 | 0 | 0 | 0 | 0 | 0 | 5 | 7 | 8 | 3 | 0 | 5 | 2 |
| Cheatgrass | 5 | 2 | 2 | 7 | 7 | 7 | 5 | 2 | 6 | 5 | 4 | 2 | 0 | 0 | 0 | 4 | 0 | 0 | 8 | 7 | 0 | 0 | 9 | 9 | 9 | 0 | 0 | 9 | 1 |
| Chickweed | 9 | 10 | 7 | 0 | 2 | 8 | 0 | 0 | 0 | 8 | 7 | 7 | 6 | 0 | 0 | 2 | 0 | 0 | 0 | 0 | 0 | 0 | 2 | 9 | 7 | 3 | 0 | 7 | 0 |
| Cocklebur | 8 | 7 | 0 | — | 0 | — | 0 | 0 | 0 | 0 | — | 0 | 0 | 0 | 0 | 1 | — | 0 | — | — | 0 | 0 | — | — | — | — | — | — | — |
| Corn | 8 | 0 | 0 | 0 | 1 | 7 | 0 | 0 | 0 | 3 | 0 | 0 | 0 | 0 | 0 | 0 | 0 | 0 | 0 | 3 | 0 | 0 | 0 | 0 | 6 | 9 | 5 | 2 | 0 |
| Cotton | 7 | 7 | 0 | 0 | 0 | 4 | 0 | 0 | 0 | 6 | 0 | 1 | 0 | 0 | 0 | 0 | 0 | 0 | 0 | 0 | 0 | 0 | 4 | 2 | 3 | 2 | 0 | 3 | 0 |
| Crabgrass | 4 | 1 | 0 | 0 | 2 | 3 | 0 | 0 | 0 | 2 | 0 | 0 | 0 | 0 | 0 | 0 | 0 | 0 | 0 | 2 | 0 | 0 | 3 | 3 | 3 | 3 | 1 | 0 | 0 |
| Giant foxtail | 0 | 2 | 0 | 0 | 6 | 8 | 0 | 0 | 0 | 3 | 0 | 0 | 0 | 0 | 0 | 0 | 0 | 0 | 0 | 4 | 0 | 0 | 3 | 6 | 5 | 1 | 2 | 2 | 0 |
| Lambsquarters | 9 | 9 | 8 | 5 | 8 | 8 | 5 | 2 | 5 | — | 3 | 9 | — | — | 2 | 5 | 0 | 0 | 0 | 8 | 0 | 0 | 10 | 10 | 9 | 4 | 8 | 9 | 8 |
| Morningglory | 8 | 7 | 0 | 0 | 0 | 3 | 0 | 0 | 0 | 0 | 0 | 3 | 0 | 0 | 0 | 2 | 0 | 0 | 0 | 2 | 0 | 0 | 3 | 2 | 7 | 2 | 0 | 4 | 0 |
| Nutsedge | — | 10 | 0 | 0 | 9 | 9 | 0 | — | 0 | 0 | — | 0 | 0 | — | 0 | — | 0 | — | — | 7 | — | 0 | 0 | 5 | 10 | 0 | 0 | 5 | 0 |
| Rape | 8 | 8 | 7 | 0 | 5 | 8 | 0 | 0 | 0 | 6 | 0 | 1 | 2 | 0 | 0 | 0 | 0 | 0 | 0 | 1 | 0 | 0 | 1 | 8 | 8 | 1 | 0 | 5 | 0 |
| Rice | 8 | 8 | 7 | 5 | 7 | 8 | 8 | 4 | 8 | 7 | 5 | 2 | 0 | 0 | 0 | 1 | 0 | 0 | 2 | 0 | 0 | 0 | 5 | 7 | 7 | 7 | 5 | 5 | 0 |
| Sorghum | 2 | 3 | 1 | 2 | 6 | 6 | 0 | 0 | 3 | 2 | 0 | 0 | 0 | 0 | 0 | 0 | 0 | 0 | 1 | 0 | 0 | 0 | 7 | 9 | 9 | 6 | 2 | 8 | 0 |
| Soybean | 8 | 7 | 0 | 0 | 2 | 5 | 0 | 0 | 0 | 2 | 0 | 5 | 3 | 0 | 2 | 1 | 0 | 0 | 4 | 1 | 0 | 0 | 2 | 6 | 5 | 3 | 3 | 4 | 0 |
| Sugar beet | 9 | 8 | 5 | 4 | 6 | 9 | 1 | 0 | 5 | 7 | 7 | 9 | 7 | 0 | 2 | 0 | 0 | 0 | 3 | 2 | 0 | 0 | 7 | 9 | 9 | 3 | 6 | 7 | 3 |
| Velvetleaf | 8 | 3 | 0 | 0 | 3 | 4 | 0 | 0 | 0 | 2 | 0 | 0 | 0 | 0 | 0 | 1 | 0 | 0 | 0 | 0 | 0 | 0 | 2 | 2 | 8 | 2 | 0 | 2 | 0 |
| Wheat | 2 | 2 | 0 | 0 | 3 | 3 | 0 | 0 | 0 | 0 | 0 | 0 | 0 | 0 | 0 | 0 | 0 | 0 | 0 | 0 | 0 | 0 | 4 | 4 | 2 | 5 | 0 | 0 | 0 |
| Wild buckwheat | 8 | 8 | 3 | 0 | 0 | 0 | 2 | 0 | 0 | 0 | 0 | 0 | 0 | 0 | 0 | 0 | 0 | 0 | 0 | 2 | 0 | 0 | 0 | 9 | — | 8 | — | — | — |
| Wild oat | 4 | 4 | 0 | 0 | 1 | 0 | 0 | 0 | 0 | 1 | 0 | 0 | 0 | 0 | 0 | 0 | 0 | 0 | 0 | 2 | 0 | 0 | 4 | 3 | 2 | 3 | 0 | 0 | 0 |

| Rate (10 g/ha) PRE- | COMPOUND | | | | | | | | | | | | | | | | | | | | | | | | |
|---|---|---|---|---|---|---|---|---|---|---|---|---|---|---|---|---|---|---|---|---|---|---|---|---|---|
| EMERGENCE | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
| Barley | 0 | 0 | 0 | 0 | 0 | — | 0 | 0 | 0 | 0 | 0 | 0 | 0 | 0 | 1 | 3 | 0 | 0 | 0 | 3 | 0 | 8 | 6 | 2 | 0 |
| Barnyardgrass | 7 | 9 | 0 | 0 | 2 | 0 | 1 | 0 | 0 | 0 | 1 | 0 | 0 | 0 | 1 | 5 | 1 | 0 | 0 | 7 | 6 | 8 | 8 | 7 | 4 |
| Bedstraw | 3 | 3 | 0 | 0 | 0 | — | 0 | 0 | 0 | 0 | 0 | 0 | 0 | 0 | 0 | 0 | 0 | 0 | 0 | 7 | 8 | 4 | 4 | 0 | 1 |
| Blackgrass | 4 | 5 | 2 | 0 | 2 | — | 2 | 0 | 0 | 4 | 3 | 0 | 0 | 0 | 1 | 4 | 0 | 0 | 0 | 2 | 3 | 7 | 8 | 4 | 2 |
| Cheatgrass | 8 | 7 | 2 | 0 | 3 | — | 2 | 0 | 0 | 0 | 0 | 0 | 0 | 0 | 3 | 6 | 0 | 0 | 0 | 7 | 8 | 9 | 8 | 7 | 8 |
| Chickweed | 5 | 3 | 9 | 0 | 0 | — | 8 | 9 | 5 | 9 | 7 | 6 | 8 | 0 | 2 | 4 | 0 | 0 | 0 | 9 | 9 | 9 | 7 | 5 | 9 |
| Cocklebur | — | — | — | — | — | — | — | — | — | — | — | — | — | — | — | — | — | — | — | — | — | — | — | — | — |
| Corn | 2 | 3 | 6 | 6 | 0 | 0 | 0 | 0 | 1 | 0 | 1 | 0 | 2 | 0 | 0 | 0 | 0 | 0 | 0 | 5 | 6 | 5 | 7 | 3 | 3 |
| Cotton | 2 | 0 | — | 0 | 0 | 0 | 0 | 2 | 2 | 0 | 2 | 0 | 2 | 0 | 0 | 1 | 0 | 0 | 0 | 8 | 7 | 7 | 8 | 5 | 5 |
| Crabgrass | 2 | 0 | 0 | 0 | 0 | 0 | 2 | 0 | 0 | 0 | 0 | 0 | 0 | 0 | 1 | 1 | 0 | 0 | 0 | 7 | 4 | 7 | 8 | 3 | 4 |
| Giant foxtail | 2 | 2 | 0 | 0 | 0 | 0 | 0 | 0 | 0 | 0 | 0 | 0 | 0 | 0 | 1 | 2 | 0 | 0 | 0 | 0 | 3 | 7 | 7 | 2 | 0 |
| Lambsquarters | 4 | 9 | 9 | 9 | 5 | — | 1 | 9 | 0 | 3 | 7 | 5 | 5 | 0 | 7 | 6 | 0 | 0 | 0 | 9 | 10 | 9 | 9 | 9 | 8 |
| Morningglory | 1 | 2 | 1 | 0 | 0 | 0 | 0 | 0 | 0 | 0 | 0 | 0 | 0 | 0 | 0 | 4 | 0 | 0 | 0 | 8 | 8 | 3 | 6 | 8 | 5 |
| Nutsedge | 6 | 9 | 10 | 0 | 0 | — | 0 | 0 | 0 | 0 | 0 | 0 | 0 | 0 | 0 | 0 | 8 | 0 | 0 | 5 | 10 | 9 | 10 | — | 10 |
| Rape | 6 | 6 | 0 | 0 | 0 | — | 0 | 1 | — | 0 | 0 | 3 | 1 | 0 | 2 | 0 | 0 | 0 | 0 | 9 | 8 | 9 | 8 | 8 | 7 |

TABLE A-continued

TEST A

| | | | | | | | | | | | | | | | | | | | | | | | | | |
|---|---|---|---|---|---|---|---|---|---|---|---|---|---|---|---|---|---|---|---|---|---|---|---|---|---|
| Rice | 5 | 8 | 2 | 2 | 0 | 0 | 0 | 0 | 1 | 0 | 0 | 0 | 2 | 0 | 2 | 5 | 0 | 0 | 0 | 8 | 8 | 10 | 8 | 5 | 7 |
| Sorghum | 7 | 7 | 6 | 3 | 2 | 0 | 0 | 0 | 1 | 0 | 0 | 0 | 1 | 0 | 1 | 2 | 0 | 0 | 0 | 7 | 2 | 9 | 8 | 3 | 3 |
| Soybean | 1 | 2 | 1 | 1 | 0 | 0 | 0 | 0 | 2 | 0 | 1 | 0 | 0 | 0 | 0 | 0 | 0 | 0 | 0 | 7 | 6 | 3 | 7 | 1 | 1 |
| Sugar beet | 5 | 5 | 3 | 3 | 0 | — | 0 | 7 | 2 | 2 | 3 | 7 | 5 | 0 | 5 | 7 | 0 | 0 | 0 | 9 | 8 | 8 | 9 | 7 | 8 |
| Velvetleaf | 2 | 4 | 0 | 0 | 0 | 0 | 0 | 0 | 0 | 0 | 0 | 0 | 0 | 0 | 0 | 1 | 1 | 0 | 0 | 8 | 5 | 7 | 8 | 3 | 6 |
| Wheat | 0 | 0 | 0 | 0 | 0 | — | 2 | 0 | 0 | 0 | 0 | 0 | 0 | 0 | 0 | 6 | 0 | 0 | 0 | 5 | 2 | 7 | 7 | 2 | 0 |
| Wild buckwheat | 10 | 3 | — | 2 | — | — | 0 | 0 | 0 | 0 | 0 | 3 | 0 | 0 | 5 | 1 | 0 | 0 | 0 | 3 | 5 | 2 | 4 | 0 | 2 |
| Wild oat | 0 | 0 | 0 | 0 | 0 | — | 2 | 0 | 0 | 0 | 2 | 0 | 0 | 0 | 1 | 2 | 0 | 0 | 0 | 6 | 5 | 6 | 5 | 2 | 2 |

| Rate (10 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 113 | 114 | 115 | 116 | 117 | 118 | 119 | 120 | 121 | 122 | 123 | 124 | 125 | 126 | 127 | 128 | 129 | 130 | 131 | 132 | 133 | 134 |
| Barley | 0 | 0 | 0 | 0 | 0 | 0 | 4 | 0 | 2 | 2 | 0 | 1 | 1 | 2 | 0 | 0 | 0 | 0 | 0 | 0 | 0 | 0 |
| Barnyardgrass | 2 | 8 | 1 | 3 | 2 | 0 | 9 | 4 | 5 | 5 | 0 | 0 | 0 | 0 | 0 | 0 | 0 | 0 | 0 | 0 | 0 | 0 |
| Bedstraw | 5 | 7 | 2 | 7 | 5 | 0 | 2 | 1 | 7 | 2 | 0 | 0 | 2 | 0 | 0 | 0 | 0 | 0 | 0 | 5 | 2 | 3 |
| Blackgrass | 4 | 6 | 5 | 3 | 2 | 0 | 7 | 5 | 4 | 2 | 5 | 6 | — | 4 | 0 | 2 | 0 | 2 | 2 | 2 | 3 | 2 |
| Cheatgrass | 6 | 7 | 7 | 7 | 3 | 2 | 7 | 7 | 7 | 7 | 4 | 7 | 4 | 2 | 0 | 0 | 0 | 2 | 3 | 2 | 0 | 0 |
| Chickweed | 0 | 5 | 3 | 5 | 9 | 2 | 9 | 8 | 8 | 9 | 4 | 8 | 8 | 8 | 0 | 0 | 0 | 3 | 8 | 5 | 3 | 0 |
| Cocklebur | — | — | — | — | 9 | — | — | — | — | — | 0 | 3 | 1 | 3 | 2 | 0 | 0 | 0 | 0 | 0 | 3 | 0 |
| Corn | 1 | 8 | 5 | 5 | 0 | 0 | 8 | 7 | 7 | 9 | 0 | 0 | 0 | 2 | 0 | 0 | 0 | 0 | 0 | 3 | 0 | 0 |
| Cotton | 0 | 3 | 0 | 8 | 8 | 0 | 8 | 3 | 8 | 6 | 2 | 3 | 0 | 1 | 0 | 0 | 0 | 0 | 0 | 0 | 0 | 0 |
| Crabgrass | 0 | 0 | 0 | 5 | 2 | 0 | 9 | 6 | 8 | 2 | 0 | 0 | 0 | 3 | 0 | 0 | 0 | 0 | 2 | 0 | 0 | 0 |
| Giant foxtail | 0 | 2 | 0 | 0 | 0 | 0 | 8 | 2 | 2 | 1 | 0 | 0 | 0 | 2 | 0 | 0 | 0 | 0 | 0 | 0 | 0 | 0 |
| Lambsquarters | — | 9 | 10 | 9 | 10 | 7 | 10 | 9 | 9 | 9 | 5 | — | 5 | 2 | — | 0 | 5 | 9 | 7 | 9 | 5 | 0 |
| Morningglory | 0 | 1 | 0 | 9 | 9 | 1 | 8 | 9 | 9 | 8 | 0 | 0 | 0 | 2 | 0 | 0 | 0 | 0 | 0 | 0 | 0 | 0 |
| Nutsedge | 0 | 0 | 3 | 6 | 8 | 0 | 2 | 8 | 8 | 3 | 0 | 0 | 0 | 0 | 0 | 0 | 0 | 0 | 2 | 4 | 0 | 0 |
| Rape | 3 | 7 | 0 | 7 | 6 | 0 | 9 | 8 | 8 | 3 | 1 | 7 | 3 | 5 | 0 | 2 | 0 | 7 | 4 | 4 | 2 | 3 |
| Rice | 1 | 7 | 3 | 7 | 5 | 0 | 9 | 9 | 8 | 9 | 2 | 2 | 0 | 4 | 0 | 0 | 0 | 0 | 0 | 0 | 0 | 0 |
| Sorghum | 0 | 4 | 6 | 4 | 1 | 0 | 8 | 5 | 7 | 9 | 0 | 0 | 0 | 2 | 0 | 0 | 0 | 0 | 0 | 0 | 0 | 0 |
| Soybean | 0 | 2 | 2 | 4 | 3 | 0 | 8 | 3 | 7 | 7 | 0 | 0 | 0 | 0 | 0 | 0 | 0 | 0 | 0 | 0 | 0 | 0 |
| Sugar beet | 2 | 5 | 5 | 8 | 8 | 2 | 9 | 8 | 8 | 8 | 8 | 5 | 7 | 8 | 7 | 4 | 2 | 5 | 4 | 8 | 7 | 2 |
| Velvetleaf | 0 | 3 | 2 | 7 | 2 | 0 | 7 | 6 | 5 | 2 | 0 | 0 | 0 | 0 | 0 | 0 | 0 | 0 | 5 | 0 | 0 | 0 |
| Wheat | 0 | 0 | 0 | 0 | 0 | 0 | 7 | 0 | 3 | 0 | 0 | 3 | 0 | 0 | 0 | 0 | 0 | 0 | 0 | 0 | 0 | 0 |
| Wild buckwheat | 0 | 1 | 0 | 3 | 3 | 0 | 3 | 1 | 5 | 3 | 0 | 5 | 2 | 0 | 2 | 0 | 3 | 2 | 4 | 3 | 5 | 3 |
| Wild oat | 0 | 2 | 2 | 0 | 0 | 0 | 5 | 2 | 5 | 3 | 5 | 4 | 2 | 2 | 0 | 0 | 0 | 0 | 2 | 2 | 0 | 2 |

| Rate (10 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 135 | 136 | 137 | 138 | 139 | 140 | 141 | 142 | 143 | 144 | 145 | 146 | 147 | 148 | 149 | 150 | 151 | 152 | 165 | 166 | 167 | 168 |
| Barley | 0 | 0 | 2 | 2 | 0 | 0 | 2 | 4 | 3 | 2 | 0 | 0 | 1 | 1 | 5 | 0 | 0 | 0 | 2 | 0 | 0 | 0 |
| Barnyardgrass | 0 | 0 | 0 | 2 | 0 | 0 | 0 | 4 | 7 | 1 | 0 | 4 | 2 | 4 | 5 | 0 | 0 | 0 | 0 | 0 | 5 | 0 |
| Bedstraw | 4 | 0 | 3 | 2 | 2 | 0 | 0 | 7 | 5 | 7 | 5 | 7 | 2 | 7 | 8 | 5 | — | 7 | 9 | 0 | 3 | 0 |
| Blackgrass | 3 | 3 | 2 | 6 | 2 | 5 | 2 | 6 | 7 | 7 | 2 | 5 | 3 | 4 | 5 | 0 | 2 | 7 | 9 | 4 | 5 | 3 |
| Cheatgrass | 7 | 7 | 7 | 8 | 8 | 7 | 7 | 9 | 8 | 2 | 0 | 8 | 8 | 8 | 10 | 8 | 2 | 8 | 10 | 7 | 7 | 5 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Chickweed | 4 | — | 6 | 5 | 0 | 7 | 0 | 7 | 7 | 7 | — | 7 | — | 8 | 8 | 7 | 4 | 7 | 10 | 9 | 9 | 10 |
| Cocklebur | 0 | 0 | 0 | 2 | 0 | 0 | 2 | 5 | 7 | 2 | 1 | 1 | 1 | 0 | 1 | 1 | 1 | 0 | — | 0 | 0 | 8 |
| Corn | 1 | 0 | 0 | 0 | 0 | 0 | 0 | 6 | 8 | 6 | 2 | 1 | 0 | 4 | 5 | 2 | 2 | 1 | 0 | 4 | 0 | 0 |
| Cotton | 0 | 0 | 0 | 2 | 0 | 0 | 2 | 5 | 6 | 2 | — | 2 | 0 | 0 | 7 | 0 | 0 | 0 | 0 | 0 | 0 | 0 |
| Crabgrass | 0 | 0 | 0 | 0 | 0 | 0 | 0 | 5 | 6 | 5 | 0 | 0 | 0 | 0 | 0 | 0 | 0 | 0 | 0 | 0 | 0 | 0 |
| Giant foxtail | 0 | 0 | 0 | 0 | 0 | 0 | 0 | 6 | 8 | 3 | 0 | 2 | 0 | 2 | 0 | 0 | 0 | 0 | 3 | 0 | 5 | 0 |
| Lambsquarters | 5 | 5 | 5 | 6 | 8 | 7 | 5 | 8 | 8 | 0 | 0 | 7 | 7 | 9 | 8 | 7 | 0 | 5 | 10 | 9 | 9 | 8 |
| Morningglory | 0 | 1 | 0 | 1 | 2 | 0 | 0 | 3 | 6 | 2 | 0 | 2 | 0 | 0 | 3 | 5 | 4 | 1 | 2 | 2 | 2 | 3 |
| Nutsedge | 0 | 0 | 0 | 0 | 0 | 0 | 4 | 8 | 9 | 6 | 0 | 0 | 4 | 9 | 7 | 0 | 0 | 0 | 0 | 0 | 0 | 10 |
| Rape | 0 | 0 | 0 | 0 | 0 | 0 | 2 | 7 | 9 | 5 | 0 | 7 | 1 | 7 | 8 | 1 | 0 | 5 | 9 | 0 | 0 | 0 |
| Rice | 3 | 0 | 2 | 7 | 0 | 0 | 7 | 9 | 9 | 9 | 8 | 10 | 9 | 8 | 9 | 7 | 5 | 9 | 6 | 5 | 8 | 6 |
| Sorghum | 4 | 0 | 1 | 0 | 0 | 0 | 2 | 6 | 5 | 5 | 2 | 4 | 0 | 2 | 3 | 0 | 0 | 2 | 0 | 0 | 0 | 0 |
| Soybean | 0 | 0 | 0 | 2 | 0 | 0 | 2 | 8 | 9 | 6 | 3 | 5 | 5 | 8 | 6 | 4 | 5 | 2 | 0 | 2 | 1 | 0 |
| Sugar beet | 7 | 7 | 7 | 7 | 7 | 7 | 3 | 9 | 8 | 3 | 0 | 8 | 6 | 8 | 8 | 7 | 2 | 5 | 9 | 2 | 3 | 0 |
| Velvetleaf | 0 | 2 | 0 | 0 | 0 | 2 | 0 | 3 | 6 | 2 | 0 | 2 | 0 | 0 | 3 | 0 | 0 | 0 | 0 | 3 | 0 | 1 |
| Wheat | 2 | 2 | 3 | 2 | 0 | 2 | 4 | 7 | 5 | 3 | 0 | 2 | 2 | 6 | 4 | 3 | 0 | 0 | 5 | 2 | 0 | 0 |
| Wild buckwheat | — | — | 0 | — | — | — | — | — | — | — | — | — | — | — | — | — | — | — | 10 | 2 | 2 | 0 |
| Wild oat | 3 | 4 | 2 | 5 | 0 | 2 | 6 | 5 | 2 | 5 | 0 | 0 | 5 | 2 | 2 | 0 | 0 | 0 | 9 | 0 | 0 | 0 |

| Rate (10 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 169 | 170 | 171 | 172 | 173 | 174 | 175 | 176 | 177 | 178 | 179 | 180 | 181 | 182 | 183 | 184 | 185 | 186 | 187 | 188 | 189 | 190 |
| Barley | 0 | 0 | 0 | 0 | 0 | 0 | 0 | 0 | 0 | 0 | 0 | 0 | 0 | 1 | 0 | 0 | 0 | 1 | 0 | 0 | 0 | 0 |
| Barnyardgrass | 0 | 0 | 0 | 1 | 0 | 3 | 0 | 0 | 0 | 0 | 0 | 0 | 2 | 9 | 5 | 2 | 5 | 4 | 1 | 0 | 0 | 0 |
| Bedstraw | 0 | 0 | 0 | 0 | 0 | 0 | 0 | 0 | 0 | 0 | 0 | 0 | 0 | 7 | 2 | 0 | 8 | 2 | 0 | 0 | 2 | 2 |
| Blackgrass | 0 | 0 | 3 | 5 | 5 | 0 | 2 | 0 | 1 | 1 | 0 | 2 | 0 | 7 | 8 | 2 | 7 | 7 | 3 | 2 | 3 | 6 |
| Cheatgrass | 2 | 3 | 2 | 0 | 2 | 2 | 3 | 2 | 0 | 0 | 0 | 3 | 0 | 8 | 7 | 7 | 8 | 10 | 7 | 5 | 5 | 2 |
| Chickweed | 8 | 7 | 0 | 2 | 3 | 0 | 1 | 2 | 0 | 0 | 0 | 4 | 0 | 5 | 5 | 5 | 5 | — | 2 | 0 | 3 | 0 |
| Cocklebur | 0 | 2 | — | 0 | 0 | 0 | 0 | 0 | 0 | 0 | 0 | 0 | 0 | 2 | 7 | 0 | 6 | 6 | 0 | 0 | 0 | 0 |
| Corn | 0 | 0 | 0 | 3 | 2 | 2 | 2 | 0 | 0 | 0 | 0 | 0 | 3 | 9 | 9 | 1 | 8 | 6 | 8 | 2 | 0 | 0 |
| Cotton | 0 | 0 | 0 | 2 | 2 | 1 | 0 | 0 | 0 | 0 | 0 | 0 | 0 | — | 0 | 0 | 2 | 2 | 3 | 0 | 0 | 2 |
| Crabgrass | 0 | 2 | 0 | 1 | 6 | 0 | 2 | 0 | 0 | 0 | 0 | 1 | 1 | 8 | 6 | 2 | 6 | 3 | 7 | 2 | 3 | 6 |
| Giant foxtail | 0 | 3 | 0 | 1 | 3 | 0 | 4 | 0 | 0 | 0 | 0 | 2 | 1 | 8 | 6 | 3 | 9 | 6 | 7 | 2 | 2 | 6 |
| Lambsquarters | 7 | 9 | 2 | 9 | 8 | 2 | 0 | 0 | 0 | 0 | 0 | 0 | 0 | 5 | 5 | 7 | 5 | 7 | 0 | 2 | 0 | 5 |
| Morningglory | 0 | 0 | 0 | 3 | 2 | 2 | 0 | 0 | 0 | 0 | 0 | 0 | 0 | 5 | 2 | 2 | 3 | 4 | 2 | 0 | 0 | 0 |
| Nutsedge | 0 | — | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 2 | 1 | 0 | 0 | 0 | 0 | 0 | 0 | 0 | 3 | 3 | 4 | 3 | 5 | 0 | 0 | 0 | 0 |
| Rice | 6 | 6 | 0 | 2 | 7 | 2 | 0 | 0 | 0 | 0 | 0 | 0 | 0 | 9 | 8 | 7 | 9 | 9 | 9 | 5 | 2 | 4 |
| Sorghum | 0 | 0 | 0 | 2 | 4 | 3 | 2 | 0 | 0 | 0 | 0 | 1 | 0 | 7 | 3 | 0 | 2 | 1 | 2 | 0 | 0 | 0 |
| Soybean | 0 | 0 | 0 | 3 | 4 | 2 | 2 | 0 | 0 | 0 | 0 | 0 | 0 | 6 | 7 | 3 | 5 | 8 | 8 | 0 | 1 | 0 |
| Sugar beet | 2 | 6 | 1 | 7 | 7 | 2 | 3 | 0 | 0 | 0 | 0 | 0 | 0 | 2 | 2 | 3 | 2 | 3 | 3 | 0 | 2 | 2 |
| Velvetleaf | 0 | 1 | 0 | 0 | 0 | 1 | 0 | 0 | 0 | 0 | 0 | 0 | 0 | 5 | 0 | 2 | 3 | 2 | 3 | 0 | 0 | 0 |
| Wheat | 0 | 0 | 0 | 0 | 4 | 0 | 3 | 0 | 0 | 0 | 0 | 0 | 0 | 7 | 3 | 0 | 0 | 2 | 6 | 0 | 0 | 0 |
| Wild buckwheat | 0 | 0 | 0 | — | — | — | — | — | — | — | — | — | — | — | — | — | — | — | — | — | — | — |
| Wild oat | 0 | 0 | 0 | 2 | 2 | 0 | 2 | 0 | 0 | 0 | 0 | 0 | 0 | 6 | 1 | 2 | 0 | 6 | 6 | 0 | 1 | 1 |

TABLE A-continued

TEST A

| Rate (10 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 191 | 192 | 203 | 204 | 205 | 206 | 207 | 208 | 209 | 210 | 211 | 212 | 213 | 214 | 215 | 216 | 217 | 218 | 219 | 220 | 221 | 222 |
| Barley | 0 | 0 | 2 | 4 | 9 | 2 | 1 | 6 | 0 | 0 | 0 | 1 | 1 | 1 | 0 | 0 | 1 | 1 | 0 | 0 | 0 | 0 |
| Barnyardgrass | 0 | 0 | 2 | 2 | 9 | 4 | 1 | 7 | 0 | 2 | 6 | 3 | 4 | 0 | 3 | 0 | 1 | 2 | 0 | 0 | 0 | 0 |
| Bedstraw | 0 | 0 | 0 | 0 | 7 | 7 | 7 | 3 | 0 | 1 | 2 | 3 | 5 | 2 | 2 | 0 | 2 | 1 | 2 | 0 | 0 | 0 |
| Blackgrass | 0 | 5 | 5 | 3 | 7 | 7 | 7 | 7 | 0 | 3 | 5 | 8 | 2 | 3 | 2 | 0 | 4 | 2 | 0 | 0 | 0 | 0 |
| Cheatgrass | 0 | 0 | 8 | 7 | 9 | 8 | 7 | 8 | 0 | 6 | 8 | 8 | 9 | 8 | 5 | 2 | 5 | 7 | 7 | 2 | 0 | 0 |
| Chickweed | 0 | 5 | 5 | 7 | 9 | 8 | 7 | 5 | 0 | 7 | 9 | — | 9 | 9 | 9 | 4 | 5 | 9 | 7 | 0 | 0 | 0 |
| Cocklebur | 0 | 0 | — | — | 10 | 10 | 8 | 2 | 0 | 0 | — | 0 | 0 | — | — | — | — | — | 0 | 0 | — | — |
| Corn | 0 | 6 | 5 | 9 | 7 | 8 | 3 | 8 | 0 | 0 | 8 | 6 | 9 | 2 | 0 | 0 | 0 | 0 | 0 | 0 | 0 | 0 |
| Cotton | 0 | 0 | 0 | 1 | 5 | 3 | 2 | 4 | 0 | 0 | 3 | 2 | 0 | 7 | 0 | 0 | 0 | 0 | 0 | 0 | 0 | 0 |
| Crabgrass | 0 | 4 | 5 | 9 | 9 | 8 | 4 | 6 | 0 | 2 | 6 | 2 | 6 | 1 | 0 | 0 | 2 | 2 | 0 | 0 | 0 | 0 |
| Giant foxtail | 0 | 6 | 0 | 8 | 9 | 7 | 2 | 8 | 0 | 2 | 8 | 4 | 2 | 1 | 0 | 0 | 2 | 2 | 0 | 0 | 0 | 0 |
| Lambsquarters | 0 | 2 | 5 | 9 | — | 9 | 5 | 5 | 0 | 3 | 9 | 8 | 9 | 9 | 9 | 6 | 3 | 9 | 2 | 0 | — | 0 |
| Morningglory | 0 | 0 | 2 | 4 | 7 | 7 | 2 | 6 | 0 | 0 | 0 | 2 | 3 | 2 | 0 | 0 | 0 | 0 | 0 | 0 | 0 | 0 |
| Nutsedge | 0 | 0 | 5 | 7 | 10 | — | 0 | 8 | 0 | 0 | 0 | 0 | 0 | 3 | 0 | 0 | 2 | 0 | 0 | 0 | 0 | 0 |
| Rape | 0 | 0 | 0 | 3 | 8 | 1 | 1 | 9 | 0 | 0 | 7 | 5 | 3 | 6 | 1 | 0 | 2 | 1 | 0 | 0 | 0 | 0 |
| Rice | 0 | 4 | 8 | 9 | 8 | 9 | 8 | 9 | 0 | 0 | 6 | 5 | 9 | 3 | 2 | 0 | 0 | 0 | 0 | 0 | 0 | 0 |
| Sorghum | 0 | 0 | 2 | 2 | 8 | 6 | 3 | 9 | 0 | 2 | 2 | 8 | 2 | 0 | 0 | 0 | 0 | 0 | 0 | 0 | 0 | 0 |
| Soybean | 0 | 3 | 4 | 4 | 5 | 7 | 5 | 4 | 0 | 2 | 6 | 2 | 7 | 7 | 0 | 0 | 0 | 0 | 0 | 0 | 0 | 0 |
| Sugar beet | 0 | 0 | 2 | 5 | 8 | 6 | 1 | 7 | 0 | 2 | 3 | 2 | 9 | 8 | 5 | 2 | 2 | 2 | 0 | 0 | 0 | 0 |
| Velvetleaf | 0 | 0 | 0 | 4 | 6 | 5 | 2 | 2 | 0 | 0 | 5 | 1 | 7 | 0 | 3 | 0 | 1 | 0 | 0 | 0 | 0 | 0 |
| Wheat | 0 | 0 | 4 | 8 | 8 | 7 | 6 | 6 | 0 | 2 | 8 | 6 | 1 | 1 | 0 | 0 | 0 | 1 | 0 | 0 | 0 | 0 |
| Wild buckwheat | — | — | 3 | 0 | 5 | 0 | 3 | 2 | 0 | 2 | 1 | 3 | 2 | 4 | 2 | 0 | 7 | 1 | 1 | 0 | 0 | 0 |
| Wild oat | 0 | 3 | 5 | 5 | 8 | 7 | 7 | 5 | 0 | 2 | 6 | 3 | 2 | 2 | 2 | 2 | 3 | 2 | 2 | 0 | 0 | 0 |

| Rate (10 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 223 | 224 | 225 | 226 | 227 | 228 | 229 | 230 | 231 | 232 | 233 | 234 | 235 | 236 | 237 | 238 | 239 | 240 | 241 | 242 | 243 | 244 |
| Barley | 0 | 0 | 0 | 0 | 0 | 0 | — | 0 | 0 | 0 | 0 | 0 | 0 | 0 | 0 | 0 | 0 | 5 | 5 | 6 | 2 | 2 |
| Barnyardgrass | 0 | 0 | 0 | 0 | 0 | 0 | 1 | 0 | 1 | 0 | 0 | 0 | 0 | 0 | 0 | 0 | 0 | 7 | 8 | 6 | 6 | 5 |
| Bedstraw | 0 | 1 | 0 | 0 | 0 | 0 | — | 0 | 0 | 0 | 2 | 2 | 0 | 0 | 0 | 2 | 0 | 2 | 3 | 4 | 7 | 5 |
| Blackgrass | 0 | 0 | 0 | 0 | 0 | 3 | — | 2 | 0 | 0 | 2 | 0 | 0 | 0 | 0 | 2 | 3 | 7 | 7 | 5 | 9 | 5 |
| Cheatgrass | 0 | 0 | 0 | 0 | 0 | 7 | — | 7 | 7 | 7 | 4 | 0 | 0 | 0 | 0 | 0 | 0 | 8 | 8 | 7 | 7 | 6 |
| Chickweed | 7 | 5 | 0 | 4 | 0 | 0 | — | 2 | 3 | 0 | 0 | 0 | 0 | 0 | 0 | 0 | 0 | 5 | 9 | 9 | 9 | 9 |
| Cocklebur | — | 0 | 0 | — | — | — | — | — | — | — | — | — | — | — | — | — | — | — | — | — | — | — |
| Corn | 0 | 0 | 0 | 0 | 0 | 0 | 2 | 1 | 6 | 2 | 0 | 0 | 0 | 0 | 0 | 0 | 0 | 9 | 9 | 6 | 9 | 8 |
| Cotton | 0 | 0 | 0 | 0 | 0 | 0 | 0 | — | 2 | 0 | — | 0 | 0 | 0 | 0 | 0 | 0 | 4 | 2 | 5 | 2 | 6 |
| Crabgrass | 0 | 2 | 0 | 0 | 0 | 2 | 0 | 0 | 4 | 0 | 0 | 0 | 0 | 0 | 0 | 0 | 0 | 9 | 9 | 9 | 9 | 9 |
| Giant foxtail | 0 | 2 | 0 | 0 | 0 | 1 | 1 | 0 | 2 | 0 | 0 | 0 | 0 | 0 | 0 | 0 | 0 | 7 | 9 | 8 | 6 | 6 |
| Lambsquarters | 7 | 3 | — | — | — | 4 | — | 3 | 3 | 2 | 0 | 0 | 0 | 0 | 0 | 0 | 0 | 5 | 9 | 9 | 9 | 9 |
| Morningglory | 0 | 0 | 0 | 0 | 0 | 0 | 2 | 1 | 0 | 1 | 1 | 0 | 0 | 1 | 0 | 0 | 0 | 6 | 4 | 5 | 5 | 3 |
| Nutsedge | 0 | 0 | 0 | 0 | 0 | — | 0 | 0 | 5 | 0 | — | 0 | 0 | — | 0 | — | 0 | 5 | 9 | 7 | 8 | 2 |
| Rape | 2 | 1 | 0 | 0 | 0 | 0 | — | 0 | 0 | 0 | 0 | 0 | 0 | 0 | 0 | 0 | 0 | 4 | 5 | 6 | 7 | 6 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Rice | 0 | 0 | 3 | 0 | 0 | 0 | 1 | 3 | 4 | 3 | 0 | 0 | 0 | 0 | 0 | 0 | 0 | 9 | 9 | 8 | 9 | 7 |
| Sorghum | 0 | 0 | 0 | 0 | 0 | 2 | 2 | 1 | 4 | 2 | 0 | 0 | 0 | 0 | 0 | 0 | 0 | 9 | 8 | 3 | 8 | 7 |
| Soybean | 0 | 2 | 2 | 0 | 0 | 0 | 3 | 2 | 6 | 2 | 0 | 0 | 0 | 0 | 0 | 0 | 0 | 7 | 5 | 4 | 5 | 3 |
| Sugar beet | 0 | 3 | 0 | 0 | 0 | 0 | — | 0 | 0 | 0 | 0 | 1 | 0 | 0 | 0 | 0 | 0 | 4 | 5 | 8 | 7 | 8 |
| Velvetleaf | 0 | 2 | 0 | 0 | 0 | 0 | 1 | 1 | 1 | 0 | 0 | 0 | 0 | 0 | 0 | 0 | 0 | 4 | 2 | 6 | 7 | 6 |
| Wheat | 0 | 0 | 0 | 0 | 0 | 0 | — | 0 | 4 | 2 | 3 | 0 | 0 | 0 | 0 | 0 | 0 | 8 | 6 | 5 | 4 | 6 |
| Wild buckwheat | 3 | 0 | 0 | 0 | 0 | 0 | — | 0 | 2 | 0 | 0 | 2 | 0 | 0 | 0 | 0 | 0 | 3 | 2 | 7 | 3 | 3 |
| Wild oat | 0 | 0 | 0 | 0 | 0 | 2 | — | 2 | 2 | 4 | 2 | 0 | 0 | 0 | 0 | 0 | 0 | 6 | 6 | 6 | 3 | 6 |

| Rate (10 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 245 | 246 | 247 | 248 | 249 | 250 | 251 | 252 | 253 | 254 | 255 | 256 | 257 | 258 | 259 | 260 | 261 | 262 | 263 | 264 | 265 | 266 |
| Barley | 7 | 0 | 0 | 0 | 0 | 0 | 0 | 0 | 1 | 0 | 0 | 4 | 5 | 0 | 0 | 0 | 7 | 0 | 0 | 0 | 0 | 0 |
| Barnyardgrass | 9 | 2 | 2 | 0 | 0 | 0 | 3 | 0 | 2 | 1 | 0 | 2 | 2 | 4 | 4 | 1 | 5 | 0 | 0 | 2 | 0 | 1 |
| Bedstraw | 8 | 5 | 0 | 2 | 0 | 0 | 7 | 4 | 2 | 0 | 3 | 7 | 6 | 5 | 2 | 0 | 3 | 0 | 0 | 2 | 0 | 0 |
| Blackgrass | 7 | 0 | 0 | 2 | 0 | 1 | 7 | 5 | 5 | 5 | 2 | 5 | 3 | 7 | 5 | 1 | 7 | 0 | 0 | 0 | 0 | 6 |
| Cheatgrass | 8 | 0 | 2 | 0 | 0 | 2 | 5 | 6 | 6 | 6 | 0 | 8 | 8 | 8 | 7 | 7 | 8 | 0 | 0 | 5 | 6 | 7 |
| Chickweed | 8 | 2 | 5 | 8 | 3 | 3 | 9 | 4 | 9 | 7 | 0 | 2 | 8 | 5 | 7 | 2 | 7 | 0 | 0 | 0 | 0 | 2 |
| Cocklebur | — | — | — | — | — | 0 | 2 | 0 | 0 | 0 | 0 | 0 | 0 | 1 | 0 | 0 | 0 | 0 | 0 | 0 | 0 | 0 |
| Corn | 9 | 0 | 0 | 2 | 0 | 0 | 3 | 5 | 7 | 2 | 0 | 7 | 5 | 8 | 7 | 2 | 8 | 2 | 0 | 2 | 2 | 0 |
| Cotton | 8 | 0 | 0 | 2 | 0 | 0 | 3 | 4 | 0 | 1 | 0 | 0 | 2 | 5 | 0 | — | 2 | 0 | 0 | 0 | 0 | 0 |
| Crabgrass | 9 | 6 | 7 | 2 | 2 | 0 | 5 | 0 | 0 | 0 | 0 | 7 | 6 | 5 | 6 | 0 | 5 | 0 | 0 | 0 | 0 | 0 |
| Giant foxtail | 9 | 2 | 6 | 2 | 2 | 0 | 5 | 2 | 0 | 0 | 0 | 5 | 6 | 9 | 5 | 1 | 8 | 0 | 0 | 0 | 0 | 0 |
| Lambsquarters | 9 | 0 | 5 | 7 | 0 | — | 9 | 5 | 9 | — | 2 | 4 | 7 | 9 | 9 | 2 | 3 | 2 | 0 | 0 | 7 | 2 |
| Morningglory | 6 | 0 | 0 | 2 | 0 | 0 | 0 | 0 | 2 | 2 | 0 | 3 | 3 | 3 | 1 | 0 | 0 | 0 | 0 | 1 | 0 | 1 |
| Nutsedge | 9 | 6 | — | 0 | — | 0 | 0 | 0 | 0 | 0 | 0 | 9 | 0 | 3 | 0 | 0 | 8 | 0 | 0 | 0 | 0 | 0 |
| Rape | 7 | 0 | 0 | 2 | 0 | 0 | 7 | 4 | 5 | 3 | 2 | 5 | 5 | 7 | 3 | 0 | 3 | 0 | 0 | 0 | 0 | 0 |
| Rice | 9 | 2 | 2 | 2 | 0 | 0 | 3 | 2 | 5 | 7 | 0 | 8 | 5 | 7 | 8 | 5 | 9 | 0 | 0 | 0 | 0 | 3 |
| Sorghum | 9 | 0 | 0 | 0 | 0 | 0 | 4 | 0 | 4 | 2 | 0 | 8 | 5 | 7 | 8 | 3 | 9 | 0 | 0 | 2 | 2 | 2 |
| Soybean | 3 | 0 | 2 | 2 | 0 | 0 | 2 | 2 | 3 | 4 | 0 | 4 | 2 | 3 | 2 | 0 | 2 | 0 | 0 | 2 | 2 | 0 |
| Sugar beet | 7 | 0 | 5 | 8 | 7 | 0 | 7 | 3 | 5 | — | 0 | 2 | 5 | 3 | 2 | 0 | 3 | 0 | 0 | 0 | 0 | 0 |
| Velvetleaf | 5 | 2 | 2 | 0 | 0 | 0 | 3 | 0 | 4 | 0 | 0 | 4 | 0 | 4 | 0 | 0 | 1 | 0 | 0 | 0 | 0 | 2 |
| Wheat | 4 | 0 | 0 | 0 | 0 | 0 | 0 | 3 | 0 | 0 | 0 | 6 | 7 | 6 | 4 | 2 | 5 | 0 | 0 | 0 | 0 | 0 |
| Wild buckwheat | 7 | 3 | — | 5 | — | 0 | — | 0 | 3 | 2 | 2 | 2 | 0 | 0 | 2 | 0 | 3 | 0 | 0 | 0 | 0 | 0 |
| Wild oat | 6 | 0 | 0 | 0 | 0 | 0 | 2 | 2 | 1 | 2 | 0 | 7 | 4 | 6 | 4 | 3 | 5 | 0 | 0 | 3 | 0 | 0 |

| Rate (10 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 267 | 268 | 269 | 270 | 271 | 272 | 273 | 274 | 275 | 276 | 277 | 278 | 279 | 280 | 281 | 282 | 283 | 284 | 285 | 286 | 287 | 288 |
| Barley | 0 | 0 | 0 | 0 | 0 | 1 | 0 | 0 | 7 | 0 | 0 | 0 | 0 | 0 | 0 | 0 | 3 | 1 | 0 | 1 | 1 | 2 |
| Barnyardgrass | 2 | 0 | 0 | 0 | 1 | 2 | 0 | 0 | 8 | 0 | 0 | 0 | 0 | 0 | 0 | 0 | 0 | 2 | 0 | 3 | 2 | 0 |
| Bedstraw | 0 | 0 | 0 | 0 | 1 | 2 | 0 | 0 | 2 | 0 | 0 | 0 | 0 | 0 | 0 | 0 | 0 | 2 | 1 | 4 | 0 | 4 |
| Blackgrass | 3 | 3 | 0 | 7 | 5 | 5 | 2 | 2 | 8 | 0 | 0 | 0 | 0 | 0 | 1 | 0 | 6 | 5 | 1 | 4 | 0 | 2 |
| Cheatgrass | 8 | 9 | 5 | 9 | 8 | 8 | 7 | 5 | 8 | 0 | 0 | 0 | 0 | 0 | 0 | 0 | 8 | 8 | 5 | 7 | 2 | 8 |

TABLE A-continued

TEST A

| | | | | | | | | | | | | | | | | | | | | | | |
|---|---|---|---|---|---|---|---|---|---|---|---|---|---|---|---|---|---|---|---|---|---|---|
| Chickweed | 0 | 2 | 0 | 0 | 6 | 8 | 0 | 0 | 8 | 0 | 0 | 0 | — | 0 | 0 | 0 | 8 | 9 | 8 | 8 | 9 | 8 |
| Cocklebur | 0 | 0 | 0 | 0 | 0 | 0 | 0 | 0 | 0 | 0 | 0 | 0 | 0 | — | 0 | 0 | 4 | 5 | 4 | 6 | 6 | 5 |
| Corn | 5 | 1 | 0 | 1 | 0 | 2 | 1 | 2 | 8 | 0 | 0 | 0 | 0 | 0 | 0 | 0 | 5 | 3 | 0 | 3 | 2 | 2 |
| Cotton | 2 | 3 | 0 | 2 | 2 | 3 | 0 | 2 | 6 | 0 | 0 | 0 | 0 | 0 | 0 | 0 | 2 | 1 | 0 | 2 | 2 | 6 |
| Crabgrass | 0 | 0 | 0 | 5 | 4 | 8 | 2 | 0 | 9 | 0 | 0 | 0 | 0 | 0 | 0 | 0 | 5 | 4 | 5 | 8 | 8 | 5 |
| Giant foxtail | 0 | 0 | 0 | 0 | 0 | 9 | 1 | 0 | 9 | 0 | 0 | 0 | 0 | 0 | 0 | 0 | 2 | 3 | 3 | 3 | 3 | 5 |
| Lambsquarters | — | 5 | 3 | — | 5 | 9 | 0 | 0 | 4 | — | 0 | — | 0 | 0 | 0 | — | — | 9 | 9 | 3 | 9 | 8 |
| Morningglory | 0 | 3 | 0 | 0 | 3 | 2 | 0 | 0 | 3 | 0 | 0 | 0 | 0 | 0 | 0 | 0 | 3 | 3 | 1 | 5 | 3 | 5 |
| Nutsedge | 0 | 0 | 0 | 8 | 0 | 0 | 0 | 0 | 10 | 0 | 0 | 0 | 0 | 0 | 0 | 0 | 0 | 2 | 0 | — | 0 | 8 |
| Rape | 1 | 1 | 0 | 0 | 0 | 0 | 0 | 0 | 2 | 0 | 0 | 0 | 0 | 0 | 0 | 0 | 8 | 8 | 6 | 8 | 9 | 6 |
| Rice | 5 | 3 | 0 | 5 | 5 | 9 | 5 | 3 | 9 | 0 | 0 | 0 | 0 | 0 | 0 | 0 | 5 | 3 | 0 | 2 | 2 | 3 |
| Sorghum | 5 | 3 | 0 | 2 | 2 | 1 | 1 | 2 | 9 | 0 | 0 | 0 | 0 | 0 | 0 | 0 | 3 | 3 | 0 | 5 | 0 | 7 |
| Soybean | 5 | 2 | 0 | 2 | 0 | 1 | 1 | 0 | 5 | 0 | 0 | 0 | 0 | 0 | 0 | 0 | 4 | 1 | 0 | 0 | 3 | 2 |
| Sugar beet | 3 | 1 | 0 | 0 | — | 3 | 0 | 0 | 2 | 0 | 0 | 0 | 1 | 0 | 0 | 3 | 7 | 8 | 4 | 5 | 8 | 7 |
| Velvetleaf | 1 | 0 | 0 | 0 | 0 | 0 | 0 | 0 | 0 | 0 | 0 | 0 | 0 | 0 | 0 | 0 | 4 | 4 | 3 | 3 | 2 | 6 |
| Wheat | 3 | 0 | 0 | 4 | 3 | 0 | 2 | 0 | 7 | 0 | 0 | 0 | 0 | 0 | 0 | 0 | 3 | 2 | 0 | 0 | 0 | 0 |
| Wild buckwheat | 0 | 0 | 0 | 5 | 6 | 0 | 0 | 0 | 0 | — | — | — | — | — | — | — | 4 | 5 | 1 | 0 | 0 | 2 |
| Wild oat | 3 | 5 | 0 | 5 | 3 | 3 | 2 | 2 | 6 | 0 | 0 | 0 | 0 | 0 | 0 | 0 | 2 | 2 | 0 | 2 | 2 | 2 |

| Rate (10 g/ha) PRE- | COMPOUND | | | | | | | | | | | | | | | | | | | | | |
|---|---|---|---|---|---|---|---|---|---|---|---|---|---|---|---|---|---|---|---|---|---|---|
| EMERGENCE | 289 | 290 | 291 | 292 | 293 | 294 | 295 | 296 | 297 | 298 | 299 | 300 | 301 | 302 | 303 | 304 | 305 | 306 | 307 | 308 | 309 | 310 |
| Barley | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 0 | 0 | 0 | 0 | 0 | 0 | 0 | 0 | 0 | 0 | 1 | 3 | 3 | 0 | 0 | 3 | 2 | 0 | 0 | 0 | 0 |
| Bedstraw | 1 | 0 | 0 | 0 | 0 | 0 | 0 | 0 | 0 | 2 | 0 | 0 | 0 | 0 | 0 | 0 | 0 | 0 | 0 | 0 | 2 | 0 |
| Blackgrass | 3 | 0 | 4 | 0 | 0 | 0 | 3 | 3 | 2 | 2 | 2 | 2 | 0 | 4 | 0 | 0 | 0 | 0 | 3 | 3 | 0 | 0 |
| Cheatgrass | 6 | 2 | 6 | 0 | 0 | 0 | 0 | 1 | 0 | 0 | 0 | 4 | 6 | 6 | 0 | 0 | 7 | 3 | 2 | 0 | 0 | 0 |
| Chickweed | 7 | 0 | 4 | 0 | 0 | 2 | 2 | 2 | 2 | — | 0 | 0 | 2 | 9 | 0 | 0 | 3 | 2 | 0 | 0 | 0 | 0 |
| Cocklebur | 0 | 0 | 0 | 0 | 0 | 0 | 0 | 0 | 0 | 0 | 0 | — | — | — | — | — | — | — | 0 | 0 | 0 | — |
| Corn | 2 | 0 | 2 | 0 | 0 | 0 | 0 | 0 | 0 | 0 | 0 | 2 | 1 | 5 | 0 | 0 | 4 | 1 | 4 | 2 | 0 | 0 |
| Cotton | 0 | 0 | 0 | 0 | 0 | 0 | 0 | 0 | 0 | 0 | 0 | 2 | 2 | 2 | 0 | 0 | 2 | 0 | — | 0 | 0 | 2 |
| Crabgrass | 3 | 0 | 4 | 0 | 0 | 0 | 2 | 0 | 0 | 0 | 0 | 5 | 2 | 5 | 0 | 0 | 7 | 3 | 0 | 0 | 0 | 0 |
| Giant foxtail | 3 | 0 | 5 | 0 | 0 | 0 | 0 | 0 | 0 | 0 | 0 | 6 | 2 | 8 | 1 | 0 | 8 | 2 | 0 | 0 | 0 | 0 |
| Lambsquarters | 7 | 5 | 6 | 0 | 0 | 0 | 2 | 4 | 10 | 4 | 3 | 3 | 9 | 9 | 0 | 0 | 5 | 5 | 2 | 3 | 3 | 5 |
| Morningglory | — | 0 | 0 | 0 | 0 | 0 | 0 | 0 | 0 | 0 | 0 | 0 | 1 | 0 | 0 | 0 | 2 | 0 | 0 | 0 | 0 | 3 |
| Nutsedge | 0 | 0 | 8 | 0 | 0 | 0 | 0 | 0 | 0 | 0 | 0 | 0 | 0 | 8 | 0 | 0 | 0 | 0 | 0 | 0 | 0 | 0 |
| Rape | 0 | 1 | 2 | 0 | 0 | 0 | 0 | 0 | 0 | 0 | 0 | 0 | 0 | 0 | 0 | 0 | 0 | 0 | 1 | 2 | 0 | 0 |
| Rice | 0 | 0 | 0 | 0 | 0 | 0 | 0 | 0 | 0 | 0 | 0 | 0 | 3 | 7 | 0 | 0 | 8 | 2 | 0 | 0 | 0 | 0 |
| Sorghum | 2 | 0 | 2 | 0 | 0 | 0 | 0 | 0 | 0 | 0 | 0 | 3 | 1 | 3 | 0 | 0 | 5 | 1 | 0 | 0 | 0 | 0 |
| Soybean | 0 | 0 | — | 0 | 0 | 0 | 0 | 0 | 0 | 0 | 0 | 1 | 3 | 2 | 0 | 0 | 2 | 0 | 0 | 1 | 0 | 2 |
| Sugar beet | 6 | 0 | 5 | 0 | 0 | 0 | 0 | 0 | 0 | 0 | 0 | 0 | 0 | 2 | 0 | 0 | 6 | 0 | 0 | 2 | 0 | 2 |
| Velvetleaf | 0 | 0 | 0 | 0 | 0 | 0 | 0 | 0 | 0 | 0 | 0 | 0 | 0 | 1 | 0 | 0 | 0 | 0 | 4 | 0 | 3 | 3 |
| Wheat | 0 | 0 | 4 | 0 | 0 | 0 | 0 | 0 | 0 | 0 | 0 | 0 | 2 | 5 | 0 | 0 | 0 | 0 | 0 | 0 | 0 | 0 |
| Wild buckwheat | 2 | 2 | 2 | 0 | 0 | 0 | 2 | 0 | 0 | 2 | 0 | 0 | 0 | 0 | 0 | 0 | 0 | 2 | — | 2 | — | — |
| Wild oat | 2 | 2 | 3 | 0 | 0 | 0 | 2 | 0 | 0 | 0 | 0 | 2 | 6 | 2 | 0 | 0 | 0 | 0 | 0 | 0 | 0 | 0 |

TABLE A-continued

TEST A

| Rate (10 g/ha) PRE- | COMPOUND | | | | | | | | | | | | | | | | | | | | |
|---|---|---|---|---|---|---|---|---|---|---|---|---|---|---|---|---|---|---|---|---|---|
| EMERGENCE | 311 | 312 | 313 | 314 | 315 | 316 | 317 | 318 | 319 | 320 | 321 | 322 | 323 | 324 | 325 | 326 | 327 | 328 | 329 | 330 | 331 | 332 |
| Barley | 0 | 0 | 0 | 0 | 0 | 0 | 0 | 0 | 0 | 0 | 0 | 2 | 8 | 3 | 0 | 0 | 2 | 0 | 0 | 0 | 0 | 0 |
| Barnyardgrass | 0 | 0 | 0 | 0 | 0 | 0 | 0 | 0 | 0 | 0 | 0 | 1 | 1 | 3 | 0 | 0 | 3 | 1 | 1 | 0 | 0 | 0 |
| Bedstraw | 0 | 0 | 0 | 0 | 0 | 0 | 2 | 0 | 0 | 0 | 0 | 1 | 8 | 5 | 0 | 0 | 5 | 0 | 0 | 0 | 0 | 0 |
| Blackgrass | 0 | 1 | 1 | 1 | 0 | 0 | 0 | 0 | 0 | 0 | 0 | 7 | 8 | 7 | 5 | 0 | 5 | 0 | 0 | 0 | 0 | 0 |
| Cheatgrass | 0 | 3 | 0 | 0 | 0 | 0 | 0 | 0 | 0 | 0 | 0 | 9 | 9 | 9 | 7 | 0 | 7 | 0 | 3 | 0 | 0 | 0 |
| Chickweed | 0 | 0 | 0 | 0 | 0 | 0 | 0 | 0 | 0 | 0 | 0 | 9 | 9 | 9 | 8 | 2 | 9 | 0 | 2 | 0 | — | — |
| Cocklebur | 3 | 2 | — | 0 | 0 | 0 | 0 | 0 | 0 | 0 | 0 | 0 | 0 | 1 | 0 | 0 | 1 | 0 | 0 | 0 | 0 | 0 |
| Corn | 0 | 0 | 0 | 0 | 0 | 0 | 0 | 0 | 0 | 0 | 0 | 9 | 8 | 9 | 7 | 0 | 9 | 2 | 2 | 0 | 0 | 0 |
| Cotton | 2 | — | 0 | 0 | 0 | 0 | 0 | 0 | 0 | 0 | 0 | 2 | 5 | 8 | 1 | 0 | 5 | 2 | 2 | 0 | 0 | 0 |
| Crabgrass | 0 | 0 | 0 | 0 | 0 | 0 | 0 | 0 | 0 | 0 | 0 | 5 | 7 | 6 | 0 | 0 | 5 | 2 | 0 | 0 | 0 | 0 |
| Giant foxtail | 2 | 2 | 0 | 0 | 0 | 0 | 0 | 0 | 0 | 0 | 0 | 3 | 8 | 8 | 0 | 0 | 6 | 0 | 0 | 0 | 0 | 0 |
| Lambsquarters | 0 | 5 | — | 10 | 0 | 0 | 0 | 0 | 0 | 0 | 0 | 9 | 9 | 9 | 3 | 2 | 9 | 0 | 3 | 0 | 0 | 0 |
| Morningglory | 5 | 3 | 0 | 0 | 0 | 0 | 0 | 0 | 0 | 0 | 0 | 2 | 5 | 3 | 1 | 1 | 2 | 0 | 0 | 0 | 0 | 0 |
| Nutsedge | 0 | 0 | 0 | 0 | 0 | 0 | 0 | 0 | 0 | 0 | 0 | 5 | 3 | 9 | — | 0 | 7 | 0 | 0 | 0 | 0 | 0 |
| Rape | 0 | 0 | 0 | 0 | 0 | 0 | 0 | 0 | 0 | 0 | 0 | 7 | 9 | 9 | 0 | 0 | 9 | 0 | 0 | 0 | 0 | 0 |
| Rice | 0 | 0 | 0 | 0 | 0 | 0 | 0 | 0 | 0 | 0 | 0 | 9 | 9 | 9 | 8 | 3 | 9 | 0 | 3 | 0 | 0 | 0 |
| Sorghum | 0 | 0 | 0 | 0 | 0 | 0 | 0 | 0 | 0 | 0 | 0 | 8 | 8 | 8 | 3 | 0 | 8 | 0 | 2 | 0 | 0 | 0 |
| Soybean | 3 | 2 | 0 | 0 | 0 | 0 | 0 | 0 | 0 | 0 | 0 | 7 | 9 | 9 | 2 | 0 | 4 | 0 | 2 | 0 | 0 | 0 |
| Sugar beet | 0 | 3 | 0 | 0 | 0 | 0 | 0 | 0 | 0 | 0 | 0 | 9 | 8 | 8 | 5 | 3 | 9 | 0 | 0 | 0 | 0 | 0 |
| Velvetleaf | 2 | 3 | 0 | 0 | 0 | 0 | 0 | 0 | 0 | 0 | 0 | 5 | 3 | 8 | 0 | 0 | 1 | 0 | 0 | 0 | 0 | 0 |
| Wheat | 0 | 0 | 0 | 0 | 0 | 0 | 0 | 0 | 0 | 0 | 0 | 5 | 8 | 6 | 2 | 0 | 0 | 0 | 0 | 0 | 0 | 0 |
| Wild buckwheat | — | — | — | — | — | 0 | — | — | — | — | 0 | — | — | — | — | — | — | — | — | — | — | — |
| Wild oat | 0 | 0 | 0 | 0 | 0 | 0 | 0 | 0 | 0 | 0 | 0 | 7 | 8 | 6 | 5 | 2 | 2 | 0 | 2 | 0 | 0 | 0 |

| Rate (10 g/ha) PRE- | COMPOUND | | | | | | | | | |
|---|---|---|---|---|---|---|---|---|---|---|
| EMERGENCE | 333 | 334 | 335 | 336 | 337 | 338 | 339 | 340 | 341 | 342 |
| Barley | 0 | 0 | 0 | 0 | 0 | 5 | 3 | 0 | 0 | 2 |
| Barnyardgrass | 0 | 0 | 0 | 0 | 0 | 2 | 4 | 0 | 0 | 0 |
| Bedstraw | 0 | 0 | 0 | 0 | 0 | 2 | 0 | 0 | 0 | 0 |
| Blackgrass | 0 | 0 | 0 | 0 | 0 | 0 | 5 | 5 | 2 | 0 |
| Cheatgrass | 0 | 0 | 0 | 0 | 0 | 9 | 9 | 7 | 3 | 8 |
| Chickweed | — | — | 0 | 0 | 0 | 9 | 9 | — | 0 | 7 |
| Cocklebur | 0 | 0 | 0 | 0 | 0 | 2 | 6 | 0 | 0 | 2 |
| Corn | 0 | 0 | 0 | 0 | 0 | 8 | 7 | 0 | 0 | 4 |
| Cotton | 0 | 0 | 0 | 0 | 0 | 4 | 6 | 0 | — | 2 |
| Crabgrass | 0 | 0 | 0 | 0 | 0 | 2 | 9 | 0 | 0 | 3 |
| Giant foxtail | 0 | 0 | 0 | 0 | 0 | 5 | 9 | 0 | 0 | 3 |
| Lambsquarters | 0 | 0 | 0 | 0 | 0 | 8 | 9 | 0 | 0 | 9 |
| Morningglory | 0 | 0 | 0 | 0 | 0 | 5 | 2 | 0 | 0 | 4 |
| Nutsedge | 0 | 0 | 0 | 0 | 0 | 6 | 4 | 0 | 0 | 0 |
| Rape | 0 | 0 | 0 | 0 | 0 | 5 | 9 | 0 | 0 | 5 |

TABLE A-continued

| TEST A | | | | | | | | | | |
|---|---|---|---|---|---|---|---|---|---|---|
| Rice | 0 | 0 | 0 | 0 | 0 | 7 | 9 | 3 | 0 | 8 |
| Sorghum | 0 | 0 | 0 | 0 | 0 | 1 | 9 | 0 | 0 | 9 |
| Soybean | 0 | 0 | 0 | 0 | 0 | 6 | 5 | 0 | 0 | 3 |
| Sugar beet | 0 | 0 | 0 | 0 | 0 | 2 | 9 | 0 | 0 | 7 |
| Velvetleaf | 0 | 0 | 0 | 0 | 0 | 2 | 5 | 0 | 0 | 2 |
| Wheat | 0 | 0 | 0 | 0 | 0 | 8 | 8 | 2 | 0 | 5 |
| Wild buckwheat | — | — | — | — | — | — | — | — | — | — |
| Wild oat | 0 | 0 | 0 | 0 | 0 | 2 | 2 | 2 | 0 | 4 |

TEST B

The compounds evaluated in this test were formulated in a non-phytoxic solvent and applied to the soil surface before plant seedlings emerged (preemergence application), to water that covered the soil surface (paddy application), and to plants that were in the one-to-four leaf stage (postemergence application). A sandy loam soil was used for the preemergence and postemergence tests, while a silt loam soil was used in the paddy test. Water depth was approximately 2.5 cm for the paddy test and was maintained at this level for the duration of the test.

Plant species in the preemergence and postemergence tests consisted of barley (*Hordeum vulgare*), bedstraw (*Galium aparine*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), duck salad (*Heteranthera limosa*), giant foxtail (*Setaria faberii*), lambsquarters (*Chenopodium album*), mornlngglory (*Ipomoea hederacea*), pigweed (*Amaranthus retroflexus*), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the proemergence portion of this test. Plantings of these species were adjusted to produce plants of appropriate size for the postemergence portion of the test. Plant species in the paddy test consisted of barnyardgrass (*Echinochloa crus-galli*), rice (*Oryza sativa*), and umbrella sedge (*Cyperus difformis*).

All plant species were grown using normal greenhouse practices. Visual evaluations of injury expressed on treated plants, when compared to untreated controls, were recorded approximately fourteen to twenty-one days after application of test compounds. Plant response ratings, summarized in Table B, are recorded on a 0 to 10 scale where 0 is no injury and 10 is complete control. A dash (-) response means no test result.

TABLE B

| Rate (125 g/ha) | 2 | 7 | 125 | 209 | 254 | 269 | 292 | 2 | 7 | 125 | 209 | 254 | 269 | 292 |
|---|---|---|---|---|---|---|---|---|---|---|---|---|---|---|
| | COMPOUND | | | | | | | | | | | | | |
| | POSTEMERGENCE | | | | | | | PREEMERGENCE | | | | | | |
| Barley Igri | 10 | 8 | 0 | 0 | 8 | 9 | 8 | 10 | 4 | 0 | 0 | 9 | 0 | 2 |
| Bedstraw | 20 | 5 | 8 | 0 | 10 | 10 | 10 | 10 | 5 | 8 | 5 | 10 | 8 | 3 |
| Blackgrass | 10 | 9 | 8 | 6 | 9 | 10 | 10 | 10 | 7 | 9 | 0 | 20 | 10 | 0 |
| Chickweed | 10 | 3 | 10 | 0 | 10 | 6 | 9 | 10 | 4 | 9 | 5 | 10 | 3 | 9 |
| Corn | 10 | 7 | 8 | 7 | 10 | 9 | 10 | 9 | 0 | 2 | 0 | 10 | 0 | 0 |
| Cotton | 7 | 6 | 10 | 0 | 9 | 7 | 9 | 5 | 0 | 3 | 0 | 9 | 2 | 0 |
| Crabgrass | 8 | 6 | 0 | 0 | 0 | 0 | 10 | 9 | 4 | 3 | 3 | 7 | 6 | 3 |
| Downy brome | 10 | 9 | 0 | 2 | 9 | 9 | 6 | 10 | 7 | 0 | 7 | 9 | 9 | 2 |
| Duck salad | — | — | 4 | 0 | 3 | 7 | 8 | — | — | — | — | — | — | — |
| Giant foxtail | 10 | 8 | 3 | 5 | 7 | 5 | 10 | 10 | 5 | 0 | 0 | 8 | 6 | 0 |
| Lambsquarters | 10 | 10 | 10 | 0 | 8 | 2 | 9 | 10 | 8 | 10 | 0 | 9 | 10 | 0 |
| Morningglory | 10 | 7 | 10 | 5 | 10 | 8 | 10 | 6 | 3 | 7 | 0 | 9 | 0 | 0 |
| Pigweed | 8 | 6 | 9 | 0 | 9 | 7 | 7 | 10 | 7 | 9 | 0 | 9 | 8 | 7 |
| Rape | 10 | 0 | 10 | 0 | 10 | 10 | 10 | 10 | 3 | 10 | 0 | 10 | 3 | 3 |
| Ryegrass | 10 | 5 | 0 | 2 | 9 | 9 | 7 | 10 | 5 | 4 | 4 | 9 | 0 | 3 |
| Sorghum | 10 | 7 | 5 | 7 | 9 | 8 | 10 | 9 | 7 | 4 | 3 | 9 | 3 | 4 |
| Soybean | 10 | 6 | 9 | 0 | 10 | 8 | 3 | 8 | 0 | 3 | 0 | 10 | 3 | 0 |
| Speedwell | 8 | 0 | 6 | 0 | 4 | 5 | 9 | 10 | 9 | 10 | 0 | 9 | 10 | 4 |
| Sugar beet | 10 | 7 | 10 | 0 | 9 | 4 | 9 | 10 | 7 | 10 | 4 | 10 | — | 6 |
| Velvetleaf | 10 | 6 | 10 | 0 | 7 | 4 | 8 | 9 | 4 | 7 | 0 | 8 | 4 | 3 |
| Wheat | 9 | 6 | 0 | 0 | 5 | 6 | 8 | 10 | 7 | 0 | 0 | 3 | 0 | 0 |
| Wild buckwheat | 10 | 4 | 9 | 0 | 10 | 10 | — | 10 | 2 | 9 | 5 | 9 | 9 | 7 |
| Wild oat | 10 | 8 | 0 | 0 | 9 | 8 | 9 | 9 | 3 | 2 | 0 | 9 | 2 | 0 |
| Barnyardgrass | 9 | 2 | 7 | 0 | 8 | 9 | 7 | — | — | — | — | — | — | — |
| Rice Japonica | 9 | 0 | 7 | 6 | 8 | 9 | 6 | — | — | — | — | — | — | — |
| Umbrella sedge | 9 | 5 | 9 | 0 | 8 | 8 | 4 | — | — | — | — | — | — | — |

| Rate (62 g/ha) | 1 | 2 | 3 | 5 | 7 | 11 | 13 | 14 | 35 | 50 | 51 | 53 | 58 | 59 | 60 | 63 | 64 | 71 | 77 | 78 | 81 | 82 | 83 | 84 | 86 | 88 | 89 | 102 | 103 | 108 | 109 | 110 | 111 | 112 | 114 | 115 | 116 |
|---|---|---|---|---|---|---|---|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | | | | | | | | | |
| | POSTEMERGENCE | | | | | | | | | | | | | | | | | | | | | | | | | | | | | | | | | | | | |
| Barley Igri | 10 | 10 | 9 | 10 | 8 | 9 | 9 | 9 | 5 | 9 | 9 | 9 | 6 | 8 | 7 | 9 | 9 | 3 | 5 | 4 | 8 | 8 | 9 | 9 | 8 | 8 | 8 | 9 | 9 | 8 | 10 | 10 | 9 | 8 | 9 | 4 | 6 |
| Bedstraw | 10 | 10 | 10 | 10 | 5 | 9 | 10 | 8 | 10 | 10 | 10 | 10 | 10 | 10 | 10 | 9 | 9 | 9 | 7 | 9 | 8 | 9 | 10 | 10 | 10 | 10 | 10 | 10 | 10 | 10 | 10 | 10 | 10 | 10 | 10 | 10 | 10 |
| Blackgrass | 9 | 10 | 10 | 10 | 8 | 9 | 9 | 7 | 10 | 10 | 9 | 9 | 9 | 9 | 9 | 10 | 10 | 7 | 7 | 8 | 10 | 10 | 10 | 9 | 9 | 9 | 10 | 9 | 9 | 10 | 10 | 10 | 10 | 10 | 9 | 9 | 9 |
| Chickweed | 9 | 10 | 10 | 10 | 0 | 10 | 9 | 9 | 10 | 9 | 10 | 9 | 9 | 10 | 10 | 10 | 10 | 9 | 7 | 9 | 9 | 10 | 10 | 10 | 9 | 9 | 10 | 9 | 9 | 20 | 10 | 10 | 10 | 9 | 9 | 9 | 10 |
| Corn | 7 | 10 | 10 | 10 | 7 | 10 | 10 | 10 | 10 | 8 | 10 | 7 | 10 | 10 | 9 | 10 | 10 | 7 | 7 | 8 | 4 | 9 | 9 | 10 | 4 | 8 | 9 | 6 | 0 | 20 | 9 | 10 | 10 | 8 | 9 | 9 | 8 |
| Cotton | 6 | 7 | 9 | 7 | 5 | 9 | 8 | 9 | 8 | 10 | 10 | 10 | 9 | 10 | 10 | 9 | 10 | 10 | 7 | 8 | 8 | 9 | 10 | 9 | 9 | 9 | 9 | 7 | 8 | 10 | 9 | 10 | 10 | 9 | 9 | 9 | 9 |
| Crabgrass | 8 | 7 | 8 | 10 | 5 | 7 | 10 | 7 | 4 | 5 | 8 | 8 | 4 | 0 | 3 | 7 | 10 | 6 | 7 | 5 | 7 | 4 | 5 | 6 | 3 | 3 | 4 | 1 | 2 | 7 | 9 | 9 | 6 | 6 | 2 | 2 | 2 |
| Downy brome | 9 | 10 | 10 | 10 | 8 | 9 | 9 | 7 | 10 | 8 | 8 | 9 | 6 | 8 | 7 | 9 | 8 | 4 | 6 | 3 | 7 | 7 | 6 | 9 | 6 | 8 | 5 | 9 | 9 | 9 | 9 | 10 | 9 | 7 | 6 | 0 | 8 |
| Duck salad | — | — | — | — | — | — | — | — | — | 10 | 10 | 10 | 8 | 10 | 10 | 9 | 10 | 10 | 7 | 9 | 4 | 9 | 9 | 3 | 9 | 9 | 9 | 6 | 9 | 10 | 9 | 10 | 8 | 10 | 4 | 4 | 7 |
| Giant foxtail | 8 | 10 | 10 | 10 | 7 | 10 | 10 | 10 | 9 | 10 | 10 | 10 | 7 | 6 | 4 | 10 | 10 | 5 | 7 | 8 | 9 | 9 | 10 | 9 | 6 | 6 | 7 | 7 | 7 | 6 | 9 | 10 | 9 | 6 | 8 | 7 | 9 |
| Lambsquarters | 10 | 10 | 10 | 10 | 9 | 10 | 10 | 8 | 10 | 10 | 10 | 10 | 9 | 10 | 10 | 16 | 10 | 10 | 10 | 10 | 9 | 9 | 10 | 10 | 10 | 9 | 10 | 10 | 10 | 10 | 10 | 10 | 10 | 10 | 9 | 10 | 9 |
| Morningglory | 7 | 10 | 10 | 10 | 6 | 9 | 10 | 10 | 10 | 10 | 10 | 10 | 10 | 10 | 10 | 10 | 10 | 10 | 10 | 10 | 10 | 10 | 10 | 9 | 9 | 10 | 10 | 10 | 9 | 10 | 8 | 10 | 10 | 10 | 8 | 10 | 10 |

TABLE B-continued

| | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| Pigweed | 8 | 7 | 7 | 10 | 4 | 9 | 10 | 6 | 10 | 10 | 10 | 10 | 10 | 10 | 10 | 10 | 10 | 10 | 10 | 10 | 9 | 10 | 10 | 9 | 9 | 8 | 10 | 9 | 10 | 10 | 10 | 10 | 10 | 10 | 7 | 6 | 9 |
| Rape | 7 | 10 | 10 | 10 | 0 | 10 | 10 | 10 | 4 | 10 | 10 | 10 | 10 | 10 | 10 | 10 | 20 | 8 | 10 | 10 | 9 | 10 | 10 | 10 | 10 | 10 | 10 | 9 | 10 | 10 | 10 | 10 | 10 | 10 | 9 | 9 | 10 |
| Ryegrass | 10 | 10 | 5 | 10 | 4 | 9 | 10 | 9 | 9 | 9 | 10 | 10 | 6 | 9 | 9 | 10 | 10 | 6 | 8 | 6 | 6 | 6 | 6 | 10 | 5 | 6 | 5 | 6 | 4 | 10 | 10 | 10 | 9 | 7 | 9 | 5 | 9 |
| Sorghum | 7 | 10 | 10 | 10 | 7 | 10 | 10 | 10 | 10 | 8 | 10 | 7 | 7 | 8 | 7 | 10 | 10 | 7 | 10 | 10 | 10 | 10 | 10 | 10 | 9 | 8 | 9 | 10 | 10 | 10 | 9 | 10 | 10 | 10 | 8 | 9 | 9 |
| Soybean | 8 | 10 | 10 | 10 | 4 | 10 | 10 | 10 | 10 | 10 | 10 | 10 | 10 | 10 | 10 | 10 | 10 | 9 | 9 | 9 | 9 | 10 | 10 | 9 | 9 | 9 | 9 | 8 | 9 | 10 | 9 | 10 | 10 | 9 | 8 | 9 | 10 |
| Speedwell | 7 | 6 | 4 | 10 | 0 | 0 | 8 | 0 | 5 | 6 | 10 | 9 | 9 | 10 | 8 | 8 | 8 | 4 | 6 | 6 | 3 | 9 | 0 | 10 | 9 | 9 | 10 | — | — | — | 10 | 10 | 9 | 10 | 9 | 8 | 10 |
| Sugar beet | 10 | 10 | 10 | 10 | 7 | 10 | 10 | 9 | 10 | 10 | 10 | 10 | 10 | 10 | 10 | 10 | 10 | 9 | 10 | 10 | 9 | 9 | 10 | 10 | 10 | 9 | 10 | 10 | 10 | 10 | 9 | 10 | 10 | 10 | 9 | 9 | 9 |
| Velvetleaf | 8 | 10 | 10 | 10 | 4 | 8 | 10 | 7 | 10 | 10 | 10 | 10 | 10 | 10 | 8 | 10 | 10 | 10 | 8 | 10 | 9 | 9 | 10 | 7 | 9 | 9 | 9 | 7 | 9 | 10 | 10 | 10 | 10 | 10 | 8 | 9 | 9 |
| Wheat | 9 | 9 | 9 | 10 | 6 | 9 | 9 | 9 | 7 | 9 | 9 | 9 | 5 | 6 | 4 | 9 | 9 | 2 | 3 | 2 | 8 | 8 | 5 | 9 | 6 | 6 | 7 | 9 | 9 | 5 | 9 | 9 | 8 | 5 | 6 | 4 | 4 |
| Wild buckwheat | — | 10 | 10 | 10 | 2 | 9 | 10 | 9 | 0 | 8 | 10 | 9 | 8 | 10 | 10 | 9 | 9 | 3 | 6 | 9 | 9 | 9 | 9 | 20 | 8 | 9 | 9 | 9 | 9 | 10 | 9 | 9 | 10 | 9 | 9 | 9 | 10 |
| Wild oat | 10 | 10 | 10 | 10 | 8 | 9 | 10 | 8 | 9 | 7 | 9 | 8 | 5 | 8 | 7 | 8 | 8 | 2 | 2 | 4 | 9 | 4 | 3 | 9 | 5 | 5 | 4 | 0 | 8 | 9 | 9 | 10 | 7 | 6 | 9 | 4 | 8 |
| Barnyardgrass | 8 | 8 | 7 | 9 | 0 | 8 | 8 | 8 | 9 | 9 | 9 | 9 | 8 | 8 | 7 | 9 | 10 | 8 | 9 | 9 | 9 | 9 | 9 | 8 | 9 | 9 | 9 | 4 | 7 | 9 | 9 | 9 | 8 | 8 | 8 | 9 | 8 |
| Rice Japonica | 8 | 8 | 8 | 9 | 2 | 8 | 8 | 7 | 8 | 9 | 9 | 9 | 8 | 9 | 9 | 8 | 9 | 9 | 9 | 9 | 9 | 9 | 9 | 9 | 9 | 8 | 8 | 6 | 6 | 9 | 9 | 9 | 9 | 8 | 8 | 7 | 7 |
| Umbrella sedge | 9 | 9 | 9 | 9 | 4 | 9 | 6 | 3 | 5 | 9 | 10 | 9 | 8 | 9 | 9 | 9 | 9 | 3 | 9 | 9 | 9 | 9 | 9 | 6 | 9 | 8 | 8 | 6 | 9 | 9 | 8 | 9 | 8 | 8 | 9 | 9 | 9 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (62 g/ha) | 117 | 118 | 119 | 120 | 121 | 122 | 125 | 166 | 167 | 170 | 172 | 173 | 203 | 208 | 209 | 211 | 212 | 213 | 214 | 217 | 218 | 219 | 225 | 229 | 230 | 231 | 232 | 252 |
| POSTEMERGENCE | | | | | | | | | | | | | | | | | | | | | | | | | | | | |
| Barley Igri | 4 | 5 | 10 | 9 | 10 | 10 | 0 | 9 | 9 | 9 | 9 | 9 | 9 | 9 | 0 | 10 | 9 | 7 | 8 | 9 | 8 | 7 | 9 | 9 | 9 | 9 | 9 | 9 |
| Bedstraw | 10 | — | 10 | 10 | 10 | 10 | 6 | 10 | 10 | — | 9 | 10 | 10 | 10 | 0 | 10 | 10 | 10 | 10 | 8 | 8 | 10 | 9 | 10 | 10 | 10 | 10 | 10 |
| Blackgrass | 9 | 9 | 10 | 10 | 10 | 10 | 8 | 9 | 9 | 9 | 10 | 10 | 9 | 10 | 5 | 10 | 9 | 8 | 9 | 9 | 8 | 8 | 8 | 10 | 9 | 9 | 10 | 10 |
| Chickweed | 10 | 3 | 10 | 10 | 10 | 10 | 9 | 10 | 10 | 10 | 9 | 9 | 10 | 9 | 0 | 10 | 8 | 20 | 10 | 9 | 10 | 10 | 10 | 10 | 10 | 10 | 10 | 7 |
| Corn | 5 | 5 | 10 | 10 | 10 | 10 | 5 | 10 | 10 | 10 | 9 | 9 | 10 | 10 | 4 | 10 | 10 | 10 | 10 | 10 | 10 | 10 | 10 | 9 | 9 | 10 | 10 | 10 |
| Cotton | 10 | 3 | 10 | 10 | 10 | 10 | 9 | 8 | 10 | 10 | 6 | 9 | 9 | 10 | 0 | 10 | 10 | 10 | 10 | 10 | 9 | 7 | 10 | 2 | — | 8 | 7 | 8 |
| Crabgrass | 0 | 0 | 8 | 7 | 9 | 7 | 0 | 8 | 8 | 10 | 8 | 9 | 10 | 10 | 0 | 7 | 7 | 8 | 5 | 8 | 6 | 4 | 9 | 6 | 4 | 9 | 9 | 7 |
| Downy brome | 0 | 0 | 10 | 9 | 9 | 9 | 0 | 9 | 9 | 9 | 9 | 9 | 10 | 9 | 0 | 10 | 9 | 8 | 8 | 9 | 8 | 7 | 10 | 9 | 9 | 9 | 10 | 10 |
| Duck salad | 6 | 5 | 9 | 9 | 9 | 9 | 4 | 9 | 9 | 9 | 7 | 5 | 9 | 10 | 0 | 10 | 9 | 9 | 10 | 9 | 8 | 6 | 8 | 8 | 8 | 0 | 0 | 6 |
| Giant foxtail | 3 | 0 | 10 | 10 | 10 | 7 | 2 | 9 | 9 | 10 | 9 | 9 | 7 | 10 | 5 | 10 | 10 | 10 | 7 | 9 | 8 | 6 | 10 | 8 | 7 | 9 | 9 | 9 |
| Lambsquarters | 5 | 3 | 10 | 10 | 10 | 10 | 10 | 10 | 10 | 10 | 9 | 9 | 10 | 10 | 0 | 10 | 10 | 10 | 10 | 10 | 10 | 10 | 10 | 10 | 10 | 10 | 10 | 9 |
| Morningglory | 10 | 9 | 20 | 10 | 10 | 10 | 10 | 10 | 10 | 10 | 9 | 10 | 10 | 10 | 4 | 10 | 10 | 10 | 10 | 10 | 10 | 10 | 9 | 9 | 10 | 9 | 10 | 10 |
| Pigweed | 8 | 7 | 10 | 10 | 10 | 10 | 8 | 10 | 10 | 10 | 9 | 9 | 10 | 10 | 0 | 10 | 7 | 10 | 10 | 10 | 20 | 10 | 10 | 10 | 9 | 10 | 10 | 8 |
| Rape | 10 | 10 | 10 | 10 | 10 | 10 | 9 | 10 | 10 | 10 | 6 | 9 | 10 | 10 | 0 | 9 | 10 | 10 | 10 | 10 | 9 | 9 | 10 | 8 | 9 | 10 | 9 | 10 |
| Ryegrass | 6 | 6 | 10 | 6 | 20 | 10 | 0 | 9 | 9 | 10 | 9 | 9 | 10 | 10 | 0 | — | 8 | 10 | 8 | 9 | 9 | 8 | 10 | 5 | 2 | 9 | 9 | 5 |
| Sorghum | 9 | 0 | 10 | 10 | 10 | 10 | 5 | 10 | 10 | 10 | 6 | 9 | 10 | 10 | 7 | 10 | 10 | 10 | 10 | 10 | 9 | 8 | 10 | 8 | 9 | 10 | 10 | 10 |
| Soybean | 9 | 1 | 10 | 10 | 20 | 10 | 9 | 9 | 10 | 10 | 9 | 9 | 10 | 9 | 0 | 10 | 10 | 10 | 10 | 9 | 10 | 10 | 10 | 9 | 9 | 10 | 9 | 8 |
| Speedwell | 10 | 9 | 10 | 8 | 10 | 0 | — | 9 | 5 | 9 | 10 | 8 | 7 | 8 | 0 | 9 | 3 | 10 | 9 | 7 | 3 | 5 | 7 | 9 | 0 | — | | 10 |
| Sugar beet | 9 | 5 | 10 | 10 | 10 | 10 | 10 | 10 | 10 | 10 | 9 | 9 | 10 | 10 | 0 | 10 | 8 | 10 | 10 | 9 | 10 | 10 | 10 | 8 | 8 | 10 | 10 | 8 |
| Velvetleaf | 9 | 4 | 10 | 10 | 10 | 9 | 9 | 9 | 10 | 10 | 9 | 8 | 10 | 10 | 0 | 10 | 10 | 10 | 7 | 10 | 10 | 9 | 10 | 9 | 10 | 9 | 8 | 8 |
| Wheat | 0 | 0 | 9 | 9 | 9 | 9 | 0 | 9 | 9 | 9 | 9 | 9 | 9 | 9 | 0 | 9 | 8 | 7 | 6 | 9 | 9 | 7 | 9 | 8 | 8 | 9 | 9 | 9 |
| Wild buckwheat | 9 | 9 | 10 | 10 | 8 | 10 | 9 | 9 | 9 | 9 | 9 | 10 | 9 | 10 | 0 | 9 | 9 | 10 | 10 | 9 | 9 | 9 | 10 | 9 | 9 | 9 | 9 | 10 |
| Wild oat | 5 | 3 | 9 | 6 | 9 | 9 | 0 | 9 | 9 | 9 | 9 | 9 | 9 | 9 | 0 | 9 | 8 | 7 | 7 | 9 | 9 | 7 | 8 | 9 | 9 | 9 | 9 | 9 |
| Barnyardgrass | 6 | 8 | 9 | 9 | 9 | 9 | 4 | 9 | 8 | 10 | 7 | 6 | 9 | 10 | 0 | 9 | 8 | 9 | 9 | 8 | 9 | 9 | 0 | 0 | 0 | 9 | 0 | 8 |
| Rice Japonica | 8 | 7 | 8 | 8 | 9 | 9 | 6 | 9 | 8 | 9 | 7 | 9 | 9 | 9 | 4 | 9 | 8 | 9 | 9 | 9 | 8 | 9 | 9 | 0 | 0 | 9 | 9 | 9 |
| Umbrella sedge | 9 | 8 | 9 | 9 | 9 | 9 | 9 | 10 | 9 | 9 | 8 | 8 | 9 | 9 | 0 | 10 | 9 | 9 | 9 | 9 | 9 | 9 | 9 | 0 | 6 | 6 | 5 | 8 |

TABLE B-continued

| Rate (62 g/ha) | 254 | 256 | 258 | 259 | 261 | 266 | 267 | 268 | 269 | 270 | 271 | 274 | 275 | 276 | 289 | 292 | 300 | 301 | 302 | 305 | 310 |
|---|---|---|---|---|---|---|---|---|---|---|---|---|---|---|---|---|---|---|---|---|---|
| | COMPOUND | | | | | | | | | | | | | | | | | | | | |
| POSTEMERGENCE | | | | | | | | | | | | | | | | | | | | | |
| Barley Igri | 8 | 9 | 10 | 9 | 10 | 9 | 9 | 9 | 9 | 10 | 10 | 9 | 9 | — | 10 | 7 | 10 | 10 | 10 | 9 | 9 |
| Bedstraw | 10 | 10 | 9 | 9 | 10 | 10 | 10 | 10 | 10 | 10 | 10 | 9 | 10 | 6 | 10 | 10 | 10 | 10 | 10 | 10 | 10 |
| Blackgrass | 9 | 9 | 9 | 9 | 10 | 10 | 10 | 10 | 10 | 10 | 10 | 9 | 10 | 9 | 10 | 10 | 10 | 10 | 10 | 10 | 10 |
| Chickweed | 10 | 10 | 10 | 9 | 9 | 6 | 10 | 10 | 2 | 8 | 10 | 0 | 10 | I | 10 | 9 | 10 | 10 | 10 | 10 | 7 |
| Corn | 9 | 10 | 10 | 10 | 10 | 10 | 10 | 10 | 9 | 10 | 10 | 10 | 10 | 8 | 10 | 10 | 9 | 10 | 10 | 10 | 9 |
| Cotton | 9 | 0 | 5 | 8 | 4 | 5 | 9 | 9 | 5 | 9 | 9 | 2 | 8 | 0 | 10 | 8 | 10 | 8 | 9 | 9 | 8 |
| Crabgrass | 0 | 9 | 10 | 7 | 10 | 0 | 4 | 3 | 0 | 10 | 10 | 5 | 10 | 3 | 8 | 9 | 9 | 9 | 10 | 10 | 4 |
| Downy brome | 8 | 9 | 9 | 10 | 9 | 9 | 10 | 10 | 9 | 10 | 10 | 9 | 9 | — | | 9 | 4 | 10 | 9 | 10 | 9 |
| Duck salad | 3 | 6 | 9 | 5 | 7 | 9 | 3 | 4 | 0 | 0 | 3 | 0 | 8 | 0 | 8 | 8 | 6 | 5 | 9 | 9 | 0 |
| Giant foxtail | 6 | 10 | 20 | 10 | 10 | 10 | 6 | 7 | 3 | 10 | 10 | 6 | 10 | 6 | 10 | 10 | 10 | 10 | 10 | 10 | 9 |
| Lambsquarters | 8 | 10 | 10 | 10 | 10 | 8 | 10 | 10 | 0 | 10 | 10 | 0 | 10 | 3 | 10 | 8 | 10 | 10 | 10 | 10 | 9 |
| Morningglory | 10 | 10 | 10 | 9 | 10 | 10 | 10 | 10 | 7 | 10 | 10 | 0 | 8 | 7 | 10 | 6 | 8 | 10 | 10 | 10 | 10 |
| Pigweed | 9 | 10 | 10 | 10 | 10 | 5 | 10 | 10 | 7 | 10 | 10 | 4 | 10 | 8 | 9 | 7 | 9 | 9 | 10 | 9 | 8 |
| Rape | 10 | 10 | 10 | 9 | 10 | 9 | 10 | 10 | 10 | 9 | 9 | 6 | 10 | 0 | 5 | 9 | 9 | 9 | 9 | 9 | 9 |
| Ryegrass | 9 | 10 | 9 | 10 | 10 | 2 | 20 | 10 | 5 | 9 | 10 | 9 | 10 | 2 | 8 | 7 | 10 | 9 | 10 | 9 | 9 |
| Sorghum | 9 | 10 | 10 | 10 | 10 | 10 | 10 | 10 | 8 | 10 | 10 | 9 | 10 | 8 | 10 | 10 | 9 | 10 | 10 | 10 | 9 |
| Soybean | 10 | 10 | 10 | 9 | 9 | 10 | 10 | 10 | 7 | 8 | 9 | 3 | 8 | 4 | 8 | 2 | 9 | 9 | 10 | 10 | 9 |
| Speedwell | 4 | 3 | 0 | 3 | 3 | 3 | 10 | 0 | 3 | 6 | 3 | 0 | 7 | 0 | 8 | 9 | 10 | 10 | 8 | 10 | 10 |
| Sugar beet | 9 | 9 | 9 | 10 | 10 | 6 | 10 | 10 | — | 9 | 9 | 7 | 9 | 5 | 10 | 9 | 9 | 10 | 10 | 10 | 10 |
| Velvetleaf | 5 | 10 | 10 | 8 | 9 | 10 | 9 | 7 | 4 | 9 | 10 | 3 | 7 | 4 | 7 | 7 | 8 | 7 | 10 | 8 | 9 |
| Wheat | 4 | 9 | 9 | 9 | 9 | 8 | 9 | 9 | 5 | 10 | 9 | 9 | 9 | — | 9 | 8 | 9 | 9 | 9 | 9 | 6 |
| Wild buckwheat | 10 | 9 | 9 | 9 | 10 | 9 | 10 | 9 | 10 | 10 | 10 | — | 10 | 0 | 9 | — | 9 | 9 | 9 | 8 | 9 |
| Wild oat | 9 | 9 | 9 | 9 | 9 | 9 | 9 | 10 | 5 | 10 | 9 | 9 | 9 | — | 9 | 8 | 10 | 10 | 10 | 9 | 9 |
| Barnyardgrass | 8 | 9 | 9 | 9 | 9 | 3 | 8 | 0 | 7 | 4 | 9 | 0 | 9 | 0 | 7 | 5 | 6 | 9 | 10 | 10 | 7 |
| Rice Japonica | 8 | 9 | 9 | 9 | 9 | 9 | 8 | 8 | 8 | 9 | 9 | 6 | 9 | 7 | 8 | 2 | 7 | 7 | 8 | 8 | 4 |
| Umbrella sedge | 8 | 9 | 9 | 5 | 9 | 4 | 5 | 5 | 7 | 10 | 9 | 3 | 9 | 0 | 8 | 3 | 9 | 9 | 9 | 8 | 3 |

| Rate (62 g/ha) | 1 | 2 | 3 | 5 | 7 | 11 | 13 | 14 | 35 | 50 | 51 | 53 | 58 | 59 | 60 | 63 | 64 | 71 | 77 | 78 | 81 | 82 | 83 | 84 | 86 | 68 | 89 | 102 | 103 | 108 | 109 | 110 | 111 | 112 | 114 | 115 | 116 |
|---|---|---|---|---|---|---|---|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | | | | | | | | | |
| PREEMERGENCE | | | | | | | | | | | | | | | | | | | | | | | | | | | | | | | | | | | | | |
| Barley Igri | 8 | 9 | 6 | 7 | 2 | 0 | 3 | 0 | 3 | 8 | 9 | 9 | 7 | 7 | 4 | 9 | 9 | 2 | 6 | 5 | 9 | 6 | 6 | 8 | 9 | 6 | 8 | 8 | 9 | 9 | 9 | 9 | 5 | 5 | 8 | 2 | 9 |
| Bedstraw | 10 | 10 | 10 | 10 | 0 | 9 | 9 | 8 | 10 | 10 | 10 | 10 | 10 | 10 | 10 | 9 | 9 | 9 | 6 | 8 | 8 | 9 | 9 | 7 | 9 | 9 | 9 | 9 | 9 | 10 | 10 | 10 | 10 | 10 | 9 | 9 | 9 |
| Blackgrass | 9 | 10 | 9 | 9 | 6 | 8 | 8 | 6 | 8 | 9 | 9 | 10 | 8 | 8 | 8 | 10 | 10 | 7 | 8 | 8 | 9 | 10 | 10 | 9 | 9 | 9 | 9 | 10 | 10 | 10 | 10 | 10 | 10 | 10 | 9 | 9 | 9 |
| Chickweed | 7 | 10 | 10 | 10 | 0 | 10 | 10 | 10 | 10 | 10 | 10 | 10 | 10 | 10 | 10 | 9 | 10 | 8 | 7 | 8 | 8 | 20 | 10 | 8 | 9 | 10 | 10 | 9 | 9 | 10 | 9 | 9 | 9 | 9 | 10 | 8 | 10 |
| Corn | 4 | 9 | 10 | 7 | 0 | 4 | 9 | 3 | 6 | 2 | 10 | 7 | 8 | 9 | 7 | 10 | 10 | 5 | 2 | e | — | — | — | 10 | 4 | 8 | 7 | 7 | 2 | 10 | 8 | 9 | 5 | 6 | 9 | 9 | 9 |
| Cotton | 4 | 4 | 7 | 8 | 0 | 4 | 9 | 3 | 7 | 8 | 10 | 9 | 5 | 9 | 9 | 9 | 9 | 9 | 4 | 8 | — | — | — | 9 | 9 | 9 | 7 | 4 | 9 | 10 | 9 | 10 | 8 | 9 | 6 | 5 | 9 |
| Crabgrass | 7 | 8 | 9 | 8 | 3 | 6 | 4 | 0 | 8 | 9 | 10 | 10 | 7 | 7 | 6 | 10 | 9 | 6 | 6 | 8 | — | — | — | 6 | 7 | 3 | 8 | 3 | 4 | 10 | 9 | 9 | 7 | 7 | 8 | 5 | 9 |
| Downy brome | 9 | 10 | 9 | 10 | 5 | 7 | 7 | 6 | 10 | 9 | 9 | 9 | 7 | 8 | 7 | 10 | 9 | 2 | 7 | 6 | 9 | 9 | 7 | 6 | 7 | 7 | 5 | 8 | 9 | 9 | 9 | 9 | 9 | 9 | 8 | 5 | 8 |
| Duck salad | — | — | — | — | — | — | — | — | — | — | — | — | — | — | — | — | — | — | — | — | — | — | — | — | — | — | — | — | — | — | — | — | — | — | — | — | — |
| Giant foxtail | 5 | 9 | 9 | 7 | 4 | 8 | 3 | 2 | 9 | 8 | 9 | 10 | 6 | 4 | 3 | 9 | 9 | 0 | 6 | 9 | — | — | — | 10 | 8 | 8 | 8 | 8 | 8 | 9 | 9 | 9 | 9 | 7 | 9 | 7 | 8 |
| Lambsquarters | 10 | 10 | 10 | 10 | 5 | 20 | 10 | 10 | 10 | 10 | 10 | 10 | 10 | 10 | 10 | 10 | 10 | 8 | 8 | 9 | 10 | 9 | 9 | 10 | 10 | 9 | 10 | 10 | 10 | 10 | 9 | 10 | 9 | 9 | 9 | 8 | 10 |
| Morningglory | 0 | 4 | 6 | 8 | 0 | 5 | 8 | 0 | 8 | 9 | 10 | 8 | 0 | 10 | 10 | 9 | 10 | 8 | 3 | 10 | — | — | — | 9 | 9 | 7 | 9 | 8 | 9 | 10 | 8 | 9 | 7 | 9 | 9 | 9 | 9 |
| Pigweed | 9 | 10 | 9 | 10 | 6 | 8 | 9 | 8 | 8 | 10 | 10 | 10 | 10 | 9 | 9 | 9 | 10 | 9 | 9 | 9 | — | — | — | 7 | 9 | 9 | 9 | 9 | 9 | 10 | 9 | 10 | 10 | 9 | 9 | 9 | 9 |

TABLE B-continued

| | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| Rape | 9 | 10 | 10 | 10 | 0 | 6 | 10 | 8 | 9 | 9 | 9 | 9 | 10 | 10 | 10 | 10 | 10 | 9 | 10 | 9 | 9 | 9 | 9 | 9 | 9 | 9 | 9 | 9 | 9 | 10 | 9 | 9 | 9 | 9 | 9 | 9 | 10 |
| Ryegrass | 9 | 6 | 3 | 10 | 3 | 8 | 7 | 4 | 10 | 9 | 9 | 10 | 8 | 10 | 8 | 10 | 10 | 6 | 5 | 8 | 9 | 6 | 9 | 9 | 1 | 6 | 8 | 1 | 2 | 10 | 10 | 9 | 8 | 9 | 9 | 5 | 9 |
| Sorghum | 9 | 9 | 9 | 9 | 6 | 9 | 9 | 6 | 9 | 9 | 10 | 9 | 10 | 10 | 8 | 9 | 10 | 7 | 8 | 10 | — | — | — | 9 | 10 | 9 | 9 | 9 | 9 | 10 | 9 | 9 | 10 | 10 | 9 | 9 | 9 |
| Soybean | 4 | 7 | 6 | 7 | 0 | 3 | 8 | 3 | 3 | 8 | 10 | 8 | 5 | 9 | 9 | 10 | 9 | 9 | 6 | 9 | — | — | — | 9 | 6 | 9 | 8 | 2 | 7 | 10 | 8 | 10 | 6 | 5 | 7 | 4 | 9 |
| Speedwell | 9 | 10 | 8 | 10 | 5 | 4 | 9 | 7 | 10 | 10 | 10 | 10 | 10 | 10 | 9 | 10 | 8 | 6 | 3 | 6 | 9 | 10 | 10 | 9 | 9 | 9 | 9 | 9 | 8 | 7 | 9 | 10 | 9 | 10 | 10 | 10 | 10 |
| Sugar beet | 9 | 10 | 10 | 10 | 0 | 9 | 9 | 9 | 10 | 9 | 9 | 9 | 10 | 10 | 10 | 10 | 10 | 9 | 9 | 9 | 9 | 9 | 9 | 9 | 9 | 9 | 9 | 9 | 9 | 10 | 10 | 9 | 9 | 9 | 9 | 9 | 9 |
| Velvetleaf | 7 | 9 | 7 | 9 | 3 | 8 | 8 | 0 | 8 | 9 | 9 | 9 | 8 | 10 | 8 | 9 | 9 | 9 | 7 | 8 | — | — | — | 8 | 8 | 7 | 9 | 7 | 9 | 9 | 9 | 10 | 9 | 10 | 9 | 8 | 9 |
| Wheat | 9 | 10 | 8 | 9 | 2 | 0 | 0 | 2 | 4 | 8 | 9 | 9 | 0 | 6 | 4 | 9 | 9 | 3 | 5 | 4 | 8 | 8 | 8 | 9 | 5 | 5 | 8 | 6 | 8 | 9 | 9 | 7 | 5 | 4 | 6 | 1 | 4 |
| Wild buckwheat | 10 | 10 | 10 | 10 | 0 | 7 | 8 | 8 | 9 | 9 | 9 | 9 | 8 | 9 | 8 | 9 | 8 | 6 | 8 | 8 | 9 | 9 | 9 | 6 | 9 | 9 | 9 | 9 | 9 | 9 | 9 | 9 | 20 | 9 | 9 | 9 | 9 |
| Wild oat | 4 | 7 | 5 | 4 | 2 | 0 | 0 | 0 | 5 | 7 | 9 | 9 | 4 | 6 | 7 | 7 | 8 | 0 | 2 | 3 | 8 | 5 | 7 | 9 | 3 | 0 | 3 | 4 | 7 | 9 | 9 | 9 | 0 | 5 | 7 | 3 | 8 |
| Barnyardgrass | — | — | — | — | — | — | — | — | — | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — | — | — | — | — | — | — | — | — | — |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (62 g/ha) | 117 | 118 | 119 | 120 | 121 | 122 | 125 | 166 | 167 | 170 | 172 | 173 | 203 | 208 | 209 | 211 | 212 | 213 | 214 | 217 | 218 | 219 | 225 | 229 | 230 | 231 | 232 | 252 |
| PREEMERGENCE | | | | | | | | | | | | | | | | | | | | | | | | | | | | |
| Barley Igri | 4 | 2 | 10 | 9 | 9 | 9 | 0 | 7 | 0 | 2 | 5 | 0 | 9 | 9 | 0 | 6 | 3 | 8 | 9 | 9 | 8 | 2 | 7 | 9 | 5 | 9 | 9 | 2 |
| Bedstraw | 9 | 9 | 9 | 9 | 10 | 10 | 8 | 9 | 9 | 10 | 8 | 8 | 8 | 10 | 3 | 10 | 10 | 10 | 10 | 9 | 9 | 10 | 9 | 9 | 9 | 10 | 10 | 9 |
| Blackgrass | 8 | 8 | 10 | 10 | 10 | 10 | 9 | 9 | 9 | 9 | 10 | 9 | 9 | 9 | 0 | 9 | 9 | 9 | 8 | 9 | 9 | 8 | 5 | 9 | 9 | 9 | 9 | 10 |
| Chickweed | 9 | 9 | 10 | 10 | 10 | 10 | 9 | 9 | 9 | 10 | 9 | 8 | 9 | 9 | 3 | 10 | 10 | 10 | 9 | 10 | 10 | 10 | 8 | 9 | 9 | 9 | 2 | 10 |
| Corn | 6 | 6 | 9 | 9 | 20 | 10 | 0 | 9 | 10 | 10 | 4 | 9 | 9 | 10 | 0 | 10 | 9 | 20 | 10 | 9 | 8 | 0 | 10 | 6 | 3 | 9 | 9 | 8 |
| Cotton | 10 | 5 | 10 | 8 | 10 | 10 | 3 | 7 | 3 | 9 | 6 | 8 | 8 | 8 | 0 | 8 | 6 | 10 | 10 | 7 | 7 | 10 | 9 | 3 | — | 9 | 8 | 3 |
| Crabgrass | 7 | 3 | 7 | 6 | 8 | 7 | 3 | 9 | 8 | 9 | 9 | 9 | 8 | 10 | 0 | 10 | 8 | 9 | 7 | 6 | 8 | 0 | 3 | 4 | 7 | 7 | 7 | 4 |
| Downy brome | 7 | 4 | 10 | 9 | 10 | 10 | 0 | 9 | 9 | 6 | 4 | 8 | 10 | 9 | 5 | 9 | 8 | 9 | 9 | 9 | 9 | 8 | — | 7 | 7 | 10 | 10 | 10 |
| Duck salad | — | — | — | — | — | — | — | — | — | — | — | — | — | — | — | — | — | — | — | — | — | — | — | — | — | — | — | — |
| Giant foxtail | 6 | 5 | 8 | 8 | 8 | 6 | 0 | 9 | 8 | 9 | 9 | 9 | 4 | 9 | 0 | 20 | 8 | 9 | 4 | 5 | 7 | 0 | 5 | 10 | 6 | 7 | 6 | 6 |
| Lambsquarters | 9 | 9 | 10 | 10 | 10 | 9 | 10 | 10 | 10 | 10 | 10 | 10 | 9 | 10 | 0 | 9 | 9 | 10 | 10 | 10 | 10 | 8 | — | 10 | 6 | 9 | 10 | 9 |
| Morningglory | 10 | 7 | 9 | 9 | 9 | 9 | 5 | 7 | 5 | 9 | 6 | 5 | 8 | 9 | 0 | 4 | 6 | 10 | 10 | 3 | 5 | 3 | 9 | 4 | 2 | 9 | 9 | 0 |
| Pigweed | 9 | 8 | 9 | 9 | 10 | 9 | 9 | 9 | 8 | 9 | 9 | 9 | 9 | 10 | 0 | 20 | 9 | 10 | 10 | 8 | 9 | 7 | 9 | 9 | 8 | 9 | 10 | 7 |
| Rape | 9 | 10 | 10 | 10 | 10 | 10 | 9 | 9 | 9 | 10 | 3 | 7 | 10 | 10 | 0 | 9 | 9 | 10 | 10 | 9 | 5 | 9 | 8 | 0 | 3 | 3 | 5 | 9 |
| Ryegrass | 8 | 8 | 10 | 9 | 10 | 10 | 2 | 9 | 9 | 9 | 5 | 9 | 9 | 10 | 3 | 8 | 4 | 9 | 7 | 8 | 6 | 7 | 0 | 2 | 0 | 9 | 8 | 5 |
| Sorghum | 9 | 5 | 9 | 9 | 10 | 10 | 0 | 9 | 9 | 9 | 6 | 9 | 10 | 10 | 3 | 10 | 9 | 10 | 10 | 10 | 9 | 4 | 9 | 9 | 9 | 10 | 9 | 9 |
| Soybean | 9 | 1 | 9 | 8 | 10 | 10 | 2 | 7 | 3 | 9 | 6 | 8 | 7 | 8 | 0 | 7 | 6 | 10 | 10 | 5 | 6 | 4 | 9 | 6 | 6 | 9 | 8 | 6 |
| Speedwell | 8 | 10 | 16 | 10 | 10 | 5 | 10 | 10 | 8 | 10 | 10 | 10 | 8 | 9 | 0 | 10 | 10 | 10 | 8 | 10 | 9 | 2 | — | 9 | 9 | 9 | 0 | 10 |
| Sugar beet | 9 | 9 | 10 | 10 | 10 | 10 | 9 | 10 | 10 | 10 | 10 | 9 | 9 | 9 | 4 | 9 | 9 | 10 | 10 | 9 | 9 | 10 | 8 | 8 | 5 | 9 | 9 | 8 |
| Velvetleaf | 9 | 7 | 9 | 9 | 10 | 9 | 7 | 8 | 7 | 9 | 6 | 7 | 9 | 10 | 0 | 8 | 5 | 10 | 7 | 8 | 8 | 5 | 9 | 9 | 4 | 9 | 5 | 5 |
| Wheat | 3 | 0 | 9 | 9 | 9 | 9 | 0 | 8 | 4 | 9 | 7 | 0 | 9 | 9 | 0 | 7 | 3 | 9 | 5 | 9 | 7 | 0 | 3 | 8 | 5 | 9 | 9 | 0 |
| Wild buckwheat | 9 | 10 | 10 | 10 | 10 | 10 | 9 | 7 | 9 | 8 | 10 | 10 | 9 | 9 | 3 | 9 | 9 | 9 | 9 | 8 | 9 | 9 | 9 | 8 | 9 | 9 | 8 | 9 |
| Wild oat | 7 | 3 | 9 | 6 | 9 | 9 | 0 | 5 | 5 | 5 | 4 | 0 | 6 | 7 | 0 | 5 | 2 | 7 | 6 | 7 | 5 | 4 | 4 | 6 | 2 | 9 | 8 | 2 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |

TABLE B-continued

| Rate (62 g/ha) | 254 | 256 | 258 | 259 | 261 | 266 | 267 | 268 | 269 | 270 | 271 | 274 | 275 | 276 | 289 | 292 | 300 | 301 | 302 | 305 | 310 |
|---|---|---|---|---|---|---|---|---|---|---|---|---|---|---|---|---|---|---|---|---|---|
| | COMPOUND | | | | | | | | | | | | | | | | | | | | |
| | PREEMERGENCE | | | | | | | | | | | | | | | | | | | | |
| Barley Igri | 7 | 9 | 8 | 6 | 9 | 3 | 9 | 9 | 0 | 9 | 9 | 2 | 10 | 0 | 5 | 0 | 4 | 5 | 9 | 9 | 0 |
| Bedstraw | 10 | 10 | 10 | 9 | 10 | 9 | 10 | 10 | 6 | 9 | 9 | 0 | 10 | 0 | 9 | 0 | 4 | 8 | 10 | 9 | 8 |
| Blackgrass | 9 | 10 | 10 | 10 | 10 | 10 | 10 | 10 | 9 | 10 | 10 | 9 | 10 | 5 | 9 | 0 | 9 | 9 | 10 | 10 | 9 |
| Chickweed | 10 | 6 | 10 | 9 | 9 | 8 | 10 | 10 | 0 | 0 | 10 | 0 | 10 | 3 | 9 | 5 | 7 | 9 | 10 | 10 | 9 |
| Corn | 10 | 9 | 10 | 10 | 9 | 7 | 10 | 9 | 0 | 9 | 7 | 0 | 10 | 0 | 6 | 0 | 5 | 2 | 3 | 7 | 4 |
| Cotton | 9 | 10 | 8 | 8 | 9 | 6 | 9 | 9 | 0 | 9 | 8 | 0 | 9 | 0 | 0 | 0 | 4 | 8 | 9 | 8 | 9 |
| Crabgrass | 6 | 8 | 9 | 8 | 9 | 5 | 7 | 6 | 1 | 9 | 9 | 3 | 10 | 0 | 2 | 2 | 5 | 7 | 9 | 7 | 0 |
| Downy brome | 9 | 10 | 10 | 10 | 10 | 9 | 10 | 10 | 3 | 10 | 10 | 9 | 10 | 0 | 7 | 0 | 8 | 9 | 10 | 9 | 0 |
| Duck salad | — | — | — | — | — | — | — | — | — | — | — | — | — | — | — | — | — | — | — | — | — |
| Giant foxtail | 6 | 8 | 9 | 9 | 9 | 4 | 6 | 6 | 0 | 9 | 9 | 5 | 9 | 3 | 7 | 0 | 8 | 7 | 9 | 9 | 0 |
| Lambsquarters | 8 | 10 | 10 | 10 | 10 | 9 | 10 | 9 | 9 | 9 | 10 | 0 | 10 | 0 | 0 | 0 | 9 | 10 | 10 | 10 | 10 |
| Morningglory | 9 | 9 | 7 | 5 | 9 | 8 | 9 | 9 | 0 | 3 | 9 | 0 | 5 | 0 | 0 | 0 | 7 | 7 | 9 | 7 | 7 |
| Pigweed | 9 | 8 | 9 | 9 | 10 | 7 | 9 | 9 | 7 | 9 | 9 | 5 | 9 | 3 | 9 | 0 | 9 | 9 | 9 | 9 | 8 |
| Rape | 10 | 9 | 9 | 9 | 9 | 7 | 9 | 9 | 2 | 9 | 8 | 0 | 9 | 0 | 1 | 0 | 6 | 6 | 10 | 4 | 3 |
| Ryegrass | 9 | 10 | 10 | 9 | 10 | 3 | 9 | 6 | 0 | 9 | 9 | 0 | 10 | 0 | 6 | 0 | 4 | 5 | 10 | 7 | 2 |
| Sorghum | 9 | 10 | 9 | 9 | 10 | 9 | 10 | 9 | 2 | 9 | 9 | 4 | 10 | 8 | 9 | 1 | 6 | 5 | 9 | 9 | 0 |
| Soybean | 9 | 8 | 7 | 6 | 7 | 6 | 8 | 8 | 0 | 3 | 4 | 0 | 6 | 0 | 0 | 0 | 3 | 3 | 6 | 5 | 5 |
| Speedwell | 9 | 9 | 7 | 8 | 9 | 9 | 10 | 8 | 9 | 9 | 9 | 0 | 10 | 6 | 10 | — | 8 | 10 | 10 | 10 | 10 |
| Sugar beet | 9 | 9 | 9 | 9 | 9 | 5 | 9 | 9 | — | 10 | 10 | 0 | 10 | 0 | 9 | 4 | 9 | 9 | 10 | 10 | 10 |
| Velvetleaf | 7 | 9 | 9 | 7 | 7 | 8 | 8 | 3 | 1 | 5 | 4 | 3 | 3 | 5 | 4 | 0 | 6 | 6 | 9 | 6 | 8 |
| Wheat | 0 | 9 | 8 | 9 | 8 | 3 | 9 | 6 | 0 | 9 | 9 | 7 | 10 | 0 | 1 | 0 | 6 | 6 | 9 | 5 | 0 |
| Wild buckwheat | 9 | 9 | 9 | 9 | 9 | 10 | 9 | 9 | 9 | 9 | 9 | — | 10 | 3 | 8 | 5 | 4 | 8 | 10 | 9 | 9 |
| Wild oat | 8 | 9 | 9 | 9 | 9 | 5 | 6 | 5 | 0 | 9 | 9 | 0 | 9 | 0 | 5 | 0 | 4 | 5 | 9 | 6 | 0 |
| Barnyardgrass | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — |

| Rate (31 g/ha) | 1 | 2 | 3 | 5 | 7 | 11 | 13 | 14 | 25 | 26 | 27 | 28 | 29 | 30 | 31 | 34 | 35 | 36 | 50 | 51 | 53 | 58 | 59 | 60 | 63 | 64 | 71 | 77 | 78 | 81 | 82 | 83 | 84 | 86 | 88 | 89 | 102 | 103 | 107 | 108 |
|---|---|---|---|---|---|---|---|---|---|---|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | | | | | | | | | | | | |
| | POSTEMERGENCE | | | | | | | | | | | | | | | | | | | | | | | | | | | | | | | | | | | | | | | |
| Barley Igri | 10 | 9 | 9 | 10 | 7 | 9 | 9 | 9 | 9 | 8 | 10 | 9 | 10 | 10 | 9 | 7 | 5 | 5 | 8 | 9 | 9 | 5 | 7 | 5 | 9 | 9 | 2 | 2 | 1 | 7 | 7 | 8 | 7 | 6 | 6 | 7 | 9 | 9 | 9 | 7 |
| Bedstraw | 10 | 10 | 10 | 10 | 3 | 8 | 9 | 8 | 10 | 10 | 10 | 10 | 10 | 10 | 7 | 8 | 10 | 10 | 8 | 10 | 9 | 10 | 10 | 10 | 7 | 9 | 7 | 5 | 7 | 6 | 9 | 10 | 9 | 10 | 10 | 10 | 9 | 9 | 10 | 10 |
| Blackgrass | 9 | 9 | 9 | 10 | 7 | 9 | 8 | 7 | 10 | 10 | 10 | 10 | 10 | 10 | 9 | 8 | 9 | 10 | 9 | 9 | 9 | 9 | 8 | 8 | 9 | 9 | 4 | 7 | 7 | 10 | 10 | 10 | 9 | 9 | 9 | 10 | 9 | 9 | 10 | 9 |
| Chickweed | 6 | 8 | 9 | 10 | 0 | 10 | 9 | 9 | 10 | 10 | 10 | 10 | 10 | 10 | 4 | 10 | 10 | 10 | 9 | 10 | 9 | 9 | 10 | 10 | 10 | 10 | 9 | 4 | 9 | 9 | 10 | 10 | 10 | 6 | 9 | 10 | 9 | 9 | 10 | 10 |
| Corn | 7 | 10 | 10 | 20 | 6 | 10 | 10 | 10 | 10 | 10 | 10 | 10 | 10 | 10 | 10 | 10 | 10 | 10 | 7 | 10 | 7 | 10 | 10 | 8 | 10 | 10 | 6 | 6 | 7 | 0 | 7 | 9 | 10 | 1 | 7 | 9 | 3 | 0 | 10 | 10 |
| Cotton | 6 | 7 | 8 | 7 | 4 | 8 | 7 | 9 | 5 | 7 | 10 | 20 | 10 | 10 | 6 | 6 | 7 | 8 | 10 | 10 | 10 | 9 | 10 | 10 | 9 | 9 | 10 | 6 | 7 | 7 | 9 | 9 | 9 | 8 | 8 | 9 | 7 | 8 | 20 | 20 |
| Crabgrass | 7 | 6 | 7 | 8 | 5 | 6 | 10 | 7 | 7 | 6 | 20 | 6 | 10 | 10 | 6 | 7 | 4 | 7 | 4 | 7 | 7 | 3 | 0 | 0 | 5 | 8 | 6 | 5 | 4 | 4 | 4 | 5 | 4 | 2 | 0 | 2 | 0 | 2 | 7 | 5 |
| Downy brome | 9 | 8 | 8 | 10 | 6 | 9 | 5 | 5 | 10 | 9 | 10 | 10 | 10 | 10 | 5 | 7 | 9 | 10 | 8 | 8 | 9 | 5 | 7 | 6 | 9 | 8 | 1 | 5 | 2 | 6 | 6 | 3 | 8 | 4 | 6 | 4 | 8 | 8 | 9 | 9 |
| Duck salad | — | — | — | — | — | — | — | — | — | — | — | — | — | — | — | — | — | — | 10 | 9 | 10 | 7 | 10 | 10 | 9 | 9 | 9 | 7 | 6 | 3 | 9 | 9 | 1 | 9 | 6 | 9 | 3 | 7 | 10 | 10 |
| Giant foxtail | 7 | 8 | 9 | 20 | 6 | 10 | 10 | 20 | 10 | 10 | 10 | 9 | 10 | 10 | 9 | 8 | 8 | 10 | 10 | 10 | 8 | 7 | 5 | 3 | 10 | 10 | 5 | 7 | 7 | 8 | 8 | 9 | 8 | 5 | 5 | 5 | 6 | 6 | 9 | 5 |
| Lambsquarters | 10 | 10 | 10 | 10 | — | 10 | 10 | 8 | 10 | 10 | 20 | 10 | 10 | 10 | 10 | 10 | 10 | 10 | 10 | 10 | 10 | 9 | 10 | 10 | 10 | 10 | 8 | 9 | 10 | 8 | 9 | 10 | 10 | 9 | 9 | 10 | 9 | 10 | 10 | 10 |
| Morningglory | 7 | 10 | 10 | 8 | 6 | 0 | 8 | 9 | 10 | 10 | 10 | 10 | 10 | 10 | 8 | 8 | 10 | 10 | 10 | 10 | 20 | 10 | 10 | 10 | 10 | 10 | 10 | 9 | 10 | 9 | 10 | 10 | 8 | 9 | 10 | 10 | 9 | 9 | 10 | 10 |
| Pigweed | 6 | 6 | 6 | 10 | 3 | 8 | 9 | 3 | 10 | 10 | 10 | 10 | 10 | 10 | 7 | 8 | 8 | 10 | 10 | 10 | 10 | 10 | 10 | 10 | 10 | 10 | 10 | 9 | 10 | 9 | 10 | 10 | 9 | 8 | 7 | 5 | 8 | 10 | 10 | 10 |

TABLE B-continued

| | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| Rape | 6 | 8 | 10 | 10 | 0 | 10 | 10 | 10 | 9 | 10 | 10 | 10 | 10 | 10 | 0 | 5 | 4 | 10 | 10 | 10 | 10 | 10 | 10 | 10 | 10 | 10 | 7 | 8 | 9 | 9 | 10 | 10 | 10 | 10 | 10 | 10 | 9 | 9 | 10 | 10 |
| Ryegrass | 10 | 9 | 4 | 10 | 4 | 9 | 8 | 5 | 10 | 10 | 10 | 10 | 10 | 10 | 9 | 9 | 9 | 10 | 9 | 10 | 9 | 5 | 9 | 8 | 8 | 9 | 3 | 4 | 4 | 5 | 5 | 5 | 8 | 4 | 6 | 4 | 5 | 3 | 10 | 10 |
| Sorghum | 7 | 10 | 10 | 10 | 7 | 10 | 10 | 10 | 10 | 10 | 10 | 10 | 10 | 10 | 10 | 7 | 10 | 10 | 7 | 10 | 6 | 7 | 7 | 7 | 10 | 10 | 6 | 8 | 10 | 10 | 10 | 10 | 10 | 9 | 8 | 9 | 9 | 10 | 10 | 10 |
| Soybean | 7 | 10 | 10 | 10 | 3 | 8 | 10 | 10 | 10 | 10 | 10 | 10 | 10 | 10 | 10 | 10 | 10 | 10 | 10 | 10 | 10 | 10 | 10 | 10 | 10 | 10 | 9 | 9 | 9 | 8 | 9 | 9 | 9 | 8 | 9 | 9 | 7 | 9 | 10 | 10 |
| Speedwell | 5 | 6 | 4 | 9 | 0 | 0 | 6 | 0 | 8 | 6 | 6 | 9 | 9 | 0 | 0 | 0 | 5 | 8 | 6 | 10 | 8 | 9 | 10 | 8 | — | 4 | 1 | 4 | 6 | 3 | 6 | 0 | 10 | 7 | 9 | 9 | — | — | — | — |
| Sugar beet | 10 | 10 | 10 | 10 | 6 | 10 | 10 | 9 | 10 | 10 | 10 | 10 | 10 | 10 | 10 | 10 | 10 | 10 | 10 | 10 | 10 | 9 | 10 | 10 | 10 | 10 | 9 | 10 | 10 | 9 | 9 | 10 | 10 | 9 | 9 | 9 | 9 | 10 | 10 | 10 |
| Velvetleaf | 7 | 8 | 10 | 9 | 4 | 8 | 9 | 6 | 7 | 9 | 10 | 10 | 10 | 10 | 7 | 6 | 7 | 10 | 10 | 10 | 10 | 10 | 10 | 7 | 10 | 10 | 9 | 8 | 10 | 8 | 9 | 10 | 7 | 8 | 7 | 8 | 4 | 9 | 10 | 8 |
| Wheat | 7 | 8 | 8 | 10 | 5 | 9 | 9 | 9 | 9 | 9 | 10 | 9 | 10 | 10 | 8 | 6 | 7 | 8 | 9 | 9 | 9 | 4 | 5 | 2 | 9 | 9 | 0 | 2 | 1 | 4 | 4 | 3 | 9 | 4 | 5 | 6 | 9 | 9 | 9 | 4 |
| Wild buckwheat | 10 | 7 | 9 | 10 | 0 | 9 | 5 | 7 | 10 | 7 | 10 | 10 | 10 | 10 | 6 | 0 | 0 | 5 | 7 | 10 | 8 | 8 | 10 | 10 | 9 | 9 | 0 | 4 | 8 | 9 | 8 | 9 | 9 | 8 | 9 | 9 | 9 | 9 | 10 | 10 |
| Wild oat | 10 | 10 | 9 | 9 | 5 | 9 | 7 | 6 | 10 | 9 | 9 | 9 | 9 | — | 9 | 8 | 9 | 9 | 7 | 9 | 7 | 4 | 7 | 5 | 7 | 7 | 0 | 0 | 2 | 7 | 4 | 2 | 9 | 3 | 4 | 2 | 8 | 8 | 9 | 9 |
| Barnyardgrass | 2 | 6 | 5 | 8 | 0 | 7 | 8 | 7 | 8 | 8 | 8 | 9 | 10 | 8 | 3 | 2 | 8 | 9 | 8 | 9 | 9 | 8 | 8 | 7 | 9 | 9 | 8 | 6 | 8 | 8 | 9 | 9 | 3 | 9 | 8 | 8 | 2 | 6 | 8 | 9 |
| Rice Japonica | 8 | 8 | 8 | 9 | 0 | 8 | 8 | 7 | 7 | 8 | 8 | 8 | 9 | 8 | 6 | 8 | 8 | 8 | 0 | 9 | 9 | 8 | 9 | 9 | 8 | 9 | 8 | 7 | 9 | 8 | 9 | 9 | 8 | 8 | 7 | 6 | 3 | 3 | 9 | 9 |
| Umbrella sedge | 8 | 9 | 9 | 8 | 4 | 8 | 4 | 2 | 9 | 9 | 9 | 10 | 9 | 8 | 8 | 2 | 3 | 8 | 9 | 10 | 9 | 8 | 9 | 9 | 9 | 9 | 3 | 9 | 9 | 8 | 8 | 9 | 4 | 8 | 6 | 7 | 3 | 9 | 9 | 8 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (31 g/ha) | 109 | 110 | 111 | 112 | 114 | 115 | 116 | 117 | 118 | 119 | 120 | 121 | 122 | 125 | 166 | 167 | 170 | 172 | 173 | 203 | 204 | 205 | 206 | 207 | 208 | 209 | 211 | 212 |
| POSTEMERGENCE | | | | | | | | | | | | | | | | | | | | | | | | | | | | |
| Barley Igri | 10 | 10 | 9 | 8 | 6 | 4 | 6 | 3 | 3 | 10 | 8 | 10 | 10 | 0 | 9 | 9 | 8 | 9 | 9 | 9 | 10 | 10 | 10 | 9 | 9 | 0 | 10 | 9 |
| Bedstraw | 9 | 10 | 10 | 10 | 10 | 10 | 10 | 10 | 9 | 9 | 10 | 10 | 10 | 3 | 9 | 10 | 10 | 9 | 10 | 9 | 9 | 10 | 10 | 10 | 10 | 0 | 9 | 10 |
| Blackgrass | 10 | 10 | 10 | 10 | 9 | 9 | 9 | 8 | 9 | 10 | 10 | 9 | 10 | 6 | 9 | 9 | 9 | 10 | 10 | 9 | 10 | 10 | 10 | 10 | 10 | 5 | 10 | 9 |
| Chickweed | 10 | 10 | 10 | 9 | 9 | 5 | 10 | 10 | 3 | 10 | 10 | 10 | 10 | 7 | 10 | 10 | 10 | 8 | 8 | 9 | 10 | 10 | 10 | 10 | 9 | 0 | 9 | 7 |
| Corn | 9 | 10 | 10 | 8 | 9 | 9 | 8 | 4 | 3 | 10 | 10 | 10 | 10 | 4 | 10 | 10 | 10 | 9 | 9 | 10 | 10 | 10 | 10 | 10 | 10 | 3 | 10 | 10 |
| Cotton | 9 | 9 | 10 | 8 | 8 | 9 | 9 | 9 | 3 | 10 | 10 | 10 | 10 | 8 | 8 | 8 | 10 | 5 | 9 | 9 | 5 | 8 | 8 | 6 | 9 | 0 | 9 | 9 |
| Crabgrass | 6 | 9 | 0 | 2 | 0 | 0 | 2 | 0 | 0 | 7 | 4 | 7 | 5 | 0 | 7 | 4 | 10 | 8 | 9 | 10 | 10 | 10 | 10 | 10 | 10 | 0 | 6 | 6 |
| Downy brome | 9 | 10 | 9 | 6 | 6 | 0 | 7 | 0 | 0 | 10 | 9 | 9 | 9 | 0 | 8 | 9 | 8 | 9 | 9 | 10 | 10 | 20 | 10 | 10 | 9 | 0 | 10 | 9 |
| Duck salad | 9 | 10 | 8 | 9 | 4 | 4 | 7 | 5 | 4 | 9 | 9 | 9 | 9 | 3 | 9 | 7 | 9 | 5 | 4 | 9 | 9 | 20 | 9 | 10 | 10 | 0 | 10 | 9 |
| Giant foxtail | 9 | 9 | 8 | 4 | 8 | 5 | 6 | 2 | 0 | 9 | 9 | 10 | 4 | 0 | 9 | 7 | 10 | 9 | 9 | 6 | 10 | 10 | 10 | 10 | 10 | 5 | 10 | 9 |
| Lambsquarters | 10 | 10 | 10 | 10 | 8 | 5 | 7 | 5 | 0 | 10 | 10 | 10 | 10 | 10 | 10 | 10 | 10 | 9 | 9 | 10 | 10 | 10 | 10 | 10 | 10 | 0 | 10 | 10 |
| Morningglory | 7 | 10 | 10 | 10 | 8 | 10 | 10 | 10 | 9 | 10 | 10 | 10 | 10 | 10 | 9 | 10 | 10 | 9 | 10 | 10 | 10 | 10 | 9 | 8 | 10 | 3 | 10 | 10 |
| Pigweed | 10 | 10 | 10 | 10 | 7 | 6 | 9 | 8 | 0 | 10 | 10 | 10 | 10 | 8 | 10 | 8 | 10 | 9 | 9 | 10 | 10 | 10 | 10 | 9 | 10 | 0 | 10 | 7 |
| Rape | 10 | 10 | 10 | 10 | 9 | 9 | 10 | 9 | 10 | 10 | 10 | 10 | 10 | 9 | 10 | 10 | 10 | 5 | 9 | 10 | 10 | 10 | 10 | 9 | 10 | 0 | 9 | 9 |
| Ryegrass | 10 | 10 | 9 | 7 | 8 | 5 | 9 | 6 | 5 | 10 | 5 | 10 | 10 | 0 | 9 | 9 | 9 | 9 | 9 | 10 | 10 | 10 | 10 | — | 10 | 0 | 9 | 7 |
| Sorghum | 9 | 10 | 10 | 9 | 8 | 9 | 9 | 9 | 0 | 10 | 10 | 10 | 9 | 4 | 10 | 10 | 10 | 6 | 9 | 10 | 10 | 10 | 10 | 10 | 10 | 6 | 9 | 10 |
| Soybean | 8 | 10 | 10 | 9 | 8 | 9 | 9 | 9 | 0 | 10 | 10 | 10 | 10 | 8 | 9 | 10 | 10 | 9 | 9 | 8 | 10 | 10 | 10 | 10 | 8 | 0 | 10 | 9 |
| Speedwell | 10 | 10 | — | 10 | 9 | 5 | 10 | 9 | — | 9 | 0 | 10 | — | 0 | 8 | 5 | 9 | 9 | 6 | 7 | 8 | 4 | 9 | 0 | 7 | 0 | 8 | 1 |
| Sugar beet | 9 | 10 | 10 | 10 | 6 | 8 | 9 | 9 | 5 | 10 | 10 | 10 | 10 | 10 | 10 | 10 | 10 | 9 | 9 | 10 | 10 | 10 | 10 | 10 | 10 | 0 | 8 | 8 |
| Velvetleaf | 10 | 10 | 10 | 10 | 8 | 9 | 9 | 9 | 4 | 10 | 10 | 10 | 8 | 9 | 9 | 9 | 10 | 8 | 8 | 10 | 10 | 10 | 9 | 8 | 10 | 0 | 10 | 10 |
| Wheat | 9 | 9 | 8 | 5 | 5 | 4 | 2 | 0 | 0 | 9 | 8 | 9 | 9 | 0 | 9 | 9 | 9 | 9 | 9 | 9 | 9 | 9 | 9 | 9 | 9 | 0 | 9 | 8 |
| Wild buckwheat | — | 9 | 9 | 9 | 9 | — | 9 | 9 | — | 10 | 10 | 8 | 9 | 8 | 8 | 9 | 9 | 9 | 9 | 9 | 9 | 10 | 10 | 9 | 9 | 0 | 8 | 9 |
| Wild oat | 9 | 10 | 7 | 6 | 6 | 4 | 8 | 5 | 3 | 9 | 6 | 9 | 9 | 0 | 9 | 9 | 9 | 9 | 9 | 9 | 10 | 10 | 9 | 9 | 8 | 0 | 8 | 7 |
| Barnyardgrass | 9 | 9 | 8 | 8 | 8 | 9 | 8 | 5 | 7 | 9 | 8 | 9 | 8 | 3 | 8 | 0 | 9 | 3 | 4 | 5 | 9 | 9 | 9 | 9 | 10 | 0 | 9 | 8 |
| Rice Japonica | 9 | 9 | 8 | 8 | 8 | 7 | 7 | 8 | 6 | 8 | 8 | 9 | 8 | 3 | 8 | 6 | 9 | 3 | 9 | 9 | 9 | 9 | 9 | 9 | 9 | 3 | 9 | 8 |
| Umbrella sedge | 8 | 9 | 8 | 8 | 8 | 9 | 9 | 9 | 8 | 9 | 8 | 9 | 9 | 9 | 10 | 9 | 8 | 7 | 8 | 9 | 9 | 9 | 9 | 9 | 9 | 0 | 9 | 9 |

TABLE B-continued

| Rate (31 g/ha) | 213 | 214 | 217 | 218 | 219 | 225 | 229 | 230 | 231 | 232 | 240 | 241 | 242 | 243 | 244 | 245 | 252 | 254 | 256 | 258 | 259 | 261 | 266 | 267 | 268 | 269 | 270 | 271 |
|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | |
| | POSTEMERGENCE | | | | | | | | | | | | | | | | | | | | | | | | | | | |
| Barley Igri | 6 | 6 | 9 | 8 | 6 | 9 | 9 | 9 | 9 | 8 | 10 | 10 | 10 | 10 | 10 | 10 | 9 | 7 | 9 | 9 | 9 | 10 | 9 | 9 | 9 | 8 | — | 10 |
| Bedstraw | 10 | 10 | 7 | 8 | 10 | 8 | 10 | 9 | 10 | 10 | 10 | 10 | 10 | 10 | 10 | 10 | 10 | 10 | 10 | 9 | 9 | 10 | 10 | 10 | 10 | 9 | 10 | 10 |
| Blackgrass | 8 | 8 | 9 | 7 | 7 | 7 | 10 | 9 | 9 | 10 | 10 | 10 | 10 | 10 | 10 | 10 | 10 | 9 | 9 | 9 | 9 | 9 | 10 | 10 | 10 | 9 | 10 | 10 |
| Chickweed | 10 | 10 | 8 | 10 | 10 | 10 | 9 | 9 | 10 | 10 | 10 | 10 | 10 | 10 | 10 | 5 | 5 | 10 | 8 | 10 | 8 | 9 | 3 | 9 | 10 | 0 | 7 | 10 |
| Corn | 10 | 10 | 10 | 9 | 10 | 10 | 9 | 9 | 10 | 10 | 10 | 10 | 10 | 10 | 10 | 10 | 10 | 9 | 10 | 10 | 10 | 20 | 10 | 10 | 10 | 9 | 10 | 10 |
| Cotton | 10 | 10 | 6 | 7 | 7 | 8 | 0 | 1 | 8 | 6 | 9 | 9 | 10 | 10 | 10 | 8 | 7 | 8 | 0 | 3 | 7 | 4 | 4 | 8 | 8 | 5 | 9 | 8 |
| Crabgrass | 6 | 4 | 7 | 4 | 3 | 8 | 4 | 1 | 7 | 7 | 9 | 9 | 10 | 10 | 10 | 9 | 7 | 0 | 9 | 10 | 4 | 7 | 0 | 3 | 2 | 0 | 10 | 10 |
| Downy brome | 8 | 7 | 9 | 7 | 6 | 9 | 9 | 8 | 9 | 10 | 10 | 10 | 10 | 10 | 10 | 9 | 10, | 8 | 9 | 9 | 10 | 9 | 9 | 20 | 10 | 8 | 8 | 10 |
| Duck salad | 9 | 9 | 6 | 4 | 0 | 2 | 4 | 6 | 0 | 0 | 7 | 8 | 9 | 8 | 8 | 9 | 0 | 3 | 3 | 6 | 4 | 4 | 8 | 3 | 3 | 0 | 0 | 0 |
| Giant foxtail | 8 | 6 | 8 | 6 | 3 | 10 | 8 | 7 | 7 | 7 | 9 | 10 | 10 | 10 | 10 | 10 | 9 | 5 | 10 | 10 | 10 | 10 | 10 | 5 | 5 | 2 | 10 | 10 |
| Lambsquarters | 10 | 10 | 10 | 10 | 10 | 10 | 10 | 0 | 10 | 10 | 10 | 10 | 10 | 10 | 9 | 9 | 4 | 2 | 10 | 10 | 10 | 10 | 8 | 20 | 0 | 0 | — | 0 |
| Morningglory | 10 | 10 | 10 | 10 | 10 | 9 | 9 | 0 | 9 | 8 | 10 | 10 | 10 | 10 | 10 | 10 | 10 | 10 | 10 | 10 | 8 | 10 | 18 | 10 | 10 | 5 | 9 | 10 |
| Pigweed | 10 | 10 | 10 | 7 | 9 | 10 | 8 | 9 | 10 | 8 | 10 | 10 | 10 | 10 | 10 | 10 | 8 | 9 | 10 | 10 | 10 | 9 | 3 | 10 | 9 | 7 | 10 | 10 |
| Rape | 10 | 10 | 9 | 9 | 9 | 10 | 8 | 9 | 9 | 7 | 10 | 10 | 10 | 10 | 10 | 10 | 9 | 10 | 10 | 10 | 9 | 10 | 9 | 10 | 9 | 9 | 9 | 9 |
| Ryegrass | 10 | 7 | 9 | 7 | 8 | 9 | 5 | 0 | 9 | 9 | 10 | 10 | 10 | 10 | 10 | 10 | 5 | 7 | 10 | 9 | 10 | 10 | 0 | 10 | 10 | 5 | 8 | 10 |
| Sorghum | 10 | 10 | 10 | 8 | 7 | 10 | 8 | 8 | 10 | 10 | 10 | 10 | 10 | 10 | 10 | 10 | 10 | 8 | 10 | 10 | 10 | 10 | 10 | 10 | 10 | 8 | 10 | 10 |
| Soybean | 10 | 10 | 8 | 10 | 10 | 10 | 9 | 8 | 9 | 9 | 9 | 10 | 9 | 9 | 9 | 10 | 8 | 10 | 7 | 10 | 9 | 8 | 10 | 10 | 10 | 5 | 7 | 8 |
| Speedwell | 10 | 7 | 3 | 0 | 3 | 6 | 6 | 0 | — | 10 | 4 | 4 | 9 | 10 | 0 | 8 | 5 | 3 | 2 | 0 | 2 | 2 | 2 | 20 | 0 | 0 | 5 | 0 |
| Sugar beet | 10 | 10 | 9 | 9 | 10 | 10 | 8 | 8 | 9 | 9 | 10 | 10 | 10 | 10 | 10 | 10 | 8 | 9 | 8 | 9 | 9 | 9 | 6 | 10 | 10 | 2 | 9 | 9 |
| Velvetleaf | 9 | 6 | 10 | 8 | 8 | 10 | 9 | 0 | 9 | 7 | 8 | 8 | 10 | 10 | 10 | 9 | 7 | 4 | 9 | 10 | 7 | 5 | 10 | 8 | 6 | 2 | 9 | 7 |
| Wheat | 6 | 4 | 9 | 9 | 6 | 7 | 8 | 6 | 9 | 9 | 9 | 9 | 10 | 10 | 9 | 9 | 9 | 3 | 8 | 9 | 9 | 8 | 8 | 9 | 8 | 4 | 9 | 9 |
| Wild buckwheat | 10 | 10 | 8 | 8 | 8 | 10 | 9 | 9 | 9 | 9 | 10 | 10 | — | 9 | — | 10 | 10 | 10 | 9 | 9 | 8 | 10 | 9 | 9 | 9 | 10 | 10 | 10 |
| Wild oat | 7 | 6 | 9 | 7 | 6 | 7 | 9 | 9 | 9 | 9 | 10 | 10 | 10 | 10 | 10 | 9 | 7 | 9 | 9 | 9 | 9 | 8 | 9 | 9 | 9 | 5 | 9 | 9 |
| Barnyardgrass | 9 | 8 | a | 8 | 8 | 5 | 0 | 0 | 6 | 0 | 7 | 7 | 9 | 9 | 9 | 9 | 3 | 7 | 6 | 9 | 9 | 9 | 0 | 3 | 0 | 6 | 0 | 3 |
| Rice Japonica | 9 | 9 | 8 | 8 | 8 | 8 | 0 | 0 | 8 | 8 | 9 | 9 | 9 | 9 | 9 | 8 | 8 | 8 | 9 | 9 | 8 | 9 | 1 | 8 | 8 | 6 | 9 | 8 |
| Umbrella sedge | 9 | 9 | 9 | 9 | 9 | 9 | 0 | 3 | 4 | 0 | 9 | 9 | 9 | 8 | 9 | 9 | 8 | 7 | 9 | 9 | 5 | 9 | 3 | 5 | 4 | 2 | 9 | 9 |

| Rate (31 g/ha) | 272 | 274 | 275 | 276 | 283 | 284 | 285 | 286 | 287 | 288 | 289 | 291 | 292 | 300 | 301 | 302 | 305 | 310 |
|---|---|---|---|---|---|---|---|---|---|---|---|---|---|---|---|---|---|---|
| | COMPOUND | | | | | | | | | | | | | | | | | |
| | POSTEMERGENCE | | | | | | | | | | | | | | | | | |
| Barley Igri | 9 | 3 | 9 | 7 | 10 | 10 | 10 | 10 | 10 | 20 | 9 | 10 | 5 | 10 | 10 | 10 | 9 | 9 |
| Bedstraw | 10 | 2 | 10 | 6 | 10 | 10 | 10 | 10 | 10 | 10 | 10 | 10 | 8 | 10 | 10 | 10 | 10 | 10 |
| Blackgrass | 10 | 9 | 10 | 9 | 10 | 10 | 10 | 10 | 10 | 10 | 10 | 10 | 9 | 10 | 20 | 10 | 10 | 9 |
| Chickweed | 10 | 0 | 10 | 1 | 10 | 10 | 10 | 10 | 10 | 10 | 10 | 10 | 8 | 10 | 10 | 10 | 10 | 6 |
| Corn | 10 | 9 | 10 | 8 | 10 | 10 | 10 | 10 | 10 | 10 | 10 | 10 | 10 | 9 | 10 | 10 | 10 | 9 |
| Cotton | 6 | 0 | 7 | 0 | 10 | 10 | 10 | 20 | 10 | 7 | 8 | 8 | 7 | 7 | 7 | 9 | 8 | 7 |
| Crabgrass | 9 | 5 | 10 | 2 | 9 | 8 | 8 | 10 | 10 | 7 | 8 | 10 | 5 | 9 | 8 | 10 | 10 | 4 |
| Downy brome | 9 | 6 | 9 | — | 10 | 10 | 10 | 10 | 10 | 9 | 9 | 10 | 3 | 10 | 9 | 10 | 9 | 9 |
| Duck salad | 0 | 0 | 7 | 0 | 9 | 9 | 8 | 9 | 9 | 9 | 7 | 8 | 2 | 5 | 4 | 8 | 7 | 0 |
| Giant foxtail | 10 | 5 | 10 | 5 | 10 | 10 | 10 | 10 | 10 | 10 | 9 | 10 | 7 | 10 | 10 | 10 | 10 | 9 |
| Lambsquarters | 10 | 0 | 9 | 0 | 10 | 10 | 10 | 10 | 10 | 10 | 9 | 10 | 8 | 10 | 10 | 10 | 10 | 9 |
| Morningglory | 10 | 0 | 7 | 7 | 9 | 10 | 10 | 10 | 10 | 10 | 9 | 9 | 5 | 7 | 9 | 10 | 10 | 10 |
| Pigweed | 10 | 4 | 10 | 7 | 10 | 10 | 10 | 10 | 10 | 9 | 9 | 10 | 7 | 8 | 9 | 10 | 8 | 7 |

TABLE B-continued

| | | | | | | | | | | | | | | | | | | |
|---|---|---|---|---|---|---|---|---|---|---|---|---|---|---|---|---|---|---|
| Rape | 9 | 0 | 9 | 0 | 10 | 10 | 10 | 10 | 10 | 10 | 3 | 10 | 9 | 9 | 9 | 9 | 9 | 9 |
| Ryegrass | 10 | 0 | 10 | 2 | 10 | 8 | 4 | 10 | 10 | 7 | 6 | 10 | 5 | 10 | 9 | 10 | 9 | 7 |
| Sorghum | 10 | 9 | 10 | 8 | 10 | 10 | 10 | 10 | 10 | 10 | 10 | 10 | 10 | 9 | 10 | 10 | 10 | 9 |
| Soybean | 7 | 2 | 7 | 3 | 9 | 10 | 10 | 10 | 10 | 10 | 8 | 9 | 1 | 9 | 9 | 10 | 9 | 9 |
| Speedwell | 0 | 0 | 6 | 0 | 8 | 8 | 0 | 10 | 2 | 10 | 6 | 0 | 8 | 10 | 10 | 6 | 10 | 10 |
| Sugar beet | 9 | 5 | 9 | 2 | 9 | 9 | 9 | 10 | 10 | 10 | 9 | 9 | 9 | 9 | 10 | 10 | 20 | 10 |
| Velvetleaf | 9 | 0 | 6 | 4 | 9 | 10 | 10 | 10 | 7 | 10 | 6 | 8 | 5 | 6 | 7 | 9 | 7 | 9 |
| Wheat | 9 | 6 | 9 | 5 | 9 | 9 | 9 | 10 | 9 | 9 | 9 | 9 | 6 | 9 | 9 | 9 | 9 | 5 |
| Wild buckwheat | — | 6 | 10 | — | 10 | 10 | 10 | 10 | 10 | 10 | — | — | — | 9 | 8 | 9 | — | — |
| Wild oat | 9 | 4 | 9 | — | 10 | 9 | 9 | 9 | 10 | 9 | 8 | 9 | 5 | 10 | 10 | 10 | 8 | 9 |
| Barnyardgrass | 5 | 0 | 9 | 0 | 9 | 7 | 5 | 9 | 9 | 9 | 3 | 8 | 3 | 5 | 9 | 10 | 9 | 3 |
| Rice Japonica | 8 | 3 | 9 | 3 | 9 | 8 | 7 | 9 | 9 | 8 | 0 | 8 | 2 | 6 | 6 | 8 | 8 | 2 |
| Umbrella sedge | 9 | 0 | 9 | 0 | 9 | 9 | 9 | 9 | 9 | 9 | 8 | 9 | 0 | 9 | 7 | 9 | 7 | 2 |

COMPOUND

PREEMERGENCE

| Rate (31 g/ha) | 1 | 2 | 3 | 5 | 7 | 11 | 13 | 14 | 25 | 26 | 27 | 28 | 29 | 30 | 31 | 34 | 35 | 36 | 50 | 51 | 53 | 58 | 59 | 60 | 63 | 64 | 71 | 77 | 78 | 81 | 82 | 83 | 84 | 86 | 88 | 89 | 102 | 103 | 107 | 108 |
|---|---|---|---|---|---|---|---|---|---|---|---|---|---|---|---|---|---|---|---|---|---|---|---|---|---|---|---|---|---|---|---|---|---|---|---|---|---|---|---|---|
| Barley Igri | 5 | 7 | 6 | 6 | 0 | 0 | 0 | 0 | 2 | 1 | 2 | 2 | 2 | 0 | 2 | 0 | 0 | 2 | 6 | 9 | 9 | 3 | 7 | 3 | 9 | 9 | 0 | 4 | 5 | 8 | 6 | 4 | 3 | 6 | 6 | 6 | 7 | 8 | 9 | 9 |
| Bedstraw | 9 | 10 | 10 | 10 | 0 | 5 | 8 | 8 | 8 | 8 | 8 | 9 | 9 | 10 | 8 | 9 | 9 | 10 | 9 | 10 | 10 | 10 | 10 | 10 | 9 | 9 | 9 | 2 | 8 | 7 | 9 | 9 | 0 | 9 | 9 | 9 | 9 | 9 | 10 | 10 |
| Blackgrass | 8 | 8 | 9 | 7 | 4 | 7 | 7 | 4 | 8 | 8 | 9 | 8 | 9 | 7 | 4 | 4 | 7 | 8 | 9 | 9 | 10 | 8 | 8 | 7 | 9 | 9 | 6 | 8 | 7 | 9 | 9 | 10 | 8 | 9 | 9 | 9 | 9 | 9 | 10 | 10 |
| Chickweed | 6 | 10 | 10 | 10 | 0 | 10 | 8 | 10 | 8 | 9 | 9 | 8 | 9 | 10 | 0 | 8 | 10 | 10 | 10 | 10 | 10 | 9 | 10 | 10 | 9 | 9 | 8 | 5 | 7 | 7 | 10 | 10 | 7 | 9 | 9 | 9 | 9 | 9 | 10 | 9 |
| Corn | 0 | 8 | 8 | 6 | 0 | 4 | 8 | 3 | 9 | 9 | 9 | 10 | 10 | 10 | 8 | 0 | 2 | 3 | 0 | 10 | 6 | 7 | 7 | 4 | 9 | 10 | 0 | 0 | 6 | — | — | — | 10 | 4 | 6 | 7 | 7 | 0 | 10 | 10 |
| Cotton | 3 | 3 | 6 | 7 | 0 | 4 | 9 | 3 | 6 | 7 | 8 | 5 | 9 | 9 | 2 | 0 | 7 | 9 | 8 | 10 | 8 | 4 | 9 | 9 | 8 | 9 | 7 | 0 | 7 | — | — | — | 8 | 9 | 9 | 7 | 4 | 9 | 10 | 10 |
| Crabgrass | 3 | 8 | 7 | 7 | 0 | 2 | 2 | 0 | 8 | 10 | 9 | 8 | 9 | 9 | 7 | 7 | 4 | 8 | 8 | 10 | 9 | 6 | 7 | 3 | 9 | 9 | 3 | 3 | 6 | — | — | — | 6 | 7 | 2 | 5 | 0 | 3 | 9 | 9 |
| Downy brome | 8 | 9 | 6 | 10 | 4 | 3 | 6 | 3 | 4 | 3 | 4 | 7 | 7 | 9 | 1 | 0 | 8 | 8 | 8 | 9 | 9 | 6 | 7 | 7 | 10 | 8 | 2 | 6 | 4 | 8 | 7 | 5 | — | 6 | 6 | 5 | 5 | 8 | 9 | 8 |
| Duck salad | — | — | — | — | — | — | — | — | — | — | — | — | — | — | — | — | — | — | — | — | — | — | — | — | — | — | — | — | — | — | — | — | — | — | — | — | — | — | — | — |
| Giant foxtail | 3 | 8 | 8 | 4 | 3 | 5 | 3 | 2 | 7 | 9 | 9 | 7 | 9 | 9 | 8 | 6 | 7 | 9 | 8 | 8 | 9 | 6 | 3 | 0 | 9 | 9 | 0 | 5 | 7 | — | — | — | 6 | 8 | 5 | 7 | 7 | 7 | 9 | 8 |
| Lambsquarters | 9 | 10 | 10 | 10 | 5 | 10 | 9 | 10 | 3 | 9 | 10 | 5 | 9 | 8 | 5 | 6 | 10 | 10 | 10 | 10 | 10 | 9 | 10 | 10 | 10 | 10 | 8 | 6 | 7 | 9 | 9 | 9 | 9 | 10 | 8 | 10 | 10 | 10 | 10 | 10 |
| Morningglory | 0 | 3 | 5 | 8 | 0 | 2 | 6 | 0 | 6 | 7 | 2 | 7 | 9 | 9 | 5 | 2 | 3 | 8 | 9 | 10 | 5 | 0 | 10 | 10 | 9 | 10 | 8 | 2 | 9 | — | — | — | 7 | 8 | 5 | 9 | a | 9 | 10 | 10 |
| Pigweed | 7 | 10 | 7 | 10 | 6 | 7 | 9 | 8 | 9 | 9 | 8 | 8 | 9 | 10 | 7 | 8 | 8 | 9 | 10 | 10 | 10 | 9 | 9 | 9 | 9 | 10 | 9 | 9 | 9 | — | — | — | 7 | 8 | 8 | 9 | 9 | 9 | 10 | 10 |
| Rape | 6 | 10 | 9 | 10 | 0 | 4 | 9 | 8 | 6 | 4 | 8 | 9 | 8 | 8 | 3 | 0 | 6 | 8 | 9 | 9 | 9 | 10 | 10 | 10 | 10 | 10 | 9 | 9 | 9 | 9 | 9 | 9 | 3 | 9 | 9 | 9 | 9 | 9 | 10 | 10 |
| Ryegrass | 6 | 4 | 2 | 8 | 0 | 5 | 7 | 3 | 5 | 8 | 5 | 9 | 4 | 8 | 3 | 0 | 6 | 7 | 9 | 9 | 10 | 7 | 10 | 8 | 10 | 9 | 6 | 5 | 8 | 6 | 5 | 5 | 4 | 5 | 6 | 8 | 1 | 2 | 10 | 10 |
| Sorghum | 7 | 8 | 9 | 9 | 4 | 8 | 9 | 5 | 10 | 10 | 9 | 9 | 10 | 10 | 7 | 5 | 9 | 9 | 8 | 10 | 9 | 10 | 10 | 8 | 9 | 10 | 7 | 9 | 10 | — | — | — | 9 | 9 | 9 | 9 | 9 | 9 | 9 | 10 |
| Soybean | 4 | 5 | 4 | 7 | 0 | 2 | 3 | 2 | 3 | 5 | 4 | 4 | 9 | 8 | 2 | 2 | 2 | 6 | 7 | 10 | 7 | 4 | 8 | 8 | 9 | 9 | 8 | 4 | 7 | — | — | — | 8 | 6 | 7 | 8 | 0 | 6 | 10 | 9 |
| Speedwell | 7 | 10 | 5 | 10 | 0 | 4 | 8 | 7 | 8 | 8 | 2 | 8 | 9 | 3 | 0 | 6 | 10 | 8 | 9 | 10 | 10 | 10 | 10 | 9 | 9 | 8 | 5 | 0 | 2 | 9 | 10 | 10 | 9 | 9 | 9 | 9 | 9 | 8 | 10 | 7 |
| Sugar beet | 8 | 10 | 10 | 10 | 0 | 9 | 8 | 8 | 9 | 9 | 8 | 9 | 9 | 10 | 2 | 9 | 10 | 10 | 9 | 9 | 9 | 10 | 10 | 10 | 10 | 10 | 9 | 9 | 9 | 9 | 9 | 9 | 4 | 9 | 9 | 9 | 9 | 9 | 10 | 10 |
| Velvetleaf | 6 | 7 | 5 | 8 | 0 | 4 | 8 | 0 | 7 | 7 | 8 | 7 | 9 | 8 | 3 | 0 | 5 | 8 | 8 | 9 | 8 | 8 | 10 | 8 | 9 | 9 | 9 | 4 | 7 | — | — | — | 7 | 8 | 6 | 8 | 7 | 8 | 10 | 9 |
| Wheat | 6 | 8 | 7 | 8 | 0 | 0 | 0 | 2 | 4 | 4 | 0 | 2 | 3 | 1 | 2 | 0 | 3 | 0 | 5 | 9 | 9 | 0 | 5 | 3 | 9 | 9 | 2 | 3 | 4 | 7 | 5 | 3 | 4 | 3 | 4 | 4 | 4 | 7 | 9 | 6 |
| Wild buckwheat | 9 | 10 | 10 | 10 | 0 | 6 | 8 | 7 | 7 | 7 | 7 | 8 | 9 | 8 | 0 | 0 | 9 | 10 | — | 9 | 9 | 8 | 9 | 8 | 9 | 8 | 5 | 6 | 7 | 9 | 9 | 8 | 5 | 9 | 9 | 8 | 9 | 9 | 9 | 9 |
| Wild oat | 3 | 5 | 3 | 3 | 0 | 0 | 0 | 0 | 5 | 4 | 0 | 3 | 4 | 3 | 2 | 3 | 4 | 3 | 5 | 9 | 8 | 3 | 6 | 6 | 6 | 5 | 0 | 0 | i | 7 | 4 | 2 | 6 | 2 | 0 | 3 | 4 | 5 | 9 | 9 |
| Barnyardgrass | — | — | — | — | — | — | — | — | — | — | — | — | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — | — | — | — | — | — | — | — | — | — | — | — | — |

TABLE B-continued

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (31 g/ha) | 109 | 110 | 111 | 112 | 114 | 115 | 116 | 117 | 118 | 119 | 120 | 121 | 122 | 125 | 166 | 167 | 170 | 172 | 173 | 203 | 204 | 205 | 206 | 207 | 208 | 209 | 211 | 212 |
| | PREEMERGENCE | | | | | | | | | | | | | | | | | | | | | | | | | | | |
| Barley Igri | 9 | 9 | 3 | 4 | 6 | 0 | 8 | 4 | 0 | 9 | 6 | 9 | 9 | 0 | 6 | 0 | 0 | 2 | 0 | 8 | 8 | 9 | 9 | 7 | 9 | 0 | 4 | 0 |
| Bedstraw | 0 | 10 | 9 | 10 | 9 | 9 | 9 | 9 | 9 | 9 | 7 | 10 | 10 | 5 | 9 | 9 | 9 | 4 | 6 | 7 | 10 | 10 | 10 | 9 | 9 | 0 | 9 | 8 |
| Blackgrass | 10 | 10 | 10 | 9 | 9 | 9 | 9 | 8 | 7 | 10 | 10 | 10 | 10 | 5 | 8 | 9 | 7 | 9 | 9 | 8 | 9 | 9 | 9 | 9 | 9 | 0 | 8 | 9 |
| Chickweed | 9 | 9 | 9 | 9 | 9 | 8 | 9 | 9 | 8 | 10 | 10 | 10 | 10 | 8 | 9 | 9 | 9 | 6 | — | 9 | 9 | 9 | 4 | 9 | 9 | 0 | 9 | 10 |
| Corn | 7 | 8 | 3 | 5 | 9 | 6 | 8 | 5 | 4 | 9 | 8 | 10 | 9 | 0 | 9 | 9 | 10 | 3 | 5 | 4 | 8 | 10 | 10 | 10 | 9 | 0 | 8 | 5 |
| Cotton | 9 | 10 | 6 | 8 | 4 | 2 | 9 | 9 | 5 | 9 | 8 | 10 | 10 | 0 | 7 | 0 | 9 | 4 | 6 | 7 | 8 | 9 | 9 | 8 | — | 0 | 6 | 5 |
| Crabgrass | 8 | 9 | 4 | 4 | 7 | 3 | 8 | 6 | 2 | 7 | 6 | 5 | 7 | 2 | 9 | 8 | 9 | 7 | 8 | 8 | 10 | 10 | 9 | 9 | 10 | 0 | 9 | 7 |
| Downy brome | 9 | 9 | 6 | 6 | 7 | 3 | 7 | 5 | 3 | 10 | 7 | 10 | 10 | 0 | 8 | 5 | 6 | 4 | 5 | 9 | 9 | 9 | 10 | 9 | 9 | 3 | 8 | 6 |
| Duck salad | — | — | — | — | — | — | — | — | — | — | — | — | — | — | — | — | — | — | — | — | — | — | — | — | — | — | — | — |
| Giant foxtail | 8 | 9 | 7 | 5 | 9 | 5 | 8 | 5 | 1 | 8 | 7 | 5 | 5 | 0 | 9 | 4 | 9 | 7 | 9 | 3 | 10 | 9 | 9 | 9 | 9 | 0 | 9 | 7 |
| Lambsquarters | 9 | 10 | 9 | 9 | 9 | 8 | 9 | 9 | 9 | 10 | 10 | 10 | 9 | 9 | 8 | 10 | 10 | 10 | 9 | 9 | 9 | 10 | 10 | 9 | 9 | 0 | 9 | — |
| Morningglory | 7 | 8 | 7 | 9 | 8 | 7 | 9 | 10 | 6 | 9 | 9 | 9 | 9 | 3 | 5 | 5 | 8 | 5 | 2 | 6 | 7 | 9 | 8 | 8 | 9 | 0 | 3 | 5 |
| Pigweed | 9 | 10 | 10 | 9 | 9 | 9 | 9 | 9 | 7 | 9 | 9 | 9 | 9 | 8 | 9 | 8 | 9 | 9 | 9 | 9 | 10 | 10 | 10 | 9 | 10 | 0 | 10 | 6 |
| Rape | 9 | 9 | 9 | 9 | 9 | 9 | 9 | 9 | 6 | 10 | 10 | 10 | 10 | 8 | 9 | 7 | 10 | 3 | 2 | 10 | 10 | 9 | 9 | 9 | 10 | 0 | 9 | 6 |
| Ryegrass | 10 | 9 | 7 | 9 | 8 | 5 | 9 | 7 | 6 | 10 | 5 | 10 | 10 | 0 | 9 | 5 | 9 | 5 | 6 | 8 | 8 | 9 | 9 | 9 | 9 | 0 | 5 | 0 |
| Sorghum | 9 | 9 | 4 | 10 | 9 | 9 | 9 | 9 | 3 | 9 | 9 | 10 | 10 | 0 | 9 | 9 | 9 | 5 | 6 | 9 | 10 | 10 | 10 | 10 | 10 | 2 | 10 | 6 |
| Soybean | 8 | 9 | 6 | 5 | 6 | 2 | 8 | 8 | 0 | 8 | 7 | 10 | 10 | 0 | 5 | 2 | 8 | 3 | 5 | 6 | 7 | 7 | 7 | 8 | 7 | 0 | 6 | 4 |
| Speedwell | 9 | 10 | 8 | 10 | 9 | 8 | 10 | 8 | 10 | 10 | 10 | 10 | 5 | 9 | 10 | — | 10 | 9 | 9 | 7 | 8 | 8 | 9 | 3 | 9 | 0 | 9 | 10 |
| Sugar beet | 9 | 9 | 9 | 9 | 9 | 7 | 9 | 9 | 8 | 10 | 10 | 10 | 10 | 9 | 10 | 9 | 10 | 9 | 9 | 9 | 10 | 10 | 9 | 9 | 9 | 4 | 9 | 6 |
| Velvetleaf | 9 | 9 | 7 | 9 | 7 | 7 | 9 | 9 | 2 | 9 | 9 | 9 | 9 | 5 | 7 | 6 | 9 | 6 | 4 | 9 | 8 | 9 | 9 | 9 | 9 | 0 | 7 | 3 |
| Wheat | 9 | 7 | 5 | 4 | 3 | 0 | 1 | 0 | 0 | 9 | 6 | 9 | 9 | 0 | 7 | 0 | 9 | 4 | 0 | 9 | 8 | 9 | 9 | 9 | 9 | 0 | 7 | 0 |
| Wild buckwheat | — | 7 | 10 | — | 9 | 9 | 9 | 9 | 9 | 10 | 10 | 9 | 10 | 9 | — | 7 | 8 | 9 | 9 | 9 | 9 | 9 | 9 | 8 | 9 | 3 | 9 | 5 |
| Wild oat | 9 | 8 | 0 | 0 | 5 | 0 | 8 | 5 | 0 | 8 | 4 | 9 | 9 | 0 | 4 | 2 | 2 | 0 | 0 | 6 | 6 | 7 | 8 | 7 | 7 | 0 | 3 | 0 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (31 g/ha) | 213 | 214 | 217 | 218 | 219 | 225 | 229 | 230 | 231 | 232 | 240 | 241 | 242 | 243 | 244 | 245 | 252 | 254 | 256 | 258 | 259 | 261 | 266 | 267 | 268 | 269 | 270 | 271 |
| | PREEMERGENCE | | | | | | | | | | | | | | | | | | | | | | | | | | | |
| Barley Igri | 7 | 6 | 6 | 6 | 0 | 5 | 9 | 0 | 9 | 9 | 9 | 9 | 6 | 9 | 8 | 9 | 0 | 5 | 9 | 8 | 4 | 9 | 1 | 9 | 5 | 0 | 6 | 9 |
| Bedstraw | 10 | 10 | 8 | 8 | 9 | 9 | 8 | 5 | 10 | 10 | 10 | 10 | 10 | 10 | 10 | 10 | 9 | 9 | 9 | 10 | 6 | 10 | 8 | 10 | 10 | 2 | 8 | 8 |
| Blackgrass | 9 | 8 | 9 | 9 | 6 | 5 | 9 | 9 | 9 | 9 | 10 | 10 | 10 | 10 | 10 | 10 | 10 | 9 | 10 | 10 | 10 | 10 | 10 | 10 | 10 | 9 | 10 | 10 |
| Chickweed | 10 | 9 | 9 | 10 | 9 | 7 | 7 | 5 | 5 | 0 | 9 | 10 | 9 | 9 | 10 | 9 | 9 | 9 | 6 | 10 | 9 | 9 | 6 | 7 | 9 | 0 | 0 | 10 |
| Corn | 10 | 10 | 4 | 5 | 0 | 7 | 4 | 2 | 4 | 5 | 9 | 9 | 9 | 10 | 10 | 9 | 8 | 4 | 9 | 10 | 10 | 9 | 5 | 5 | 3 | 0 | 9 | 4 |
| Cotton | 10 | 10 | 5 | 7 | 7 | 9 | 2 | 2 | 9 | 5 | 6 | 5 | 6 | 10 | 9 | 6 | 0 | 9 | 5 | 8 | 7 | 9 | 3 | 8 | 8 | 0 | 8 | 3 |
| Crabgrass | 8 | 6 | 5 | 5 | 0 | 2 | 3 | 5 | 7 | 5 | 9 | 9 | 9 | 7 | 9 | 8 | 2 | 6 | 7 | 8 | 7 | 7 | 5 | 7 | 5 | 0 | 8 | 9 |
| Downy brome | 9 | 8 | 9 | 9 | 7 | 5 | 7 | 4 | 9 | 10 | 10 | 10 | 9 | 10 | 10 | 10 | 8 | 9 | 9 | 8 | 10 | 10 | 7 | 10 | 10 | — | 8 | 10 |
| Duck salad | — | — | — | — | — | — | — | — | — | — | — | — | — | — | — | — | — | — | — | — | — | — | — | — | — | — | — | — |
| Giant foxtail | 8 | 3 | 4 | 4 | 0 | 3 | 7 | 4 | 6 | 4 | 8 | 9 | 9 | 7 | 9 | 8 | 3 | 5 | 7 | 8 | 7 | 8 | 4 | 6 | 3 | 0 | 5 | 9 |
| Lambscluarters | 10 | 10 | — | 10 | 8 | — | 9 | — | 9 | 9 | 10 | 10 | 9 | 10 | 9 | 10 | 7 | 8 | 9 | 10 | 10 | 9 | 9 | 9 | 9 | 9 | 8 | 8 |
| Morningglory | 10 | 9 | 3 | 4 | 2 | 9 | 2 | 0 | 9 | 8 | 7 | 7 | 6 | 9 | 9 | 8 | 0 | 9 | 5 | 7 | 2 | 8 | 8 | 8 | 9 | 0 | 2 | 6 |
| Pigweed | 10 | 9 | 7 | 8 | 6 | 7 | 9 | 5 | 8 | 9 | 9 | 9 | 10 | 10 | 10 | 9 | 5 | 8 | 7 | 9 | 9 | 9 | 7 | 9 | 8 | 5 | 9 | 9 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rape | 10 | 10 | 8 | 4 | 6 | 5 | 0 | 3 | 0 | 0 | 9 | 9 | 9 | 10 | 10 | 10 | 8 | 10 | 9 | 8 | 4 | 9 | 4 | 6 | 9 | 0 | 5 | 8 |
| Ryegrass | 9 | 7 | 6 | 6 | 5 | 0 | 2 | 0 | 8 | 7 | 10 | 10 | 9 | 10 | 10 | 10 | 3 | 7 | 9 | 9 | 9 | 9 | 0 | 6 | 4 | 0 | 4 | 6 |
| Sorghum | 10 | 8 | 9 | 6 | 2 | 9 | 8 | 7 | 10 | 9 | 9 | 9 | 9 | 10 | 10 | 10 | 3 | 9 | 10 | 9 | 9 | 10 | 9 | 9 | 9 | 2 | 5 | 9 |
| Soybean | 10 | 9 | 3 | 6 | 2 | 7 | 4 | 2 | 8 | 7 | 7 | 9 | 7 | 9 | 10 | 7 | 4 | 8 | 7 | 7 | 5 | 5 | 5 | 7 | 8 | 0 | 2 | 2 |
| Speedwell | 10 | 8 | 9 | — | 0 | 9 | 8 | 5 | 6 | 0 | 10 | 10 | 8 | 10 | 0 | 10 | 10 | 8 | 9 | 7 | 6 | 9 | 7 | 10 | 2 | 9 | 8 | 7 |
| Sugar beet | 10 | 10 | 9 | 9 | 9 | — | 5 | 4 | 9 | 9 | 10 | 10 | 9 | 9 | 10 | 9 | 4 | 9 | 9 | 7 | 9 | 9 | 3 | 9 | 9 | — | 10 | 7 |
| Velvetleaf | 10 | 7 | 7 | 5 | 2 | 9 | 7 | 2 | 9 | 5 | 7 | 7 | 9 | 9 | 8 | 7 | 3 | 5 | 7 | 8 | 7 | 7 | 8 | 8 | 3 | 0 | 2 | 3 |
| Wheat | 9 | 4 | 5 | 6 | 0 | — | 7 | 3 | 9 | 8 | 9 | 5 | 5 | 9 | 9 | 9 | 0 | 0 | 9 | 5 | 8 | 8 | 0 | 8 | 4 | 0 | 7 | 9 |
| Wild buckwheat | 9 | 9 | 6 | 8 | 8 | 9 | 4 | 9 | 7 | 6 | 9 | 9 | 10 | — | 9 | 9 | 8 | 9 | 9 | 9 | 7 | 9 | 8 | 9 | 9 | 8 | 9 | 9 |
| Wild oat | 6 | 5 | 5 | 3 | 2 | 2 | 2 | 0 | 9 | 5 | 8 | 5 | 6 | 9 | 8 | 8 | 0 | 7 | 8 | 8 | 5 | 9 | 2 | 5 | 4 | 0 | 7 | 7 |
| Barnyardgrass | — | — | — | — | — | — | — | — | — | — | — | — | — | — | — | — | — | — | — | — | — | — | — | — | — | — | — | — |
| Riice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |

| | COMPOUND | | | | | | | | | | | | | | | | | |
|---|---|---|---|---|---|---|---|---|---|---|---|---|---|---|---|---|---|---|
| Rate (31 g/ha) | 272 | 274 | 275 | 276 | 283 | 284 | 285 | 286 | 287 | 288 | 289 | 291 | 292 | 300 | 301 | 302 | 305 | 310 |
| | PREEMERGENCE | | | | | | | | | | | | | | | | | |
| Barley Igri | 2 | 0 | 9 | 0 | 9 | — | 0 | 10 | 2 | 2 | 5 | 4 | 0 | 3 | 1 | 5 | 8 | 0 |
| Bedstraw | 8 | 0 | 10 | 0 | 10 | 10 | 4 | 10 | 10 | 10 | 8 | 3 | 0 | 2 | 6 | 9 | 8 | 7 |
| Blackgrass | 10 | 8 | 10 | 4 | 10 | 10 | 9 | 10 | 10 | 9 | 9 | 8 | 0 | 8 | 9 | 10 | 10 | 8 |
| Chickweed | 10 | 0 | 10 | 0 | 10 | 10 | 10 | 10 | 10 | 10 | 9 | 8 | 2 | 4 | 9 | 10 | 9 | 7 |
| Corn | 2 | 0 | 10 | 0 | 9 | 9 | 4 | 6 | 4 | 4 | 2 | 4 | 0 | 3 | 1 | 3 | 3 | 4 |
| Cotton | 7 | 0 | 8 | 0 | 6 | 8 | 7 | 9 | 9 | 7 | 0 | 3 | 0 | 4 | 7 | 8 | 7 | 8 |
| Crabgrass | 10 | 0 | 9 | 0 | 6 | 8 | 2 | 9 | 9 | 8 | 0 | 7 | 0 | 4 | 4 | 7 | 7 | 0 |
| Downy brome | 10 | 0 | 10 | 0 | 10 | 10 | 3 | 10 | 20 | 9 | 7 | 8 | 0 | 5 | 8 | 10 | 8 | 0 |
| Duck salad | — | — | — | — | — | — | — | — | — | — | — | — | — | — | — | — | — | — |
| Giant foxtail | 9 | 1 | 9 | 2 | 8 | 8 | 3 | 9 | 8 | 7 | 7 | 8 | 0 | 7 | 4 | 9 | 9 | 0 |
| Lambsquarters | 7 | 0 | 9 | 0 | 10 | 10 | 10 | 9 | 10 | 10 | 0 | 8 | 0 | 3 | 9 | 10 | 10 | 10 |
| Morningglory | 0 | 0 | 4 | 0 | 6 | 5 | 5 | 9 | 9 | 6 | 0 | 0 | 0 | 2 | 5 | 5 | 7 | 5 |
| Pigweed | 10 | 0 | 9 | 0 | 9 | 9 | 8 | 9 | 9 | 9 | 9 | 9 | 0 | 9 | 8 | 9 | 9 | 8 |
| Rape | 8 | 0 | 9 | 0 | 8 | 9 | 9 | 10 | 10 | 9 | 0 | 6 | 0 | 5 | 6 | 8 | 3 | 0 |
| Ryegrass | 8 | 0 | 9 | 0 | 10 | 8 | 3 | 10 | 9 | 5 | 3 | 7 | 0 | 2 | 0 | 8 | 3 | 0 |
| Sorghum | 6 | 2 | 10 | 5 | 9 | 9 | 2 | 9 | 9 | 8 | 6 | 6 | 0 | 5 | 4 | 8 | 9 | 0 |
| Soybean | 0 | 0 | 3 | 0 | 7 | 3 | 2 | 9 | 6 | 3 | 0 | 0 | 0 | 0 | 2 | 5 | 3 | 5 |
| Speedwell | 0 | 0 | 9 | — | 10 | 10 | 4 | 10 | 2 | 10 | 10 | 9 | 4 | 7 | 10 | 10 | 10 | 10 |
| Sugar beet | 9 | 0 | 10 | 0 | 9 | 10 | 9 | 10 | 10 | 10 | 7 | 9 | 0 | 9 | 9 | 10 | 10 | 10 |
| Velvetleaf | 6 | 2 | 3 | 2 | 5 | 8 | 5 | 9 | 2 | 8 | 3 | 5 | 0 | 5 | 5 | 8 | 5 | 6 |
| Wheat | 8 | 0 | 9 | 0 | 9 | — | 0 | 10 | 8 | 5 | 0 | 2 | 0 | 4 | 5 | 9 | 0 | 0 |
| Wild buckwheat | — | — | 10 | 0 | 9 | 10 | 10 | 9 | 9 | 9 | 8 | 3 | 2 | 4 | 7 | 9 | 9 | 9 |
| Wild oat | 2 | 0 | 8 | 0 | 9 | 2 | 2 | 9 | 4 | 1 | 2 | 4 | 0 | 2 | 3 | 3 | 0 | 0 |
| Barnyardgrass | — | — | — | — | — | — | — | — | — | — | — | — | — | — | — | — | — | — |
| Rice Japonica | — | — | — | — | — | — | — | — | — | — | — | — | — | — | — | — | — | — |
| Umbrella sedge | — | — | — | — | — | — | — | — | — | — | — | — | — | — | — | — | — | — |

TABLE B-continued

| Rate (16 g/ha) | 1 | 2 | 3 | 5 | 7 | 11 | 13 | 14 | 25 | 26 | 27 | 28 | 29 | 30 | 31 | 34 | 35 | 36 | 50 | 51 | 53 | 58 | 59 | 60 | 63 | 64 | 71 | 77 | 98 | 81 | 82 | 83 | 84 | 86 | 88 | 89 | 102 | 103 | 107 | 108 |
|---|---|---|---|---|---|---|---|---|---|---|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | | | | | | | | | | | | |
| | POSTEMERGENCE | | | | | | | | | | | | | | | | | | | | | | | | | | | | | | | | | | | | | | | |
| Barley Igri | 6 | 9 | 7 | 10 | 6 | 9 | 9 | 9 | 9 | 8 | 9 | 8 | 10 | 10 | 8 | 7 | 3 | 4 | 8 | 8 | 9 | 4 | 7 | 4 | 7 | 8 | 0 | 1 | 0 | 7 | 6 | 6 | 5 | 5 | 6 | 6 | 8 | 8 | 9 | 7 |
| Bedstraw | 9 | 8 | 9 | 10 | 0 | 5 | 8 | 4 | 10 | 10 | 10 | 10 | 10 | 10 | 7 | 5 | 10 | 10 | 8 | 10 | 8 | 10 | 10 | 10 | 7 | 7 | 7 | 4 | 6 | 5 | 8 | 9 | 8 | 9 | 9 | 10 | 8 | 9 | 10 | 10 |
| Blackgrass | 8 | 8 | 9 | 10 | 5 | 8 | 8 | 5 | 10 | 20 | 10 | 9 | 10 | 10 | 7 | 4 | 8 | 9 | 9 | 9 | 9 | 9 | 8 | 7 | 9 | 9 | 4 | 6 | 7 | 10 | 9 | 10 | 9 | 9 | 8 | 9 | 9 | 9 | 10 | 9 |
| Chickweed | 6 | 5 | 7 | 10 | 0 | 9 | 9 | 9 | 10 | 10 | 10 | 5 | 10 | 10 | — | 10 | 10 | 10 | 8 | 10 | 9 | 7 | 10 | 10 | 10 | 10 | 9 | 3 | 5 | 7 | 10 | 10 | 9 | — | 9 | 8 | 9 | 9 | 10 | 10 |
| Corn | 7 | 8 | 10 | 10 | 6 | 10 | 10 | 10 | 10 | 10 | 10 | 10 | 10 | 10 | 9 | 10 | 10 | 10 | 7 | 10 | 6 | 10 | 9 | 7 | 10 | 10 | 5 | 4 | 7 | 0 | 5 | 9 | 8 | 0 | 4 | 8 | 2 | 0 | 10 | 10 |
| Cotton | 5 | 6 | 7 | 6 | 3 | 6 | 6 | 8 | 4 | 7 | 9 | 8 | 10 | 10 | 4 | 5 | 6 | 8 | 10 | 10 | 10 | 8 | 10 | 10 | 8 | 9 | 9 | 4 | 7 | 5 | 5 | 9 | 8 | 4 | 8 | 4 | 3 | 7 | 10 | 10 |
| Crabgrass | 7 | 5 | 6 | 7 | 4 | 5 | 7 | 6 | 6 | 5 | 7 | 4 | 10 | 10 | 4 | 6 | 3 | 6 | 3 | 6 | 6 | 3 | 0 | 0 | 3 | 7 | 5 | 4 | 3 | 2 | 4 | 5 | 3 | 2 | 0 | 0 | 0 | 0 | 5 | 2 |
| Downy brome | 8 | 7 | 6 | 10 | 6 | 8 | 5 | 4 | 10 | 9 | 10 | 10 | 10 | 20 | 5 | 7 | 7 | 9 | 6 | 8 | 9 | 4 | 7 | 4 | 8 | 7 | 0 | 3 | 0 | 6 | 5 | 3 | 3 | 3 | 5 | 3 | 7 | 7 | 8 | 4 |
| Duck salad | — | — | — | — | — | — | — | — | — | — | — | — | — | — | — | — | — | — | 10 | 9 | 9 | 7 | 10 | 10 | 8 | 9 | 9 | 5 | 5 | 0 | 9 | 9 | 0 | 7 | 4 | 8 | 2 | 4 | 10 | 10 |
| Giant foxtail | 6 | 8 | 8 | 8 | 6 | 9 | 10 | 10 | 10 | 10 | 10 | 7 | 10 | 10 | 8 | 7 | 8 | 10 | 7 | 7 | 8 | 4 | 4 | 0 | 8 | 10 | 3 | 6 | 6 | 6 | 8 | 8 | 7 | 5 | 4 | 2 | 5 | 4 | 9 | 3 |
| Lambsquarters | 10 | 10 | 10 | 10 | 9 | 10 | 10 | 5 | 10 | 10 | 10 | 10 | 10 | 10 | 9 | 10 | 10 | 10 | 10 | 10 | 10 | 9 | 10 | 10 | 10 | 10 | 7 | 8 | 10 | 6 | 9 | 10 | 10 | 9 | 8 | 10 | 9 | 10 | 10 | 10 |
| Morningglory | 6 | 10 | 10 | 7 | 6 | 7 | 6 | 7 | 10 | 10 | 10 | 10 | 10 | 10 | 7 | 7 | 10 | 10 | 10 | 10 | 8 | 10 | 10 | 10 | 10 | 10 | 10 | 7 | 10 | 9 | 10 | 10 | 7 | 9 | 10 | 10 | 7 | 9 | 10 | 10 |
| Pigweed | 5 | 5 | 4 | 10 | 2 | 8 | 9 | 0 | 7 | 7 | 10 | 20 | 10 | 10 | 6 | 8 | 7 | 10 | 10 | 10 | 10 | 7 | 10 | 8 | 10 | 10 | 10 | 8 | 10 | 7 | 10 | 10 | 8 | 6 | 4 | 3 | 8 | 9 | 10 | 10 |
| Rape | 5 | 6 | 8 | 10 | 0 | 8 | 10 | 10 | 9 | 10 | 10 | 10 | 10 | 10 | 0 | 4 | 2 | 10 | 10 | 10 | 10 | 10 | 10 | 10 | 10 | 10 | 5 | 7 | 9 | 9 | 10 | 8 | 9 | 10 | 9 | 10 | 9 | 8 | 10 | 10 |
| Ryegrass | 9 | 5 | 3 | 10 | 4 | 9 | 4 | 3 | 10 | 10 | 10 | 10 | 10 | 10 | 7 | 9 | 7 | 10 | 7 | 9 | 9 | 2 | 9 | 4 | 7 | 9 | 2 | 3 | 2 | 5 | 5 | 3 | 4 | 0 | 4 | 4 | 3 | 2 | 10 | 9 |
| Sorghum | 7 | 8 | 10 | 10 | 7 | 8 | 10 | 8 | 10 | 10 | 10 | 10 | 10 | 10 | 8 | 7 | 10 | 10 | 7 | 10 | 6 | 6 | 6 | 6 | 10 | 10 | 5 | 7 | 8 | 10 | 10 | 10 | 10 | 9 | 7 | 8 | 9 | 10 | 10 | 9 |
| Soybean | 7 | 9 | 8 | 10 | 2 | 8 | 10 | 8 | 10 | 10 | 10 | 10 | 10 | 10 | 7 | 10 | 10 | 10 | 10 | 10 | 10 | 10 | 10 | 10 | 10 | 10 | 9 | 8 | 9 | 8 | 8 | 9 | 9 | 8 | 8 | 9 | 6 | 8 | 10 | 10 |
| Speedwell | 4 | 5 | 0 | 9 | 0 | 0 | 5 | 0 | 6 | 6 | 5 | 8 | 8 | 0 | 0 | 0 | 3 | 4 | 5 | 9 | 7 | 9 | 10 | 8 | 4 | 0 | 1 | 3 | 3 | — | — | — | 8 | 7 | 9 | 7 | — | — | — | — |
| Sugar beet | 9 | 10 | 10 | 10 | 5 | 9 | 9 | 8 | 8 | 9 | 10 | 10 | 10 | 10 | 8 | 9 | 10 | 10 | 9 | 10 | 10 | 9 | 10 | 10 | 10 | 10 | 7 | 10 | 10 | 6 | 9 | 10 | 9 | 9 | 9 | 9 | 9 | 9 | 10 | 10 |
| Velvetleaf | 6 | 7 | 6 | 8 | 3 | 6 | 8 | 3 | 7 | 9 | 10 | 9 | 9 | 10 | 5 | 6 | 7 | 6 | 10 | 10 | 10 | 10 | 8 | 6 | 10 | 10 | 8 | 6 | 8 | 6 | 9 | 9 | 5 | 7 | 7 | 7 | 2 | 8 | 10 | 7 |
| Wheat | 7 | 8 | 6 | 10 | 5 | 9 | 9 | 9 | 9 | 7 | 10 | 5 | 10 | 10 | 7 | 6 | 6 | 6 | 6 | 8 | 9 | 0 | 2 | 1 | 7 | 8 | 0 | 0 | 0 | 4 | 3 | 2 | 4 | 3 | 5 | 5 | 9 | 8 | 8 | 4 |
| Wild buckwheat | 10 | 6 | 9 | 10 | 0 | 9 | 5 | 3 | 10 | 6 | 20 | 10 | 10 | 10 | 6 | 0 | 0 | 4 | 7 | 10 | 8 | 6 | 10 | 10 | 6 | 8 | 0 | 4 | 7 | 9 | 7 | 8 | 9 | 8 | 8 | 9 | 8 | 7 | 9 | 10 |
| Wild oat | 9 | 10 | 8 | 9 | 5 | 8 | 4 | 3 | 9 | 9 | 9 | 6 | 9 | 9 | 8 | 7 | 8 | 9 | 5 | 9 | 7 | 2 | 7 | 4 | 5 | 6 | 0 | 0 | 0 | 7 | 0 | 0 | 7 | 2 | 4 | 2 | 6 | 5 | 9 | 8 |
| Barnyardgrass | 0 | 0 | 0 | 7 | 0 | 4 | 5 | 2 | 7 | 8 | 8 | 8 | 9 | 7 | 0 | 1 | 6 | 8 | 8 | 9 | 9 | 8 | 7 | 6 | 9 | 9 | 0 | 0 | 7 | 4 | 8 | 8 | 3 | 8 | 8 | 8 | 1 | 2 | 8 | 8 |
| Rice Japonica | 6 | 6 | 7 | 8 | 0 | 5 | 7 | 6 | 5 | 6 | 2 | 8 | 8 | 8 | 0 | 8 | 4 | 5 | 0 | 9 | 9 | 8 | 9 | 9 | 8 | 8 | 8 | 3 | 8 | 6 | 8 | 8 | 5 | 8 | 3 | 6 | 2 | 2 | 9 | 8 |
| Umbrella sedge | 6 | 9 | 9 | 8 | 0 | 7 | 0 | 1 | 9 | 9 | 9 | 9 | 8 | 7 | 0 | 2 | 0 | 4 | 9 | 9 | 9 | 8 | 9 | 9 | 8 | 9 | 0 | 5 | 9 | 4 | 7 | 8 | 2 | 5 | 0 | 6 | 0 | 7 | 9 | 8 |

| Rate (16 g/ha) | 109 | 110 | 111 | 112 | 114 | 115 | 116 | 117 | 118 | 119 | 120 | 121 | 122 | 125 | 166 | 167 | 170 | 172 | 173 | 203 | 204 | 205 | 206 | 207 | 208 | 209 | 211 | 212 |
|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | |
| | POSTEMERGENCE | | | | | | | | | | | | | | | | | | | | | | | | | | | |
| Barley Igri | 10 | 10 | 9 | 7 | 6 | 3 | 5 | 2 | 0 | 10 | 5 | 9 | 0 | 0 | 8 | 9 | 5 | 9 | 9 | 8 | 10 | 10 | 9 | 9 | 9 | 0 | 9 | 8 |
| Bedstraw | — | 10 | 10 | 9 | 10 | — | 10 | 10 | 9 | 9 | 9 | 10 | 10 | 0 | 9 | 10 | 10 | 9 | 9 | 8 | 9 | 10 | 9 | 10 | 10 | 0 | 9 | 10 |
| Blackgrass | 10 | 10 | 10 | 10 | 9 | — | 9 | 8 | 7 | 20 | 10 | 9 | 9 | 4 | 9 | 9 | 9 | 10 | 10 | 9 | 10 | 10 | 10 | 10 | 10 | 5 | 10 | 8 |
| Chickweed | 9 | 10 | 9 | 8 | 8 | — | 0 | 10 | 3 | 10 | 10 | 10 | 10 | 4 | 10 | 10 | 10 | 6 | 6 | 8 | 10 | 10 | 10 | 9 | 8 | 0 | 8 | 6 |
| Corn | 7 | 9 | 10 | 8 | 9 | 9 | 5 | 3 | 0 | 10 | 10 | 10 | 10 | 3 | 10 | 10 | 10 | 8 | 9 | 10 | 10 | 10 | 10 | 10 | 9 | 0 | 9 | 10 |
| Cotton | 9 | 9 | 10 | 8 | 8 | 9 | 9 | 9 | 3 | 10 | 10 | 10 | 10 | 8 | 7 | 7 | 10 | 5 | 8 | 7 | 5 | 8 | 7 | 6 | 9 | 0 | 6 | 7 |
| Crabgrass | 6 | 7 | 0 | 0 | 0 | 0 | 0 | 0 | 0 | — | 0 | 5 | 4 | 0 | 5 | 3 | 10 | 6 | 9 | 9 | 10 | 10 | 10 | 10 | 9 | 0 | 5 | 5 |
| Downy brome | 9 | 10 | 9 | 6 | 5 | 0 | 2 | 0 | 0 | 10 | 8 | 9 | 7 | 0 | 7 | 9 | 6 | 9 | 9 | 10 | 10 | 10 | 10 | 10 | 9 | 0 | 9 | 9 |
| Duck salad | 9 | — | 7 | 9 | 4 | 3 | 6 | 5 | 4 | 8 | 7 | 9 | 8 | 1 | 8 | 7 | 9 | 2 | 3 | 8 | 9 | 10 | 9 | 9 | 10 | 0 | 10 | 8 |
| Giant foxtail | 7 | 8 | 7 | 2 | 7 | 4 | 5 | 0 | 0 | — | 9 | 9 | 4 | 0 | 7 | 7 | 10 | 8 | 9 | 6 | 9 | 10 | 10 | 10 | 10 | 5 | 8 | 8 |
| Lambsquarters | 10 | 10 | 10 | 10 | 6 | — | 7 | — | 0 | 10 | 10 | 20 | 8 | 8 | 10 | 10 | 10 | 9 | 9 | 10 | 10 | 10 | 10 | 10 | 10 | 0 | 10 | 10 |
| Morningglory | 7 | 10 | 10 | 10 | 8 | 10 | 10 | 10 | 9 | 10 | 10 | 10 | 10 | 0 | 8 | 9 | 9 | 9 | 9 | 10 | 10 | 10 | 7 | 7 | 10 | 0 | 10 | 10 |
| Pigweed | 10 | 10 | 10 | 10 | 6 | 5 | 8 | 8 | 0 | — | 10 | 10 | 10 | 8 | 8 | 5 | 10 | 9 | 9 | 10 | 10 | 10 | 10 | 9 | 10 | 0 | 10 | 5 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rape | 10 | 10 | 10 | 10 | 9 | 9 | 9 | 9 | 9 | 10 | 10 | 10 | 10 | 9 | 10 | 10 | 10 | 0 | 7 | 10 | 10 | 10 | 10 | 9 | 10 | 0 | 8 | |
| Ryegrass | 10 | 10 | 9 | 7 | 8 | 3 | 9 | 5 | 4 | 10 | 4 | 10 | 9 | 0 | 8 | 9 | 8 | 9 | 9 | 10 | 10 | 10 | 10 | 6 | 10 | 0 | 4 | 3 |
| Sorghum | 9 | 9 | 10 | 9 | 8 | 8 | 9 | 8 | 0 | — | 10 | 10 | 9 | 3 | 10 | 10 | 10 | 6 | 9 | 10 | 10 | 10 | 10 | 10 | 10 | 5 | 7 | 10 |
| Soybean | 8 | 10 | 10 | 9 | 8 | 9 | 9 | 9 | 0 | 10 | 10 | 10 | 10 | 8 | 9 | 8 | 10 | 9 | 9 | 8 | 10 | 10 | 10 | 10 | 7 | 0 | 10 | 9 |
| Speedwell | 6 | 9 | 5 | 9 | 9 | — | 10 | 0 | 7 | — | 0 | 10 | 0 | 0 | 8 | 4 | 9 | 9 | 6 | 5 | 8 | 3 | 8 | 0 | 5 | 0 | 8 | 0 |
| Sugar beet | — | 10 | 10 | 9 | 6 | — | 9 | 9 | 4 | 10 | 10 | 10 | 10 | 9 | 10 | 10 | 10 | 8 | 9 | 10 | 10 | 10 | 10 | 9 | 10 | 0 | 8 | 7 |
| Velvetleaf | 8 | 10 | 10 | 8 | 8 | 9 | 9 | 9 | 2 | — | 10 | 10 | 8 | 8 | 9 | 9 | 9 | 7 | 7 | 10 | 10 | 10 | 8 | 7 | 9 | 0 | 10 | 8 |
| Wheat | 9 | 9 | 8 | 5 | 5 | 4 | 0 | 0 | 0 | 9 | 7 | 9 | 8 | 0 | 8 | 8 | 9 | 9 | 9 | 7 | 9 | 9 | 9 | 8 | 8 | 0 | 8 | 7 |
| Wild buckwheat | 9 | 9 | 8 | 9 | 8 | — | 9 | 9 | 8 | 10 | 10 | 8 | 9 | — | 7 | 8 | 9 | — | 9 | 9 | 9 | 10 | 9 | 7 | 9 | 0 | 7 | 9 |
| Wild oat | 9 | 10 | 6 | 5 | 6 | 3 | 5 | 4 | 0 | 8 | 4 | 9 | 8 | 0 | 8 | 9 | 5 | 9 | 9 | 8 | 10 | 9 | 9 | 9 | 6 | 0 | 6 | 6 |
| Barnyardgrass | 9 | 9 | 8 | 7 | 8 | 9 | 7 | 4 | 5 | 8 | 5 | 0 | 8 | 0 | 2 | 0 | 9 | 0 | 0 | 1 | 9 | 9 | 9 | 8 | 9 | 0 | 9 | 6 |
| Rice Japonica | 8 | 8 | 8 | 8 | 8 | 7 | 7 | 7 | 5 | 7 | 6 | 8 | 8 | 0 | 6 | 5 | 9 | 0 | 4 | 9 | 9 | 9 | 9 | 9 | 9 | 0 | 9 | 8 |
| Umbrella sedge | 8 | 8 | 8 | 8 | 7 | 9 | 9 | 8 | 8 | 9 | 8 | 9 | 8 | 9 | 10 | 9 | 7 | 5 | 7 | 9 | 9 | 9 | 9 | 9 | 9 | 0 | 9 | 9 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (16 g/ha) | 213 | 214 | 217 | 218 | 219 | 225 | 229 | 230 | 231 | 232 | 240 | 241 | 242 | 243 | 244 | 245 | 252 | 254 | 256 | 258 | 259 | 261 | 266 | 267 | 268 | 269 | 270 | 271 |
| | POSTEMERGENCE | | | | | | | | | | | | | | | | | | | | | | | | | | | |
| Barley Igri | 5 | 6 | 9 | 7 | 6 | 9 | 8 | 8 | 8 | 8 | 9 | 9 | 10 | 10 | 9 | 9 | 9 | 5 | 9 | 9 | 8 | 10 | 8 | 9 | 8 | 6 | 9 | 9 |
| Bedstraw | 10 | 10 | 6 | 8 | 10 | 8 | 9 | 9 | 9 | 9 | 10 | 10 | 10 | 10 | 10 | 10 | 10 | 9 | 10 | 9 | 8 | 10 | 9 | 10 | 10 | 8 | 10 | 10 |
| Blackgrass | 8 | 7 | 8 | 7 | 7 | 6 | 9 | 9 | 9 | 10 | 10 | 10 | 10 | 10 | 10 | 10 | 10 | 9 | 9 | 9 | 9 | 9 | 10 | 10 | 9 | 9 | 10 | 10 |
| Chickweed | 10 | 10 | 6 | 9 | 10 | 9 | 8 | 3 | 6 | 10 | 10 | 10 | 10 | — | 10 | 4 | 4 | 10 | 8 | 10 | 8 | 9 | 3 | 9 | 9 | 0 | 6 | 10 |
| Corn | 10 | 9 | 10 | 9 | 7 | 10 | 9 | 9 | 10 | 9 | 10 | 10 | 10 | 10 | 10 | 10 | 10 | 10 | 10 | 10 | 10 | 10 | 10 | 10 | 10 | 6 | 10 | 10 |
| Cotton | 9 | 10 | 6 | 4 | 6 | 7 | 0 | 0 | 5 | 4 | 6 | 9 | 8 | 8 | 9 | 7 | 6 | 8 | 0 | 2 | 3 | 2 | 1 | 7 | 7 | 1 | 8 | 8 |
| Crabgrass | 4 | 3 | 6 | 3 | 0 | 7 | 3 | 0 | 7 | 6 | 6 | 8 | 10 | 10 | 9 | 8 | 2 | 0 | 8 | 9 | 3 | 6 | 0 | 0 | 0 | 0 | 9 | 9 |
| Downy brome | 7 | 7 | 0 | 7 | 6 | 9 | 7 | 5 | 9 | 9 | 9 | 10 | 10 | 10 | 10 | 9 | 10 | 7 | 9 | 9 | 9 | 9 | 8 | 10 | 8 | 6 | 8 | 10 |
| Duck salad | 9 | 9 | 0 | 0 | 0 | 0 | 0 | 2 | 0 | 0 | 6 | 7 | 8 | 8 | 5 | 9 | 0 | 3 | 2 | 3 | 0 | 0 | 0 | 1 | 2 | 0 | 0 | 0 |
| Giant foxtail | 6 | 5 | 7 | 5 | 0 | 8 | 7 | 6 | 6 | 5 | 8 | 10 | 10 | 10 | 10 | 9 | 8 | 2 | 9 | 10 | 9 | 10 | 7 | 4 | 5 | 0 | 8 | 9 |
| Lambsquarters | 10 | 20 | 10 | 10 | 10 | 10 | 8 | 10 | 9 | 10 | 10 | 9 | 10 | 10 | 7 | 9 | 0 | 0 | 10 | 10 | 10 | 9 | 4 | 7 | 0 | 0 | 10 | 10 |
| Morningglory | 10 | 10 | 10 | 10 | 7 | 9 | 9 | 9 | 8 | 7 | 10 | 10 | 10 | 10 | 10 | 10 | 10 | 9 | 10 | 10 | 7 | 10 | 10 | 9 | 10 | 5 | 8 | 9 |
| Pigweed | 10 | 10 | 7 | 7 | 8 | 10 | 8 | 9 | 10 | 4 | 10 | 10 | 10 | 10 | 10 | 10 | 5 | 8 | 9 | 10 | 10 | 9 | 2 | 10 | 9 | 5 | 10 | 9 |
| Rape | 10 | 10 | 9 | 7 | 8 | 10 | 6 | 7 | 9 | 6 | 10 | 10 | 10 | 10 | 10 | 10 | 9 | 9 | 10 | 10 | 8 | 10 | 7 | 9 | 9 | 8 | 9 | 9 |
| Ryegrass | 8 | 6 | 9 | 6 | 7 | 5 | 4 | 0 | 9 | 8 | 10 | 10 | 10 | 10 | 10 | 10 | 4 | 4 | 10 | 9 | 10 | 9 | 0 | 10 | 9 | 4 | 8 | 9 |
| Sorghum | 10 | 10 | 10 | 7 | 4 | 9 | 8 | 8 | 10 | 10 | 10 | 10 | 10 | 10 | 10 | 10 | 9 | 8 | 10 | 10 | 10 | 10 | 9 | 10 | 10 | 7 | 10 | 10 |
| Soybean | 10 | 10 | 7 | 9 | 7 | 10 | 8 | 8 | 9 | 9 | 9 | 10 | 9 | 9 | 9 | 9 | 8 | 9 | 7 | 10 | 8 | 8 | 10 | 9 | 10 | 3 | 5 | 7 |
| Speedwell | 10 | 7 | 3 | 0 | 3 | 5 | 2 | — | — | — | 4 | 4 | — | 10 | 0 | 6 | 3 | 0 | 0 | 0 | 0 | 0 | — | 8 | 0 | 0 | — | 0 |
| Sugar beet | 10 | 10 | — | 9 | 10 | 10 | 6 | 3 | 9 | 8 | 10 | 9 | 10 | 10 | 10 | 10 | 7 | 9 | 8 | 9 | 9 | 8 | 2 | 10 | 10 | 0 | 9 | 9 |
| Velvetleaf | 9 | 4 | 8 | 8 | 8 | 8 | 8 | 6 | 8 | 6 | 6 | 8 | 10 | 10 | 9 | 8 | 4 | 3 | 9 | 9 | 5 | 3 | 7 | 8 | 4 | 0 | 6 | 7 |
| Wheat | 6 | 3 | 9 | 5 | 5 | 6 | 7 | 5 | 9 | 8 | 9 | 9 | 10 | 10 | 9 | 9 | 8 | 0 | 8 | 8 | 7 | 7 | 3 | 9 | 7 | 3 | 9 | 9 |
| Wild buckwheat | 10 | 10 | 7 | 8 | 8 | 8 | 6 | 9 | 9 | 9 | 10 | 10 | 10 | 9 | — | 10 | 7 | 9 | 9 | 9 | 3 | 10 | 8 | 9 | 9 | — | 10 | 10 |
| Wild oat | 6 | 6 | 9 | 5 | 5 | 5 | 8 | 8 | 8 | 0 | 10 | 10 | 10 | 10 | 9 | 9 | 7 | 6 | 9 | 9 | 8 | 8 | 7 | 9 | 7 | 4 | 9 | 9 |
| Barnyardgrass | 9 | 5 | 3 | 6 | 5 | 3 | 0 | 0 | 2 | 0 | 0 | 6 | 9 | 9 | 7 | 9 | 2 | 1 | 6 | 7 | 8 | 9 | 0 | 0 | 0 | 0 | 0 | 0 |
| Rice Japonica | 8 | 8 | 8 | 8 | 8 | 8 | 0 | 0 | 7 | 6 | 6 | 7 | 8 | 9 | 9 | 8 | 5 | 7 | 9 | 8 | 8 | 9 | 0 | 8 | 6 | 5 | 5 | 3 |
| Umbrella sedge | 9 | 9 | 8 | 8 | 8 | 7 | 0 | 0 | 2 | 0 | 7 | 8 | 9 | 8 | 8 | 9 | 8 | 7 | 8 | 9 | 3 | 9 | 2 | 4 | 2 | 0 | 9 | 8 |

TABLE B-continued

| Rate (16 g/ha) | 272 | 274 | 275 | 276 | 283 | 284 | 285 | 286 | 287 | 288 | 289 | 291 | 292 | 300 | 301 | 302 | 305 | 310 |
|---|---|---|---|---|---|---|---|---|---|---|---|---|---|---|---|---|---|---|
| | COMPOUND | | | | | | | | | | | | | | | | | |
| | POSTEMERGENCE | | | | | | | | | | | | | | | | | |
| Barley Igri | 9 | 3 | 8 | 7 | 10 | 10 | 10 | 10 | 10 | 10 | 9 | 9 | 3 | 9 | 9 | 10 | 9 | 9 |
| Bedstraw | 10 | 0 | 10 | 5 | 10 | 10 | 10 | 10 | 10 | 10 | 10 | 10 | 7 | 9 | 10 | 10 | 10 | 10 |
| Blackgrass | 10 | 9 | 10 | 9 | 10 | 9 | 10 | 10 | 10 | 10 | 10 | 10 | 9 | 10 | 10 | 10 | 10 | 8 |
| Chickweed | 10 | 0 | 8 | 0 | 10 | 10 | 10 | 10 | 10 | 10 | 10 | 10 | 8 | 10 | 9 | 10 | 9 | 6 |
| Corn | 10 | 3 | 10 | 8 | 10 | 10 | 10 | 10 | 10 | 10 | 10 | 10 | 10 | 9 | 9 | 10 | 9 | 9 |
| Cotton | 5 | 0 | 5 | 0 | 10 | 10 | 10 | 10 | 10 | 7 | 8 | 7 | 5 | 5 | 7 | 8 | 5 | 6 |
| Crabgrass | 9 | 2 | 10 | 0 | 9 | 8 | 8 | 10 | 9 | 7 | 7 | 9 | 5 | 8 | 8 | 10 | 8 | 2 |
| Downy brome | 9 | 6 | 9 | 6 | 10 | 10 | 10 | 10 | 10 | 9 | 9 | 9 | 3 | 9 | 9 | 9 | 8 | 8 |
| Duck salad | 0 | 0 | 5 | 0 | 8 | 6 | 2 | 6 | o | 9 | 0 | 6 | 0 | 4 | 0 | 7 | 5 | 0 |
| Giant foxtail | 10 | 2 | 10 | 3 | 10 | 10 | 10 | 10 | 10 | 10 | 9 | 10 | 6 | 9 | 9 | 10 | 10 | 8 |
| Lambsquarters | 9 | 0 | 9 | 0 | 10 | 10 | 10 | — | 10 | 10 | 8 | 9 | 5 | 10 | 10 | 10 | 9 | 8 |
| Morningglory | 9 | 0 | 7 | 6 | 8 | 10 | 10 | 10 | 10 | 10 | 8 | 8 | 1 | 6 | 8 | 9 | 8 | 10 |
| Pigweed | 10 | 2 | 9 | 5 | 10 | 10 | 10 | 10 | 10 | 8 | 7 | 9 | 7 | 7 | 9 | 9 | 8 | 6 |
| Rape | 9 | 0 | 9 | 0 | 10 | 10 | 10 | 10 | 10 | 10 | 0 | 9 | 9 | 9 | 9 | 9 | 9 | 9 |
| Ryegrass | 10 | 0 | 10 | 0 | 10 | 7 | 3 | 10 | 9 | 6 | 5 | 9 | 4 | 9 | 9 | 10 | 9 | 4 |
| Sorghum | 10 | 3 | 10 | 8 | 10 | 10 | 10 | 10 | 10 | 10 | 10 | 10 | 9 | 8 | 9 | 10 | 10 | 8 |
| Soybean | 6 | 0 | 6 | 0 | 9 | 9 | 9 | 10 | 10 | 10 | 8 | 8 | 0 | 8 | 9 | 10 | 8 | 9 |
| Speedwell | 0 | 0 | 3 | 0 | 7 | 7 | 0 | 10 | 0 | 10 | 4 | 0 | 8 | 9 | 10 | 5 | 10 | 9 |
| Sugar beet | 9 | 0 | 9 | 2 | 8 | 8 | 9 | 10 | 10 | 10 | 9 | 9 | 9 | 9 | 10 | 10 | 9 | 10 |
| Velvetleaf | 8 | 0 | 5 | 1 | 8 | 10 | 10 | 10 | 5 | 10 | 4 | 6 | 4 | 5 | 5 | 8 | 7 | 9 |
| Wheat | 9 | 6 | 9 | 4 | 9 | 9 | 9 | 10 | 9 | 9 | 9 | 9 | 2 | 9 | 9 | 9 | 9 | 4 |
| Wild buckwheat | 10 | 6 | — | — | 10 | 10 | 10 | 10 | 10 | 10 | — | 9 | 9 | 9 | 8 | 9 | 7 | 8 |
| Wild oat | 9 | 4 | 9 | 6 | 10 | 9 | 9 | 9 | 9 | 9 | 8 | 9 | 4 | 9 | 10 | 10 | 8 | 9 |
| Barnyardgrass | 3 | 0 | 7 | 0 | 8 | 3 | 0 | 9 | 9 | 9 | 0 | 2 | 0 | 4 | 6 | 9 | 9 | 0 |
| Rice Japonica | 8 | 0 | 8 | 1 | 8 | 3 | 3 | 9 | 9 | 8 | 0 | 3 | 2 | 6 | 5 | 4 | 7 | 0 |
| Umbrella sedge | 9 | 0 | 6 | 0 | 9 | 9 | 9 | 8 | 8 | 9 | 8 | 7 | 0 | 0 | 5 | 8 | 5 | 0 |

| Rate (16 g/ha) | 1 | 2 | 3 | 5 | 7 | 11 | 13 | 14 | 25 | 26 | 27 | 28 | 29 | 30 | 31 | 34 | 35 | 36 | 50 | 51 | 53 | 58 | 59 | 60 | 63 | 64 | 71 | 77 | 78 | 81 | 82 | 83 | 84 | 86 | 88 | 89 | 102 | 103 | 107 | 108 |
|---|---|---|---|---|---|---|---|---|---|---|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | | | | | | | | | | | | |
| | PREEMERGENCE | | | | | | | | | | | | | | | | | | | | | | | | | | | | | | | | | | | | | | | |
| Barley Igri | 4 | 6 | 4 | 3 | 0 | 0 | 0 | 0 | 0 | 0 | 0 | 0 | 0 | 0 | 0 | 0 | 0 | 0 | 5 | 9 | 9 | 1 | 6 | 2 | 8 | 8 | 0 | 1 | 3 | 6 | 5 | 4 | 2 | 4 | 5 | 6 | 5 | 6 | 9 | 8 |
| Bedstraw | 7 | 9 | 10 | 10 | 0 | 5 | 8 | 7 | 8 | 8 | 8 | 8 | 9 | 10 | 2 | 6 | 9 | 10 | 9 | 10 | 10 | 8 | 10 | 9 | 9 | 9 | 9 | 0 | 8 | 6 | 9 | 9 | 0 | 9 | 9 | 9 | 8 | 9 | 10 | 10 |
| Blackgrass | 7 | 7 | 6 | 5 | 0 | 6 | 6 | 0 | 8 | 8 | 9 | 7 | 7 | 4 | 3 | 3 | 7 | 7 | 8 | 8 | 9 | 7 | 8 | 6 | 9 | 9 | 5 | 6 | 7 | 9 | 9 | 9 | 8 | 9 | 9 | 9 | 8 | 9 | 9 | 9 |
| Chickweed | 6 | 10 | 9 | 9 | 0 | 10 | 8 | 10 | 5 | 9 | 9 | 7 | 9 | 9 | 0 | 7 | 10 | 10 | 9 | 10 | 10 | 9 | 10 | 10 | 9 | 8 | 7 | 2 | 7 | 6 | 9 | 10 | 2 | 8 | 9 | 9 | 5 | 9 | 9 | 9 |
| Corn | 0 | 6 | 7 | 3 | 0 | 4 | 6 | 2 | 8 | 9 | 5 | 9 | 10 | 10 | 8 | 0 | 2 | 2 | 0 | 9 | 3 | 4 | 6 | 3 | 9 | 9 | 0 | 0 | 4 | — | — | — | 9 | 3 | 3 | 7 | 2 | 0 | 10 | 9 |
| Cotton | 0 | 3 | 5 | 7 | 0 | 3 | 6 | 2 | 5 | 7 | 7 | 5 | 9 | 8 | 0 | 0 | 7 | 8 | 7 | 10 | 8 | 3 | 9 | 9 | 8 | 9 | 6 | 0 | 6 | — | — | — | 8 | 9 | — | 4 | 2 | 8 | 10 | 10 |
| Crabgrass | 0 | 6 | 6 | 6 | 0 | 0 | 0 | 0 | 7 | 9 | 8 | 7 | 9 | 9 | 2 | 4 | 4 | 8 | 7 | 10 | 9 | 5 | 4 | 0 | 9 | 9 | 0 | 0 | 5 | — | — | — | 2 | 4 | 0 | 5 | 0 | 0 | 8 | 8 |
| Downy brome | 6 | 7 | 5 | 10 | 4 | 0 | 5 | 0 | 2 | 2 | 3 | 5 | 5 | 5 | 0 | 0 | 1 | 7 | 5 | 9 | 9 | 5 | 7 | 6 | 9 | 8 | 0 | 5 | 2 | 6 | 7 | 5 | 3 | 5 | 4 | 5 | 3 | 6 | 9 | 7 |
| Duck salad | — | — | — | — | — | — | — | — | — | — | — | — | — | — | — | — | — | — | — | — | — | — | — | — | — | — | — | — | — | — | — | — | — | — | — | — | — | — | — | — |
| Giant foxtail | 2 | 7 | 6 | 3 | 0 | 5 | 0 | 0 | 6 | 8 | 8 | 7 | 8 | 9 | 6 | 4 | 2 | 8 | 7 | 8 | 9 | 4 | 0 | 0 | 9 | 9 | 0 | 3 | 5 | — | — | — | 2 | 7 | 5 | 5 | 4 | 5 | 9 | 7 |
| Lambsquarters | 9 | 9 | 9 | 10 | — | 8 | 9 | 8 | 3 | 8 | 7 | 5 | 9 | 8 | 5 | — | 10 | 10 | 10 | 10 | 10 | 8 | 10 | 10 | 10 | 10 | 8 | 2 | 6 | 9 | 9 | 9 | — | 10 | 6 | 9 | 9 | 9 | 10 | 10 |
| Morningglory | 0 | 0 | 5 | 7 | 0 | 1 | 2 | 0 | 6 | 6 | 2 | 5 | 9 | 9 | 0 | 0 | 3 | 8 | 9 | 9 | 5 | 0 | 10 | 10 | 8 | 9 | 8 | 0 | 8 | — | — | — | 5 | 8 | 5 | 6 | 7 | 7 | 10 | 10 |
| Pigweed | 6 | 9 | 7 | 8 | 4 | 3 | 5 | 5 | 7 | 8 | 8 | 8 | 9 | 9 | 7 | 8 | 7 | 9 | 10 | 10 | 10 | 9 | 9 | 9 | 9 | 9 | 9 | 8 | 8 | — | — | — | 3 | 8 | 8 | 8 | 8 | 9 | 9 | 10 |

TABLE B-continued

| | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| Rape | 6 | 8 | 8 | 10 | 0 | 3 | 8 | 6 | 5 | 2 | 5 | 3 | 7 | 8 | 2 | 0 | 3 | 7 | 9 | 9 | 9 | 10 | 10 | 10 | 10 | 10 | 9 | 8 | 9 | 9 | 9 | 9 | 3 | 9 | 9 | 9 | 9 | 9 | 9 | 10 |
| Ryegrass | 4 | 2 | 0 | 6 | 0 | 3 | 5 | 2 | 3 | 4 | 4 | 4 | 3 | 4 | 0 | 0 | 4 | 6 | 9 | 9 | 9 | 7 | 10 | 8 | 9 | 9 | 3 | 2 | 5 | 4 | 4 | 5 | 4 | 5 | 5 | 6 | 0 | 0 | 10 | 9 |
| Sorghum | 4 | 7 | 8 | 8 | 3 | 3 | 5 | 4 | 10 | 10 | 9 | 9 | 10 | 10 | 3 | 3 | 9 | 8 | 7 | 10 | 9 | 9 | 8 | 7 | 9 | 9 | 6 | 5 | 7 | — | — | — | 9 | 9 | 9 | 8 | 8 | 9 | 9 | 10 |
| Soybean | 3 | 4 | 3 | 6 | 0 | 0 | 0 | 0 | 3 | 3 | 4 | 2 | 9 | 8 | 0 | 2 | 0 | 5 | 6 | 8 | 6 | 3 | 7 | 7 | 8 | 8 | 7 | 2 | 6 | — | — | — | 7 | 5 | 7 | 6 | 0 | 2 | 10 | 8 |
| Speedwell | 6 | 9 | — | 10 | 0 | 4 | 8 | 6 | 8 | 8 | 0 | 7 | 9 | 0 | 0 | 5 | 8 | 7 | 9 | 10 | 10 | 8 | 10 | 8 | 9 | 8 | 2 | 0 | 0 | 9 | 9 | 9 | 7 | 9 | 9 | 9 | 9 | 8 | 10 | 7 |
| Sugar beet | 6 | 8 | 7 | 10 | 0 | 8 | 8 | 7 | 5 | 9 | 8 | 8 | 9 | 10 | 2 | 6 | 10 | 10 | 9 | 9 | 9 | 9 | 10 | 10 | 10 | 10 | 9 | 2 | 9 | 9 | 9 | 9 | 3 | 9 | 9 | 9 | 9 | 9 | 10 | 10 |
| Velvetleaf | 3 | 7 | — | 8 | 0 | 1 | 5 | 0 | 7 | 7 | 7 | 7 | 8 | 8 | 0 | 0 | 5 | 5 | 7 | 9 | 7 | 6 | 10 | 7 | 8 | 9 | 9 | 0 | 6 | — | — | — | 4 | 7 | 4 | 5 | 5 | 8 | 10 | 9 |
| Wheat | 5 | 6 | 4 | 7 | 0 | 0 | 0 | 0 | 2 | 2 | 0 | 0 | 2 | 1 | 0 | 0 | 0 | 0 | 5 | 9 | 9 | 0 | 5 | 3 | 7 | 8 | 0 | 0 | 1 | 5 | 4 | 3 | 3 | 3 | 2 | 3 | 2 | 5 | 8 | 0 |
| Wild buckwheat | 9 | 9 | 9 | 10 | 0 | 4 | 8 | 5 | 4 | 7 | 2 | 5 | 8 | 8 | 0 | 0 | 9 | 9 | 8 | 9 | 9 | 3 | 9 | 8 | 9 | 8 | 5 | 1 | 6 | 9 | 9 | 8 | 0 | 8 | 9 | 8 | 8 | 9 | 9 | 9 |
| Wild oat | 1 | 3 | 0 | 2 | 0 | 0 | 0 | 0 | 2 | 2 | 0 | 2 | 2 | 2 | 0 | 0 | 3 | 0 | 4 | 9 | 7 | 2 | 6 | 6 | 5 | 4 | 0 | 0 | 0 | 5 | 4 | 2 | 3 | 2 | 0 | 0 | 2 | 3 | 7 | 7 |
| Barnyardgrass | — | — | — | — | — | — | — | — | — | — | — | — | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — | — | — | — | — | — | — | — | — | — | — | — | — |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (16 g/ha) | 109 | 110 | 111 | 112 | 114 | 115 | 116 | 117 | 118 | 119 | 120 | 121 | 122 | 125 | 166 | 167 | 170 | 172 | 173 | 203 | 204 | 205 | 206 | 207 | 208 | 209 | 211 | 212 |
| PREEMERGENCE | | | | | | | | | | | | | | | | | | | | | | | | | | | | |
| Barley Igri | 8 | 6 | 2 | 0 | 5 | 0 | 7 | 3 | 0 | 9 | 6 | 9 | 8 | 0 | 2 | 0 | 0 | 0 | 0 | 5 | 8 | 8 | 5 | 6 | 8 | 0 | 3 | 0 |
| Bedstraw | 9 | 10 | 9 | 10 | 9 | 9 | 9 | 9 | 7 | 9 | — | 9 | 10 | 5 | 9 | 7 | 9 | 3 | 0 | 5 | 8 | 10 | 9 | 9 | 9 | 0 | 9 | 2 |
| Blackgrass | 10 | 10 | 9 | 9 | 9 | 9 | 9 | 7 | 5 | 10 | 10 | 10 | 9 | 5 | 8 | 8 | 7 | 7 | 9 | 7 | 9 | 9 | 9 | 8 | 8 | 0 | 8 | 7 |
| Chickweed | 9 | 9 | 8 | 9 | 8 | 8 | 9 | 9 | 7 | 10 | 10 | 10 | 10 | 8 | 9 | 9 | 9 | 2 | 2 | 7 | 9 | 9 | 8 | 9 | 9 | 0 | 9 | 10 |
| Corn | 5 | 8 | 2 | 3 | 9 | 4 | 8 | 4 | 3 | 9 | 7 | 10 | 9 | 0 | 6 | 4 | 10 | 2 | 3 | 3 | 7 | 10 | 10 | 9 | 8 | 0 | 6 | 5 |
| Cotton | 10 | 9 | 9 | 5 | 8 | 2 | 2 | 9 | 9 | 3 | 7 | 6 | 10 | 9 | 0 | 5 | 0 | 9 | 4 | — | 6 | 4 | 8 | 8 | 7 | 0 | 4 | 4 |
| Crabgrass | 8 | 6 | 0 | 3 | 7 | 2 | 8 | 2 | 0 | 6 | 5 | 2 | 5 | 0 | 8 | 4 | 8 | 5 | 5 | 7 | 8 | 10 | 8 | 8 | 8 | 0 | 8 | 5 |
| Downy brome | 9 | 9 | 4 | 6 | 5 | 3 | 6 | 4 | 2 | 10 | 5 | 8 | 8 | 0 | 5 | 4 | 6 | 4 | 0 | 8 | 9 | 9 | 9 | 8 | 9 | 0 | 8 | 3 |
| Duck salad | — | — | — | — | — | — | — | — | — | — | — | — | — | — | — | — | — | — | — | — | — | — | — | — | — | — | — | — |
| Giant foxtail | 8 | 9 | 4 | 3 | 8 | 4 | 8 | 2 | 0 | 8 | 6 | 2 | 2 | 0 | 7 | 2 | 8 | 7 | 7 | 0 | 9 | 9 | 8 | 9 | 9 | 0 | 8 | 4 |
| Lambsquarters | 9 | 10 | 9 | 9 | 9 | 8 | 9 | 8 | 9 | 10 | 10 | 10 | 9 | 9 | 8 | 9 | 9 | 9 | 9 | 8 | 9 | 10 | 10 | 9 | 9 | 0 | 9 | — |
| Morningglory | 6 | 7 | 6 | 8 | 8 | 7 | 9 | 10 | 5 | 8 | 8 | 9 | 9 | 2 | 5 | 2 | 8 | 3 | 2 | 4 | 7 | 9 | 8 | 8 | 8 | 0 | 0 | 4 |
| Pigweed | 9 | 10 | 9 | 9 | 9 | 9 | 9 | 8 | 6 | 9 | 8 | 9 | 9 | 8 | 8 | 6 | 9 | 9 | 8 | 8 | 10 | 10 | 10 | 9 | 10 | 0 | 9 | 6 |
| Rape | 9 | 9 | 7 | 9 | 9 | 8 | 9 | 9 | 4 | 10 | 10 | 10 | 10 | 8 | 9 | — | 9 | 2 | 0 | 10 | 9 | 9 | 6 | 8 | 10 | 0 | 8 | 1 |
| Ryegrass | 9 | 9 | 4 | 7 | 8 | 3 | 8 | 5 | 4 | 8 | 5 | 9 | 9 | 0 | 6 | 3 | 6 | 2 | 5 | 7 | 8 | 9 | 9 | 8 | 9 | 0 | 3 | 0 |
| Sorghum | 9 | 9 | 4 | 5 | 9 | 7 | 9 | 9 | 0 | 9 | 4 | 9 | 9 | 0 | 9 | 9 | 9 | 4 | 4 | 7 | 9 | 9 | 10 | 10 | 10 | 0 | 10 | 5 |
| Soybean | 8 | 6 | 4 | 3 | 3 | 0 | 8 | 6 | 0 | 8 | 5 | 10 | 7 | 0 | 5 | 0 | 8 | 2 | 3 | 4 | 6 | 7 | 7 | 6 | 6 | 0 | 5 | 3 |
| Speedwell | 9 | 10 | 8 | 9 | 9 | 8 | 10 | 7 | 9 | 10 | 9 | 10 | 4 | 8 | 10 | 2 | 10 | 9 | 9 | 4 | 7 | 7 | 9 | 3 | 9 | 0 | 9 | 9 |
| Sugar beet | 9 | 9 | 9 | 9 | 9 | 7 | 9 | 9 | 4 | 10 | 10 | 10 | 10 | 9 | 10 | 9 | 10 | 6 | 6 | 8 | 10 | 9 | 9 | 9 | 9 | 2 | 9 | — |
| Velvetleaf | 9 | 7 | 7 | 3 | 7 | 7 | 9 | 8 | 0 | 8 | 7 | 8 | 8 | 3 | 6 | 4 | 9 | 4 | 4 | 7 | 7 | 8 | 9 | 8 | 8 | 0 | 7 | 2 |
| Wheat | 8 | 7 | 3 | 2 | 0 | 0 | 0 | 0 | 0 | 8 | 6 | 9 | 8 | 0 | 3 | 0 | 6 | 2 | 0 | 5 | 8 | 6 | 9 | 8 | 9 | 0 | 5 | 0 |
| Wild buckwheat | — | 7 | — | 9 | 9 | 9 | 9 | 9 | 9 | 10 | 10 | 9 | 10 | 8 | 5 | 7 | 8 | 9 | 9 | 9 | 9 | 9 | 8 | 7 | 8 | 3 | 8 | 4 |
| Wild oat | 7 | 8 | 0 | 0 | 4 | 0 | 7 | 4 | 0 | 6 | 3 | 9 | 8 | 0 | 2 | 0 | 0 | 0 | 0 | 5 | 6 | 7 | 4 | 5 | 5 | 0 | 2 | 0 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |

TABLE B-continued

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (16 kg/ha) | 213 | 214 | 217 | 218 | 219 | 225 | 229 | 230 | 231 | 232 | 240 | 241 | 242 | 243 | 244 | 245 | 252 | 254 | 256 | 258 | 259 | 261 | 266 | 267 | 268 | 269 | 270 | 271 |
| | PREEMERGENCE | | | | | | | | | | | | | | | | | | | | | | | | | | | |
| Barley Igri | 4 | 4 | 5 | 4 | 0 | 2 | 8 | 0 | 8 | 4 | 7 | 7 | 4 | 7 | 5 | 9 | 0 | 4 | 8 | 4 | 2 | 9 | 0 | 8 | 4 | 0 | 6 | 8 |
| Bedstraw | 10 | 10 | 2 | 5 | 8 | 7 | 3 | 0 | 8 | 7 | 9 | 9 | 10 | 10 | 10 | 10 | 6 | 9 | 9 | 9 | 0 | 9 | 7 | 9 | 9 | 0 | 5 | 8 |
| Blackgrass | 8 | 7 | 8 | 7 | 5 | 5 | 5 | 6 | 8 | 7 | 10 | 10 | 10 | 10 | 10 | 10 | 9 | 8 | 10 | 10 | 9 | 9 | 9 | 9 | 9 | 8 | 9 | 10 |
| Chickweed | 10 | 9 | 3 | 10 | 9 | 7 | 2 | 5 | 0 | 0 | 9 | 10 | 9 | 9 | 10 | 8 | 9 | 9 | 0 | 9 | 0 | 9 | 4 | 6 | 3 | 0 | 0 | 8 |
| Corn | 10 | 10 | 3 | 3 | 0 | 3 | 1 | 0 | 0 | 5 | 9 | 9 | 9 | 10 | 10 | 9 | 6 | 4 | 8 | 5 | 8 | 9 | 0 | 5 | 3 | 0 | 4 | 3 |
| Cotton | 10 | 10 | 5 | — | 2 | 9 | 0 | 0 | 8 | 4 | 3 | 3 | 5 | 10 | 9 | 6 | 0 | 9 | 3 | 5 | 5 | 4 | 0 | 7 | 8 | 0 | 8 | 2 |
| Crabgrass | 7 | 4 | 3 | 3 | 0 | 0 | 2 | 2 | 4 | 4 | 8 | 9 | 9 | 7 | 9 | 8 | 0 | 0 | 6 | 4 | 7 | 5 | 2 | 5 | 4 | 0 | 7 | 7 |
| Downy brome | 8 | 7 | 9 | 6 | 5 | 4 | 5 | 0 | 9 | 10 | 9 | 10 | 9 | 10 | 9 | 9 | 6 | 8 | 9 | 8 | 9 | 9 | 4 | 10 | 9 | 0 | 8 | 10 |
| Duct salad | — | — | — | — | — | — | — | — | — | — | — | — | — | — | — | — | — | — | — | — | — | — | — | — | — | — | — | — |
| Giant foxtail | 7 | 2 | 3 | 4 | 0 | 2 | 4 | 1 | 3 | 3 | 6 | 9 | 9 | 7 | 9 | 7 | 0 | 0 | 6 | 8 | 5 | 6 | 0 | 5 | — | 0 | 5 | 7 |
| Lambsquarters | 10 | 9 | 7 | — | 8 | 8 | — | 4 | 4 | 2 | 10 | 10 | 9 | 9 | 9 | 10 | 7 | 7 | 8 | 10 | 9 | 9 | 9 | 9 | 8 | 2 | 7 | 8 |
| Morningglory | 10 | 9 | 2 | 3 | 0 | 7 | 0 | 0 | 8 | 7 | 6 | 5 | 6 | 9 | 8 | 8 | 0 | 9 | 3 | 4 | 2 | 8 | 2 | 7 | 7 | 0 | 0 | 6 |
| Pigweed | 10 | 9 | 7 | 8 | 6 | 6 | 9 | 5 | 8 | 8 | 8 | 9 | 10 | 10 | 10 | 9 | 5 | 8 | 5 | 8 | 8 | 8 | 2 | 7 | 7 | 0 | 9 | 9 |
| Rape | 10 | 10 | 6 | 3 | 5 | 4 | 0 | 0 | 0 | 0 | 9 | 9 | 7 | 10 | 9 | 9 | 6 | 9 | 9 | 7 | 3 | 9 | 3 | 6 | 5 | 0 | 0 | 0 |
| Ryegrass | 7 | 5 | 5 | 2 | 2 | 0 | 0 | 0 | 3 | 2 | 7 | 9 | 9 | 10 | 8 | 10 | 0 | 6 | 9 | 9 | 8 | 6 | 0 | 6 | 0 | 0 | 4 | 3 |
| Sorghum | 10 | 8 | 9 | 5 | 0 | 9 | 7 | 2 | 9 | 9 | 9 | 9 | 9 | 10 | 10 | 9 | 3 | 8 | 9 | 7 | 8 | 9 | 5 | 9 | 8 | 0 | 2 | 3 |
| Soybean | 9 | 8 | 2 | 4 | 2 | 7 | 1 | 0 | 8 | 8 | 5 | 6 | 7 | 9 | 8 | 5 | 2 | 8 | 4 | 5 | 4 | 2 | 2 | 5 | 6 | 0 | 0 | 0 |
| Speedwell | 10 | 5 | 9 | — | 0 | 9 | 7 | 5 | 0 | 0 | 9 | 10 | 4 | 10 | 0 | 10 | 10 | 8 | 8 | 0 | 4 | 9 | 6 | 10 | 0 | 9 | 8 | 4 |
| Sugar beet | 10 | 9 | 8 | 7 | 8 | 8 | 0 | 4 | 4 | 3 | 9 | 9 | 9 | 9 | 9 | 9 | 4 | 9 | 9 | 7 | 8 | 8 | 1 | 8 | 8 | — | 9 | 5 |
| Velvetleaf | 10 | 7 | 5 | 4 | 0 | 8 | 5 | 0 | 8 | 2 | 6 | 7 | 6 | 9 | 8 | 7 | 0 | 2 | 6 | 8 | 5 | 3 | 6 | 5 | 3 | 0 | 2 | 3 |
| Wheat | 7 | 2 | 5 | 6 | 0 | 0 | 5 | 3 | 9 | 5 | 8 | 5 | 3 | 9 | 4 | 9 | 0 | 0 | 8 | 4 | 7 | 7 | 0 | 3 | 0 | 0 | 6 | 8 |
| Wild buckwheat | 9 | 9 | 2 | 0 | 8 | 8 | 4 | 4 | 0 | — | 9 | 9 | 8 | 9 | 9 | 8 | 3 | 9 | 9 | 9 | 7 | 9 | 7 | 8 | 8 | 3 | 8 | 9 |
| Wild oat | 5 | 4 | 3 | 2 | 0 | 0 | 0 | 0 | 3 | 2 | — | 4 | 3 | 9 | 3 | 8 | 0 | 3 | 8 | 4 | 2 | 6 | 0 | 5 | 0 | 0 | 7 | 6 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |

| | COMPOUND | | | | | | | | | | | | | | | | | |
|---|---|---|---|---|---|---|---|---|---|---|---|---|---|---|---|---|---|---|
| Rate (16 g/ha) | 272 | 274 | 275 | 276 | 283 | 284 | 285 | 286 | 287 | 288 | 289 | 291 | 292 | 300 | 301 | 302 | 305 | 310 |
| | PREEMERGENCE | | | | | | | | | | | | | | | | | |
| Barley Igri | 1 | 0 | 9 | 0 | 9 | 9 | 0 | 9 | 0 | 9 | 0 | 3 | 0 | 0 | 0 | 0 | 3 | 0 |
| Bedstraw | 8 | 0 | 10 | 0 | 10 | 8 | — | 10 | 10 | 10 | 6 | 2 | 0 | 0 | 5 | 7 | 7 | 4 |
| Blackgrass | 10 | 6 | 10 | 0 | 10 | 10 | 9 | 10 | 9 | 9 | 9 | 7 | 0 | 7 | 7 | 9 | 9 | 0 |
| Chickweed | 10 | 0 | 10 | 0 | 10 | 10 | 10 | 10 | 10 | 10 | 8 | 8 | 2 | 3 | 9 | 10 | 6 | 4 |
| Corn | 0 | 0 | 5 | 0 | 4 | 4 | 2 | 6 | 0 | 3 | 2 | 2 | 0 | 2 | 0 | 2 | 3 | 2 |
| Cotton | 5 | 0 | 7 | 0 | 5 | 5 | 6 | 9 | 8 | 7 | 0 | 3 | 0 | 2 | 3 | 8 | 5 | 8 |
| Crabgrass | 8 | 0 | 8 | 0 | 6 | 6 | 0 | 8 | 7 | 7 | 0 | 5 | 0 | 0 | 0 | 7 | 3 | 0 |
| Downy brome | 9 | 0 | 9 | 0 | 10 | 9 | 0 | 10 | 10 | 9 | 5 | 4 | 0 | 3 | 3 | 7 | 3 | 0 |
| Duck salad | — | — | — | — | — | — | — | — | — | — | — | — | — | — | — | — | — | — |
| Giant foxtail | 9 | 0 | 9 | 0 | 6 | 6 | 1 | 9 | 4 | 6 | 2 | 8 | 0 | 2 | 2 | 9 | 5 | 0 |
| Lamsquarters | 7 | 0 | 6 | 0 | 9 | 10 | 9 | 9 | 10 | 10 | 0 | 8 | 0 | 2 | 9 | 10 | 8 | 0 |
| Morningglory | 0 | 0 | 2 | 0 | 5 | 5 | 2 | 9 | 5 | 5 | 0 | 0 | 0 | 0 | 3 | 3 | 6 | 2 |
| Pigweed | 10 | 0 | 9 | 0 | 9 | 9 | 8 | 9 | 9 | 9 | 8 | 9 | 0 | 7 | 7 | 9 | 8 | 3 |

TABLE B-continued

| | | | | | | | | | | | | | | | | | | |
|---|---|---|---|---|---|---|---|---|---|---|---|---|---|---|---|---|---|---|
| Rape | 7 | 0 | 9 | 0 | — | 9 | 6 | 10 | 10 | 9 | 0 | 5 | 0 | 4 | 4 | 4 | 0 | 0 |
| Ryegrass | 5 | 0 | 6 | 0 | 10 | 2 | 0 | 9 | 4 | 5 | 0 | 4 | 0 | 0 | 0 | 4 | 0 | 0 |
| Sorghum | 2 | 0 | 10 | 2 | 9 | 6 | 0 | 9 | 5 | 4 | 2 | 4 | 0 | 2 | 2 | 5 | 8 | 0 |
| Soybean | 0 | 0 | 2 | 0 | 2 | 0 | 1 | 9 | 2 | 3 | 0 | 0 | 0 | 0 | 0 | 4 | 0 | 2 |
| Speedwell | 0 | 0 | 7 | 5 | 10 | 10 | 2 | 10 | 0 | 10 | 9 | 7 | — | 5 | 10 | 10 | 10 | 9 |
| Sugar beet | 9 | 0 | 9 | 0 | 9 | 8 | 9 | 10 | 10 | 10 | 7 | 9 | 0 | 6 | 9 | 10 | 9 | — |
| Velevtleaf | 3 | 0 | 2 | 0 | 5 | 7 | 5 | 9 | 0 | 7 | 0 | 2 | 0 | 3 | 3 | 6 | 5 | 6 |
| Wheat | 6 | 0 | 9 | 0 | 9 | 9 | 0 | 9 | 3 | 4 | 0 | 2 | 0 | 2 | 4 | 2 | 0 | 0 |
| Wild buckwheat | — | — | 10 | — | 9 | 9 | 9 | 9 | 9 | 9 | 7 | 3 | 0 | 3 | 6 | 9 | 8 | 9 |
| Wild oat | 0 | 0 | 4 | 0 | 7 | 0 | 0 | 0 | 2 | 0 | 2 | 3 | 0 | 0 | 0 | 0 | 0 | 0 |
| Barnyardgrass | — | — | — | — | — | — | — | — | — | — | — | — | — | — | — | — | — | — |
| Rice Japonica | — | — | — | — | — | — | — | — | — | — | — | — | — | — | — | — | — | — |
| Umbrella sedge | — | — | — | — | — | — | — | — | — | — | — | — | — | — | — | — | — | — |

| | COMPOUND | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| Rate (8 g/ha) | 1 | 2 | 3 | 5 | 7 | 11 | 13 | 14 | 25 | 26 | 27 | 28 | 29 | 30 | 31 | 34 | 35 | 36 | 50 | 51 | 53 | 58 | 59 | 60 | 63 | 64 | 71 | 77 | 78 | 81 | 82 | 83 | 84 | 86 | 88 | 89 | 102 | 103 | 107 | 108 |
| POSTEMERGENCE | | | | | | | | | | | | | | | | | | | | | | | | | | | | | | | | | | | | | | | | |
| Barley Igri | 5 | 6 | 5 | 8 | 5 | 9 | 8 | 7 | 7 | 8 | 9 | 8 | 10 | 9 | 7 | 5 | 2 | 3 | 7 | 7 | 8 | 2 | 5 | 2 | 7 | 6 | 0 | 0 | 0 | 2 | 4 | 5 | 4 | 5 | 3 | 5 | 8 | 8 | 8 | 6 |
| Bedstraw | 8 | 8 | — | 10 | 0 | 3 | 3 | 3 | 9 | 10 | 10 | 10 | 10 | 10 | 5 | 3 | 7 | 10 | 8 | 9 | 7 | 9 | 10 | 10 | 6 | 7 | 5 | 2 | 5 | 5 | 7 | 9 | 7 | 6 | 8 | 10 | 8 | 8 | 10 | 10 |
| Blackgrass | 5 | 8 | 7 | 9 | 5 | 7 | 6 | 3 | 8 | 10 | 10 | 9 | 9 | 10 | 6 | 3 | 7 | 5 | 9 | 8 | 8 | 8 | 7 | 6 | 9 | 9 | 2 | 5 | 6 | 9 | 9 | 9 | 9 | 8 | 8 | 9 | 9 | 8 | 10 | 8 |
| Chickweed | 5 | 5 | 6 | 9 | 0 | 9 | 8 | 8 | 9 | 10 | 10 | 3 | 10 | 10 | — | 8 | 3 | 9 | 8 | 10 | 8 | 4 | 10 | 10 | 6 | 9 | 9 | 1 | 3 | 5 | 10 | 9 | 7 | 2 | 8 | 5 | 5 | 8 | 10 | 10 |
| Corn | 6 | 8 | 10 | 10 | 6 | 9 | 10 | 9 | 9 | 10 | 10 | 10 | 10 | 10 | 8 | 10 | 10 | 10 | 6 | 9 | 6 | 8 | 9 | 4 | 7 | 10 | 3 | 3 | 7 | 0 | 4 | 6 | 6 | 0 | 1 | 7 | 0 | 0 | 10 | 10 |
| Cotton | 4 | 4 | 6 | 6 | 2 | 5 | 4 | 6 | 3 | 4 | 7 | 6 | 9 | 9 | 3 | 0 | 4 | 7 | 9 | 10 | 10 | 7 | 9 | 10 | 6 | 8 | 8 | 3 | 6 | 5 | — | 9 | 8 | 4 | 7 | 4 | 2 | 7 | 10 | 10 |
| Crabgrass | 6 | 5 | 5 | 7 | 3 | 4 | 6 | 6 | 5 | 4 | 6 | 3 | 7 | 8 | 4 | 6 | 3 | 5 | 3 | 5 | 5 | 0 | 0 | 0 | 3 | 6 | 3 | 3 | 0 | 2 | 2 | 5 | 2 | 0 | 0 | 0 | 0 | 0 | 5 | 0 |
| Downy brome | 6 | 5 | 4 | 10 | 5 | 6 | 2 | 2 | 10 | 8 | 9 | 7 | 10 | 10 | 2 | 5 | 3 | 7 | 6 | 7 | 9 | 2 | 6 | 2 | 8 | 7 | 0 | 1 | 0 | 3 | 2 | 2 | 0 | 3 | 5 | 0 | 7 | 6 | 8 | 3 |
| Duck salad | — | — | — | — | — | — | — | — | — | — | — | — | — | — | — | — | — | — | 9 | 9 | 9 | 7 | 10 | 10 | 8 | 8 | 9 | 0 | 4 | 0 | 6 | 7 | 0 | 7 | 0 | 7 | 0 | 0 | 10 | 9 |
| Giant foxtail | 6 | 6 | 8 | 7 | 6 | 8 | 6 | 9 | 10 | 10 | 10 | 6 | 10 | 10 | 7 | 7 | 7 | 8 | 6 | 6 | 8 | 3 | 3 | 0 | 7 | 9 | 0 | 5 | 6 | 5 | 6 | 7 | 4 | 4 | 2 | 0 | 4 | 2 | 6 | 2 |
| Lambsquarters | 9 | 10 | 10 | 10 | 8 | 9 | 8 | 5 | 10 | 10 | 10 | 9 | 10 | 10 | 9 | 5 | 10 | 10 | 10 | 10 | 10 | 7 | 10 | 10 | 10 | 10 | 5 | 8 | 8 | 5 | 8 | 10 | 9 | 9 | 8 | 9 | 9 | 9 | 10 | 10 |
| Morningglory | 6 | 10 | 7 | 6 | 6 | 6 | 4 | 6 | 10 | 10 | 10 | 10 | 10 | 10 | 6 | 7 | 9 | 10 | 10 | 10 | 8 | 10 | 8 | 9 | 9 | 10 | 9 | 7 | 8 | 8 | 10 | 10 | 7 | 8 | 9 | 10 | 7 | 8 | 10 | 10 |
| Pigweed | 3 | 4 | 3 | 10 | 0 | 7 | 8 | 0 | 7 | 6 | 10 | 8 | 10 | 9 | 6 | 7 | 7 | 8 | 9 | 10 | 8 | 3 | 10 | 8 | 10 | 10 | 10 | 7 | 9 | 7 | 8 | 10 | 8 | 4 | 2 | 2 | 7 | 9 | 10 | 8 |
| Rape | 2 | 5 | 7 | 10 | 0 | 6 | 10 | 10 | 3 | 6 | 9 | 9 | 10 | 10 | 0 | 3 | 0 | 9 | 10 | 10 | 10 | 9 | 10 | 10 | 10 | 10 | 5 | 7 | 8 | 8 | 9 | 7 | 9 | 9 | 9 | 10 | 9 | 7 | 10 | 9 |
| Ryegrass | 6 | 3 | 0 | 9 | 4 | 5 | 3 | 2 | 10 | 10 | 9 | 8 | 10 | 9 | 0 | 5 | 4 | 7 | 5 | 9 | 8 | 0 | 9 | 4 | 7 | 8 | 0 | 2 | 2 | 0 | 4 | 0 | 0 | 0 | 3 | 0 | 3 | 2 | 10 | 7 |
| Sorghum | 6 | 7 | 8 | 10 | 7 | 7 | 10 | 7 | 10 | 10 | 10 | 10 | 10 | 10 | 8 | 7 | 8 | 10 | 7 | 9 | 6 | 6 | 4 | 4 | 10 | 10 | 4 | 7 | 7 | 10 | 9 | 10 | 9 | 9 | 7 | 8 | 9 | 9 | 10 | 9 |
| Soybean | 6 | 7 | 7 | 10 | 0 | 7 | 10 | 8 | 8 | 10 | 10 | 10 | 10 | 10 | 6 | 7 | 10 | 10 | 10 | 10 | 10 | 10 | 10 | 10 | 9 | 10 | 9 | 7 | 8 | 7 | 8 | 9 | 8 | 6 | 8 | 9 | 5 | 8 | 10 | 10 |
| Speedwell | 4 | 4 | 0 | 8 | 0 | 0 | 2 | 0 | 5 | 2 | 0 | 5 | 8 | 0 | 0 | 0 | 0 | 0 | 4 | 9 | 7 | 9 | 10 | 6 | — | — | 0 | 2 | 2 | 2 | 4 | 0 | — | — | 8 | 4 | — | — | — | — |
| Sugar beet | 9 | 10 | 9 | 10 | 3 | 9 | 9 | 6 | 6 | 8 | 10 | 9 | 10 | 10 | 6 | 8 | 9 | 10 | 9 | 10 | 9 | 7 | 10 | 10 | 10 | 10 | 3 | 9 | 8 | 6 | 9 | 10 | 9 | 8 | 9 | 9 | 9 | 9 | 10 | 10 |
| Velevtleaf | 5 | 5 | 5 | 7 | 0 | 4 | 6 | 0 | 6 | 8 | 8 | 8 | 7 | 10 | 4 | 5 | 6 | 6 | 10 | 10 | 10 | 10 | 7 | 5 | 9 | 10 | 7 | 3 | 7 | 5 | 9 | 9 | 4 | 6 | 2 | 6 | 1 | 7 | 10 | 6 |
| Wheat | 5 | 4 | 0 | 9 | 4 | 9 | 8 | 8 | 8 | 4 | 9 | 5 | 10 | 9 | 4 | 4 | 4 | 4 | 5 | 8 | 9 | 0 | 0 | 0 | 7 | 7 | 0 | 0 | 0 | 0 | 3 | 2 | 2 | 2 | 4 | 3 | 8 | 6 | 8 | 3 |
| Wild buckwheat | 9 | 6 | 6 | — | 0 | 8 | 2 | 3 | 8 | 6 | 9 | 9 | 10 | 10 | 0 | 0 | 0 | 3 | 6 | 10 | 7 | 5 | 10 | 10 | 6 | 7 | 0 | 2 | 5 | 9 | 7 | 8 | 4 | 5 | 8 | 8 | 5 | 5 | 9 | 10 |
| Wild oat | 8 | 7 | 7 | 7 | 4 | 8 | 2 | 2 | 8 | 8 | 8 | 6 | 7 | 9 | 6 | 5 | 7 | 8 | 4 | 8 | 6 | 2 | 5 | 3 | 5 | 5 | 0 | 0 | 0 | 4 | 0 | 0 | 5 | 0 | 2 | 0 | 5 | 5 | 9 | 7 |
| Barnyardgrass | 0 | 0 | 0 | 5 | 0 | 3 | 3 | 0 | 3 | 7 | 4 | 8 | 6 | 5 | 0 | 0 | 0 | 7 | 5 | 9 | 9 | 7 | 7 | 5 | 8 | 8 | 0 | 0 | 5 | 2 | 8 | 8 | 3 | 8 | 0 | 2 | 0 | 2 | 8 | 7 |
| Rice Japonica | 3 | 2 | 0 | 8 | 0 | 0 | 4 | 4 | 3 | 3 | 0 | 8 | 8 | 8 | 0 | 6 | 0 | 5 | 0 | 9 | 9 | 7 | 8 | 9 | 7 | 8 | 8 | 0 | 6 | 0 | 6 | 7 | 3 | 6 | 0 | 2 | 0 | 0 | 9 | 8 |
| Umbrella sedge | 5 | 8 | 9 | 6 | 0 | 3 | 0 | 0 | 9 | 8 | 9 | 7 | 2 | 4 | 0 | 2 | 0 | 0 | 9 | 9 | 9 | 8 | 9 | 9 | 8 | 9 | 0 | 4 | 9 | 0 | 7 | 8 | 0 | 3 | 0 | 4 | 0 | 3 | 9 | 8 |

TABLE B-continued

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate (8 g/ha) | 109 | 110 | 111 | 112 | 114 | 115 | 116 | 117 | 118 | 119 | 120 | 121 | 122 | 125 | 166 | 167 | 170 | 172 | 173 | 203 | 204 | 205 | 206 | 207 | 208 | 209 | 211 | 212 |
| | POSTEMERGENCE | | | | | | | | | | | | | | | | | | | | | | | | | | | |
| Barley Igri | 10 | 10 | 8 | 6 | 6 | 3 | 4 | 0 | 0 | 9 | 5 | 7 | 5 | 0 | 6 | 9 | 4 | 9 | 9 | 7 | 9 | 10 | 9 | 7 | 7 | 0 | 9 | 7 |
| Bedstraw | 8 | 9 | 9 | 9 | 9 | 10 | 10 | 10 | 9 | 8 | 9 | 10 | 10 | 0 | 9 | 9 | 9 | 6 | 9 | 7 | 9 | 10 | 9 | 8 | 10 | 0 | 8 | 9 |
| Blackgrass | 10 | 10 | 10 | 10 | 9 | 9 | 8 | 7 | 6 | 10 | 10 | 9 | 9 | 0 | 8 | 8 | 9 | 10 | 10 | 9 | 10 | 10 | 10 | 10 | 9 | 2 | 9 | 8 |
| Chickweed | 9 | 9 | 6 | 8 | 7 | 5 | 10 | 10 | 0 | 9 | 10 | 10 | 10 | 0 | 10 | 9 | 10 | 5 | 4 | 7 | 9 | 10 | 10 | 7 | 7 | 0 | 8 | 5 |
| Corn | 4 | 9 | 9 | 8 | 9 | 9 | 4 | 0 | 0 | 10 | 10 | 10 | 10 | 0 | 10 | 10 | 10 | 8 | 8 | 10 | 10 | 10 | 10 | 10 | 9 | 0 | 8 | 10 |
| Cotton | 8 | 8 | 10 | 8 | 7 | 8 | 9 | 9 | 3 | 9 | 10 | 10 | 8 | 7 | 5 | 7 | 9 | 5 | 5 | 6 | 4 | 8 | 4 | 6 | 7 | 0 | 4 | 6 |
| Crabgrass | 4 | 4 | 0 | 0 | 0 | 0 | 0 | 0 | 0 | 0 | 0 | 3 | 3 | 0 | 5 | 3 | 10 | 5 | 8 | 8 | 10 | 10 | 10 | 9 | 8 | 0 | 3 | 4 |
| Downy brome | 9 | 9 | 8 | 5 | 4 | 0 | 2 | 0 | 0 | 9 | 7 | 8 | 6 | 0 | 7 | 9 | 4 | 8 | 9 | 9 | 9 | 10 | 10 | 10 | 5 | 0 | 9 | 6 |
| Duck salad | 9 | 9 | 0 | 6 | 4 | 0 | 6 | 5 | 2 | 8 | 6 | 8 | 7 | 0 | 8 | 6 | 8 | 0 | 0 | 7 | 9 | 9 | 9 | 9 | 9 | 0 | 9 | 8 |
| Giant foxtail | 6 | 7 | 4 | 0 | 6 | 3 | 4 | 0 | 0 | 7 | 6 | 7 | 2 | 0 | 5 | 4 | 10 | 8 | 9 | 5 | 8 | 10 | 10 | 10 | 10 | 0 | 8 | 7 |
| Lambsquarters | 10 | 10 | 10 | 10 | 5 | 5 | 5 | 0 | 0 | 10 | 10 | 10 | 4 | 7 | 10 | 10 | 10 | 9 | 9 | 10 | 10 | 10 | 10 | 9 | 10 | 0 | 10 | 10 |
| Morningglory | 5 | 10 | 10 | 10 | 7 | 9 | 10 | 10 | 8 | 10 | 10 | 10 | 10 | 10 | 8 | 7 | 9 | 9 | 8 | 9 | 10 | 10 | 7 | 7 | 10 | 0 | 8 | 10 |
| Pigweed | 8 | 8 | 10 | 10 | 6 | 3 | 7 | 5 | 0 | 10 | 10 | 10 | 10 | 8 | 4 | 5 | 10 | 8 | 9 | 10 | 10 | 10 | 10 | 5 | 10 | 0 | 8 | 3 |
| Rape | 10 | 10 | 10 | 10 | 9 | 9 | 9 | 9 | 9 | 10 | 10 | 10 | 10 | 9 | 9 | 9 | 10 | 0 | 6 | 9 | 10 | 10 | 9 | 9 | 10 | 0 | 6 | 8 |
| Ryegrass | 10 | 10 | 7 | 6 | 7 | 3 | 9 | 5 | 4 | 9 | 3 | 9 | 8 | 0 | 8 | 8 | 8 | 6 | 9 | 8 | 10 | 10 | 10 | 6 | 7 | 0 | 3 | 2 |
| Sorghum | 9 | 8 | 10 | 9 | 7 | 8 | 9 | 7 | 0 | 9 | 10 | 9 | 8 | 2 | 9 | 10 | 10 | 6 | 8 | 10 | 10 | 10 | 10 | 10 | 10 | 3 | 7 | 10 |
| Soybean | 8 | 10 | 10 | 8 | 8 | 8 | 8 | 9 | 0 | 10 | 10 | 10 | 10 | 5 | 8 | 8 | 8 | 8 | 9 | 7 | 10 | 10 | 10 | 8 | 6 | 0 | 9 | 6 |
| Speedwell | 6 | 8 | 4 | 9 | 9 | 2 | 10 | 0 | 4 | 9 | 0 | 10 | 0 | 0 | 7 | 0 | 9 | 9 | 2 | 5 | 4 | 3 | 8 | 0 | 3 | 0 | 7 | 0 |
| Sugar beet | 9 | 10 | 10 | 8 | 6 | 5 | 9 | 9 | 3 | 10 | 10 | 10 | 10 | 7 | 10 | 10 | 10 | 8 | 9 | 10 | 10 | 10 | 10 | 8 | 10 | 0 | 8 | 7 |
| Velvetleaf | 8 | 9 | 10 | 8 | 8 | 9 | 9 | 6 | 0 | 10 | 10 | 10 | 6 | 8 | 8 | 7 | 9 | 6 | 5 | 7 | 8 | 10 | 7 | 5 | 7 | 0 | 8 | 8 |
| Wheat | 9 | 9 | 6 | 5 | 4 | 4 | 0 | 0 | 0 | 9 | 5 | 9 | 5 | 0 | 8 | 8 | 8 | 9 | 9 | 5 | 8 | 9 | 7 | 7 | 6 | 0 | 7 | 4 |
| Wild buckwheat | 8 | 9 | — | 7 | 7 | 8 | 9 | 9 | 8 | 10 | 10 | 8 | 9 | — | 6 | 6 | 9 | 9 | 8 | 8 | 9 | 9 | 9 | 7 | 7 | 0 | 7 | 8 |
| Wild oat | 9 | 9 | 6 | 5 | 5 | 0 | 4 | 3 | 0 | 8 | 4 | 9 | 8 | 0 | 8 | 8 | 5 | 6 | 8 | 7 | 9 | 9 | 9 | 8 | 5 | 0 | 5 | 4 |
| Barnyardgrass | 8 | 8 | 6 | 6 | 8 | 8 | 6 | 3 | 3 | 6 | 3 | 8 | 2 | 0 | 0 | 0 | 8 | 0 | 0 | 1 | 5 | 8 | 9 | 7 | 9 | 0 | 9 | 6 |
| Rice Japonica | 8 | 8 | 7 | 8 | 8 | 7 | 7 | 6 | 4 | 6 | 3 | 8 | 7 | 0 | 4 | 0 | 8 | 0 | 0 | 9 | 6 | 9 | 8 | 9 | 9 | 0 | 8 | 8 |
| Umbrella sedge | 8 | 8 | 8 | 7 | 7 | 9 | 9 | 8 | 7 | 9 | 8 | 8 | 8 | 9 | 9 | 9 | 6 | 2 | 4 | 7 | 9 | 9 | 9 | 9 | 9 | 0 | 9 | 8 |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate (8 g/ha) | 213 | 214 | 217 | 218 | 219 | 225 | 229 | 230 | 231 | 232 | 240 | 241 | 242 | 243 | 244 | 245 | 252 | 254 | 256 | 258 | 259 | 261 | 266 | 267 | 268 | 269 | 270 | 271 |
| | POSTEMERGENCE | | | | | | | | | | | | | | | | | | | | | | | | | | | |
| Barley Igri | 4 | 4 | 8 | 5 | 3 | 8 | 7 | 6 | 6 | 7 | 9 | 9 | 10 | 9 | 7 | 9 | 6 | 5 | 8 | 9 | 7 | 9 | 6 | 9 | 6 | 5 | 9 | 9 |
| Bedstraw | 10 | 10 | 5 | 7 | 9 | 7 | 9 | 6 | 9 | 9 | 9 | 10 | 10 | 10 | 10 | 10 | 10 | 9 | 9 | 9 | 5 | 9 | 9 | 10 | 9 | 6 | 9 | 10 |
| Blackgrass | 7 | 7 | 7 | 6 | 6 | 5 | 9 | 9 | 9 | 9 | 10 | 10 | 10 | 10 | 10 | 10 | 9 | 8 | 9 | 9 | 9 | 9 | 9 | 10 | 9 | 9 | 10 | 10 |
| Chickweed | 10 | 10 | 3 | 8 | 8 | 8 | 7 | 3 | 4 | 10 | 10 | 10 | 10 | 10 | 10 | 0 | 3 | 9 | 8 | 9 | 3 | 7 | 0 | 7 | 9 | 0 | 5 | 10 |
| Corn | 9 | 8 | 8 | 7 | 7 | 9 | 8 | 8 | 8 | 8 | 10 | 10 | 10 | 10 | 10 | 10 | 9 | 7 | 10 | 10 | 9 | 10 | 9 | 9 | 10 | 6 | 10 | 10 |
| Cotton | 8 | 10 | 6 | 4 | 4 | 6 | 0 | 0 | 5 | 4 | 4 | 8 | 8 | 8 | 8 | 7 | 3 | 8 | 0 | 0 | 0 | 0 | 0 | 7 | 6 | 0 | 7 | 7 |
| Crabgrass | 3 | 2 | 5 | 2 | 0 | 6 | 2 | 0 | 5 | 4 | 6 | 8 | 8 | 9 | 8 | 8 | 2 | 0 | 7 | 8 | 0 | 4 | 0 | 0 | 0 | 0 | 8 | 7 |
| Downy brome | 7 | 6 | 7 | 7 | 4 | 6 | 5 | 5 | 8 | 8 | 9 | 9 | 10 | 10 | 10 | 8 | 9 | 6 | 9 | 9 | 9 | 9 | 7 | 9 | 8 | 5 | — | 10 |
| Duck salad | 7 | 8 | 0 | 0 | 0 | 0 | 0 | 2 | 0 | 0 | 5 | 6 | 8 | 7 | 4 | 7 | 0 | 2 | 0 | 0 | 0 | 0 | 0 | 0 | 0 | 0 | 0 | 0 |
| Giant foxtail | 5 | 3 | 6 | 5 | 0 | 6 | 6 | 5 | 5 | 3 | 8 | 10 | 9 | 9 | 10 | 8 | 6 | 0 | 9 | 10 | 9 | 10 | 6 | 3 | 2 | 0 | 6 | 9 |
| Lambsquarters | 10 | 10 | 10 | 10 | 10 | 10 | 8 | 9 | 9 | 10 | 9 | 9 | 10 | 10 | 5 | 8 | — | 0 | 9 | 10 | 10 | 8 | — | — | 0 | 0 | 10 | 10 |
| Morningglory | 10 | 10 | 10 | 9 | 4 | 8 | 8 | 9 | 8 | 7 | 9 | 10 | 10 | 10 | 10 | 10 | 8 | 9 | 9 | 10 | 6 | 10 | 10 | 8 | 9 | 4 | 8 | 8 |
| Pigweed | 9 | 9 | 5 | 6 | 7 | 8 | 7 | 8 | 10 | 4 | 10 | 9 | 10 | 10 | 10 | 10 | 5 | 8 | 8 | 9 | 9 | 9 | 2 | 9 | 8 | 5 | 10 | 9 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rape | 10 | 10 | 9 | 7 | 7 | 9 | 3 | 6 | 9 | 5 | 9 | 10 | 10 | 10 | 10 | 10 | 9 | 9 | 9 | 10 | 8 | 10 | 6 | 9 | 9 | 6 | 8 | 9 |
| Ryegrass | 8 | 6 | 5 | 4 | 6 | 3 | 0 | 0 | 9 | 6 | 10 | 9 | 10 | 10 | 9 | 9 | 0 | 4 | 9 | 9 | 9 | 9 | 0 | 8 | 7 | 0 | 5 | 9 |
| Sorghum | 10 | 10 | 8 | 6 | 3 | 8 | 8 | 8 | 9 | 10 | 9 | 10 | 10 | 10 | 10 | 10 | 9 | 8 | 10 | 10 | 10 | 10 | 9 | 10 | 9 | 6 | 10 | 10 |
| Soybean | 10 | 10 | 6 | 8 | 7 | 7 | 8 | 8 | 9 | 9 | 8 | 10 | 9 | 9 | 9 | 9 | 8 | 9 | 5 | 9 | 7 | 7 | 8 | 9 | 9 | 0 | 5 | 7 |
| Speedwell | 10 | 7 | 2 | 0 | 3 | 3 | — | 0 | — | — | 3 | 3 | — | 10 | 0 | 4 | 2 | 0 | 0 | 0 | 0 | 0 | 0 | 7 | 0 | 0 | 2 | 0 |
| Sugar beet | 10 | 10 | 8 | 9 | 9 | 9 | 2 | 2 | 9 | 7 | 9 | 9 | 10 | 10 | 10 | 9 | 5 | 9 | 6 | 9 | 9 | 7 | 0 | 9 | 9 | 0 | 9 | 9 |
| Velvetleaf | 8 | 3 | 5 | 5 | 7 | 6 | 7 | 6 | 8 | 5 | 5 | 7 | 9 | 8 | 8 | 8 | 4 | 0 | 7 | 8 | 3 | 2 | 2 | 7 | 3 | 0 | 4 | 4 |
| Wheat | 5 | 0 | 8 | 4 | 3 | 3 | 5 | 4 | 9 | 8 | 9 | 9 | 10 | 10 | 6 | 8 | 5 | 0 | 7 | 7 | 7 | 7 | 3 | 8 | 4 | 3 | 9 | 9 |
| Wild buckwheat | 10 | 9 | 3 | 7 | 7 | 6 | 5 | 6 | 8 | 8 | 10 | 10 | 10 | 9 | 8 | 9 | — | 9 | 9 | 9 | 0 | 10 | 7 | 9 | 9 | 6 | 10 | 10 |
| Wild oat | 5 | 4 | 8 | 4 | 4 | 4 | 6 | 7 | 8 | 7 | 9 | 9 | 10 | 10 | 9 | 9 | 4 | 6 | 8 | 9 | 8 | 7 | 5 | 8 | 7 | 4 | 9 | 9 |
| Barnyardgrass | 8 | 3 | 0 | 1 | 3 | 0 | 0 | 0 | 0 | 0 | 0 | 2 | 6 | 8 | 0 | 8 | 0 | 0 | 0 | 4 | 5 | 8 | 0 | | 0 | 0 | 0 | 0 |
| Rice Japonica | 8 | 8 | 7 | 7 | 6 | 5 | 0 | 0 | 2 | 0 | 3 | 0 | 7 | 8 | 5 | 8 | 4 | 6 | 8 | 0 | 7 | 8 | 0 | 6 | 0 | 2 | 3 | 2 |
| Umbrella sedge | 9 | 9 | 2 | 4 | 3 | 0 | 0 | 0 | 0 | 0 | 7 | 8 | 8 | 7 | 8 | 8 | 6 | 3 | 8 | 9 | 0 | 8 | 0 | 2 | 0 | 0 | 8 | 4 |

| | COMPOUND | | | | | | | | | | | | | | | | | |
|---|---|---|---|---|---|---|---|---|---|---|---|---|---|---|---|---|---|---|
| Rate (8 g/ha) | 272 | 274 | 275 | 276 | 283 | 284 | 285 | 286 | 287 | 288 | 289 | 291 | 292 | 300 | 301 | 302 | 305 | 310 |
| POSTEMERGENCE | | | | | | | | | | | | | | | | | | |
| Barley Igri | 9 | 0 | 8 | 6 | 9 | 10 | 9 | 10 | 10 | 9 | 8 | 9 | 2 | 9 | 9 | 10 | 9 | 7 |
| Bedstraw | 9 | 0 | 6 | 2 | 10 | 10 | 10 | 10 | 10 | 10 | 9 | 9 | 6 | 9 | 10 | 10 | 10 | 9 |
| Blackgrass | 10 | 8 | 10 | 8 | 10 | 9 | 9 | 10 | 9 | 10 | 10 | 10 | 9 | 9 | 10 | 9 | 10 | 7 |
| Chickweed | 10 | 0 | 6 | 0 | 10 | 10 | 10 | 10 | 10 | 10 | 9 | 9 | 8 | 9 | 9 | 10 | 9 | 5 |
| Corn | 10 | 0 | 10 | 8 | 10 | 10 | 10 | 10 | 10 | 10 | 10 | 9 | 9 | 8 | 9 | 10 | 9 | 8 |
| Cotton | 5 | 0 | 4 | 0 | 10 | 8 | 10 | 9 | 9 | 6 | 7 | 7 | 4 | 4 | 4 | 7 | 2 | 4 |
| Crabgrass | 7 | 0 | 8 | 0 | 8 | 5 | 6 | 9 | 8 | 4 | 7 | 8 | 4 | 6 | 6 | 9 | 7 | 2 |
| Downy brome | 9 | 4 | 9 | 5 | 10 | 9 | 10 | 10 | 10 | 9 | 9 | 9 | 2 | 9 | 9 | 9 | 8 | 5 |
| Duck salad | 0 | 0 | 2 | 0 | 8 | 5 | 0 | 3 | 3 | 9 | 0 | 2 | 0 | 3 | 0 | 3 | 2 | 0 |
| Giant foxtail | 10 | 0 | 10 | 0 | 10 | 9 | 10 | 10 | 10 | 9 | 9 | 10 | 4 | 9 | 8 | 9 | 9 | 6 |
| Lambsquarters | 9 | 0 | 9 | 0 | 9 | 10 | 10 | 10 | 9 | 10 | 8 | 9 | 5 | 10 | 10 | 10 | 9 | 7 |
| Morningglory | 8 | 0 | 6 | 5 | 6 | 10 | 10 | 10 | 10 | 10 | 7 | 8 | 0 | 3 | 7 | 9 | 7 | 9 |
| Pigweed | 8 | 0 | 8 | 5 | 10 | 8 | 8 | 10 | 10 | 8 | 7 | 9 | 7 | 5 | 8 | 8 | 7 | 5 |
| Rape | 9 | 0 | 9 | 0 | 10 | 10 | 10 | 10 | 10 | 10 | 0 | 9 | 9 | 9 | 9 | 9 | 9 | 9 |
| Ryegrass | 10 | 0 | 9 | 0 | 9 | 4 | 0 | 10 | 8 | 5 | 4 | 9 | 3 | 8 | 7 | 9 | 5 | 0 |
| Sorghum | 10 | 0 | 10 | 8 | 10 | 10 | 10 | 10 | 10 | 10 | 9 | 10 | 9 | 7 | 9 | 10 | 10 | 8 |
| Soybean | 6 | 0 | 5 | 0 | 9 | 9 | 9 | 10 | 10 | 10 | 8 | 8 | 0 | 8 | 8 | 10 | 8 | 8 |
| Speedwell | — | 0 | 0 | 0 | 5 | 6 | 0 | 10 | 0 | 9 | 4 | 0 | 5 | 8 | 10 | 0 | 9 | 9 |
| Sugar beet | 9 | 0 | 9 | 0 | 8 | — | 9 | 10 | 10 | 10 | 9 | 8 | 9 | 9 | 9 | 10 | 9 | 10 |
| Velvetleaf | 3 | 0 | 1 | 0 | 7 | 10 | 10 | 9 | 1 | 9 | 2 | 6 | 2 | 2 | 2 | 6 | 4 | 8 |
| Wheat | 9 | 5 | 9 | 4 | 9 | 9 | 9 | 10 | 5 | 8 | 7 | 9 | 0 | 8 | 8 | 9 | 8 | 3 |
| Wild buckwheat | 10 | — | 10 | 0 | 10 | — | 10 | 10 | 10 | 10 | — | 9 | 7 | 8 | 8 | 6 | — | 8 |
| Wild oat | 9 | 3 | 9 | 4 | 10 | 9 | 5 | 9 | 9 | 9 | 6 | 9 | 4 | 9 | 9 | 9 | 7 | 5 |
| Barnyardgrass | 0 | 0 | 0 | 0 | 6 | 0 | 0 | 6 | 7 | 8 | 0 | 0 | 0 | 4 | 3 | 7 | 6 | 0 |
| Rice Japonica | 8 | 0 | 8 | 0 | 7 | 3 | 2 | 3 | 7 | 8 | 0 | 2 | 0 | 0 | 3 | 3 | 6 | 0 |
| Umbrella sedge | 8 | 0 | 4 | 0 | 9 | 8 | 6 | 0 | 0 | 9 | 6 | 3 | 0 | 0 | 2 | 6 | 2 | 0 |

TABLE B-continued

| | COMPOUND | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| Rate (8 g/ha) | 1 | 2 | 3 | 5 | 7 | 11 | 13 | 14 | 25 | 26 | 27 | 28 | 29 | 30 | 31 | 34 | 35 | 36 | 50 | 51 | 53 | 58 | 59 | 60 | 63 | 64 | 71 | 77 | 78 | 81 | 82 | 83 | 84 | 86 | 88 | 89 | 102 | 103 | 107 | 108 |
| | PREEMERGENCE | | | | | | | | | | | | | | | | | | | | | | | | | | | | | | | | | | | | | | | |
| Barley Igri | 2 | 5 | 3 | 0 | 0 | 0 | 0 | 0 | 0 | 0 | 0 | 0 | 0 | 0 | 0 | 0 | 0 | 0 | 4 | 6 | 6 | 0 | 6 | 0 | 7 | 7 | 0 | 0 | 0 | 4 | 3 | 0 | 0 | 3 | 3 | 5 | 5 | 4 | 8 | 4 |
| Bedstraw | — | 4 | 6 | 10 | 0 | 5 | 7 | 5 | 5 | 6 | 3 | 5 | 5 | 8 | 2 | 3 | 3 | 8 | 8 | 10 | 9 | 7 | 10 | 9 | 7 | 9 | 8 | 0 | 7 | 5 | 9 | 9 | 0 | 8 | 4 | 9 | 7 | 9 | 10 | 10 |
| Blackgrass | 5 | 6 | 6 | 3 | 0 | 4 | 3 | 0 | 7 | 7 | 7 | 5 | 5 | 4 | 2 | 0 | 5 | 6 | 7 | 8 | 9 | 7 | 7 | 6 | 9 | 9 | 5 | 3 | 5 | 8 | 9 | 9 | 7 | 9 | 9 | 9 | 6 | 8 | 9 | 9 |
| Chickweed | 4 | 8 | 9 | 7 | 0 | 8 | 8 | 10 | 2 | 8 | 4 | — | 9 | 8 | 0 | 4 | 8 | 10 | 9 | 10 | 10 | 9 | 10 | 10 | 7 | 8 | 7 | 0 | 5 | 3 | 9 | 9 | 0 | 5 | 7 | 9 | 3 | 6 | 9 | 9 |
| Corn | 0 | 4 | 3 | 0 | 0 | 4 | 0 | 0 | 4 | 4 | 4 | 4 | 6 | 8 | 2 | 0 | 0 | 2 | 0 | 7 | 0 | 0 | 5 | 2 | 4 | 9 | 0 | 0 | 3 | — | — | — | 8 | 2 | 1 | 4 | 0 | 0 | 10 | 9 |
| Cotton | 0 | 2 | 2 | 7 | 0 | 2 | 5 | 2 | 4 | 6 | 7 | 5 | 8 | 8 | 0 | 0 | 4 | 7 | 6 | 9 | 7 | 0 | 9 | 9 | 6 | 8 | 5 | 0 | 4 | — | — | — | 8 | — | 5 | 2 | 0 | 8 | 10 | 10 |
| Crabgrass | 0 | 5 | 5 | 5 | 0 | 0 | 0 | 0 | 4 | 8 | 7 | 6 | 7 | 8 | 0 | 2 | 2 | 5 | 6 | 9 | 9 | 4 | 3 | 0 | 8 | 8 | 0 | 0 | 4 | — | — | — | 2 | 4 | 0 | 4 | 0 | 0 | 8 | 7 |
| Downy brome | 5 | 6 | 0 | 6 | 0 | 0 | 3 | 0 | 0 | 0 | 0 | 4 | 3 | 4 | 0 | 0 | 4 | 4 | 5 | 8 | 9 | 3 | 6 | 5 | 9 | 8 | 0 | 2 | 0 | 5 | 5 | 4 | 2 | 0 | 3 | 5 | 2 | 5 | 8 | 5 |
| Duck salad | — | — | — | — | — | — | — | — | — | — | — | — | — | — | — | — | — | — | — | — | — | — | — | — | — | — | — | — | — | — | — | — | — | — | — | — | — | — | — | — |
| Giant foxtail | 0 | 5 | 3 | 3 | 0 | 2 | 0 | 0 | 2 | 7 | 4 | 3 | 7 | 9 | 4 | 2 | 0 | 6 | 6 | 7 | 8 | 3 | 0 | 0 | 9 | 9 | 0 | 0 | 3 | — | — | — | 2 | 4 | 2 | 5 | 3 | 2 | 8 | 6 |
| Lambsquarters | 8 | 8 | 8 | 10 | 0 | 6 | 8 | 7 | 0 | 7 | 2 | 5 | 5 | 8 | 5 | 6 | 10 | 10 | 9 | 10 | 9 | 7 | 10 | 10 | 9 | 10 | 7 | 2 | 5 | 9 | 9 | 9 | 5 | — | — | 9 | 5 | 9 | 10 | 9 |
| Morningglory | 0 | 0 | 3 | 6 | 0 | 0 | 0 | 0 | 5 | 6 | 2 | 4 | 5 | 7 | 0 | 0 | 3 | 5 | 9 | 9 | 5 | 0 | 9 | 9 | 6 | 9 | 7 | 0 | 7 | — | — | — | 4 | 5 | 3 | 6 | 4 | 7 | 10 | 9 |
| Pigweed | 4 | 7 | 6 | 6 | 0 | 3 | 4 | 2 | 7 | 8 | 8 | 8 | 8 | 9 | 2 | 7 | 6 | 8 | 10 | 10 | 9 | 7 | 9 | 9 | 9 | 9 | 9 | 8 | 8 | — | — | — | 2 | 7 | 7 | 8 | 8 | 9 | 9 | 9 |
| Rape | 4 | 4 | 6 | 5 | 0 | 0 | 7 | 6 | 4 | 2 | 3 | 5 | 4 | 8 | 0 | 0 | 0 | 5 | 7 | 9 | 9 | 9 | 10 | 10 | 10 | 9 | 8 | 5 | 8 | 9 | 9 | 8 | 0 | 9 | 8 | 9 | 7 | 7 | 9 | 9 |
| Ryegrass | 0 | 0 | 0 | 0 | 0 | 0 | 3 | 0 | 0 | 2 | 2 | 4 | 0 | 3 | 0 | 0 | 3 | 3 | 7 | 9 | 9 | 3 | 10 | 7 | 6 | 8 | 0 | 0 | 1 | 4 | 4 | 3 | 3 | 4 | 4 | 5 | 0 | 0 | 10 | 9 |
| Sorghum | 3 | 4 | 4 | 8 | 0 | 0 | 2 | 3 | 7 | 9 | 5 | 9 | 10 | 9 | 2 | 0 | 4 | 5 | 6 | 9 | 8 | 5 | 7 | 6 | 9 | 9 | 4 | 4 | 6 | — | — | — | 9 | 9 | 5 | 8 | 7 | 9 | 9 | 9 |
| Soybean | 0 | 3 | 2 | 5 | 0 | 0 | 0 | 0 | 3 | 3 | 3 | 2 | 6 | 4 | 0 | 0 | 0 | 4 | 5 | 7 | 5 | 2 | 6 | 6 | 7 | 7 | 6 | 0 | 4 | — | — | — | 6 | 5 | 5 | 4 | 0 | 0 | 10 | 8 |
| Speedwell | — | 7 | 5 | 10 | 0 | 4 | 7 | 6 | 7 | 8 | 0 | 7 | 9 | 0 | 0 | 3 | 7 | 6 | 9 | 10 | 10 | 3 | 10 | 8 | 7 | 7 | 0 | 0 | 0 | 7 | 9 | 9 | 6 | 9 | 9 | 8 | 8 | 7 | 10 | 2 |
| Sugar beet | 5 | 8 | 7 | 10 | 0 | 4 | 8 | 6 | 3 | 8 | 3 | 5 | 5 | 9 | 0 | 5 | 8 | 9 | 9 | 9 | 9 | 8 | 10 | 10 | 10 | 10 | 9 | 0 | 9 | 9 | 9 | 9 | 0 | 9 | 9 | 9 | 9 | 9 | 10 | 10 |
| Velvetleaf | 0 | 4 | 3 | 6 | 0 | 0 | 4 | 0 | 7 | 6 | 4 | 5 | 8 | 3 | 0 | 0 | 3 | 5 | 6 | 9 | 7 | 5 | 9 | 6 | 8 | 9 | 8 | 0 | 6 | — | — | — | 3 | 6 | 2 | 3 | 5 | 6 | 10 | 8 |
| Wheat | 2 | 5 | 3 | 5 | 0 | 0 | 0 | 0 | 2 | 0 | 0 | 0 | 0 | 0 | 0 | 0 | 0 | 0 | 5 | 6 | 6 | 0 | 4 | 0 | 6 | 6 | 0 | 0 | 0 | 3 | 3 | 0 | 0 | 0 | 0 | 0 | 2 | 0 | 7 | 0 |
| Wild buckwheat | 6 | 9 | 9 | 10 | 0 | 2 | 7 | 3 | 2 | 2 | 0 | 5 | 5 | 7 | 0 | 0 | 7 | 7 | 8 | 9 | 9 | 3 | 8 | 8 | 8 | 7 | 5 | 0 | 6 | 7 | 8 | 7 | 0 | 8 | 3 | 7 | 8 | 8 | 9 | 9 |
| Wild oat | 0 | 0 | 0 | 0 | 0 | 0 | 0 | 0 | 0 | 0 | 0 | 0 | 0 | 0 | 0 | 0 | 0 | 0 | 3 | 8 | 6 | 0 | 6 | 4 | 0 | 3 | 0 | 0 | 0 | 5 | 0 | 2 | 0 | 0 | 0 | 0 | 2 | 3 | 6 | 4 |
| Barnyardgrass | — | — | — | — | — | — | — | — | — | — | — | — | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — | — | — | — | — | — | — | — | — | — | — | — | — |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (8 g/ha) | 109 | 110 | 111 | 112 | 114 | 115 | 116 | 117 | 118 | 119 | 120 | 121 | 122 | 125 | 166 | 167 | 170 | 172 | 173 | 203 | 204 | 205 | 206 | 207 | 208 | 209 | 211 | 212 |
| | PREEMERGENCE | | | | | | | | | | | | | | | | | | | | | | | | | | | |
| Barley Igri | 8 | 6 | 0 | 0 | 2 | 0 | 5 | 2 | 0 | 9 | 3 | 7 | 0 | 0 | 0 | 0 | 0 | 0 | 0 | 2 | 5 | 4 | 3 | 4 | 8 | 0 | 2 | 0 |
| Bedstraw | 9 | 10 | 3 | 9 | 9 | 8 | 9 | 9 | 0 | 4 | 2 | 8 | 8 | 3 | 9 | 7 | 8 | 3 | 0 | 3 | 7 | 9 | 9 | 8 | 9 | 0 | 8 | 0 |
| Blackgrass | 10 | 9 | 9 | 8 | 8 | 8 | 8 | 7 | 5 | 10 | 10 | 9 | 6 | 4 | 7 | 6 | 3 | 7 | 8 | 6 | 8 | 9 | 9 | 8 | 8 | 0 | 7 | 6 |
| Chickweed | 9 | 9 | 8 | 8 | 8 | 7 | 9 | 8 | 6 | 10 | 9 | 10 | 9 | 7 | 9 | 9 | 7 | — | 0 | 2 | 9 | 9 | 7 | 9 | 8 | 0 | 9 | 7 |
| Corn | 5 | 7 | 2 | 2 | 8 | 4 | 7 | 4 | 3 | 8 | 5 | 10 | 7 | 0 | 5 | 2 | 6 | 0 | 3 | 0 | 5 | 7 | 9 | 6 | 7 | 0 | 5 | 5 |
| Cotton | 6 | 8 | 5 | 5 | — | 0 | 9 | 8 | 0 | 7 | 6 | 9 | 8 | 0 | 4 | 0 | 8 | 2 | 3 | 5 | 0 | 7 | 7 | 6 | 4 | 0 | 3 | 0 |
| Crabgrass | 7 | 4 | 0 | 0 | 5 | 2 | 7 | 0 | 0 | 5 | 5 | 0 | 5 | 0 | 7 | 4 | 6 | 3 | 3 | 5 | 7 | 10 | 5 | 7 | 8 | 0 | 7 | 5 |
| Downy brome | 8 | 9 | 0 | 3 | 5 | 2 | 5 | 3 | 0 | 9 | 5 | 8 | 5 | 0 | 4 | 4 | 5 | 0 | 0 | 7 | 9 | 7 | 8 | 7 | 8 | 0 | 6 | 2 |
| Duck salad | — | — | — | — | — | — | — | — | — | — | — | — | — | — | — | — | — | — | — | — | — | — | — | — | — | — | — | — |
| Giant foxtail | 7 | 8 | 3 | 0 | 8 | 3 | 6 | 0 | 0 | 6 | 5 | 0 | 0 | 0 | 6 | 0 | 6 | 5 | 5 | 0 | 7 | 9 | 6 | 6 | 8 | 0 | 6 | 2 |
| Lambsquarters | 9 | 10 | 9 | 9 | 8 | 6 | 9 | 8 | 8 | 10 | 10 | 10 | 9 | 9 | 2 | 8 | 9 | 9 | 7 | 7 | 8 | 10 | 8 | 8 | 7 | 0 | 8 | 6 |
| Morningglory | 6 | 5 | 5 | 5 | 7 | 7 | 9 | 9 | 3 | 8 | 8 | 9 | 8 | 0 | 4 | 0 | 7 | 2 | 0 | 3 | 6 | 9 | 7 | 7 | 8 | 0 | 0 | 4 |
| Pigweed | 9 | 9 | 8 | 8 | 9 | 9 | 9 | 8 | 6 | 9 | 8 | 8 | 8 | 5 | 8 | 6 | 9 | 5 | 5 | 7 | 10 | 9 | 8 | 8 | 9 | 0 | 8 | 3 |

TABLE B-continued

| Rate (8 g/ha) | 213 | 214 | 217 | 218 | 219 | 225 | 229 | 230 | 231 | 232 | 240 | 241 | 242 | 243 | 244 | 245 | 252 | 254 | 256 | 258 | 259 | 261 | 266 | 267 | 268 | 269 | 270 | 271 |
|---|---|---|---|---|---|---|---|---|---|---|---|---|---|---|---|---|---|---|---|---|---|---|---|---|---|---|---|---|
| Rape | 9 | 9 | 6 | 9 | 9 | 7 | 9 | 9 | 4 | 10 | 9 | 10 | 10 | 5 | 8 | 4 | 9 | 0 | 0 | 8 | 8 | 9 | 5 | 3 | 9 | 0 | 8 | 0 |
| Ryegrass | 9 | 9 | 3 | 4 | 8 | 0 | 8 | 5 | 0 | 8 | 4 | 8 | 0 | 0 | 5 | 0 | 5 | 0 | 0 | 3 | 7 | 8 | 8 | 7 | 8 | 0 | 0 | 0 |
| Sorghum | 7 | 9 | 4 | 5 | 8 | 4 | 9 | 9 | 0 | 8 | 4 | 9 | 8 | 0 | 8 | 4 | 9 | 3 | 2 | 4 | 8 | 9 | 9 | 10 | 10 | 0 | 6 | 3 |
| Soybean | 6 | 5 | 3 | 1 | 2 | 0 | 8 | 5 | 0 | 8 | 5 | 8 | 6 | 0 | 2 | 0 | 6 | 0 | 0 | 3 | 3 | 6 | 6 | 4 | 4 | 0 | 3 | 2 |
| Speedwell | 9 | 9 | 7 | 9 | 9 | 7 | 10 | 7 | 9 | 10 | 9 | 10 | 3 | 7 | 10 | 0 | 9 | 8 | 4 | 0 | 3 | 7 | 8 | 0 | 8 | 0 | 8 | 5 |
| Sugar beet | 9 | 9 | 9 | 9 | 9 | 7 | 9 | 9 | 3 | 10 | 10 | 10 | 10 | 8 | 9 | 7 | 9 | 4 | 5 | 6 | 9 | 9 | 9 | 8 | 8 | 0 | 8 | 4 |
| Velvetleaf | 5 | 5 | 5 | 3 | 7 | 5 | 9 | 6 | 0 | 7 | 6 | 8 | 6 | 0 | 4 | 4 | 8 | 2 | 0 | 3 | 5 | 7 | 8 | 7 | 8 | 0 | 6 | 0 |
| Wheat | 6 | 6 | 3 | 2 | 0 | 0 | 0 | 0 | 0 | 7 | 3 | 9 | 3 | 0 | 0 | 0 | 0 | 0 | 0 | 3 | 5 | 4 | 8 | 7 | 8 | 0 | 4 | 0 |
| Wild buckwheat | — | — | 8 | 7 | 8 | 9 | 9 | 8 | 8 | 10 | — | — | 10 | 8 | 3 | 6 | 7 | — | 3 | 4 | 9 | 8 | 8 | 5 | 7 | 3 | 8 | 0 |
| Wild oat | 5 | 7 | 0 | 0 | 2 | 0 | 5 | 3 | 0 | 5 | 2 | 8 | 4 | 0 | 0 | 0 | 0 | 0 | 0 | 2 | 4 | 4 | 3 | 3 | 3 | 0 | 0 | 0 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |
| PREEMERGENCE | | | | | | | | | | | | | | | | | | | | | | | | | | | | |
| Barley Igri | 3 | 2 | 4 | 0 | 0 | 0 | 3 | 0 | 5 | 2 | 5 | 3 | 4 | 2 | 2 | 8 | 0 | 4 | 8 | 0 | 0 | 7 | 0 | 6 | 2 | 0 | 4 | 4 |
| Bedstraw | 10 | 9 | 2 | 0 | 8 | 0 | 2 | 0 | 6 | 3 | 9 | 8 | 9 | 9 | 9 | 10 | 6 | 9 | 8 | 6 | 0 | 7 | 0 | 9 | 7 | 0 | 3 | 3 |
| Blackgrass | 7 | 5 | 7 | 5 | 4 | 4 | 0 | 2 | 8 | 5 | 9 | 10 | 9 | 10 | 10 | 10 | 9 | 7 | 9 | 9 | 7 | 9 | 3 | 9 | 3 | 3 | 9 | 9 |
| Chickweed | 10 | 8 | 0 | 9 | 8 | — | 0 | 3 | 0 | 0 | 9 | 9 | 9 | 9 | 10 | 8 | 5 | 9 | 0 | 9 | 0 | 7 | 0 | 0 | 0 | 0 | 0 | 2 |
| Corn | 10 | 6 | 2 | 2 | 0 | 2 | 0 | 0 | 0 | 3 | 6 | 9 | 6 | 10 | 10 | 9 | 4 | — | 5 | 5 | 4 | 6 | 0 | 5 | 3 | 0 | 2 | 0 |
| Cotton | 10 | 9 | 3 | 2 | 0 | 8 | 0 | 0 | 5 | 2 | 3 | 2 | 5 | 10 | 5 | 4 | 0 | 7 | 2 | 3 | 5 | 3 | 0 | 2 | 3 | 0 | 7 | 0 |
| Crabgrass | 5 | 0 | 2 | 2 | 0 | 0 | 2 | 0 | 2 | 3 | 6 | 9 | 5 | 5 | 7 | 6 | 0 | 0 | 4 | 4 | 5 | 3 | 0 | 2 | 0 | 0 | 3 | 7 |
| Downy brome | 7 | 7 | 6 | 5 | 3 | 0 | 0 | 0 | 9 | 5 | 9 | 6 | 8 | 8 | 6 | 9 | 4 | 7 | 9 | 7 | 9 | 9 | 0 | 9 | 9 | 0 | 5 | 3 |
| Duck salad | — | — | — | — | — | — | — | — | — | — | — | — | — | — | — | — | — | — | — | — | — | — | — | — | — | — | — | — |
| Giant foxtail | 6 | 0 | 0 | 4 | 0 | 0 | 2 | 0 | 0 | 2 | 4 | 8 | 4 | 6 | 5 | 5 | 0 | 0 | 5 | 7 | 3 | 5 | 0 | 4 | 0 | 0 | 2 | 5 |
| Lambsquarters | 10 | 9 | — | 7 | 5 | 7 | 6 | — | 0 | 0 | 10 | 10 | 8 | 9 | 9 | 10 | 7 | 7 | 4 | 9 | 8 | 9 | 8 | 0 | 6 | 0 | 5 | 6 |
| Morningglory | 9 | 9 | 0 | 2 | 0 | 2 | 0 | 0 | 4 | 5 | 5 | 5 | 3 | 9 | 6 | 7 | 0 | 9 | 0 | 2 | 0 | 2 | 0 | 3 | 7 | 0 | 0 | 2 |
| Pigweed | 9 | 9 | 6 | 7 | 6 | 3 | 2 | 2 | 3 | 4 | 8 | 9 | 8 | 9 | 8 | 8 | 2 | 7 | 5 | 8 | 5 | 8 | 0 | 7 | 0 | 0 | 7 | 7 |
| Rape | 10 | 10 | 4 | 0 | 5 | 0 | 0 | 0 | 0 | 0 | 9 | 9 | — | 9 | 9 | 9 | 5 | 8 | 8 | 4 | 0 | 5 | 0 | 0 | 2 | 0 | 0 | 0 |
| Ryegrass | 7 | 3 | 3 | 0 | 0 | 0 | 0 | 0 | 0 | 0 | 5 | 6 | 6 | 9 | 7 | 9 | 0 | 3 | 9 | 8 | 6 | 6 | 0 | 0 | 0 | 0 | 3 | 2 |
| Sorghum | 10 | 8 | 7 | 5 | 0 | 7 | 5 | 0 | 9 | 9 | 9 | 7 | 4 | 10 | 10 | 9 | 0 | 6 | 9 | 4 | 8 | 9 | 3 | 9 | 7 | 0 | 0 | 0 |
| Soybean | 8 | 7 | 0 | 2 | 2 | 4 | 0 | 0 | 7 | 5 | 2 | 4 | 6 | 8 | 5 | 3 | 0 | 7 | 0 | 2 | 3 | 0 | 0 | 3 | 3 | 0 | 0 | 0 |
| Speedwell | 10 | 3 | 9 | 0 | 0 | 6 | 6 | 5 | 0 | 0 | 9 | 9 | 0 | 10 | 0 | 9 | 9 | 8 | 7 | 0 | 0 | 8 | 2 | 4 | 0 | 0 | 7 | 4 |
| Sugar beet | 10 | 9 | 7 | 6 | 8 | 6 | 0 | 2 | 2 | 2 | 9 | 9 | 9 | 9 | 9 | 9 | 2 | 9 | 8 | 5 | 8 | 7 | 2 | 4 | 6 | — | 9 | 5 |
| Velvetleaf | 9 | 3 | 2 | 3 | 0 | 7 | 2 | 0 | 7 | 0 | 4 | 2 | 5 | 8 | 6 | 4 | 0 | 2 | 2 | 5 | 2 | 0 | 3 | 3 | 0 | 0 | 0 | 2 |
| Wheat | 5 | 0 | 4 | 3 | 0 | 0 | 0 | 2 | 7 | 3 | 5 | 5 | 3 | 5 | 2 | 3 | 0 | 0 | 7 | 3 | 4 | 5 | 0 | 0 | 0 | 0 | 5 | 5 |
| Wild buckwheat | 9 | 9 | 2 | 0 | 7 | 2 | 0 | 0 | 0 | 5 | 9 | 9 | — | — | 9 | 8 | 3 | 9 | 9 | 9 | 6 | 9 | — | 0 | 8 | — | 5 | 6 |
| Wild oat | 4 | 3 | 2 | 0 | 0 | 0 | 0 | 0 | 0 | 0 | 4 | 4 | 3 | 6 | 0 | 3 | 0 | — | 8 | 3 | 0 | 6 | 0 | 2 | 0 | 0 | 2 | 0 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |

COMPOUND

| Rate (8 g/ha) | 272 | 274 | 275 | 276 | 283 | 284 | 285 | 286 | 287 | 288 | 289 | 291 | 292 | 300 | 301 | 302 | 305 | 310 |
|---|---|---|---|---|---|---|---|---|---|---|---|---|---|---|---|---|---|---|

PREEMERGENCE

TABLE B-continued

| | | | | | | | | | | | | | | | | | | |
|---|---|---|---|---|---|---|---|---|---|---|---|---|---|---|---|---|---|---|
| Barley Igri | 0 | 0 | 9 | 0 | 3 | 1 | 0 | 1 | 0 | 0 | 0 | 2 | 0 | 0 | 0 | 0 | 0 | 0 |
| Bedstraw | 0 | 0 | 8 | 0 | 9 | 7 | 3 | 10 | 9 | 10 | 2 | 0 | 0 | 0 | 2 | 5 | 4 | 2 |
| Blackgrass | 9 | 0 | 10 | 0 | 9 | 9 | 5 | 10 | 9 | 9 | 9 | 5 | 0 | 5 | 3 | 8 | 6 | 0 |
| Chickweed | 9 | 0 | 9 | 0 | 9 | 10 | 10 | 10 | 10 | 10 | 7 | 5 | 0 | 0 | 5 | 10 | 4 | 4 |
| Corn | 0 | 0 | 2 | 0 | 3 | 2 | 0 | 6 | 0 | 3 | 0 | 0 | 0 | 0 | 0 | 1 | 2 | 0 |
| Cotton | 2 | 0 | 7 | 0 | 3 | 3 | 3 | 9 | 8 | 6 | 0 | 1 | 0 | — | 0 | 3 | 2 | 4 |
| Crabgrass | 7 | 0 | 7 | 0 | 3 | 3 | 0 | 8 | 3 | 7 | 0 | 3 | 0 | 0 | 0 | 4 | 2 | 0 |
| Downy brome | 8 | 0 | 9 | 0 | 6 | 3 | 0 | 7 | 5 | 9 | 4 | 3 | 0 | 0 | 0 | 3 | 0 | 0 |
| Duck salad | — | — | — | — | — | — | — | — | — | — | — | — | — | — | — | — | — | — |
| Giant foxtail | 8 | 0 | 4 | 0 | 3 | 4 | 0 | 7 | 3 | 4 | 0 | 5 | 0 | 0 | 0 | 5 | 2 | 0 |
| Lambsquarters | 0 | 0 | 4 | 0 | 9 | 10 | 9 | 9 | 9 | 10 | 0 | 7 | 0 | 0 | 6 | 8 | 6 | — |
| Morningglory | 0 | 0 | 0 | 0 | 5 | 4 | 2 | 8 | 2 | 4 | 0 | 0 | 0 | 0 | 0 | 3 | 4 | 0 |
| Pigweed | 8 | 0 | 5 | 0 | 8 | 8 | 8 | 8 | 8 | 8 | 7 | 8 | 0 | 5 | 5 | 8 | 8 | 3 |
| Rape | 6 | 0 | 2 | 0 | 5 | 5 | 2 | 9 | 9 | 9 | 0 | 2 | 0 | 1 | 3 | 2 | 0 | 3 |
| Ryegrass | 2 | 0 | 4 | 0 | 8 | 0 | 0 | 7 | 2 | 2 | 0 | 3 | 0 | 0 | 0 | 0 | 0 | 0 |
| Sorghum | 0 | 0 | 9 | 0 | 7 | 3 | 0 | 9 | 5 | 3 | 0 | 2 | 0 | 0 | 0 | 2 | 7 | 0 |
| Soybean | 0 | 0 | 0 | 0 | 0 | 0 | 0 | 6 | 0 | 2 | 0 | 0 | 0 | 0 | 0 | 0 | 0 | 0 |
| Speedwell | 0 | 0 | 7 | 2 | 9 | 10 | 0 | 10 | 0 | 10 | 9 | 7 | 0 | 3 | 9 | 9 | 9 | 4 |
| Sugar beet | 7 | 0 | 7 | 0 | 9 | 6 | 4 | 10 | 10 | 10 | 7 | 6 | 0 | 0 | 9 | 8 | 9 | 9 |
| Velvetleaf | 1 | 0 | 0 | 0 | 4 | 3 | 2 | 8 | 0 | 6 | 0 | 0 | 0 | 2 | 0 | 4 | 3 | 2 |
| Wheat | 5 | 0 | 9 | 0 | 4 | 4 | 0 | 0 | 0 | 2 | 0 | 0 | 0 | 0 | 2 | 0 | 0 | 0 |
| Wild buckwheat | — | — | — | 0 | 9 | 9 | 8 | 7 | 9 | 9 | 5 | 0 | 0 | 0 | 4 | 8 | 8 | 5 |
| Wild oat | 0 | 0 | 4 | 0 | 0 | 0 | 0 | 0 | 0 | 0 | 0 | 2 | 0 | 0 | 0 | 0 | 0 | 0 |
| Barnyardgrass | — | — | — | — | — | — | — | — | — | — | — | — | — | — | — | — | — | — |
| Rice Japonica | — | — | — | — | — | — | — | — | — | — | — | — | — | — | — | — | — | — |
| Umbrella sedge | — | — | — | — | — | — | — | — | — | — | — | — | — | — | — | — | — | — |

| | COMPOUND | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| Rate (4 g/ha) | 1 | 3 | 5 | 11 | 13 | 14 | 25 | 26 | 27 | 28 | 29 | 30 | 31 | 34 | 35 | 36 | 50 | 51 | 53 | 58 | 59 | 60 | 63 | 64 | 71 | 77 | 78 | 81 | 82 | 83 | 84 | 86 | 88 | 89 | 102 | 103 | 107 | 108 | 109 | 110 |
| | POSTEMERGENCE | | | | | | | | | | | | | | | | | | | | | | | | | | | | | | | | | | | | | | | |
| Barley Igri | 5 | 5 | 5 | 8 | 2 | 4 | 5 | 6 | 8 | 5 | 8 | 8 | 5 | 2 | 0 | 2 | 4 | 7 | 8 | 0 | 4 | 1 | 6 | 6 | 0 | 0 | 0 | 2 | 3 | 3 | 3 | 3 | 3 | 3 | 8 | 7 | 7 | 3 | 3 | 3 |
| Bedstraw | 5 | 9 | 9 | 0 | 2 | 2 | 7 | 10 | — | 5 | 10 | 10 | 5 | 2 | 7 | 9 | 7 | 9 | 5 | 8 | 9 | 9 | 5 | 4 | 4 | 0 | 4 | 4 | 6 | 8 | 0 | 6 | 7 | 9 | 7 | 8 | 10 | 10 | 8 | 9 |
| Blackgrass | 5 | 7 | 7 | 7 | 3 | 0 | 8 | 9 | 7 | 7 | 9 | 9 | 5 | 2 | 7 | 5 | 8 | 7 | 8 | 6 | 6 | 4 | 8 | 9 | 0 | 4 | 3 | 8 | 9 | 8 | 9 | 8 | 8 | 8 | 8 | 8 | 9 | 6 | 10 | 10 |
| Chickweed | 0 | 0 | 8 | 8 | 5 | 5 | 8 | 10 | 10 | 2 | 10 | 10 | — | 5 | 0 | 9 | 8 | 9 | 6 | 4 | 10 | 10 | 5 | 7 | 7 | 0 | 0 | 4 | 8 | 8 | 6 | 0 | 4 | 4 | 5 | 7 | 10 | 10 | 5 | 8 |
| Corn | 6 | 10 | 10 | 7 | 10 | 8 | 8 | 10 | 10 | 8 | 10 | 10 | 7 | 8 | 10 | 10 | 5 | 8 | 6 | 7 | 6 | 3 | 4 | 10 | 2 | 2 | 6 | 0 | 2 | 5 | 4 | 0 | 0 | 5 | 0 | 0 | 10 | 10 | 3 | 8 |
| Cotton | 3 | 3 | 5 | 3 | 3 | 0 | 0 | 2 | 6 | 4 | 8 | 8 | 0 | 0 | 3 | 6 | 8 | 10 | 8 | 6 | 9 | 9 | 5 | 8 | 7 | 0 | 4 | 4 | 3 | 9 | 2 | 2 | 7 | 2 | 0 | 6 | 10 | 9 | 8 | 6 |
| Crabgrass | 5 | 4 | 6 | 3 | 3 | 5 | 4 | 3 | 5 | 0 | 6 | 6 | 3 | 4 | 3 | 4 | 0 | 4 | 5 | 0 | 0 | 0 | 0 | 2 | 3 | 3 | 0 | 0 | 2 | 5 | 0 | 0 | 0 | 0 | 0 | 0 | 2 | 0 | 2 | 2 |
| Downy brome | 4 | 4 | 9 | 4 | 0 | 0 | 6 | 4 | 7 | 6 | 10 | 9 | 0 | 2 | 0 | 5 | 4 | 5 | 8 | 0 | 4 | 0 | 6 | 6 | 0 | 0 | 0 | 3 | 2 | 0 | 0 | 0 | 4 | 0 | 4 | 5 | 6 | 0 | 9 | 9 |
| Duck salad | — | — | — | — | — | — | — | — | — | — | — | — | — | — | — | — | 9 | 9 | 9 | 6 | 10 | 9 | 0 | 8 | 5 | 0 | 0 | 0 | 1 | 2 | 0 | 0 | 0 | 4 | 0 | 0 | 9 | 8 | 8 | 9 |
| Giant foxtail | 6 | 6 | 6 | 8 | 6 | 7 | 7 | 8 | 8 | 6 | 10 | 10 | 7 | 6 | 6 | 7 | 4 | 5 | 7 | 3 | 0 | 0 | 7 | 8 | 0 | 3 | 5 | 2 | 6 | 7 | 2 | 3 | 2 | 0 | 2 | 0 | 4 | 0 | 4 | 5 |
| Lambsquarters | 8 | 10 | 10 | 9 | 5 | 5 | 8 | 10 | 10 | 9 | 10 | 10 | 5 | 2 | 9 | 10 | 10 | 10 | 10 | — | 10 | 10 | 10 | 10 | 1 | 6 | 7 | 5 | 6 | 9 | 9 | 6 | 8 | 9 | 9 | — | 10 | 10 | 10 | 10 |
| Morningglory | 6 | 6 | 6 | 5 | 4 | 6 | 7 | 10 | 10 | 10 | 10 | 10 | 5 | 6 | 8 | 9 | 10 | 10 | 8 | 8 | 7 | 8 | 9 | 10 | 8 | 5 | 7 | 7 | 9 | 9 | 6 | 6 | 7 | 20 | 7 | 8 | 10 | 10 | 3 | 10 |
| Pigweed | 3 | 2 | 10 | 7 | 7 | 0 | 6 | 5 | 10 | 7 | 8 | 8 | 6 | 7 | 6 | 8 | 7 | 10 | 7 | 3 | 10 | 8 | 8 | 10 | 8 | 7 | 9 | 3 | 8 | 10 | 6 | 0 | 0 | 0 | 7 | 8 | 10 | 8 | 8 | 8 |
| Rape | 0 | 3 | 10 | 4 | 9 | 9 | 3 | 5 | 6 | 8 | 10 | 10 | 0 | 2 | 0 | 8 | 10 | 10 | 9 | 8 | 10 | 10 | 9 | 9 | 5 | 6 | 7 | 8 | 9 | 6 | 9 | 7 | 8 | 10 | 9 | 6 | 10 | 9 | 9 | 10 |
| Ryegrass | 3 | 0 | 7 | 4 | 0 | 0 | 9 | 9 | 7 | 6 | 8 | 6 | 0 | 2 | 2 | 5 | 5 | 8 | 7 | 0 | 8 | 2 | 6 | 6 | 0 | 0 | 0 | 0 | 3 | 0 | 0 | 0 | 2 | 0 | 0 | 0 | 10 | 5 | 9 | 10 |
| Sorghum | 6 | 7 | 10 | 6 | 8 | 7 | 10 | 10 | 10 | 10 | 10 | 10 | 8 | 7 | 6 | 10 | 6 | 8 | 6 | 5 | 3 | 3 | 9 | 9 | 3 | 6 | 7 | 9 | 9 | 9 | 9 | 9 | 7 | 7 | 8 | 9 | 9 | 8 | 9 | 8 |
| Soybean | 5 | 7 | 10 | 6 | 8 | 7 | 7 | 7 | 10 | 8 | 10 | 10 | 5 | 6 | 7 | 10 | 10 | 8 | 9 | 9 | 9 | 10 | 8 | 10 | 8 | 6 | 6 | 6 | 7 | 8 | 4 | 5 | 8 | 9 | 4 | 7 | 10 | 10 | 6 | 10 |
| Speedwell | 4 | 0 | 7 | 0 | 0 | 0 | 4 | 2 | 0 | 3 | 7 | 0 | 0 | 0 | 0 | 0 | 4 | 9 | 5 | 7 | 10 | 2 | 4 | 0 | 0 | 0 | 0 | — | 0 | — | 2 | 0 | 8 | 0 | — | — | — | — | 6 | 8 |

TABLE B-continued

| | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| Sugar beet | 6 | 6 | 10 | 8 | 8 | 5 | 6 | 6 | 10 | 6 | 10 | 10 | 5 | 5 | 9 | 10 | 9 | 10 | 7 | 6 | 10 | 10 | 10 | 10 | 3 | 6 | 7 | 6 | 9 | 9 | 8 | 8 | 8 | 8 | 9 | 9 | 10 | 10 | 8 | 9 |
| Velvetleaf | 4 | 4 | 6 | 3 | 0 | 0 | 5 | 5 | 7 | 7 | 7 | 8 | 4 | 2 | 5 | 6 | 10 | 10 | 10 | 9 | 7 | 0 | 8 | 9 | 6 | 0 | 6 | 4 | 7 | 8 | 3 | 4 | 2 | 3 | 0 | 4 | 10 | 5 | 7 | 8 |
| Wheat | 4 | 0 | 9 | 9 | 3 | 3 | 6 | 4 | 7 | 4 | 8 | 9 | 2 | 2 | 2 | 3 | 4 | 6 | 9 | 0 | 0 | 0 | 6 | 5 | 0 | 0 | 0 | 0 | 0 | 2 | 0 | 2 | 2 | 0 | 8 | 6 | 7 | 0 | 9 | 9 |
| Wild buckwheat | 7 | 5 | 9 | 8 | 0 | 0 | 6 | 4 | 9 | 6 | 10 | 10 | 0 | 0 | 0 | 2 | 5 | 10 | 6 | 3 | 10 | 7 | 5 | 5 | 0 | 0 | 4 | 8 | 5 | 8 | 4 | 5 | 5 | 2 | 4 | 4 | 9 | 10 | 8 | — |
| Wild oat | 7 | 6 | 6 | 6 | 0 | 0 | 7 | 5 | 7 | 3 | 6 | 8 | 5 | 3 | 4 | 6 | 3 | 6 | 6 | 0 | 5 | 2 | 4 | 5 | 0 | 0 | 0 | 0 | 0 | 0 | 3 | 0 | 0 | 0 | 3 | 5 | 8 | 6 | 9 | 9 |
| Barnyardgrass | 0 | 0 | 0 | 1 | 0 | 0 | 0 | 6 | 2 | 8 | 4 | 0 | 0 | 0 | 0 | 0 | 2 | 7 | 8 | 6 | 7 | 2 | 6 | 8 | 0 | 0 | 0 | 0 | 5 | 6 | 2 | 7 | 0 | 0 | 0 | 0 | 6 | 5 | 8 | 8 |
| Rice Japonica | 2 | 0 | 6 | 0 | 0 | 0 | 1 | 0 | 0 | 6 | 5 | 0 | 0 | 0 | 0 | 5 | 0 | 8 | 0 | 6 | 8 | 9 | 5 | 7 | 7 | 0 | 0 | 0 | 3 | 6 | 2 | 0 | 0 | 2 | 0 | 0 | 8 | 8 | 8 | 7 |
| Umbrella sedge | 2 | 8 | 3 | 0 | 0 | 0 | 8 | 5 | 9 | 7 | 0 | 0 | 0 | 2 | 0 | 0 | 8 | 9 | 9 | 7 | 9 | 9 | 1 | 9 | 0 | 2 | 3 | 0 | 4 | 8 | 0 | 0 | 0 | 2 | 0 | 0 | 9 | 8 | 7 | 8 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (4 g/ha) | 111 | 112 | 114 | 115 | 116 | 117 | 118 | 119 | 120 | 121 | 122 | 166 | 167 | 170 | 172 | 173 | 203 | 204 | 205 | 206 | 207 | 208 | 211 | 212 | 213 | 214 | 217 | 218 |
| | POSTEMEGENCE | | | | | | | | | | | | | | | | | | | | | | | | | | | |
| Barley Igri | 7 | 5 | 5 | 2 | 3 | 0 | 0 | 9 | 4 | 5 | 5 | 5 | 7 | 3 | 8 | 9 | 5 | 9 | 10 | 9 | 6 | 5 | 8 | 7 | 3 | 3 | 7 | 4 |
| Bedstraw | 9 | 8 | 8 | 10 | 10 | 10 | 8 | 8 | 7 | 10 | 10 | 5 | | 9 | 6 | 8 | 6 | 6 | 9 | 7 | 7 | 7 | 6 | 7 | 10 | 9 | 3 | 5 |
| Blackgrass | 10 | 9 | 9 | 9 | 8 | 5 | 5 | 9 | 10 | 8 | 9 | 8 | 8 | 7 | 10 | 9 | 7 | 10 | 10 | 10 | 9 | 8 | 8 | 8 | 7 | 7 | 6 | 5 |
| Chickweed | 5 | 6 | 3 | 4 | 9 | 10 | 0 | 9 | 9 | 10 | 10 | 8 | 7 | 9 | 4 | 3 | 6 | 9 | 10 | 8 | 5 | 7 | 5 | 5 | 10 | 10 | 0 | 7 |
| Corn | 9 | 7 | 8 | 7 | 4 | 0 | 0 | 9 | 10 | 10 | 10 | 9 | 10 | 10 | 7 | 8 | 9 | 9 | 10 | 10 | 9 | 9 | 8 | 9 | 9 | 7 | 7 | 6 |
| Cotton | 8 | 6 | 5 | 8 | 8 | 9 | 2 | 8 | 10 | 8 | 6 | 3 | 5 | 8 | 5 | 4 | 3 | 3 | 6 | 3 | 4 | 6 | 3 | 6 | 8 | 7 | 4 | 4 |
| Crabgrass | 0 | 0 | 0 | 0 | 0 | 0 | 0 | 0 | 0 | 0 | 0 | 4 | 0 | 9 | 5 | 8 | 7 | 9 | 10 | 8 | 8 | 6 | 2 | 3 | 3 | 0 | 4 | 0 |
| Downy brome | 7 | 5 | 3 | 0 | 0 | 0 | 0 | 8 | 3 | 5 | 5 | 2 | 8 | 0 | 7 | 9 | 5 | 8 | 9 | 9 | 8 | 3 | 8 | 5 | 6 | 5 | 7 | 6 |
| Duck salad | 0 | 0 | 3 | 0 | 6 | 5 | 0 | 6 | 0 | 3 | 2 | 8 | 0 | 8 | 0 | 0 | 3 | 5 | 9 | 1 | 9 | 9 | 8 | 7 | 6 | 8 | 0 | 0 |
| Giant foxtail | 4 | 0 | 6 | 3 | 2 | 0 | 0 | 6 | 6 | 4 | 0 | 5 | 3 | 10 | 7 | 9 | 5 | 7 | 10 | 8 | 10 | 8 | 6 | 6 | 4 | 0 | 5 | 4 |
| Lambsquarters | 10 | 9 | 5 | 2 | 5 | 0 | 0 | 10 | 8 | 9 | 2 | 10 | 10 | 10 | 9 | 9 | 9 | 10 | 10 | 10 | 8 | 10 | 10 | 10 | 10 | 10 | 9 | 10 |
| Morningglory | 10 | 10 | 7 | 9 | 9 | 10 | 7 | 10 | 10 | 10 | 10 | 7 | 4 | 8 | 8 | 7 | 8 | 7 | 10 | 7 | 6 | 10 | 6 | 10 | 8 | 10 | 7 | 7 |
| Pigweed | 10 | 10 | 3 | 0 | 6 | 4 | 0 | 9 | 10 | 10 | 10 | 2 | 4 | 10 | 8 | 8 | 8 | 10 | 10 | 10 | 4 | 10 | 5 | 3 | 9 | 7 | 3 | 5 |
| Rape | 10 | 10 | 9 | 9 | 9 | 9 | 8 | 9 | 10 | 10 | 10 | 7 | 9 | 10 | 0 | 0 | 8 | 10 | 10 | 9 | 9 | 8 | 6 | 8 | 10 | 10 | 8 | 5 |
| Ryegrass | 5 | 6 | 7 | 0 | 7 | 2 | 2 | 8 | 3 | 9 | 6 | 3 | 7 | 7 | 3 | 7 | 4 | 8 | 10 | 6 | 4 | 5 | 3 | 0 | 7 | 4 | 4 | 3 |
| Sorghum | 9 | 9 | 7 | 8 | 8 | 7 | 0 | 9 | 10 | 9 | 8 | 9 | 9 | 10 | 5 | 8 | 10 | 10 | 10 | 10 | 10 | 10 | 7 | 8 | 10 | 8 | 7 | 6 |
| Soybean | 9 | 8 | 7 | 8 | 8 | 9 | 0 | 9 | 10 | 10 | 10 | 8 | 7 | 8 | 7 | 8 | 7 | 9 | 10 | 9 | 7 | 5 | 8 | 6 | 10 | 10 | 5 | 7 |
| Speedwell | 4 | 7 | 9 | 2 | 10 | 0 | — | 9 | 0 | 10 | 0 | 6 | 0 | 9 | 9 | 0 | 5 | 4 | 0 | 6 | 0 | 0 | 4 | 0 | 9 | 6 | 0 | 0 |
| Sugar beet | 9 | 8 | 3 | 5 | 9 | 9 | 3 | 9 | 10 | 10 | 10 | 9 | 9 | 10 | 7 | 9 | 8 | 9 | 9 | 9 | 5 | 8 | 6 | 7 | 10 | 10 | 7 | 9 |
| Velvetleaf | 8 | 7 | 7 | 8 | 9 | 5 | 0 | 9 | 10 | 9 | 5 | 7 | 7 | 9 | 5 | 4 | 6 | 7 | 9 | 6 | 4 | 6 | 3 | 5 | 8 | 3 | 3 | 5 |
| Wheat | 5 | 3 | 4 | 3 | 0 | 0 | 0 | 9 | 4 | 5 | 5 | 5 | 5 | 8 | 7 | 9 | 3 | 7 | 8 | 7 | 7 | 3 | 7 | 3 | 3 | 0 | 6 | 3 |
| Wild buckwheat | 7 | 7 | 5 | 7 | 9 | 9 | 5 | 10 | 7 | 8 | 9 | 5 | 5 | 8 | 8 | 8 | 7 | 8 | 9 | 7 | 3 | 7 | 5 | 7 | 10 | 7 | 2 | 7 |
| Wild oat | 6 | 4 | 4 | 0 | 3 | 3 | 0 | 4 | 2 | 9 | 6 | 6 | 8 | 4 | 5 | 7 | 5 | 8 | 9 | 8 | 8 | 4 | 4 | 3 | 4 | 4 | 6 | 3 |
| Barnyardgrass | 6 | 5 | 7 | 4 | 4 | 0 | 2 | 0 | 0 | 6 | 2 | 0 | 0 | 7 | 0 | 0 | 1 | 3 | 7 | 7 | 2 | 8 | 7 | 3 | 2 | 2 | 0 | 0 |
| Rice Japonica | 7 | 8 | 8 | 6 | 6 | 5 | 4 | 0 | 2 | 7 | 0 | 4 | 0 | 7 | 0 | 0 | 8 | 4 | 8 | 6 | 8 | 9 | 6 | 6 | 6 | 7 | 7 | 4 |
| Umbrella sedge | 7 | 3 | 6 | 8 | 8 | 8 | 0 | 9 | 8 | 7 | 3 | 9 | 9 | 4 | 0 | 2 | 6 | 9 | 9 | 7 | 2 | 8 | 9 | 8 | 8 | 8 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (4 g/ha) | 219 | 225 | 229 | 230 | 231 | 232 | 240 | 241 | 242 | 243 | 244 | 245 | 252 | 256 | 258 | 259 | 261 | 266 | 267 | 268 | 270 | 271 | 272 | 274 | 275 | 276 | 283 | 284 |
| | POSTEMERGENCE | | | | | | | | | | | | | | | | | | | | | | | | | | | |
| Barley Igri | 0 | 6 | 6 | 5 | 5 | 4 | 9 | 8 | 10 | 7 | 5 | 8 | 6 | 8 | 8 | 6 | 7 | 4 | 4 | 5 | 9 | 8 | 9 | 0 | 7 | 5 | 9 | 9 |
| Bedstraw | 8 | 4 | 9 | 6 | 8 | 7 | 8 | 9 | 10 | 9 | 10 | 10 | 9 | 8 | 9 | 5 | 9 | 7 | 9 | 9 | 6 | 9 | 7 | 0 | 6 | 0 | 9 | 10 |
| Blackgrass | 5 | 4 | 9 | 9 | 9 | 9 | 10 | 10 | 10 | 10 | 10 | 9 | 9 | 9 | 8 | 8 | 8 | 9 | 9 | 9 | 8 | 9 | 10 | 2 | 9 | 4 | 9 | 9 |
| Chickweed | 7 | 8 | 2 | 0 | 0 | 8 | 9 | 8 | 10 | 10 | 10 | 0 | 0 | 7 | 9 | 3 | 7 | 0 | 2 | 3 | 4 | 9 | 9 | 0 | 5 | 0 | 9 | 10 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Corn | 6 | 7 | 8 | 8 | 7 | 7 | 10 | 10 | 10 | 10 | 10 | 9 | 9 | 10 | 10 | 9 | 10 | 9 | 8 | 9 | 10 | 10 | 10 | 0 | 10 | 4 | 9 | 10 |
| Cotton | 3 | 3 | 0 | 0 | 5 | 2 | 4 | 7 | 7 | 7 | 8 | 5 | 0 | 0 | 0 | 0 | 0 | 0 | 5 | 1 | 3 | 3 | 2 | 0 | 0 | 0 | 5 | 8 |
| Crabgrass | 0 | 5 | 0 | 0 | 2 | 1 | 6 | 5 | 8 | 9 | 7 | 6 | 0 | 7 | 7 | 0 | 0 | 0 | 0 | 0 | 7 | 7 | 7 | 0 | 7 | 0 | 7 | 5 |
| Downy brome | 3 | 4 | 0 | 3 | 7 | 7 | 8 | 8 | 9 | 9 | 9 | 6 | 8 | 9 | 8 | 8 | 8 | 5 | 8 | 6 | 7 | 9 | 9 | 0 | 9 | 3 | 9 | 9 |
| Duck salad | 0 | 0 | 0 | 0 | 0 | 0 | 5 | 2 | 4 | 7 | 0 | 5 | 0 | 0 | 0 | 0 | 0 | 0 | 0 | 0 | 0 | 0 | 0 | 0 | 0 | 0 | 5 | 4 |
| Giant foxtail | 0 | 5 | 4 | 4 | 4 | 0 | 8 | 10 | 9 | 8 | 7 | 7 | 5 | 7 | 10 | 5 | 10 | 4 | 0 | 0 | 5 | 7 | 10 | 0 | 9 | 0 | 8 | 8 |
| Lambsquarters | 8 | 10 | 7 | 8 | — | 10 | 9 | 8 | 10 | 10 | 4 | 8 | 0 | 9 | 10 | 8 | 8 | 0 | 7 | 0 | 8 | 9 | 9 | 0 | 6 | 0 | 8 | 9 |
| Morningglory | 0 | 6 | 8 | 8 | 8 | 7 | 9 | 10 | 10 | 9 | 10 | 10 | 7 | 9 | 10 | 5 | 8 | 9 | 8 | 8 | 7 | 8 | 5 | 0 | 3 | 4 | 5 | 10 |
| Pigweed | 6 | 8 | 1 | 6 | 9 | 3 | 10 | 7 | 10 | 10 | 8 | 9 | 5 | 8 | 8 | 8 | 8 | 0 | 8 | 7 | 10 | 8 | 8 | 0 | 8 | 2 | 9 | 7 |
| Rape | 6 | 9 | 0 | 2 | 8 | 5 | 9 | 9 | 10 | 10 | 9 | 9 | 8 | 8 | 9 | 7 | 9 | 4 | 8 | 9 | 8 | 9 | 8 | 0 | 9 | 0 | 10 | 9 |
| Ryegrass | 4 | 0 | 0 | 0 | 4 | 3 | 10 | 7 | 10 | 10 | 4 | 8 | 0 | 9 | 9 | 8 | 8 | 0 | 8 | 3 | 4 | 4 | 8 | 0 | 9 | 0 | 8 | 0 |
| Sorghum | 3 | 7 | 8 | 8 | 9 | 9 | 9 | 10 | 10 | 10 | 10 | 10 | 9 | 10 | 10 | 10 | 9 | 9 | 9 | 9 | 10 | 9 | 9 | 0 | 9 | 8 | 10 | 9 |
| Soybean | 7 | 6 | 7 | 3 | 8 | 6 | 8 | 8 | 9 | 9 | 9 | 8 | 8 | 5 | 9 | 7 | 4 | 8 | 8 | 9 | 4 | 7 | 5 | 0 | 4 | 0 | 9 | 8 |
| Speedwell | 0 | 3 | 0 | 0 | — | — | 0 | 3 | 6 | 10 | 0 | 3 | 0 | 0 | 0 | 0 | 0 | 0 | 5 | 0 | 0 | 0 | 0 | 0 | 0 | 0 | 3 | 5 |
| Sugar beet | 8 | 8 | 2 | 2 | 8 | 5 | 9 | 8 | 10 | 10 | 10 | 8 | 0 | 6 | 8 | 9 | 7 | 0 | 9 | 8 | 9 | 9 | 9 | 0 | 5 | 0 | 8 | 8 |
| Velvetleaf | 6 | 5 | 5 | 4 | 7 | 4 | 5 | 6 | 9 | 8 | 7 | 7 | 0 | 6 | 7 | 0 | 0 | 0 | 5 | 0 | 0 | 0 | 3 | 0 | 0 | 0 | 7 | 8 |
| Wheat | 0 | 3 | 3 | 3 | 7 | 4 | 8 | 9 | 9 | 8 | 4 | 5 | 5 | 7 | 7 | 6 | 7 | 0 | 6 | 4 | 9 | 8 | 8 | 0 | 8 | 2 | 9 | 9 |
| Wild buckwheat | 7 | 6 | 4 | 5 | 8 | 7 | 9 | 9 | — | 9 | — | 9 | — | 9 | 8 | 0 | 9 | 7 | 5 | 7 | 9 | 9 | 9 | — | 10 | — | 9 | — |
| Wild oat | 3 | 2 | 4 | 6 | 5 | 4 | 9 | 9 | 10 | 10 | 9 | 8 | 4 | 7 | 8 | 7 | 7 | 4 | 6 | 7 | 8 | 5 | 9 | 0 | 8 | 0 | 10 | 7 |
| Barnyardgrass | 1 | 0 | 0 | 0 | 0 | 0 | 0 | 0 | 5 | 6 | 0 | 7 | 0 | 0 | 0 | 0 | 6 | 0 | 0 | 0 | 0 | 0 | 0 | 0 | 0 | 0 | 2 | 0 |
| Rice Japonica | 2 | 0 | 0 | 0 | 0 | 0 | 0 | 0 | 7 | 6 | 4 | 8 | 3 | 6 | 0 | 5 | 8 | 0 | 0 | 0 | 0 | 0 | 6 | 0 | 7 | 0 | 6 | 2 |
| Umbrella sedge | 0 | 0 | 0 | 0 | 0 | 0 | 7 | 7 | 7 | 6 | 3 | 7 | 0 | 6 | 8 | 0 | 1 | 0 | 0 | 0 | 7 | 3 | 3 | 0 | 3 | 0 | 8 | 7 |

| | COMPOUND | | | | | | | | | | |
|---|---|---|---|---|---|---|---|---|---|---|---|
| Rate (4 g/ha) | 285 | 286 | 287 | 288 | 289 | 291 | 300 | 301 | 302 | 305 | 310 |
| | POSTEMERGENCE | | | | | | | | | | |
| Barley Igri | 9 | 10 | 9 | 8 | 7 | 9 | 9 | 9 | 9 | 8 | 4 |
| Bedstraw | 10 | 10 | 9 | 10 | 9 | 8 | 8 | 8 | 9 | 7 | 5 |
| Blackgrass | 9 | 9 | 9 | 9 | 10 | 10 | 9 | 9 | 9 | 9 | 6 |
| Chickweed | 10 | 10 | 10 | 10 | 9 | 7 | 8 | 9 | 9 | 9 | — |
| Corn | 10 | 10 | 10 | 10 | 9 | 9 | 7 | 8 | 10 | 8 | 7 |
| Cotton | 8 | 9 | 8 | 3 | 5 | 3 | 2 | 0 | 5 | 0 | 0 |
| Crabgrass | 3 | 8 | 8 | 0 | 5 | 8 | 5 | 4 | 8 | 5 | 0 |
| Downy brome | 9 | 9 | 5 | 8 | 8 | 9 | 7 | 8 | 9 | 7 | 0 |
| Duck salad | 0 | 1 | 1 | 8 | 0 | 0 | 0 | 0 | 0 | 0 | 0 |
| Giant foxtail | 9 | 9 | 10 | 8 | 7 | 8 | 8 | 7 | 9 | 7 | 5 |
| Lambsquarters | 9 | 10 | 9 | 10 | 8 | 9 | 9 | 9 | 9 | 9 | 4 |
| Morningglory | 10 | 10 | 10 | 10 | 7 | 7 | 2 | 6 | 9 | 4 | 9 |
| Pigweed | 8 | 8 | 10 | 8 | 7 | 8 | 5 | 7 | 8 | 7 | 2 |
| Rape | 9 | 10 | 10 | 10 | 0 | 9 | 7 | 9 | 9 | 9 | 9 |
| Ryegrass | 0 | 9 | 4 | 4 | 0 | 8 | 6 | 4 | 4 | 0 | 0 |
| Sorghum | 10 | 10 | 10 | 10 | 9 | 9 | 7 | 8 | 9 | 9 | 8 |
| Soybean | 9 | 10 | 10 | 9 | 8 | 7 | 7 | 8 | 10 | 6 | 8 |
| Speedwell | 0 | 10 | 0 | 8 | 0 | 0 | — | 10 | — | 6 | 8 |
| Sugar beet | 9 | 10 | 10 | 9 | 8 | 7 | 9 | 9 | 10 | 9 | 9 |
| Velvetleaf | 10 | 8 | 0 | 8 | 0 | 4 | 0 | 0 | 6 | 0 | 6 |
| Wheat | 9 | 9 | 4 | 8 | 7 | 6 | 7 | 5 | 9 | 5 | 0 |
| Wild buckwheat | 10 | — | 10 | 10 | 5 | 9 | 8 | 3 | 6 | — | 8 |
| Wild oat | 5 | 9 | 5 | 8 | 5 | 8 | 7 | 8 | 9 | 4 | 2 |

TABLE B-continued

| | | | | | | | | | | | |
|---|---|---|---|---|---|---|---|---|---|---|---|
| Barnyardgrass | 0 | 4 | 4 | 7 | 0 | 0 | 3 | 0 | 2 | 2 | 0 |
| Rice Japonica | 2 | 2 | 2 | 7 | 0 | 0 | 0 | 2 | — | 4 | 0 |
| Umbrella sedge | 0 | 0 | 0 | 7 | 0 | 0 | 0 | 0 | 2 | 0 | 0 |

| | COMPOUND | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| Rate (4 g/ha) | 1 | 3 | 5 | 11 | 13 | 14 | 25 | 26 | 27 | 28 | 29 | 30 | 31 | 34 | 35 | 36 | 50 | 51 | 53 | 58 | 59 | 60 | 63 | 64 | 71 | 77 | 78 | 81 | 82 | 83 | 84 | 86 | 88 | 89 | 102 | 103 | 107 | 108 | 109 | 110 |
| | PREEMERGENCE | | | | | | | | | | | | | | | | | | | | | | | | | | | | | | | | | | | | | | | |
| Barley Igri | 0 | 0 | 0 | 0 | 0 | 0 | 0 | 0 | 0 | 0 | 0 | 0 | 0 | 0 | 0 | 0 | 3 | 5 | 6 | 0 | 5 | 0 | 5 | 5 | 0 | 0 | 0 | 2 | 3 | 0 | 0 | 0 | 3 | 0 | 3 | 3 | 4 | 0 | 6 | 5 |
| Bedstraw | 2 | 4 | 7 | 4 | 4 | 3 | 2 | 2 | 0 | 2 | 5 | 2 | 0 | 0 | 3 | 8 | 7 | 10 | 8 | 7 | 9 | 9 | 6 | 9 | 8 | 0 | 4 | 0 | 8 | 9 | 0 | 6 | 4 | 9 | 2 | 8 | 10 | 10 | 8 | 6 |
| Blackgrass | 4 | 4 | 0 | 2 | 0 | 0 | 4 | 4 | 4 | 3 | 4 | 2 | 0 | 0 | 4 | 5 | 7 | 7 | 9 | 5 | 7 | 4 | 9 | 9 | 3 | 2 | 3 | 7 | 9 | 9 | 3 | 8 | 8 | 8 | 4 | 8 | 9 | 9 | 9 | 9 |
| Chickweed | 0 | 6 | 6 | 8 | 8 | 7 | 0 | 2 | — | — | 9 | 5 | 0 | 3 | 6 | 8 | 9 | 10 | 9 | 7 | 9 | 10 | 5 | 7 | 7 | 0 | 3 | 0 | 9 | 9 | 0 | 4 | 7 | 7 | 3 | 6 | 9 | 9 | 8 | 9 |
| Corn | 0 | 2 | 0 | 4 | 0 | 0 | 4 | 2 | 4 | 2 | 4 | 4 | 0 | 0 | 0 | 0 | 0 | 7 | 0 | 0 | 4 | 2 | 3 | 9 | 0 | 0 | 0 | — | — | — | 5 | 0 | 0 | 0 | 0 | 0 | 10 | 8 | 4 | 6 |
| Cotton | 0 | 2 | 5 | 0 | 3 | 0 | 4 | 5 | 6 | 5 | 8 | 7 | 0 | 0 | 0 | 6 | 4 | 9 | 7 | 0 | 9 | 9 | 4 | 8 | 4 | 0 | — | — | — | — | 4 | 3 | 2 | 0 | 0 | 3 | 10 | 9 | 6 | 4 |
| Crabgrass | 0 | 3 | 4 | 0 | 0 | 0 | 2 | 6 | 4 | 4 | 5 | 8 | 0 | 0 | 0 | 2 | 5 | 8 | 7 | 3 | 0 | 0 | 5 | 8 | 0 | 0 | 4 | — | — | — | 0 | 1 | 0 | 1 | 0 | 0 | 7 | 6 | 4 | 3 |
| Downy brome | 2 | 0 | 6 | 0 | 0 | 0 | 0 | 0 | 0 | 3 | 0 | 0 | 0 | 0 | 3 | 3 | 3 | 7 | 7 | 2 | 6 | 3 | 9 | 8 | 0 | 0 | 0 | 4 | 4 | 3 | 0 | 0 | 3 | 4 | 0 | 4 | 7 | 2 | 8 | 5 |
| Duck salad | — | — | — | — | — | — | — | — | — | — | — | — | — | — | — | — | — | — | — | — | — | — | — | — | — | — | — | — | — | — | — | — | — | — | — | — | — | — | — | — |
| Giant foxtail | 0 | 0 | 0 | 0 | 0 | 0 | 0 | 3 | 2 | 2 | 7 | 4 | 2 | 0 | 0 | 3 | 4 | 7 | 7 | 0 | 0 | 0 | 8 | 8 | 0 | 0 | 0 | — | — | — | 0 | 0 | 0 | 2 | 0 | 0 | 7 | 4 | 4 | 6 |
| Lambsquarters | 4 | 6 | 10 | 4 | 7 | 6 | 0 | 5 | 0 | 3 | 5 | 5 | 5 | 6 | 8 | 8 | 9 | 10 | 9 | 5 | 10 | 8 | 9 | 10 | 7 | 0 | 2 | 8 | 9 | 8 | 3 | — | 0 | 8 | 3 | 1 | 9 | 9 | 8 | 9 |
| Morningglory | 0 | 3 | 3 | 0 | 0 | 0 | 4 | 4 | 1 | 3 | 4 | 3 | 0 | 0 | 0 | 3 | 7 | 9 | 3 | 0 | 8 | 9 | 6 | 8 | 5 | 0 | 6 | — | — | — | 2 | 2 | 2 | 3 | 0 | 3 | 9 | 8 | 6 | 5 |
| Pigweed | 0 | 5 | 5 | 0 | 2 | 0 | 7 | 7 | 7 | 7 | 8 | 9 | 0 | 0 | 3 | 8 | 10 | 10 | 9 | 6 | 8 | 9 | 9 | 9 | 8 | 4 | 7 | — | — | — | 0 | 7 | 2 | 7 | 7 | 8 | 9 | 9 | 9 | 9 |
| Rape | 2 | 3 | 0 | 0 | 6 | 4 | 4 | 2 | 2 | 4 | 4 | 4 | 0 | 0 | 0 | 4 | 7 | 9 | 9 | 8 | 10 | 9 | 9 | 9 | 6 | 4 | 6 | 6 | 9 | 8 | 0 | 6 | 7 | 9 | 6 | 7 | 9 | 9 | 9 | 8 |
| Ryegrass | 0 | 0 | 0 | 0 | 0 | 0 | 0 | 0 | 0 | 2 | 0 | 0 | 0 | 0 | 0 | 0 | 5 | 9 | 7 | | 8 | 6 | 4 | 6 | 0 | 0 | 0 | 0 | 4 | — | 0 | 3 | 0 | 0 | 0 | 0 | 9 | 5 | 7 | 6 |
| Sorghum | 0 | 2 | 6 | 0 | 0 | 2 | 5 | 3 | 3 | 4 | 10 | 4 | 0 | 0 | 2 | 3 | 4 | 9 | 6 | 4 | 7 | 5 | 9 | 9 | 0 | 3 | 3 | — | — | — | 9 | 9 | 5 | 6 | 5 | 7 | 9 | 9 | 6 | 9 |
| Soybean | 0 | 0 | 2 | 0 | 0 | 0 | 2 | 0 | 2 | 0 | 5 | 2 | 0 | 0 | 0 | 2 | 4 | 7 | 3 | 0 | 6 | 5 | 2 | 6 | 4 | 0 | 3 | — | — | — | 4 | 2 | 4 | 1 | 0 | 0 | 9 | 7 | 5 | 4 |
| Speedwell | 0 | 3 | 10 | 4 | 7 | 5 | 7 | 7 | 0 | 4 | 9 | 0 | 0 | 0 | 5 | 4 | 9 | 10 | 10 | 3 | 10 | 5 | 5 | 5 | 0 | 0 | 0 | 6 | 9 | 7 | 6 | 8 | 8 | 7 | 3 | 3 | 10 | 2 | 9 | 9 |
| Sugar beet | 5 | 6 | 9 | 3 | 7 | 3 | 0 | 4 | 0 | 5 | 4 | 5 | 0 | 4 | 8 | 8 | 8 | 9 | 9 | 8 | 9 | 10 | 9 | 9 | 8 | 0 | 8 | 8 | 9 | 9 | — | 8 | 9 | 8 | 7 | 9 | 10 | 10 | 9 | 9 |
| Velvetleaf | 0 | 0 | 3 | 0 | 0 | 0 | 3 | 5 | 2 | 3 | 8 | 2 | 0 | 0 | 0 | 2 | 4 | 9 | 7 | 4 | 9 | 6 | 7 | 9 | 8 | 0 | 4 | — | — | — | 0 | 6 | 2 | 2 | 4 | 5 | 10 | 8 | 5 | 3 |
| Wheat | 0 | 3 | 0 | 0 | 0 | 0 | 0 | 0 | 0 | 0 | 0 | 0 | 0 | 0 | 0 | 0 | 0 | 5 | 6 | 0 | 3 | 0 | 5 | 5 | 0 | 0 | 0 | 0 | 3 | 0 | 0 | 0 | 0 | 0 | 0 | 0 | 5 | 0 | 6 | 5 |
| Wild buckwheat | 5 | 4 | 7 | 0 | 3 | 0 | 0 | 0 | 0 | 2 | 4 | 5 | 0 | 0 | 7 | 7 | 8 | 9 | 8 | 2 | 8 | 8 | 8 | 7 | 4 | 0 | 4 | 4 | 8 | — | 0 | 7 | 3 | 6 | 2 | 8 | 9 | 9 | — | — |
| Wild oat | 0 | 0 | 0 | 0 | 0 | 0 | 0 | 0 | 0 | 0 | 0 | 0 | 0 | 0 | 0 | 0 | 2 | 5 | 3 | 0 | 5 | 3 | 0 | 2 | 0 | 0 | 0 | 3 | 0 | 2 | 0 | 0 | 0 | 0 | 0 | 0 | 3 | 0 | 4 | 4 |
| Barnyardgrass | — | — | — | — | — | — | — | — | — | — | — | — | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — | — | — | — | — | — | — | — | — | — | — | — | — |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (4 g/ha) | 111 | 112 | 114 | 115 | 116 | 117 | 118 | 119 | 120 | 121 | 122 | 166 | 167 | 170 | 172 | 173 | 203 | 204 | 205 | 206 | 207 | 208 | 211 | 212 | 213 | 214 | 217 | 218 |
| | PREEMERGENCE | | | | | | | | | | | | | | | | | | | | | | | | | | | |
| Barley Igri | 0 | 0 | 0 | 0 | 4 | 0 | 0 | 7 | 3 | 6 | 0 | 0 | 0 | 0 | 0 | 0 | 0 | 3 | 0 | 0 | 2 | 7 | 0 | 0 | 2 | 0 | 3 | 0 |
| Bedstraw | 3 | 8 | 8 | 7 | 9 | 9 | 0 | 0 | 2 | 4 | 8 | 0 | 2 | 8 | 0 | 0 | 0 | 3 | 8 | 8 | 6 | 8 | 5 | 0 | 9 | 9 | 0 | 0 |
| Blackgrass | 8 | 7 | 8 | 7 | 8 | 5 | 4 | 9 | 9 | 3 | 5 | 6 | 2 | 3 | 5 | 8 | 5 | 8 | 8 | 8 | 4 | 8 | 4 | 4 | 6 | 3 | 6 | 5 |
| Chickweed | 7 | 8 | 8 | 7 | 8 | 8 | 4 | 9 | 9 | 9 | 9 | 8 | 8 | 7 | 0 | 0 | 2 | 8 | 9 | 5 | 3 | 8 | 8 | 7 | 9 | 8 | 0 | 8 |
| Corn | 2 | 0 | 6 | 0 | 6 | 0 | 0 | 7 | 4 | 10 | 7 | 4 | 2 | 0 | 0 | — | 0 | 4 | 0 | 7 | 3 | 0 | 3 | 5 | 8 | 0 | 0 | 0 |
| Cotton | 4 | 3 | 2 | 0 | 9 | 8 | 0 | 7 | 6 | 9 | 8 | 3 | 0 | 7 | 0 | 0 | 3 | 0 | 7 | 5 | 4 | 3 | 0 | 0 | 10 | 8 | 3 | 0 |
| Crabgrass | 0 | 0 | 3 | 0 | 5 | 0 | 0 | 5 | 3 | 0 | 2 | 6 | 4 | 2 | 0 | 0 | 3 | 6 | 8 | 4 | 5 | 7 | 5 | 3 | 3 | 0 | 0 | 0 |
| Downy brome | 0 | 0 | 4 | 0 | 5 | 0 | 0 | 8 | 2 | 5 | 5 | 0 | 0 | 0 | 0 | 0 | 6 | 5 | 6 | 7 | 5 | 7 | 4 | 0 | 7 | 6 | 5 | 5 |
| Duck salad | — | — | — | — | — | — | — | — | — | — | — | — | — | — | — | — | — | — | — | — | — | — | — | — | — | — | — | — |

TABLE B-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| Giant foxtail | 0 | 0 | 6 | 0 | 5 | 0 | 0 | 6 | 3 | 0 | 0 | 4 | 0 | 2 | 3 | 2 | 0 | 5 | 7 | 5 | 3 | 7 | 3 | 0 | 4 | 0 | 0 | 2 |
| Lambsquarters | 9 | 9 | 8 | 5 | 9 | 8 | 5 | 10 | 9 | 8 | 8 | 0 | 2 | 8 | 9 | 0 | 3 | 8 | 10 | 3 | 3 | 7 | 7 | — | 9 | 8 | 6 | — |
| Morningglory | 5 | 5 | 7 | 6 | 9 | 9 | 2 | 8 | 7 | 9 | 7 | 2 | 0 | 7 | 0 | 0 | 0 | 4 | 7 | 5 | 6 | 7 | 0 | 2 | 8 | 8 | 0 | 0 |
| Pigweed | 8 | 8 | 8 | 7 | 8 | 8 | 5 | 9 | 8 | 8 | 7 | 8 | 6 | 9 | 5 | 5 | 4 | 9 | 9 | 7 | 5 | 9 | 7 | 3 | 9 | 9 | 2 | 5 |
| Rape | 5 | 5 | 8 | 5 | 9 | 8 | 3 | 9 | 7 | 8 | 10 | 4 | 4 | 8 | 0 | 0 | 6 | 5 | 8 | 3 | 2 | 8 | 5 | 0 | 10 | 8 | 3 | 0 |
| Ryegrass | 0 | 0 | 6 | 0 | 7 | 2 | 0 | 0 | 0 | 3 | 0 | 2 | 0 | 0 | 0 | 0 | 0 | 4 | 5 | 8 | 4 | 7 | 0 | 0 | 5 | 0 | 0 | 0 |
| Sorghum | 0 | 3 | 7 | 4 | 8 | 5 | 0 | 7 | 2 | 8 | 7 | 4 | 4 | 8 | 2 | 0 | 3 | 6 | 7 | 9 | 9 | 10 | 3 | 0 | 10 | 7 | 5 | 3 |
| Soybean | 0 | 1 | 0 | 0 | 7 | 3 | 0 | 7 | 4 | 7 | 5 | 0 | 0 | 2 | 0 | 0 | 0 | 0 | 5 | 4 | 0 | 2 | 0 | 0 | 7 | 6 | 0 | 0 |
| Speedwell | 3 | 9 | 8 | 7 | 10 | 3 | 7 | 10 | 8 | 8 | 0 | 9 | 0 | 9 | 7 | 4 | 0 | 0 | 3 | 3 | 0 | 7 | 7 | 0 | 9 | 3 | 0 | 0 |
| Sugar beet | 9 | 9 | 9 | 6 | 9 | 9 | 3 | 10 | 8 | 9 | 9 | 0 | 4 | 9 | 4 | 2 | 2 | 7 | 8 | 8 | 2 | 8 | 7 | 4 | 9 | 9 | 4 | 5 |
| Velvetleaf | 4 | 3 | 6 | 5 | 9 | 6 | 0 | 5 | 2 | 8 | 0 | 2 | 2 | 7 | 0 | 0 | 0 | 3 | 6 | 7 | 4 | 8 | 5 | 0 | 8 | 0 | 0 | 0 |
| Wheat | 3 | 0 | 0 | 0 | 0 | 0 | 0 | 6 | 0 | 8 | 3 | 0 | 0 | 0 | 0 | 0 | 0 | 3 | 3 | 6 | 2 | 7 | 4 | 0 | 4 | 0 | 3 | 2 |
| Wild buckwheat | 6 | — | 8 | 8 | 8 | 8 | — | 10 | 8 | 9 | 9 | 3 | 4 | 6 | 0 | — | 1 | 8 | 8 | 7 | 3 | 7 | 3 | 0 | 9 | 8 | 0 | 0 |
| Wild oat | 0 | 0 | 2 | 0 | 4 | 2 | 0 | 4 | 0 | 0 | 0 | 0 | 0 | 0 | 0 | 0 | 0 | 3 | 3 | 0 | 2 | 2 | 0 | 0 | 2 | 0 | 0 | 0 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |
| | COMPOUND | | | | | | | | | | | | | | | | | | | | | | | | | | | |
| Rate (4 g/ha) | 219 | 225 | 229 | 230 | 231 | 232 | 240 | 241 | 242 | 243 | 244 | 245 | 252 | 256 | 258 | 259 | 261 | 266 | 267 | 268 | 270 | 271 | 272 | 274 | 275 | 276 | 283 | 284 |
| | PREEMERGENCE | | | | | | | | | | | | | | | | | | | | | | | | | | | |
| Barley Igri | 0 | 0 | 0 | 0 | 0 | 2 | 4 | 4 | 0 | 0 | 0 | 3 | 0 | 4 | 0 | 0 | 5 | 0 | 4 | 0 | 3 | 2 | 0 | 0 | 7 | 0 | 0 | 0 |
| Bedstraw | 3 | 0 | 0 | 0 | 3 | 2 | 5 | 6 | 7 | 8 | 8 | 9 | 4 | 3 | 6 | 0 | 5 | 0 | 5 | 0 | 0 | 0 | 0 | 0 | 5 | 0 | 8 | 7 |
| Blackgrass | 0 | 0 | 0 | 0 | 3 | 5 | 9 | 10 | 9 | 9 | 10 | 9 | 6 | 9 | 9 | 6 | 9 | 3 | 8 | 3 | 6 | 8 | 6 | 0 | 9 | 0 | 9 | 6 |
| Chickweed | 6 | 2 | 0 | 0 | 0 | 0 | 4 | 9 | 9 | 8 | 10 | 8 | 5 | 0 | 7 | 0 | 0 | 0 | 0 | 0 | 0 | 0 | 7 | 0 | 0 | 0 | 9 | 10 |
| Corn | 0 | 0 | 0 | 0 | 0 | 3 | 4 | 8 | 4 | 10 | 8 | 6 | 0 | 2 | 5 | 0 | 4 | 0 | 0 | 0 | 0 | 0 | 0 | 0 | 0 | 0 | 3 | 0 |
| Cotton | 0 | 4 | 0 | 0 | 3 | 0 | 0 | 1 | 4 | 7 | 5 | 4 | 0 | 0 | 0 | — | 2 | 0 | 0 | 0 | 3 | 0 | 0 | 0 | 2 | 0 | 2 | 2 |
| Crabgrass | 0 | 0 | 0 | 0 | 0 | 0 | 4 | 5 | 3 | 3 | 4 | 5 | 0 | 0 | 3 | 0 | 2 | 0 | 2 | 0 | 0 | 3 | 4 | 0 | 3 | 0 | 0 | 0 |
| Downy brome | 2 | 0 | 0 | 0 | 6 | 2 | 4 | 5 | 7 | 5 | 4 | 9 | 3 | 7 | 6 | 4 | 6 | 0 | 8 | 6 | 0 | 0 | 3 | 0 | 9 | 0 | 2 | 0 |
| Duck salad | — | — | — | — | — | — | — | — | — | — | — | — | — | — | — | — | — | — | — | — | — | — | — | — | — | — | — | — |
| Giant foxtail | 0 | 0 | 0 | 0 | 0 | 0 | 1 | 3 | 2 | 4 | 3 | 4 | 0 | 3 | 4 | 0 | 4 | 0 | 4 | 0 | 0 | 2 | 8 | 0 | 2 | 0 | 0 | 1 |
| Lambsquarters | 2 | 0 | 6 | 3 | 0 | 0 | 9 | 9 | 8 | 8 | 9 | 9 | — | 4 | 9 | 8 | — | 3 | 0 | 0 | — | 6 | 0 | 0 | 3 | 0 | 9 | 9 |
| Morningglory | 0 | 0 | 0 | 0 | 1 | 2 | 4 | 2 | 2 | 8 | 4 | 5 | 0 | 0 | 0 | 0 | 0 | 0 | 2 | 2 | 0 | 0 | 0 | 0 | 0 | 0 | 3 | 4 |
| Pigweed | 5 | 0 | 0 | 0 | 0 | 0 | 7 | 8 | 8 | 8 | 7 | 8 | 0 | 0 | 7 | 3 | 7 | 0 | 6 | 0 | 2 | 3 | 2 | 0 | 3 | 0 | 8 | 8 |
| Rape | 3 | 0 | 0 | 0 | 0 | 0 | 6 | 6 | 3 | 9 | 7 | 8 | 3 | 4 | 3 | 0 | 3 | 0 | 0 | 0 | 0 | 0 | 2 | 0 | 2 | 0 | — | 3 |
| Ryegrass | 0 | 0 | 0 | 0 | 0 | 0 | 4 | 4 | 3 | 6 | 2 | 2 | 0 | 4 | 5 | 4 | 4 | 0 | 0 | 0 | 0 | 0 | 0 | 0 | 3 | 0 | 3 | 0 |
| Sorghum | 0 | 3 | 4 | 0 | 9 | 9 | 3 | 4 | 2 | 10 | 10 | 9 | 0 | 8 | 4 | 7 | 8 | 3 | 8 | 5 | 0 | 0 | 0 | 0 | 4 | 0 | 2 | 0 |
| Soybean | 0 | 2 | 0 | 0 | 4 | 2 | 0 | 1 | 6 | 7 | 0 | 2 | 0 | 0 | 0 | 0 | 0 | 0 | 2 | 0 | 0 | 0 | 0 | 0 | 0 | 0 | 0 | 0 |
| Speedwell | 0 | — | 2 | 4 | 0 | 0 | 8 | 9 | 0 | 9 | 0 | 9 | 7 | 7 | 0 | 0 | 3 | 2 | — | 0 | 0 | 3 | 0 | 0 | 0 | 0 | — | 9 |
| Sugar beet | 7 | 5 | 0 | 0 | 0 | 2 | 8 | 9 | 7 | 9 | 9 | 9 | 1 | 0 | 5 | 2 | 6 | 0 | 1 | 0 | 2 | — | 0 | 0 | 7 | 0 | 6 | 6 |
| Velvetleaf | 0 | 2 | 2 | 0 | 3 | 0 | 2 | 2 | 2 | 8 | 4 | 0 | 0 | 0 | 3 | 0 | 0 | 2 | 0 | 0 | 0 | 2 | 0 | 0 | 0 | 0 | 4 | 2 |
| Wheat | 0 | 0 | 0 | 0 | 2 | 2 | | 5 | 0 | 4 | 0 | 3 | 0 | 6 | 3 | 0 | 5 | 0 | 0 | 0 | 3 | 0 | 0 | 0 | 4 | 0 | 0 | 0 |
| Wild buckwheat | 3 | 2 | 0 | 0 | 0 | 3 | 9 | 9 | — | 9 | 8 | 7 | 0 | 9 | 9 | — | 9 | 7 | — | 8 | 5 | 6 | 5 | — | — | 0 | 9 | 8 |
| Wild oat | 0 | 0 | 0 | 0 | 0 | 0 | 4 | 0 | 0 | 3 | 0 | 0 | 0 | 5 | 2 | 0 | 4 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |

COMPOUND

TABLE B-continued

| Rate (4 g/ha) | 285 | 286 | 287 | 288 | 289 | 291 | 300 | 301 | 302 | 305 | 310 |
|---|---|---|---|---|---|---|---|---|---|---|---|
| | PREEMERGENCE | | | | | | | | | | |
| Barley Igri | 0 | 0 | 0 | 0 | 0 | 0 | 0 | 0 | 0 | 0 | 0 |
| Bedstraw | — | 9 | 8 | 10 | 0 | 0 | 0 | 2 | 4 | 0 | 2 |
| Blackgrass | 4 | 4 | 5 | 7 | 8 | 3 | 3 | 2 | 4 | 3 | 0 |
| Chickweed | 9 | | | | | | | | | | |
| 9 | 10 | 9 | 7 | 2 | 0 | 5 | 5 | 0 | 0 | | |
| Corn | 0 | 5 | 0 | 0 | 0 | 0 | 0 | 0 | 0 | 2 | 0 |
| Cotton | 2 | 7 | 4 | 2 | 0 | 0 | 0 | 0 | 2 | 0 | 0 |
| Crabgrass | 0 | 6 | 0 | 4 | 0 | 2 | 0 | 0 | 0 | 0 | 0 |
| Downy brome | 0 | 4 | 0 | 8 | 0 | 2 | 0 | 0 | 0 | 0 | 0 |
| Duck salad | — | — | — | — | — | — | — | — | — | — | — |
| Giant foxtail | 0 | 7 | 0 | 0 | 0 | 3 | 0 | 0 | 2 | 0 | 0 |
| Lambsquarters | 5 | 9 | 9 | 10 | 0 | 5 | 0 | 4 | 7 | 0 | 0 |
| Morningglory | 0 | 7 | 0 | 2 | 0 | 0 | 0 | 0 | 0 | 0 | 0 |
| Pigweed | 7 | 8 | 8 | 8 | 7 | 6 | 3 | 0 | 7 | 5 | 0 |
| Rape | 0 | 9 | 9 | 8 | 0 | 2 | 0 | 0 | 0 | 0 | 0 |
| Ryegrass | 0 | 4 | 0 | 0 | 0 | 0 | 0 | 0 | 0 | 0 | 0 |
| Sorghum | 0 | 8 | 2 | 0 | 0 | 2 | 0 | 0 | 0 | 5 | 0 |
| Soybean | 0 | 4 | 0 | 0 | 0 | 0 | 0 | 0 | 0 | 0 | 0 |
| Speedwell | 0 | 10 | 0 | 10 | 9 | 2 | 0 | 5 | 8 | 0 | 4 |
| Sugar beet | 4 | 9 | 9 | 8 | 5 | 3 | 0 | 7 | 6 | 4 | 2 |
| Velvetleaf | 0 | 8 | 0 | 3 | 0 | 0 | 0 | 0 | 0 | 2 | 0 |
| Wheat | 0 | 0 | 0 | 0 | 0 | 0 | 0 | 2 | 0 | 0 | 0 |
| Wild buckwheat | 7 | 4 | 8 | 8 | 5 | 0 | 0 | 4 | 7 | 7 | — |
| Wild oat | 0 | 0 | 0 | 0 | 0 | 0 | 0 | 0 | 0 | 0 | 0 |
| Barnyardgrass | — | — | — | — | — | — | — | — | — | — | — |
| Rice Japonica | — | — | — | — | — | — | — | — | — | — | — |
| Umbrella sedge | — | — | — | — | — | — | — | — | — | — | — |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate (2 g/ha) | 25 | 26 | 27 | 28 | 29 | 30 | 31 | 34 | 36 | 107 | 204 | 205 | 206 | 207 | 240 | 241 | 242 | 243 | 244 | 245 | 272 | 283 | 284 | 285 | 286 | 287 | 288 | 291 |
| | POSTEMERGENCE | | | | | | | | | | | | | | | | | | | | | | | | | | | |
| Barley Igri | 3 | 5 | 6 | 5 | 6 | 7 | 4 | 0 | 2 | 4 | 7 | 10 | 7 | 4 | 8 | 6 | 9 | 6 | 4 | 8 | 5 | 9 | 8 | 8 | 9 | 9 | 8 | 7 |
| Bedstraw | 6 | 6 | 8 | 4 | 10 | 7 | 5 | 0 | 8 | 10 | 5 | 5 | 4 | 6 | 7 | 6 | 8 | 9 | 9 | 9 | 0 | 8 | 9 | 10 | 10 | 8 | 10 | 5 |
| Blackgrass | 7 | 9 | 7 | 7 | 6 | 5 | 4 | 0 | 4 | 9 | 10 | 10 | 10 | 9 | 9 | 9 | 9 | 10 | 9 | 9 | 9 | 9 | 9 | 9 | 9 | 9 | 8 | 10 |
| Chickweed | 5 | 6 | 9 | 0 | 9 | 10 | 0 | 2 | 8 | 10 | 8 | 10 | 6 | 5 | 5 | 6 | 8 | 9 | 10 | 0 | 9 | 9 | 10 | 10 | 9 | 10 | 9 | 5 |
| Corn | 7 | 10 | 10 | 7 | 10 | 10 | 6 | 7 | 10 | 10 | 8 | 9 | 10 | 7 | 10 | 9 | 10 | 10 | 10 | 9 | 9 | 9 | 10 | 10 | 10 | 9 | 9 | 9 |
| Cotton | 0 | 2 | 4 | 2 | 7 | 6 | 0 | 0 | 3 | 10 | 0 | 4 | 2 | 0 | 1 | 3 | 2 | 5 | 8 | 4 | 0 | 3 | 7 | 6 | 5 | 5 | 3 | 0 |
| Crabgrass | 3 | 2 | 4 | 0 | 5 | 5 | 0 | 3 | 3 | 0 | 8 | 10 | 7 | 7 | 5 | 4 | 7 | 8 | 4 | 4 | 6 | 5 | 3 | 0 | 7 | 7 | 0 | 5 |
| Downy brome | 4 | 2 | 4 | 6 | 9 | 5 | 0 | 0 | 4 | 3 | 8 | 9 | 9 | 7 | 5 | 5 | 9 | 9 | 8 | 4 | 7 | 7 | 5 | 6 | 8 | 0 | 6 | 6 |
| Duck salad | — | — | — | — | — | — | — | — | — | 7 | 0 | 9 | 0 | 3 | 0 | 0 | 0 | 5 | 0 | 2 | 0 | 2 | 0 | 0 | 0 | 0 | 2 | 0 |
| Giant foxtail | 6 | 7 | 7 | 6 | 10 | 9 | 6 | 5 | 7 | 2 | 6 | 9 | 7 | 7 | 5 | 8 | 9 | 8 | 6 | 6 | 10 | 7 | 6 | 9 | 9 | 7 | 7 | 7 |
| Lambsquarters | 6 | 10 | 10 | 8 | 10 | 10 | 5 | 0 | 8 | 10 | 10 | 10 | 9 | 8 | 8 | 7 | 10 | 10 | 3 | 8 | 7 | 8 | 9 | 9 | 9 | 6 | 8 | 9 |
| Morningglory | 7 | 8 | 9 | 10 | 8 | 10 | 4 | 5 | 7 | 10 | 7 | 10 | 6 | 5 | 8 | 8 | 8 | 8 | 9 | 8 | 3 | 4 | 5 | 10 | 7 | 9 | 8 | 5 |
| Pigweed | 5 | 4 | 8 | 6 | 7 | 7 | 5 | 6 | 7 | 10 | 10 | 10 | 9 | 3 | 9 | 7 | 10 | 10 | 7 | 8 | 7 | 9 | 7 | 8 | 6 | 10 | 7 | 7 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rape | 3 | 2 | 6 | 7 | 7 | 8 | 0 | 0 | 6 | 9 | 5 | 9 | 9 | 7 | 7 | 9 | 10 | 8 | 8 | 9 | 3 | 9 | 7 | 6 | 9 | 10 | 9 | 7 |
| Ryegrass | 4 | 6 | 3 | 5 | 7 | 0 | 0 | 0 | 2 | 8 | 6 | 10 | 6 | — | 7 | 2 | 5 | 10 | 0 | 4 | 2 | 3 | 0 | 0 | 2 | 0 | 2 | 5 |
| Sorghum | 10 | 9 | 10 | 9 | 10 | 10 | 8 | 6 | 10 | 8 | 10 | 10 | 10 | 10 | 9 | 10 | 10 | 10 | 10 | 10 | 9 | 9 | 9 | 9 | 10 | 10 | 10 | 8 |
| Soybean | 6 | 6 | 10 | 7 | 10 | 10 | 3 | 3 | 8 | 10 | 8 | 10 | 7 | 6 | 5 | 8 | 9 | 9 | 8 | 6 | 4 | 6 | 8 | 9 | 10 | 9 | 8 | 5 |
| Speedwell | 2 | 0 | 0 | 2 | 5 | 0 | 0 | 0 | 0 | — | — | 0 | 3 | 0 | 0 | 2 | 0 | 9 | 0 | 0 | 0 | 0 | 3 | 0 | 9 | 0 | 7 | 0 |
| Sugar beet | 5 | 4 | 6 | 6 | 10 | 10 | 4 | 3 | 9 | 10 | 8 | 7 | 9 | 4 | 9 | 8 | 9 | 10 | 10 | — | 6 | 6 | 8 | 9 | 10 | 10 | 9 | 7 |
| Velvetleaf | 4 | 4 | 5 | 5 | 7 | 7 | 3 | 0 | 5 | 9 | 7 | 8 | 3 | 2 | 5 | 6 | 6 | 7 | 6 | 5 | 0 | 7 | 8 | 10 | 6 | 0 | 8 | 2 |
| Wheat | 5 | 4 | 3 | 4 | 6 | 8 | 0 | 0 | 2 | 3 | 4 | 7 | 6 | 4 | 7 | 5 | 7 | 5 | 3 | 4 | 4 | 9 | 8 | 5 | 9 | 3 | 7 | 6 |
| Wild buckwheat | 6 | — | 7 | 5 | 9 | 9 | 0 | 0 | 2 | 9 | 6 | 8 | 0 | 3 | 9 | — | 9 | 6 | — | 9 | 9 | 8 | 8 | — | 9 | 10 | 10 | — |
| Wild oat | 5 | 4 | 5 | 0 | 4 | 6 | 0 | 0 | 4 | 6 | 7 | 9 | 7 | 6 | 8 | 8 | 9 | 10 | 7 | 4 | 5 | 8 | 6 | 2 | 9 | 0 | 4 | 5 |
| Barnyardgrass | 0 | 0 | 2 | 7 | 1 | 0 | 0 | 0 | 0 | 4 | 0 | 5 | 0 | 0 | 0 | 0 | 3 | 3 | 0 | 5 | 0 | 0 | 0 | 0 | 0 | 0 | 2 | 0 |
| Rice Japonica | 0 | 0 | 0 | 5 | 0 | 0 | 0 | 0 | 0 | 7 | 3 | 3 | 3 | 6 | 0 | 0 | 6 | 2 | 0 | 7 | 1 | 2 | 0 | 1 | 1 | 2 | 3 | 0 |
| Umbrella sedge | 2 | 5 | 8 | 7 | 0 | 0 | 0 | 2 | — | 8 | 7 | 9 | 3 | 0 | 0 | 3 | 7 | 3 | 0 | 0 | 2 | 8 | 5 | 0 | 0 | 0 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (2 g/ha) | 25 | 26 | 27 | 28 | 29 | 30 | 31 | 34 | 36 | 107 | 204 | 205 | 206 | 207 | 240 | 241 | 242 | 243 | 244 | 245 | 272 | 283 | 284 | 285 | 286 | 287 | 288 | 291 |
| | PREEMERGENCE | | | | | | | | | | | | | | | | | | | | | | | | | | | |
| Barley Igri | 0 | 0 | 0 | 0 | 0 | 0 | 0 | 0 | 0 | 3 | 2 | 0 | — | 0 | 2 | 0 | 0 | 0 | 0 | 3 | 0 | 0 | 0 | 0 | 0 | 0 | 0 | 0 |
| Bedstraw | 0 | 0 | 0 | 0 | 3 | 0 | 0 | 0 | 7 | 10 | 0 | 7 | 5 | 2 | 3 | 2 | 6 | 7 | 7 | 9 | 0 | 5 | 7 | 2 | 9 | 6 | 4 | 0 |
| Blackgrass | 0 | 0 | 0 | 2 | 3 | 0 | 0 | 0 | 3 | 9 | 7 | 8 | 7 | 0 | 8 | 5 | 9 | 7 | 7 | 8 | 4 | 6 | 5 | 2 | 3 | 3 | 6 | 0 |
| Chickweed | 0 | 0 | — | 5 | 7 | 4 | 0 | 0 | 6 | 9 | 8 | 8 | 5 | 2 | 0 | 6 | 9 | 8 | 9 | 5 | 3 | 9 | 9 | 7 | 9 | 9 | 9 | 0 |
| Corn | 2 | 0 | 4 | 2 | 4 | 2 | 0 | 0 | 0 | 10 | 2 | 0 | 3 | 3 | 3 | 2 | 3 | 10 | 5 | 5 | 0 | 3 | 0 | 0 | 4 | 0 | 0 | 0 |
| Cotton | 3 | 5 | 5 | 4 | 5 | 5 | 0 | 0 | 6 | 10 | 0 | 4 | 3 | 3 | 0 | 0 | 4 | 6 | 2 | 3 | 0 | 0 | 0 | 0 | 6 | 3 | 0 | 0 |
| Crabgrass | 0 | 3 | 3 | 2 | 4 | 7 | 0 | 0 | 0 | 7 | 4 | 7 | 3 | 3 | 0 | 3 | 0 | 0 | 0 | 2 | 3 | 0 | 0 | 0 | 3 | 0 | 0 | 0 |
| Downy brome | 0 | 0 | 0 | 0 | 0 | 0 | 0 | 0 | 0 | 5 | 2 | 4 | — | 3 | 3 | 0 | 0 | 0 | 3 | 5 | 3 | 0 | 0 | 0 | 4 | 0 | 5 | 0 |
| Duck salad | — | — | — | — | — | — | — | — | — | — | — | — | — | — | — | — | — | — | — | — | — | — | — | — | — | — | — | — |
| Giant foxtail | 0 | 2 | 0 | 0 | 3 | 3 | 0 | 0 | 0 | 5 | 3 | 5 | 3 | 0 | 0 | 0 | 0 | 0 | 0 | 3 | 2 | 0 | 0 | 0 | 5 | 0 | 0 | 0 |
| Lambsquarters | 0 | 2 | 0 | 2 | 2 | 0 | 2 | 3 | 7 | 9 | 7 | 7 | 0 | 3 | 8 | 7 | 7 | 8 | 3 | 9 | 0 | 9 | 0 | — | — | 9 | 8 | 0 |
| Morningglory | 3 | 2 | 0 | 3 | 2 | 0 | 0 | 0 | 0 | 9 | 3 | 6 | 3 | 0 | 0 | 0 | 2 | 7 | 0 | 2 | 0 | 0 | 3 | 0 | 5 | 0 | 0 | 0 |
| Pigweed | 7 | 2 | 4 | 3 | 4 | 8 | 0 | 0 | 3 | 9 | 6 | 8 | 6 | 0 | 5 | 8 | 3 | 8 | 7 | 7 | 0 | 8 | 5 | 2 | 7 | 7 | 8 | 2 |
| Rape | 3 | 0 | 0 | 2 | 1 | 0 | 0 | 0 | 3 | 8 | 2 | 5 | — | 0 | 5 | 4 | 3 | 5 | 4 | 3 | 0 | 3 | 3 | 0 | 2 | 3 | 5 | 0 |
| Ryegrass | 0 | 0 | 0 | 0 | 0 | 0 | 0 | 0 | 0 | 9 | 0 | 3 | — | 2 | 2 | 4 | 0 | 2 | 2 | 0 | 0 | 0 | 0 | 0 | 2 | 0 | 0 | 0 |
| Sorghum | 4 | 2 | 0 | 4 | 5 | 4 | 0 | 0 | 0 | 9 | 4 | 4 | 9 | 8 | 2 | 0 | 0 | 10 | 9 | 6 | 0 | 0 | 0 | 0 | 4 | 0 | 0 | 2 |
| Soybean | 2 | 0 | 2 | 0 | 4 | 0 | 0 | 0 | 0 | 8 | 0 | 4 | 3 | 0 | 0 | 0 | 2 | 5 | 0 | 0 | 0 | 0 | 0 | 0 | 3 | 0 | 0 | 0 |
| Speedwell | 4 | 2 | 0 | 0 | 8 | 0 | 0 | 0 | 3 | 10 | 0 | 0 | 3 | 0 | 5 | 4 | 0 | 8 | 0 | 9 | 0 | 9 | 7 | 0 | 8 | 0 | 10 | 0 |
| Sugar beet | 0 | 0 | 0 | 3 | 4 | 4 | 0 | 3 | 7 | 10 | 7 | 8 | 7 | 2 | 8 | 8 | 7 | 9 | 9 | 8 | 0 | — | 6 | 3 | 6 | 8 | 7 | 0 |
| Velvetleaf | 2 | 4 | 0 | 0 | 4 | 0 | 0 | 0 | 0 | 9 | 3 | 3 | 5 | 0 | 0 | 0 | 0 | 7 | 2 | 0 | 0 | 4 | 0 | 0 | 6 | 0 | 2 | 0 |
| Wheat | 0 | 0 | 0 | 0 | 0 | 0 | 0 | 0 | 0 | 3 | 2 | 0 | — | 0 | 2 | 2 | 0 | 0 | 0 | 0 | 0 | 0 | 0 | 0 | 0 | 0 | 0 | 0 |
| Wild buckwheat | 0 | 0 | 0 | 0 | 3 | 0 | 0 | 0 | 5 | 8 | 7 | 3 | 7 | 3 | 9 | 9 | — | 4 | — | 7 | — | 4 | 8 | 4 | 4 | 5 | 2 | 0 |
| Wild oat | 0 | 0 | 0 | 0 | 0 | 0 | 0 | 0 | 0 | 0 | 2 | 0 | — | 0 | 3 | 0 | 0 | 0 | 0 | 0 | 0 | 0 | 0 | 0 | 0 | 0 | 0 | 0 |
| Barnyardgrass | — | — | — | — | — | — | — | — | — | — | — | — | — | — | — | — | — | — | — | — | — | — | — | — | — | — | — | — |
| Rice Japonica | — | — | — | — | — | — | — | — | — | — | — | — | — | — | — | — | — | — | — | — | — | — | — | — | — | — | — | — |
| Umbrella sedge | — | — | — | — | — | — | — | — | — | — | — | — | — | — | — | — | — | — | — | — | — | — | — | — | — | — | — | — |

TEST C

Plastic pots were partially filled with silt loam soil. The soil was then saturated with water. Japonica rice (*Oryza sativa*) seedlings at the 2.0 and 2.5 leaf stage, seeds selected from barnyardgrass (*Echinochloa crus-galli*), duck salad (*Heteranthera limosa*), umbrella sedge (*Cyperus difformis*), and tubers selected from arrowhead (Safittaria spp.), waterchestnut (Eleocharis spp.), were planted into this soil. After planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table C, are reported on a 0 to 10 scale where 0 is no effect and 10 is complete control. A dash (-) response means no test result.

TABLE C

| Rate (64 g/ha) | COMPOUND 6 | COMPOUND 58 |
|---|---|---|
| PADDY | | |
| Barnyardgrass | 5 | 9 |
| Duck salad | — | 10 |
| Japonica rice | 8 | 8 |
| Umbrella sedge | 9 | 9 |
| Waterchestnut | 8 | 8 |

| Rate (16 g/ha) | COMPOUND 6 | 27 | 58 | 205 |
|---|---|---|---|---|
| PADDY | | | | |
| Arrowhead | — | — | — | 7 |
| Barnyardgrass | 0 | 2 | 6 | 10 |
| Duck salad | — | 10 | 10 | — |
| Japonica rice | 6 | 6 | 6 | 7 |
| Umbrella sedge | 7 | 9 | 9 | 9 |
| Waterchestnut | 4 | 6 | 7 | 8 |

| Rate (4 g/ha) | COMPOUND 6 | 27 | 58 | 205 |
|---|---|---|---|---|
| PADDY | | | | |
| Arrowhead | — | — | — | 3 |
| Barnyardgrass | 0 | 2 | 0 | 9 |
| Duck salad | — | 10 | 9 | — |
| Japonica rice | 1 | 1 | 4 | 7 |
| Umbrella ledge | 2 | 9 | 9 | 9 |
| Waterchestnut | 3 | 4 | 6 | 8 |

| Rate (32 g/ha) | COMPOUND 6 | 27 | 58 | 205 |
|---|---|---|---|---|
| PADDY | | | | |
| Arrowhead | — | — | — | 8 |
| Barnyardgrass | 3 | 4 | 5 | 10 |
| Duck salad | — | 10 | 10 | — |
| Japonica rice | 7 | 8 | 7 | 8 |
| Umbrella sedge | 8 | 9 | 9 | 10 |
| Waterchestnut | — | 7 | 8 | 8 |

| Rate (0 g/ha) | COMPOUND 6 | 27 | 58 | 205 |
|---|---|---|---|---|
| PADDY | | | | |
| Arrowhead | — | — | — | 5 |
| Barnyardgrass | 0 | 2 | 4 | 10 |
| Duck salad | — | 10 | 10 | — |
| Japonica rice | 5 | 5 | 5 | 7 |
| Umbrella sedge | 5 | 9 | 9 | 9 |
| Waterchestnut | 3 | 5 | 6 | 8 |

| Rate (2 g/ha) | COMPOUND 27 | 205 |
|---|---|---|
| PADDY | | |
| Arrowhead | — | 1 |
| Barnyardgrass | 0 | 4 |
| Duck salad | 3 | — |
| Japonica rice | 0 | 5 |
| Umbrella sedge | 0 | 9 |
| Waterchestnut | 2 | 5 |

Test D

Compounds evaluated in this test were formulated in a non-phytoxic solvent and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test. Plantings of these crops and weed species were adjusted to produce plants of appropriate size for the postemergence test. All plant species were grown using normal greenhouse practices. Crop and weed species include winter barley (*Hordeum vulgare* cv. 'Igri'), bedstraw (*Galium aparine*), blackgrass (*Alopecurus myosuroides*), chickweed (*Stellaria media*), downy brome (*Bromus tectorum*), field violet (*Viola arvensis*), green foxtail (*Setaria viridis*), kochia (*Kochia scoparia*), lambsquarters (*Chenopodium album*), Persian speedwell (*Veronica persica*), rape (*Brassica napus* cv. 'Jet Neuf'), ryegrass (*Lolium multiflorum*), sugar beet (*Beta vulgaris* cv. 'US1'), sunflower (*Helianthus annuus* cv. 'Russian Giant'), spring wheat (*Triticum aestivum* cv. 'ERA'), winter wheat (*Triticum aestivum* cv. 'Talent'), wild buckwheat (*Polygonum convolvulus*), wild mustard (*Sinapis arvensis*), wild oat (*Avena fatua*), and wild radish (*Raphanus raphanistrum*). Blackgrass and wild oat were treated postemergence at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table D, are based upon a 0 to 10 scale where 0 is no effect and 10 is complete control. A dash response (-) means no test result.

TABLE D

| Rate (250 g/ha) | COMPOUND 36 |
|---|---|
| PREEMERGENCE | |
| Blackgrass (1) | 10 |
| Blackgrass (2) | 10 |
| Chickweed | 10 |
| Downy brome | 10 |
| Field violet | 10 |
| Galium (1) | 10 |
| Green foxtail | 10 |
| Kochia | 10 |
| Lambsquarters | 10 |
| Persn Speedwell | 9 |
| Rape | 10 |
| Ryegrass | 10 |
| Sugar beet | 10 |
| Sunflower | 10 |
| Wheat (Spring) | 10 |
| Wheat (Winter) | 10 |
| Wild buckwheat | 10 |
| Wild mustard | 10 |
| Wild oat (1) | 10 |
| Wild oat (2) | 10 |
| Wild radish | 10 |
| Winter Barley | 10 |

| | COMPOUND | | | | | | | | | | | | | | | |
|---|---|---|---|---|---|---|---|---|---|---|---|---|---|---|---|---|
| Rate (125 g/ha) | 36 | 59 | 60 | 83 | 89 | 107 | 108 | 214 | 229 | 230 | 232 | 244 | 252 | 269 | 288 | 289 |
| POSTEMERGENCE | | | | | | | | | | | | | | | | |
| Blackgrass (1) | — | 10 | 7 | 10 | 10 | 10 | 7 | 10 | 7 | 8 | 10 | 10 | 10 | 4 | 10 | 10 |
| Blackgrass (2) | — | 10 | 7 | 10 | 9 | 10 | 6 | 10 | 7 | 9 | 10 | 10 | 10 | 4 | 10 | 10 |
| Chickweed | — | 10 | 10 | 10 | 8 | 10 | 10 | 10 | 7 | 6 | 9 | 10 | 4 | 0 | 10 | 10 |
| Downy brome | — | 7 | 7 | 5 | 3 | 7 | 5 | 10 | 7 | 9 | 10 | 10 | 10 | 5 | 10 | 10 |
| Field violet | — | 10 | 9 | 8 | 2 | 10 | 10 | 10 | 6 | 8 | 8 | 10 | 8 | 0 | 9 | 6 |
| Galium (1) | — | 10 | 10 | 10 | 9 | 10 | 10 | 10 | 9 | 9 | 10 | 10 | 10 | 4 | 10 | 9 |
| Galium (2) | — | 10 | 10 | 10 | 8 | 10 | 10 | 10 | 9 | 9 | 10 | 10 | 10 | 3 | 10 | 10 |
| Green foxtail | — | 9 | 7 | 9 | 5 | 10 | 5 | 8 | 6 | 9 | 5 | 10 | 10 | 3 | 10 | 10 |
| Kochia | — | 10 | 10 | 10 | 2 | 10 | 10 | 10 | 3 | 6 | 4 | 6 | 4 | 6 | 10 | 10 |
| Lambsquarters | — | 8 | 6 | 7 | 5 | 10 | 4 | 6 | 7 | 10 | 3 | 7 | 4 | 0 | 10 | 8 |
| Persn Speedwell | — | 10 | 3 | 0 | 2 | 10 | 0 | 4 | 0 | 0 | 3 | 2 | 4 | 0 | 7 | 4 |
| Rape | — | 10 | 10 | 10 | 10 | 10 | 10 | 10 | 10 | 10 | 10 | 10 | 10 | 7 | 10 | 7 |
| Ryegrass | — | 10 | 8 | 7 | 4 | 10 | 10 | 10 | 5 | 2 | 10 | 10 | 6 | 3 | 9 | 9 |
| Sugar beet | — | 10 | 10 | 10 | 9 | 10 | 10 | 10 | 6 | 8 | 9 | 10 | 5 | 2 | 10 | 10 |
| Sunflower | — | 10 | 10 | 10 | 10 | 10 | 10 | 10 | 10 | 10 | 10 | 10 | 10 | 6 | 10 | 10 |
| Wheat (Spring) | — | 6 | 4 | 7 | 3 | 8 | 5 | 5 | 7 | 6 | 10 | 10 | 8 | 2 | 10 | 10 |
| Wheat (Winter) | — | 5 | 3 | 6 | 3 | 7 | 4 | 5 | 8 | 7 | 10 | 10 | 8 | 2 | 10 | 10 |
| Wild buckwheat | — | 10 | 10 | 8 | 4 | 10 | 10 | 10 | 6 | 7 | 5 | 10 | 3 | 10 | 10 | 6 |
| Wild mustard | — | 10 | 10 | 10 | 10 | 10 | 10 | 10 | 10 | 10 | 10 | 10 | 10 | 10 | 10 | 10 |
| Wild oat (1) | — | 10 | 8 | 4 | 2 | 10 | 8 | 10 | 10 | 10 | 10 | 10 | 9 | 3 | 10 | 10 |
| Wild oat (2) | — | 9 | 8 | 3 | 2 | 10 | 7 | 10 | 10 | 10 | 10 | 10 | 8 | 2 | 10 | 10 |
| Wild radish | — | 10 | 10 | 10 | 10 | 10 | 10 | 10 | 9 | 9 | 10 | 10 | 10 | 9 | 10 | 10 |
| Winter Barley | — | 9 | 7 | 7 | 4 | 9 | 7 | 9 | 10 | 10 | 10 | 10 | 8 | 4 | 10 | 10 |
| PREEMERGENCE | | | | | | | | | | | | | | | | |
| Blackgrass (1) | 10 | 10 | 9 | 9 | 8 | 10 | 8 | 9 | 6 | 8 | 8 | 10 | 9 | 2 | 9 | 9 |
| Blackgrass (2) | 10 | 10 | 9 | 10 | 7 | 10 | 8 | 8 | 8 | 7 | 6 | 10 | 9 | 2 | 8 | 9 |
| Chickweed | 10 | 10 | 10 | 10 | 10 | 10 | 10 | 10 | 10 | 9 | 8 | 10 | 10 | 4 | 10 | 10 |
| Downy brome | 10 | 9 | 8 | 6 | 2 | 9 | 8 | 10 | 10 | 8 | 10 | 10 | 9 | 3 | 8 | 9 |
| Field violet | 10 | 10 | 10 | 10 | 10 | 10 | 10 | 10 | 8 | 9 | 5 | 10 | 10 | 0 | 10 | 9 |
| Galium (1) | 10 | 10 | 10 | 10 | 10 | 10 | 10 | 10 | 10 | 9 | 8 | 10 | 8 | 2 | 10 | 9 |
| Galium (2) | — | 10 | 10 | 10 | 10 | 10 | 10 | 10 | — | 8 | 8 | 10 | 9 | 2 | 10 | 9 |
| Green foxtail | 10 | 10 | 10 | 10 | 6 | 10 | 8 | 10 | 6 | 3 | 8 | 10 | 7 | 0 | 8 | 10 |
| Kochia | 9 | 10 | 10 | 10 | 8 | 10 | 10 | 9 | 4 | 2 | 4 | 10 | 3 | 0 | 10 | 8 |
| Lambsquarters | 10 | 10 | 10 | 10 | 10 | 10 | 10 | 10 | 7 | 9 | 2 | 10 | 10 | 0 | 10 | 6 |
| Persn Speedwell | 7 | 10 | 9 | 10 | 8 | 10 | 10 | 8 | 5 | 4 | 5 | 8 | 9 | 0 | 10 | 8 |
| Rape | 10 | 10 | 10 | 10 | 10 | 10 | 10 | 10 | 6 | 2 | 6 | 10 | 8 | 2 | 10 | 2 |
| Ryegrass | 10 | 10 | 9 | 10 | 6 | 10 | 10 | 8 | 0 | 0 | 7 | 10 | 5 | 0 | 9 | 8 |
| Sugar beet | 10 | 10 | 10 | 10 | 10 | 10 | 10 | 10 | 6 | 9 | 5 | 10 | 6 | 2 | 10 | 9 |
| Sunflower | 10 | 10 | 10 | 10 | 10 | 10 | 10 | 10 | 3 | 0 | 10 | 10 | 9 | 0 | 10 | 10 |
| Wheat (Spring) | 7 | 9 | 7 | 5 | 2 | 10 | 7 | 3 | 10 | 6 | 9 | 10 | 6 | 0 | 9 | 5 |
| Wheat (Winter) | 7 | 9 | 7 | 4 | 2 | 10 | 8 | 3 | 10 | 7 | 9 | 10 | 6 | 0 | 9 | 4 |
| Wild buckwheat | 10 | 10 | 10 | 10 | 8 | 10 | 10 | 10 | 5 | 7 | 6 | 10 | 2 | 0 | 10 | 8 |
| Wild mustard | 10 | 10 | 10 | 10 | 10 | 10 | 10 | 10 | 7 | 7 | 10 | 10 | 10 | 6 | 10 | 9 |

TABLE D-continued

| | | | | | | | | | | | | | | | | |
|---|---|---|---|---|---|---|---|---|---|---|---|---|---|---|---|---|
| Wild oat (1) | 9 | 10 | 10 | 4 | 2 | 10 | 9 | 8 | 8 | 6 | 10 | 10 | 4 | 0 | 6 | 6 |
| Wild oat (2) | 9 | 10 | 10 | 5 | 3 | 10 | 9 | 8 | 9 | 6 | 10 | 10 | 4 | 2 | 6 | 5 |
| Wild radish | 10 | 10 | 10 | 10 | 10 | 10 | 10 | 10 | 4 | 5 | 7 | 10 | 10 | 3 | 10 | 8 |
| Winter Barley | 10 | 10 | 9 | 10 | 4 | 10 | 10 | 10 | 10 | 9 | 9 | 10 | 8 | 3 | 8 | 5 |
| | COMPOUND | | | | | | | | | | | | | | | |
| Rate (64 g/ha) | 36 | 59 | 60 | 83 | 89 | 107 | 108 | 214 | 229 | 230 | 232 | 244 | 252 | 269 | 288 | 289 |
| POSTEMERGENCE | | | | | | | | | | | | | | | | |
| Blackgrass (1) | — | 9 | 6 | 10 | 9 | 10 | 6 | 8 | 5 | 7 | 10 | 10 | 10 | 2 | 10 | 10 |
| Blackgrass (2) | — | 9 | 5 | 9 | 7 | 10 | 5 | 8 | 6 | 8 | 10 | 10 | 10 | 2 | 10 | 10 |
| Chickweed | — | 10 | 10 | 10 | 4 | 10 | 10 | 10 | 5 | 4 | 8 | 10 | 3 | 0 | 10 | 10 |
| Downy brome | — | 6 | 5 | 3 | 2 | 5 | 3 | 10 | 6 | 8 | 10 | 10 | 10 | 4 | 10 | 10 |
| Field violet | — | 10 | 7 | 6 | 0 | 10 | 10 | 8 | 4 | 7 | 6 | 10 | 6 | 0 | 8 | 5 |
| Galium (1) | — | 10 | 9 | 8 | 7 | 10 | 10 | 10 | 8 | 8 | 10 | 10 | 9 | 2 | 10 | 8 |
| Galium (2) | — | 10 | 9 | 9 | 6 | 10 | 10 | 10 | 7 | 7 | 10 | 10 | 9 | 2 | 10 | 8 |
| Green foxtail | — | 8 | 5 | 7 | 3 | 10 | 3 | 7 | 4 | 7 | 3 | 10 | 10 | 0 | 10 | 10 |
| Kochia | — | 10 | 10 | 10 | 0 | 10 | 10 | 9 | 2 | 4 | 3 | 5 | 2 | 4 | 10 | 10 |
| Lambsquarters | — | 7 | 3 | 6 | 2 | 8 | 2 | 4 | 6 | 8 | 2 | 5 | 3 | 0 | 8 | 7 |
| Persn Speedwell | — | 10 | 2 | 0 | 0 | 10 | 0 | 2 | 0 | 0 | 0 | 0 | 2 | 0 | 4 | 2 |
| Rape | — | 10 | 10 | 10 | 10 | 10 | 10 | 10 | 10 | 10 | 10 | 10 | 10 | 4 | 10 | 5 |
| Ryegrass | — | 10 | 7 | 6 | 2 | 10 | 10 | 8 | 3 | 0 | 10 | 10 | 4 | 2 | 8 | 8 |
| Sugar beet | — | 10 | 10 | 10 | 7 | 10 | 10 | 10 | 5 | 6 | 7 | 10 | 4 | 0 | 10 | 9 |
| Sunflower | — | 10 | 10 | 10 | 10 | 10 | 10 | 10 | 10 | 10 | 10 | 10 | 10 | 3 | 10 | 10 |
| Wheat (Spring) | — | 4 | 2 | 5 | 2 | 6 | 2 | 4 | 6 | 5 | 9 | 10 | 7 | 0 | 9 | 10 |
| Wheat (Winter) | — | 4 | 2 | 4 | 2 | 5 | 2 | 4 | 7 | 6 | 10 | 10 | 7 | 0 | 9 | 10 |
| Wild buckwheat | — | 10 | 10 | 6 | 2 | 10 | 10 | 10 | 4 | 6 | 2 | 10 | 0 | 9 | 10 | 5 |
| Wild mustard | — | 10 | 10 | 10 | 10 | 10 | 10 | 10 | 10 | 10 | 10 | 10 | 10 | 10 | 10 | 10 |
| Wild oat (1) | — | 8 | 6 | 2 | 0 | 10 | 5 | 9 | 10 | 10 | 10 | 10 | 8 | 2 | 10 | 10 |
| Wild oat (2) | — | 8 | 6 | 2 | 0 | 10 | 5 | 10 | 10 | 10 | 10 | 10 | 6 | 0 | 10 | 10 |
| Wild radish | — | 10 | 10 | 10 | 10 | 10 | 10 | 10 | 7 | 7 | 10 | 10 | 10 | 7 | 10 | 10 |
| Winter Barley | — | 7 | 5 | 6 | 2 | 7 | 5 | 8 | 9 | 9 | 9 | 10 | 6 | 3 | 9 | 10 |
| PREEMERGENCE | | | | | | | | | | | | | | | | |
| Blackgrass (1) | 10 | 10 | 7 | 8 | 6 | 9 | 7 | 7 | 3 | 4 | 5 | 10 | 8 | 0 | 7 | 8 |
| Blackgrass (2) | 10 | 10 | 9 | 9 | 6 | 9 | 6 | 7 | 5 | 4 | 4 | 10 | 8 | 0 | 6 | 8 |
| Chickweed | 10 | 10 | 10 | 10 | 10 | 10 | 10 | 10 | 6 | 4 | 5 | 10 | 8 | 2 | 10 | 9 |
| Downy brome | 10 | 9 | 7 | 4 | 0 | 8 | 6 | 10 | 9 | 6 | 9 | 10 | 7 | 0 | 6 | 7 |
| Field violet | 10 | 10 | 10 | 10 | 8 | 10 | 10 | 10 | 5 | 7 | 3 | 10 | 9 | 0 | 10 | 6 |
| Galium (1) | 10 | 10 | 10 | 10 | 10 | 10 | 10 | 10 | 9 | 7 | 4 | 10 | 6 | 0 | 10 | 7 |
| Galium (2) | — | 10 | 10 | 10 | 10 | 10 | 10 | 10 | — | 7 | 4 | 10 | 7 | 0 | 10 | 8 |
| Green foxtail | 10 | 10 | 8 | 10 | 5 | 10 | 7 | 9 | 4 | 2 | 6 | 10 | 6 | 0 | 6 | 8 |
| Kochia | 7 | 10 | 10 | 10 | 5 | 10 | 10 | 8 | 2 | 0 | 3 | 9 | 2 | 0 | 10 | 6 |
| Lambsquarters | 10 | 10 | 10 | 10 | 10 | 10 | 10 | 10 | 4 | 4 | 0 | 10 | 9 | 0 | 10 | 3 |
| Persn Speedwell | 4 | 10 | 9 | 9 | 6 | 10 | 10 | 7 | 4 | 2 | 3 | 6 | 8 | 0 | 10 | 7 |
| Rape | 10 | 10 | 10 | 10 | 10 | 10 | 10 | 10 | 3 | 0 | 3 | 10 | 6 | 0 | 10 | 0 |
| Ryegrass | 10 | 10 | 8 | 8 | 3 | 10 | 9 | 6 | 0 | 0 | 5 | 9 | 2 | 0 | 7 | 5 |
| Sugar beet | 10 | 10 | 10 | 10 | 10 | 10 | 10 | 10 | 4 | 7 | 3 | 10 | 4 | 0 | 10 | 8 |
| Sunflower | 10 | 10 | 10 | 10 | 10 | 10 | 10 | 10 | 0 | 0 | 8 | 10 | 5 | 0 | 10 | 7 |
| Wheat (Spring) | 5 | 8 | 6 | 3 | 0 | 8 | 6 | 3 | 9 | 3 | 8 | 8 | 4 | 0 | 7 | 3 |
| Wheat (Winter) | 5 | 7 | 5 | 3 | 0 | 8 | 6 | 2 | 10 | 4 | 7 | 8 | 5 | 0 | 8 | 2 |
| Wild buckwheat | 10 | 10 | 10 | 10 | 6 | 10 | 10 | 10 | 2 | 5 | 4 | 10 | 0 | 0 | 10 | 6 |
| Wild mustard | 8 | 10 | 10 | 10 | 10 | 10 | 10 | 10 | 3 | 3 | 8 | 10 | 10 | 3 | 10 | 7 |
| Wild oat (1) | 6 | 10 | 9 | 3 | 0 | 10 | 8 | 6 | 7 | 4 | 7 | 10 | 2 | 0 | 5 | 5 |
| Wild oat (2) | 7 | 10 | 9 | 3 | 0 | 10 | 8 | 6 | 6 | 4 | 8 | 10 | 2 | 0 | 5 | 4 |
| Wild radish | 10 | 10 | 10 | 10 | 10 | 10 | 10 | 8 | 3 | 2 | 4 | 10 | 8 | 0 | 10 | 5 |
| Winter Barley | 9 | 10 | 8 | 8 | 2 | 10 | 10 | 8 | 9 | 6 | 6 | 10 | 5 | 2 | 7 | 4 |
| | COMPOUND | | | | | | | | | | | | | | | |
| Rate (32 g/ha) | 36 | 59 | 60 | 83 | 89 | 107 | 108 | 214 | 229 | 230 | 232 | 244 | 252 | 269 | 288 | 289 |
| POSTEMERGENCE | | | | | | | | | | | | | | | | |
| Blackgrass (1) | — | 8 | 5 | 8 | 6 | 8 | 4 | 6 | 4 | 6 | 9 | 10 | 9 | 0 | 9 | 10 |
| Blackgrass (2) | — | 7 | 4 | 7 | 4 | 8 | 4 | 7 | 4 | 6 | 10 | 10 | 8 | 0 | 8 | 10 |
| Chickweed | — | 10 | 10 | 10 | 2 | 10 | 10 | 10 | 4 | 2 | 4 | 10 | 2 | 0 | 8 | 10 |
| Downy brome | — | 5 | 4 | 2 | 0 | 3 | 2 | 8 | 4 | 6 | 9 | 10 | 8 | 2 | 10 | 10 |
| Field violet | — | 10 | 4 | 4 | 0 | 10 | 8 | 5 | 2 | 5 | 5 | 10 | 4 | 0 | 6 | 2 |
| Galium (1) | — | 10 | 8 | 7 | 4 | 10 | 10 | 9 | 7 | 6 | 9 | 10 | 7 | 0 | 9 | 7 |
| Galium (2) | — | 10 | 8 | 8 | 3 | 10 | 10 | 10 | 6 | 6 | 9 | 10 | 8 | 0 | 8 | 6 |
| Green foxtail | — | 7 | 3 | 6 | 0 | 10 | 0 | 5 | 3 | 6 | 2 | 10 | 8 | 0 | 10 | 10 |
| Kochia | — | 10 | 9 | 8 | 0 | 10 | 8 | 7 | 0 | 2 | 0 | 3 | 0 | 2 | 10 | 10 |
| Lambsquarters | — | 6 | 0 | 5 | 0 | 6 | 0 | 2 | 4 | 6 | 0 | 2 | 2 | 0 | 6 | 5 |
| Persn Speedwell | — | 10 | 0 | 0 | 0 | 9 | 0 | 0 | 0 | 0 | 0 | 0 | 0 | 0 | 2 | 0 |
| Rape | — | 10 | 10 | 10 | 10 | 10 | 10 | 10 | 8 | 9 | 10 | 10 | 9 | 2 | 10 | 3 |
| Ryegrass | — | 10 | 6 | 5 | 0 | 10 | 9 | 6 | 2 | 0 | 8 | 10 | 2 | 0 | 7 | 5 |

TABLE D-continued

| | | | | | | | | | | | | | | | | |
|---|---|---|---|---|---|---|---|---|---|---|---|---|---|---|---|---|
| Sugar beet | — | 10 | 10 | 10 | 5 | 10 | 10 | 10 | 3 | 3 | 4 | 10 | 3 | 0 | 9 | 7 |
| Sunflower | — | 10 | 10 | 10 | 10 | 10 | 10 | 10 | 10 | 10 | 10 | 10 | 10 | 0 | 10 | 10 |
| Wheat (Spring) | — | 3 | 0 | 3 | 0 | 4 | 0 | 2 | 5 | 4 | 8 | 10 | 4 | 0 | 8 | 10 |
| Wheat (Winter) | — | 4 | 0 | 3 | 0 | 3 | 0 | 2 | 6 | 3 | 8 | 10 | 4 | 0 | 8 | 10 |
| Wild buckwheat | — | 10 | 8 | 3 | 0 | 10 | 10 | 10 | 2 | 3 | 0 | 10 | 0 | 7 | 8 | 3 |
| Wild mustard | — | 10 | 10 | 10 | 10 | 10 | 10 | 10 | 10 | 10 | 10 | 10 | 10 | 7 | 10 | 10 |
| Wild oat (1) | — | 7 | 5 | 0 | 0 | 8 | 4 | 8 | 8 | 8 | 10 | 10 | 4 | 0 | 10 | 10 |
| Wild oat (2) | — | 7 | 5 | 0 | 0 | 7 | 4 | 9 | 8 | 8 | 10 | 10 | 3 | 0 | 9 | 10 |
| Wild radish | — | 10 | 10 | 10 | 10 | 10 | 8 | 10 | 4 | 5 | 10 | 10 | 10 | 5 | 10 | 8 |
| Winter Barley | — | 6 | 2 | 5 | 0 | 5 | 3 | 6 | 8 | 7 | 7 | 9 | 3 | 2 | 7 | 10 |
| PREEMERGENCE | | | | | | | | | | | | | | | | |
| Blackgrass (1) | 9 | 9 | 6 | 7 | 3 | 8 | 5 | 5 | 0 | 3 | 2 | 10 | 6 | 0 | 4 | 6 |
| Blackgrass (2) | 9 | 9 | 7 | 7 | 4 | 8 | 5 | 6 | 2 | 2 | 2 | 9 | 6 | 0 | 3 | 5 |
| Chickweed | 10 | 10 | 10 | 10 | 8 | 10 | 10 | 9 | 3 | 2 | 2 | 10 | 5 | 0 | 10 | 8 |
| Downy brome | 10 | 8 | 6 | 3 | 0 | 7 | 4 | 8 | 7 | 4 | 7 | 10 | 4 | 0 | 4 | 4 |
| Field violet | 10 | 10 | 10 | 10 | 6 | 10 | 10 | 10 | 2 | 3 | 2 | 10 | 6 | 0 | 10 | 3 |
| Galium (1) | 9 | 10 | 10 | 10 | 10 | 10 | 10 | 10 | 5 | 5 | 3 | 10 | 4 | 0 | 9 | 5 |
| Galium (2) | — | 10 | 10 | 10 | 10 | 10 | 10 | 10 | — | 3 | 2 | 10 | 4 | 0 | 8 | 4 |
| Green foxtail | 9 | 9 | 7 | 9 | 2 | 9 | 6 | 7 | 2 | 0 | 4 | 10 | 5 | 0 | 4 | 7 |
| Kochia | 4 | 10 | 9 | 8 | 2 | 10 | 9 | 5 | 0 | 0 | 2 | 7 | 0 | 0 | 10 | 5 |
| Lambsquarters | 10 | 10 | 10 | 10 | 7 | 10 | 10 | 9 | 2 | 2 | 0 | 10 | 7 | 0 | 10 | 2 |
| Persn Speedwell | 2 | 10 | 8 | 6 | 5 | 10 | 8 | 5 | 2 | 0 | 0 | 4 | 5 | 0 | 10 | 5 |
| Rape | 10 | 10 | 10 | 10 | 10 | 10 | 10 | 10 | 0 | 0 | 0 | 10 | 4 | 0 | 10 | 0 |
| Ryegrass | 8 | 10 | 7 | 6 | 2 | 10 | 7 | 4 | 0 | 0 | 2 | 7 | 0 | 0 | 5 | 3 |
| Sugar beet | 10 | 10 | 10 | 10 | 9 | 10 | 10 | 10 | 2 | 4 | 2 | 10 | 3 | 0 | 10 | 6 |
| Sunflower | 10 | 10 | 10 | 10 | 10 | 10 | 10 | 9 | 0 | 0 | 4 | 10 | 3 | 0 | 10 | 4 |
| Wheat (Spring) | 3 | 6 | 5 | 2 | 0 | 6 | 4 | 2 | 8 | 2 | 4 | 5 | 3 | 0 | 4 | 0 |
| Wheat (Winter) | 3 | 6 | 4 | 2 | 0 | 7 | 4 | 2 | 8 | 2 | 4 | 6 | 3 | 0 | 6 | 0 |
| Wild buckwheat | 7 | 10 | 10 | 10 | 4 | 10 | 10 | 10 | 0 | 2 | 2 | 8 | 0 | 0 | 8 | 4 |
| Wild mustard | 7 | 10 | 10 | 10 | 10 | 10 | 10 | 10 | 0 | 0 | 4 | 10 | 8 | 0 | 10 | 5 |
| Wild oat (1) | 3 | 10 | 8 | 2 | 0 | 10 | 7 | 3 | 4 | 2 | 4 | 8 | 0 | 0 | 3 | 3 |
| Wild oat (2) | 3 | 10 | 8 | 0 | 0 | 10 | 7 | 4 | 5 | 2 | 5 | 8 | 0 | 0 | 3 | 2 |
| Wild radish | 7 | 10 | 10 | 10 | 10 | 10 | 10 | 7 | 2 | 0 | 2 | 10 | 6 | 0 | 10 | 3 |
| Winter Barley | 4 | 9 | 7 | 7 | 0 | 10 | 10 | 6 | 8 | 3 | 3 | 8 | 3 | 0 | 5 | 2 |

| | COMPOUND | | | | | | | | | | | | | | | |
|---|---|---|---|---|---|---|---|---|---|---|---|---|---|---|---|---|
| Rate (16 g/ha) | 36 | 59 | 60 | 83 | 89 | 107 | 108 | 214 | 229 | 230 | 232 | 244 | 252 | 269 | 288 | 289 |
| POSTEMERGENCE | | | | | | | | | | | | | | | | |
| Blackgrass (1) | 5 | 7 | 3 | 6 | 3 | 7 | 3 | 4 | 3 | 4 | 7 | 9 | 7 | 0 | 7 | 9 |
| Blackgrass (2) | 4 | 6 | 2 | 5 | 2 | 6 | 2 | 3 | 2 | 3 | 8 | 9 | 5 | 0 | 6 | 8 |
| Chickweed | 5 | 10 | 10 | 8 | 0 | 10 | 10 | 10 | 2 | 0 | 2 | 10 | 0 | 0 | 6 | 8 |
| Downy brome | 10 | 3 | 3 | 0 | 0 | 2 | 0 | 6 | 3 | 5 | 7 | 10 | 5 | 0 | 8 | 10 |
| Field violet | 5 | 9 | 2 | 2 | 0 | 10 | 6 | 3 | 0 | 2 | 3 | 8 | 2 | 0 | 3 | 0 |
| Galium (1) | 7 | 9 | 7 | 4 | 2 | 10 | 10 | 7 | 6 | 3 | 7 | 8 | 6 | 0 | 7 | 5 |
| Galium (2) | — | 10 | 6 | 5 | 2 | 10 | 10 | 8 | 5 | 3 | 6 | 8 | 7 | 0 | 7 | 4 |
| Green foxtail | 10 | 6 | 0 | 4 | 0 | 7 | 0 | 3 | 2 | 4 | 0 | 10 | 6 | 0 | 8 | 8 |
| Kochia | 4 | 10 | 6 | 6 | 0 | 10 | 7 | 6 | 0 | 0 | 0 | 2 | 0 | 0 | 9 | 9 |
| Lambsquarters | 5 | 4 | 0 | 2 | 0 | 4 | 0 | 0 | 2 | 4 | 0 | 0 | 0 | 0 | 4 | 4 |
| Persn Speedwell | 0 | 10 | 0 | 0 | 0 | 6 | 0 | 0 | 0 | 0 | 0 | 0 | 0 | 0 | 0 | 0 |
| Rape | 10 | 10 | 10 | 9 | 10 | 8 | 10 | 10 | 6 | 7 | 10 | 10 | 7 | 0 | 10 | 2 |
| Ryegrass | 10 | 9 | 3 | 3 | 0 | 10 | 7 | 4 | 0 | 0 | 6 | 8 | 0 | 0 | 5 | 3 |
| Sugar beet | 10 | 10 | 10 | 10 | 4 | 10 | 10 | 10 | 2 | 0 | 2 | 10 | 0 | 0 | 8 | 6. |
| Sunflower | 10 | 10 | 10 | 10 | 10 | 10 | 10 | 10 | 10 | 10 | 10 | 10 | 10 | 0 | 9 | 10 |
| Wheat (Spring) | 6 | 2 | 0 | 2 | 0 | 2 | 0 | 0 | 3 | 2 | 6 | 7 | 2 | 0 | 7 | 8 |
| Wheat (Winter) | 4 | 3 | 0 | 2 | 0 | 2 | 0 | 0 | 3 | 2 | 6 | 8 | 2 | 0 | 6 | 8 |
| Wild buckwheat | 2 | 10 | 5 | 2 | 0 | 10 | 8 | 10 | 0 | 0 | 0 | 8 | 0 | 4 | 6 | 0 |
| Wild mustard | 10 | 10 | 10 | 10 | 10 | 10 | 10 | 10 | 9 | 10 | 10 | 10 | 10 | 6 | 10 | 10 |
| Wild oat (1) | 10 | 5 | 3 | 0 | 0 | 5 | 2 | 6 | 7 | 6 | 10 | 10 | 2 | 0 | 9 | 9 |
| Wild oat (2) | 9 | 5 | 4 | 0 | 0 | 5 | 2 | 7 | 6 | 6 | 10 | 10 | 2 | 0 | 8 | 10 |
| Wild radish | 9 | 10 | 10 | 10 | 10 | 8 | 5 | 10 | 3 | 4 | 10 | 10 | 10 | 2 | 10 | 5 |
| Winter Barley | 4 | 5 | 0 | 3 | 0 | 3 | 2 | 3 | 6 | 5 | 6 | 6 | 2 | 0 | 5 | 9 |
| PREEMERGENCE | | | | | | | | | | | | | | | | |
| Blackgrass (1) | 6 | 8 | 5 | 5 | 2 | 6 | 3 | 4 | 0 | 0 | 0 | 8 | 5 | 0 | 2 | 2 |
| Blackgrass (2) | 8 | 8 | 6 | 6 | 2 | 6 | 3 | 4 | 0 | 0 | 0 | 7 | 4 | 0 | 2 | 2 |
| Chickweed | 10 | 10 | 10 | 9 | 6 | 10 | 10 | 8 | 0 | 0 | 0 | 10 | 3 | 0 | 10 | 6 |
| Downy brome | 8 | 7 | 5 | 2 | 0 | 5 | 3 | 6 | 3 | 2 | 5 | 9 | 2 | 0 | 2 | 2 |
| Field violet | 8 | 10 | 10 | 10 | 5 | 10 | 10 | 10 | 0 | 0 | 0 | 8 | 3 | 0 | 10 | 0 |
| Galium (1) | 7 | 10 | 10 | 9 | 8 | 10 | 8 | 8 | 2 | 2 | 0 | 9 | 2 | 0 | 4 | 3 |
| Galium (2) | — | 10 | 10 | 10 | 8 | 10 | 10 | 9 | — | 0 | 0 | 9 | 2 | 0 | 5 | 3 |
| Green foxtail | 7 | 8 | 5 | 7 | 0 | 7 | 3 | 4 | 0 | 0 | 2 | 9 | 3 | 0 | 2 | 5 |
| Kochia | 2 | 10 | 8 | 5 | 0 | 8 | 7 | 2 | 0 | 0 | 0 | 3 | 0 | 0 | 7 | 3 |
| Lambsquarters | 10 | 10 | 9 | 10 | 4 | 10 | 9 | 7 | 0 | 0 | 0 | 8 | 4 | 0 | 8 | 0 |
| Persn Speedwell | 0 | 10 | 7 | 4 | 3 | 10 | 6 | 4 | 0 | 0 | 0 | 2 | 3 | 0 | 10 | 2 |
| Rape | 8 | 10 | 10 | 10 | 8 | 10 | 9 | 10 | 0 | 0 | 0 | 9 | 2 | 0 | 8 | 0 |

TABLE D-continued

| | | | | | | | | | | | | | | | | |
|---|---|---|---|---|---|---|---|---|---|---|---|---|---|---|---|---|
| Ryegrass | 4 | 9 | 5 | 4 | 0 | 10 | 5 | 3 | 0 | 0 | 0 | 6 | 0 | 0 | 2 | 0 |
| Sugar beet | 9 | 10 | 10 | 10 | 5 | 10 | 10 | 10 | 0 | 2 | 0 | 10 | 2 | 0 | 9 | 4 |
| Sunflower | 8 | 10 | 10 | 10 | 7 | 10 | 10 | 6 | 0 | 0 | 2 | 10 | 0 | 0 | 9 | 2 |
| Wheat (Spring) | 0 | 4 | 3 | 0 | 0 | 5 | 3 | 0 | 5 | 0 | 2 | 2 | 2 | 0 | 2 | 0 |
| Wheat (winter) | 0 | 4 | 3 | 0 | 0 | 4 | 3 | 0 | 6 | 0 | 2 | 3 | 2 | 0 | 3 | 0 |
| Wild buckwheat | 5 | 10 | 9 | 8 | 3 | 10 | 9 | 10 | 0 | 0 | 0 | 4 | 0 | 0 | 7 | 2 |
| Wild mustard | 5 | 10 | 10 | 10 | 10 | 10 | 10 | 10 | 0 | 0 | 2 | 10 | 6 | 0 | 10 | 3 |
| Wild oat (1) | 0 | 8 | 6 | 0 | 0 | 10 | 6 | 2 | 2 | 0 | 3 | 5 | 0 | 0 | 2 | 0 |
| Wild oat (2) | 0 | 9 | 6 | 0 | 0 | 10 | 6 | 2 | 2 | 0 | 3 | 4 | 0 | 0 | 2 | 0 |
| Wild radish | 6 | 10 | 10 | 10 | 10 | 10 | 9 | 5 | 0 | 0 | 0 | 7 | 4 | 0 | 10 | 0 |
| Winter Barley | 2 | 8 | 5 | 4 | 0 | 9 | 9 | 3 | 4 | 2 | 2 | 5 | 2 | 0 | 3 | 0 |

| | COMPOUND | | | | | | | | | | | | | | | |
|---|---|---|---|---|---|---|---|---|---|---|---|---|---|---|---|---|
| Rate (8 g/ha) | 36 | 59 | 60 | 83 | 89 | 107 | 108 | 214 | 229 | 230 | 232 | 244 | 252 | 269 | 288 | 289 |
| POSTEMERGENCE | | | | | | | | | | | | | | | | |
| Blackgrass (1) | 3 | 4 | 2 | 3 | 2 | 3 | 0 | 2 | 2 | 2 | 4 | 7 | 4 | 0 | 6 | 8 |
| Blackgrass (2) | 2 | 4 | 0 | 2 | 0 | 3 | 0 | 2 | 0 | 2 | 5 | 7 | 3 | 0 | 4 | 6 |
| Chickweed | 3 | 10 | 10 | 6 | 0 | 10 | 9 | 10 | 0 | 0 | 0 | 10 | 0 | 0 | 4 | 6 |
| Downy brome | 9 | 2 | 2 | 0 | 0 | 0 | 0 | 5 | 2 | 3 | 5 | 9 | 2 | 0 | 7 | 9 |
| Field violet | 3 | 8 | 0 | 0 | 0 | 8 | 3 | 0 | 0 | 0 | 2 | 6 | 0 | 0 | 2 | 0 |
| Galium (1) | 4 | 8 | 4 | 2 | 0 | 10 | 10 | 5 | 3 | 0 | 3 | 4 | 3 | 0 | 5 | 2 |
| Galium (2) | — | 7 | 4 | 2 | 0 | 10 | 9 | 5 | 4 | 0 | 3 | 5 | 4 | 0 | 4 | 2 |
| Green foxtail | 9 | 4 | 0 | 3 | 0 | 3 | 0 | 2 | 0 | 2 | 0 | 8 | 4 | 0 | 7 | 6 |
| Kochia | 2 | 10 | 3 | 4 | 0 | 10 | 5 | 4 | 0 | 0 | 0 | 0 | 0 | 0 | 7 | 7 |
| Lambsquarters | 4 | 2 | 0 | 0 | 0 | 2 | 0 | 0 | 0 | 2 | 0 | 0 | 0 | 0 | 2 | 2 |
| Persn Speedwell | 0 | 10 | 0 | 0 | 0 | 3 | 0 | 0 | 0 | 0 | 0 | 0 | 0 | 0 | 0 | 0 |
| Rape | 10 | 10 | 9 | 7 | 9 | 6 | 8 | 10 | 3 | 3 | 9 | 10 | 4 | 0 | 10 | 0 |
| Ryegrass | 9 | 7 | 2 | 2 | 0 | 10 | 5 | 2 | 0 | 0 | 4 | 5 | 0 | 0 | 3 | 2 |
| Sugar beet | 10 | 10 | 9 | 10 | 2 | 10 | 10 | 10 | 0 | 0 | 0 | 10 | 0 | 0 | 7 | 5 |
| Sunflower | 10 | 10 | 10 | 10 | 10 | 10 | 10 | 10 | 9 | 8 | 10 | 10 | 10 | 0 | 8 | 10 |
| Wheat (Spring) | 3 | 0 | 0 | 0 | 0 | 0 | 0 | 0 | 0 | 0 | 3 | 5 | 0 | 0 | 5 | 7 |
| Wheat (Winter) | 2 | 0 | 0 | 0 | 0 | 0 | 0 | 0 | 0 | 0 | 4 | 5 | 0 | 0 | 4 | 7 |
| Wild buckwheat | 0 | 8 | 3 | 0 | 0 | 9 | 5 | 8 | 0 | 0 | 0 | 7 | 0 | 2 | 5 | 0 |
| Wild mustard | 8 | 10 | 10 | 10 | 10 | 10 | 9 | 10 | 7 | 9 | 8 | 10 | 10 | 4 | 10 | 10 |
| Wild oat (1) | 7 | 4 | 2 | 0 | 0 | 4 | 0 | 4 | 4 | 5 | 9 | 10 | 0 | 0 | 8 | 8 |
| Wild oat (2) | 7 | 3 | 2 | 0 | 0 | 3 | 0 | 5 | 5 | 4 | 8 | 10 | 0 | 0 | 6 | 7 |
| Wild radish | 6 | 10 | 9 | 10 | 9 | 7 | 3 | 10 | 0 | 3 | 8 | 10 | 10 | 0 | 10 | 5 |
| Winter Barley | 2 | 4 | 0 | 0 | 0 | 2 | 0 | 2 | 4 | 2 | 3 | 4 | 0 | 0 | 4 | 6 |
| PREEMERGENCE | | | | | | | | | | | | | | | | |
| Blackgrass (1) | 4 | 7 | 4 | 3 | 0 | 3 | 0 | 2 | 0 | 0 | 0 | 6 | 2 | 0 | 0 | 0 |
| Blackgrass (2) | 4 | 7 | 5 | 4 | 0 | 3 | 0 | 2 | 0 | 0 | 0 | 5 | 2 | 0 | 0 | 0 |
| Chickweed | 9 | 10 | 10 | 7 | 3 | 10 | 10 | 6 | 0 | 0 | 0 | 10 | 2 | 0 | 8 | 4 |
| Downy brome | 5 | 6 | 2 | 0 | 0 | 4 | 2 | 3 | 0 | 0 | 3 | 7 | 0 | 0 | 0 | 0 |
| Field violet | 6 | 10 | 10 | 8 | 2 | 10 | 10 | 9 | 0 | 0 | 0 | 6 | 0 | 0 | 8 | 0 |
| Galium (1) | 5 | 10 | 10 | 8 | 5 | 9 | 5 | 6 | 0 | 0 | 0 | 6 | 0 | 0 | 2 | 2 |
| Galium (2) | — | 10 | 10 | 8 | 4 | 10 | 7 | 7 | — | 0 | 0 | 7 | 0 | 0 | 3 | 0 |
| Green foxtail | 5 | 7 | 2 | 4 | 0 | 5 | 0 | 2 | 0 | 0 | 0 | 6 | 2 | 0 | 0 | 3 |
| Kochia | 0 | 9 | 7 | 3 | 0 | 6 | 5 | 0 | 0 | 0 | 0 | 0 | 0 | 0 | 5 | 2 |
| Lambsquarters | 7 | 10 | 8 | 9 | 2 | 9 | 6 | 4 | 0 | 0 | 0 | 7 | 2 | 0 | 7 | 0 |
| Persn Speedwell | 0 | 10 | 6 | 2 | 2 | 10 | 3 | 3 | 0 | 0 | 0 | 0 | 2 | 0 | 8 | 0 |
| Rape | 6 | 10 | 10 | 10 | 7 | 10 | 6 | 10 | 0 | 0 | 0 | 5 | 0 | 0 | 6 | 0 |
| Ryegrass | 2 | 8 | 3 | 3 | 0 | 8 | 3 | 2 | 0 | 0 | 0 | 4 | 0 | 0 | 0 | 0 |
| Sugar beet | 6 | 10 | 10 | 9 | 2 | 10 | 9 | 9 | 0 | 0 | 0 | 10 | 0 | 0 | 7 | 3 |
| Sunflower | 4 | 10 | 10 | 10 | 3 | 10 | 10 | 5 | 0 | 0 | 0 | 10 | 0 | 0 | 5 | 0 |
| Wheat (Spring) | 0 | 3 | 2 | 0 | 0 | 3 | 2 | 0 | 2 | 0 | 0 | 0 | 0 | 0 | 0 | 0 |
| Wheat (Winter) | 0 | 3 | 2 | 0 | 0 | 3 | 2 | 0 | 3 | 0 | 0 | 0 | 0 | 0 | 0 | 0 |
| Wild buckwheat | 3 | 10 | 8 | 6 | 0 | 9 | 7 | 8 | 0 | 0 | 0 | 2 | 0 | 0 | 5 | 0 |
| Wild mustard | 2 | 10 | 10 | 10 | 10 | 10 | 10 | 9 | 0 | 0 | 0 | 9 | 3 | 0 | 10 | 2 |
| Wild oat (1) | 0 | 7 | 4 | 0 | 0 | 8 | 4 | 0 | 0 | 0 | 2 | 2 | 0 | 0 | 0 | 0 |
| Wild oat (2) | 0 | 7 | 5 | 0 | 0 | 8 | 5 | 0 | 0 | 0 | 2 | 2 | 0 | 0 | 0 | 0 |
| Wild radish | 4 | 10 | 9 | 10 | 10 | 9 | 6 | 4 | 0 | 0 | 0 | 4 | 2 | 0 | 8 | 0 |
| Winter Barley | 0 | 7 | 2 | 3 | 0 | 7 | 7 | 2 | 2 | 0 | 0 | 3 | 0 | 0 | 0 | 0 |

| | COMPOUND | | | | | | | | | | | | | | | |
|---|---|---|---|---|---|---|---|---|---|---|---|---|---|---|---|---|
| Rate (4 g/ha) | 36 | 59 | 60 | 83 | 89 | 107 | 108 | 214 | 229 | 230 | 232 | 244 | 252 | 269 | 288 | 289 |
| POSTEMERGENCE | | | | | | | | | | | | | | | | |
| Blackgrass (1) | 0 | 2 | 0 | 2 | 0 | 0 | 0 | 0 | 0 | 0 | 2 | 5 | 2 | 0 | | |
| Blackgrass (2) | 0 | 2 | 0 | 0 | 0 | 0 | 0 | 0 | 0 | 0 | 3 | 6 | 2 | 0 | | |
| Chickweed | 0 | 10 | 8 | 3 | 0 | 7 | 5 | 7 | 0 | 0 | 0 | 9 | 0 | 0 | 2 | 4 |
| Downy brome | 7 | 0 | 0 | 0 | 0 | 0 | 0 | 3 | 0 | 0. | 4 | 7 | 0 | 0 | | |
| Field violet | 2 | 5 | 0 | 0 | 0 | 5 | 2 | 0 | 0 | 0 | 0 | 4 | 0 | 0 | 0 | 0 |
| Galium (1) | 2 | 4 | 2 | 0 | 0 | 7 | 7 | 2 | 2 | 0 | 0 | 2 | 0 | 0 | | |
| Galium (2) | — | 4 | 2 | 0 | 0 | 10 | 6 | 2 | 2 | 0 | 0 | 3 | 2 | 0 | 3 | 0 |

TABLE D-continued

| | | | | | | | | | | | | | | | | |
|---|---|---|---|---|---|---|---|---|---|---|---|---|---|---|---|---|
| Green foxtail | 7 | 2 | 0 | 2 | 0 | 0 | 0 | 0 | 0 | 0 | 0 | 4 | 2 | 0 | 6 | 3 |
| Kochia | 0 | 8 | 2 | 2 | 0 | 6 | 3 | 3 | 0 | 0 | 0 | 0 | 0 | 0 | | |
| Lambsquarters | 2 | 0 | 0 | 0 | 0 | 0 | 0 | 0 | 0 | 0 | 0 | 0 | 0 | 0 | | |
| Persn Speedwell | 0 | 8 | 0 | 0 | 0 | 2 | 0 | 0 | 0 | 0 | 0 | 0 | 0 | 0 | 0 | 0 |
| Rape | 9 | 10 | 4 | 5 | 8 | 5 | 7 | 6 | 0 | 0 | 7 | 10 | 3 | 0 | 10 | 0 |
| Ryegrass | 5 | 5 | 0 | 0 | 0 | 10 | 3 | 0 | 0 | 0 | 2 | 3 | 0 | 0 | 2 | 0 |
| Sugar beet | 7 | 10 | 6 | 9 | 0 | 10 | 10 | 7 | 0 | 0 | 0 | 10 | 0 | 0 | 6 | 2 |
| Sunflower | 10 | 10 | 10 | 10 | 7 | 10 | 9 | 10 | 7 | 7 | 10 | 10 | 9 | 0 | 6 | 7 |
| Wheat (Spring) | 0 | 0 | 0 | 0 | 0 | 0 | 0 | 0 | 0 | 0 | 2 | 3 | 0 | 0 | 4 | 5 |
| Wheat (Winter) | 0 | 0 | 0 | 0 | 0 | 0 | 0 | 0 | 0 | 0 | 2 | 3 | 0 | 0 | 3 | 5 |
| Wild buckwheat | 0 | 6 | 0 | 0 | 0 | 5 | 3 | 6 | 0 | 0 | 0 | 5 | 0 | 0 | | |
| Wild mustard | 6 | 10 | 10 | 10 | 10 | 10 | 7 | 9 | 3 | 8 | 6 | 8 | 8 | 2 | 10 | 0 |
| Wild oat (1) | 4 | 2 | 0 | 0 | 0 | 2 | 0 | 2 | 2 | 3 | 6 | 8 | 0 | 0 | | |
| Wild oat (2) | 4 | 2 | 0 | 0 | 0 | 2 | 0 | 2 | 3 | 2 | 6 | 9 | 0 | 0 | 5 | |
| Wild radish | 5 | 10 | 7 | 10 | 7 | 5 | 2 | 7 | 0 | 0 | 5 | 10 | 8 | 0 | 9 | 4 |
| Winter Barley | 0 | 2 | 0 | 0 | 0 | 0 | 0 | 0 | 2 | 0 | 0 | 2 | 0 | 0 | 2 | 5 |
| PREEMERGENCE | | | | | | | | | | | | | | | | |
| Blackgrass (1) | 2 | 6 | 2 | 2 | 0 | 0 | 0 | 0 | 0 | 0 | 0 | 3 | 0 | 0 | 0 | 0 |
| Blackgrass (2) | 2 | 6 | 3 | 3 | 0 | 0 | 0 | 0 | 0 | 0 | 0 | 3 | 0 | 0 | 0 | 0 |
| Chickweed | 6 | 9 | 8 | 5 | 2 | 10 | 9 | 3 | 0 | 0 | 0 | 8 | 0 | 0 | 6 | 2 |
| Downy brome | 2 | 5 | 0 | 0 | 0 | 2 | 0 | 2 | 0 | 0 | 0 | 3 | 0 | 0 | 0 | 0 |
| Field violet | 3 | 9 | 9 | 6 | 0 | 8 | 8 | 7 | 0 | 0 | 0 | 3 | 0 | 0 | 7 | 0 |
| Galium (1) | 2 | 9 | 8 | 6 | 2 | 6 | 3 | 4 | 0 | 0 | 0 | 4 | 0 | 0 | 0 | 0 |
| Galium (2) | — | 9 | 8 | 6 | 3 | 7 | 5 | 4 | — | 0 | 0 | 4 | 0 | 0 | 2 | 0 |
| Green foxtail | 2 | 6 | 0 | 2 | 0 | 2 | 0 | 0 | 0 | 0 | 0 | 5 | 0 | 0 | 0 | 0 |
| Kochia | 0 | 8 | 5 | 0 | 0 | 4 | 2 | 0 | 0 | 0 | 0 | 0 | 0 | 0 | 2 | 0 |
| Lambsquarters | 4 | 8 | 7 | 6 | 0 | 6 | 5 | 3 | 0 | 0 | 0 | 3 | 0 | 0 | 5 | 0 |
| Persn Speedwell | 0 | 10 | 5 | 0 | 0 | 10 | 2 | 2 | 0 | 0 | 0 | 0 | 0 | 0 | 6 | 0 |
| Rape | 4 | 10 | 10 | 8 | 4 | 8 | 5 | 8 | 0 | 0 | 0 | 3 | 0 | 0 | 4 | 0 |
| Ryegrass | 0 | 7 | 2 | 2 | 0 | 6 | 2 | 0 | 0 | 0 | 0 | 2 | 0 | 0 | 0 | 0 |
| Sugar beet | 4 | 10 | 10 | 8 | 0 | 10 | 8 | 8 | 0 | 0 | 0 | 8 | 0 | 0 | 6 | 0 |
| Sunflower | 2 | 10 | 10 | 9 | 0 | 10 | 10 | 3 | 0 | 0 | 0 | 7 | 0 | 0 | 2 | 0 |
| Wheat (Spring) | 0 | 2 | 0 | 0 | 0 | 2 | 0 | 0 | 0 | 0 | 0 | 0 | 0 | 0 | 0 | 0 |
| Wheat (Winter) | 0 | 2 | 0 | 0 | 0 | 2 | 0 | 0 | 0 | 0 | 0 | 0 | 0 | 0 | 0 | 0 |
| Wild buckwheat | 0 | 8 | 7 | 4 | 0 | 8 | 4 | 5 | 0 | 0 | 0 | 0 | 0 | 0 | 4 | 0 |
| Wild mustard | 0 | 10 | 10 | 10 | 7 | 10 | 9 | 7 | 0 | 0 | 0 | 8 | 0 | 0 | 10 | 0 |
| Wild oat (1) | 0 | 6 | 2 | 0 | 0 | 4 | 2 | 0 | 0 | 0 | 0 | 0 | 0 | 0 | 0 | 0 |
| Wild oat (2) | 0 | 5 | 2 | 0 | 0 | 4 | 3 | 0 | 0 | 0 | 0 | 0 | 0 | 0 | 0 | 0 |
| Wild radish | 2 | 9 | 7 | 10 | 9 | 8 | 4 | 2 | 0 | 0 | 0 | 2 | 0 | 0 | 6 | 0 |
| Winter Barley | 0 | 6 | 0 | 0 | 0 | 5 | 5 | 0 | 0 | 0 | 0 | 2 | 0 | 0 | 0 | 0 |

| | COMPOUND | | | | | |
|---|---|---|---|---|---|---|
| Rate (2 g/ha) | 36 | 107 | 108 | 232 | 252 | 289 |
| POSTEMERGENCE | | | | | | |
| Blackgrass (1) | 0 | 0 | 0 | 0 | 0 | 0 |
| Blackgrass (2) | 0 | 0 | 0 | 0 | 0 | 0 |
| Chickweed | 0 | 3 | 2 | 0 | 0 | 2 |
| Downy brome | 3 | 0 | 0 | 2 | 0 | 3 |
| Field violet | 0 | 3 | 0 | 0 | 0 | 0 |
| Galium (1) | 0 | 3 | 3 | 0 | 0 | 0 |
| Galium (2) | — | 3 | 3 | 0 | 0 | 0 |
| Green foxtail | 4 | 0 | 0 | 0 | 0 | 0 |
| Kochia | 0 | 3 | 0 | 0 | 0 | 2 |
| Lambsquarters | 0 | 0 | 0 | 0 | 0 | 0 |
| Persn Speedwell | 0 | 0 | 0 | 0 | 0 | 0 |
| Rape | 5 | 3 | 5 | 5 | 0 | .0 |
| Ryegrass | 2 | 7 | 0 | 0 | 0 | 0 |
| Sugar beet | 3 | 9 | 9 | 0 | 0 | 0 |
| Sunflower | 9 | 10 | 5 | 10 | 5 | 4 |
| Wheat (Spring) | 0 | 0 | 0 | 0 | 0 | 2 |
| Wheat (Winter) | 0 | 0 | 0 | 0 | 0 | 2 |
| Wild buckwheat | 0 | 2 | 2 | 0 | 0 | 0 |
| Wild mustard | 4 | 10 | 3 | 4 | 5 | 7 |
| Wild oat (1) | 2 | 0 | 0 | 2 | 0 | 2 |
| Wild oat (2) | 3 | 0 | 0 | 3 | 0 | 2 |
| Wild radish | 3 | 2 | 0 | 2 | 5 | 0 |
| Winter Barley | 0 | 0 | 0 | 0 | 0 | 3 |
| PREEMERGENCE | | | | | | |
| Blackgrass (1) | — | 0 | 0 | 0 | 0 | 0 |
| Blackgrass (2) | — | 0 | 0 | 0 | 0 | 0 |
| Chickweed | — | 8 | 7 | 0 | 0 | 0 |
| Downy brome | — | 0 | 0 | 0 | 0 | 0 |
| Field violet | — | 6 | 5 | 0 | 0 | 0 |
| Galium (1) | — | 4 | 0 | 0 | 0 | 0 |

TABLE D-continued

| | | | | | | |
|---|---|---|---|---|---|---|
| Galium (2) | — | 5 | 2 | 0 | 0 | 0 |
| Green foxtail | — | 0 | 0 | 0 | 0 | 0 |
| Kochia | — | 2 | 0 | 0 | 0 | 0 |
| Lambsquarters | — | 5 | 3 | 0 | 0 | 0 |
| Persn Speedwell | — | 8 | 0 | 0 | 0 | 0 |
| Rape | — | 5 | 2 | 0 | 0 | 0 |
| Ryegrass | — | 3 | 0 | 0 | 0 | 0 |
| Sugar beet | — | 9 | 5 | 0 | 0 | 0 |
| Sunflower | — | 9 | 9 | 0 | 0 | 0 |
| Wheat (Spring) | — | 0 | 0 | 0 | 0 | 0 |
| Wheat (Winter) | — | 0 | 0 | 0 | 0 | 0 |
| Wild buckwheat | — | 6 | 3 | 0 | 0 | 0 |
| Wild mustard | — | 9 | 7 | 0 | 0 | 0 |
| Wild oat (1) | — | 2 | 0 | 0 | 0 | 0 |
| Wild oat (2) | — | 2 | 0 | 0 | 0 | 0 |
| wild radish | — | 6 | 2 | 0 | 0 | 0 |
| Winter Barley | — | 3 | 2 | 0 | 0 | 0 |

What is claimed is:

1. A compound of the formula

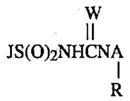

wherein:

J is

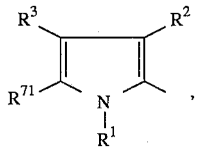

J-1

,

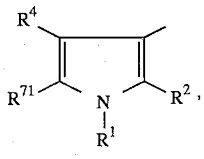

J-2

, or

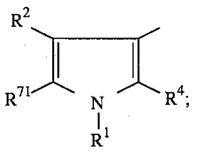

J-3

W is O or S;

R is H or $CH_3$;

$R^1$ is H; $CH_3$; $CH_2OCH_3$; $CH_2OC_2H_5$; $CH_2CN$; $CH_2SCH_3$, $CH_2SC_2H_5$; $C_2$–$C_6$ alkyl optionally substituted with one $C_1$–$C_2$ alkoxy, $C_1$–$C_2$ alkylthio, CN or one or more halogens; $C_3$–$C_4$ alkenyl; $C_3$–$C_4$ haloalkenyl; $C_3$–$C_6$ cycloalkyl; $C(O)R^5$; $N(CH_3)_2$; or $Q^1$;

$R^2$ is $C_1$–$C_4$ alkyl optionally substituted with one CN, $C_2$–$C_3$ alkylcarbonyl, methoxycarbonyl, $C_1$–$C_2$ alkoxy, $C_1$–$C_2$ alkylthio, $C_1$–$C_2$ alkylsulfonyl, $S(O)_2NR^6R^7$, OH or one or more halogens; $C_2$–$C_4$ alkenyl optionally substituted with one $C_1$–$C_2$ alkoxy, $C_1$–$C_2$ alkylthio, CN or one or more halogens; CN; $C(O)R^8$; $C(O)OR^9$; $C(O)NR^{10}R^{11}$; $C(R^{12})$=$NOR^{13}$; $C(R^{14})$ $(OR^{15})$ $(OR^{16})$; $S(O)_nR^{17}$; $S(O)_2NR^{18}R^{19}$; $NO_2$; halogen; or $OR^{73}$;

$R^3$ is H, halogen or $C_1$–$C_4$ alkyl;

$R^4$ is H, $C_1$–$C_4$ alkyl optionally substituted with one CN, $C_2$–$C_3$ alkylcarbonyl, methoxycarbonyl, $C_1$–$C_2$ alkoxy, $C_1$–$C_2$ alkylthio, $C_1$–$C_2$ alkylsulfonyl, $S(O)_2NR^6R^7$, OH or one or more halogens; $C_2$–$C_4$ alkenyl optionally substituted with one $C_1$–$C_2$ alkoxy, $C_1$–$C_2$ alkylthio, CN or one or more halogens; CN; $C(O)R^8$; $C(O)OR^9$; $C(O)NR^{10}R^{11}$; $C(R^{12})$=$NOR^{13}$; $S(O)_nR^{17}$; $S(O)_2NR^{18}R^{19}$; or halogen;

$R^5$ is $C_1$–$C_4$ alkyl, $C_1$–$C_4$ alkoxy or $NR^{20}R^{21}$;

$R^6$ is H, $C_1$–$C_2$ alkyl or $OCH_3$;

$R^7$ is $C_1$–$C_2$ alkyl; or $R^6$ and $R^7$ can be taken together as —$(CH_2)_3$— or —$(CH_2)_4$—;

$R^8$ is H, $C_1$–$C_3$ alkyl or cyclopropyl;

$R^9$ is $CH_3$; $C_2$–$C_3$ alkyl optionally substituted with one $C_1$–$C_2$ alkoxy, OH, CN or one or more halogens; $C_3$–$C_4$ alkenyl; or propargyl;

$R^{10}$ is H, $C_1$–$C_3$ alkyl or $OCH_3$;

$R^{11}$ is $C_1$–$C_3$ alkyl; or $R^{10}$ and $R^{11}$ can be taken together as —$(CH_2)_3$—, —$(CH_2)_4$—, —$(CH_2)_5$— or —$(CH_2)_2O(CH_2)_2$—;

$R^{12}$ is H, $C_1$–$C_3$ alkyl, allyl, halogen, CN, $N_3$, $C_1$–$C_2$ alkoxy, $C_1$–$C_2$ alkylthio or SCN;

$R^{13}$ is $C_1$–$C_3$ alkyl or allyl;

$R^{14}$ is H or $C_1$–$C_3$ alkyl;

$R^{15}$ and $R^{16}$ are independently $C_1$–$C_2$ alkyl;

$R^{17}$ is $C_1$–$C_4$ alkyl, optionally substituted with one $C_1$–$C_2$ alkoxy, $C_1$–$C_2$ alkylthio, CN or one or more halogens; $C_3$–$C_4$ alkenyl; or cyclopropylmethyl;

$R^{18}$ is H, $C_1$–$C_3$ alkyl or $OCH_3$;

$R^{19}$ is H or $C_1$–$C_2$ alkyl; or $R^{18}$ and $R^{19}$ can be taken together as —$(CH_2)_3$—, —$(CH_2)_4$— or —$(CH_2)_5$—;

$R^{20}$ and $R^{21}$ are independently $C_1$–$C_2$ alkyl; or $R^{20}$ and $R^{21}$ can be taken together as —$(CH_2)_3$—, —$(CH_2)_4$—, —$(CH_2)_5$— or —$(CH_2)_2O(CH_2)_2$—;

$R^{71}$ is H, halogen or $CF_3$;

$R^{73}$ is $C_1$–$C_4$ alkyl optionally substituted with one or more halogens, CN, $C_1$–$C_2$ alkoxy, or $C_1$–$C_2$ alkylthio; $C(O)R^{74}$; $SO_2R^{75}$; $C_3$–$C_4$ alkenyl; or propargyl;

$R^{74}$ is $C_1$–$C_4$ alkyl optionally substituted with $C_1$–$C_2$ alkoxy, one or more halogens, or CN; $C_3$–$C_4$ alkenyl; or $C_1$–$C_3$ alkoxy;

$R^{75}$ is $C_1$–$C_3$ alkyl or $CF_3$;

n is 0, 1 or 2;

$Q^1$ is

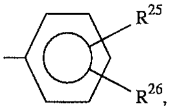, 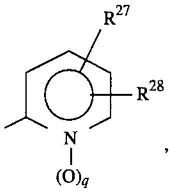, 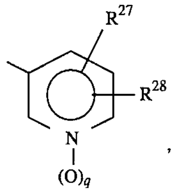,

Q1-1 Q1-2 Q1-3

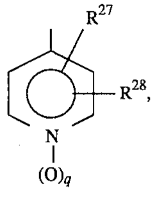, 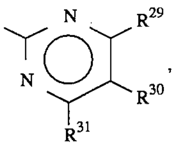, 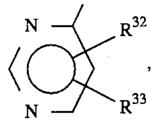,

Q1-4 Q1-5 Q1-6

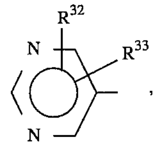, 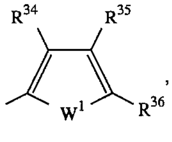, 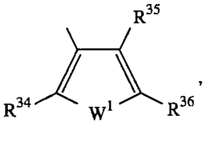,

Q1-7 Q1-8 Q1-9

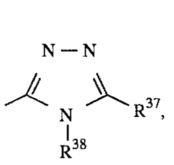 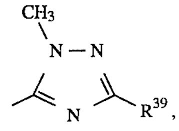 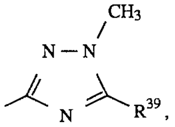

Q1-10 Q1-11 Q1-12

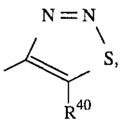 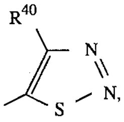 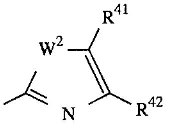

Q1-13 Q1-14 Q1-15

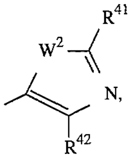 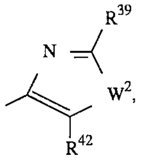 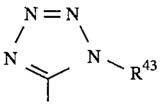 or

Q1-16 Q1-17 Q1-18

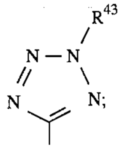

Q1-19

A is

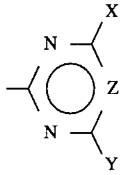 or 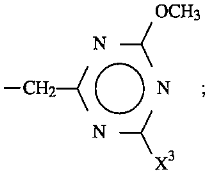 ;

A-1 A-6

X is H, $C_1$–$C_4$ alkyl, $C_1$–$C_4$ alkoxy, $C_1$–$C_4$ haloalkyl, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

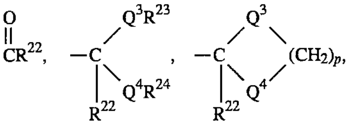

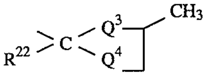

or $N(OCH_3)CH_3$;

p is 2 or 3;

$Q^3$ and $Q^4$ are independently O or S;

$R^{22}$ is H or $C_1$–$C_3$ alkyl;

$R^{23}$ and $R^{24}$ are independently $C_1$–$C_3$ alkyl;

Z is N; and $X^3$ is $CH_3$ or $OCH_3$;

q is 0 or 1;

$R^{25}$ and $R^{26}$ are independently H, $CH_3$ or Cl;

$R^{27}$ and $R^{28}$ are independently H, F, or $CH_3$;

$R^{29}$ is H, $CH_3$ or $OCH_3$;

$R^{30}$ is H or $CH_3$;

$R^{31}$, $R^{32}$ and $R^{33}$ are independently H, $CH_3$ or $OCH_3$;

$R^{34}$, $R^{35}$ and $R^{36}$ are independently H, $CH_3$, $CH_2CH_3$, Cl, Br, $OCH_3$ or $OCH_2CH_3$;

$R^{37}$ is H or $C_1$–$C_2$ alkyl;

$R^{38}$ is $CH_3$;

$R^{39}$ is H, $C_1$–$C_2$ alkyl, $OCH_3$ or $SCH_3$;

$R^{40}$ is H, $CH_3$ or $CH_2CH_3$;

$R^{41}$ and $R^{42}$ are independently H, or $CH_3$;

$R^{43}$ is H, $CH_3$, $CH_2CH_3$ or $C_3H_7$;

$W^1$ is O or S;

$W^2$ is O, S or $NR^{44}$;

$R^{44}$ is H or $CH_3$;

and their agriculturally suitable salts; provided that:

(a) when W is S, then R is H, A is A-1 and Y is $CH_3$, $OCH_3$, $OCH_2CH_3$, $CH_2OCH_3$, $CH_2CH_3$, $CF_3$, $SCH_3$, $OCH_2CH{=}CH_2$, $OCH_2C{\equiv}CH$, $OCH_2CH_2OCH_3$, $CH(OCH_3)_2$ or

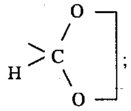

(b) when the total number of carbon atoms of X and Y is greater than four, then the number of carbons of $Q^1$ is less than or equal to eight;

(c) when A is A-6 then R is H;

(d) when J is J-1, A is A-1 and X and/or Y is alkyl, then $R^2$ is other than CN or $NO_2$.

2. A compound of claim 1 wherein:

W is O;

$R^1$ is H, $C_1$–$C_6$ alkyl, allyl, $CH_2OCH_3$, $CH_2OC_2H_5$, $CH_2SCH_3$ phenyl, 2-pyridyl, 3-pyridyl, 4-pyridyl, $C(O)OCH_3$ or $C(O)N(CH_3)_2$;

X is $C_1$–$C_2$ alkyl, $C_1$–$C_2$ alkoxy, F, Cl, Br, I, $CH_2F$, $CF_3$, $CH_2Cl$ or $CH_2Br$; and Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH{=}CH_2$, $OCH_2C{\equiv}CH$, $OCH_2CH_2OCH_3$, $CH_2SCH_3$, $C(O)R^{22}$,

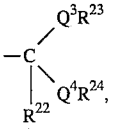 , 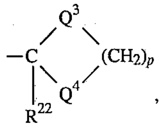 , 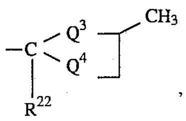 , cyclopropyl, $C{\equiv}CH$ or $C{\equiv}CCH_3$.

3. A compound of claim 2 wherein:

$R^3$ is H, $CH_3$, Cl or Br; and $R^4$ is H, $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)NR^{10}R^{11}$, $C(R^{12}){=}NOR^{13}$, $C(R^{14})$ $(OR^{15})$ $(OR^{16})$, $S(O)_nR^{17}$, $S(O)_2NR^{18}R^{19}$, F, Cl or Br;

$R^8$ is H or $C_1$–$C_2$ alkyl;

$R^9$ is $C_1$–$C_2$ alkyl or $CH_2CH_2Cl$;

$R^{10}$ is H or $CH_3$;

$R^{11}$ is $CH_3$;

$R^{12}$ is H, $CH_3$, $C_2H_5$ or Cl;

$R^{13}$ is $CH_3$;

$R^{14}$ is H or $C_1$–$C_2$ alkyl;

$R^{15}$ and $R^{16}$ are $CH_3$;

$R^{17}$ is $C_1$–$C_2$ alkyl;

$R^{18}$ is H or $CH_3$;

$R^{19}$ is $CH_3$; and n is 0 or 2.

4. A compound of claim 3 wherein:

$R^2$ is $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)NR^{10}R^{11}$, $C(R^{12}){=}NOR^{13}$, $C(R^{14})$ $(OR^{15})$ $(OR^{16})$, $S(O)_nR^{17}$, $S(O)_2NR^{18}R^{19}$, F, Cl, Br, or $OR^{73}$.

5. A compound of claim 4 wherein:

R is H; and $R^{71}$ is H.

6. A compound of claim 5 wherein:

J is J-1.

7. A compound of claim 5 wherein:

J is J-2.

8. A compound of claim 5 wherein:

J is J-3.

9. A compound of claim 6 wherein:

$R^2$ is $C_1$–$C_2$ alkyl, $CH_2CN$, $CH_2OCH_3$, CH2$SCH_3$, $CH_2S(O)_2CH_3$, $C(O)R^8$, $C(O)OR^9$, $C(O)N(CH_3)_2$, $S(O)_2CH_3$, $S(O)_2C_2H_5$, $S(O)_2N(CH_3)_2$, $C_1$–$C_2$ alkoxy, $OC(O)CH_3$, or $OSO_2CH_3$;

$R^4$ is H, $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)N(CH_3)_2$, $S(O)_2CH_3$, $S(O)_2C_2H_5$ or $S(O)_2N(CH_3)_2$;

$R^8$ is $C_1$–$C_2$ alkyl;

$R^9$ is $C_1$–$C_2$ alkyl.

10. A compound of claim 7 wherein:

$R^2$ is $C_1$–$C_2$ alkyl, $CH_2CN$, $CH_2OCH_3$, $CH_2SCH_3$, $CH_2S(O)_2CH_3$, $C(O)R^8$, $C(O)OR^9$, $C(O)N(CH_3)_2$, $S(O)_2CH_3$, $S(O)_2C_2H_5$, $S(O)_2N(CH_3)_2$, $C_1$–$C_2$ alkoxy, $OC(O)CH_3$, or $OSO_2CH_3$;

$R^4$ is H, $C_1$–$C_2$ alkyl, $CH_2CN$, $CH_2OCH_3$, $CH_2SCH_3$, $CH_2S(O)_2CH_3$, $Q^2$, $C(O)R^8$, $C(O)OR^9$, $C(O)N(CH_3)_2$, $S(O)_2CH_3$ or $S(O)_2N(CH_3)_2$;

$R^8$ is $C_1$–$C_2$ alkyl;

$R^9$ is $C_1$–$C_2$ alkyl.

11. A compound of claim 8 wherein:

$R^2$ is $C_1$–$C_2$ alkyl, $CH_2CN$, $CH_2OCH_3$, $CH_2SCH_3$, $CH_2S(O)_2CH_3$, $C(O)R^8$, $C(O)OR^9$, $C(O)N(CH_3)_2$, $S(O)_2CH_3$, $S(O)_2C_2H_5$, $S(O)_2N(CH_3)_2$, $C_1$–$C_2$ alkoxy, $OC(O)CH_3$, or $OSO_2CH_3$;

$R^4$ is H, $C_1$–$C_2$ alkyl, $CH_2CN$, $CH_2OCH_3$, $CH_2SCH_3$, $CH_2S(O)_2CH_3$, $C(O)R^8$, $C(O)OR^9$, $C(O)N(CH_3)_2$, $S(O)_2CH_3$ or $S(O)_2N(CH_3)_2$;

$R^8$ is $C_1$–$C_2$ alkyl;

$R^9$ is $C_1$–$C_2$ alkyl.

12. A compound of claim 9 wherein:

A is A-1;

X is $CH_3$, $OCH_3$, $OCH_2CH_3$, or Cl; and

Y is $CH_3$, $OCH_3$, $NHCH_3$ or $N(CH_3)_2$.

13. A compound of claim 10 wherein:

A is A-1;

X is $CH_3$, $OCH_3$, $OCH_2CH_3$, or Cl; and

Y is $CH_3$, $OCH_3$, $NHCH_3$ or $N(CH_3)_2$.

14. A compound of claim 11 wherein:

A is A-1;

X is $CH_3$, $OCH_3$, $OCH_2CH_3$, or Cl; and

Y is $CH_3$, $OCH_3$, $NHCH_3$ or N $(CH_3)_2$.

15. The compound of claim 1 which is: (1-methylethyl)2-[[(4-methoxy-6-methyl-1,3,5-triazin-2-yl)aminocarbonyl] aminosulfonyl]-1-methyl-1H-pyrrole-3-carboxylate.

16. An agriculturally suitable composition for controlling the growth of undesired vegetation comprising a herbicidally effective amount of a compound in any of claims 1, 2, 3, 4 or 5 and at least one of the following surfactants: solid diluent or liquid diluent.

17. A method for controlling the growth of undesired vegetation which comprises applying to the locus to be protected a herbicidally effective amount of a compound in any of claims 1, 2, 3, 4 or 5.

* * * * *